(12) United States Patent
Hung et al.

(10) Patent No.: US 10,619,158 B2
(45) Date of Patent: Apr. 14, 2020

(54) MODULATION OF HUNTINGTIN EXPRESSION

(71) Applicant: Ionis Pharmaceuticals, Inc., Carlsbad, CA (US)

(72) Inventors: Gene Hung, Carlsbad, CA (US); C. Frank Bennett, Carlsbad, CA (US); Susan M. Freier, San Diego, CA (US); Holly Kordasiewicz, San Diego, CA (US); Lisa Stanek, Cambridge, MA (US); Don W. Cleveland, Del Mar, CA (US); Seng H. Cheng, Natick, MA (US); Lamya Shihabuddin, Brighton, MA (US)

(73) Assignee: IONIS Pharmaceuticals, Inc., Carlsbad, CA (US)

( * ) Notice: Subject to any disclaimer, the term of this patent is extended or adjusted under 35 U.S.C. 154(b) by 0 days.

(21) Appl. No.: 16/270,983

(22) Filed: Feb. 8, 2019

(65) Prior Publication Data

US 2019/0249177 A1    Aug. 15, 2019

Related U.S. Application Data

(63) Continuation of application No. 15/596,249, filed on May 16, 2017, now Pat. No. 10,202,603, which is a continuation of application No. 15/005,712, filed on Jan. 25, 2016, now Pat. No. 9,683,236, which is a continuation of application No. 14/528,656, filed on Oct. 30, 2014, now Pat. No. 9,273,315, which is a continuation of application No. 13/395,188, filed as application No. PCT/US2010/048532 on Sep. 10, 2010, now Pat. No. 8,906,873.

(60) Provisional application No. 61/241,853, filed on Sep. 11, 2009.

(51) Int. Cl.
*C07H 21/04* (2006.01)
*C12N 15/113* (2010.01)

(52) U.S. Cl.
CPC ........ *C12N 15/113* (2013.01); *C12N 2310/11* (2013.01); *C12N 2310/113* (2013.01); *C12N 2310/315* (2013.01); *C12N 2310/321* (2013.01); *C12N 2310/3341* (2013.01); *C12N 2310/341* (2013.01); *C12N 2310/345* (2013.01); *C12N 2310/346* (2013.01)

(58) Field of Classification Search
None
See application file for complete search history.

(56) References Cited

U.S. PATENT DOCUMENTS

| | | |
|---|---|---|
| 5,595,756 A | 1/1997 | Bally et al. |
| 5,686,288 A | 11/1997 | MacDonald et al. |
| 5,700,922 A | 12/1997 | Cook |
| 5,801,154 A | 9/1998 | Baracchini et al. |
| 5,998,148 A | 12/1999 | Bennett et al. |
| 6,043,060 A | 3/2000 | Imanishi |
| 6,147,200 A | 11/2000 | Manoharan et al. |
| 6,582,908 B2 | 6/2003 | Fodor et al. |
| 6,670,461 B1 | 12/2003 | Wengel et al. |
| 7,320,965 B2 | 1/2008 | Sah et al. |
| 7,374,927 B2 | 5/2008 | Palma et al. |
| 2001/0053519 A1 | 12/2001 | Fodor et al. |
| 2003/0109476 A1 | 6/2003 | Kmiec |
| 2003/0144242 A1 | 7/2003 | Ward et al. |
| 2003/0228597 A1 | 12/2003 | Cowsert et al. |
| 2004/0092465 A1 | 5/2004 | Dobie |
| 2004/0096880 A1 | 5/2004 | Kmiec |
| 2004/0137471 A1 | 7/2004 | Vickers et al. |
| 2004/0146902 A1 | 7/2004 | Ecker et al. |
| 2005/0042646 A1 | 2/2005 | Davidson |
| 2005/0096284 A1 | 5/2005 | McSwiggen |
| 2005/0101013 A1 | 5/2005 | Freier et al. |
| 2005/0191638 A1 | 9/2005 | McSwiggen |
| 2005/0245475 A1 | 11/2005 | Khvorova et al. |
| 2005/0255086 A1 | 11/2005 | Davidson |
| 2005/0255487 A1 | 11/2005 | Khvorova et al. |
| 2006/0051769 A1 | 3/2006 | Barts |
| 2007/0031844 A1 | 2/2007 | Khvorova et al. |
| 2007/0099860 A1 | 5/2007 | Sah |
| 2007/0299027 A1 | 12/2007 | Hung et al. |
| 2008/0015158 A1 | 1/2008 | Ichiro |
| 2008/0039415 A1 | 2/2008 | Stewart et al. |
| 2008/0039418 A1 | 2/2008 | Freier |
| 2008/0274989 A1 | 11/2008 | Davidson et al. |
| 2009/0092981 A1 | 4/2009 | Swayze et al. |

FOREIGN PATENT DOCUMENTS

| | | |
|---|---|---|
| CA | 2526893 | 11/2004 |
| JP | 2009-513144 | 4/2009 |
| JP | 2009-524431 | 7/2009 |
| RU | 2297833 | 4/2007 |

(Continued)

OTHER PUBLICATIONS

Anderson et al., "An Overview of Psychiatric Symptoms in Huntington's Disease" Current Psychiatry Reports (2001) 3:379-388.

(Continued)

*Primary Examiner* — Kimberly Chong

(74) *Attorney, Agent, or Firm* — McDonnell Boehnen Hulbert & Berghoff LLP

(57) ABSTRACT

Provided herein are methods, compounds, and compositions for reducing expression of huntingtin mRNA and protein in an animal. Such methods, compounds, and compositions are useful to treat, prevent, delay, or ameliorate Huntington's disease, or a symptom thereof.

16 Claims, 10 Drawing Sheets

Specification includes a Sequence Listing.

(56) References Cited

FOREIGN PATENT DOCUMENTS

| | | |
|---|---|---|
| WO | WO 1994/026764 | 11/1994 |
| WO | WO 1999/050409 | 10/1999 |
| WO | WO 2000/003720 | 1/2000 |
| WO | WO 2001/079283 | 10/2001 |
| WO | WO 2003/013437 | 2/2003 |
| WO | WO 2003/009835 | 8/2003 |
| WO | WO 2003/064625 | 8/2003 |
| WO | WO 2004/044123 | 5/2004 |
| WO | WO 2004/048601 | 6/2004 |
| WO | WO 2004/101787 | 11/2004 |
| WO | WO 2004/013280 | 12/2004 |
| WO | WO 2005/027980 | 3/2005 |
| WO | WO 2005/045032 | 5/2005 |
| WO | WO 2005/083436 | 9/2005 |
| WO | WO 2005/105995 | 11/2005 |
| WO | WO 2005/116204 | 12/2005 |
| WO | WO 2006/128141 | 11/2006 |
| WO | WO 2007/022470 | 2/2007 |
| WO | WO 2007/051045 | 5/2007 |
| WO | WO 2007/120883 | 10/2007 |
| WO | WO 2007089584 | 11/2007 |
| WO | WO 2008/005562 | 1/2008 |
| WO | WO 2008/018795 | 2/2008 |
| WO | WO 2009/008725 | 1/2009 |
| WO | WO 2011/097388 | 8/2011 |

OTHER PUBLICATIONS

Bennett et al., "Antisense oligonucleoties as a tool for gene functionalization and target validation" Biochimica Biophysica Acta (1999) 1489:19-30.

Boado et al., "Antisense-mediated down-regulation of the human huntington gene" Journal of Pharmacology and Experimental Therapeutics (2000) 295:239-243.

Boffa et al., "Isolation of active genes containing CAG repeats by DNA strands invasion by a peptide nucleic acid" PNAS (1995) 92:1901-5.

Borovecki et al., "Genome-wide expression profiling of human blood reveals biomarkers for Huntington's disease" Proc. Natl. Acad. Sci. USA (2005) 102:11023-11028.

Branch et al., "A good antisense molecule is hard to find," TIBS (1998) 23:45-50.

Caplen et al., "Rescue ofpolyglutamine-mediated cytotoxicity by double-stranded RNA-mediated RNA interference" Human Molecular Genetics (2002) II (2): 175-184.

Chang et al., "Structural Analysis of Complementary DNA and Amino Acid Sequences of Human and Rat Androgen Receptors" PNAS (1988) 85:7211-7215.

Shin "On the Preparation and Utilization ofIsolated and Purififed Oligonucleotides." Document purportedly located on a CD-ROM and contributed to the public collection of the Katherine R. Everett Law Library of the University ofNorth Carolina on Mar. 14, 2002.

Crooke et al., "Basic Principles of Antisense Therapeutics" Antisense Research and Application (1998) Chapter 1:1-50.

Davidson et al., "Molecular medicine for the brain: silencing of disease genes with RNA interference" Lancet Neural. (2004) 3:145-149.

Diaz-Hernandez et al., "Full Motor Recovery Despite Striatal Neuron Loss and Formation of Irreversible Amyloid-Like Inclusions in a Conditional Mouse Model of Huntington's Disease" J Neurosci(2005) 25:9773-9781.

Drouet et al., "Sustained effects of nonallele-specific Huntingtin silencing" Ann Neural. (2009) 65(3): 276-285.

Eder et al., "Inhibition of LNCaP Prostate Cancer Cells by Means of Androgen Receptor Antisense Oligonucleotides" Cancer Gene Therapy (2000) 7(7):997-1007.

Gagnon et al., "HD Therapeutics—CHDI Fifth Annual Conference" IDrugs 13( 4): 219-223 (2010).

Gonzalez-Alegre et al., "Technology Insight: therapeutic RNA interference—how far from the neurology clinic?" Nature Clinical Practice 3:394-404.

Gryaznov et al., "Oligodeoxyribonucleotide N3'->P5' Phosphoramidates Synthesis and Hybridization Properties" JAm. Chem. Soc. (1994) 116:3143-3144.

Haque et al., "Antisense gene therapy for neurodegenerative disease" Experimental Neurology (1997) 144:139-146.

Harper et al., "Ten years ofpresymptomatic testing for Huntington's disease: the experience of the UK Huntington's Disease Prediction Consortium" J. Med. Genet. 37:567-571, 2000.

Harper et al., "RNA interference improves motor and neuropathological abnormalities in a Huntington'sdisease mouse model" PNAS (2005) I 02:5820-5825.

Hasholt et al., "Antisense downregulation of mutant huntingtin in a cell model" Journal of Gene Medicine (2003) 5:528-538.

Hersch et al., "Translating Therapies for Huntington's Disease from Genetic Animal Models to Clinical Trials" NeuroRX (2004) 1:298-306.

Hersch et al., "Neuroprotection for Huntington's disease: Ready, set, slow" Neurotherapeutics (2008) 5(2):226-236.

Liu et al., "Specific inhibition of Huntington's disease gene expression by siRNAs in cultures cells" Proceedings of the Japan Academy. Series B, Physical and Biological Sciences (2003) 79B:293-298.

MacDonald et al., "A novel gene containing a trinucleotide repeat that is expanded and unstable on Huntington's disease chromosomes" Cell (1993) 72(6):971-983.

Machida et al., "rAAV-mediated shRNA ameliorated neuropathology in Huntington disease model mouse" Biochem. Biophys. Res. Commun. (2006) 343:190-197.

Macmillan et al., "Molecular analysis and clinical correlations oftheHuntington's disease mutation" Lancet (1993) 342:954-958.

Maher et al., "Comparative hybrid arrest by tandem antisense oligodeoxyribonucleotides or oligodeoxyribonucleoside rnethylphosphonates in a cell-free system" Nuc. Acid. Res. (1988) 16:3341-3358.

Martin et al., "38. Ein neuer Zugang zu 2'-0-Alkylribonucleosiden und Eigenschaften deren Oligonucleotide" Helv. Chim. Acta (1995) 78:486-504.

Nellemann et al., "Inhibition of Huntington synthesis by antisense oligonucleotides" Molecular and Cellular Neurosciences (2000) 16:313-323.

New England BioLabs, Inc. Catalogue (1998): 121, 284.

Nguyen et al., "Clioquinol down-regulates mutant huntingtin expression in vitro and mitigates pathology in a Huntington's disease mouse model" PNAS (2005) 102:11840-11845.

Nikiforov et al., "The Use ofPhosphorothioate Primers and Exonuclease Hydrolysis for the Preparation of Single-stranded PCR Products and their Detection by Solid-phase Hybridization" PCR Methods and Applications (1994) 3:285-291.

Pakula et al., "Genetic analysis of protein stability and function" Annual review of genetics 23: 289-310 (1989).

Reynolds et al., "Rational siRNA design for RNA interference" Nature Biotechnology (2004) 22:326-330.

Sanghvi et al., "Heterocyclic Base Modifications in Nucleic Acids and Their Applications in Antisense Oligonucleotides" Antisense Research and Applications (1993) pp. 273-288.

Sewell et al., "Phase I Trial of ISIS 104838, a 2'-Methoxyexthyl Modified Antisense Oligonucleotide Targeting Tumor Necrosis Factor-Alpha" The Journal of Pharmacology and Experimental Therapeutics (2002) 303(3):1334-1343.

Sheehan et al., "Biochemical properties ofphosphonoacetate and thiophosphonoacetate oligodeoxyribonucleotides" Nucleic Acids Research (2003) 31 :4109-4118.

Uhlmann et al., "Antisense oligonucleotides: a new therapeutic principle" Chemical Reviews (1990) 90:543-584.

Vickers et al., "Efficient Reduction of Target RNAs by Small Interfering RNA and Rnase H-dependent Antisense Agents. A comparative analysis." J Bioi. Chem. (2003) 278:7108-7118.

Wang et al., "Clinico-pathological rescue of a model mouse of Huntington's disease by siRNA" Neurosci. Res. (2005) 53:241-249.

(56) References Cited

OTHER PUBLICATIONS

Woolf et al., "Specificity of antisense oligonucleotides in vivo" Proc. Natl. Acad. Sci. USA (1992) 89:7305-7309.
Yen et al., "Sequence-specific cleavage of Huntingtin mRNA by catalytic DNA" Annals of Neurology (1999) 46 (3)366-373.
International Search Report for Application No. PCT/US2007/002215 dated Nov. 16, 2007.
International Search Report for Application No. PCT/US2007/002171 dated Sep. 26, 2007.
International Search Report for Application #PCT/US2010/048532 dated Jan. 26, 2011.

SEQUENCE LISTING

```
<160> NUMBER OF SEQ ID NOS: 56

<210> SEQ ID NO 1
<211> LENGTH: 13481
<212> TYPE: DNA
<213> ORGANISM: Homo sapiens

<400> SEQUENCE: 1
gctgccggga cgggtccaag atggacggcc gctcaggttc tgcttttacc tgcggcccag      60
agccccattc attgccccgg tgctgagcgg cgccgcgagt cggcccgagg cctccgggga     120 ctccgtgcc gggcgggaga ccgccatggc gaccctggaa aagctgatga aggccttcga     180
gtccctcaag tccttccagc agcagcagca gcagcagcag cagcagcagc agcagcagca     240
gcagcagcag cagcagcagc aacagccgcc accgccgccg ccgccgccgc cgcctcctca     300
gcttcctcag ccgccgccgc aggcacagcc gctgctgcct cagccgcagc cgccccgcc     360 gccgccccg ccgccacccg gcccggctgt ggctgaggag ccgctgcacc gaccaaagaa     420
agaactttca gctaccaaga aagaccgtgt gaatcattgt ctgacaatat gtgaaaacat     480
agtggcacag tctgtcagaa attctccaga atttcagaaa cttctgggca tcgctatgga     540
actttttctg ctgtgcagtg atgacgcaga gtcagatgtc aggatggtgg ctgacgaatg     600
cctcaacaaa gttatcaaag cttttgatgga ttctaatctt ccaaggttac agctcgagct     660
ctataaggaa attaaaaaga atggtgcccc tcggagtttg cgtgctgccc tgtggaggtt     720
tgctgagctg gctcacctgg ttcggcctca gaaatgcagg ccttacctgg tgaaccttct     780
gccgtgcctg actcgaacaa gcaagagacc cgaagaatca gtccaggaga ccttggctgc     840
agctgttccc aaaattatgg cttcttttgg caatttttgca aatgacaatg aaattaaggt     900
tttgttaaag gccttcatag cgaacctgaa gtcaagctcc cccaccattc ggcggacagc     960
ggctggatca gcagtgagca tctgccagca ctcaagaagg acacaatatt tctatagttg    1020
gctactaaat gtgctcttag gcttactcgt tcctgtcgag gatgaacact ccactctgct    1080
gattcttggc gtgctgctca ccctgaggta tttggtgccc ttgctgcagc agcaggtcaa    1140
ggacacaagc ctgaaaggca gcttcggagt gacaaggaaa gaaatggaag tctctccttc    1200
tgcagagcag cttgtccagg tttatgaact gacgttacat catacacagc accagacca    1260 caatgttgtg accggagccc tggagctgtt gcagcagctc ttcagaacgc ctccacccga    1320
```

```
gcttctgcaa accctgaccg cagtcggggg cattgggcag ctcaccgctg ctaaggagga    1380
gtctggtggc cgaagccgta gtgggagtat tgtggaactt atagctggag ggggttcctc    1440
atgcagccct gtccttcaa gaaaacaaaa aggcaaagtg ctcttaggag aagaagaagc    1500
cttggaggat gactctgaat cgagatcgga tgtcagcagc tctgccttaa cagcctcagt    1560
gaaggatgag atcagtggag agctggctgc ttcttcaggg gtttccactc cagggtcagc    1620
aggtcatgac atcatcacag aacagccacg gtcacagcac acactgcagg cggactcagt    1680
ggatctggcc agctgtgact tgacaagctc tgccactgat ggggatgagg aggatatctt    1740
gagccacagc tccagccagg tcagcgccgt cccatctgac cctgccatgg acctgaatga    1800
tgggacccag gcctcgtcgc ccatcagcga cagctcccag accaccaccg aagggcctga    1860
ttcagctgtt acccccttcag acagttctga aattgtgtta gacggtaccg acaaccagta    1920
tttgggcctg cagattggac agccccagga tgaagatgag gaagccacag gtattcttcc    1980
tgatgaagcc tcggaggcct tcaggaactc ttccatggcc cttcaacagg cacatttatt    2040
gaaaaacatg agtcactgca ggcagccttc tgacagcagt gttgataaat tgtgttgag    2100 agatgaagct actgaaccgg gtgatcaaga aaacaagcct tgccgcatca aggtgacat    2160 tggacagtcc actgatgatg actctgcacc tcttgtccat tgtgtccgcc tttatctgc    2220 ttcgttttg ctaacagggg gaaaaatgt gctggttccg gacagggatg tgagggtcag    2280
cgtgaaggcc ctggccctca gctgtgtggg agcagctgtg gccctccacc cggaatcttt    2340
cttcagcaaa ctctataag ttcctcttga caccacggaa tacctgagg aacagtatgt    2400 ctcagacatc ttgaactaca tcgatcatgg agacccacag gttcgaggag ccactgccat    2460
tctctgtggg accctcatct gctccatcct cagcaggtcc cgcttccacg tgggagattg    2520
gatgggcacc attagaaccc tcacaggaaa tacattttct ttggcggatt gcattccttt    2580
gctgcggaaa acactgaagg atgagtcttc tgttacttgc aagttagctt gtacagctgt    2640
gaggaactgt gtcatgagtc tctgcagcag cagctacagt gagttaggac tgcagctgat    2700
catcgatgtg ctgactctga ggaacagttc ctattggctg gtgaggacag agcttctgga    2760
aacccttgca gagattgact tcaggctggt gagcttttg gaggcaaaag cagaaaactt    2820
acacagaggg gctcatcatt atacagggct tttaaaactg caagaacgag tgctcaataa    2880
tgttgtcatc catttgcttg gagatgaaga ccccagggtg cgacatgttg ccgcagcatc    2940
actaattagg cttgtcccaa agctgtttta taaatgtgac caaggacaag ctgatccagt    3000
agtggccgtg gcaagagatc aaagcagtgt ttacctgaaa cttctcatgc atgagacgca    3060
gcctccatct catttctccg tcagcacaat aaccagaata tatagaggct ataacctact    3120
accaagcata acagacgtca ctatggaaaa taacctttca agagttattg cagcagtttc    3180
tcatgaacta atcacatcaa ccaccagagc actcacattt ggatgctgtg aagctttgtg    3240 tcttcttttcc actgccttcc cagtttgcat ttggagttta ggttggcact gtggagtgcc    3300
tccactgagt gcctcagatg agtctaggaa gagctgtacc gttgggatgg ccacaatgat    3360
tctgaccctg ctctcgtcag cttggttccc attggatctc tcagcccatc aagatgcttt    3420
gattttggcc ggaaacttgc ttgcagccag tgctcccaaa tctctgagaa gttcatgggc    3480
ctctgaagaa gaagccaacc cagcagccac caagcaagag gaggtctggc cagccctggg    3540
ggaccgggcc ctggtgccca tggtggagca gctcttctct cacctgctga aggtgattaa    3600
catttgtgcc cacgtcctgg atgacgtggc tcctggaccc gcaataaagg cagccttgcc    3660
```

```
ttctctaaca aacccccctt ctctaagtcc catccgacga aaggggaagg agaaagaacc   3720
aggagaacaa gcatctgtac cgttgagtcc caagaaaggc agtgaggcca gtgcagcttc   3780
tagacaatct gatacctcag gtcctgttac aacaagtaaa tcctcatcac tggggagttt   3840
ctatcatctt ccttcatacc tcaaactgca tgatgtcctg aaagctacac acgctaacta   3900
caaggtcacg ctggatcttc agaacagcac ggaaaagttt ggagggtttc tccgctcagc   3960
cttggatgtt ctttctcaga tactagagct ggccacactg caggacattg ggaagtgtgt   4020
tgaagagatc ctaggatacc tgaaatcctg ctttagtcga gaaccaatga tggcaactgt   4080
ttgtgttcaa caattgttga agactctctt tggcacaaac ttggcctccc agtttgatgg   4140
cttatcttcc aaccccagca agtcacaagg ccgagcacag cgccttggct cctccagtgt   4200
gaggccaggc ttgtaccact actgcttcat ggccccgtac acccacttca cccaggccct   4260
cgctgacgcc agcctgagga acatggtgca ggcggagcag gagaacgaca cctcgggatg   4320
gtttgatgtc ctccagaaag tgtctaccca gttgaagaca aacctcacga gtgtcacaaa   4380
gaaccgtgca gataagaatg ctattcataa tcacattcgt ttgtttgaac tcttgttat    4440
aaaagcttta aaacagtaca cgactacaac atgtgtgcag ttacagaagc aggttttaga   4500
tttgctggcg cagctggttc agttacgggt taattactgt cttctggatt cagatcaggt   4560
gtttattggc tttgtattga acagtttga atacattgaa gtgggccagt tcagggaatc   4620
agaggcaatc attccaaaca tctttttctt cttggtatta ctatcttatg aacgctatca   4680
ttcaaaacag atcattggaa ttcctaaaat cattcagctc tgtgatggca tcatggccag   4740
tggaaggaag gctgtgacac atgccatacc ggctctgcag cccatagtcc acgacctctt   4800
tgtattaaga ggaacaaata agctgatgc aggaaaagag cttgaaaccc aaaaagaggt   4860
ggtggtgtca atgttactga gactcatcca gtaccatcac gtgttggaga tgttcattct   4920
tgtcctgcag cagtgccaca aggagaatga agacaagtgg aagcgactgt ctcgacagat   4980
agctgacatc atcctcccaa tgttagccaa acagcagatg cacattgact ctcatgaagc   5040
ccttggagtg ttaaatacat tatttgagat tttggcccct tcctccctcc gtccggtaga   5100
catgcttta cggagtatgt tcgtcactcc aaacacaatg gcgtccgtga gcactgttca   5160
actgtggata tcgggaattc tggccatttt gagggttctg atttcccagt caactgaaga   5220
tattgttctt tctcgtattc aggagctctc cttctctccg tatttaatct cctgtacagt   5280
aattaatagg ttaagagatg gggacagtac ttcaacgcta gaagaacaca gtgaagggaa   5340
acaaataaag aatttgccag aagaaacatt ttcaaggttt ctattacaac tggttggtat   5400
tcttttagaa gacattgtta caaaacagct gaaggtggaa atgagtgagc agcaacatac   5460
tttctattgc caggaactag gcacactgct aatgtgtctg atccacatct tcaagtctgg   5520
aatgttccgg agaatcacag cagctgccac taggctgttc cgcagtgatg gctgtggcgg   5580
cagtttctac accctggaca gcttgaactt gcgggctcgt tccatgatca ccacccaccc   5640
ggccctggtg ctgctctggt gtcagatact gctgcttgtc aaccacaccg actaccgctg   5700
gtgggcagaa gtgcagcaga ccccgaaaag acacagtctg tccagcacaa agttacttag   5760
tccccagatg tctggagaag aggaggattc tgacttggca gccaaacttg gaatgtgcaa   5820
tagagaaata gtacgaagag gggctctcat tctcttctgt gattatgtct gtcagaacct   5880
ccatgactcc gagcacttaa cgtggctcat tgtaaatcac attcaagatc tgatcagcct   5940
ttcccacgag cctccagtac aggacttcat cagtgccgtt catcggaact ctgctgccag   6000
cggcctgttc atccaggcaa ttcagtctcg ttgtgaaaac ctttcaactc caaccatgct   6060
```

```
gaagaaaact cttcagtgct tggaggggat ccatctcagc cagtcgggag ctgtgctcac   6120
gctgtatgtg gacaggcttc tgtgcacccc tttccgtgtg ctggctcgca tggtcgacat   6180
ccttgcttgt cgccgggtag aaatgcttct ggctgcaaat ttacagagca gcatggccca   6240
gttgccaatg aagaactca acagaatcca ggaataccct cagagcagcg ggctcgctca   6300
gagacaccaa aggctctatt ccctgctgga caggtttcgt ctctccacca tgcaagactc   6360
acttagtccc tctcctccag tctcttccca cccgctggac ggggatgggc acgtgtcact   6420
ggaaacagtg agtccggaca aagactggta cgttcatctt gtcaaatccc agtgttggac   6480
caggtcagat tctgcactgc tggaaggtgc agagctggtg aatcggattc ctgctgaaga   6540
tatgaatgcc ttcatgatga actcggagtt caacctaagc ctgctagctc catgcttaag   6600
cctagggatg agtgaaattt ctggtggcca aagagtgcc cttttgaag cagcccgtga   6660 ggtgactctg gcccgtgtga gcggcaccgt gcagcagctc cctgctgtcc atcatgtctt   6720
ccagcccgag ctgcctgcag agccggcggc ctactggagc aagttgaatg atctgtttgg   6780
ggatgctgca ctgtatcagt ccctgcccac tctggcccgg ccctggcac agtacctggt   6840 ggtggtctcc aaactgccca gtcatttgca ccttcctcct gagaaagaga aggacattgt   6900
gaaattcgtg gtggcaaccc ttgaggccct gtcctggcat ttgatccatg agcagatccc   6960
gctgagtctg gatctccagg cagggctgga ctgctgctgc ctggccctgc agctgcctgg   7020
cctctggagc gtggtctcct ccacagagtt tgtgacccac gctgctccc tcatctactg   7080 tgtgcacttc atcctggagg ccgttgcagt gcagcctgga gagcagcttc ttagtccaga   7140
aagaaggaca ataccccaa aagccatcag cgaggaggag gaggaagtag atccaaacac   7200
acagaatcct aagtatatca ctgcagcctg tgagatggtg gcagaaatgg tggagtctct   7260
gcagtcggtg ttggccttgg gtcataaaag gaatagcggc gtgccggcgt ttctcacgcc   7320
attgctaagg aacatcatca tcagcctggc ccgcctgccc cttgtcaaca gctacacacg   7380
tgtgccccca ctggtgtgga agcttggatg gtcacccaaa ccgggagggg atttttggcac   7440 agcattccct gagatccccg tggagttcct ccaggaaaag gaagtctttta aggagttcat   7500 ctaccgcatc aacacactag gctggaccag tcgtactcag tttgaagaaa cttgggccac   7560
cctccttggt gtcctggtga cgcagcccct cgtgatggag caggaggaga gcccaccaga   7620
agaagacaca gagaggaccc agatcaacgt cctggccgtg caggccatca cctcactggt   7680
gctcagtgca atgactgtgc ctgtggccgg caacccagct gtaagctgct tggagcagca   7740
gccccggaac aagcctctga agctctcga caccaggttt ggggaggaagc tgagcattat   7800 cagagggatt gtggagcaag agattcaagc aatggtttca aagagagaga atattgccac   7860
ccatcattta tatcaggcat gggatcctgt cccttctctg tctccggcta ctacaggtgc   7920
cctcatcagc cacgagaagc tgctgctaca gatcaacccc gagcgggagc tggggagcat   7980
gagctacaaa ctcggccagg tgtccataca ctccgtgtgg ctggggaaca gcatcacacc   8040
cctgagggag gaggaatggg acgaggaaga ggaggaggag gccgacgccc ctgcaccttc   8100
gtcaccaccc acgtctccag tcaactccag gaaacaccgg gctggagttg acatccactc   8160
ctgttcgcag ttttttgcttg agttgtacag ccgctggatc ctgccgtcca gctcagccag   8220
gaggaccccg gccatcctga tcagtgaggt ggtcagatcc cttctagtgg tctcagactt   8280
gttcaccgag cgcaaccagt ttgagctgat gtatgtgacg ctgacagaac tgcgaagggt   8340 gcaccctca gaagacgaga tcctcgctca gtacctggtg cctgccacct gcaaggcagc   8400
```

```
tgccgtcctt gggatggaca aggccgtggc ggagcctgtc agccgcctgc tggagagcac    8460
gctcaggagc agccacctgc ccagcagggt tggagccctg cacggcgtcc tctatgtgct    8520
ggagtgcgac ctgctggacg acactgccaa gcagctcatc ccggtcatca gcgactatct    8580
cctctccaac ctgaaaggga tcgcccactg cgtgaacatt cacagccagc agcacgtact    8640
ggtcatgtgt gccactgcgt tttacctcat tgagaactat cctctggacg tagggccgga    8700
attttcagca tcaataatac agatgtgtgg ggtgatgctg tctggaagtg aggagtccac    8760
cccctccatc atttaccact gtgccctcag aggcctggag cgcctcctgc tctctgagca    8820
gctctcccgc ctggatgcag aatcgctggt caagctgagt gtggacagag tgaacgtgca    8880
cagcccgcac cgggccatgg cggctctggg cctgatgctc acctgcatgt acacaggaaa    8940
ggagaaagtc agtccgggta gaacttcaga ccctaatcct gcagccccg acagcgagtc    9000 agtgattgtt gctatggagc gggtatctgt tcttttgat aggatcagga aaggctttcc    9060
ttgtgaagcc agagtggtgg ccaggatcct gccccagttt ctagacgact tcttcccacc    9120
ccaggacatc atgaacaaag tcatcggaga gtttctgtcc aaccagcagc catacccca    9180 gttcatggcc accgtggtgt ataaggtgtt tcagactctg cacagcaccg gcagtcgtc    9240 catggtccgg gactgggtca tgctgtccct ctccaacttc acgcagaggg ccccggtcgc    9300
catggccacg tggagcctct cctgcttctt tgtcagcgcg tccaccagcc cgtgggtcgc    9360
ggcgatcctc ccacatgtca tcagcaggat gggcaagctg gagcaggtgg acgtgaacct    9420
tttctgcctg gtcgccacag acttctacag acaccagata gaggaggagc tcgaccgcag    9480
ggccttccag tctgtgcttg aggtggttgc agccccagga agcccatatc accggctgct    9540
gacttgttta cgaaatgtcc acaaggtcac cacctgctga gcgccatggt gggagagact    9600
gtgaggcggc agctggggcc ggagcctttg gaagtctgcg cccttgtgcc ctgcctccac    9660
cgagccagct tggtccctat gggcttccgc acatgccgcg ggcggccagg caacgtgcgt    9720
gtctctgcca tgtggcagaa gtgctctttg tggcagtggc caggcaggga gtgtctgcag    9780
tcctggtggg gctgagcctg aggccttcca gaaagcagga gcagctgtgc tgcacccat    9840 gtgggtgacc aggtccttc tcctgatagt cacctgctgg ttgttgccag ttgcagctg    9900 ctcttgcatc tgggccagaa gtcctccctc ctgcaggctg gctgttggcc cctctgctgt    9960
cctgcagtag aaggtgccgt gagcaggctt tgggaacact ggcctgggtc tccctggtgg    10020
ggtgtgcatg ccacgccccg tgtctggatg cacagatgcc atggcctgtg ctgggccagt    10080
ggctgggggt gctagacacc cggcaccatt ctcccttctc tcttttcttc tcaggattta    10140
aaatttaatt atatcagtaa agagattaat tttaacgtaa ctctttctat gcccgtgtaa    10200
agtatgtgaa tcgcaaggcc tgtgctgcat gcgacagcgt ccggggtggt ggacagggcc    10260
cccggccacg ctccctctcc tgtagccact ggcatagccc tcctgagcac ccgctgacat    10320
ttccgttgta catgttcctg tttatgcatt cacaaggtga ctgggatgta gagaggcgtt    10380
agtgggcagg tggccacagc aggactgagg acaggccccc attatcctag gggtgcgctc    10440
acctgcagcc cctcctcctc gggcacagac gactgtcgtt ctccacccac cagtcaggga    10500
cagcagcctc cctgtcactc agctgagaag gccagccctc cctggctgtg agcagcctcc    10560
actgtgtcca gagacatggg cctcccactc ctgttccttg ctagccctgg ggtggcgtct    10620
gcctaggagc tggctggcag gtgttgggac ctgctgctcc atggatgcat gccctaagag    10680
tgtcactgag ctgtgttttg tctgagcctc tctcggtcaa cagcaaagct tggtgtcttg    10740
gcactgttag tgacagagcc cagcatccct tctgcccccg ttccagctga catcttgcac    10800
```

```
ggtgacccct tttagtcagg agagtgcaga tctgtgctca tcggagactg ccccacggcc    10860
ctgtcagagc cgccactcct atccccaggc caggtccctg gaccagcctc ctgtttgcag    10920
gcccagagga gccaagtcat taaaatggaa gtggattctg gatggccggg ctgctgctga    10980
tgtaggagct ggatttggga gctctgcttg ccgactggct gtgagacgag gcaggggctc    11040
tgcttcctca gccctagagg cgagccaggc aaggttggcg actgtcatgt ggcttggttt    11100
ggtcatgccc gtcgatgttt tgggtattga atgtggtaag tggaggaaat gttgaactc     11160 tgtgcaggtg ctgccttgag accccccaagc ttccacctgt ccctctccta tgtggcagct   11220
ggggagcagc tgagatgtgg acttgtatgc tgcccacata cgtgaggggg agctgaaagg    11280
gagcccctcc tctgagcagc ctctgccagg cctgtatgag gcttttccca ccagctccca    11340
acagaggcct cccccagcca ggaccacctc gtcctcgtgg cggggcagca ggagcggtag    11400
aaaggggtcc gatgtttgag gaggccctta aggaagcta ctgaattata acacgtaaga     11460
aaatcaccat tccgtattgg ttgggggctc ctgtttctca tcctagcttt ttcctggaaa    11520
gcccgctaga aggtttggga acgaggggaa agttctcaga actgttggct gctccccacc    11580
cgcctcccgc ctcccccgca ggttatgtca gcagctctga cagcagta tcacaggcca      11640 gatgttgttc ctggctagat gtttacattt gtaagaaata acactgtgaa tgtaaaacag    11700
agccattccc ttggaatgca tatcgctggg ctcaacatag agtttgtctt cctcttgttt    11760
acgacgtgat ctaaaccagt ccttagcaag gggctcagaa caccccgctc tggcagtagg    11820 tgtccccac ccccaaagac ctgcctgtgt gctccggaga tgaatatgag ctcattagta     11880
aaaatgactt cacccacgca tatacataaa gtatccatgc atgtgcatat agacacatct    11940
ataattttac acacacacct ctcaagacgg agatgcatgg cctctaagag tgcccgtgtc    12000
ggttcttcct ggaagttgac tttccttaga cccgccaggt caagttagcc gcgtgacgga    12060
catccaggcg tgggacgtgg tcagggcagg gctcattcat tgcccactag gatcccactg    12120
gcgaagatgg tctccatatc agctctctgc agaagggagg aagactttat catgttccta    12180
aaaatctgtg gcaagcaccc atcgtattat ccaaattttg ttgcaaatgt gattaatttg    12240
gttgtcaagt tttgggggtg ggctgtgggg agattgcttt tgttttcctg ctggtaatat    12300
cgggaaagat tttaatgaaa ccagggtaga attgtttggc aatgcactga agcgtgtttc    12360
tttcccaaaa tgtgcctccc ttccgctgcg ggcccagctg agtctatgta ggtgatgttt    12420
ccagctgcca agtgctcttt gttactgtcc accctcattt ctgccagcgc atgtgtcctt    12480
tcaaggggaa aatgtgaagc tgaaccccct ccagacaccc agaatgtagc atctgagaag    12540
gccctgtgcc ctaaaggaca ccccctcgccc ccatcttcat ggaggggtc atttcagagc    12600 cctcggagcc aatgaacagc tcctcctctt ggagctgaga tgagcccac gtggagctcg     12660 ggacggatag tagacagcaa taactcggtg tgtggccgcc tggcaggtgg aacttcctcc    12720
cgttgcgggg tggagtgagg ttagttctgt gtgtctggtg ggtggagtca ggcttctctt    12780
gctacctgtg agcatccttc ccagcagaca tcctcatcgg gctttgtccc tcccccgctt    12840
cctccctctg cggggaggac ccgggaccac agctgctggc cagggtagac ttggagctgt    12900
cctccagagg ggtcacgtgt aggagtgaga agaaggaaga tcttgagagc tgctgaggga    12960
ccttggagag ctcaggatgg ctcagacgag gacactcgct tgccgggcct gggcctcctg    13020
ggaaggaggg agctgctcag aatgccgcat gacaactgaa ggcaacctgg aaggttcagg    13080
ggccgctctt cccccatgtg cctgtcacgc tctggtgcag tcaaaggaac gccttcccct    13140
```

| | |
|---|---:|
| cagttgtttc taagagcaga gtctcccgct gcaatctggg tggtaactgc cagccttgga | 13200 |
| ggatcgtggc caacgtggac ctgcctacgg agggtgggct ctgacccaag tggggcctcc | 13260 |
| ttgtccaggt ctcactgctt tgcaccgtgg tcagagggac tgtcagctga gcttgagctc | 13320 |
| ccctggagcc agcagggctg tgatgggcga gtcccggagc cccacccaga cctgaatgct | 13380 |
| tctgagagca agggaagga ctgacgagag atgtatattt aatttttta ctgctgcaaa | 13440 |
| cattgtacat ccaaattaaa ggaaaaaaat ggaaaccatc a | 13481 |

```
<210> SEQ ID NO 2
<211> LENGTH: 172001
<212> TYPE: DNA
<213> ORGANISM: Homo sapiens

<400> SEQUENCE: 2
```

| | |
|---|---:|
| cctgcagggg cctctccagc tcactggggg tggggtgggg gtcacacttg gggtcctcag | 60 |
| gtcgtgccga ccacgcgcat tctctgcgct ctgcgcagga gctcgcccac cctctccccg | 120 |
| tgcagagagc cccgcagctg ctccccgca gggctgtccg ggtgagtatg gctctggcca | 180 |
| cgggccagtg tggcgggagg gcaaacccca aggccacctc ggctcagagt ccacggccgg | 240 |
| ctgtcgcccc gctccaggcg tcggcggggg atcctttccg catgggcctg cgcccgcgct | 300 |
| cggcgccccc tccacggccc cgccccgtcc atggccccgt ccttcatggg cgagcccctc | 360 |
| catggccctg cccctccgcg cccaccccct ccctcgcccc acctctcacc ttcctgcccc | 420 |
| gcccccagcc tccccaaccc tcaccggcca gtcccctccc ctatcccgtc cgcccctcag | 480 |
| ccgccccgcc cctcagccgg cctgcctaat gtccccgtcc ccagcatcgc ccgcccccgc | 540 |
| cccgtctccg ccccgcccct caggcggcct cctgctgtg cccgccccg gcctcgccac | 600 |
| gcccctacct caccacgccc cccgcatcgc cacgcccccc gcatcgccac gcctcccta | 660 |
| ccatgcagtc ccgccccgtc ccttcctcgt cccgcctcgc cgcgacactt cacacacagc | 720 |
| ttcgcctcac cccattacag tctcaccacg ccccgtcccc tctccgttga gccccgcgcc | 780 |
| ttcgcccggg tggggcgctg cgctgtcagc ggccttgctg tgtgaggcag aacctgcggg | 840 |
| ggcagggggcg ggctggttcc ctggccagcc attggcagag tccgcaggct agggctgtca | 900 |
| atcatgctgg ccggcgtggc cccgcctccg ccggcgcggc cccgcctccg ccggcgcagc | 960 |
| gtctgggacg caaggcgccg tgggggctgc cgggacgggt ccaagatgga cggccgctca | 1020 |
| ggttctgctt ttacctgcgg cccagagccc cattcattgc cccggtgctg agcggcgccg | 1080 |
| cgagtcggcc cgaggcctcc ggggactgcc gtgccgggcg ggagaccgcc atggcgaccc | 1140 |
| tggaaaagct gatgaaggcc ttcgagtccc tcaagtcctt ccagcagcag cagcagcagc | 1200 |
| agcagcagca gcagcagcag cagcagcagc agcagcagca acagccgcca ccgccgccgc | 1260 |
| cgccgccgcc gcctcctcag cttcctcagc cgccgccgca ggcacagccg ctgctgcctc | 1320 |
| agccgcagcc gccccgccg ccgccccgc gccacccgg cccggctgtg ctgaggagc | 1380 |
| cgctgcaccg accgtgagtt tgggcccgct gcagctccct gtcccggcgg gtcccaggct | 1440 |
| acggcgggga tggcggtaac cctgcagcct gcggggccggc gacacgaacc cccggccccg | 1500 |
| cagagacaga gtgacccagc aacccagagc ccatgaggga cacccgcccc ctcctggggc | 1560 |
| gaggccttcc cccacttcag ccccgctccc tcacttgggt cttcccttgt cctctcgcga | 1620 |
| ggggaggcag agccttgttg gggcctgtcc tgaattcacc gagggagtc acggcctcag | 1680 |
| ccctctcgcc cttcgcagga tgcgaagagt tggggcgaga acttgttct ttttatttgc | 1740 |
| gagaaaccag ggcgggggtt cttttaactg cgttgtgaag agaacttgga ggagccgaga | 1800 |

```
tttgctcagt gccacttccc tcttctagtc tgagagggaa gagggctggg ggcgcgggac   1860
acttcgagag gaggcggggt ttggagctgg agagatgtgg gggcagtgga tgacataatg   1920
cttttaggac gcctcggcgg gagtggcggg gcagggggg ggcggggagt gagggcgcgt    1980
ccaatgggag atttcttttc ctagtggcac ttaaaacagc ctgagatttg aggctcttcc   2040
tacattgtca ggacatttca tttagttcat gatcacggtg gtagtaacac gattttaagc  2100
accacctaag agatctgctc atctaagcct aagttggtct gcaggcgttt gaatgagttg   2160
tggttgccaa gtaaagtggt gaacttacgt ggtgattaat gaaattatct taaatattag   2220
gaagagttga ttgaagtttt ttgcctatgt gtgttgggaa taaaaccaac acgttgctga   2280
tggggaggtt aattgccgag ggatgaatga ggtgtacatt ttaccagtat tccagtcagg   2340
cttgccagaa tacgggggt ccgcagactc cgtgggcatc tcagatgtgc cagtgaaagg    2400
gtttctgttt gcttcattgc tgacagcttg ttacttttg gaagctaggg gtttctgttg    2460
cttgttcttg gggagaattt ttgaaacagg aaaagagaga ccattaaaac atctagcgga   2520
accccaggac tttccctgga agtctgtgtg tcgagtgtac agtaggagtt aggaagtact   2580
ctggtgcagt tcaggccttt ctcttacctc tcagtattct atttccgatc tggatgtgtc   2640
ccagatggca tttggtaaga atatctctgt taagactgat taattttag taatatttct    2700
tgttctttgt ttctgttatg atccttgtct cgtcttcaaa gtttaattag aaaatgattc    2760
ggagagcagt gttagcttat ttgttggaat aaaatttagg aataaattat tctaaaggat   2820
ggaaaaactt tttggatatt tggagaaatt ttaaaacaat ttggcttatc tcttcagtaa   2880
gtaatttctc atccagaaat ttactgtagt gcttttctag gaggtaggtg tcataaaagt   2940
tcacacattg catgtatctt gtgtaaacac taaacagggc tcctgatggg aaggaagacc   3000
tttctgctgg gctgcttcag acacttgatc attctaaaaa tatgccttct ctttcttatg   3060
ctgatttgac agaacctgca tttgcttatc ttcaaaatat gggtatcaag aaatttcctt   3120
tgctgccttg acaaggaga tagattttgt ttcattactt taaggtaata tatgattacc    3180
ttatttaaaa aatttaatca ggactggcaa ggtggcttac acctttaatc cgagcacttt   3240
gggaggccta ggtggacgaa tcacctgagg tcaggagttt gagaccagcc tggctaacat   3300
ggtgaaaccc tgtctctact aaaaatacaa aaattagctg gtcatggtgg cacgtgcctg   3360
taatccaagc tacctgggag gctgaggcag gaaaatcgct tgaacccggg aggcagagtc   3420
tgcagtgagt tgagatcacg ccactgcact ccagcctggg tgacagagcg agactctatc   3480
tcaaaaaaaa ttttttttaa tgtattattt ttgcataagt aatacattga catgatacaa   3540
attctgtaat tacaaagggg caataattaa aatatcttcc ttccaccct ttcctctgag     3600
tacctaactt tgtccccaag aacaagcact atttcagttc ctcatgtatc ctgccagata   3660
taacctgttc atattgtaag atagatttaa aatgctctaa aaacaaaagt agtttagaat   3720
aatatatatc tatatatttt ttgagatgta gtctcacatt gtcacccagg ctggagtgca   3780
gtgatacaat ctcggctcac tgcagtctct gcctcccagg ttcaaatgct tctcctgcct   3840
cagccttctg agtagctggg attacaggcg cccaccacca tgtccagcta atttttgtat   3900
ttttagtaga gatggggttt caccatgttg gccaggctgg tcttgaactc ctgaccttgt   3960
gatctgtcca cctcggcctc ccaaagtgct gggattacag gtgtgagcca ccatgcctgg   4020
ctagaataat aactttttaaa ggttcttagc atgctctgaa atcaactgca ttaggtttat   4080
ttatagtttt atagttattt taaataaaat gcatatttgt catatttctc tgtatttgc    4140
```

```
tgttgagaaa ggaggtattc actaattttg agtaacaaac actgctcaca aagtttggat    4200
tttggcagtt ctgttcacgt gcttcagcca aaaaatcctc ttctcaaagt aagattgatg    4260
aaagcaattt agaaagtatc tgttctgttt ttatggctct tgctctttgg tgtggaactg    4320
tggtgtcacg ccatgcatgg gcctcagttt atgagtgttt gtgctctgct cagcatacag    4380
gatgcaggag ttccttatgg ggctggctgc aggctcagca atctagcat  gcttgggagg    4440 gtcctcacag taattaggag gcaattaata cttgcttctg gcagtttctt attctccttc    4500
agattcctat ctggtgtttc cctgacttta ttcattcatc agtaaatatt tactaaacat    4560
gtactatgtg cctggcactg ttataggtgc agggctcagc agtgagcaga caaagctctg    4620
ccctcgtgaa gctttcattc taatgaagga catagacagt aagcaagata gataagtaaa    4680
atatacagta cgttaatacg tggaggaact tcaaagcagg aaggggata  gggaaatgtc    4740 agggttaatc gagtgttaac ttattttat  ttttaaaaaa attgttaagg gctttccagc    4800
aaaacccaga aagcctgcta gacaaattcc aaaagagctg tagcactaag tgttgacatt    4860
tttattttat tttgttttgt tttgttttt  ttgagacagt tcttgctcta tcagccaggc    4920
tggagtgcac tagtgtgatc ttggctcact gcaacctctg cctcttgggt tcaagtgatt    4980
ctcatgcctc agcctcctgt ttagctggga ttatagacat gcactgccat gcctgggtaa    5040
tttttttttt ttccccgag  acggagtctt gctctgtcgc ccaggctgga gtgcagtggc    5100
gcgatctcag ctcactgcaa gctccgcttc ccgagttcac gccattctcc tgcctcagtc    5160
tcccaagtag ctgggactac aggcgcctgc caccacgtcc agctaatttt tttgtatttt    5220
taatagagac ggggtttcac cgtgttagcc aggatgatct tgatctcctg acctcgtcat    5280
ccgccgacct tgtgatccgc ccacctcggc ctcccaaagt gctgggatta caggcatgag    5340
ccactgtgcc cggccacgcc tgggtaattt ttgtatttt  agtagagatg gggttttgcc    5400
atgatgagca ggctggtctc gaactcccgg cctcatgtga tctgcctgcc ttggcctccc    5460
aaagtgctag gattacaggc atgagccacc atacctggcc agtgttgata ttttaaatac    5520
ggtgttcagg gaaggtccac tgagaagaca gcttttttt  ttttttttt  tggggttggg    5580 gggcaaggtc ttgctctttta acccaggctg gaatgcagta tcactatcgt agctcacttc    5640
agccttgaac tcctgggctc aagtgatcct cccacctcaa cctcacaatg tgttgggact    5700
ataggtgtga gccatcacac ctggccagat gatggctttt gagtaaagac ctcaagcgag    5760
ttaagagtct agtgtaaggg tgtatgaagt agtggtattc cagatggggg gaacaggtcc    5820
aaaatcttcc tgtttcagga atagcaagga tgtcatttta gttgggtgaa ttgagtgagg    5880
gggacatttg tagtaagaag taaggtccaa gaggtcaagg gagtgccata tcagaccaat    5940
actacttgcc ttgtagatgg aataaagata ttggcatttta tgtgagtgag atgggatgtc    6000
actggaggat tagagcagag gagtagcatg atctgaattt caatcttaag tgaactctgg    6060
ctgacaacag agtgaagggg aacaccggca aaagcagaaa ccagttagga agccactgca    6120
gtgctcagat aagcatggtg ggttctgtca gggtaccggc tgtcggctgt gggcagtgtg    6180
aggaatgact gactggattt tgaatgcgga accaactgca cttgttgaac tctgctaagt    6240
ataacaattt agcagtagct tgcgttatca ggtttgtatt cagctgcaag taacagaaaa    6300
tcctgctgca atagcttaaa ctggtaacaa gcaagagctt atcagaagac aaaaataagt    6360
ctggggaaat tcaacaataa gttaaggaac ccaggctctt tcttttttt  tttttttgaaa    6420 cggagtttcg ctcttgtcac ccgggctgga gtgcaatgat gtgatctcag ctcactaaaa    6480
cctctacctc ctgggttcaa gtgattcttc tgcctcagcc tcccaagtaa ctgggattac    6540
```

```
aggcgtatac caccatgccc agctaatttt tgtgttttta gtagagatgg ggtttcacca    6600
tgttggccag gctggtctcg aacttctgac ctcaggtgat ccactcgcct cagcctgcca    6660
aagtgctggg attacaggtt tgggccactg cacccggtca gaacccaggc tctttcttat    6720
acttaccttg caaacccttg ttctcatttt ttccctttgt attttttattg ttgaattgta    6780 atagttcttt atatattctg gatactggat tcttatcaga tagatgattt gtaaaaactc    6840
tcccttcctt tggattgtct ttttactttc ttgatagtgt cttttgaagt gtaaaagttt    6900
ttaattttga tgaagtcgag tttatctatt ttgtctttgg ttgctgtgct tcaagtgtca    6960
tatctaagaa atcattgtct aatccaaagt caaaaaggtt tactcctatg ttttcttcta    7020
agaattttag agttttacat ttaagtctga tccattttga gttaattttt atatatggtt    7080
caggtagaag tccaacttta ttcttttcca tgtggttatt cagttgtccc agcactgttt    7140
gttgaagaga ctattctttc cccatggaat tatcttagta cccttgttga aaattaatcg    7200
tccttaattg tataaattta tttctagact gtcagttcta cctgttggtc tttatgtcga    7260
tcctgtgcca gtaccataca gtcttgatta ctgaagtttg tgtcacagtt taaattcatg    7320
aaatgtgagt tctccaactt tgttcctttt caagattgat ttggccatgc tgggtccctt    7380
gcatttccgt acgaattgta ggatcagctt gtcagtttca acaaagaagc caagtaggat    7440
tctgagaggg attgtgttga atctgtagat caacttgggg agtattcgca tcttaacaat    7500
attgtcttcc acctatgaac atgggcaaac tttgtgtaaa tggtcagatt gtaagtattt    7560
cgggctgtgt gggcacagtg tctctgtcac agctacgcgg ctctgccatt gtagcatgaa    7620
agtagccata agcaatatgt atgagtgtct gtgttccaat agaattttat taatgacaag    7680
gaagtttgaa tttcatataa ttttcacctg tcatgagata gtatttgatt attttggtca    7740
accatttaaa aatgtaaaaa catttcttag cttgtgaact agccaaaaat atgcaggtta    7800
tagttttccc actcctaggt taaaatatga taggaccaca tttggaaagc atttcttttt    7860
tttttttttt tttttttttt gagacggagt ttcactcttg ttgcccaggc tggagtgcag    7920
tggcgcgatc tcggctcact gcaacctctg cctcccaggt tcaagacatt ctcctgcacg    7980
gcctccctag tagctgggat tacaggcatg cgccaccaca cccagctaat tttgtatttt    8040
tagtagagac ggggtttctc catgttggtc aggctggtct tgaactcctg acctcaggtg    8100
atccacccgc ctcagcctcc caaagtgctg ggattacagg gtgtgagcca ccacaccctg    8160
ctggaaagca tttctttttt ggctgttttt gttttttttt taaactagtt ttgaaaatta    8220
taaaagttac acatatacat tataaaaata tcttcaagca gcacagatga aaacaaagc    8280 ccttcttgca agtctgtcat ctttgtctaa cttcctaaga acaaaagtgt tcttgtgtc    8340 ttcttcccag attttaatat gcatatacaa gcatttaaat gtgtcatttt ttgtttgctt    8400
gactgagatc acattacata tgtatttttt tacttaacaa tgtgtcatag atattgttcc    8460
atagcagtac ctgtaattct tattaattgc tatgtaatat tttagaattt cttttttaaaa    8520 gaggactttt ggagatgtaa aggcaaaggt ctcacatttt tgtggctgta gaatgtgctg    8580
gtgacatatt ctctctacct tgagaagtcc ccatccccat cacctccatt tcctgtaaat    8640
aagtcaacca cttgataaac tacctttgaa tggatccaca ctcaaaacat ttagtcttat    8700
tcagacaaca aggaggaaaa ataaaatacc ttataaagca ctgtttaata ttgtattaaa    8760
ttggatcaat ttgggggcta gaatgtatgt tagagacatg atatgtccat aggtccttgc    8820
tatcacagtg aggtctcagg gacagtcgtt tggtatcatt tgggatctca taagcagact    8880
```

```
ctctctgctt gacctgacaa atcagagtct gtgttttaac aggttcagtg agtgacttac    8940
atgcacattg gagtttggga agctccactg taggtgctta gaccttacct ttgttgttgc    9000
taataacaat gcaagcattt gggaggaaga cctgtgttgc tcatatgtgt ccaggtgtag    9060
ctgaggtggc cttgcttatc tgctgtaggg ccgttgagca tttctgtagc tgtgatgagt    9120
gagctgaggt gagcctgcgg agagctccca gccattggta gtgggactcg cttagatgaa    9180
ctggaaggac cctttcatct gagcagccac tatggagaaa aacaaccgaa tgaggggaga    9240
gacaatgtgc aattttattt agggcacaaa ggagagctgt ggttagaagg tgacatttga    9300
gtggaaaggg ggcaagccat gtgtatagcg ggagaagaga ggtccaggca gagttaacag    9360
aaggcagaaa tgctttccat gtttgagaac cagtaaggag gccagtggct gaagtaaggt    9420
gaagggcaga ataaggatg aggctgcgag agatgagagg ttagagacga gcgtcttgtg    9480
caccaagata agcttgtgtg gtcaaaacaa gtagtttaat ttatgttttt aaagatcat    9540
tttggctggg cacaatggtt catgcctgta ataccagtag tttgagacgg tgtggtggga    9600
ggattgcctg aggccagacg accagcatag ccaacatagc agcacctata aggtctctac    9660
aaaaaacttt aaaaaattag ctgggcatag tggtgtgtgc ctgtagtccc agctactcag    9720
gaggctgagg aggctggagg attgcttgag tccaggagtt tgaggctgca gtgagctatg    9780
attatgccac tacactacaa cctgggcaag agagtgagac cctgtctcta aatatacaca    9840
cacacacaca cacacacaca cacacacaca cacacacaca cacacacaca catatatatg    9900
tatatatatg catttagatg aaaagatcac tttgacaata ccacatgctg gtgaggattt    9960
agaaaaacta ggtcacttat tgctggtggg aatataatat agtacggcca ctctggaaaa    10020
cagtttggca gtttgtcata aaactgaaca taccgttagt atacagccca gcagcaacta    10080
caatcctggg cattaatcct agagaaatga aaccttaatg ttcacataaa aacctatact    10140
caagtatgca tagcagcttt acccataata tctaagaact ggaatcagct cagatgtcct    10200
tcaacaggtg aatggttaaa ctactcagta ataaaaagga atgagctact gatagcatgc    10260
aacagtttag gtgaagttat gctaatgaaa aaagccaatc ccaaaaggtt atacatactg    10320
tatgattcta tgttttttttg caatggcaca gttttaggga tggagaatag attagtggtt    10380
gcctggggtt agagatgggg tagtagagta ggttagtggt ggcagaggag agaaaagaga    10440
gggaggtgaa tgtggttata aaaggacaac acagggaat acttgtaatg gaatgctttt    10500
gtctttttt ttttttttt tttttggcg acagagtctt gctctgttgc ccaggctgga    10560
gtgcagtggc atgatctttt ctcactgcaa cctctgcctc ctgggttcaa gtgatacttg    10620
tgtctcagtc tcccatgttc agagtgaaac aaaccagagg taatgttcat ccaaataatc    10680
caacacacat gacattaaaa catcaagatc aggtcggacg tggtggctca tgcctgtaat    10740
cccagcactt tgggaggcc aaggtgggca gatcacttga ggtcaggagt tcgagaccag    10800
ccgggccaac atgatgaaac ccatcttga ctaaaaatac aaaaattagc cgggcatggt    10860
ggtgtgcacc tgtagtccca gctacttggg aggctgagg aagagaactg cttgaacccg    10920
agggcagag gttgcagtga gctgagagtg cgccattgca cttcagcctg tgtgacagag    10980
taagactcca tctccaaaaa aaaaaaacca agatcaatta aaatacagca ttactgggcc    11040
gggtgtggtg gctcacacct gtaatcccag cactttggga ggccgagatg gcagatcac    11100
gaggtcagga gatccagacc atcccggcta cacggtgaa accccgtctc tactaaaaaa    11160
tacaaaaaat tagccgggta tagtggtggg tgcctgtagt cccagctact tgggaggctg    11220
aagcaggaga atggtgtgaa cccgggaggc agagctggca gtgagctgag atcgcgccac    11280
```

```
tgcactccag cctgggcgac agagcaagac tccgtctcgg gggaaaaaaa aaaataaata    11340
aatagaatgc tgtagtgtcc ttgagtttac atgcccctcc ttacgcttgt gtgcccgtgc    11400
agattgcttg attacacaat tagaggaggc tggcggagga ttgttttaat tttttttttt    11460
ttgagacagt ctggctctgt tccccaggct agagtgcaat ggcgcaatct tggtgcactg    11520
caacctctgc ctcctgggtt caagcagttc ttctgccgca gcctcccgag tagctgggat    11580
tataggcgcc cgccaccacg cccaactatt ttttgtattt ttagtagagc agcgtttcac    11640
catgctggcc aggctggtct cgaactcctg acctcagatg atctgctgcc ccagcctccc    11700
aaagtgctgg gattacaggc gtgagccaca cctggccgtt tgttttaatt ttgaaggtga    11760
agtgaaagtg actacattta ccaaaagtga ttgaaaagcc aggactgttc ttaccctgtt    11820
tttccagttc ttgctcagag caaggtggtt cttttttcac ttaatcacca tacttacttt    11880
tcatgtagaa caagtcagtt tgagttatca gttcatcatc ttaactaaat tccatggggg    11940
aaggaattag ttttagtttc ttaaacttcc aggtttgctt attggacaaa atgagatagc    12000
aaggcagtgt ttttaagtta gattttttat ttctttggta atacaatttt ctcagaaact    12060
tagtagtctt ttagtttagt tgttttagt tggtcctatg ttttggatca ccctctctcta   12120 ctttattttg atagtgccaa ctgtgaagac atctgaagcc ataggtttgg atgggaagga    12180
ggcatcttta gcctgatcat cttcgccagg ctgtttatct cctttgctt ggctgagaag     12240 tcttaatagg aggcttattc ccagctattt ggggacatag aagcagttag ccattgctta    12300
tattttactg aggtctgtgt ggtatgttga ttgtagtcag ttaacgattt tgagaactga    12360
aggcagcctg gtatatatag agtaggtatt agactgtgtt tcttctaatt gaatttccca    12420
tctcttgtaa tctatgccat catcttctgt actgctgaga aagaaagaaa gtttctaatc    12480
aaactatacc actggttgta agatgcagtt tggctttagt gatgttaaca catgattcaa    12540
acgtgaaatt gattgagtat tggtgaaata cagaggagat ttaaagccag aagacctggg    12600
tttaaatgct ggctgtatga cttcatatct gtgtgatctt gggcatgtca tggttggcac    12660
ttcaatttct tctctctata atgggggaag tgaggccagt catggtggct catacctata    12720
atcccagtgc tttgggaggc caagatggga agatcgcttg aggccaggag tttgagcaat    12780
tgggcaacat cgtgaggccc cgtctctaca aaatattttg aaaaaattag ccaggcccag    12840
tggtgcgtgc ctgtggtccg cgccactcag gaggctgaga cgggaggatc ctttcagcct    12900
aggagtttaa ggctaaagtg agccatgatt gtgctatcgt actccagcct gggcagcaga    12960
gcaagatcct gactctaaaa aaaagtaaaa taaagtaaaa tgggggaaat gaactgcttt    13020
agtaacatca tctgtttttt ctgtgagcag cgtagcttga cagccattgg tgaactcgtg    13080
ccctgtgctt ccctgtccag atccccattc tgcccgcaac atggagtata acggtttatt    13140
catagtagtc gagaaacact cactgaatga atgaatgagg tgtagaacta agtggagtgg    13200
gtaattcaac acatattaat ttccttcttt tttttatttt tagaaagaaa gaactttcag    13260
ctaccaagaa agaccgtgtg aatcattgtc tgacaatatg tgaaaacata gtggcacagt    13320
ctgtcaggta attgcacttt gaactgtcta gagaaaataa gaactttgta tattttcagt    13380
cttaatgggc tagaatattc tttgtgtccc agctatttta aatggattca gaaatccatt    13440
taagatgaag aaggacccct ttcccatatt tctggctata tacaaggata tccagacact    13500
gaaatgaata atgttccctt tttgtaatct tttatgcaaa aattaaaacc attatggtaa    13560
ttgaacaaca tgtttatgtt tagttaacac ccttagcaac tatagttatt ttaaaaccat    13620
```

```
ctatggtttg atattttgc atttgttgca atagtaggaa cagcacaaga cagttcagtt    13680
tgtctctctt atttgctttt tcttggcagt ttgctgtcct attgtacctc tgctcctagc    13740
agtggctgga gcccactcct ctgtgcttcg ggattagtgg ggatcgtggg gcattgactg    13800
taggtcagct ttccttgctt gatctttctc actgggatga actagcagca ccttcttttg    13860
tagctgcttt gcttttgact atctttctga ccgttgttcc tagtagctgt agatggtaaa    13920
tatatttagg cctgtttcca atggctcagt aggagacata ttcacctatg atatctgaat    13980
tctgttaccc acatgggcat gcgtgaaata gttgccttgc cttactttcc cttggaataa    14040
ataattcatg ttattctcct ggtagaagct agaaaaagcc tttatagtca gtcagaaaaa    14100
aatttttaga caaataatct tgattttagt actgacaaaa acgtgtggtg attcttttt     14160
taatttttt ttgagacgga gtttcactct tgttgcccag gctggagtgc aatggcgtga    14220
tctcggctca ctgcaacctc tgcctcctgg gttcaagtga ttctcctgcc tcagcctccc    14280
aagtagctgg agttacaggc atgtgctact gtgcccagct aattttgtat ttttagtaga    14340
gatgttggtc aggctgatct cgaactccca accttaggtg atctgcccgc tcagcctcc     14400
caaagtgctg ggattacagg cgtgagccag ggcgcccggt gattcatttg tttttcaaa    14460
aaatttcctc ttggccattg cttttcactt ttgttttttt ttttttttg agacggagtc    14520
acgatctgtc acccaggctg gagtgcagtg gcatgatctt ggcttactgc aagctctgcc    14580
tcccaggttc acgccattct cctgcttcag cctggcgagt agctgggact acaggtgctc    14640
gccaccacac ccggctaatt ttttgtattt ttagtagaga tggggtttca ccgtggtctt    14700
gatctcctga cctcatgacc cgctcaactc agcctcccaa agtgctggga ttacaggcgt    14760
gagccaccgc gcccggccct ctcttgtctt tttattgtgg taaaatgcac ataaaattga    14820
ctgtcttaac cattttagg ggtacagttc agtatatata ttcgtaatgt tgtacagcca    14880
tcactgccat ctacttcata agttttttctt ctgtcaaaac tgaacatctg tcttcattaa    14940
actccctatc atccattctt tcctgtagtc ccttttctact ttctgtctgt atgagtgtaa    15000
ctgctctgga gacctcatgt aagtggattc ctacaggatt tgtgttttt ttttggtgat    15060
ctgcttattt ttaatgcctc tgtgcatttg tattatatac tttcaaagtg atttcacaaa    15120
accgtttcat tttaggttaa ctcatttctg ttgtttgtga aatactgtgt atgattctgt    15180
tctgtttctg tctaatttgt ggaaatgttg tgggaagaaa atgaaataac aaatgagcat    15240
atgtcctgaa aataaaaata taaaaattct aagttagcat gctattgtag aatacaacgc    15300
tatgataaaa gtaggaaaaa aaaaggtttg aattctatct ctgctacctg tgtaagctgg    15360
gtgactttag ataagctgta acgtgtttga gccttactgg ctcatttttg aaatgtaatc    15420
cctagttaca cagttcttgt gggatcagat ggtacatgtg aaacactgtg aaaaagcaac    15480
tgcatagata tgttcattag ccacctgagc gggaagcgta tcccattgcg atgcccatca    15540
tccaaagcta tatgttatct ttactttttt tttttgaga cagagtcttg ctctgttgcc    15600
caggctagag tgcagtggtg caatctcagc tcactgcaag ctccacctcc cgggttcacg    15660
ctattctcct gccccagcct cccaagtagc tgggactaca ggcacccgcc accatgcctg    15720
gctaaatttt tgtattttta gtagagatgg ggtttcaccg tgttagccag gatggtcttg    15780
atctcctgac ctcgtgatcc gcccgcctcg gcctcccaaa gtgctgggat tacaggcgtg    15840
agccactgcc cctggccatc tttacttttt ttgtgaaatg actttaaata cttggcaaac    15900
atttggtcat tgttcatctg atctccacca tccaggtctc agagaacata atttctctct    15960
gaaagcttat tgacccagga aataagatct ctttcaatct gagtgcgtca ggctttattc    16020
```

```
ttgtcatttt gtcttttgat aattttcaaa tggaattcat ggaatgttgg cttatattca   16080
tatattagta aagtatgttg agacatctta agattgattt gtggttctat atgccatatt   16140
aaatcaaaat aatagctgtt aatggttttc acattagtct gtctcttgtt tttatggagt   16200
aatgctgaga gttcattatg cttgttctac agaagagcat gttaaaagga gttttggag    16260 tcagagaggt tattcttggt ttcataggat acactctata cttttaggg atttcagagt    16320 atatagctga aggtgatatt ttatgtaaat atgttttatg gaaacttatt gctcatcgct   16380
gtttcctgtt aactctccta aaatataatt aaacttttgg aactttttta tagcttttgt   16440
gctagactaa tttttgtctc taatgaggtt atataaatgg cagcttctga cgttttcaat   16500
gtaggaagtc atttaaaact tcatgtatat tgtgaaaatg tagtctgctt taagctctct   16560
aaagtggtct aagttactgg ttcctaagta tggatgagca tcaaaatcat ctggaaaatt   16620
tgttaaaaat acagtaatga aggcacctca ctgtcctttt tcccaaacat acttctgcat   16680
tctgtttgag taggtaggga ctacacattt ttcacaagta tcctcttggg aatacccagg   16740
aatgcttact tgagcaacct cttactaata tgtaccttga taaggtggct aggtaaacat   16800
aaatatacaa aaatccatag atctcccata tattagcata aatcagctag aaaatataac   16860
gtttaaagat ctagttcaca gtagcaccaa tatatcgaac tctaaggaat cgataaatat   16920
gcaaaaactt tataaaaact tctgttaatg tttctgaaag atataggtga ccactttcta   16980
gataggaaga ttttatatta ctaagttgaa ttttctctaa attaacacag aaatttaaaa   17040
taatcttgat caaaattcta gtagaggtat ttttgaactt gttcactgca agaataaata   17100
cataattgca aagaatatct caaaatcatc accaggcctg gtgtggtggc ccatgcctgt   17160
aatcccagca ctttgggagg ctgaggcagg cagatcacct gaggtcaaga gtttgagacc   17220
agctggacca gtgcggtgaa acactgcctc tactaaaaat acaaaaatta gctgggtgtg   17280
gtggtgcatg cctgtagtcc cagctacttg ggaggctgag gcaggagaat tgcttgaacc   17340
caggaggtac aggttgcggt gagcctagat cgcaccactg cattccagcc tgggcgacaa   17400
gagcaaaatt ctgtctcaag aaaaagaga aaaagaaaa agaaatcaac actaatatgg    17460
tgagacttaa tgtatgtgac attaaaatag tgattggatg ttaaaacagg tatagaacag   17520
aaagaagagt gtatgtgtgt atctgtatga atttatgatg ggtgtaacat atatgtatta   17580
gggaaatgag ggaaatgata catttctctg actttgggag aacattatat ctctacctca   17640
tattgcaaac aaacataaag ttcagattaa ttacctaaat gtgaaaaaat gaataatttt   17700
ctttaaaaaa tgtaatctta gtttgaggaa ggttaacatt ataaggaaa aaactgtttt    17760 gagtggaata tagttcaata tgtcaaaatc caccttcaac aaaattgaaa gtaaattgaa   17820
cttggggaaa gtattgacag catatagatc aaaggttact agcctgtgta aagagcagtt   17880
ataaatatcg ttaagaaaaa cactgtcgac ctgtcggcac cttgttctcc gactcccagc   17940
ctccagaact gtgacgagta agtgcttatt gtttaaacca cccagtctgt atgtggtatt   18000
ttgttataga aactcaagct gattaggaca ctagtaatca gtagactgaa actgaaacaa   18060
aaataagaac cttttttacc tgtcaaattg gcaaacatta agaatattca gattttgtc    18120 agaggtgata caaccttcta agaaggcaat ttgggaaaat ataagctttt agattattat   18180
atgtctgacc tagcagtttt acctctaggg tgcttacccc taggaaagtg tgtaatgata   18240
ttggtgcagt gcccttcatc ccattagaaa attaaaaata accttaatgg cctaccacta   18300
aaaggggatt gaaaatttaa gatatatttta tttatgtgtt tattgagatg gagtcttgca   18360
```

```
ctgtccgcct gggccagagt gcaatggtgc gatctcggct cactgcaacc tctgcttccc   18420
gggttcatgt gattctcctg cctcagcctc ctgagtagct gggattacag gctcacacca   18480
ccgcacccgg ctaattttt  gtattttag  tagagatggg gtttcactgt gttggccaga   18540
ctggtctcga actcctgacc tcatgatccg cgccctcgg  cctcccagtg ttgggattac   18600
aggtgtgagc cactgcgcct ggccagatac atttatacaa gagaatgtta gttaacattc   18660
atagatattt atattttgtt tactttttat taaaaaaatt ttttttagag acaggatctt   18720
actctgtcac ccaggcagga tgcagttgca caatcatagc ccactgcagc ctgaactcct   18780
gggcttaagt gatccttctg cctcagcctt tgagtacct  ggggactttt aggcagtgct   18840
actatacctg gctaattttt aaatgtttta tagatgagat cttgctgtat tgcccaggct   18900
ggtctagaat tcctgggccc aagtgatcct cccaccttgg cctcccaaag cgctgagatt   18960
acaggcatga gccaccactt ctgaccaata gatatttata tttgtgactg gaaaatatat   19020
taacaatgtg ttaaaaaatt cagttaaaaa ataatgaaag attttttgctt ctggctaaga   19080
tagaataaca aggacagcat ttatcttctt gccttgaaat agttgaaaac ggaagaaata   19140
tatgtaacag tggttttcaa gttattgggc atcaggcaaa gaagaatagt tatcccagga   19200
aaatgaatgt ggagagccct acaatttcct tacattactg cctggtcatg gcaagaggaa   19260
aaactgagag gagactgagg ctgagccagt ggtttgctgg gttgaggagg cagagctggg   19320
agtgcagaga tgcaaggtgg tgagagccca tatggaagaa taccagggaa gagagctgca   19380
gagggagctc cggagacctg caccctgccc tctcagtacc ctgtcatgtg tgtagctgag   19440
tactgacgag cacttgcttg tgcggaaatg acccagggct ggaggtagag ccacctgaaa   19500
ggattagaag gaacagttgc tgaaagtcac acagggccag gaagaatttc taatcacacc   19560
agttggagtg gaaaacctca gctctcatag agcaggtagg gtactcagaa gggtttgccc   19620
acctagcccc agactaagtt tcgttactct gaccctacct aatattaaaa agagattaat   19680
taaattgttc gcaacaaaaa taatatattt cagtgtttgt aacacgtaga agtgaattgt   19740
atgacaatag cataaaggct ggaagagcag aaattgacat gtatttgcgc tgggcagaat   19800
aatgctcccc tctttcccca aaagatatca agtcctaatc cctggagcct gtaaatatta   19860
ctttatatgg aaaattgttt tatgatgtga ttaaattcag gatcttgaga tgaggggct   19920
atcttggatc atctgggtag gcactaaatg caatcacata tatataaaaa ggaggcagag   19980
ggagatttta cacacagaga gaaggccctg tgaagatgga acagaaagat ttgaaggtgc   20040
tggccttgaa aattggagtg atgaagctat aagccaagga atgcagcagc caccaaagct   20100
ggaagaggca cggagcagtt ctcatttaga gcctactcca gagggaatgt ggtgctgcca   20160
attccttttt ttttttttt  tttaagatat catttacccc tttaagttgg ttttttttt    20220
ttttttttt  ttttagtatt tattgatcat tcttgggtgt tcttggaga  ggggatttg    20280
gcagggtcat aggacaatag tggagggaag gtcagcagat aaacatgtaa acaaaggtct   20340
ctggtttttcc taggcagagg gccctgccac gttctgcagt gtttgtgtcc ctgggtactt   20400
gagattaggg agtggtgatg actcttaacg agtatgctgc cttcaagcat ctgtttaaca   20460
aagcacatct tgcaccgccc ttaatccatt taacccttag tggacacagc acatgtttca   20520
gagagcacgg ggttggggt  aaggttatag attaacagca tcccaaggca gaagaatttt   20580
tcttagtaca gaacaaaatg gagtgtccta tgtctacttc tttctacgca gacacagtaa   20640
caatctgatc tctctttctt ttcccacatt tcctcctttt ctattcgaca aaactgccac   20700
cgtcatcatg gactgttctc aatgagctat tgggtacacc tcccagatgg ggtggcggcc   20760
```

```
gggcagaggg gctcctcact tcccagatgg ggcggccggg cagaggcgcc ccccaacctc   20820
ccagacgggg cggcggctgg gcgggggctg ccccccacct cccggacggg gcgggtggcc   20880 gggcggggc tgcccaccac ctcccggacg gggcggctgg ccgggcgggg gctgcccccc    20940
acctcccgga cggggcgggt ggccgggcgg gggctgcccc ccacctcccg gacggggcgg   21000
ctggccgggc gggggctgcc ccccacctcc cggacggagc ggctgccggg cggaggggct   21060
cctcacttcc cggacggggc ggctgctggg cggaggggct cctcacttct cagacgggc    21120 ggctggtcag agacgctcct cacctcccag acggggtggc agtggggcag agacattctt   21180
aagttcccag acggagtcac ggccgggcag aggtgctctt cacatctcag acggggcggc   21240
ggggcagagg tgctccccac ttcccagacg atgggcggcc gggcagagat gctcctcact   21300
tcctagatgg gatgacagcc gggaagaggc gctcctcact tcccagactg gcagccagg    21360 cagaggggct cctcacatcc cagacgatgg gcggccaggc agaaacgctc ctcacttcct   21420
agacggggtg gcggctgggc agaggccgca atcttggcac tttgggaggc caaggcaggc   21480
ggctgggagg tgaaggttgt agtgacccga gatcacgcca ctgcactcca gcctgggcaa   21540
cactgagcac tgagtgagcg agactccgtc tgcaatcccg gcacctcggg aggccgaggc   21600
tggcagatca cttgcagtca ggagctggag accagcccgg ccaacacggc gaaacccgt    21660 ctccaccaaa aaacacgaaa accagtcaga catggcggtg cgtgcctgca atcccaggca   21720
cttggcaggc tgaggcagga gaatcaggta gggaggttgc agtgagtaga gatggtggca   21780
gtacagtcca gccttggctc ggcatcagag ggagactgtg cgagggcgag ggcgagggcg   21840
agggaattcc ttaatttcag tttagtgata ctaattttgg actctggcct ctaaaactgt   21900
gaaagaaaaa atttttttgtt tgtttgtttc ttttaagcca catagtttgt ggtaatttgt   21960
tacagcagct gcaggaaact aatttatgct gcatgtgaaa tggtgtaata aggtagattg   22020
tgatgaagat acatagtata aacaattaag caacaactaa aagcacaaca aggaattata   22080
gctaatgaac caaaaaagga gattagaata ataaaaatgg tgaatcccaa agaagccaga   22140 aatagggaa gaggcaaata aaggaaagaa agagcttgat ggtagatttc aacctaacta    22200
tgtcaaaaag gacattacat gtaaaaggca gcgattttc agattgaatg gaaaagtaag    22260
actcggtata tgctgctgcc tgcaagaaac acattctaaa tataaaggca aaaataacct   22320
acaggtaaca gaacgaaaag aagttcactg tgcttacaag aattagatgc aagctagact   22380
ggttctgtta atatcagaca aagtggattt caaagcaaag gctcttgccc aggatgagat   22440
ggtcatttca taatgatgaa ggggattcgt tcatcagcct ggcatagcaa gctgaaatgt   22500
ttatgcaccg gactacagag ctaaaataca tgaagcaaag cctgacagaa ctacaagtag   22560
aaacagacaa atccacagtg atagagattt cagtagccgc tctcaatgat ttgtagaaca   22620
cgtagccata atatctggat ctagaacact tgaccaacac tgtcccctgt gcaacctcat   22680
tggcatttac aggacactcc acccagcacc agcagaagag acactctctc aagtgctcac   22740
agaatgtttg ccaagataga gcagatgctg gccataaaa caagtctcta aattaaaagc    22800
attcaaatta ttcagagtat gttttctgac ctcagtatca ttaagttgga atatattata   22860
ggaagataac ctgaaaaagc ctcagatatg tggaaaaacc catttccaca tggcccatgg   22920
gtcagaagtg aagtcaaaag ggaaatttga aagtcttttg gattgactga tataaaaaca   22980
atagatttct aaacttgtgg ggtgctgtta cagcatagta aatggaaatt tctagcatta   23040
aatgcctgtt ttaggaaaga aagatttcaa atcaatgacc tcagcttcta cctttggaaa   23100
```

```
cttgaaaatg acaagcaaat ggaatccaga gttaccagaa gggccaggta cggtggctta   23160
tgcctgcagt tctgccactt tgggaggccg aggcaggtgg attgtttgag actggcagtt   23220
gaagaccagc ctgggcagcc tagggagacc ccatatctac aaaaaacaaa aaaattagcc   23280
aggtgtggtg gcatgtgcct gtagtcccag ctaaccagga gtctaaggtg ggaggattgc   23340
ttgagtctgg gaggttgagg ctgcagtgaa ctgtgattgt gccactgtgt tccatcctgg   23400
gcaacagaat gagaccctgt ctcaaaaaca aaacagtta ctagaagaat ggacatcata    23460
aagataggag cagaagtcag taaaatagaa aacaaaaata cataggaaat caataaaacc   23520
aaaagctggt tcatcaagaa catcaataaa ttggtaaagc tgataggaaa acagtgaag    23580 tcacaaaatta gcaatatcag gaatgaggga gatgacagta gtatagatta tatagatatt  23640
aaaaggactg tatgaggcag gtgtggtggt tcacgcctgt aatcccagca ccttgggagg   23700
ccgaggtgga cagatcacct gaggtcagga gtttgggacc agcctggcca acatggtgaa   23760
actctgtctc tactaaaaat acaaaaatta gttggtcgtg gtgctgtgtg cctgtaatcc   23820
cagctacttg ggaggctgag gcaggagaat tgcttgaacc tgggaggcgg aggttgcagt   23880
gagctgagat tgtgccgttg cactccagcc tgggtgacag agcaagactc catctcaaaa   23940
caaataaata aataaaaagg actatatggt aatattatga caactttat gccaataaat    24000 ttgacaactt atagatgaaa tggatgagtt ccttgaaaga cacagaaact attaaagctc   24060
tctcaagaag atatagataa gctgattagc cctatatcta ttttattgaa tttaaatgta   24120
aaaatcaata tttagttact ggaaaacttt taagtgtggt tggaaatggt atacgaactt   24180
tttcaactga attttatgaa gtctaatcac aggtaaaggt tttctgatga aaatttagtg   24240
tctgaattga gatatactgt aaaaaatgtt atatatctta attatttctt cacattaatt   24300
acatgttgaa ataatacttt gggtgtattg ggttaaatta aatattatga aaatcttgcc   24360
tgttttcttt ttacttttga tgcgtcagct aggaaatata aaagtgtagc tcacattctg   24420
tttctgttga cagtactgct ttggagcaca gtgtttgaat gatctatcat ttcaaagacc   24480
tttcctcagt tcgttattca tggctgtctg tattccacat agataaggtc tgaaatactg   24540
ctaagtggca tgttttgttt tatgctttta taagtttgtt gatcattact gatgtggact   24600
tttggtgcct cttaggctca ttgctatctt ccaaccattg tttgcaattt ttacctagag   24660
ataaagagaa agagacattt ggtttcagag tagttagatt gggatcatga aagagcaacc   24720
tcattttgat gcttcaaaaa tagcacatcc cccgtattac tgggatttgc tattcttggg   24780
attacttcaa gaacatcctt gtgttactgg tttggatgct tctgaatgct gtgaagtcag   24840
tttcatgtac atggctcatc agtttagctc tctcttggct ttgtttagac agttggagca   24900
tgatggccta aacagcttct ttcaattaaa cattttaaaa tagtttacaa atagtaaaca   24960
aactccagtt tttgtgactc tttgtctcgc acaacaaaaa cacaatctga ccatgatcat   25020
ctggcatctt agggtgaaat atggttatac tttggcccat accgaaagca agattaaaaa   25080
ggggcaggag agatagactg ctgaactgat tttcaaggtt ccaagaatat tgtaggttaa   25140
gagtaaaagt aaactttggg tagaaagcag tgggttgtct aggattgaag tatctgaagt   25200
ttttaaacga aaatttaaaa agaaaaatga gaattgcctt acaagtacaa tctcttcttt   25260
tttaaaaaat aaactttatt ttgaaatagt tttagattta tagaaaaaaa ttagataggg   25320
taggaagttt tcatataccc tacatccagt taccccagtt attatcatcc taatttagtg   25380
tgagacattt tcatgtttaa tgaatcaata ttgatatgct attaacttaa gtccagactt   25440
tattcagatt ttcttaattt ctatgtaatg tccttttctt gttccagaat tccatgcagg   25500
```

```
acaccggata cctcattaca tttcattgtc atgtcacctt aggctcctct tgacagtttc   25560
tcttcttttt ttgcttagaa attctccaga atttcagaaa cttctgggca tcgctatgga   25620 acttttctg ctgtgcagtg atgacgcaga gtcagatgtc aggatggtgg ctgacgaatg    25680
cctcaacaaa gttatcaaag taagaaccgt gtggatgatg ttctcctcag agctatcatt   25740
gttgtaggct gagagaagaa gcgatcattg agtgttcttc tgttttgagt ccctgaggat   25800
gtctgcactt ttttcctttc tgatgtatgg tttggaggtg ctctgttgta tggtttggag   25860
gtgctctgtt gtatggtttg gaggtgctct attgtatggt ttggaggtgc tctgttgtat   25920
ggtttggagg tgctcttgta tggtttggag gtgctcttgt atggtttgga ggtgctctgt   25980
tgtatggttt ggaggtggtc ttgtatggtt tgcaggtgct ctattgcatg gtttgcaggt   26040
gctctattgt atggtttgga agtgctcttg tatggtttgg aggtgctctt gtatggtttg   26100
gagatgctct attgtatggt ttgcaggtgc tctattgtat ggtttggaag tgctcttgta   26160
tggtttggag gtgctcttgt atggtttgga ggtgctctgt tgtatggttt ggaggtgctc   26220
tgttgtatgg tttggaggtg ctcttgtatg gtttggaggt gctctattgt atggtttgga   26280
gatgctctgg tatctgcctg cattgcttgc cacacctgcc cggtcagaag cgctatgtt    26340 gacaattgtg cctgcacggt gcctaggtca atgaagggaa ccgatggtag ccactggatg   26400
ctcctgggaa aatgtcacta caggcaccag agaagccaga gctatgccca aatttctatg   26460
agtctcagtt ttcttaacca taaaatggga tcaatgtttt tgtggcatgt gtatgagtgt   26520
gtgtctgtgt atgtgtgagg attaaattgt gtatgtgtga ggactaattg ccactactgg   26580
atcctcaaag tggtaagaag tgttcttatt aataatgaca tccttacact cttacccagc   26640
aagattgatg ggtgtggcac tgcttctctt tttccatcac atggtttcca tggtatcctt   26700
ttgcccaggg aatctttgct ttgtggctag cactttgttg tttggctaat cacgctttct   26760
gtggtcagga cgctggcttc tctggagcca tgggattcta gctccctgtc ttgtccctag   26820
agtggtcact gtcttctctc tccgcttgca attcctgctt tgctcgcatc tcacttatgc   26880
agtgacgtat atcagtttca ccttgttctc cgtgcctgct gatcattggc accacttgca   26940
tggtgccatt tagggcctgc ttccagttaa gcttgcttct ccacaggcct aaatatcctt   27000
gcttgcttct tttattctca ctggcaggac cagggcggtc tgtctttgca tgagacaggg   27060
tctcgctcag tcacccaggc tggagtgcag tggctgatca cggctcattg cagccttgag   27120
ctaccgggct caagctatcc tcctggcttg gccccttgag tagctgggac tacaggcgtg   27180
caccaccatg cccagctaat ttttaaaatt atttgtagag atgggatctc gccaggttgc   27240
ccaggctggt cttgaacgcc tgggctcaag tgatcctccc tccttggttt cccaaagtgc   27300
tgggatcaca ggtgtgagcc actgtgcctg gcccttgatg tttcagttct tgatatttga   27360
tcctcagagt cagaaaatct aaaaagaggg ctatcccagg ttgccttggt tcatggcaaa   27420
tgggacgtta agagggcaga gagaatatga acagaaactg ttctaatatt ggtcatttaa   27480
tgtgtaagta ttgttctttt ttaaacctcc ttcatttttt ttccaggaat tgctggacac   27540
agtggcttgg tgtgtgtctg aggactgtag gccatggccc taggttgtgg ttttaggtct   27600
caggtgctct tcctggctgt ctccttgctt ctttcccatg tcctcttctt tgtttccagc   27660
catttctccc ttatgcttaa gtttggtgca gcagggtttg gctgctctca gattcctgct   27720
tcctcagatg ctgtagttgt caggcccagc gggctggcag cgggatcagg atctggctag   27780
gtttgctctc actgtggcag agtaggggga ggcgtgggag agcacgtgtg accccaggcc   27840
```

```
agctgtaggg agcataggca tggtcacgta gccttcaggt cctagacttt gtcttctcat    27900
gagtatggct gtgtgtgtat ggtgaaaact aggttctact tagcccaaga aaatgggcac    27960
attttgcatg tggtttctgt agagaaatgc actgggtatc tgacatagcc tggcagcatg    28020
cctccctcag gtaggttagt ctcaggcggt gaagcacgtg tgtccagcaa gaacttcata    28080
tgtggcataa agtctccgtt ctgtgaggtg ctggcaaatc accaccaccg tcaagaggct    28140
gaagtgattt ttgtctaggg aggcaggaaa ggcttcctgg agtcagcagc cagtaggtga    28200
aagagtagat tggagacctt cttaatcatc accgcctctt gtctcaaggg gtgccaggaa    28260
gctgtgnagg ctgaacccat cttatgctgc cagagagtgg gacaccatga gggtcaggtc    28320
aaggggttgt accttgtttg gtagagaatt aggggctctt gaagactttg gatgtggtca    28380
ggggagtgta tcatttagga agagtgaccc ggtgaggacg tggggtagag gaggacaggt    28440
gggagggagt ccaggtggga gtgagtagac ccagcaggag tgcagggcct cgagccagga    28500
tggtggcagg gctgtgagga gaggcagcca cctgtgtgtc tgcggaagca ggggcaagag    28560
ggaagaggcc agcagcgtgc tgccatcacc cagcgactgg cgtagattgt gagagaccat    28620
tccctgctct taggaggggc tgagttttag ttttctcttg ttatacaata agcttggtat    28680
ttgtttacaa aacatttgta aagctaaatc aaggtttgat aaggcttcta gttttattta    28740
agaagtaatg ttgaaataaa tgtttgtcca attcgctttg ctcatttaag gactttcagt    28800
acaaactgca acaacaggat taggatttaa acgtttctga gatgttttta ctcctcagaa    28860
tttcccagaa tgtgatctgg ttttgatttt caagcttgct gacccaatag gttaacccac    28920
aagttttacg aagaccatct cagtccactt acatcaactg cccatgccac ggttaaagag    28980
atcatcgact gatgtttggc acagcttcct ccctcttggg tgggcaagca tttggaagag    29040
aaggctccta tgggtgagag tgggcacca aagtcttccc tgtcccatcc cctagcttga    29100
gaagcccttc tctaatgtgg actttgtgcc gttagcatcg ttactagctt gaagttgacc    29160
atctggacgt actttctggt ttagcctcac aagtgagcaa ggagggttga gagatgtgct    29220
gtgaggaatg tggggcccca gctggcagca ggctctgggt caggggggca gggaccacgg    29280
gcatacctga cagtgaggag gggccacacc tgcagaaaag gatgcaggac tccgccttgg    29340
gaagtgttct aggccagagc gagggtctgt ggtttataag tacacccaca gtgctcggga    29400
ccctgcagat gtccagggtg ccgtctgagc ccgtatcatc caacagaatg ttctgctagt    29460
gaagattaaa gatttactcc aggggcttta ggatttatta tatatatata aatcctatat    29520
atataatttt ttttttttt tttttgaga tggagtttcg ctcttgttgc ccaggctgga    29580
gtgcaatggc gtgatcttgg ctcactgcaa cctccgcctc ccgggttcaa actattctcc    29640
tgcctcagcc tctcgagtag ctgggattac aggcgcccac caccacccc ggctaatttt    29700
tgtattttt agtagagacg gagtttctcc atgttggtca ggctggtctt gaactcctga    29760
cctcaggtga tctgcccgcc ttggcctccc aaagtgctgg gattacaggc atgagccacc    29820
ccacctggcc aggatttatt gtatttgaac catctaccat tttaattttg atgttatgta    29880
gtatttgatg ataatgaaag ttaaattgtt tttcttttca tttttctgtt taagtgaatg    29940
acctgtatct agtttattca gtaacttcct gcatatattt gtttctttca ttcttaatga    30000
atatattctt aatttagttg ctattatgtt ttgctttgcc ccaaaattga aatcttagtt    30060
tccttttagc tcgttttaga actagtgatg ggatgtgtct tccataaatc tcttgtgatt    30120
tgttgtaggc tttgatggat tctaatcttc caaggttaca gctcgagctc tataaggaaa    30180
ttaaaaaggt gggccttgct tttctttttt aaaaatgttt taaatttaa attttatag    30240
```

```
gtacacgtat tttgtaggta catgtaaatg tatatattta tggggtacat gagatatttt    30300
gatacaggta tacaatacat aataatcaca ccatggaaag ttggatatcc atgccctcaa    30360
gcatttatcc tttgtgttac aaacaatcca gttacatgct ttacttattt tattttattt    30420
ttgagacaga gtcttgcttt cacccatgct agagtacagt ggcatgacct ggctcactg    30480 caacctccgc ctcccgggtt caaccgaact ttgggctggt ctcgaactcc tgacctcagg    30540
tgatccgccc gcctcggcct cccaaagtgt gggattaca ggcgtgagcc actgtgccgg    30600
gcctgattgt acattttaaa ataactaaaa cagtcagggc acagtggctc atgcctgtaa    30660
tcccagcatt tgggaggct gaggcaggtg atcacctgag atcaggagtt cgagaccagc    30720
ctggccaaca tggagaaacc ctgtctctac taaaaataca aaattagcc aagtgtggtg    30780 gcgggcgcct gtaatcctgg ctactcggga ggctgaggta ggggaatcgc ttgaacctgg    30840
gggtggaggt tgcagtgagc cgagatcacg ccactgcatt ccagcctgag cgacagagtg    30900
agactttgtc tcaaaaaata aaatgaaat aaaattgggc cgggtgtggt ggctcacacc    30960
ttagtcccag cactttggga acctgaggca ggtggatgct tgagaccagg agtttgagac    31020
cagcatgggc aacatggcaa aacgctgtct gtacagaaat tagctgggtg tggtggtgca    31080
caactatagt ctcagctact tgggagattg aggtgggagg attaattgag cctggaaggt    31140
tgaatctata ggtagctgag attgtgccac tgcccttcag cctgggcgac caagtgagac    31200
cctgtctcaa aagaaaaaca aaaaacaaa aaacaaacca ctattatcga ctatatatta    31260
ttgtctatga tccctctgct gtgctgtcga ataccaggtc ttgggccctt atttccatca    31320
ctgagcaaac ttcactctgt taagcagcag gtgtgggatt tcatcgttat tcagtaattc    31380
acaatgttag aaggaaatgc tgtttggtag acgattgctt tacttttctt caaaaggtta    31440
ctctttatta gatgagatga gaattaaaaa tggtaactta ctttatatct ttataattga    31500
agcccactag accttaaagt agttaccaga tgtttatgc atttaaatgg ccttttctct    31560
aaaattagaa agtaacaagg aaagaaaatg cttcgtttct atgcaaccct cttggtgact    31620
agtatgtgac tcttaatgca accctcattg caccccctca gaatggtgcc cctcggagtt    31680
tgcgtgctgc cctgtggagg tttgctgagc tggctcacct ggttcggcct cagaaatgca    31740
ggtaagttgt acactctgga tgttggtttt tgtcgggggc cagctgctac tgatccttta    31800
tgtctcagct cagatgtcat ttcaaaagtc tgctctgccc tctccaaatt gcagtcgacc    31860
ttgccctgtt tatgtttccc tcatagcact aatccatgtc agaaattgtc acgtacagtc    31920
tatctgtgtg cttgttgatt ttctatccca cccttccgca agagacttat gggatgtgtg    31980
ccccaggaca gcagggggtct tactgtctta tgctctgttg cagcccagca gcgataacag    32040
tgtctgcaca tagtacttgc ttaaaagata cttgccaaat tgttgaaggt tgaggtacca    32100
atttcattat tgctgactat aggagttata gcaaaatatc catttgtctg ttacatgagt    32160
taaaaatatg gttgttgcac tgtgaatagt ttggtttagt caaaacagtt gtatcttaac    32220
ggattgagaa acaaaagcag gaccactttt catcagctcc ctccttctcc ttaaccagca    32280
atacatgctg atgctgatat cccatagacc ctcagctcca tcctgagtca ctgggaatgt    32340
ggtctaaacc ctcactatta atatgaactg agtttcaata agaatcttat atgggtcggg    32400
catagtggct cataccttg atcccagcac ttcaggaggc caaggcaggt ggattgcttg    32460
acccagacta ggcaacatgg tgaaacgccg cctctacaaa aaatacaaaa cttagccagg    32520
catggtggtg cgtgcctgtg gtcacagcca ctcgagaggc tgaggtggga ggatcacttg    32580
```

```
agcctgggag gtggaggtcg tgttgagcca agatcgcacc actgcactcc agcctgggca   32640
acagagtgag acctgtctca aaaaaaccaa aatccagaaa agaacttata tggctgcaga   32700
ggtataatca ctaaggaaat ttccttttgt ataatctttt ttcttttact atcatttaaa   32760
aaaatgtgtt atatttctga agcaacacat ccaggttctg cacatagcag ccaaagtgac   32820
cttaaagaat ataactgggt cttgtcattc ccttatttaa actcttgtac ccatttccca   32880
gtgccgttta gatagagatt ccagactcgt caatggctct gtcacctcag acaccctgca   32940
ttgactcatt agtctgatta gagtcaggtt tttcttcctc ctgatggttt ttttttcccc   33000
cttagttctc agcggaacag tcacttcctt agggaggttt ccccagccac cctctgaggc   33060
cgtgcttgtt gccagactct gccactagag ggcagggctg caccactcct ggcacctcgc   33120
acccggcctg ccctgtcact ctgtgtgttg ggtgaattcc tgtgatctgt gactcactgc   33180
tctgtgtcct acacattcgg cttttcttct ctccccacaa ccccatttta taattctcct   33240
ttttcaggaa agctttattc ccatttaaaa attttgttt ttaaaatggt attttcttac   33300
acttattttc taattaaaaa tgagtgtttt aagaagtatt atgatttact gcaaataatt   33360
tttaacccca gccttttaga tcctctgtga tcataagaga aatgaaggat gtctcccaac   33420
acttgagctt catccacatt tcatcctcct gttctttcag ctgagttttc cccatcccat   33480
tagggactgt tggaatataa aactggcttt tccctaacag ggaatgaatt gcttctgttt   33540
ctcctgaagg agagctggaa gaatgacttg cgttcttttg catacacagg ccttacctgg   33600
tgaaccttct gccgtgcctg actcgaacaa gcaagagacc cgaagaatca gtccaggaga   33660
ccttggctgc agctgttccc aaaattatgg cttcttttgg caattttgca aatgacaatg   33720
aaattaaggt atgattgttg cctcaggtca caaacatgcg agtgatgctg tgagtgagtc   33780
tgtggagggt gagggcttct gaacagggag tcctgtggga gtgcttcttg gggtatgttg   33840
tatgtcgtaa tttagactac catcatttgt gttatttttg aggcacctaa ggacttcttt   33900
ccacttctca tttcttactg tggggtgaag agttgaattg ggagatggtt tctagatgca   33960
aattgaaaag gcatttttcc agagcagatt tgttttcggc gtactagagt gactctttaa   34020
cctagctgcg ggaagatgac tgtgccaaga ctgcaggtag gagaaagctc actgacgagg   34080
ccttgtgggt ctgaacgtcc tgcagctatc agagcctgtt ggcttcctgt tgtgcattcc   34140
aacaaatcat cttcaaaccc actttagtgt tttgtttata atgtccagaa atagtgaccc   34200
tgtcacatgc tctacagatt acaggattct tagcctcttc cttttggta ggtcagtcct   34260 gggtttgagc ccaagtgacc ctcctgggag gtgatgatac acactgggta gagtggaatc   34320
agatggactt ggattagaat tctgtcctct ttactagtta ttttcctcta ggcaaactgc   34380
ccaacagctc taagctattt ccttcgtatt ctgaaaaata agccttaatg ggacccatat   34440
agggcaactc tgagagtaaa ataaaggaat atgtgttaga gtgtagcata gtcacccacg   34500
ggaagggctt agatgttagc tgctactgct cttattagct gaatgatttg gaataaactg   34560
ttagcctctc tcatgttttt tctcttgagc ttcgaagttt tcttgttaat actaaggaga   34620
tattcaaact agtcatgggg ttttggaatg acgaagggag atgatgaatc taaagaattt   34680
agtgtaatat ttcttcatgc tcagtaaatg gtagttctg ctgctgttat ttttattacc   34740
atctctttgg aatgggagta ggtgctcctt tgtggtcaga ggctgtgaga gctccacagc   34800
gccagtttgc ccatctgtac actgggtct gttgaaggca gtcccctctg tgatatctct   34860
ggctgtcaga gctcagatga tagatggtat ttttgtactc ttagttctca tcatttcat   34920 gatttcgatc accatttgag tatgatgatg ctaacacttt gttgaacgta gaatccgtta   34980
```

```
attacttcct tcctgaacct ttggcattaa aaaaaatcta ttctgctacc tctctgctca   35040
tttatggtta ttcaaattta ttatcaagag cctggtacag tggcttgtgc ctataattgt   35100
agctacttgg gaggctgagg taggaggatt gcttgaggcc aggagtttga ccagcctg    35160
ggcaagatag tgagaccta  tctctaaaaa aactgaaaaa aaattagctg acatgatgg    35220
catgtgcctg tggtcctagc tactcaggag gctgagacag gaggctcggt tgagcccagg   35280
agttggagtt cgaggctaca ctgagctgtg attgtgccac cacactccag catgggtggt   35340
aaaacaagat gccatttctt aaaaaaaaaa aatatatata tatatattat caatgaaatt   35400
cagtagtacc aacaggatta taaacaaaga tagtagttcc cttcctactt tttctcttaa   35460
tccttgtgtc tcacaggcaa acataactct tagtatttct tccaatattt actttcatgt   35520
ttctttcttt ctttcttttt ttttctttga gatggagttt tgctcttgtt gccaaggctg   35580
gagtgcaatg acgcaatctt ggctcaccac aacctctgtc tcccgggttc aagcgattct   35640
cctgcctcag cctcctagta gctgggatta caggcatgca tcaccacgct cggctaattt   35700
tgtactttta gtagagatgg ggtttctccg ggttggtcag gctggtctcg aactcctgac   35760
ctcaggtgat cctcccacct cagcctccca aagtgctggg attacaggcg tgagccactg   35820
cgcccagcaa cttccacatt tctaaataac atgcttctac tgctattttt tttttcaatt   35880
ttagacattt ttttacttc actatagttc tatcagaatt cagtgtgtac gttattatgc   35940
ctaagtaaat agtcatggtt gcttacgtat tatatttctt tgattgtgtt tcttatttga   36000
tgagaaagct gtgttttttg ctctgggttg aaactggaga gaggacctgg ggaggaggag   36060
gaggacagat gaagttggtg actgtacctt catggccata gctgggttct cagcacccgg   36120
ggatctgctg atcacctact cataggccag gcccctatcg aagttctagg tgacccagtg   36180
ctggggacgg gggggccacc tgcaaggtct aatcatggag gtgggggcta cagtgttggc   36240
ttgtgctggg gccagcatcc ttaggaaggc atcttggagg tggaggagac agccgcccac   36300
ttcttgattg gggccttcag cagcaccagc ttcttgggca ggctggtgct ggcttcatc    36360
accatgtcgt gttcaatctt cttccagatc ctgacttcta ggttcagctt tcctcagacc   36420
ctggttcctt tcagaggcca ttgctgctgc cttgctcttt gctggcttgt gccttgatta   36480
tatgtctttg tacaactttt tgttttcctg gagttaatct tcacatctgt tttcttggag   36540
ttaatcgtta cctctatatc gcttgcttat tattctttgg ccttttttgtc ttctcacacc   36600
ttccaacttc tttgtaatat gtgtttagta caattttca tgacaggtag tttactgaat   36660
cagttttcc ccagtgtggt catccaactt gagttatcca gctctctgcc ccagtctggg    36720
caggttgatc ttcaggtctg tagtacactt gtatcctagg acttctcttt gccattagcc   36780
tggaatttcc tttgcagttc tcccgttgga tgcccagttc ctagatgcca tatgttttc    36840
tatcgtctag tagcttcctg agagaagatg aatgggaggg aaattgtatg aggttttgca   36900
ttcataaaaa tgccattttt tttcctgtac acttggctgg gtatggtgtt ctggggtaga   36960
aatcatttc cctcagaaat gcaaagtctt tgccctgttg tcttaaaatc tccaacgtga    37020
cccgattcct taacctatga atgtacttt ctttggaagc tttccatttt tggggaggtg    37080
aagtgctagg tacttagtag gccttttaat ttggaaactt acatcccttc agttctggga   37140
aaatttcctt aacatttctc tgagaagttc ttgcctttta ttttctgtgt tctctcctga   37200
aattggttag ttggatgttg gtcctcctag attgactcac atcttacctt tttcttttct   37260
ttttctggta cttttagat atccatctca aactcttcta ttcattgtta tgttttaac    37320
```

```
ttctttcttt tctttgtctc ttgatggggt cttgccctgt tgcccaggtt gtggtgcagt    37380
ggtgcgatca tagctcactg cagcctcaaa ttcctgggct caagcagctg ttctgcctca    37440
ccctcccaag tagttgggac tacaggtatg caccaccacg tccagctatt ttctttactt    37500
tttttttttt tttttttgaga tggagtccta ctctgtcgcc caggctagag tgcggtggtg    37560
ggattttggc tcacttaagc ctctgcctcc caggttcaag cagttctcct gcctcagcct    37620
ctcaagtagc tgggattaca ggtgtgcacc accatgcccg gctaattttt gtattttag     37680 tagagccaga gtttcaccat gttggccagg ctggtctcga acgcctgacc tcaggtgatc    37740
cgcctgcctt ggcctccgaa agtgccggga ttacaggcgt gagcccatca ttagatcttt    37800
aaataccagt atctataagt cttttcctct tgagtcagct agtatccctg aaggaaatt     37860 actcattttc ctgcttggag gctataagct tggctatgtt tatcctgcaa ccggggactg    37920
gaagggaggg gactgacagt gttgctggtc agggtgccct cttactttt gttttctgtg     37980 tgcatctcac gtctgtcctc agcctatgta aacacctctt gagattatcc ctctcaatct    38040
ttgccggagg tgggggaggg gctgcttcct gggctgcctt ggattggagg gaagacctca    38100
ggtgagtggg tgggaatttg cccaaggagc catgagacca gccactattt caccctctcc    38160
atccctccac tttcagatgt atgtggcgcc tccaaagccc gagctcttct tggcgtctgt    38220
ggcttcaata agcttgcttt ttgctggtat ccctcctacc ctccctgtc cccagcaaag     38280 cttgcatttg aacttcttcc tacgggctaa caaatcagtc agttatgtag ctcttgttac    38340
tttttagctt ccgaagtttt gttgacaccc gtagtctgct aatgtccctg ttctgttctt    38400
tctgttcgtg taaatatatg ctttatacaa cttctttaca tgattttgt ggggtttctg     38460 ggtagcagag cttcacaagt tcaatccagc gtgttggatt agaaatctcc caccctctgg    38520
tttattctta ttctcaaaat tacctgccaa acactgatac tcccttgttt ttccttttcc    38580
tgacaggaaa tgtacatacc atacaggaca gaaatcatta gtgtatccct tggtgaataa    38640
ccacaaagtg aacttaaccc ttgtaaccgc cacccaggtc aagacagaat attaccaagc    38700
actcagaagc ctctccccta ttcccccgtc actgctcctg ccttcctccc caaggtcatg    38760
actgctggct tctaattcca gagtctgttt ttaaattctg tgtacataga ccatggatta    38820
agtgttcttt ttgtctggtt tattttggtc gacattaagt tcatgagagt cttctatatt    38880
atcgtgtgta ttagtattcc tgtagttta ggagcttcat agcattccat tgtagggata     38940
taccacagtt tattcattgt attatcactg ggttgtttct agttcttggc tattgcgagc    39000
agtgctactg tgaccactct taggtgtgtc ttttggagta catgtgcagg tttccatctt    39060
gcacagctag aggtggagtt gttgggtgat agggtgtgtg catctcagct gcagtagaaa    39120
ctgccaaata gctttccttg agtgcttgta ccagctcacc cttttgccac tgtgtatggg    39180
gattccagga gctctggtcc tcgctagcac ttggaattgc tgatgctttt actcttagcc    39240
ttcctgatgg gtgttttctg gaatcacatt atgattttaa tttccattcc ttaaagtacc    39300
cttggctctg aagtttaatg attcatgcat ctcttcccctt ttgaagtact cttacaggta   39360
tgttgtgcat gtgttgaaaa gtggcactat ctattctaaa atacagtatg cctcctctgt    39420
gtttgaacag ttgtagcgtg gccttggggc ctcctgttag ctggcttgga aagggattc     39480 ttgggattgt agagattaga cctgaggagg ccccttggag ctctctgact aaattttatt    39540
ctttattatt ccaaactatt taagctcacc gtgtgctgac tcatcataat aatgagtagc    39600
tctcattgtg cttgtctatt tggactcata caatgatttt ttttttttct ttgagacaga    39660
gtcttgctct gttgcctagg ctggagtgca gtggcacaat ctcggctcac tgcagcctcc    39720
```

```
acctcccagg ttcaagtgat tcttgtgcct cagcttctca agtagctgag actgcaggtg   39780
cgtaccacca tgcctggcta atgtttgtat tttagtagag acggggtttt caccatgttg   39840
gccaggttgg tctcaaactc ctgacctcaa gtgatctgcc ttcttcagcc tcccaaagtg   39900
ctgggattac aggtgtgagc cactgagctt ggccaaagta gttttttaag atgttagtat   39960
cttttcttgc agctaaaaaa gtttgtcaga gatgattcta ctttgttctc caggtgtttt   40020
ctcagggaga aattggaggc agtaagccac tgggggagtc ctgtggctgg ggggtggggt   40080
agtcctgtgg ctccttgtca gggagtcctg tggctggcaa ggagagaagt cctgtggctg   40140
ggttgggagg gagtcctgtg gctggggtct catcctgtgc ctaacagtgt ccagaggtgc   40200
cgagaccagc tcagtcgggg agaccctaac ccagcagcgc tagaggaatt aaagacacac   40260
acacagaaat atagaggtgt gaagtgggaa atcaggggtc tcacagcctt tagagctgag   40320
agccctgaac agagatttac ccacatattt attaatagca aaccagtcat tagcattgtt   40380
tctatagatg ttaaattaac taaaagtatc cctatatggga aacgagggga tgggccgaat   40440
taaaagaaga ggttgggcta gttaaccgca gcaggagcat gtccttaagg cacagatcgc   40500
tcatgctatt gtttgtggct taagaatgcc tttaagcggt tttccaccct gggtgggcca   40560
ggtgttcctt gccctcattc ctgtcaaccc acaaccttcc agtgtgggca ttagggccat   40620
tatgaacatg ttacagtgct tcagagattt tgtttatggc cagttttggg gccagtttat   40680
ggccagattt tggggggcct gctcccaata cagaggtctc gtgtaaattc cctgggaggc   40740
gataagcctc tgagaaacag actatgctaa ccacgccatg aaagagaaac ttatttataa   40800
atcagatgcc agttactagt ttactgctta tttgcccagg cgtagctctg acagagtccc   40860
cgactcatag tgcttgctca gtgcatgctg aacaatgatt ggaatcaagt catggctcag   40920
agcatagttt tgaataatgg gaaatggatg ttcttaagta acatagtcac caagataatg   40980
cgactagctg ggtcacccct tttcaatttt aggatatttt tatcaagatt taaatggcca   41040
tcattagagt tatagcactt tctcctttgg attgtcctag aggcccatga gaaagtattc   41100
cctaatttct taggagaaca gtttgtgggt agtatgcggt catgtccagt taaattgcag   41160
atatttccga tcgaagatgt tccagtcctg agaacttcgt gacattagca ggacttctac   41220
aagccatctc ttagggtggg gcatttactg cagttggcta gtactctttt ctccttaact   41280
ttgtcatttg ttgattttttt tttaactgtc cccaaatact gtgggcagag tgtatctaga   41340
attgaggcct ccaccattgc ggagaggaca tggatgctga gcagtcccct gagtgaaggt   41400
tataaagaag caaatagact acacatgtct gtaaactgct cttgagtgtc ccaaatttgg   41460
ggtacttcag ttcagctgta ggaaaagcct caaactgttt atactttgca agaattggaa   41520
acttctaatt cacgttaagt tttatgtaat acatgataag cttcatagga gcttcatctt   41580
ttatctactt ggacttttgc ttccgtaggt tttgttaaag gccttcatag cgaacctgaa   41640
gtcaagctcc cccaccattc ggcggacagc ggctggatca gcagtgagca tctgccagca   41700
ctcaagaagg acacaatatt tctatagttg gctactaaat gtgctcttag gtaaggtgga   41760
ggcatatgag tggaagagtc tccagcatgt actcaagata gacctttgaa ataaataaaa   41820
ccagatgatc cctcagcttc tagaccaggc tatttggcac tggttgattg aatgtgaact   41880
gcactggggc tgctgtgagc ccgcatgggt ctctgtgacc ctgcagatgc agccgtgccc   41940
agggactggg cagtgggtgt gggctggtgt gagccctgtc tgccacccag ggcctggccc   42000
tctgtctgtg tcggccatga ctatggtgag tcttgtaggc ttgagactgt gcctcgggtt   42060
```

```
cctgcgggtt ctctgtaggt cagttgacag tttctcctgt tgtttgggta actgtggaaa  42120
cgaacactgg caagtgctga agcgagcatg tggacgtgcg atatgaaata acgacctggc  42180
tttcaaaggc agtgaggctc tctggaaagg accttgctga gctagggatg tgggtgtgta  42240
gccattccca gtgggcctca tggcgtactc gttcatgatc atgtttgtgc catcttgatc  42300
tctcaggatc tcttcttttt taacagatta agccgggaat ctccaaacag tgagtcagat  42360
gttaagatgt cttgcttcca cccccacagg cttactcgtt cctgtcgagg atgaacactc  42420
cactctgctg attcttggcg tgctgctcac cctgaggtat ttggtgccct tgctgcagca  42480
gcaggtcaag gacacaagcc tgaaaggcag cttcggagtg acaaggaaag aaatggaagt  42540
ctctccttct gcagagcagc ttgtccaggt aggagcacag ggtttactct aggccctgca  42600
tgtgaatgac tgacattcaa gaaccgatt aatttggaag agaagcggca gaaccgagag  42660
ttagaggtgt ggactctgga gctgcgctgc tcgtttccaa ccctaggtgc tgacctctag  42720
ctgtcttccc tctgtatgtc cctgtcaccg tgagtcaaat gcgggtgatg cctcctcagg  42780
tgccgtgtta cctaagcctc tcagagacca ctgctaccct gtttctaaaa ccagaggtca  42840
cgatatgtgt tcatccaccc agtaaatact gattgagcac ccactgtgtg ctaggctctg  42900
ggataggggc tgggtataca atggtgagta tttcagctgc agcttctgcc ccgtggaggc  42960
tgtggcctag cacactggtc taggcacggt ggtatatgct cactcaagga gatagggacg  43020
tggtcgtttg gggtgtcgga acaaaatgtc ggaacttctc tttccaatgc agagaaacct  43080
tgcagtaatt ctaatgtact gtgattggca gttgacttca gttctttgta gcacgcttac  43140
tcaggttatt tcactaacta tgtaaccatg cagcctcatt ttaagcaatt ggattttttg  43200
aactttactt aaaatgttat gtcagggttt ttattgtgct taatgtgtgc catttagcta  43260
agttttgtag gatacgaaat tgtaagtggc ttaaaatgat tcttaataga atcatgaatt  43320
gaagataatg ctaataattt aagcactgag ttaggtagtg tttgtaaaat gcttagaatg  43380
cttcctggca catgttaagg ccatgtaagt gctgcgtgtt gataaacagc tgagcaaaag  43440
tggactctta agaaagtatt ggggctgaga gttctgttcc aaccagctgc cctttggtta  43500
tttttcagaa taaaagcaga gtctcatggg atatgacatt tatatttcct tcacaaaaaa  43560
cactgctgag tgttttgttg agtaaaaagg gtgtagccat ggtaataata catttaaaat  43620
atagtttatt tcatctttac cttgccttgt tttttttta agctagcttt ttattgagaa  43680
ttccacacat acaaaagtat caactcatga ccagttatat ttcatttata atcctacttc  43740
tccctttttt tattatttga aagcaaaccc caattatcct cttatttcat ctataagtat  43800
ttcagtatct ctatagatga ggactcttct ttattttaa aactttattt ttaaaatgat  43860
ggtcagatgc agtgttcatg cctgtaatcc cagaactttg ggaggccaag ctgggcggat  43920
cacttgaacc tgggagtttg agaccagccc gggaaacatg gcgaaacccc atgtcttaaa  43980
gaaaaaaatc agccaagtgt ggtgatgcat gcctgtagtc ccagctactt gggaggctga  44040
gatgggaggg tcacatgagc ctggaagatc aaggctgcag tgatccatga ttgtaccact  44100
gcactccatc ctgggtgatg gagcaagatt ctgtctcaaa aaacaaaac tgcaaaacaa  44160 cgtcacaaaa cagtgccatt gttagacctg aaaatattaa acatttccta catcaaatac  44220
ccaccaactc attatcaatt tttctctcta ctcttttgga atcagcatct aaataaaatt  44280
ggtcgataag gattgtaaat ctctttgatg aactggttcc cctccatccc agttttttc  44340 ccttagagtt catttattga gaaaccagat tgtttgtctt ctaagttttc ctgtggtctg  44400
atatactgct tccatctcca ctgtgtaaat taacacctt ttctcttctc tgtattccct  44460
```

```
gtaaatcaat aattggagga aaagccttgt cagatttagt gtatatttta tatctgagtc    44520
cagtatttct tatataatat tttaagataa gtgtactctt ttaaaaagta ttgaaactat    44580
atgctcaatt tttttaact gatgcttta agaaggctgc ttgatcataa aagtttagag      44640
atcattggtc tgatgggaaa agcaaataat tactaaaccg tttagcaagg ttgaggtgca    44700
catggtgggg cctggagaag ttcagtcatg agccgtcact tatgggcacg tggaatctga    44760
cccggcacag agttgggaga agacaggagc tttatagaca gaaaatgtgg tctttgctaa    44820
gtcccaggag tgaaagggtg agacagtgct cacagcacac gagtgtgggt gcgtagacag    44880 agcaaggtg ggtcctgaaa aggcctgcag gctttctcat agattagcaa gagtgctggt     44940
tacggaggtt tctaacattt gtgaacagat cgaaactgtg ttaaattggg attgcagtaa    45000
tcctggaagg acaggdatag agggtgaagg ggaaaaaagg gtatggatgt gagacttaat   45060
tgctgatttt cttaagacct ttctccaaag taaataaatg atgtggcaca ttttgaact     45120 ggcaaattct aaactctaga tatgattatc tctataacat atcttactcc atcttctttt    45180
gactaaaaac tgttcttaat taaattacca tgagacgttc aattcagcaa atgtagtttg    45240
gctaaccata tttaattaga atttaatata atcctaggcc tggccaaact attaagcaag    45300
tgtgggcaaa atattgataa ttttagatat gcaggaactt agtttgcttt ccatgtgtgc    45360
ttttcgaaaa aggaataaat tgaaaaatag aggaagccct gaaatccaag aagcaaactc    45420
tctcacctag gcatgcagta aaagcaattc taggatgatt gctgtttggc gcgtagttcg    45480
tattagaaac cattcttctt gaataaatag tatgtttaag aagctgggca gagggaaggc    45540
atatgcatat attatcaaca aggagggaga aaaaggcaat tagtaaccat ccataggagg    45600
gtcagcaaga tttataaagg aaatttgtga tccaagtatg aagcaaaata aggtgcagaa    45660 taaatttaa gcaagtaata gattagagta agagaaccca tttgaccatt aaccttggga    45720
cattctcttt caaatgacat ggagtagtac tgaaatcttt ctttctttct gagtctaggt    45780
tattgtgact ggactcagaa agaaatattt cattattgca gtgaataaca tttgtgaaca    45840
ttattgttca taaattatgc agtgaataac atttatgaac acgtgatgtg taagatacat    45900
actgtttatt tttagttaag ttttttggct caacttctag gcagagaaca ttaaatgtaa    45960
atagtgttac ctaggagcat gtaaatggaa atctccatag tatgaaagca gtgctgttgc    46020
taacagaatt taggaggggg cagatgaggt gaaggaaatg tgggtgctga tttccttatt    46080
acattgagag gagccaggag attctttgtt caaaatggat ggcttaagaa gtcaaagtat    46140
aagctgatta cgtagagcag gtacccaaaa atgttttgtg taaggggcca gatagtaaat    46200
attttcagtc ttgcaggcca tcccaagtct gtggcagcta ctcaacacta cctttgtagc    46260
atgaaagcag ccacaggcag cccataaatg tggctctgtt ccggtgaaac tttaggtaca    46320
aaagcaggtg caggccagac ctgacctgtg cactgtggtt tgctgacctg ggattcaggg    46380
gtatagaagt taccatcaga agagctaaaa gtgagacttt ttactttata ctcttctaca    46440
ctgtctgatt ttgaaaaaaa gaaacatgta ttttataata ttaaagatag ggttggcaaa    46500
tagcaaataa aaatacagaa taccagtgaa atttgaactt cagatacatt atgagtaatt    46560
ttatggtgta agtatattcc aaatcatgtg ggacatactt acactacaaa attatttgtt    46620
gtttgtttac agtttaaatt tgagtgcctt gtatttatc tggcaactgt aattaaaggg     46680
aaaaagaata aattcattat gttcatataa tgtgatatag caggggtccc caaccccag    46740 gctgcagagt ggtactggtc catgggtccc caaccccag gctgcagagc ggtattggtc     46800
```

```
catggcctgt taggaaccag gctgcccagc aggaagtgag cagcaggtga gctggcattc    46860
ccacctgagc accgcctcct gtcagatcag tggcagcatt agattcccat aggagtgcaa    46920
accctattgt gaactgcaca tgtgaggggt ctaggttgtg cgctccttat gagaatctaa    46980
tgcctgatga tctgaggtgg aacagtctcg tcttgaaacc atcccctggc cctgtggaaa    47040
aattgtctcc catgaaacca gtctctggtg ccagaaaggt tgggtagcac tgtgatatag    47100
tattaaaagt gctaataaat atggcatact gcctttaaaa tgtctggtag ctcttctca    47160 gtggcactca taatagtgtt ttttgatttt taaatgtgtg tcaagctgac tctcccctcc    47220
gtgtatgctg ggctttattt tccctttcct agtcaccagt tttgggaaat agagatcttc    47280
attctcatgc tgctcctcta gtgcaagtgc tccatttatt tttaaggaat taatataaca    47340
aaaaatcatg ggaatttaga aaacaacatg gaagctaatg atcacattgg tggaagtgat    47400
agggaaatat ttaggggag aagttaaggt ataaactttg tcaatgaagt cctattaaaa    47460
acaacaaaaa agtgaagctt aggatgcatt ttataaactc tgaccagaac acctgtgttt    47520
ctctgtttct aggtttatga actgacgtta catcatacac agcaccaaga ccacaatgtt    47580
gtgaccggag ccctggagct gttgcagcag ctcttcagaa cgcctccacc cgagcttctg    47640
caaaccctga ccgcagtcgg gggcattggg cagctcaccg ctgctaagga ggagtctggt    47700
ggccgaagcc gtagtgggag tattgtggaa cttataggca agttattagc aaggtctact    47760
cttacaatta actttgcagt aatactagtt acactctatt gattatgggc ctgccctgtg    47820
ctaagcagtc tgcattccat cttccttgcc aaaacttata atacaaattt catctttatt    47880
ttataaatag gggagttggg ctgggtgtgg tggctcacgc ctgtaatttc agcactttgg    47940
aaggatcgct tcagcccagg agtttgagac aacctggcca agtgagaccc tgtctctaca    48000
aaaaaaaaaa aaaaaaaaa attagctggg catggtggca catgcctgta gtcccagctg    48060
ctttggaggc tgaggtggta ggattgctta agcccaagag gttgaggctg cagtgaatct    48120
tgatggcagc tgcactgagc ctggtgacag agcaagatgc tgtctcaaaa taaatttaaa    48180
aataaaataa gagaattaaa gtttagcagg ttgggtggca aaatgaggcc acacatttaa    48240
agcccctcct cctgattctt ttctctgcct tggctgcctc ctgtggcatt ttaggtgctg    48300
agaaatgaaa acagtaggga aaatagttcc aggatcctca tgttaatttg ccagaaatgg    48360
catcttcaag tcgtcagagg gatctgagag ttccttcctg gcctgacttg agaaaatccg    48420
tctgtcccca gctctgcgtc tgcctccact gcccagtcac ctcctctcca tgctcttggg    48480
gctgggccct accccaccat gcagtgctgc cctggagcag tgagcttggt gggtcctgtc    48540
tggcatgaga gctgcctttg ggagctggat cccagcctct accactgggt ctggtgccta    48600
gcaggctatg gataaacttc tgctgactcc ggcctctcct aagccactgc aacgtggtcg    48660
gtgtagtgca cagtgtgtgt gcagcgtggc cttactcaca gcctccacat tagagagaat    48720
ctgactgaag tcttactgct gcctcgtgtg aacataaatg tttgccagaa ccatgagcag    48780
gaaatgttaa tctgccttgt ttcctgtcct ttacacggaa gaattttttt ctgtatggaa    48840
tgcgtgcctt acaaataatg agtggaaata cccatcgcta atgaaaagtt atacttgact    48900
gttagtcagc taaataatct gagatttcta atacttttaa tttggctttt acaatgcaat    48960
ttatcttagc ttttttgatt tcttaggtca tatctttaga actatatatt tgaatgttaa    49020
tgtaattttc atattgaaat taaaatgttg aactgcgatg ttaagtgttt cctgtggaaa    49080
aacgttcaca ttttctctag ttttaaagtt gaatcaagct gtttgaagat tttcacattt    49140
cttctagatt ttatcagctt gttactttat ctgtcacttt ctgtgatttg cagctggagg    49200
```

```
gggttcctca tgcagccctg tcctttcaag aaaacaaaaa ggtgattatt tcagaaatca   49260
gagtcttgtg ttgaatctta ctgattttct tgtatttctg taatgtaatg tatcttgtat   49320
ttcttgtaat actgtattgg actctgtgta tatctcttct cagatgagtg attatatgtg   49380
tgaatgttgc tggaatctga taaccaggcc tgaatagttt tgtagggtgg cttttaaaaa   49440
ttactttcat atcagaattg ctttgtcata aattttgaac gcatcataaa tttctaatgt   49500
tcggggtcag cagactttt ttgtaaaggg acagagtgta aacatcttag ctttatgggc   49560
catatggtct cttttgcaac attcagctct gccctgtgac aggaatgcag ttgtaaagac   49620
atgagctact ggccagctat gttccagtag aactttactt acagaaacag acaggctgta   49680
gtttgccaat acctgcctta gggaatgtgt tgttatattt tgtgagttac cttctcagta   49740
aattttattt agtattagtc aggaatatta ttaagtagct tcttttccag cctggtcaac   49800
atagtgagac ccggtctcta ccaaaacaaa acaaaacaaa aaacagcca cgcatgtggc   49860 atgtgcctgt agcctcagct gctgctcagg gggctgaggc aagaggattg tttgagccca   49920
ggagtttgag gtcacagtga gctgtagtca tgccactgca ctccagccta ggcaacagaa   49980
tgagaccttg tgtcttaaaa aaaaaaagtt tcctttgttg ggttatttta atttggacct   50040
ggttatcatt tttcagccat atttaacttt gtacatatca gaatgttctg ataaaactta   50100 actttttatta aagtgtttgt gatataatct gctagttttg gtacacatta tcttttgcaa   50160
tgccagttat tttcttttcc agtgtgggtt tgcataggaa aagaattgct gtcactttct   50220
attttgaaat cttaaaagac tgatcctttt ttgtgtcatg atttgagtat ttaattgaga   50280
gcctaatgcc taatattatt tgcagtatta aatgggatct taacaggaat agcattctag   50340
ccttcattga attaagtaaa catttcttaa gagaacttgg aatctataat atttgcgtca   50400
tcatagtatg agatacttaa tcaagtttga gattttagtg aaacattgtt tagaagccaa   50460
aaggattcta ggaaaaatta atgtctatat tcttgaatta ggagagattt tgggacgtgt   50520
gactaagtta cgctgacact tgtttgtttc ttagtcgctt tttccagtgg cggtgagaac   50580
gaagatgact gattcacatt gctcagatga gtttatcctc ttctggctgg gacatgggat   50640
atatcctgtc tcttttaagc ctttttggta tttttccccc attgagagct gtgtcttcaa   50700
actcttctgt tatagctgga aaatccttt taagtgaaat ctgcccaaat tataagacag   50760
atgaaggtag agttgtgttg gatataggat tagggtgaaa gtagtggggg tgtcctggag   50820
cctctcttct ggtggcagcc tagctcttgt gcctttgagg aaattaccct ggggacggct   50880
ctgtggaaca tatttgcaaa ccactgattt ggaagataga gatggctttt gttaagatct   50940
gaattcacct ttttggcatt ttatttgatt tctcaaggta aagaacttat tttgtaataa   51000
agttccctat tatttagtag ataggccaag ttgctgtgtt aattccatgt agattttggg   51060
tttcctttgc tcattttttc actcttaatc tcacatcatt gtaagtttat ggaagttatc   51120
atacttctga cttttttcttt gaagagcaga aattagaaat tcccaataat tattttgata   51180
gtgtcattta atgacactca catgtgatgt agccacaaag atttaatgag ttcagtttta   51240
aatcatatta agactgttgg tttcatttgt tctcattaat gtaattctga agatgaacaa   51300
taaaatgtat tttagaact ttcaaatgaa atattttc atccttccag atcatataat   51360
gcttaagttc tgattgttaa tcataaagtc tagaaaatta aagataata aaatgaaagt   51420 gactttagg tattagagtt ttattataaa ttctggtgtg tcattggagc tatgacatga   51480
atatttcaaa ggccaatagc attggatctt tacagttata acttaccatt tttaagttta   51540
```

```
agtagtaata tagattattt aataatcaaa atcaataaat attaattatt aaaatgtttt    51600
gtggtatagt ttgagaatca ttgcttttaa ctttttccat ataggtttat tgactttaat    51660
agcattctaa acataacatc tctacattct ttgtgtttaa tactgtggag gtataaaaat    51720
acttatatat gatgataaac tatattagag taaattaaat attcttatga gtttcatttt    51780
agagtgcatt tacttaattt tgaagtcctt attttagca aactaaaagg aatgttggta     51840
cattatttac taggcaaagt gctcttagga gaagaagaag ccttggagga tgactctgaa    51900
tcgagatcgg atgtcagcag ctctgcctta acaggtagtt ctcactagtt agccgctggt    51960
gtggaccttc actgtctgcc ttccacccct tgcccttcct gctcgtcccc ctgcacctgg    52020
tggacagcac gactgggggc agcagtggag ccaggttgct taaatggggc atattcgggc    52080
ttcttttata atacttactc tgaagcttgt gtgtctgtgg tgtttgcatc atatatttgt    52140
tgttttccat ggtttaggct gttttaaaat taggtttatg gcttgagcat agggctttgt    52200
gagtagggga tggcaggtcg aaacatctca tgagttggat gggttatgct ggggttggg    52260
aaatgggatg aaaaattatg ggatgaaaaa ttgcctatgg atagtttaac ttgaaagaat    52320
ctgccttgt ttacagatag ttatcttttt tcttttttga gatagagtct cacactgtca     52380
cccagtgcag atacccagtg tcactggagt gcagtggtgt gctcttggtg cactgcagcc    52440
tccgccttct gggttccagc gattctcctg cctcagcctc ccaagtagct gggactacag    52500
gtgcccgcca ccacgcttgg ctaattttg tattttttg tggagacggg ttttgccat      52560
gttggtcagg ctggtcttga actcctgacc tcaagtgatc tgcctgcctc agcctccac    52620
agtgccggga ttacaggagt gagccactgt gcccggccag ttacagatac ttatctaatg    52680
aaattctctg tgtactttat aaaagatgag gattaactga aggtactaat aactggatta    52740
tatgagggtg gttttggttg tataatccta tctaaaagaa tattttagct ataactgaaa    52800
gtaagactta aatatttaga gaggaaaatc tgaataattc tagtagtaat tatttattta    52860
caaaataaaa atagatttt ttttgattac acaaattaaa caacaataaa acatcacagc     52920
aatccggata ctataaagct cacatgctta ccgacccaac tgccccagga gtgaccactg    52980
ccaacagctt catgtcgacc ttttgccat aattttata tagccttttt tgttttaaa      53040
tggtaattta gaaagtcaac taggaaaatg tgttacaggt ttatcttcca ggagaatagg    53100
actggagtcg agatcttgaa tgtggcttgg aagaaggcaa gcccacccca gagagatgag    53160
ttgacagttg tttctgacca ctgcttgctt agagggcctg cgtgtctgtg accgcctagc    53220
tttgcgcccc tgactaggct gccccttaat tacaaatgtc tttatatatt gctccagcta    53280
aggcttggag tagtcggtta agaacttgaa cttcggtttt tgcagtgaaa cagcatttga    53340
gaatatcacc ttctgataag ccttatttta taaggtgggt actgtagtgg gaggcagtgt    53400
gagagatgct tgaaggatgc actgctgtcc tgcatttcag catcttcagg atgctgtgca    53460
gctgaaacat ttgataacgg tggaactgtt cgttattttg caagcctgtg attccctatt    53520
gaatgttttc tctcgccatt tgacaaatga gtgtttctct gtcttcagcc tcagtgaagg    53580
atgagatcag tggagagctg gctgcttctt caggggtttc cactccaggg tcagcaggtc    53640
atgacatcat cacagaacag ccacggtcac agcacacact gcaggcggac tcagtggatc    53700
tggccagctg tgacttgaca agctctgcca ctgatgggga tgaggaggat atcttgagcc    53760
acagctccag ccaggtcagc gccgtcccat ctgaccctgc catggacctg aatgatggga    53820
cccaggcctg gtcgcccatc agcgacagct cccagaccac caccgaaggg cctgattcag    53880
ctgttacccc ttcagacagt tctgaaattg taagtgggca gaggggcctg acatctttt     53940
```

```
ttttatttttt tatttgagac agagtctcac tccatagtgc agtggaggcc gggcacaggg    54000
gctcatgcct gtaatcccag cactttggga gactgaggca ggcggatcac ttgaggtcag    54060
gagttcgaga ccagcctggc caacatggtg aaaccctgtc tctactaaaa atacaaaaat    54120
tagttgggcg tggtggcaca tgtctgtagt cccagctgtt agggaggctg aggcaggaga    54180
attgcttgag cctgggaggc agaggttgca atgagccgag atcgtgacac tgcactccag    54240
cccgggcaac agagcaagac tccatttcaa aaaaataaa aaataaagt gcagtggctc    54300
gttctcagcc cactgcaact tctgcctccc aggctcgagc gattctcccg cctcagcctc    54360
ctgagtaggt gggattacag gtgggcacca ccacactcag ctaatgtttg tattttcagt    54420
agagacaggg tttcaccatg ttggccaggc tggtctcaaa ctcctgacct tagatgatcc    54480
acccaccttg gcctcctaaa gtattgggat tatagttgtg agccaccatg cccggccctg    54540
ccacctgcca tcttttgagt tcttccctgg agacctagac ctgaaccctc ctgcttgttc    54600
tcttgttatc taatacccct attgacagcg cagcttagat cattaatgga gagcttgacc    54660
tcatctgata ccttcactga aggaaacaac ttagtgtctt ttgtgttgaa cactgaggta    54720
aaaaattgga atagttgatt atatgaactc tgctaaaatt gagtgcattt tacatttttt    54780
aaggccttgt tgggccctgg ttaaataatt attttttaaaa atccttaagg agcctattat    54840
aaacagatct gtggtcttaa tgaaatgtga ttaatactgt gcattatttt aagaactttt    54900
gacttttcaa aaaacttta caacatttcc catttgatag cggcataggt ttaagcactt    54960
ctcatctcta agttagtgga caaaaaaccc tcatggatag tctaataatg tttgctacaa    55020
gtccatgttg agttttatac tccattttat tttcagtttt aaaaactgtg gttaaatatg    55080
tgtaacataa aatttatgtt cttaaccatt ttttgcgtat acagttcgct ggtattaaat    55140
acatttaaat aatgtcatgg aatcattgct accacccatc tctgtaacct tttgatcatg    55200
taacactgaa gctctgttcc cattgaactc tattcctcct ttcccgccaa gtccctggca    55260
accacgattc ttctttctgt cttctgaatt tgactacttt gggttctcat atactttagg    55320
agtcacacag tatttgtttt acttagcata atgtccccaa agctcatgca tgttgtagcc    55380
tatgttagaa cttcctaatg tttcaggcca aatactattc cattgtatgg ataggccaca    55440
ttttgctttt ccattcctct gtccatggac acttgtattg cttcatgttt tagccattgt    55500
gaatcatgct gttatgaacg tgggtgtaca gatagctcct ggagactctg ctttccattt    55560
ttttggctaa atacccagaa atggagttgc ttttacattc caattttaat ttaaaacatt    55620
catatcattg agtgttttac ttaatagtat agtagttaac aaacttaata aaatagtatt    55680
ttggtaataa tttgctggta gtccattgtt cagttttttt aggtaaatta cacaggacat    55740
ttcaagtgga catgaaacat cttgtgatgt ggaatcatgc cccaagctga tggctaaaca    55800
tatgaaatac catacccctaa atttagtaga tttagtcttt gcaatttagg agataacctg    55860
ttatattgtt aggttttgt cgaaaagctt tgtcctcata tttccaactt gctgtaaaat    55920
ttgtttgtga agacaaatat ttttgtatgg gttttttctt tttcatatta aaagaaatg    55980
tccacattgg aattttttg gagtttttag agctaataga gcttttcata atgtagtggg    56040
aatgagtgat cagtaagctc ttagcagttt ccatgcgtgc atttctgtgc cttgaaataa    56100
atgacagatg agtacatttg tgttctgtgt gtaaaatgtg ctctttcctc attgcacttc    56160
catgttggag ggcttgtctc ttggtgatca cacttcaaaa ttctcacagc ccccccttgaa    56220
ccgtttaggt gttagacggt accgacaacc agtatttggg cctgcagatt ggacagcccc    56280
```

```
aggatgaaga tgaggaagcc acaggtattc ttcctgatga agcctcggag gccttcagga    56340
actcttccat gggtatgtgg actacaggtg atgcgctaca aagtggtttg tattcagacc    56400
tggacatctt aattatatct ttgcttccaa gaagaagtcc tttgatactg ttttctgagt    56460
tctgaatagc tgatgaaaat gaccaattga ggaataatca tacttttttct tgatctaaat   56520 cttatacttt tgagttatct tagcataaat gtataattgt attttaagtg gaaatttgtc    56580
acttaatctt gatttctctg tttttaaagc ccttcaacag gcacatttat tgaaaaacat    56640
gagtcactgc aggcagcctt ctgacagcag tgttgataaa tttgtgttga gagatgaagc    56700
tactgaaccg ggtgatcaag aaaacaaggt gagggacata ggcttgagac gacttggtgt    56760
ttctgagctt gtgtgaggat ttaaaatcgc cctggctact gtctacttta ttgctttccc    56820
atccctgggc ctttaaattt ccccttaaa taccagctct tcccaggcct gttgttttct     56880
gcctttccag gtactaccca cagccttgag aattgcctga gttctgcctc ctttgagagt    56940 gtgcccaga caaatctatt ctgtactgaa tgtttccttg tctgatttct tggatcattc     57000
atttgatggt tgcgtatggc ctgcaacgtt tcttgttttg gttctactga actgttctaa    57060
aagtctctct tcatattatc tttttacatg taaatgtaac tgtcttcact tttaattcct    57120
caaggacaag gaatagcgtt tcacagttcg tcccatcaat cagaattata gcctttggca    57180
tctccctatc taccaggccc acttcctctt agatttgggc ttccccaggc tgttgccttt    57240
ccccaagtag cttctgcttg tcctgtagaa gacctttcat gctttgcttc tgcagcagcc    57300
gttcctgaat gcctagtgtc aactgccttc ttaccacgcc caccctccct gcatgctgca    57360
tttatcccct gccacagccc tgtgaccctg tgtcctgctg cctctgactt gtctgtttct    57420
gcttggccat ggtctctgtg aggtcaggtg tgcatatggg cacaaaccag ggcatctctt    57480
tatccccagc acctggctta agtgctgctc tggaactatc tgttgaatga actaatgcat    57540
gaatgtattg ttgagtatga gacaaacaag tgtcattgtc tcctttctag ccttgccgca    57600
tcaaaggtga cattggacag tccactgatg atgactctgc acctcttgtc cattgtgtcc    57660 gcctttatc tgcttcgttt ttgctaacag ggggaaaaaa tggtgagtac aaaagggat     57720 gtgcacagtt gaaggaaata actaggtttc agaggtcagc ttggtggcct gttttttgcct   57780 tgcgtgcagc agaggaagta gaatctgagg atgagtttgg ttttcactag ccgaggggag    57840
ggaggaaatg atgggagcag gtaggttatt gggtctggtt ttgttcattt gaaaacaatc    57900
tgttgtttga ggctgaaggt ggcttgggtg atttcttggc agtgctggtt ccggacaggg    57960
atgtgagggt cagcgtgaag gccctggccc tcagctgtgt gggagcagct gtggccctcc    58020
acccggaatc tttcttcagc aaactctata aagttcctct tgacaccacg gaataccctg    58080
gtatgttaaa agttcacatc ttattttctc agatttaatc attattgtaa aaactatttc    58140
agtattgact atttagtttt tagagcagta agtgttttga gttcatttgg gatatttgac    58200
ctgcgttgta gctcttcaga aaacacatga atagtgaagt tctttgtttc atgggttccc    58260
tttagatgaa acccatagag gagaaaagta gaaacctcag cacgtaagag ccaacatata    58320
tacacatcgg atttaaacct aaagcacaaa ttgtgcctgg tcgcagtggc gctgagtcgc    58380
actcagccag gccaggcatt cacactcagg gtgagtggga accaggactg gctgaggcag    58440
cagtggaccc aagtctccat cgcgcccatg cttactatgg agccttctcg ttctctcttt    58500
ttctttgggt gagagggtac acttgtgttt ttgaatttat atgaggtaag tgtgtaatag    58560
ggttttttct aatcttttt aagtggaatc tggaatttta atcagattta ttatctgaca     58620
acctagaatt ataatccaga aagtctgtgg tattgaggac atattggcaa tatgatgaat    58680
```

```
ctctaattct taaatcctga aactttttt tttttaatca cttagggtta ttatagtgaa    58740
gtcatttctg aatttggatc ttctcttcac acctcttttt ctctttcctg agaattaagc    58800
ttttgtttcg agttagaaag ttgatagtag ggaattgttc catggctgag caatttatct    58860
ccacagagga acagtatgtc tcagacatct tgaactacat cgatcatgga gacccacagg    58920
ttcgaggagc cactgccatt ctctgtggga ccctcatctg ctccatcctc agcaggtccc    58980
gcttccacgt gggagattgg atgggcacca ttagaaccct cacaggtaac ggccagtttt    59040
tcagctgtgt ttttctagt tatgcttact aaggtttaag tttagatgat gatgtttgtt    59100
gcttgttctt ctggttagga aatacatttt ctttggcgga ttgcattcct ttgctgcgga    59160
aaacactgaa ggatgagtct tctgttactt gcaagttagc ttgtacagct gtgagggtga    59220
gcataatctt ctgtggaacc atttcttcac ttagtggaca ttttatcatt gctacaatta    59280
aaattggagc ttaataggaa atatttccat gcactctaaa gctgtaacca gtaataccca    59340
ccatgtatcc atctctcagc tttagaaaga aaacgttgcc agtaaagtta atgcttcata    59400
aacttcagtt taagttctaa ttctcagaat atttgtttga aatagacctc ttcctaaagg    59460
atatatttag aaataaccta tcattaagtg taaagtctgt tgaatatgct gggcacggtg    59520
actcacacct gtaatctgac cactttggga ggccaaggtg aaggattgc ttgagcccag    59580
gagttcaaga ctatgggcaa catagttgac cctgtcccta cagaaaatta aaaaaaaaa    59640
aaaaaaagt agctgggtat ggtggtgcat acctgtagtc tcagctactc gggaagctga    59700
ggtggagggg ggattgcttg agccccagag atcaaggctg cagtaaggcg tggttacacc    59760
actgccctct agcctgggca acagagtgag actgtctcaa aaataatagt aataataatc    59820
agttgaatta aaaaaaaaa aaaaaaacc actgtgctag gcccatagta tggtaagagt    59880
taaagtgagc cttagggatt atttactcaa cctctgtttc tgtataaagt ggaataggct    59940
caattctta agtgatagca tgttgaacct ttccatacca actggctcat aagtcacaac    60000
tggccagtca acaagagtaa aaattaactg gtaaaaatca aagcaaaaaa cctacaattg    60060
tcaaatttgt gggataactc cccctttaa aatgtcatgc ctgacagtaa tttctctcta    60120
gtttccaggt tttcagtcag ttgtgtcttt tttgagcaga aggaagcatg ctaagagctc    60180
aatcttgtgg ctagctgggg gtcttttgtgt cagccatgca tgtgatggtg cccctgggtg    60240
cttgggctg caggggaggg gtacagcagt aggggcctgt tctgttctct cgtgctgtgg    60300
agtacatagt gacatagtgg ggtggtcctt ggtgtaggtc ccttgttcct accctgggt    60360
ctgagattta tttagaagtg gtgttggggc tgtgcggcag gcccctctgt aactgatcaa    60420
tgtttgtgaa gttgctgttt gagagttgaa accatgacat aagcagaaat ggaaggaaga    60480
aagaaccagt tatgtgaaag ggacacattt acttttaagc ttgtatttac tgagataaag    60540
tattcttaat caatgttctt gagaggtgtg ggaaaaatgc aacatcctgg ttgcagttaa    60600
acccagaaca ttgtgtgttg aagagtgacg gttctcaaac cgtcaagacg cgggtactga    60660
gtgggactaa cctgctgtcc tcttgccttg gaccttgtgt tccagaactg tgtcatgagt    60720
ctctgcagca gcagctacag tgagttagga ctgcagctga tcatcgatgt gctgactctg    60780
aggaacagtt cctattggct ggtgaggaca gagcttctgg aaacccttgc agagattgac    60840
ttcaggtaag tgagtcacat ccattagatt tcatgaacta agctcaattg aaagttctgg    60900
gatcacttga tgcaaggaat gatgttatca agtaccctgt ccatcagaaa tccgagtggt    60960
ttaggtagat gacagtgatt ttctcctccc agtggctttt tgctgaactt tgccctatgc    61020
```

```
ttggaatttt attttatttt attatttatt tagagacaag atcttgctct gtcgcccagg   61080
cttgaatgca gtagcacaat catagctcac tgaagctttg aactctagga ctcaagtggt   61140
cctcctgcct cagcctcccg attagctagg agaataggtg tgtgccgtca cactggctaa   61200
tattttttgt agaaatgggg tcttgctatg ttgcccaggc tggtctcaaa ctcctgggct   61260
tgattgatcc tccatcttgg cctcccaaag tgctgggatt acaggcatga gccactgtgc   61320
ctggcctaga attttaaaat ataagtagaa gagtagattt tttttttttgg tagtcctcgt   61380 catttaagta ttctggatag tgggaataaa agagcttaga attttcatc tttgtcttaa   61440 acttttaaaa aaatgtagct tatattaatt ctgcttgttt aaaaagaata tactcttcat   61500
tatactgaac ctaggtaaga cagctggttt atattttgtt gcaattaaaa aacgtgagct   61560
gtggttgcag tgagccaaga ttgtggccat tgcacttcag cctggcaaca gagtgagact   61620
tggcctcaaa aaaaaaaaaa taacatgagc tgtgttggca cttcatttt ctaagagtag   61680 ttttggctgg agaagttttc tttcagtact ttctttttaga agggaaattt tcctttataa   61740
tttagggttt gtttttttt tttccaagcc acctttata gagcccttgt gggttatttc   61800
atttaatcct tagaatgttt ataaatctgg gcttgttctc ggctccaccc acagataggg   61860
acgctgagcg tgcatgagtg ggcagcaaga tagcaggtta tggagggccc agctcacccc   61920
ttctgtggct tgagccaatt ttatagggca cttacagagt cttttgaaat agtatttatt   61980
ttgaagaaaa agaaaaacag tttactgagt actgtcttat tgagtctgga attgtgagag   62040
gaatgccacc tctatttatt taaagccatt ggccttttt gttgttttga gtaagtgctg   62100
cccaaggtcc ttccagggca cctggatgag cctgctctgg agcaagctgg cggtaagtgt   62160
ttactgagta actaaatgat ttcattgtta aatgtgctct tttgttaggc tggtgagctt   62220
tttggaggca aaagcagaaa acttacacag aggggctcat cattatacag gggtaagcgg   62280 tttattttg tgagatgctg ttttaccttc aagaaggtga agtgaggct ttccttgtgg   62340 aatttctcta aatgcattcg tcatgttttta gatgtttatt tcacagttta tatcatgaaa   62400
gttataatct tgtcatatgg atttaagtct agtaatgttg agttctttct cactagcttt   62460
ccaaaatatc ttacctaaaa tttagtcaaa tacaagatta tgtttatttt tattatcctt   62520
ctctctaaag cttttaaaac tgcaagaacg agtgctcaat aatgttgtca tccatttgct   62580
tggagatgaa gaccccaggg tgcgacatgt tgccgcagca tcactaatta ggtatttacc   62640
aatattttat ctcttttcct ttttttggttg aagtactaaa agatacgaga atggaaagag   62700
agggaagaat tcaaaggatg tagagcagta ttcctgaatc tgagctcatt tcagccattc   62760
tattcttaaa ctataatgaa aaaaaaatcc aaaaaagtct aaaattataa ttaaaaaaac   62820
aacaaaatac taactgtcca ttgtaaaaag taatgcactt tcattgtaaa aatttttggac   62880 tatagagaat agtactaaga agaaaaaaaa aatcaccttc aattctgctg ccacctggag   62940
gtaatcactg ttaatatttt gctatatact ctatgagttt cttgttcaaa atcaggtcaa   63000
aattacatgc aattttgtaa tctgacaatt tccacttaat attttattag catttttcctg   63060 ttatgaaaca gtaattttag ttatgggtcg ttgttttgct atgcggttgg gataaaattt   63120
tatatacttt ttttggcaat tacttattat acataaatgt ttgtgtatag ttttcttttt   63180
ctgagaattc ctggaagttg agttaccagg cccggctttg aatttttttt tttattttttt   63240 ttttgagaca gagtcctgct ctattgtcca ggtgctatct cggctcactg caacctctgt   63300
ctccctggtt caagcgattc tcctgcctca gcctcccgag tagctgggat tacagggggca   63360 caccaccacg cccaattaat ttttgtattt ttagtagaga cagggtttca cgatattggc   63420
```

```
caggctggtc tcgaacttct gaccccgtga tccacctgca ttggcctccc aaagtgctgg   63480
gattacaggc gtgagccatg cgcctggcc aggctttaaa tttaaaacaa atcttctaat   63540
agctttatgg aggttataat ttacatttct tgaaatgtac tcactttgag tgtatagtaa   63600
actccaattt tatcacattt ctgtcacccc aaatgtatcc ttgtgcccat ttgctgtaac   63660
ctccggttcc tgccccaact cctaggcagc cactcatcta ttttctgtcc cttaagattt   63720
gtgttttcgc caggcgctca tgcctgtaat cccagcactt tgggaggccg aggttggtgg   63780
atcacttgag gtcaggagtt cgagaccagc ctggccaaca tggtgaaacc ttgtctctac   63840
taaaaataca aaaattagtc ggatgtggtg gcacacgcct gtaatcccag ctactcggga   63900
ggctgaggca ggagaatcac ttgaacctgg gaggcggagg ttgcagtgag cagagatcgc   63960
gccactgcct tccaacctgg gcaacagaga gagactgtct caaaacaaac aaagatttgt   64020
attttctgga cattttatag tactggggtc atagtataga tggacttttg catttggctt   64080
cttttactta attgtgagat tggttcttgt tgtagcatgt atcagtagtt tgttcatttt   64140
tattggcgaa agtattctat tatatgaata ataccatatt ttatctatcc atcagatgga   64200
tattatagag ttcatgtttt ggctaattta tgaattatgg tactgtgaac atttgcctgc   64260 aagatttgt gtagacatgt cttcatttct cttgagtaga tcacctagaa gtggattttt   64320
aaataatttt ggtacttact gtgaaactgc tcttcaaaaa cataccattg ttccttcctt   64380
ccttccttcc ttccttcctt ccttctttcc ttcctccctt cctccctccc ttccctactt   64440
ccctctccct ttccctttcc cttccccttt tccttccc ttcccgcctg cctgcctgcc   64500
tgccttcctt ccttccttcc ttcgtttctt tctacatata cacatttttt taaatttcaa   64560 tggttttgg ggtacaagtg gttttggtt acatggctga attttggtta catggtgaag   64620
tctgagattt tagtacacct gtcacccgag tagtgtacct tgtacccaat atgtagtttt   64680
ttgtccctca ccttccagcc ttccgccttg tgagtctcca atgtccatta taccacactg   64740
tatgcccttg cgtacccaca gctcagctcc cacttctgag aacatatagc agaaacatgc   64800
caaagtatac tcccactacc agaatgtgat tgtgcctgat tcttctcacc agtacaaata   64860
tttcaaaaaa agttaaatat gtatcagttt tttgggcaga agttgatact tctctttatt   64920
tatttatttt ttttgagata gggtctcatt ctatgatgcc caggctggag tgtggtggtg   64980
cgatctcggc tcactgcagt ctctgcctcc caggttcaag tgattccac gtcagcctcc   65040 caggaagctg gaattacagg cgagggccac cactgccagc taattttgt attttttggt   65100 agagatgggg tttcaccatg ttggccagac tggtctcaag ctcctgacct caagtgatcc   65160
acctgccttg gccttccaaa gtgctgggat tacaggcgtg agctaccaca cccggctgat   65220 atttctttt aaaataactt accttctttt gaaagtaata catgtttaat gaacagaatt   65280
taaggaaaat ataaaaaaac gaaataatct ttgtaatcaa actactgaaa agaaaaccaa   65340
agttacattt tggtgcatat tctttttcat tttcatcatt gtaatttgca tttctttgat   65400
tacttgtgag acactccttt catttactta ataggtttat atgacttgcc tattcagaga   65460
ttttgcagct ttaccatttt ctgcaaatga tagcaacttc ttttgtttg tttgtttgtg   65520 gagacagagt ctcgctctgt cactcaggca ggaatgcagt ggtggaatct ggctcattg   65580 caactattgc ctcctgggtt caagcgattt tcctgcctca gcctcccaag tagctgggat   65640
tacaggagtg tgccaccatg cccggctaat ttttgtatct ttagtagaga tggggttttg   65700
ccatgttggc cgggctgatc ttgaactcct ggcctcaagc ggtcccctg tctcggcctc   65760
```

```
ccaaagtgct gggattacag gcgtgagcac cgtacccagc cagtagttac ttcttatatt   65820
ctagaaaaaa ttctactcat gatcaagtct ccatgaggaa agagacttta attgaagatc   65880
atggggcttg cagaccaata tgataaaata gttcattgtt tctaaaagta ttactgagtg   65940
ttgatggcag atatgaaccc ttttgttttt gtaggaaaat gttacccgta ttctccattt   66000
gaattcagtt tagatttgtt aggaatcgca gcttaagctt tgccatctgg gagtgtttgg   66060
gacagttttg cagacaaaat tgcaaaagtg cctaaggaat gcagctggca ttcagacctg   66120
ctctgtgctc agtactctgt ggacagacac tgttcagcac ttgttgatca aaggtttag    66180
aaagagaact ttcaaagttg ttttttaatt aaagcattta atagtgtaaa tagaaaggga   66240
ttaaatttta tgacagacaa agaaagtac agcacccagc tgggcgtggg ggctcacgcc    66300
tgtaatccag cactatgggg ggctgaggtg ggtggatcac gaggtcagga gttcaagagt   66360
tcaagaacag cctggccaag gtgatgaaac cctgtctcta ctaaaactac aaaaattagc   66420
cgggcgcggt ggcaggcgcc tgtaatccca gctactcagg aggctgaggc aggagaatca   66480
cttgaacctg gacggcagag gttgcagtga gccaagattg caccattgta ctccggcctg   66540
ggccacagag tgacattctg tctcaaaaaa aaaaaaaaa gaaaaaaaga agtacagca    66600
cccagttatg tccgagtggg tgcatgagag tgaccctgag attggagaca cgctgtcac    66660
gtgcttgaag aacgccacct gagaaggggg gcgagaagtg gtgtccgctg gtaaccagag   66720
gtgttggctt agccatctgc agggaggagg gtggtctatc acaggtgagt ttcatctact   66780
ttcttaagca aattaaccct acttttgtgt taggcttgtc ccaaagctgt tttataaatg   66840
tgaccaagga caagctgatc cagtagtggc cgtggcaaga gatcaaagca gtgtttacct   66900
gaaacttctc atgcatgaga cgcagcctcc atctcatttc tccgtcagca caataaccag   66960
gtatgctgac ccagtggcat cttcacattg tcgggaaaat gcccttttcct gatgcctttc   67020
tttaggcttt aattgaaaac atttatttt ctagaaaaaa gcttcagctc aggatgtttg    67080
agtgtaggtc agtcctttga taggatatta tcattttgag gattgaccac accacctctg   67140
tatttaagct ctgccacaat cactcagctg tgacactgta aatctcttaa tagtttatta   67200
cattccatgt gctgacagtt gtattttgt ttgtgacact tacgtattat ctgttaaaac    67260
attttcactt tagttgtgtt acctttaaag aggattgtat tctatcatgc ctgttgattt   67320
tttggtgagc gggctattaa agtcagtgtt atttagggtt atccactagt tcagtgattt   67380
gcgagattat cattcacatt tattgtggag cttttgaata tcgtgtcaaa tggccacata   67440
tatcccattc ttatctgctt cttaggtgag tgggacacag tgctttaatg aagctataat   67500
cttcagaatt ctagcttgca gagaagattg cagaagtgat aagacttgtg ctttttaatt   67560
ttgtctttta aatgttattt taaaaattgg ctttatatga tactcttttt ttctgctgag   67620
taacagtgtt ttacaaaact tggactaaat gacttctaag cttaaatgat cacttgatgc   67680
tttttttctg aattaggaac tcagcttatc aaatatcaaa gtcataattc ctgaataaat   67740
aacgtctttt ttcatgtaaa gactgcttta aaaacacat ggaaggctgg gtgcggtggc    67800
tcacgcctgt aatcctaaca ctttgggagg cccaggtggg caggtcgctt gagctcaggg   67860
gttcaagacc acccagggca acatggcaaa acccacctct actcaaatac aaaaaattag   67920
ccaggcgtgg tggcgggccc ctgtaatccc agctactcgg gaggctgagg gatgagaatc   67980
acttgagccc cggaggcaga ggttgcagtg agccaagatt gtgccattgc actcccagct   68040
tgggctacag agtgagactc tgtctcaaaa aaagacacac acacaaacaa aaaaacatg    68100
gagacatttt tttggccacc ttaatatttc ccctcagata atttcctttg tttaaactca   68160
```

```
gaactggcat tttctctctt ggagaagatt caggacaaat actcctttaa gataagtaga    68220
agcagtgaaa gaggatttga ttatcaggaa tttgataagc ttagaataaa ttgttgcttc    68280
ttaatgtcat ttcagaagat gaatatttat taatagatgc caactgagat atcattaaaa    68340
ttgattacta actactactt ggaaaagtct cccagttcca aacttcagca ggcctcttga    68400
caattcagct gtggtcaatt gggtcttgcg tgatagatac aatgaccaat tgtgcagcag    68460
agtgtgctgc ttagctgcct attctgttag cattcatgtg ttaacttaaa atcataatct    68520
ccttagtttt gttgagtgtc tccgtggaca agacactgtg agggatacaa aatcagattg    68580
gctttattca aaccactggg gtattataat tcatttataa tttattttat ttttgccttt    68640 tttccatgt gttctaaagg aattagagtt tgtatataac tataatgggg gatagaaatt     68700
gacatgtgcc atgaagggaa tgcaaaaaag tgccgtggga gatgagaagt ggagaaagga    68760 atttctttt tcttggaagc aggaataact tcatgaagca tgtatttcaa cttaaacaga     68820
tagtaggcaa cgctgtaagg ggagtatggc tgcagcaaaa gtgttcgggg cagactggga    68880
ggaagggagg gaataaaattc agccattgtt atggaataat gatcaaaatt tattttcagc   68940
ccgtttcact taaaagttga gactgcttaa ctttttttaa tctttaatct taaacttttta   69000 aatgccattt gatctttaaa aatatatgtt ttaatagtgt attttaagtc tctatatttt    69060
tgttattaga atatatagag gctataacct actaccaagc ataacagacg tcactatgga    69120
aaataacctt tcaagagtta ttgcagcagt ttctcatgaa ctaatcacat caaccaccag    69180
agcactcaca gtaagtctct ttcttgatcg gtcttactga cattgtaata gttttggta    69240 gcttgtatgg ccagttagtt gtatggtcat cttacggtga ggtgcttgtc ttacagctct   69300
tacttatcca tgaggcttgc taagaaattg tgcttctgtg aaaagaatct cagcttactc    69360
caggaatgta aatgactatg ttttttctga ttattaaagt aatacacgcc caaaataaaa    69420
aaattcagcc aatttaggaa gacacaacaa ttaaaataag ccaggcatgg tggctcatgc    69480
ctgtaatccc agcactttgg gaggccaagg ttggggggctc acttgaggtc aggagtcgga   69540
taccagcctg gccaacgtgg tgaaacccca tctctactaa aaatacaaaa attagctggg    69600
cgtggtggcg ggcgcctgta atcccagcta ctcaggaggc tgaggcagga gaatcgcttg    69660
aacctgggag gtagaggttg cagtgagctg aggtcaagcc actgcactcc agcctgtgca    69720
atagagcgag actctgtctc aaaaaaaaaa aaaaaaaag aaaagaaaaa agtaaactac    69780
tgtcacctgc attggtaatg tatcagaagt ttaaaatgtc tagattataa ttaactcagt    69840
gacctggtaa tatatactaa gggaaaaata tttataattt acattttac atttttattt     69900 ttttaatttt attattttt tttgagaca gagttttgct cttgttgccc aggctggagt     69960
gcaatggcat gatctcagct caccacaacc tccacctccc gggttcaagc aattctcctg    70020
cctcagcctc ctgagtagct gggattacag gcatgcacca ccatgcccgg ctaattttgt    70080 attttagta gagacagggt ttctccatgt tggtcaggct ggtctcaaac tcccaacctc      70140
aggtgatccg ccctcctcga ccccccaaag tgctgggatt acaggtgtga gccaccatgc    70200
ctggccttac attttatatt aagaattta tgttgctgac attagaaaag aaccataata      70260
tccaagaatc caagaataat taaattatgt acatatgcta gtatatagtg tgatgctttg     70320
gagaattttt aacaatatgg agatgtataa tctggattgt aatattgagt gaaaaaggc     70380 agaatacaaa cctggtgggg gtatagtcgg atttcagtta agaaaaataa tatttacata    70440
tatacatttc tcacactggc agataatcac caagataaat tttgggattg tggatgattt    70500
```

```
ttttcttctt tatattttc  agatattctc  aaattttcta  aaatgagcaa  gtataacttt  70560
tgttatcaga  aaaaaataat  atacaaaagt  aatgttaatt  tgctggtgac  caggttaaac  70620
cttttattt   ttatttttg   agatggaatc  tcactctgtt  gcccaggcta  gagcacagtg  70680
gcatgatctt  ggctcactgc  agcctccgct  tcctgggttc  aaatgattct  ctggccccag  70740
cctcctgagt  ggctggaatt  acaggcgtgt  ggcaccacac  ctggctaatt  tttgtatttt  70800
tagtagaggt  agggtttcac  caggttggtc  aggctggtct  cgaactcctg  acctcgtgat  70860
ccacccacct  cggcctccca  aagtgctggg  attacaggcg  tgagctactg  cgcccagcca  70920
gacctttta   ttttatttga  caaaagaaat  acttccatgt  tatagaagac  taaatattgt  70980
ttgggctgtc  tgcagtatgg  tcttcccttg  atttgttcaa  aatatcgtaa  actttgctta  71040
tttatttta   ttgtggccga  ctgtgtcggg  cactgttgta  ggcttgggat  ggaaaaacag  71100
gattcctgcc  cttagggttt  ctgcaggctg  gtcagggaga  cgatgtggta  agctggagct  71160
cagctcctaa  ggatgtgcag  gggcagttga  gaggcggaag  ggtgggagat  cattccaggg  71220
tgtgggcagc  acaggaacct  ctcttcattg  ggatataatt  gccattctga  taacacgtgt  71280
ttgaggtgtc  taaagtagga  agttgtacca  tggtgggaca  gatatcctgt  ggttatcata  71340
cacagatctc  agttttcttc  tcattgtttg  tacttttat   aaagggtaac  aggagatata  71400
attcaataaa  cctttgtggt  gtttgggtgt  gattttattg  tttctttctt  ctcagtttgg  71460
atgctgtgaa  gctttgtgtc  ttcttccac  tgccttccca  gtttgcattt  ggagtttagg  71520
ttggcactgt  gggtatgtat  tttcctcagt  atatattaat  agttgtctac  aacagtatga  71580
cataaacata  gttattagga  tgcccttttt  ctttcttttt  aagtctttta  tcaatttggc  71640
tttttggaaa  aatatctgat  ggaatacttg  tttctgctat  attagctgtg  tgagactagt  71700
gacaggagct  gtgggaaatg  aatgccaaat  gttcttaggc  attgatggga  atttcagggt  71760
gtggtcttca  agttcattta  agggaatttt  catatgctgg  caaaaggctt  ttctcattag  71820
cttgactctt  tccaaaatta  tttgctgtga  attagaagtt  taggaaccct  ttttcactta  71880
attgtgacct  agcatacgaa  atggtgatga  tttaggaact  actgttcttg  tattaacagc  71940
ttttattaa   aaatgatttt  cctccagtag  atggccctac  tagcatctgg  gaaataattt  72000
caagtcttct  ccagcattca  ggaataggct  ttcattttgt  gtatcaatta  ctgagaatga  72060
ttttggtgac  tcacatcaca  tttgagaagt  aaacctgcag  atttcttgtg  tgtgtcagca  72120
aatgaccaac  tgatatttgc  ttgaagtgga  ttacattatc  tgctctagaa  tgattgcttt  72180
cccaccttcc  tcacatacag  actgagcagc  tacggtttct  aatcataggt  ctggcactag  72240
acttcacttc  tgggcaactt  tggcattgga  gtaaaatgta  ttaatttaaa  gaaagttaaa  72300
aatccgttca  agtaaacata  cagttctaat  acttttaca   atttaaaata  tagatttaaa  72360
tgataaaata  aaaagaaaa   tatgggtaga  caccataatc  ctcgtttctg  catctgttca  72420
caagggttg   atatttatga  gttctattct  ccatatccat  tctatgttct  cttaatgctc  72480
agtcagcacc  tcaggtggtt  ggagttcaat  gcttggtagt  ttgacttaca  ctgtcttttc  72540
tagggattg   agccctgggt  agtcctgctt  atttgaggtt  gcaatttgtc  tttcaataac  72600
ttttactaca  agatatggcg  tgttaaagga  taccattggg  gaaccaacat  aataatatca  72660
ggaaaactaa  ccacgtcaga  cctgccccat  tgtgtatcaa  gtacactatt  tttccatagt  72720
aataaagagt  tcaccccagc  caattctctt  ttatttgtg   cctgtttact  caatggcatt  72780
aacatgccca  aatgtctggg  tagctgtctc  atctccagtt  cagcagaacc  attgtcatat  72840
gccctagtaa  aagcattcct  tcattggaca  cttaggcccc  aatactttca  ttcagatcta  72900
```

```
ctacctgatt tcatttctca aatgattttt atggagctct gatttatagg aaagatgtta   72960
gttgattaaa aataaaacaa tttctgagct ggtataaaat gtattgtgac atgccttcct   73020
cttggaattg caagagaaag gaagactgtt gtttgcttaa aaattgtcta taatttgact   73080
ttgcaaatgt ctgcttccag agtgcctcca ctgagtgcct cagatgagtc taggaagagc   73140
tgtaccgttg ggatggccac aatgattctg accctgctct cgtcagcttg gttcccattg   73200
gatctctcag cccatcaaga tgctttgatt ttggccggaa acttgcttgc aggtactggt   73260
actgagttga aacagggact ccaggacttg gattttgatt tccttagggg aatgggggt    73320 ggtgagcata tgaggggaaa atactataag gtcattgcca gtgatggctt gtcccttag    73380 tcaaatttca gatgttacct atatgcataa acacatgcag ttggcagctg ttctgtgctg   73440
agtattttaa agtagcctct tcccaatata gcccctcagt taactacaag taaactcatt   73500
ttgaatttca ttttaatggg caccatatgc cagtactccc tcgggcactg ggatgttaag   73560
aaagtataat gtatggactt cattctcaag ttagttttag attagagggg gatacacgta   73620
aacaaaagtg cagtggtcac acagagtggc cctaatcact ctccttgggc agatttatgg   73680
gctggtagga aagagcacaa cacggagagg gtgtagcacc ttggcgatga taatggagga   73740
tgtggccagc aaggaagacg gagtccattg aaattgattt tgggagaagt tgccaatctc   73800
catgaaagaa ttggggcctg tgctatttgc ttcaggggc tataggagag tttcgtgaaa    73860
gggactaaaa gatgagtatt ttaataagat cattcatcca acttgaacat gggctggagg   73920
agaaggtagg gagactcagg agattaatgt tgatgctaag gcaagataat ggctttggga   73980
ctgtagggaa gacactgatt gtaagagaat gaaggaggca gaattgccag gcctggttca   74040
ccaactgaac ttcggttgtg aagacaaaga aacctgggat gacttacat cctgggcagg    74100 tgtgtggtgg tgacagtcat ggaaattggg aacacagatt tgtgcgggaa acatcagttt   74160
cagtttgagt ttggcttatc agttgaatat caggcacaga tgtctggcca actctcaaca   74220
tagggtctta aatgacttca gttccccaag caatttgtcc ttcccatgct attggggtgg   74280
agaggtaatg tctgtgccca tatcacagcc agtgctccca aatctctgag aagttcatgg   74340
gcctctgaag aagaagccaa cccagcagcc accaagcaag aggaggtctg gccagccctg   74400
ggggaccggg ccctggtgcc catggtggag cagctcttct ctcacctgct gaaggtgatt   74460
aacatttgtg cccacgtcct ggatgacgtg gctcctggac ccgcaataaa ggtaatgtcc   74520
cacttgggtg ctggattcat acagccttaa tgactatggg tttccagact acctttgttt   74580
agtaatctgt cccttcttta ttctcttttt gctttaaatg aacaaaattg ctcagattgt   74640
gacactaaat ttaacatcaa aatgtgacca tgtggatggg tgcagtggct cgtgcctgtt   74700
attccagcac tttgggagac tgaggcaagt ggatcacttg aggccaagag ttcgagacca   74760
gcctgggcaa catcacgaaa ccccctctct actaaaaata caaaaaatta gatgggttgg   74820
gccgggcgtg gtggctcaag cctgtaatcc cagcactttg ggaggccgag gtgggcggat   74880
cacgaggtca agagatcaag accatcctgg ctaacacagt gaaaccccgt ctctactaaa   74940
aatacaaaaa aattatctga gcatggtggc gggcgcctgt agtcccagct gctcgggagg   75000
ctgaggcagg agaatggcgt gaatccggga ggcggagctt gcagtgagcc gagatcgtgc   75060
cactgcactc cagcctgggt gacagagcga gactccgtct caaaaaaaaa attagatggg   75120
catggtggtg cgtgcctgta atcccagcta cttgggaggc tgaggcaaga gagttgcttg   75180
aacctgggag gcggagtttg cagtaagcct tgattgtgcc gctgcactcc agcctgggtg   75240
```

```
acagagtcag actctttcca aaagaagaaa aaaatgtgac catgtgtttt atagctcttt   75300
tagtatcatc agtcactgtt atccctaaga gggaaatacc tagctttagt tttaggtttc   75360
cagcattagc caagaaagct cagaattgat gttcctggcc aagtacctca ttgctgtctc   75420
cttaaatctt ggttaatggc tactgtcctg gctagcatag ttatggagca tttccatggt   75480
tgtagaatgt tctgccaatc tcagggacag ttttgctttt ctgtgaagca ataaaatcaa   75540
cttcaaaaca aatgttaact atttgtacaa tggatttaag atagaccagt tcacatactt   75600
tttttttttt tttttttga gatggagttt cattcttgtt gcctgggctg gagtgcaatg   75660
gtgtgatctc agctcactgc aacttctgcc tcctgggttc aaacgattct tctgcctcag   75720
cctctcgagg cagattacag ctgggattac aggcatgcac caccacccc agctaatttt    75780 tttgtagttt tagtagagac ggggtttcac catgttggtc aggttggtct caaactcctg   75840
acctgaagtg atctatccgc ttcggcctcc caaagtgttg ggattacggg catgagccac   75900
cacgcccagc ctaagataga ccagttcact tactgtttat atctgattac tctctctttg   75960
ccttgtcttc tacctttaaa aatctcccta ctaacttccc attctccttt agctgccatc   76020
agtcttctcc cttctctgca aacatctctg gagagtccca gcctcagccc acagagcttc   76080
ccactgctct gaggtggacc ttgtttgcaa ggcttctttg gctctcttgg cctggaccct   76140
gtctactact tcagccatcc ttccttaacc cctgctggtg gtttctgttg ccacactcca   76200
tagcagcgtt tcccgcccag atcatgtctt tacatctctg ggcactgctc tggtcctgcc   76260
tgcctttccc tctttgtatc ctgcaggctg ctaccccat cttgagtgtc ctcttcagtt    76320
ggctttcaga gggcctcctg ggtgttccct tacccacttg ccactcccca gtcactgggt   76380
tcagtccttc ctgcccacca gcacatgctt tctaggctct gtcctaggcc gtcttctctc   76440
tttgtagtct ctgggccagt gctgttctag agagtggcag aatttttctat aaccatggca  76500 gtgctccata gctatgccag gcaagacagt agccactaaa cacatatagc tgttgagccc   76560
ttgaaatgca gctagtgtga ctgaagaact gaaccccgat tcggtttaat tttcattaaa   76620
tttaaattta aataacctta tgtgggtagt ggctccagta ttgggcaggg cagcctgaga   76680
gtcggggctg ttctcctgtc ttcagtgtct agatgaggga cctcagagga cctgtctctg   76740
gagctgcagt tcaatgtagc cagctgcccc gtgacactta catatagctg atttgtggat   76800
atgtcagaca cggtgtgatg agctcagctt tctgtcctcc tccccacatc tgcccctgcc   76860
ccatttaccc cactttgtgt cttatcaagc tagaaacagg tcaccacaag tcttcatttc   76920
cactcaccaa gtcttttgtt tcccctacta aatattttgc gagaagaaag tgtgtaccttt 76980 tgtattcaca tacatgtaca tgcacatata catgcacata tgcagggggtc cccaacctct  77040 gttaaaaacc ggactgcagg ccgtgcgtgg tggctcacgc ctgtaattcc agaactttgg   77100
gaggccgaga ccagtgcatc acaaggtcag gagatcgaga ccattccggc tcacacggtg   77160
aaaccccgtc tctactaaaa atacaaaaaa aaattagccg ggtgtggtgg cgggcgccca   77220
tagtcccagc tacctgggag gctgatgcag gagaacggcg tgaacctggg aggcggagct   77280
tgcagtgagc cgagattgtg ccattgcact ccagcctggg cgacagagcg agactctgtc   77340
tcaaaaacaa aacaaaacaa aaaaaaaaaa aaccaggctg cacaggaaga agtgagcaag   77400
cattaccatc tgagctctat ctcctctcag gccagtggtg gcattagatt ctcataggag   77460
cgtgtatgag ttcgttctca cacttctgta aagacatacc tgagacatat aaagaaaaga   77520
ggtttaattg gctcacagtt ctgcaggctg tacaggcttc tgtttctggg aaggcctcag   77580
gaaacttgca gtcatggcag aaggtgaagg ggaagtaggc acatcttcac atggcccaca   77640
```

```
ggaaaaagag agaaggagag agagagagag acagagagag agagagaaaa agaaagattg    77700
agagggagag aggagggaga aaggagagtg cctgtagggg gagttgctac acaaaggagc    77760
accaggggga tggtgctcaa ccattagaaa ctaccccat gatccaatca cctcccacca    77820
ggccccacct ccgacactgg agattacaat tcagcatgag atttgggtgg ggacacagag    77880
ccaaaccata tcagagcatg aaccctattg tgaactgcac atttgaggga tctaggttgc    77940
atgctcctta tgagaatcta atgcctgatg atgatttgag gtggaacagt ttcatcccga    78000
aaccatcccc cgccaaccct ggtttgtgga aaaattgtct tccacagaac cggtccctgg    78060
tgccaaaaag tttggggacc tctgcacata tgcatgcacc tgtacatgga cacataatac    78120
atgtacatat gcatacttta tattctctgc cacttctggt ccagactgat atactatctc    78180
atttggatta ctgcactagc cttttgtttt ggaaacagca tttttaaaa aatttaattt    78240 aattttttg agatagggtg tcattctgtt gcccagcttg gagtgcagtg tcatgatcat    78300
agctcactgc ggcctcgatc tcccaggctc aagtgatcct tctgcctcag ccttctcagt    78360
agttgggact acaggcatac ccaccatgcc cagctaattt tttgatttt ttttttttt    78420 gagacagagt ctcagcctgt cgcccaggct ggagtgggtt ggcgcgatct cagctcactg    78480
caacttctgc ctcccaggtt caagtgattc tcctgcctca gcctcccgag tagttgggat    78540
tacaggcgcc tgccaccaca cccagctaac ttttgtatt tttagtagag acggggtttc    78600
accatgttgg ccaggctggt ctcgaacttg tgacctcgtg attagcccgc ctcggcctcc    78660
caaagtgctg ggattacagg cgtgagctac cgctcccagc caggaaacag cattcttgag    78720
ataattcata taattcaccc atttaaagta tataattcat tctctttagt atgcccacag    78780
agttgtacag ccatcaccag aatcagtttt agaacccata aaggaactct gtactcttta    78840
cccaaaacct ccatgcctcc agctgcaggc agccactaac ctgccttctg tctctgtgac    78900
tctacgtctt ctggacatta ctgtggatgg gctcatacag tcagtgagct tgtgactggt    78960
gccttctacc aagcagggtt ttcagtgtag cagcctctct gtttttcttt ttttttaaa    79020 ttgtgacgga acttctgcct cccggggttca agcgattctc ctgcctcagc ctcccgagtg    79080
gctgggacta caggcccatg tcaccatgcc tggctaattt ttttttttt tttttttagt    79140 agagatgggt ttcaacatgt tagccagggt ggtctcgatc tcctgacttc atgatccgcc    79200
tgcctcggcc tcccaaagtg ctgggattac aggcgtgagc caccatgccc ggctaacctt    79260
tcatttactg tctgcatttc ttccctgatg ccttccagtc catgcacccg attgtagcca    79320
ttcatcctat tatggtttaa ggtgactgtc ttagtcagca tgggttgcca taacaaaata    79380
ccatagcctg ggtggcttca acaacagaat ttacttctca cacttctgga ggttgggaag    79440
tccaagatcc aggactttcg ccttgccctc atgtggtgag ggggtgagga agctctgtgg    79500
ggcctcttat atatggatgc taatctcatt catgagggt ctgccctcat gacccagtca    79560
cctcccaaag gccccacctc ctaataccat caccctggta attaagtttc agtgtataaa    79620
tttgggggac tatagacatt gaaaccataa caagcacttt tctaagatca gggagtgagt    79680
aagtagcaga gctaggacct caattccaca tgtcagtcat cttgccttca ctctgctcca    79740
tgatggctgc ctcctagagc attgggagtc tcgatgttct atatgctctc atgtgttgtg    79800
tattggagat agttgaggct ttatgaatac atctggattt gttgacttct agctttgctg    79860
gtaaccagct gtgaccttga ataagttact tcatctctga gcctgtttcc tcttttagaa    79920
acaggagttt aaaatgctgc tttgggttgg gcacggtggc tcatgcctgt aattccagca    79980
```

-continued

| | |
|---|---|
| ctttgggagg ctgagatggg aggatcactg gagcttggag ttcgagacca gcctgggcat | 80040 |
| catagtgtga gatcctgtct cctcaagaaa ttaaaaaatt agctgggtga tgtggcgtgt | 80100 |
| gcctgtggtc ccatctactc tggaggctga ggtgggagga ttgcttgagc ccaggaggtt | 80160 |
| gaggctacaa tgaaatatga ttgcacccca tcctgggtga cgagtgagac cctgtctcaa | 80220 |
| aaaagaaaaa aaaatgctg ctttgtaccc ctttcatgtc atggcgtcat ggccaacata | 80280 |
| gaatgccctg gttgtttgct gttggagggc atgggcctgg gggctccctg agggctcctt | 80340 |
| ccatcttcaa ctcattctct gtgcacctgt taggaagttg tgggccagtc cctaccatgt | 80400 |
| atcattgtgt gggtaaaagt aaataaaatg tgtacagtgt ctgaactgta catatcaggg | 80460 |
| tccaagaaca aaatgagtga catgggttag ctcttttttaa taaatggtaa aaccaaatat | 80520 |
| tctaattttc agttttgtta tacttccatc acatgttttt gtttttttgt ttttttgtttt | 80580 |
| tgttttttcta ttttaggcag ccttgccttc tctaacaaac ccccttctc taagtcccat | 80640 |
| ccgacgaaag gggaaggaga aagaaccagg agaacaagca tctgtaccgt tgagtcccaa | 80700 |
| gaaaggcagt gaggccagtg caggtaggaa acagcgtggg gaagggaggg acatgagtgc | 80760 |
| agcatctgtc atgtagaaac ataggattta agtaacttgg tgttttagag aaataaaatat | 80820 |
| aatacacatc agtaaagtga gagaaagttt ctccaggtgc ggttcaagat attagaaact | 80880 |
| aatgactgat gtacacagac caccttttgg tctgaagcat ttctaagtgc cactggctga | 80940 |
| catgcagccc ctacagcctc caggcttcca gccctagcat ggagcatcac tctcctatgc | 81000 |
| ttccctggtt gcaggtgatg gctggagagg cctcctgatt ttcagtaagg gaagtggtgt | 81060 |
| agatgcttag gaatagatgt agtgagtgaa aaaactgatt ctgatatgtc aaaaattctg | 81120 |
| attggaaatg gaatatttac atttggaaga gctaaaggcg agagaaagtg gggataaagt | 81180 |
| catctgagtt ggaggagctt aaaccattca caagtttgga ggacctttt ttacccatga | 81240 |
| aaaggtcaga acagaagggg ctaggattta ggtgtgactg cagtttattg aattcccatc | 81300 |
| catactgctc tcggtgggca gtggcagggg caggagagga gcctggcaaa gcatgaagtg | 81360 |
| actgctgctg cctctgctat ctgggacgcc tggccacctg tctgtacagt ctccctccag | 81420 |
| acccattctc acgctgtctc ttggcaccca ggggccagtg atggttctcc catttgttt | 81480 |
| gtgtatatag catttatatc aaggctattt atttatttat ttatttatt tattt tatttt | 81540 |
| tttgagacag agtctcactc tgtcacccag gctggagtgc agtggtgcaa tctcggctca | 81600 |
| gtgcaagctc tgcctcctgg gttcaagcaa ttctcctgcc tcagcctcct gagtagctgg | 81660 |
| gactacaggt gtgcaccacc acacctggct aattttttgt attttttatt agtggagacg | 81720 |
| gggtttcacc ttgttggcca ggatggtctt gatctcctga cctcgtgatc cgtccacctc | 81780 |
| agcctctcaa agtgctggga ttacaggcat gagtcactgt acccggccta tttatttatt | 81840 |
| tttaattgac aaaattgtat atatctgtaa tatacaacat gatgtttgaa atatgtgtac | 81900 |
| attggccagg cgtggtggct cacaccttt atcccagcac tttgggaggc tgaggtgggc | 81960 |
| ggattacgag gtcgggggtt taaggccaaa ctggccagca tggtgaagag gtgccctac | 82020 |
| taaaaatacc ccaaaaaaaa aaaaaaaaa aaaagccgg gcatggtggc tcgcgccagt | 82080 |
| cgtcccagct acttgggagg ctgaggcagg agaattgctt gaatctggca ggtggaggtt | 82140 |
| gcagtgagct gagttcatgc cactgcactc tagcctgggc gatagagcga gactccgtct | 82200 |
| caaaaaaaaa aaaaaaagaa gaaatacata tgcattgtgg aatggctaat taacctgtgc | 82260 |
| atcacctcac gtatcattgt tttgtggtga gaacacttaa aatctactct ttcagtgatt | 82320 |
| ttcttgcata tggtacattg ctattaactg cagtcaccat gctatacagt agatctcttg | 82380 |

```
aactcattcc tcctgtctat aaatgaaatt ttgtatcctt gaccaacaca ttcaaggttt    82440
tttttgagat ggagtcttct tcacccaggc tggagtacca tggcacgatc tcatctcact    82500
gcaacctccg cctcccaggt tcaagcaatt ctcctgcctc agcctcctga gtagctggga    82560
ttacaggcac atgctactgc acctggctaa ttttttgtatt tttagtagaa gtggagtttc    82620
accatgttgg ccaggctggt ctcgaactcc tgacctcaag tgatccgcct gccttggcct    82680
gccaaagtgc tgggattaca ggtgtgagcc actgcacccg gcctcaagcg ttttaaaaga    82740
tgctcttttc taaggattga ctgtagtaca ggaggaagat tgacctgttg aaaagcctca    82800
gcctttacaa gtgtaaaatt atcagtatat tactatcatc tttctgatga attaaataaa    82860
ctaaggactc caagtcaaaa gtcttcaaac tgaagtagaa tagttgtata tagtgcttgg    82920
cactttaata tttagtatcg gtttaatgat aatgtttgtg cctttgccgt ctttaaaaca    82980
tttttacatc atccctgttt gattacttgg tgtgctcatg aagttgttgg ccactaagga    83040
atcttaggct cagagaggtt ctggaattgg ccagtggtcc ttgaatcagc tgctcctatg    83100
attctctaac tgatttctca caaagcaaac aagcaatcat aacaaaacaa ctgtgcacac    83160
tgctcttctt attttgttat ttaaaaagta cttaggctct acttatgttt gttagtcaat    83220
ttctcattac ttctagttaa tcaaaaggtc agaggaaata cttgaatatt ttcatactag    83280
aatactttaa aaaatcatga tttccagtaa tctctttaaa acttggcaag ttattttgat    83340
ctaaaagttt atcttttgtg tgcatatttt taaagcttct agacaatctg atacctcagg    83400
tcctgttaca acaagtaaat cctcatcact ggggagtttc tatcatcttc cttcatacct    83460
caaactgcat gatgtcctga aagctacaca cgctaactac aaggtatggg cctctgcatc    83520
ttttaaaaat atatatgcac acatacttac gtctaatgga tagttgatgt ttttcttatg    83580
atttgtagga tgtataagcc ctttgagata tgagttacat ttagttttttt caagtttgtt    83640 tgtcttttcag ctttgtttat gatagcttct atcatacagg tgttttggat tttcatattg    83700
tttgtactca cagctaagat tgattacagt gacagagcta ggatgtgcag ccaggttata    83760
gggggaagtg gccctggtgg agtctggagg gatccgtgta caggcttcct tccctcccgt    83820
gaggctcaca caaaaataca gcaacatgct ggtcctgcag gtaccctctg cctaacatga    83880
gccacaattc cagactcaca gaagaaaagc aggtgttcgg cataaaccat gtgtttcaaa    83940
tagtctgggc atggtgagcc acttgttatc agctagggaa agtttatgtc agcgtaagaa    84000
actgttcacc agatacccccc aagagccagc cttctgtgtct agggatgttt tagttttta    84060 gttcattttt tttttttaact ttaaaattttt ctgttcatct gcaatttgtt agatatgaag    84120
tatgtgtcta atttaattttt tgttttttggt tgtccccaat aatgtttaca gaagaatttt    84180
tctgcactaa ttggcttgag ttacttacat tctcatagtt ctctagtttc agtagtttca    84240
tttattattt tgttatatca atctatctgt ctgctcatct attagaagca tccttgtttt    84300 tttttttttct ttttagaca gagtcttgct ctgtccccag gttggagtgc agtggtgcaa    84360
ccatgcctcc ctgcagtctc agggctcaag tgatcctccc acctcagctc ctgagtacct    84420
gggactaccg gcatgtgcca ccacacccag ctaattttta cattttttgt agagacaggg    84480
tctccctaag ttgcctgggc tggtctcaag ctcctggctt aagtaatcct ccctccttgg    84540
cctcccaaag tgctgggatt acaggtgtga gcaactgcac ccggctacaa gtatacttct    84600
taattattgt agcttaatgg tatttatgag gggatcagtt ccctgttgt tctttagaat    84660 tttctggata ttcttcttta ttgattttgg gatgtgaaca atagaatcaa cttctacttg    84720
```

-continued

```
tagattgatt tagggagaac ttatacctca gatgttaagt caccctgtcc agaatgtggg    84780
atgctttcct atttgttcag aacttttta  attacctcag aagcacatga aatttaaagg    84840 atttaaaaa  aaacttaaag attatttcac atagctcttg cacatttctt gataaatgaa    84900
tcctcaggta ttcctctgtt tttgttacta atagttactt cttatgggtt ttttttcccc    84960
tgaaaatcat ttatcaaacg tatgtggctt attttctgaa ggatgtttga taattttgga    85020
agatatgaaa gtcttcatat tttacaaggt ttgaggtctc tttaagctgc atggttctca    85080
tgtcagctcc caaagcagaa gacggcatgt tgaaaaatgc cgtagagaag atacttcttt    85140
tccacctgtt ttcaactcat atcatcttga atttcagggc acctttccat gctcctagtg    85200
cttgctatct gtttattatt ttccttcctg aatacctga  actccagcat gttctgctgt    85260
aattctggcc tccctggcat cttggactcc tgtttccttt gctctgtcat ccccgcggtc    85320
agctcctgct gcgcagcttc tcagctgaag tgcgtttgga gtgcctggcg tgtcttgctg    85380
gatctttgag tattgcctct ggtttccttg gttccttctg ctgagttgct cagcgtctcc    85440
actccccatt tcttgtgtgg cccttcctgc actcctctga ttccttttgt cttccctggt    85500
ttcttgcttt ggtttcgagt ctccacagaa ctttttgcagc tcttctgaag acctggaagc    85560
tttttcatct taattctcat ctcatgacct cttttccctt ctttgagagc tagaacttcc    85620
catggtgaac ttctctttcc agaattccat gccttctttt ccctcccact tacctgttgt    85680
ccaggagagg tcagattgct gtgcatattg gaggagaacc cttcttccc  tgggctcttc    85740 atctcacatg acatcaccac atcacctcgt tccttggacc ctcagtggtg tcactgctgg    85800
atttttcttt cctttggctg gccttagggc acacccaggt tgactagcgt agtcatggta    85860
tttagatcca ctcacatttt cagtttctgt gtctgtctct tgcctgcttc tgacttcgcc    85920
cagagaaagc ttctctttca caagggttct tagatttatg ttcactgagc accttctttt    85980
ctgaggcagt gttttaccaa tatttatttt cctagtcagt ctcgccttac cttttcttgtt   86040 atgcatgtct ttggtcctga cccattctct gagtctgtaa aatagaattg ctgtataatt    86100
taattacatg aaatccttta gaatcttaac acatcttaca cctgatttaa tattttattg    86160
tatccaaatt gaaccaaccc tatgtgaatt tgacagtgat ttctcccagg gatcctagtg    86220
tataaggaat aggacttagt attttctatt ttttgatata ccacatacca gatactgatt    86280
atgatggaca tttaaccctt ttttctcatt atgaaagaaa gttaggaatt atttcttcca    86340
gtagcgccag tgtaacctga aagcctttga aagagtagtt tttgtatagc tatctgaaag    86400
gaatttcttt ccaaaatatt tttccagtgc tgacaacaaa cacgcagaca cacctgcaa    86460 ggtgagtgta cggcgccgca cagtggaggc atctgctgca gccgtcgatg tttgtgtctt    86520
tggttgtaca ttatgagatc gtgacagggc cagtaaccgt gtgttctctc cttcaccttc    86580
ccaaggtcac gctggatctt cagaacagca cggaaaagtt tggagggttt ctccgctcag    86640
ccttggatgt tctttctcag atactagagc tggccacact gcaggacatt gggaaggttt    86700
gtgtcttgtt ttttctcctt gggttgtggc tggcacactt gatgtgcgtc ttctgggctg    86760
agttcatcta ggatggagcc tggttctcca gggtgcctcc gggagactcc tccctgcccc    86820
acgtgcttgc gtcacaggac ccaagtctga ctctgcctta gccatgaagt ttaggggaa    86880 gtttctattt gtattctatt tttgtctgtt atcatgtatt agcttagacc cagtttagtt    86940
tggaaaatca gtgggtttca aaatgtgttt gtagagtcct ttatttctta acttgaccttt   87000 ttcaagtgga aaggggcaaa acagacgggt aaggggggcgg ggcggaggt  gtgacttgct   87060 cttttgtgcc tgaggaagta acagagctgg ggttgacagt catattctct gacacagata   87120
```

```
gtctctgact tatctcacag aaagtcagcg gcagagcctg agttaaaagt ctcgtagatt   87180 ttcttttttct tttttttggt ggctaatttc agttttattt atatttgttt atttatttat   87240
tatactttaa gttctgggtt acatgtgcag aatgtgcagt tttgttacat aggtatacac   87300
gtgccatgat ggtttgctgc acccatcaac ccatcaccta cattaggtat ttctcctaat   87360
gttatccctc ccccagtccc ctcactcccc atgggcccg gtgtgtgatg ttctcctccc    87420
tgtgcccatg tgttctcatt gttcaatttc cacttgtgag tgagaacatg cggtgtttgg   87480
ttttctgatc ttgtgatagt ttgctgagaa tgatggtttc cagcatcatc catgtgcctg   87540
caaaggacat gaactcatcc tttttatgg ctgtatagta ttccatggtg tatatgtgcc    87600 acatttctt aatccagtct atcattgatg acattcggg ttggttccaa gtctttgcta     87660
ttgtgactag tgccacaata aacatacatg tgcatgtgtc tttatcgtag aatgatttat   87720
aatcctttgg gtatatgccc agtaatggga ttgctgggtc aaatggtatt tctagttcta   87780
gacctttgag gaatcgccag actgtcttcc acaatagttg aactaattta cactcccacc   87840
aacagtgtaa aagtgttcct attttttccac aacctctcca gcatctgttg tttcgtgact  87900
ttttaacgat cgccatccta actggcgtga gatggtatct cattgtgatt ttgatctgca   87960
tttctctaat gaccagtggt gatgagcatt ttttcgtatg tctgttggct gcataaatgt   88020
cttcttttgc gaagtgtctg ttcatatcct ttgtccattt tttgatgggg ttgtttgctt   88080 tttttcgta aatttgttta agttctttgt agattctgga tgttaatctt ttgtcagatg    88140
ggtagattgc aaaaatttta tcccattctg taggttgcct gttcactctg atgatagttt   88200
cttttgctat gcagaagctc tttagtttaa ttagatcccg tttgtcaatt ttggcttttg   88260
ttgccattgc ttttggtgtt ttagacatga agtctttgcc tatgcctatg tcctgaatgt   88320
tatggcccag gttttcttct aggattttta tggtcctagg tcttatgttt aagtctttga   88380
tccatcttga gttgatttttt gtgtaaggta taaggaaggg gtccagtttc agttttctgc   88440
atgtggctag ccagttttcc caacaccatt tattaaatag ggaatctttt ccccattgct   88500
tatgtgtgtc aggtttgtca agatcagat gattgtagat gtgtggtggt atttctgagg   88560
cctctgttct gttccattgg tctatatatc tgttttggta ccagtaccat gcagttttgg   88620
ttactgtagt gttgtagtat agtttgaagt caggtagtgt gatgcctcca gctttgttct   88680
tctagcccag gattgtcttg gctatgcagg ctctttttttg gttccatatg aagttttaaaa  88740 tagttttttc caattctgtg aagaaagtca gtgatagctt gatgggggga tagcattgaa   88800
tctataaatt actttgggca gcaaggccat tttcacgata ttgattcgtc ctatccatga   88860
acatggaatg ttttttctatt tgtttgtgtc ctctcttatt tccttgagca gtggtttgta   88920
gttctccttg aagaggtcct tcacatccct tgtaagttgt cttcctaggt gtttcattcc   88980
cttagtagca tttgtgaatg ggagttcact catgatttgg ctctctgttt gtctgttatt   89040
ggtgtatagg aatgcttgtg attttttgcac attgattttg tatcctgaga ctttgctgaa   89100
gttgctaatc agcttaagga gattttgagc tgaaccaata gggttttcta aatatacaat   89160
catgtcatct gcaaacaggg acagtttttac ttcctctctt cctatttgaa taccctttat   89220
tgctttctct tgcctgattg cgctggccag aacttccaat actatgttga ataggagtgg   89280
tgagagaggg catccttgtc ttgtgccggt tttcgaaggg aatgcttcca gttttttgccc   89340 attcagtatg atattagctg tgggtttgtc ataaatagct cttactatgt tgagatacgt   89400
tccatcgata cctagtttat tgagagtttt tagcatgaaa ggctgttgaa ttttgtcaaa   89460
```

```
ggccttttct gcatctgttg agataatcat atggttttg ttgttggttc tgtttatgtg   89520
atggattacg tttattgatt tgcgtatgtt gaaccagcct tgcattccag ggatgaagct   89580
gacttgattg tggtggataa gcttttgat gtgctgctgg attcagtttg ccagtatttt   89640
attgaggatt ttcacatcga tgttcatcag ggatattggc ctaaaattct cttttttgt   89700
tgtgtctctg ccaggctttg gtatcaggat gatgctggcc tcataaaatg agttagggag   89760
gattctctct ttttctattg attggaatag tttcagaagg aatggtacca tctcctcttt   89820
gtacctctgg tagaattcgg ctgtgaatcc atcctggact tttttggtt agtaggctat   89880
taactattgc ctcaagttta gaacctgtta tcagtctatt cagagattca gcttttttct   89940
ggtttagtct tgggagggtg tatgtgtcca ggaatttatc catttcttct agattttcta   90000
gtttatttgg gtagagatgt ttatagtatt ctctgatggt agtttgtatt tctgtgggat   90060
cggtggtgat atccccttta tcgttttat tgagtctatt tgattcttct ctcttttctt   90120
ctttattagt cttgctagcg gtctacctat tttattgatc ttttcaaaaa accagcacct   90180
ggattcattg atttttttg gagggttttt tttcgtgtct ctatctcctt cagttctgct   90240
ctgatcttag ttatttttg tcttctgcta gcttttgaat tgtttgctc ttgcttttct   90300
agttctttta attgtgatgt tagggtgtta attttagatc ttttctgctt tctcttgtgg   90360
gcatttagtg ctataaattt ccctctacac actgctttaa atgtgtccca gagattctgg   90420
tatgttgtgt cttcgttctc attggtttcc aagaaaattt ttatttctgc cttcatttcg   90480
ttatttaccc agtagtcatt caagagcagg ttgttcagtt tccatgtagt tgtgtggttt   90540
tgagtgagat tctcaatcct gagttctaat ttgattgcac tgtggtctga cagacagttt   90600
gttgtgattt ctgttctttt acatttgctg aggagtgttt tacttccaac tatgtggtca   90660
gttttagaat aagtgcaatg tggtgctgag aagaatgtat gttctgttga tttggggtgc   90720
agagttctgt agatgtctat taggtccgct tggtccagtg ctgagttcaa gtcctggata   90780
tccttgttaa ttttctggct cattgatctg cctaatattg acagtgggt gttaaagtct   90840
cccactatta ccgggtggga gtctctttgt aggtctctaa gaacttgctt catgaatctg   90900
ggtgctcctg tattgggggc gtgtatattt aggatagtta gctcttcttg ttgaattgat   90960
cccttaccca ttatgtaatg gccttctttg tctcctttga actttgttga tttaaagtct   91020
gttttatcag agactaggat tgcaatccct gcttttttt tgctttccat ttgcttgtta   91080
gatcttcctc catcccttta ttttgagcca atgagtgtct ttgcatgtga gatgggtctc   91140
ctgaatacag cacaccaatg ggtcttgact ctttatccaa tttgccagtc tgtgtctttt   91200
aattggggca tttagcccat ttacatttaa ggttaatatt gctatgtgtg aatttgatcc   91260
tgtcattatg atcctagttg gttattttgc ccgttaactg atgcagtttc ttcatagcgt   91320
cagtagtctt tacaatttgg catgttttg cagtggctgg tactggttgt tccttttccat   91380
gtttagtgct tccttcagga gctcttgtaa ggcaggcctg gtggtgacaa aatctctgca   91440
tttgcttgtc tgtaaaggat tttatttctc gttcacttat gaagcttagt ttggctggat   91500
atgaaattct gggttgaaaa tactttttt aaagaatgtt gaatattggc tcccactctt   91560
ttctggcttg taggatttct gcagagagat ctgctgttag tctgatgggc ttcccttgt   91620
gggtaacccg acctttctct ctggctgccc tttccttcat ttcaatcttg gtggatctga   91680
tgattatgtg tcttgggtt gctcttctcg aggagtatct ttgtggtgtt ctctgtatt   91740
cctgaatttg aatgttggtc tgccttgcta ggttggggaa gttctcctgg ataatatcct   91800
gaagagtgtt ttctaacttg gttctattct ccccatcact ttcaggtaca ccaatcaaac   91860
```

```
gtagatttgg tcttttcaca tagtcccata tttcttggag gcttggttca tttcttttca   91920
ctcttttttc tctaatcttg tcttctcgct ttatttcatt aatttgatct tcaatcactg   91980
atatcctttc ttctgcttga ttgaatcggc tgtcgaagct tgtgtatact tcacaaaatt   92040
ctcgttctgt ggttttttagc tccatcaggt catttaagct cttctctaca ctggttattc   92100
tagccattag tctaacattt ttttcaaggt ttttagcttc cttgtgatgg gttagaacat   92160
gctcctttag ctcggagaag tttgttatta ccgaccttct gaagcctact tctgtcaatt   92220
catcaaactc attctccatc cagttttgtt cccttgctgg tgaggagttg tgatcctttg   92280
gaggagaaga ggtgttctgg tttttggaat tttcagcctt tctgctatgg tttctcccca   92340
tcattgtggt tttatctacc tttggtcttt gatgttggtg acctacggat ggggttttgg   92400
tgtgggtgtc cttttgttg atgttgatgc tattcctttc tgtttgttag ttttccttct   92460
aacagacagg cccctcagct gcaggtctgt tggagtttgc tggaggtcca ctccaggccc   92520
tgtttgcctg ggcatcacca gcagaggctg cagaacagca atattgctg cctgatcctt   92580
cctctggaaa catcgtccca gagcacgaag gtgtctgcct gtatgaggtg tttgttggcc   92640
cctactggga ggtgtctccc agtcaggcta catgggggtc agggaccac ttgaggcagt   92700
ctgttcatta tcggagcttg aatgccgtac cgggagaacc actgctctct tcagagctgt   92760
caggcacgta tgtttaaatc tggagaagct gtctgctgcc ttttgttcag atgtgccctt   92820
cccccagagg tggaatctag agaggcagta ggccttgctg agctgcagtg ggctctgccc   92880
agttcgagct tccctgctgc tttgtttaca ctgtgagcat agaaccacct actctagcct   92940
cagcagtggt ggacacccct cccccagcca agctcctgca tcccaggtcg atttcagagt   93000
gctgcgctag cagtgagcaa ggccccatgg gcgtgggacc cgctgagcca ggcacaggag   93060
agaatctcct ggtctgctgg ttgtgaagac tgtgggaaaa gtgcagtatt tgggcaggag   93120
tgtactgctc cttcaggtac agtcactcat ggcttccttt ggcttggaaa gggaagtccc   93180
ccgacccctt gtgcttccca ggtgaggcaa caccccgccc tgcttcggct tgccctccgt   93240
gggctgcacc cactgtccag caagtcccag tgagatgaac taggtacctc agttggaaat   93300
gcagaaatca cctgtcttct gtgtcgatct cactgggagc tgtagactgg agctgttcct   93360
attcggccat tttggaagca tccttgttt tttgaggtgg agtcttgctc tgtcgcccag   93420
gctgacgtgc atcggcacaa tctcggccca ctgcaacctt tgcctcctgg tttcaagcga   93480
ttctcctacc tcagcctccg gagtagctgg gattacaggc acctgccacc atgcctggct   93540
aattttttgt atttttagtg gagatggggt ttcaccacat tggccaggct agtctcgaac   93600
tcctgacctt gtgatccacc cacctcagcc tcctagagtg ctgggatcac aggtgtcagc   93660
caccacgccc agccatattt tcagatctcc ctctctttgc cctaaaccac tgtgcttaat   93720
aagtagtttt tagtggccag cagtctccat gtataacaca ttttagcaaa atggaaaata   93780
ctatatgttt taaatttgaa cgtgagatta tactgaaata aaaatcatct aactgggatt   93840
ctttaaatag taagattttc ttttttgtat gtgggttttt tttaaccttt attattatga   93900
ctgtcatata tagaaatggc tgttttcag ttacagtcag tgaatgtatc aaatgctgcc   93960
ttatccaaat aataaaagta aattattaat aagtcacaat ttaatgaaga ttgatgttag   94020
ttgatcttta tattcttgaa atcagccata tggttgtgtg tgtatgtata tattttaaa    94080
ggtacataaa gataataagc tcatctctga aaattttac atttggcata agaataactg   94140
gataattaag catcttattc tctggcctgt gtctttacag ttaaaggtag atttactcac   94200
```

```
ctctcctttt ttgttttct aagttcatct ttttgctgt ttcaagacag aggcccattt    94260
tagctttctc gcatatcctt ttgtttgtac tttggaagcc tcacctgctt aattgttgag    94320
ttttttatccg tggtctttta gagggggata tgtagggtag aagctttcac aggttcttgt   94380
ttgcacttgg cccctgactg ttttgaggaa tctccctcac tgactcacag catggcaagg    94440
tttcagatct ctttctgcca cacagcagtt ctgaggcagc tggaaagata tccagatgct    94500
tagattgtca ggccaggctt gagatataca aactattgag ccttatctgt gaccttgctt    94560
aggtgaaggc atcagagccc ctgcaccaac atgcataggc ctctgcatgt gtgcggggct    94620
gggtgttgag gtctgagcac aagtgtagct ggagaggtga gcttgatgtg gcgacgggta    94680
tgagcaggtt ttcttcagac ttctgtgagt ttacctagtt ccaggattta aaggcacaga    94740
gactttagaa ttaaaataga atcattttct ttttctaaat agcaacacta ggaataaaaa    94800
ataataattc cacattcttg acaggtaatg ttttttcttg tcttctaatc cttatttatt    94860
ccatactcat tttatacat aattgaaatg tattatgcat tggatttttc ttttgcatta     94920
tattatagac gattttcat gtaactcctt actgttccat tttatatgtt ttgtctggtt     94980
taagactta tctgcaaacc gggaaactgt ctctacaaaa agaaaaacaa aaatagttgg     95040
ccgcagtggc atgcgtctgt ggtcccagct actcggggct gaggtgggag gattgcttga    95100
gccttgggag gttgaggctg caaagagcca tgatcatgcc attgcactcc agcatgggtg    95160
acagacttta tactgtctgt tttgggtgat ttgataatga tatgccctga tgtagttttt    95220
ttatatcttg tgtttcttgt gcctgggttt attgaggttg ggtctgtggc ttcatagtat    95280
ttttaaagtt tggaaaattt taggccattc tttctttctt tctttctttt tttttttttt    95340
gagacagtgt ctcgctctgt cgcctgcgtt ggagtgcagt gacactatct tggctcactg    95400
caagctctgc ctcctgggtt cacgccattc tcctgcctca gcctcctgag tagctgggac    95460
tacaggcgcc tgccaccacg cctggctaat tttttgtatt tttagtagag acgaggtttc    95520
actgtgttag ccaggatggt ctcaatctcc tgacctcgtg atctgcccgc ctgggcctcc    95580
caaagtgctg ggattacagg cgtgagccac tgcacccagc taggccatta tttcttcaaa    95640
gattttttt ctgccctgcc tccctccttt tttccctctc ttaaagggc tgtgatttcc      95700
tgaatgattg cttagtgttg tcccatagct tactgatgct cttttcagtg tttgattgtt    95760
ttatgtgttt tctgttttgt atagtttcta ttattgtgtt ttcaagttct ctgatctttt    95820
cttctacagt gtctactctg ttgttaatct gttaatctgt tgttaatcct gtccagcgta    95880
ttttttttt tgttttgaa acagtctcac tctgttgccc aggctggagt ttagtggtgc      95940
gatatcagct cactgcaacc tccacctccc aggctcaagc aattcttctg cctcagcctc    96000
ccgagtagct gggactatag gcacgtgcca ccacacctgg ctaatttgtg tattttatt     96060
agagatgggg tttcaccatg ttggccaaac tggccttgaa ctcctgacct caggtgattc    96120
atccgcctcg gtctcccaaa gtgttgggat ataggcatg agccaccgtg tctgcccct     96180
gttcagtgta tatcactaat tttgttttta tctctagaag tttgatttag gtcttttaaa    96240
aatgtctccc tgtgtttctg tttagctttg tgaacacaat tgtaataact gttttaatat    96300
ccttctctgc tagttctaag atcttctaat aacttcccag ttcttggtgt ttctcattgg    96360
ttgattgata ctcctcgttt tgggttgtat tttcctgcct cttgtatgg ctgccaattt     96420
tttattggat gcccaacctt gtgaatttta ctttgttgga tgctatatat ttttgtgttc    96480
ccatagatct tcttgagctt tgttctgagg ttagttgagt tacatataga tggtttactc    96540
ttttgggtct tgctttataa tttgtcagat gggttggagc agtgcttagt ttaggactaa    96600
```

```
tttttttttt ggactaatta ttcctctttta ggaataatta ggtaccatgc ttaggaggca   96660
agaccatcct gagtactcta cctaatgaac cagaaagttt gggttttcca gtccgcctgc   96720
tgagaacagt gactttctag ccctgtgtga gcgctgagct ctgctccttc taatcctttc   96780
caatgcttct ttccctggcc tcagggagtt ttctcacaca catatctctg ctgagtactc   96840
gagagggacc ttccccagat ctccagagct ctctctgtct tgttttctct tctctggtgc   96900
tctgtcttat gaactgtggc tgtccttggtc tccttagatt ctcagcacct cttcaattca   96960
gagggttgcc tgtccctcct ccttgtgcca cagcctagga actctctcaa agcagcgagt   97020
tggggcagcc ataggggctga cttagtctct cgtctcccag ggatcactgt ccttcattgc   97080
tcatgtccag tgtcttgagg actctgggtt ttgtctgttt tgttttttgg tttgctttgg   97140
ttgtctcagg caggagggta aacccagtcc ctcaccctca ttgtgctcag tagtggaagt   97200
ctcactctat tacattagat attagtattt gtagcagagc cctggttccc tggtacttgg   97260
ggagctcttg aaaggccaga aacagcatgc tttctcacct tttccagggc ttcagttttct   97320 ggtgcacatc aagcattcca tacacatttg ttaaagtcct ttgttagaca agtagtgatt   97380
cacaggttct atttgtaatt ttttcagtta acatgtattg ggtatctgct gggagctagt   97440
aaaaacaaaa agtggtgtgt gacaaattca attctgacaa gaacaacctt aaacacttag   97500
aatatacttt gagcatatca gaattttaaa aatgtgtggc ccttgagtat ttgaaaccaa   97560
caagaatcta ttgcttatta gtagaggata ttttgttaaa caagtggaga gagaggcatt   97620
ttcagtctaa ttggtgttgg cttttagcag ctgatggaaa ccagttcgtg attagccagg   97680
cagtggtgaa acaggctgtg cattctgaat gcctaggtat ctaggcattc agaatggtgg   97740
cgctctttga gttagcatct tcttctttct tgattcttttt ttttttttt ttgagatgga   97800 cttttcgctct tgttgcccag gtaacaactc cagtgcaatg gcgccatctc ggctcactgt   97860
aacctctgcc tccctggttc aagcgattct cctgcctcag cctctcaagt agctgggatt   97920
acaggtgtgc gccaccacgc ctggctaatt ttgtattttt ggtagagatg gggtttcact   97980
atattggtca ggctggtctt gaactcctga cctcaagtga tgcacctgcc tcgatctccc   98040
aaaatgctgg gattacaggc gtgagccacc actcccagcc ccttcttgat tcttgaaaag   98100
gacattgggt gctgtacatc tcgttataga tgttgataaa aatgcttgtg agaagagtaa   98160
cattaaggta gttatttggt cattttttgca gattatttta agacaattct aggactgatt   98220
tgtggtaaat cacacattgc tgtatcatag ttgtgttcac tgaacatatt caggggctct   98280
acagatgcag ggctcttagc tgctttgcac acttctgaat tcctgccctg cgaacaggac   98340 tggatacccta atagacaaca ggtacttgat aacagtttat tgaattaatg agtgaatgaa   98400
cagatacata aatgcatgaa agaatggttg taatgtatat aacttggatt tcaagacttt   98460
ttactgactg ttcaaaataa gaaattgaaa actttcctct gattttcctc tactatttac   98520
acaatttaaa tggaagttat cttgtacctt caatttctgt ctaggattcg tacaataacg   98580
ggtcatctct gagtcgctta atgtctcact tgtctttcta cagtgtgttg aagagatcct   98640
aggatacctg aaatcctgct ttagtcgaga accaatgatg gcaactgttt gtgttcaaca   98700
agtaagagct tcattctttt cctcttctgt taagacgttc gggtatgaca gcaaaacgct   98760
gctactcctt aagaggcagg cgctgttggc ataatcagct gggaggattg tggggtccag   98820
cgcagcactt tttggctcag tccatgattg agccaagagg ccatccttcc cttcactccc   98880
caggaggacg aggtctgtca ctgtggaggg cagaggacac cagaagctcc tctgcaacct   98940
```

```
cgctagttaa cttccagtcc ctcggagttt ctgtttagaa tgctcaatct catttagaat   99000
tgcaaggaaa cccaaaacgc ctatttaagg tacaaacagc acttcataca atatctcatg   99060
aggtattaat agtgattcac aggaagaatt tcacgctgtg agtctttgct aacatatcca   99120
gttatttaca gatggatttg atatttgtgt gggagattct taaaagtgtt gttcacgcca   99180
cattgttgat gcctcatttt tttcactgta gttgttgaag actctctttg gcacaaactt   99240
ggcctcccag tttgatggct tatcttccaa ccccagcaag tcacaaggcc gagcacagcg   99300
ccttggctcc tccagtgtga ggccaggctt gtaccactac tgcttcatgg ccccgtacac   99360
ccacttcacc caggccctcg ctgacgccag cctgaggaac atggtgcagg cggagcagga   99420
gaacgacacc tcggggtaac agttgtggca agaatgctgt cgttggtgga agcacgaaag   99480
agcaagcagg aaatactttg taaaagaata aaaacgaaaa atgttagcga acatcttcta   99540
atagtctgct gtattcagag aactctagga gatatatatg gttgatgcaa agatgattta   99600
aggcatagcc cggccttcca agaagtgtgt ggccagtgag tgagatgggc ttgggactta   99660
cacatctcag aggtgggggt agaggaggag gaacactgag tgggctgaga agcagccagc   99720
tctcattgcc aaagtgtgtc agcaaaccag aatgcagttc ataatgtccc cacccattca   99780
aagcacagga cctgtagagt ggtgtggcat gtgttggtgg cacttttcag gcctgtaaca   99840
aggatgaaag aacagcttca tagcagcaca gtagtgctgg tgttcagagg tgtgtgaagg   99900
ccatagaagc atcttggata tattaccttg tgttttgtca gctttatgac tagaagtctc   99960
ttttcactta aatttgtttt tttttttttt gagacggagt cttgctctgt cgcccaggct  100020
ggagtgcagt ggtgcaatct cagctcactg caagctctgc atcctgggtt catgccattc  100080
tcctgcctca gcctcccgag tagctgggac tacaggcgcc tgccatcacg cctggctaac  100140
ttttttttgt attttttagta gagacggggt ttcaccatgt tagccaggat ggtctcgatc  100200
tcctgacctc gtgatctgcc cgtcccggcc tcccaaagtg ctgggattac aggcgtgagc  100260
caccgcgccc ggcctctttt cacttaaatt tatgtttgtg ttttttaatgc ctagtataca  100320 ggacttctta aattgcctta agtatgaaca ggtatttgag ttgctaatct gtatagtagc  100380
aataatagaa tcccttgttt ttccttttat aaatttagcg attaaatagc tacaattaaa  100440
acactagagt caggagtcaa ggaaaatacc catgttccag gctgtatgtt agtgatgtac  100500
ttactatata ttggagtttc aggagtaagt ctgtttcaat gctttctgta accatttggg  100560
gtattaataa gcatgtgagt gtgtgcatgt ttgggttaat ttcatatatg tttcttagaa  100620
gggatatcat tgatgtaaat attttaaagg cttgtcctcc aaaaaaatca tgtaatttct  100680
tctaaattac tgatctttta aatgaccttc acctttctct caaatctcac ttaagactgg  100740
gctgagtagt cagtttcctg tagcagaaaa aagctcagac ttgagtagcc ttctgcgagt  100800
gaggagactt gatggctgtc aggcagctgt aaactctaaa tagagtgtca ttatctgaag  100860
agggcgatgc tgccacactg agtggccttt caagttgttt ctcaatctga cacgttctga  100920
tcgtgtgaat gtgaaattgg tttgagcagg agtatatctg agtgcagagg agattattta  100980
aagatattct cattctctgc ttcccttttta ttcccatttg gcagatggtt tgatgtcctc  101040
cagaaagtgt ctacccagtt gaagacaaac ctcacgagtg tcacaaagaa ccgtgcagat  101100
aaggtaaatg gtgccgtttg tggcatgtga actcaggcgt gtcagtgcta gagaggaaac  101160
tggagctgag actttccagg tattttgctt gaagcttta gttgaaggct tacttatgga  101220
ttctttcttt ctttttttct tttttataga atgctattca taatcacatt cgttgtttg   101280 aacctcttgt tataaaagct ttaaaacagt acacgactac aacatgtgtg cagttacaga  101340
```

```
agcaggtttt agatttgctg gcgcagctgg ttcagttacg ggttaattac tgtcttctgg   101400
attcagatca ggtttgtcac tttatctttt catccatcat acctgttcct aatttagtac   101460
aaattaccct aaaagacact gaaatctact ttaaagaaat gtggtctgca tgtttccctc   101520
atcagttgct gctgcttatc tttttcatgc acctagctgg tgcagaaggc ctggggcata   101580
gccagcctca gcaagtcagc atccttgccc cagctccctg gactcaaggc taacctgggg   101640
ttggctgtta gggatttcca aaggtttgtc ccatccactt gcctcccctc caaaataagt   101700
ttgaatttaa attgtgagat acaattaaga tttattgttt ggggaacatt tttgcaaaat   101760
ctagagttag tttaaacaga ttatcaatta ttaccataat tgatcatctg cagtttcaag   101820
ctatctaaca ggttcactta cctctttaaa aaggaatgga atttagcagg acagtaactg   101880
agacccgtgc tcctggagtc catgtgggag ctgtgtggct ctgcacaagc atttgcacgc   101940
ttcccctctt gactgcatta ccttcctcct atagttgctg tgggcaccag attctggcta   102000
gtcctgtccc ttcatgatgc acattttcct caagattcgt cccagttaaa tcactgcaga   102060
tgaaactgcc ttttcatcgt caaaatttaa ctgtcatttt tgagccgtga tcttgggcta   102120
ctttcttatg tggggtagga atatttgtga gttagaaata ttacttct ctatttcctt   102180 ctagacgtaa atctgttaat cctgtcagca ctgttactca cctgaaaggg tctgtttccc   102240
taggagaact gagggcactc ggtcaacact gattttccac agtgggtatt ggggtggtat   102300
ctgcttgttt tttttgttgt tgttgtttgt ttttttttgt ttttttttg agatgggagtc   102360 tcgctctgtc acccaggctg gagtgcaggg gtgcgatctc ggctcactgc cagctccgcc   102420
tcagaggttc acgccattct cctgcctcag cctcccgagt agctgggact acaggcaccc   102480
accactacgc caggctaatt ttttgtattt ttagtagaga cgaggtttca ctgtgttagc   102540
caggatggtc tccatctcct gacctcgtga tctgcccgcc tcggcctccc aaagtgctgg   102600
gatgacaggc gtgagccacc gcgcccggcc tggggtctgc ttttaatgaa ggaggcatca   102660
aggggtgggc tttgcgttgg cctgatgctt tcatctttct ttcacaaaac ctgtccgaag   102720
aaaatccgtc taaatgggcc attgctctcc tcaggaaata gtcattggga acttcttttc   102780 cttctcctttg acactaggag gctgactggg gagaagccct ggtctatggc tgtgggcagc   102840
aggggctgag aggagcaggc tctcagggggg gcacgggtac cccaagggaa gccagagccc   102900
tgatttgttc cattctagta agaacaaaga ctgctctggt ttcatgtttg ttctgattgc   102960
ctttcatcaa ccggtcccct ttctcccagt tcttaagatt cagtacagtg acagttttat   103020
gaacaagaat agaacactag aacagacaaa ccattgaact ctatgctgat aaagatttat   103080
tgagctcctg ctgtatgttt gcattctgcc cagaggctct gagaaaacca ggccatatgc   103140
tccatgcttt atccatggaa gctccccgtc aggttgggaa agctgacagc tgcagggaat   103200
acagtgtgac acaaaactgg ctcccatgca gcccttacgt gtcgcctctc agatggttgg   103260
gggacgaagg tcgactcctt tgggtatctt attactaaac cagtttcagg gaatctgtgc   103320
caccctatct gccattaacg tgaacagatg agtccccaag gtgtaatttt gggtattgtc   103380
tgatgtctct tggaatttat tatttgtttt tccaatgaga tttcacctca gggtatagta   103440
aagttgttga ggggattcct ggatgtgttc tgcaattatc taggctgatt tcagaataga   103500
gttatgctta tagtcaaatt tatcagctgt caagaatttt atttaaaatt tatgcagata   103560
agcaggagga aaagaagcct ggttttaca ttttaatcct attattgatg tgaaattta   103620 ttttccttcc tgtaggtgtt tattggcttt gtattgaaac agtttgaata cattgaagtg   103680
```

```
ggccagttca ggtaatagca ttttattatt ttagattttt ttcttcttct tgtgtactta 103740
catgtaattt aggttattaa gtgaatgttt aaactactgt taggcatttt tgctgttttc 103800
tttaaatgga aatctgacta acatactgtg catttttgct tctcttaaaa attaatgtat 103860
atctcaagac ttgtttggaa gtagttatgt atctgaaaat tccatatgtt gtcagtattc 103920
attgcacatt tcaaagcatt taattgtgtt gacagatggt ggaatgaaat cttgtggtgg 103980
agcactagtt tttaaatctt cttagagaaa gcagttttat ataatgttgt ctttagtaat 104040
tattatgcat ttgtattctc tgcagctttt tcttgctaga tgttgaggtt ttaatacttc 104100
ttgctagtcc attacaggtt tataattatt aaaagttaaa attcttttag tacctaaaat 104160
gcttaataaa cattgtaatt aggaaaattt agtgcagaag gaaagtgttc ccagattccc 104220
tggggtctgg aaacatagtg tttattctaa ttacatgaca cctccactgt gttttgggge 104280 aagttactgt ttctcttttg agtttcaatt tcttcaagag caaagaggca gaggagagct 104340
aggaagatcg tagctgctgt gccctgtgc cgtcgggtgc cttctacctg ctgcctccga 104400 accttacac atgtccctgc tctgcgcgag ggcacagatg ggatgcactg tggcaggggt 104460
ggggttagag tagatcacgg acacctgtta gcttgatgtg tgcttgctgt caaggttgaa 104520
tcatgaatta ttttatgttg cttatattga tatgtatctt aattttaaaa gaaaggtcta 104580
aatggatgtt tttgttttta gggaatcaga ggcaatcatt ccaaacatct ttttcttctt 104640
ggtattacta tcttatgaac gctatcattc aaaacagatc attggaattc ctaaaatcat 104700
tcagctctgt gatggcatca tggccagtgg aaggaaggct gtgacacatg gtaacgggac 104760
acacctttca ctgtcgtctt cggtgtcgtg atgtgcttgg cagtgttcgt tttcatatac 104820
ccactttgaa cgttgtcagt ggcagccatg tgcttctcag gctctgcatg tgtgtctgtg 104880
tatgtgaagg tactggttag agacgtttca aaagagaaga gagcatattc tttactctca 104940
gcaatttgta atcttctcag ggaaaaaaat tcaagaaaca gtaagataac ctaaggtaca 105000
gatagattct gaatataaag ttcctgttca ttcacatgaa acgctaaaag ttcttcactt 105060
gatcttagcc aaaaggccaa gaagcgatgc aacactaaaa attcttaaat cgaacttgcc 105120
gtgaattaaa ttttgatctc tcatccagtg gtattggaga tatagtttga cttgggttca 105180
gggctttctg ttttgcctga tgattttgct ggagcttaaa taaggaaccc aggagatggc 105240
cagctgtgca agccccagc ctgtggaagg agctagtgtg gttttatgaa tgagttcaa 105300 atctttcttt gagcttttg aactgatctt ccagcattgc cctattgacc cctccctgac 105360
tcctttgctg gaatctgtag gcttttgaac tttgacaggg acacatccta agacccttgc 105420
aaactcccag atgtgagaat ggcactacta cttagagtct tttcgactca gcgtgtgtgc 105480
agaagagcat caaccgggct gtgttgcgag gcagggcctt ggctgacctc tcagtgttta 105540
catagctaag ccagttagtg tttgccacgg cctcacaagg gcttcagatt cacacagcca 105600
aagtatagat tattaaaggc ataggtgttt ggtttcctgg acttggaggg tctttggaca 105660
gaaaatcagt aggcaaccac acccagtact ttgtgctggg aagcttggtc atctgtgaga 105720
gggtcagaga gtatacccat gcgtgcatgc caccgaaggg tcagtgagta ttcctgtgtg 105780
tgcatgtctc agggccggag agagtatgtg tcactgagag gtcagagtgt ttgtgtgtgt 105840
gtcaaagagg gttgcattgt gcccttcact gaggggtcag agggtgcctc gcgtgtgtgt 105900
gtgtgtacgt gtgtgtgtgt cactgagggg tcagagtgtg cctgtgtgtg tgcttgtgtg 105960
tgcgtacatg tcactgaggg gtcagagtgt gcctctgtgt gtgtgctcat gtgtgtgcat 106020
acgtgtcact gaggggtcag agtgtgcctc tgtgtgtgct catttgtgag cgtatgtgtc 106080
```

```
actgaggggg tcagagtgtg cctctgtgtg tgtgctcatg tgtgagcgta tgtgtcactg   106140 aggggtcag agtgtgcctc tgtgtgtgtg ctcatgtgtg agcgtatgtg tcactgaggg   106200
gtcagtgttc ctatgtgctc atgacattga gggtcagagt gtgcctgtgt gccaatgaaa   106260
ggcatttctt atatttttt atatgtggtc atagtagacc agttaattta ttttgactcc   106320
tgtgttagac caaaataaga cttggggggaa agtcccttat ctatctaatg acagagtgag   106380
tttacttaaa aaagcataat aatccagtgg ctttgactaa atgtattatg tggaagtctt   106440
tattgtcttt tcagatgaat caagtagatt attcttgaga ccaggaatgt tgctgttttg   106500
gttatttgga aagttttatc attttcaaat tgacttttga atttgagtca ccttttttca   106560
gaagtggtgt taaattatag gagccctagg ttttttttct tttttagaa gtcatcacaa   106620 aatgatcagt gttcagagga agagctttga ccttccacat ggtataatga ttgataacct   106680
taattcatct cttaccataa accaagtatg tgtaagggtt ttctttattt cttgaaagca   106740
ttttgtagat gttgagagca gttttccaaa tgtaatttcc atgaaatgcc tgataagggt   106800
acccttttgt ccccacagcc ataccggctc tgcagcccat agtccacgac ctctttgtat   106860
taagaggaac aaataaagct gatgcaggaa aagagcttga aacccaaaaa gaggtggtgg   106920
tgtcaatgtt actgagactc atccagtacc atcaggtaag aggaatgtat gttggaactg   106980
tcgtggatac tttattgacc cgtgcagatg gaaggaagtg ccatgtggta acgctcactg   107040
ttaactgtgt tactttgaac caggtttggg ctttctgggg cctgggtaga tgccggtgca   107100 ggggatggg gagggaggcg ggggtggg ggtgtggtg gagttgggga ggtgcagtgg   107160
caggaggtgt tgttggtgtg tatcctttt ttttttttga gatggagtct ctctccgtcg   107220
cccaggctgg agtgtggtgg cacgatcttg gctcattgca agctccacct cccgggttta   107280
agcaattctc ctgcctccac ctcccgagta gctgggatta caggcatgca ccaccatgcc   107340
cagcaaattt tttttttgt attttagta gagatggggt ttcaccatga tggccaagct   107400
gtttcgaact cctgacctca agtgatcctc ctgccttggc ctcccaaagt gctaggatta   107460
caggcgtgag ccaccatgcc cagcctggtg tttatcttta aagtgggcac agccacagga   107520
gttcacctga ctcctggtct gagagtcacg agatcgttca agatagtgag gccctcttt   107580 ccaaaacgag gaccaaaaat caattgacag tgttggtcaa gatggtagaa accttaaaat   107640
gatagaaatc tcaactctga aataaaaact ttatttgtat atttatttac cactatttg   107700 acatagggct aaggtctttt tctttgagct gatttctggt tttgttttct taaagtggca   107760
taagaattca aagacatttt gaggaaggct gagtgcagaa atctctcttt ttaaatgact   107820
tctcctttct tttaacttgc actgttgtct agccctcact tattttgtca attcttttta   107880
gctgtttgtc tttgaatctt cataaagcca tagcttttct cataagaagc agcacttct   107940 ttgttcattc atatttaat gaaccctgt agtatttaat taaatactta atgcctaatt   108000
aaatcacata attgcaatgc aaaagtacat gtatcataaa gaggtctgaa aatgagcaac   108060
tggcaagcag gtggtggcag gcagagctgc ttgggtgggt gggtgtcatg gagaggagtt   108120
catcagccac atgttcagtg agctctggat atgtctgttt agaaatgatc actaataaac   108180
ttgtgctcaa ccatgtatac ctctgggaag caggtgctct tcagtagatt gcctctgcag   108240
agaacacaga attgaagtga atgtccacaa aggcaatgag ccacctgcag aatagtttag   108300
tcaaggctgt gtttgaagtt tgccaaagat taatatacat ttgattttca tgttgtgcct   108360
tttctctgat tgtgaaatat tacaaattct atacaaataa caatgatggc aaatcctcct   108420
```

```
gagcaaagtg tgcaccttgt atgtgccta gaggaacttg tgtttcgttc tgattcccct    108480
acatttctca tgtcatagag tgggggttgc attagtgtcc ccctgtcctc gctgggatca    108540
catctgtttg gatcctagag tcttccagct gaactgggac aagtataaca gacggacacg    108600
taggggtgga aaggcgtctc ttggcagcag actttctaat tgtgcacgct cttataggtg    108660
ttggagatgt tcattcttgt cctgcagcag tgccacaagg agaatgaaga caagtggaag    108720
cgactgtctc gacagatagc tgacatcatc ctcccaatgt tagccaaaca gcaggtttgt    108780
ccccgcagcc ttggcttgtt gttgcatagt gatggtagct taaggtcctt gtgaaaggtg    108840
ggtggctgga atcagctctt ccttcagtcc taatctgtgc cttgatagca gttctccgtg    108900
ctagtcatgg gacagctgac ttcatttctt ctcacaatgc catctcaggt tggtattgcc    108960
cacctacttt acagggggga tcccacagct ccgagaggtt atggaggtga tcaggcagca    109020
cacagcttta gagtgctggg gtgagggcgg gccaaggcta actctaaagc ccgaaccctt    109080
acctcctaca ctgcctcctg cattctggtc aacccagtgt tttatttggt ggttagattt    109140 ttgttttgt taccttactg cttgtaattt agcagttttc ctttcctttc ccttcctttc    109200
ctttccgaca gggtctcact ctgtcaccca ggctagagtg cagtcgtgta atctcactgc    109260
aacaacctct gcctcccagg ttcaaccaat tctcccacct cagcctcctg agtagcaagg    109320
accacaggtg tgcaccacta cgcctggcta gttttttgta ttttagtag agatgaggtc    109380 tcgctgtgtt gcccaggctg gttttaaact cctgggcgca agtgatccac caaccttggc    109440
ctgccaaagt gctggcatta caggtgtgag ccacctcgcc tggcctattc atcactaatc    109500
agaatttcta tgatcaaatg acatgaatca ttgtttccac aactgcagtg gaaggaaatg    109560
gcctggcagt gccagtttca gaagcagcct gcccccagtc aggcacaggc cactgtgccc    109620
ccagtgtagc agcacctctg tagctcacag agaagggtgg tggggacctc cttgaggcag    109680
ctctgccaga aaatctcatg agctgcctgg cacagcttga ggttgccttt taagtggact    109740
cagcaaatac atgtttgttc atcttgatta tacacaataa acaactactc tgtatagtac    109800
gagtagtccg tggttttttgg catttgattt aaacttagag gcatgtgata ttgatgttac    109860
tgccttcatg actgcacccc cattctgatt tcataatgga atgttatctt gagaccagtt    109920
agacaacagg acagggatct tggcttctgg tgagattgac agcagtttta gtgtggtcag    109980
ggtctccctg cctacagatg gttttagaat ggtgccctgg aagctttatc ccattctttt    110040
ctgtgcgtaa tctgagtaga gtggagatcg aaggcctgaa tacatagtaa ataccctgact    110100 taatatctgc cgcaatggaa attgtgtgat acaacatttta tgaaacgctt agtgcagcac    110160
ctgccaggta gctcaccaca ggtgcatgtt gcattcagaa gtagtgctag atactatcct    110220
gttactggca gtgcatacat cagtgatcaa agcagattaa agaaagaccc cctgccttct    110280
tggagtgaag atttttgttgg gatgcgggta agggacaga caatagaaaa gcaagtgagt    110340
gaagtctata ccatggcggc tgatcaggaa caccgtacag aagaatccag gagggaagag    110400
agttaggtgg tgtctgcggt gggagtggca ttgttcagct ggtgatgaga agaagctttg    110460
gtgatctggt gacatttgag tgaatttgca gaaaggaaag atacaagcct aggagatacc    110520
tggggaagga acattccagg cagagcaaat agcagtgcaa aggccctggc ggggggcgga    110580
catgctgtta gggtacaagc aatgagggtg gaggagtggg gcagccatgg ggagggaagg    110640
gagtgaggcc tggtggggtg aggccagtgt ggaggagcct tgagagggtt tgcgctgatg    110700
tggtgtaggt tttagcagga tcattcttat tcctgagttg agaatagcct tgaggggag    110760 gtgagggcag agcagggcca cccatgtgag acccggcact ggagtggaat ggcccaagtc    110820
```

```
agcatccctt ggcagcatga aagcaaaacc agcaaggttt gctggtggct tagatgtggc  110880
atgtgagaga gagcagggct ttgggggtga tttcagggtg aggacagggt ggctgtggac  110940
aaggtagggc agacattggg ggcagcagga ggtcagagcc tgtctggatg tagcagttga  111000
gaccccatag gtgcctaatg aggtgaggcc agcatcaggt gtatgagcct ggagttgtcg  111060
agagactgtg gggcaggggg tcagcatctg agatgtccac tcacagtgga cccagactgg  111120
ctggagagga ggaggagctt gaataccgag cctgctgagt cccagctcca aggtcaggta  111180
ggtgagggga gccagtgctg gggcagggggg agtaggcagg tgtggggttc ctaaagccaa  111240
gattttttt aaggcatttt gtgcaggagg gcgacatctg ctgtcagcac cttgggaact  111300
tggcccaggt ttggcagcac cgagggcact gatgagtgct tttggaggag caagggagc   111360
caaaccctaa tgggaatgtg ttcctgaaag gacaggagag agacttggga aaaggtttta  111420
cttgaagagg gaacggagaa atagggcagt agccagagga ggagaggagt cggcaatggg  111480
ttaagttggc agaaatgaag gcctgtttac gcactgaggg cagaagcaac agggaggatc  111540
agttcatgac acaggagaca caaatcgccg ttgtggtgtt cacagacatg ggttaggatt  111600
ggctgcatgg atgacagagc actgtgggtt ctcccagagt tgctggggag gaggcagagt  111660
tggtgagcac aggcgagggt ccaggatgca ggaatcctgg agctcaagtc agttgttccc  111720
ttgttgtaag atgtggccag tgttgtgagc ttcacatctg tgccttgaaa aacaccacat  111780
ctgtttgcag agttgtttac tatgtataca cactcagtag aaacaaaaat tggaaacagt  111840
cagtgcccac catcaataag taatggttga acacactgtg gtataagctt agactatttt  111900
agcttgggct atttttgcatg attaaaaatg ttctggccag gtgtggtggc tcatgcctgt  111960
aatcccagca ctttgggagg ccaaggcagg cagattgctt gagctcagga gtttgagacc  112020
agcctgggca acatggtgaa accctgtctc tactagaaat acaaaaagta gctgggtgtg  112080
gtggtgtgcg cctgtagtcc tggctaactc aggaggctga ggtgggagga tcacttgagc  112140
ccattcgtgc gccactgcac tcctggggca cagagtgaga ctctgttaga aagagagaga  112200
gagaaagaag agagagggag ggaggaagga aggaagaaa taaatggaag aaatggaagg  112260
gaggaagggg agggaggaag gaagaaagga agttcagcca gttgccttgg gagttctcca  112320
ttgcactggg ttaagtgaga agagcagaga cgtttatgat ttttcaaaac aactaaaaca  112380
aaacctctgt gggtgagggg gcaaggatat ggctatagga acatgggca gattaagaaa   112440
gggatataca cacaccactt agcatttgtt acaactgttg tgggagggat ggagtgcaga  112500
aaaagaaaaa aaaagtgca caccatccca tgtatgtgta tacaaaggga cgcttggaag  112560
actggtcccc aaaatgttgg taatgattgt gtcagggtgc tgcagtgcta gttgattttt  112620
tttcacactt ttgtatattt gagtctttta cagaaagcat ttattattta tgtaataaaa  112680
atctaaatga caagatttct gttatgggaa aaatgtagct atacagtgtt gttgtaaaaa  112740
tgtttgcttg gttcaccact gaacttaaaa tgcttttaaa tgagggaagg tgacgatgag  112800
atgattatga tgatttgccc ttgagttaca tagctggtgt acaggaagct gtcgtttctt  112860
ttggcttacg tagaaatgtt tgtggtgtct aattccacag atgcacattg actctcatga  112920
agcccttgga gtgttaaata cattatttga gattttggcc ccttcctccc tccgtccggt  112980
agacatgctt ttacggagta tgttcgtcac tccaaacaca atggtgagtc tctcgcctgg  113040
ctcagcagat gaatctggac ggcttgttca ggctctgatt actgggacca cccccagaat  113100
gtctgagtca gtcagtttgg gtagggcttc ttgagagttt gcttttttt tttttttttt  113160
```

```
ttttggtgtg ggggtggtgc ggaacagagt ctcactctgt cgcccaggct ggagtacagt    113220
gtcatgatct cggctcactg caagctctgc cttccagctt cacaccattc tcctgcctca    113280
gcctcccgag ttgctgggac tacaagcgcc caccaccacg cccggctaat tttttttgtat   113340 ttttagtaga gatggggttt caccgtgtta gccaggatgg tcttgatctc ctgacctcgt    113400
gacccgccca tctcagcctc ccaaagtgct gggattacag gcgtgagcca ccgcacccgg    113460 ccttttatt tttttggag atggagcctt gctctgtcac ccaggctgga gtacagtggc     113520
gctacctcga ctcactgcaa cctccgcctc ccgggttcaa gcaattttcc tgcctcagcc    113580
tcccgagtag ctgggactac aggtgcgtgc cactgtgccc ggctaatttt ttgtattttt    113640
agtagagacg gggtttcact gtgttagcca ggatggtcgc gatctcctga ccttgtgatc    113700
cgcccgcctc ggcctcccaa agtgttggga ttacaggtgg ctctcgcacc aagccaagag    113760 tttgcattt tagcaaattc ccaggtgaaa ctaatgcctg cttttctggg agcacacttt     113820
gggactcagt gatagagagg tttattggta ggatagtaaa ataggagtta ttttctttca    113880
caaaattggc aattggggga aatttaatct tcctttttc ttcagctgtg acttatgtat      113940
tatgtttatt ttaggcgtcc gtgagcactg ttcaactgtg gatatcggga attctggcca    114000
ttttgagggt tctgatttcc cagtcaactg aagatattgt tctttctcgt attcaggagc    114060
tctccttctc tccgtattta atctcctgta cagtaattaa taggttaaga gatggggaca   114120
gtacttcaac gctagaagaa cacagtgaag ggaaacaaat aaagaatttg ccagaagaaa    114180
cattttcaag gtatgctttc tatctgagcc tataactaac ccatgccttt tgggaagtca    114240
cgtgatgttt cacagtcagt aagtctggaa taatacctgg tcttgcttca cttctgagtt    114300
gggtaaagaa gtctgtatca gtgtaatttt ctaatccgtc ctgcattatc tatggctctt    114360
ggttcatacc tgtcttgaag ttctgtcatg ttctgtctct tgtcctcagt agagatgcta    114420
cagcagtggc tcgcctcagg cagggcaggg cagtggggtg gctgtcctgg gggcaggcag    114480
taggggcacg ctgacgtcag ggaagttgaa acccaagaga agccagtaaa agtgagtctc    114540
agattgtcac catgtgctgg cagttttaca cgctgtcagt aataaaagtc ttctccctgc    114600
agggcagcct gcctccaata aatacgtgta gtatcaaatc ctgtcttccc tcataaattg    114660
tttggaagct ccccaaggac agtgatgagg cactcgtaag tgcttgctgc ctagatgggt    114720
ccctctccac ctttgctaga ttctgagcat tcactgagtt agagctgctt ctgcaaatgt    114780
gctgcttctg ctaagtggct gtgacttcat gcagccttca cttggtttgt catcagtgga    114840
gatgccctgt gttgtcgaag gagataagcc cagtaagcct gctgggcacc ttttggtttg    114900
caggttcagc aggcagccca tggctttccc tgtgtcgcat tgaagcagct ggctaaaatt    114960
gatgatacat taaattcctg tgacagatga tcagcttgta tttgtgtaat ggtgtacagt    115020
tcacaaagct taaaaaatg ctacctgcca tttcatcctc agtgaggaag gtgatacaca     115080
gagagaccaa gtgactgtgt ccacggcgac ggcgctctgc atttcacttt agcggttaat    115140
gtactctacc tatattttta ctttatattt accatatatc ttttcatgta tacttggcgt    115200 aagtgctttta tagtagtcac ctaattcact gtcatctttt ttgtttcttg gaaggtttct   115260
attacaactg gttggtattc ttttagaaga cattgttaca aaacagctga aggtggaaat    115320
gagtgagcag caacatactt tctattgcca ggaactaggc acactgctaa tgtgtctgat    115380
ccacatcttc aagtctggta ggtgaatcac attagtcttc ctggagtgtc tcgttcccca    115440
ttctgcacta tacactctca gagtgtagga gctgtgctgc ccggtagaaa ctctgccttg    115500
cccagtgtgc cagttgaaaa tatttgttgc tgtaagagta cacctgatac catgtgaccc    115560
```

```
agcagttcca ctcttgggta tatacccaaa agaatggaaa gcagggtggt gaaaagatat   115620
ttgcatgcca gcattcatag cagcattatt cacgatagct aaaatgtgga accaactgaa   115680
gtgtccctcg atggatgaat ggataagcaa aatctggtgt atatttacag tggaatatta   115740
ttcagcctta aaaaaaggac attctgacac atgctacaac atgggtgacc cttaaggaca   115800
ttatgctaaa tgaaataagc cagtcacaaa aggacaaata ctatgtgatt ccacttacat   115860
gagggacctg gagtagttaa ttcatagata tagaaagtag aatggtggtt gccagggct    115920
gcagggagg ggagttattt ttacaagatg aagagagtta ttctagaaat gaatggtggt    115980
gatggttgta taacattatg aatgtactta atgctactga actgtacagt taaaaatagt   116040
taagaggacc aggtgtcatg gctcatgcct gaaatccaag cactttgaga ggccaaggca   116100
ggaggattgc ttgagccaag gagtttgaga ccagcctcag caacatggta ggaccccatc   116160
tgtacaaaca aactagccgg ggatagtggt gtgcatgtgg tcccagctac tcaggagact   116220
gaggctggag gatcgcttga gcccaggagg ttaagtctct agtgagatgt gttcatgcca   116280
ctgcactcca gcctcggcta tagagtaaga ccctgcctca aaaaacaaa acaaaacaag    116340
acaagagcca aaaatggtta agatgggcca atcacagtgg cttatgcctg taatcccaac   116400
actttgggag gtcaaggtaa aaggatcact tgaagccagg agcttgggac cagcctgagc   116460
aacatatcga gacccctatc tctacaaaga aaatcaaaaa ctagctagat atggtgggca   116520
catgcctgta gtcccagcta cttgggaggc tgaggtggga ggatctcttg agctcaggag   116580
ttcgaggctg cagggagcta ttattgcact ccagcctggg ctacagaatg ataccctgcc   116640
tcttattaaa aaaaaatcca aaaaaaaaaa aaagtaaacc tgagagcttc ctcctcctgt   116700
gttaaatttg gaggccaaga tgttttttgt acttttacaa atgatcaagg acggtgaagg   116760
ttgggcatgg tagctcacac ctgaaatccc agcactttgg gaggctgagg cggggtgatc   116820
gcttgagctt gagaccagcc tggacaacat agcaagagac cccatctcca caaaaataaa   116880
aaaataaaaa aaaatagcca ggagtagtgg catgagcctg agcccaggag gtcaagctgt   116940
agtgagccat gatcatgcca ctgcactcca gcctgggcga gatcgagacc atgtctctag   117000
agaaagaaaa tgacaaggac agtgaaccca agaaagtcat aagatgccag ctgtgcagca   117060
agcatggaaa gcagccagtc caaattagga cagtgtgttt tccaagaaga acgatcgttt   117120
gtaatgagaa tgctttgctt taaataaatg actaaatagc tagaagccta gttctagggg   117180
ataggcacgt ctttcttctc tcaagaaaat agaaaggcaa ttctaatttc tagtaacagc   117240
aaacagcatt aagtcatggt ccaaatatga ggcaaaccaa aatgtggctt gattgttcag   117300
cagttgatct gttggaagcc cttgatatta aaaaggttct cctttaagcg gcttaggagt   117360
cacgatcaaa gacctataga aagagatgcc atccttctag gatccttggc tctcttggga   117420
actagattca gatagtcata atgtaaatac tgcttgagct ttctttcttt ctttctttct   117480
ttcttttttt ttttgagaca gagtttcact cttgttgccc atcctggagt gcaatggtgc   117540
catctcggct caccgcaacc tctgcctccc aggttcaagc aattctcctg cctcagcctc   117600
ccgagtagct gggattacgg gcatgcacca ccacgcctgg ctaatttttt gtatttttag   117660
tagagacagg gtttctccat gttgaggctg gtctcgaact cctgacctca ggtgatccac   117720
ccgcctcggc ctcccaaagt gctgggatta caggtgtgag ccaccgcacc cggcccgagc   117780
tttcattttt gaaatcaatg tatgactgaa acactgaaga cttactgact taattatggt   117840
ttcagaacag aatgaaaatg tcttcggttc tgatgaatat aaaaggaaaa ctaaccaagt   117900
```

-continued

```
taatttggca agtagatggt agagatagag gtggggagtg gaaggggaac taaaatcttc    117960
acctagcatt gttgggatta tatggttaca tcatctgaag ttgacagacc aaaatataga    118020
ggcttcagag gtctccaaat agaactaaac atgtaattca gattgttagg aggtagtata    118080
aatgagctaa atctcatctt tattacggta gagttaatgg gtgatgtcta aagttgtctg    118140
aagtctataa atcatgacaa attatgatgt ggtgattgta ttcaacagtc tttcagttgc    118200
agggataaaa ccccagttta aactagagta agagaaagaa tgtgttggtt taagctcctg    118260
gaaagtgcag gcaagggtag ttggtaggac tgcatctagt gttgtaattc tgtggtctgc    118320
attgtatatt tatgcatctc agctctgctt tcttcttttc atttatataa ttttaaatt    118380
ttattttaaa datagggtct cactttgtcg cctaggctga agtgcagtgg catgaagtgc    118440
agtgcgaggc tcactctagc ctcgaactcc tgggctctag agttcttcct gcctcagcct    118500
tctaagtagc tgagacaata ggcatgtacc aacatgcctg gataggtttt aaaatttttt    118560
tgtagaaatg gaagtcttgc tgtgttgccc aggcgggtct ttaactctta gcttcaggcg    118620
atcctcctgc ctctgcctcc caaaatgctg aggttatagg tgtcacccac cacgcccagt    118680
ctcatctctg cttcctgtgt tagttttgtt ctctggtggg ctgttttcac atgaccgaag    118740
atgacctcta gcaggctgtg ttctcagccc ctcaagtagg cctatgtgat tggccttgca    118800
tgagtaatat gggtgaccat aaaccctga atgctctggt ccacatgggc caaatgggag    118860
actgacagc attccattga tgaggagtg gggctggtct ccgggagtaa gggagaggag    118920
cacatgcagt aactgatggt ctgctgcaag ggatagcagc acagcagtta gaattttgga    118980
ggtaactacc agaactgaaa acagaaatga taacaagtag ttgccttaaa aagggatggg    119040
agcagggtgc ttttgtgatc aaagctcctt tctcttactg gattttgta cacattttgc    119100
atacatatct tagagtaaaa gatagcattt tcagccttgg tccatttgag gatactcttg    119160
gcgtggcccg cctccatgct agcaggctct ggttgtgcca agttcagttg agcatcctgg    119220
ctcttgcctg cacggaactt ccagtcagtg cgtcagtatc acaagtcttg atatttccta    119280
tgaagaagaa cagtagtgca gtgacagacg aaatgggtgg gcaggcagag gcaggatttc    119340
tgagggagag aagtagctag cttttttgcag agaagagttc cggcacccaa gagagcagct    119400
gagagtacag gcaggcaggc aggatgccgg tagggcccgg ccgcacggcg ccacagaatc    119460
ctggagaaag gggcctcttc atggcctctg cattcagctg ctgtcaccct ccgcacaggc    119520
catggccaaa atttaatttt catagtggac tctagttttt gagccttact tgctattatt    119580
gaaataattt tcttgtttct ttttaaagat cttcggatta tgcttcactg accactgtaa    119640
taagtttaaa gttgagaaaa tatggcttgt taatgaatga taggtcaatt ttagtatgtt    119700
ggtcatttta atattttgcc accagttggt ttggatttga tgccaggagg agacagcctc    119760
atttctaagg actagtcttg cctttgtggg ataagggtgg tgtgttctgt gtccttctac    119820
atgtccgagc gatctctgtg cagctcaaat gtggtcactg tcttattgcg ctgatttcct    119880
ctccttccat ctcacaattg aggcaaaata ttgttactgt tgaagtgttg tccaatagga    119940
cttccagcag agacaggatg tctgcactgt ctaatttagt tgcctttagc cacatgtggt    120000
gttctgtacc tgaaatgtgg ctggtctgat tggatagctt aatttataat tttatttaat    120060
tttaattaac ttaaatttaa acagctctgt gtggatagtg gctcctgtat gagacagtgc    120120
aggtctgttg agaagcagct ttactggtgg gagtggaggg cttggagagg gcacgtgggt    120180
ttcctgctgg tatctttga ccttatttaa tctgcccaac atttgcaagt aagttgtgtg    120240
tgtgtgtata tataaatgtg tgtttctgtc ttcttgtttc ctttgactgc atttatttga    120300
```

```
aagacactag gtggcagaat tactgtattt gattggtttc aagataagag ttgaaataat   120360
tcatctcgtg tttttatata agtaaggtgt gtttagcatg taaaattggt aatatgtatt   120420
cacgtactgc ttaaacaaag gctatgaatt ccacccataa accgaaaatg aagacccttta  120480
aatttgtcca tttcaggcgt gggtacttct taaataatac ctggttcagg aactagtcag   120540
aatggcaccc ttgactttt gtttcctgct tttcctcttg ttgggagagg agggtattca    120600
tcccaaagtg gtttgcctat ttcacattcc atctaggata agcagaatag ccaagaaaga   120660
tagctgtcct cctgtttaca acatttgggg taaccagcat ccctctcttt tggtccaaga   120720
tagactggtt tagaaacaga tgatggcacc agaggcccag gaggtggaaa catcagcttt   120780
gtttgttgtc catgtggctg aattagagct gtctggcctt gtagcctcaa cacggccttc   120840
cagctttgct caccgtgatt ttcaaggaca catcttgtgc tcttccctgc ctgccatcca   120900
gactataccc agtcagggtg gcaggagctg ctgcccttc ctccctgagt cctggtcgtg    120960
ggtggtggag atgtgccatg acgctcacgg aggcatgctc accccttcct ctgtggcaga   121020
ggggatggct gcacgacagc tcttccctgt cctttccaaa gcgtctgtgg ttccactttt   121080
tgggcaaag caggaatact ggaagagaga gaaagtggtc cttctatag taataaagtt     121140
gacattgatt caagttcatg cttggggaaa ggacagggct actaacaatt ataatgctgg   121200
gagcaatgga atttctcat gggtatgtgg taggttaat tttaattatc ccagttaatt     121260
cttagaactg ctctgtgaag tatttcccgc tttgtgctta agttctaaaa gatcctgtgc   121320
caaaaccaag aatgaaaacc caagcattct ttcttgccca tcgatctttc tctcatcagg   121380
ccacttcttg ggttgatagt ggtgagtgta gccgctgcca ctttcagaat acccaccatg   121440
ggccccagtc actgtgtggc gtggagaaga gatggttctc tctgtgtcat agctgaacaa   121500
gcccagccca gagaggtttc tgccctagga gctctcgatg gtggaattgg gatgcgatcc   121560
cacatcctgc ctgttttgaa aacagcattc tttatttcca attcctgctt ccattgttcc   121620
ttttaatatt tctttgttta gctcacaaaa acacggcttg cggagctgct gcgtgcagct   121680
gtagctgttt ctctgggtgc agcctgcatc cgccttcctg cccgcctcct ttcctgcact   121740
gccatcgtgg tctccgggca cttggtccct ttctcttccc ctgagtccct ttggctcccc   121800
tgtgccaccc ttgtgatcca caggctctgc cttctttctg tctcagactg ctgctcatca   121860
ctactcggga ccctaggaag ggaggttcca ccgagaagca tcttctcatc tcagccacgt   121920
tctcagtgcc actgttgtct ttgttaggta atggtagcta ctgtaacaaa taaaccaaca   121980
tttccatggc ttcacaccag agaaggttgt ttcttggttt tatgacaatg tattgagggt   122040
gttcttggtt cacggatggt tttcctccat gtgggaattc ggggacccag gctccttcc    122100
ttcttttggt tctgttctcc aggccttcac atcctctgtg tctggttggg gacaaggaga   122160
gggaaggtaa agaaggcttt gtggccttgg ataagtgaca ggcatgcctt tgctggtgtt   122220
ctctcgtggt gacaggtcac agccccaccc tgtaaaaggg gactgagaga cgtcgtcctg   122280
ctgcttccca gcagcagcac tgtggtctct gatgtgtttt ctgtgaggat aaaaacaggt   122340
gattccagga tgaggaaagt cagggaaacc cttggaagga ggggaccagg cgggtgtcac   122400
catgggatta gtggtggctt cagaatgagc tgcagcgagt gccatgcctt ctaaagcttt   122460
tgctattctg atatgcccac accatgccca gcaggtgtct gccttgctct ccgcagagag   122520
agtgatgaat cctctctatg agcctctgtc cagttgttcc tccctccacc tggaagggac   122580
cctgggttcc tcataacatc ccagcggaac aggggaccct ctatcctgtc cccaagttca   122640
```

```
tcctcatcct cctgccggct tcctggcccc tcttatgtct gcttcctgac gccacatcct  122700
tctggattct ctggaattga attttgcctt tgatgcttat ttaaaaatat ccattgcagg  122760
ccaggtgtgg tggctcacac ctgtaatcct gtgcactttg ggaagccaag gtgggcagat  122820
tgcttgagcc caggagtttg agattagcct gagcaacatg ttgaaatcct gtttctatag  122880
aaaatacaaa aattagctgg gcatggtggc gcacacctat actcccagct actcaggaac  122940
ctgagacagg aggatcaatt gagcccngga ggcaaagct acagtgggct gtgatcgtgc  123000
cactgtactc cagtctggtc aaacagagtg agaccctgtc tgaaaaaaa aaaaaaatcc  123060 attgcatact tcaccgtagc gaaacatgta tgtcttacct ttcctttcct gcctgtagct  123120
gctcttttac acttaacagc cacactaagc cagccttaaa tgaaaacaa accagcactt  123180 cctgtgccct cctgcttcct tcatgagggg tccctccctc tgtgtacact ccattctcat  123240
tgcccatggt ggtttgtttc cctcttgttt ctcaagccat ggcagcctgc ctcttgccct  123300
ctttactaaa aaggcctttg cagaggctgc ctgtgttctt tctttctagg tctctctcat  123360
cctaggccct ccagcttgat tctgtggagc tgccctcttg tcactcagta gcttgtgggg  123420
tcttctctgt ctagccactt aattgattgt gttcctcgag ttgctgtcca tggtctctcg  123480
ttactgtttt ctctgtgttt ctgcctctct ccttggcctt ggtaggtcca tcccctttgt  123540
gaccttggct gttgctctca tggacaactt tctcttgctg gtccttgtag tcctggcatc  123600
cagcttctcg acacgggact tgtcctgcca gtacctcaga cttgcactta aaattgaact  123660
agcaccactg tcactctcca gggcctcttc ttgttaatta gatcattagg gatgttcaga  123720
atcccagcat catagtatgt tcctcctccc gctaccccag gaaccctaac cttacctcct  123780
cctctctatc tactaggagg tggccctcag agtccgtctc atcttccacc tgaacttccc  123840
taataggctc cagcagctgc cacccgggg gctgagtact tcctccatgc cttgtgcagt  123900
gctgagccct ttacctgggt tctcctgttt gctccttatt acagccctgc gaacagatac  123960
tgctcttaat tccatcttac acctaaggaa gctgaggccc caggtaaggt gcatccaagg  124020
tcacccaggt agtagacagt agagccacga tctgaaccag gcagtctgat tcagagcctg  124080
tgttgacact cagccaccta gaacacagct tggattgtgg gtttctatta cctgttcaaa  124140
acccctacat cccgggtctg tccctgcacg tgctctgtgg cctggctgca tcttccttga  124200
aggcagtgca tgcctcttca ctcagggggc ccatgcagga acagagggcc ccacagaagg  124260
atgaggccag tgcagaatgg gctggagggg acaatgctga ccaggaagca agtgtagaga  124320
aatcccagga aacctggagg agccagagac aaggcattag aactcctcgt cgtgacctgg  124380
tctgcattct ctgagtgtgc tgcttctgtt agctcgcttc cttggtctca ggttatagtt  124440
taaggcattg tggagcccta aaaagcctgt actctgtttt tacctgtttt aggaccctt  124500 cactttgggg atgtgttgat tttttttttt tttttttttt tttttttgag atagagtctc  124560
gctccattgc ccaggctaga gtgcagtggc acgatcttgg ccactgctgc ccctgcctcc  124620
tgggttcaag caattcttgt gctcccgcct cccaaatacc tgggattaca ggcacccgcc  124680
accacactcg gccaattttt gtattttag tggagacagg gttttaccat gttggtcagg  124740
ctggtctcga actcctgacc tcaagtgatc tgcccacctt ggcctcccaa agtgctgtga  124800
ttataggcgt gagccaccac acccggcctg aaatttaaat cagaaataaa attttgatcc  124860
caacagtgat gccaggcagc ccagatctgg gggagagggt ggccttggcc agctgggcct  124920
ttctctgttt cccaagtctt gctgcctctc cctgctgggc tttgcagcct gtgcatgtct  124980
ctgtgccttt gaccttgttt atccaaagga gaggatagaa tgaagtcatg attcctggag  125040
```

```
ccctgagaag gatgctgtgg agaaatttgc cggtagaatc tagctgagtg tgttgctgag  125100
gtgccagcat tgtgtgtggg gaggctgacc gcttggcctg cctaggccca ggatgctcca  125160
tggccgggca cagaggccac ttggctgtca ggtgtcagga gcctgcagag ggcacacaga  125220
gcctggaccg caggggggtc ctgctttctc acctggcctc cttcagcatt tctgtccctc  125280
agtccttagc aagcccagga gctgttgagt ttggcaggtg ccgagtgctg ttcctgcctg  125340
tgtagctgtg gctcagtcct gtgggggccc cgctgtggcc cgagtgcagt gattcgaggc  125400
gctgagtgtt ccctgactcc ttctccagga gctgtgttca gactttcgca gctcttggct  125460
tggagctcct ggagggcttg gcattgccga ccaatgtgga ggtcgacagt gagagaggag  125520
gaatgctagc tttcttgacc agtccattaa ataagtggga tattggccag gcacggcggc  125580
tcacgcctta atcccagcac tttgggaggc tgaggcgggt ggatcacgag ctcaggagtt  125640
caagaccagc ctggccaaca tggtgaaacc ccctctatac taaaaataca atattagct  125700 gggcgtggtg gcaggcgcct gtaatcctag ctacttggga ggctgaggca ggagaacagc  125760
ttgaaaccgg aaggtggagt ttgcagtgag ccaagattgc gccactgcac tccaacctgg  125820
gcaacaagag caaaactcta tctcaaaaaa aaaaaaaaa gtaggatatc tgtttctgct  125880
tagaaaaatc agaattttct aaatgccagg tgttctgaat acgtaagtat gggagacgac  125940
tcagcctgtt tcattttat gtaaaatctt cgcgtagcca tgtggcactg gaccgagatg  126000
aaagcaaaga catttctcct taactttgtt tctaggaatg ttccggagaa tcacagcagc  126060
tgccactagg ctgttccgca gtgatggctg tggcggcagt ttctacaccc tggacagctt  126120
gaacttgcgg gctcgttcca tgatcaccac ccacccggcc ctggtgctgc tctggtgtca  126180
gatactgctg cttgtcaacc acaccgacta ccgctggtgg gcagaagtgc agcagacccc  126240
gaagtaggtt cataatgccc cacagcccag ggcgccagcc cagcaccctg tcctgagact  126300
cccagtaacc tgagctttgg ccaccgttaa agcattttca ttttccattt tttgtgaggg  126360
cttgtgaaat ttctgctgca tattaatatt cctttcatgg acagcatatt attgggacaa  126420
acatgcggtc cagctaaagg cattcaaaat agcagttgct ttctaaatgc gattttcttt  126480
ggcaggttct ttgacaccat tgcatcttgt gggatatgct tgtcatgctc tgtggctcct  126540
actaagttct agtccttaaa ttggttccat agccagacat gttgcaatgt cttaacctca  126600
ttataaagta aatgtggttc tggttatcct tagataatga agtaacagtg tagcaaattt  126660
caaaacctct tggaaatgtt attttaccat tcaaaaaggc ttactaaggt tctcgttatg  126720
ggtggccctc ttttgcaaa aggttttcag gcttaagctc catttctagg tgctccaaca  126780
ctccattatt tgtatatgta tggaaataaa agctgtgacc accccaaacc ctggccccg   126840 cccagctgaa tcctcagcac agtatttctg gaaggctcaa gatcccacgc tggggaaaag  126900
aagttctgga gacaaaagag ggcaggtgct gccgtgcctc tctgctcagt atggatactg  126960
gaccttgtgc tgccagggct cccagtaggg ccagttcatg gcactcagct ggaaagtcca  127020
ctgttgggag gcattcttaa ccatccactc tgtgccgtat gtagtggggt ctggtcattc  127080
tgttggagga gacagaccag tgacgacatt tgaaatgctt ggtggatgtc ttaggcctgt  127140
tacgatgact gagcactgtg ggggcaggag acagaaagtc agtgtctcct agttctgtgc  127200
tgctttaacg tgcatagaaa tcagctgcgg attcagcaga tcactccttt tctgacagat  127260
gggcctgctt actctgatgt tatatcagaa agctctgaat ctgggaattg tgtcccctga  127320
attggagtaa cagaaatgct tagatgatga gtgtttaaaa gaaataaacc aaaggtaaat  127380
```

```
ttagtttgga attcagcaag cgtcttcatt cagccctctg agggcaaact acagctttt    127440
gtaaatgtag gtaaattctg tgactgtttc gtgaccccct ctgatccagt tttccttat    127500
aaccttctgt attgttcctt ctattatcct gaaataacat taatagatta ggctgggcgt    127560
ggtggctcat gcctataatc ccagcacctt gggaagccaa ggcgggcaga tcacctgagg    127620
ccaggacttc gagaccagcc tggccaacat gatgaaatgc tgtctctact gaaaataaca    127680
aaaattagcc gagcatggtg acaggtgcct gtagtccctg ctactcagaa ggctgaggcg    127740
ggagaatcgc ttgaacctag gaggaaaagg ttgcagtgag ctgagatcgc gccactgcac    127800
tctagcctgg gtgacagagt gagactccat ctcaaaaaaa aaaaaaaaaa aaaaaaatta    127860
atggatcaat ggattttaa cctaataatt aaatttcaaa aatatcgtt ctttaatggt     127920
aatgtaaagg taaattaag ataatatgta acaagcatgt gagtgtctaa ggtgtccccg     127980
tggtggaagg aaaaaataaa tccccataag tgtccaagat gcccatagag agcagagctg    128040
ttctggttta accccctgct cttagcactg tgttttttcca gctgtgggtg gtgggggatg   128100
agtatctttt tatttccatg agatgagaaa atgaattac tagaagtgtg aaatacaaaa     128160
cacagctgct cttttttag ccatagactc agcagccata aaattgctgt atccagttgc     128220
agaaattcct gctgcttact cttgaccctc tctcggtttg tgtgcatctc ctctcaggct    128280
ggctcccaga tgggagctgg ctccaggcga cactgggtgc tctgctccag gaggtcctta    128340
tgtgggtcct gccctagcct agccctctc ttatggactc tgtcactgtg ggtttatgat     128400
tcactctcaa tctgtcttac ctcttggtga actgttagag tcctgcctat actttggcgc    128460
ttgtgggtgt gttgtggtac acatgatgtg ttggtcactt cccagctcat cttgttctga    128520
gtcaccctag atttgggaca ttcattcgcc accagtaccg ggcggtgtat ggcctgagat    128580
ttggggggggc ttgtgctgct acaaattggg gctgaatttg agttgacagt ggaccttctt   128640
tatgtctact gctcatattt gaattgcaaa tactgcctct tctctttcag aggctcatta    128700
ccctatagct gtattattgc aaagtgcaca attacagctt gagtgtaagt cacactgcgc    128760
tggcaggacg gcccactgag aaagggcacg tttcctgttc gttagttttc acattgacac    128820
ataatttaca atacagtaaa atgtactttt ctatcaactg tagtcagtaa cagcccccct    128880
cccccaacca catcaagata tagaggagtg ctgtcacttc aaacagttcc ctcttcctct    128940
gccacatcct gcccctcccc aggtctaacc accaatccgt gctctgtccc tctgttcagc    129000
ccattgcaga aggccataga aatagaatct ataggctagg tgtggtggct catgcctgta    129060
atcccagtat tttgagaggc tgaagtggga ggatgacttg aggctgggag ttcaagacta    129120
gcctgggctg cctagcaaga ccccatctcc agaaaaaaaa aatttaaaaa ttacaatcac    129180
gtccctgtag ttcagctgct tgggaggctg aggcaggagg atcacttgag ctcaggagtt    129240
agaggttaca gtgagctatg atcgtgccac tgtgctccag cctaggtgac acagcaagac    129300
gttgtctctg gggaaaaaag aaagaaacgg aaccacgcgg tgtgcagcct tctgagtctg    129360
gccccttcg gtgagcagtg tctaaagttc tgtcgcgtgt tgcccacgcg tcggtggctc     129420
gctccttgca actgctgagc attgtatggc taggctgtag tttgttttca cttcaccagt    129480
tgggaaacag agaaaaggca ctttttaaaa agtttaaatc tgtagaattt tggttttac    129540
cagttctctt ctaaatcctg agggattaca ggaaaagttg ttgtatttca gaatattctt    129600
agcttgatgt gacctctgtc cccgttaagg ccctttgccg caatgggaag gacgtcgctc    129660
ggtcagaccc tgaaggtcag aggggcagtt tgggagtgtg tcaacatttt aactgtatgg    129720
actagagcca agagtctcaa ggtttataat tcccacgtat tcaaaagaa aaaaacaata     129780
```

```
aagtgagaag tcagtgtaga gtgaaataac ctgtgttagt ggggaagaag tgtttttaaa   129840
caggatttcc ataacgtata acatcaacat gtttagagtg gtgatgtttc attgggaaac   129900
gaacagtaaa acatgaaagc agggaggttt tcattctggc agttggcaac tttcacggca   129960
gatggagaat ttcaaaagca attgctcaat tatcaaacat agccagtgtg agttctgaaa   130020
taaaggtgct gattgaatgt gcagctttat ggtggatttt gctattcagg caagcatttt   130080
aattttctgc ctgttaaatt ctgttttctt tagtttttca tatgtggttt attgtagctt   130140
aggaatagat aactgagagt atatattaca catacaacat tctgatatgg caatatttaa   130200
aacaacttgt ctgttttaga actagaatta aacataatca tcttcagtat tttgcaaata   130260
agctcactgc catccagaaa cattgtcaat gcatctgttg ctccttctag aagacacagt   130320
ctgtccagca caaagttact tagtccccag atgtctggag aagaggagga ttctgacttg   130380
gcagccaaac ttggaatgtg caatagagaa atagtacgaa gagggctct cattctcttc   130440 tgtgattatg tcgtaagttt gaaatgcctg taaacgggt tgaggaggt ggggaccagg   130500 agaacatcct gtgtagatga cacttgcatg gaccctctgg aacccagacc gcccggtgtc   130560
ctgccaagct ccatcgaaac taaatctaga atgaatgttt acttctgctg tgacatataa   130620
ttggagacca ggcctggcct tccagtcact ggattctaag ttggactgtg agagtttttg   130680
cagctgactc atttatcaaa tgcccggcta ttggctcacg cctacatgat gctgggtatg   130740
tttgttaatt tgagggaagc aatggaataa taataactaa tgatttaaaa aacaaagtaa   130800
gtgcattgac tgtagtgggg ttctgatttt aaattttttt aaaaattaat accaggagca   130860
gtggcttatg cctaaattcc agcaactcga gaggctgagg taggaagatc acttgagccc   130920
aggagtttga gacaagcctg ggctatggtg tgagacaccc atctctaaaa aaataaaaaa   130980
taaaaaatta tccaagtgtg gtggctcgtg cctgtaatca cagctctttg agaagctgag   131040
ggcggaggat ggcttgagcc tgggagttcg agaccagcct ggcaacacag agaaaccctg   131100
cctctaccaa aaaagaaag agaggaagaa agaaaaatta gcctggcgtg gtggtgcatg   131160
cctgtggtcc cagccacctg agagactgag aagggaggat tgcttgagcc cagaagtttg   131220
aggctgcagt gagctgtgac tgtgtcactg cactccggcc tgggtgacaa ggcgagaccc   131280
ctgctctaaa ataattttt taagttaatt tgtagaaaag gtgttagatg ttctttgtca   131340
cattttatga tggattcctg tttaaatgcc gttctcttta aagaaaaaaa ataacttgt   131400 gggagttttt aaccataaaa ctagcatcac atatttacca tggagaattt acaaaaaaac   131460
aaataaacgg aggaaaataa aacctcctgt aatcatacta ctcagagata acttgctgtt   131520
agattttggt ctagatttaa tacttttct atatttatat taaaaatatt taaaacatat   131580
gcatttcttt gtcacaaaca tggtatctta tagatactac tgtcacatag caaacagtg   131640 ttaaatattc tgaatcagaa aaggaagccg actctccaac tgaaagaggt gttatcctag   131700
agactttttc tggtgatgac aatttattaa tagtcacttt ttgctttact ttctctattg   131760
aagtagtttt tctattttgt tctacttta aggataatat aatttataat gctgttttc   131820 acagaaatat aagaaaaaag atactaattt tataagttaa taaagtttga tcatcccaaa   131880
tccaaaaatc tgaaatccaa aatgctccaa attctgaagc ttttgagtg ctgacattat   131940 gttcaaagga aatgttcatt ggaaggtttc agattttcgg atttagggag ctcaacaaat   132000
aagtataatg cacatatttc aaaacctgaa aaaaatccta aattcagaat acttctgatc   132060
ccaaacattt cagataaggg ttattcaacc tgtactgtca gatgatccca aatgaaaaat   132120
```

```
attaatcgtt aaccaaatat caaggaattg atcacatttt acagtttctg cctaggatta   132180
tgaatcaaga tgaaaaggct ctgcatgttt aaaaatatat attttttattt tcttataaat   132240 cttaaatatc tacacttaag atttatttga tatgtgggat ccattcatat tttggattca   132300
acagttctgt caaaactgtg gcagtgatag gggattcttt ttttcccact gaactatcac   132360
aaaattggaa aaagagtaat tggagaaccc cactggctta gccggcccga agcccgggag   132420
agggcaggca gtgctgtgga tggggtcatc ccagcgcaac gctgcccctg ctacctgcgg   132480
atctcgctga ggcctgcctt tgtcctttga cccttggcca tttgttagtg tctctgagag   132540
ctggactgct gtaccctact tccccagggg gcctaacttc acacagcctc tgccgcagtg   132600
cgtggttgga ggtgacggcc ttggtaaatc gagtttccta cctcctcaat tatttgtgct   132660
catacactgt atattttag tgaggtttat atttgggatg tgttttctcc ttcttaccct   132720
ttctggcctt tctatggcat taatacctgg tctcttcttg tgtacttgaa aatgaatctc   132780
tcatcatatt tttccttagt gtcagaacct ccatgactcc gagcacttaa cgtggctcat   132840
tgtaaatcac attcaagatc tgatcagcct ttcccacgag cctccagtac aggacttcat   132900
cagtgccgtt catcggaact ctgctgccag cggcctgttc atccaggcaa ttcagtctcg   132960
ttgtgaaaac ctttcaactg tacgtcttca tcctgccgac tattgccagt tgcagttttc   133020
cctgccttaa aaatggagta ttgaaatttt taactttaat ttctgatttg caaaatagtc   133080
atcttttgtt cttttccttc ttgctgttag ccaaccatgc tgaagaaaac tcttcagtgc   133140
ttggagggga tccatctcag ccagtcggga gctgtgctca cgctgtatgt ggacaggctt   133200
ctgtgcaccc ctttccgtgt gctggctcgc atggtcgaca tccttgcttg tcgccgggta   133260
gaaatgcttc tggctgcaaa tttacaggta ttgggaagag aaaccctgat attgatttat   133320
attgaaaatt tagcaggcca agcaaaacag gtggctggct ttttcctccg taagtatggt   133380
cttgacatgg tcaccgatag aaacatggaa acatctgcaa acttgccgtt actcgtgtgt   133440
ccgatctgac tgtttcttgt atttttttct agtctgccct tactaggatg aactgtacac   133500
atcagttcat ccttttaaa tgagcatgag gttatttgg gttgttaggt gttacaaaca   133560
cactaatgtg ttttttgtcta ttagagcagc atggcccagt tgccaatgga agaactcaac   133620
agaatccagg aataccttca gagcagcggg ctcgctcaga ggtaatgctg gaaacacagg   133680
tcgtccttgt gttaggacaa cccaggatat aaaggatata gatttgtacg ggaataaatt   133740
cacaggacaa gaaatcgatg tgccttatag gtgggtttac tgcagaagtg ccataataga   133800
accttcctac ttttaaaaca accagatctc actttctaaa gagtaaagga tgaccggcag   133860
gatcacgtct gtgacgtgag tggaggcagt ttgcactcct ggtggctgtt tgagaggtag   133920
catttagaat gcctgtattc actgtcctgt gatgagtggg aaaataggtt atcaggttta   133980
tcttagcaaa atcaaagcat gtcatctaat tgctaaacaa gagttggcaa atctgagaga   134040
cattactcaa tccttggcat gcaggactta catctgcatc ctgttgccat tttatgtctt   134100 caaagcatt aatcatttag ttgtgtttgc aaagtctttg agaagccttt gtcagaaatc   134160
cctacatctc ctatgtgagt gtatttccat gactgcagaa taagttaaac ttttaccttt   134220
ttccttccct tgcggggcgg ggtgggggc agggattgtg tgtgtgagag ggagagagag   134280
acagcagaga aggagaatat aattatcatg ctgtgtactt tgagctgaaa ctgcaaaaaa   134340
ggaaaaacac acaaaaatta ttatgctttt cagtctttag agtaccttgt ctattatgct   134400
tttcagtctt tagagtacct tgttgatggt gttttttaaat gggattgggc acaattaggt   134460
ggacagtttg ggatgatttt tcagtctgta gggccaagct cttttgtaat ttgcattatg   134520
```

```
aagttgtcac tctcatagca gatggcggga gataaactat tattacttt tgaccctaga   134580 cttagtcttc agtccagatg agggagatta aaagattata aatatcttgt gccagatgag   134640
gtgattttat tttgaaatga ccatgaattc ctatcagttg tcttactggg atatttgata   134700
gtggaatttg tgcatttgag tcttagatga tctgttttac attattaag aaagccttta   134760 ttagctttta tactgtgtat tgcctgttgc agtgtttgag tataaatgaa atttctggaa   134820
aatattaatg gagtacaaac tgtgatactt aaaagtaaac tagggcctgc atttgtatca   134880
tgacctgttt gagtattgat gagaagatag ctgtgaagaa aaaggtttaa acaagtgtat   134940
tttcctttaa gaagccacta atagtgcatc tccttagagt gtatatttct agaatcctag   135000
tgtgcagagt ttagactaag actaaaaaaa aaaaaaaaca aattatactg taatttcatt   135060
tttatttgta ttttagacac caaaggctct attccctgct ggacaggttt cgtctctcca   135120
ccatgcaaga ctcacttagt ccctctcctc cagtctcttc ccacccgctg acggggatg    135180 ggcacgtgtc actggaaaca gtgagtccgg acaaagtaag tgtccagcgt gtctgcatgg   135240
gaggcacagg gcgctgagtg cctctgtcac ctgtggcaga tacagagagt gcagaggagg   135300
tgccgtggac ccaaggagtt ctggcgctcg gctcggctca gtgaagctgt ggttagagac   135360 gtgggggggcc atcaaggtct gagggagcca agcagtgctg atgtgggacc cttttggtag   135420
gagtgtgggg tgagtagtta gtgggtgaat caaggaatag tcggccgtgg cctgcaggcc   135480
cctgactgca caggccttca agcacatgtc aatgccgtta gcctccctcc atctcctcat   135540
accttctggc cacctgtgag ttgcactgcc actgccagcc attctggtat gttgtcagca   135600
cctccactgc tcatacctca tggttaggga ccacctggag ccttggtaga gccttggtag   135660
agccttggta ctctactttc ctggacaaag ttcagcttat gaatatgaat ttagatttca   135720 aaaccagca gcccaagtat aagaaagcga aggttcagtc ctgccttctt aggctctatt   135780
cgctaagcac ctgccctgcc ctggttgctg gggagagatg agtaaagcag acaacccagg   135840
agaggatggc aaaggggccg ctaacccta gtggtttagc tatatttgga aggcctattg   135900
gaagttcacc aggtgaaggg ggaggctgtg agggtgccca ggcaggtaac agaagtccaa   135960
aggggaaaac ctgtggtgtg gtgagccgta tagccacagc ctgccggccg gcagccctct   136020
cagcctagtg cggtgttccc aagcactggc ctaggcctgt agctccaggg atgtgaagtc   136080
cccttgaacg ccgcccatca tgttcccctt atccatttt ttcttcccag gactggtacg   136140
ttcatcttgt caaatcccag tgttggacca ggtcagattc tgcactgctg gaaggtgcag   136200
agctggtgaa tcggattcct gctgaagata tgaatgcctt catgatgaac tcggtacggg   136260
gggagcagtg gaggcaagga atcctcagct tttcttgtga cttccaagtg ggatttgtct   136320
catcatcatg tgacccactt gttgacaaca catgttgggg actccagtct gggcagggac   136380
gggatgtcgg agagactcca ctctgaatgg ggccgggaag tggggaggac tccatttcag   136440
atggggtcgg gacatggggg ttatgctgat cgagacagaa aagcacattg tttcagccac   136500
attagaatcc acggaggtgt tgttttgaaa tccagctggc cccaaggctg ggtgtatggt   136560
ttgggatgag aactatctgg cctccactgg aggaacaaac acaggatgtt atcatctaag   136620
ctccatggcc aagacagaat ggaagtcaag gttgcgtatt tgccgtagac ttcaacacag   136680
tgtcgtaatg cgtgacgtca ataacttgtt tctagtgtct tggaagttga tctttagtcg   136740
taaaagagac ccttggatgc agcgagattt cctctactca cacctctgtt agatgtagtg   136800
aggttcttca ccccccaacc ccagatgtca gagggcaccc tgcgcagagc taggaggcca   136860
```

```
tgcaaagcct tggtgtccct gtccctcacc cgtgggcagg tcctgtgagc agtgggggg   136920 ccacctcttg ggtatggtgc agccatggcc caagcagggc ttcttctcag acctactagg  136980
acgggagaaa cctcctggtg ctttagccct gcgttgatat gcagcaaatg ggagggaagt  137040
gggcacctgg gaggacaaat gcctgtagag gccgggagtg acggcaggtg ttcatgaaaa  137100
gagaccttgt ggggagggca acacaacagt gtgttctgat gtactgaaga gctcaactga  137160
aaacaacagg agaattagcc caaaatccat ttactaaaat tgtttatctt tttttttttt  137220
tttgagacaa agtctcgctg ttgtccccca ggctggagtg caatggcgct atcttggctc  137280
actgcaacct ccgcctcctg ggttcatacg attctcctgc ctcagcctcc caaatagctg  137340
gtattaacag gcatgcacca ccacgcccgg ctaattttg tatttttagt agagacggga  137400
tttcaccatg ttggccaggc tggtctcaaa ctcctgacct caggtgatcc gcccacctcg  137460
gcctcccaaa gtgctgggat tataggcctg agccaccacg cccggcctaa aattgtttat  137520
cttaagattc atgcagtgaa agctaactta ctgagtgata aatttgctta gtgatctgtt  137580
tattaggttt tccaaatttg ctaattgggc tttgaacagc tgtaaaagtt ctgactgtaa  137640
aagaaagctt caacttttgg cattcatgat gcttttctga gtattaaact aagatagatg  137700
ttttacctga aggatcggcc accaatcttt aaatggctaa acaaagggt tgctaaaaca   137760 taatccaaat tgacataaga ataccattt ttccaaccaa aattttggca ttcatatggc    137820 tactttacg tatttcagct gcatttgaac atctttttca aactttaggg tggttggtgt     137880
atcactgagg tcttggatga cactttagct ttgattttgt ttttatgaat taaaattgtc    137940
ataccaaaat ttttatttca agcaaatcca agagcataaa aaattaaaat attacttaaa   138000
atactaagag agaacagata tatattttac taagcatatg ttgaatgaaa ttgttcaaat  138060
atttataaca ggcatagagt agaattttct taaaaatatt tttgatggta taccaatttg  138120
tattttctca gaaacatttg ccttattctt ttttctgttg tgttttttctt acctgattga   138180 aagctcataa tctgttgtta ttgttttgtta acctttaatg ctctgatttc aggagttcaa   138240
cctaagcctg ctagctccat gcttaagcct agggatgagt gaaatttctg gtggccagaa  138300
gagtgccctt tttgaagcag cccgtgaggt gactctggcc cgtgtgagcg gcaccgtgca  138360
gcagctccct gctgtccatc atgtcttcca gcccgagctg cctgcagagc cggcggccta   138420
ctggagcaag ttgaatgatc tgtttggtaa ttaaaattaa aatttatctt atttttaaaa    138480
agcattccag ggccagtata gtactttgca ccaagtaaat gtacaataaa ggcagtggat  138540
ctaatacatt gaaagcgttt acagaggtag ctaaagagca gcacgggtgt cctcggctca   138600
gaatttcttc ctgtgtgttt gccactttgc cattcattga catggtcatg gacatagggc   138660
tctaagccct tgaggaaggc tgggccagac ctcaggggag atgcagcccc aaaccacgtg  138720
cagtcctgtg gacggatgtg tagatgtgcc actgaggaac aatgtcttga gctttcatca   138780
gattctcaga gaattgcttg actgcctttc gaagttgatg catctgtgct cacgtttgca  138840
cccacccacg aggtccttct gtttcagggg atgctgcact gtatcagtcc ctgcccactc  138900
tggcccgggc cctggcacag tacctggtgg tggtctccaa actgcccagt catttgcacc  138960
ttcctcctga gaaagagaag gacattgtga aattcgtggt ggcaacccctt gaggtaagag  139020 gcagctcggg agctcagtgt tgctgtgggg aggggcatg gggctgacac tgaagagggt    139080
aaagcagttt tatttgaaaa gcaagatctc tgaccagtcc agtcactttt ccatctcagc   139140
ctggcagtaa gtcttgtcac cgtcaagtta ttgtagccat ccttcaccct cacctcgcca  139200
ctcctcatgg tggcctgtga ggtcagccag gtcccttct catctgcacc taccatgtta    139260
```

```
ggtggatcct aattttagag acatgaaaaa taatcatctg gaagtacttt atgtcttaag   139320
ttggcctgga catgtcagcc aaggaatact tacttggttt gtgttagtgc ttgtaattcg   139380
cccccagaat gtgtacacgt tctggatgca ttaaagtctg gcctgtatcc ttaaagggcc   139440
atcgctgtgc tgcctgccct cagcaaggac acactttgca gacccacaga ggctccgcct   139500
ccacctcaca ccaaagaaag ggaggagtcc aaagggcatc agtgccatta ctcacaaaat   139560
gataaataca cccttattct gaaccacgtg gagtcatatg gtttgtgatc cctgtccttc   139620
aggtttcagc ttagtgggga agtgggaaag tcagcgtgtg atcacagcac agggtgattg   139680
ctgctgatta tattatgtgc ctgctgtatg caggatgaaa tactttatat gcgtcatctt   139740
atttgactct cacaaccccc tgtgagatag gctctgttac tcccatttga caggtgagga   139800
aagcaaggct tagagaattt cagtgacttg cccaggtcct ctgagctagg aagtagccat   139860
tctggcattt gaacccaagg cctgctatcc ctagaaccca cgctctcaaa ttcaacctat   139920
gacagaggca agccctggtg ctgtgggagc cccaaggaag agcctctggc ctggtggcca   139980
cgtagcccag gagagatttc tacaggagcc cacagcgctg aaggagagag aggcagcaga   140040
gtaagggggc tttgtggcag agaggggact ggcactttgg ggaataggtg ggtcaggact   140100
gaatgtaatg gagccatgtc agagctgtcc ttctggaagg gcaagggcac ctggacgcgc   140160
tgcccctcag tgctttggac ggttccacaa ctgtgattca cacggcttcc ccaaacgaag   140220
gtacacgagt gggcattctg tgactcggta cttccctttta ggcctgtcc tggcatttga   140280
tccatgagca gatcccgctg agtctggatc tccaggcagg gctggactgc tgctgcctgg   140340
ccctgcagct gcctggcctc tggagcgtgg tctcctccac agagtttgtg acccacgcct   140400
gctccctcat ctactgtgtg cacttcatcc tggaggccgg tgagtccccg tccatgaacg   140460
gtgggttcct atcatagttc ctgtctgctt caccatgttt ttattttgtg ctgcctgttt   140520
gccaggtact aagctaggaa ttggggatgg agaggtagat aaaatatgca tcaggaaggg   140580
ctgggcccca tctcttactc tccaatatat tggagtctac actggaattt aactggaatt   140640
tgcttttttta gtcattttat ttagattttg aagtttcagc tttcatcaaa aatacctcta   140700
aactttatgt ctctgtgatc tttggtctta gctgttttat gtatttagtc ttatatgatc   140760
ataagattaa taacattaca ttcagaagat tatttgtttt ctgtcagagt taaaatgttt   140820
gtttttatac tgcattgtaa tattaacgta ctgtaaaata aaagtggctt gttcttttca   140880
aggaacagta tcctcaacaa gggtcattag ccacaatttt taaaaaattg gacgtcatag   140940
tttacatgtt agagggcgtt ttgaagcttt gtatttttaa attaaatgtt atagagtgat   141000
gttttcatgt ttcataattg ttttcatctg tgcatttgta gccaacttga aaacaaagat   141060
ccagggatta ctacttaaaa gccagacttc ttggaggtta tagtgatgat tttgatagta   141120
tcttgagccg tctcataata acctcagggt gagagatggc caacaggaga cagtcgaggg   141180
acttagaaat ctgaatgaaa tctgaagttc aaatcttcag acatatacca ctaaccaaga   141240
gattggtacc tcagtctagt attgtctgtt tgtctaaaat tggttctaag gaatctaggc   141300
tagtctgtct atcccttttca acttttgtga ggctgcacaa atgtaaaatg ttgaataaaa   141360
agcactgatg gaagtgtgta gaaattcttc tctttgttct gttgtaattt tagttgcagt   141420
gcagcctgga gagcagcttc ttagtccaga aagaaggaca aatacccaa aagccatcag   141480
cgaggaggag gaggaagtag atccaaacac acagagtaag tctcaggacc cattttttttc   141540
ttacatgttg ttcctccagg acttaaaaat cattcacaga gacgtgcacc gcggtgagtg   141600
```

```
tggactcctg gaagcgcacc gtagctccgc tgtgtcctgc tgctcctccc tagctgtcag   141660
ggaggctgta gtccattgct ttgccagctc ttttgtttcc gagtgaacac cttatccgta   141720
cacatgcggc tgtctctgac cctacagacc agctgggatg ccactggggg agcgctccct   141780 tcccccgca cttcccacac tctgcagtta ttctgagatc cttgagggca gggaacaggt   141840
ttgtcttctt tgtgttctca gaaattaatg ctcggcctct ggtcagcaag caacaacctt   141900
ttgttgagtg ataatgaata aataaatgtt tcccacatga gtattcagta acctcagtgt   141960
caggttcagc catctgtttt ggtggatatt taaaagaaaa ttccgctttt cctacagaaa   142020
aaaaaaaaaa tccaaatccc agtgatttaa gccagttata gacttagaca tatactacgg   142080
cttttcatgc actttcctcc caattctaga gtaggtattt tactaggaaa atggtggcag   142140
tgcctgttgg gaggaagatt ctttggccaa gtgtcttttg ttcttgccag gcccctagg   142200 ctgctggggt gcttcagctt ctttagccca gtgtctggtg gggaatggcc cctgttgcct   142260
gtcccacaga ggtgggggtg cctcacctgg agcctgtcca cacattttac acagcacgct   142320
tacctggagc atcaggcatc ttttccatgc tctgtggctc aggaaacacg ccttttcaat   142380
catgagtgca ccagtgcttt tgggcttttt ctccccgctt ttgtgcaatc ctggttgtgg   142440
atggagtttt cctgtcttta gtcttctgca tagtactttt ctcttctggt tcccggttca   142500
aggttttgta attagagaat gacccagaag caatggcatt ttaatgcaca gccaaggact   142560
tctctgaatt tgtatctcaa acctctgtgg gtccttcagg cttcagtttg tgatttcatg   142620
atttcttgtt gctacctaag gaatatgaaa cacccacct ccctactctg catcttccag   142680
ccgagtggca cctcaggctg tggatcctgt gcttctgtgg tgaggataag aatagtgcca   142740
accgtgtgga ttgaaatcaa tcagttaatc cctccatgta aagcacctgg aacggatgac   142800
agtcttgtta tgaatactca acaaatgcta tcatgatttt tagttagatt tccattgctt   142860
taaaacagtt gagacatctt ggcggtttga gttagagcaa cgggccctga agtgggttct   142920
gtttgggtga agatgattat gcttattccc catggccctc tttaggcaag agtgggaagc   142980
tttctttgtt tttttaatca cctcgatagg acgttacttc ttaaaggtca tccaataaat   143040
attaataggc cgggcgcggt ggctcacgcc tgtaatccca gcactttggg aggccgaggc   143100
gggcggatca cgaggtcagg agatcgagac catcccagct aaaacggtga aaccccgtct   143160
ctactaaaaa tacaaaaaat tagccgggcg tagtggcggg cgcctgtagt cccagctact   143220
tgggaggctg aggcaggaga atggcgtgaa cccgggaggc ggagcttgca gtgagccgag   143280
atcccgccac tgcactccag cctgggcgac agagcaagac tccgtctcaa aaaaaaaaa   143340 aaatattaat aaagccaact cgttagcgtg gggcttaatt gcttaagtcc aatgagaagt   143400
ccttctctat cctaggaagt tgcccaaact gtagaatctc gtggcctgtg ggtaatagcc   143460
acgtaataca cactcactgc ctcaacaaat catatttag taggtatgat attctagact   143520
caagacacca ttctgtggat cttcccaagg gtgtgaagtg tccacagcgt ctgccttggg   143580
agtttccatg cccaccagaa ccatgcccca agcccctcaa gcactctgac ctaggaaagc   143640
cagtgaagca aggatgacaa catggcccctt tgatactagc tgagggacag acacaggtcc   143700
tgggagacca gagaaagacg aggggcagag gaggtgtcct aaaggaagtc tgaggctgag   143760
gagccacagg atggcttcca gctgtcacag gctgctgctg gccttatcac agagagtggg   143820
ccagagggct gggaaccaag gccagagctc aggttcagga ccattccagc aatcccagca   143880
gaaaatgggg agaattgtat ggtataggcg gatatgaagg tagaatctgc aggccttcag   143940
tggccaactc agagtctaag tggattccac agttacagct tgagcagctg gttgtaggtc   144000
```

```
atgctttcta cactgggcat ataggatgtg ttttttaaaa agtcctctct taaccgttgc    144060
ttgtttagat cctaagtata tcactgcagc ctgtgagatg gtggcagaaa tggtggagtc    144120
tctgcagtcg gtgttggcct tgggtcataa aaggaatagc ggcgtgccgg cgtttctcac    144180
gccattgcta aggaacatca tcatcagcct ggcccgcctg ccccttgtca acagctacac    144240
acgtgtgccc ccactggtga gtctgctcgt tccttgcaga agaccaagta cggtgaaagg    144300
caccggtagg ccctgggctg ggcacacgtg agagggcggg acagaatccc cgcagcccag    144360
aggctgcctg ctgtggttct ggtgcccact gtggttctgg tgccaggctg ctttcctcag    144420
gcaccacgtg tggaggtcgc tagtagaaat actgggtttt ctaaaatgaa ctgaggccct    144480
acatccctaa gagattagtg ttagacctga ttctagagca actagaccac tttgcttaat    144540
agcagaccag aaaccacacc ccctcgagtg agtgagattt cctttggag ataattcatg    144600 tttttctaca cagttttgca gttgtcttca gaattggttt aaagtaggtg ttattgccag    144660
gcgcagtagc tcatgcctgt aatcccagca ctttgggaag ccaaggtggg cggatcactt    144720
gaggtcagga tttcgagacc agcctggcca acatggtgaa accccatctc tactaaaaat    144780
ataaaaatta gccaggtgtg gtggtgtacg cctgtaatcc cagctactca ggagactgag    144840
acaggagaat cgcttgaacc caggaggcga aggttgcagt aagccgagat cgcgccactg    144900
cactctagcc tgggcaacag agcaagactc cgtctcaaaa aaaaaaaagg taggtgttat    144960
tgatcagaac ccttgtttca gataacatga ggagcttagc ttgaggagag tgagggttga    145020 tggagggga ctgacttctg cccagtgaaa tggcatcatc tcccaccagc ccgctgaaat     145080
aagatgatgg ggcctgttcc ttagggcctg cagcatcctc aggcaggaaa gaaaggccga    145140
cctggcaggg tgtgagccag caggtgtagg tcagggagaa tggagccagg tcccagggaa    145200
gaggcttgtg gctgcctgag aagggtgcgt gcctgcctgt gtgtgtgtgt gcacgtgtgt    145260
gtatgtatgc tggagagtct agggaggctt gctccaagga cgcagtattg tttgatcctg    145320
agagataagg attctgccgc agggaatgaa ggtattccag atggcgggct tattccgaag    145380
aagaggccag tgcctggcgg tgctggaagc agttgcagaa cagggagttg taggctttcc    145440
tgggaagaga gcagcagggg tgctggagaa gcaggccaca cttgctgcat ggggttgctc    145500
tcggccccac tcttggtgca cagcgagtca ctgtgggttc attagcatct ggttatgaga    145560
cagtaactgc tcctttggag gggctcgtgg agaccatgca ggagggcacg gtcttgaggt    145620
catgccgtcc agagcacacc tgaggatagg ccaggacggg ctgcacgctg taggtaaaat    145680
tcctccagca agctcttcac tggcattgag gagttccctg agtgcggtca tctgaaaggc    145740
agctgtaaca ggcactgcag tctctccctg ggtgggtacc agagaggagc atagggagc    145800 ataaccgatt taaagagagg gctttcctgt ggtgaggtaa gagattagct ggtcattatc    145860
atagagcccc ctctgccttt gtgcagatgg gctgtgggaa tcctggggtt ccgttgggtc    145920
ctttgtcacc tcactgaagg catgtaagct gagctggcca gaccgtgagc tgatcctgcc    145980
acttgaacag catcaagcct gcctctggat tcttctgtgc atggcacttg tctgagcacc    146040
tcacgcacag agaactggac ttcagagttt acagaaataa gctgtatggt tcattttcat    146100
gcctgcttgc caataaacat atctgagctg aacctcattg aacgcctgcc tttattctag    146160
cacagcacct gctgtttgtg ggcgaggggt gctgtctcta actcctgcct gcttctccca    146220
gcactccctg agtggggtgt gccagcagcc tcaggatgag gacaggaagt gggagggcag    146280
agcagatttg ggagggccac ttgatgggga aggaagtccc aggaagcagt tggagctgtt    146340
```

```
ttctggggga gaaggtgcca gctctgggac agtgttgggg tagtgaggag ggagcccagt 146400
ggagagaagt cgggcttcct gcttcctcac agtatgtctg tcctgactca actcggatga 146460
tgtcacttcc ttttcatctt ctcaggtgtg gaagcttgga tggtcaccca aaccgggagg 146520
ggattttggc acagcattcc ctgagatccc cgtggagttc ctccaggaaa aggaagtctt 146580
taaggagttc atctaccgca tcaacacact aggtactctt ggggcctctc cttcaggtca 146640
ccattgtcgg acatctaccg ggaggaaatc cagagccccc agtactggga tcttctcatt 146700
tgactccaga aaagatttaa gcatgataat aatacaaacc tatgtgaata cattttgcag 146760
tgttggcaaa actccttta tactgagaaa atagatccca gttcctgtgt tttgtggctt 146820
gaatcccagc tttgtgtatt ccgggcttgt ttgaagtcag gaaaggttca tgtgtagtgg 146880
acaacgtgag accaaattct gccttagatt ttgcatttag gctaaacagt ggcagcactt 146940
gtctcagaat gttttcttgt gttcaccagt ctgatcctgt tgtgtctcag tggtccattt 147000
tctcatatgg gaacaagcag acgggagcag atgagtcag gtttcttggc actcgccttc 147060
cccagagcct agaggcagca tggggagaaa gcaggcttgg ggctcagaca gtcctggtct 147120
gcttccagcc ctcctacctg agcagcgcag ggcaagtccg tctaacctct agagaccctc 147180
agttttgtca tatgtaaaat gggggtcgtg tctatttcat agaattgttg cagatttaga 147240
aattacattt ctaaacaaat gttacccctt atttctaaat aagtgtctaa atgaataagt 147300
caccactttt gccctattt gatggcaaga ggtgtgatct tgtggtggga ctgtaatcag 147360
tcagttctca gtgactgtgc cctgctgtgg tgtttcctgg aatgttcctg tcttgtccta 147420
gaaagtctgg caggggcacc ctgactccac tgtccagtcc tctccccagt ccctcgggct 147480
tctgcagatt tgaggcttgt ttggatccca gaaggttgtg gcaggagaca ccttgcctct 147540
actttccect ttataattca atgtccaaag agagccctga gcaggtacct cacgccagct 147600
gcctcacgga gctcctcctc ttcctggctg tgaggatcgg tatcagtggc ctcctgctct 147660
ctcccccttg cctaacacga gcaccttgc ttacttgggt gccttgctc ttgaactgcc 147720
catcggacgt gcgtgaccca agactgtgcc gcagtccttg ccttgtctgt gctcattttc 147780
tttgttcatt ttttcctg taacgtaaat tgttatattt gtctgtatct gtgtctgaat 147840
cagtcctgca cgctctcctt ctctctgtct cttgttcttt ctttacccg tttatcacgg 147900
ggaccccgat gtccattgct ctagttctcc tgtcctaagc accccatccc gtctctctgg 147960
ccttaccaca agtggcgtgg ctgcctcaga catcatgatg gggacatgaa gcacagctgt 148020
cagaaacaac tgttcgttag atacactcga atgcagctca tcaataggga tggagggtct 148080
gtcggatgta ttttcactga atccccgttc ctaccttgat acactctttt taatctattc 148140
ttctagacag gtcagaggaa ccattacttt gacttttaaa ttttttagcag ctttattgag 148200
gtagaattca catactacag atttcaccca ctctaagcgg acagcttggt ggccattagt 148260
tttatccaca gagttgtgca gccagctgca cagtctcagg gctggactcc agggaagatt 148320
ttagcccatt tagtgagtgg ggcagaagtg gccctggccc tgcacgaggt tgcctgcatg 148380
ggcgtccctg ccctgtccct gtgtctgctc cactgggggt tgaccaggct gccagggccg 148440
acttgggcct gtgccacctg cctctcatgt gtctcggaca gtgcagccga tgtctatact 148500
tcggtttcct caatgatgaa atggagggga tagtgttccc cgcatcatag aactgtgtga 148560
ggtttaaggg actcactgcc cttggcgtgg agccttctcc aggggccgtg ctgtgtcggc 148620
gtagctgtca gctctccgtt acaggcttga gaagggttga cactctctca tgtaacattt 148680
atatttctag gctggaccag tcgtactcag tttgaagaaa cttgggccac cctccttggt 148740
```

```
gtcctggtga cgcagcccct cgtgatggag caggaggaga gcccaccaga agtaaggcca   148800
caccctgtgc tggttggcac atgggcagtt atggccgctt gcaggccttt ggtggggaat   148860
aaaataaggc agcaagctgg tgttctttt ttctcttacc ttattttga aagagtagct     148920 gaatggtgtc ttgactgata ttccagagca gggacaaagc ctgctgaggt ctggggctg    148980 cgattaccaa tggctggaat gcattttatt acggtgcatt ccatgttaag gatcaatacg   149040
attgtgccct ttctggaaaa tatcttttag tttatcaata ttcagaggag tgtaggttga   149100
attaaaatga aaaggcactt tataaaggcc atgagtagta cctggtttca tttttctaat   149160
gtcttgcaga gattttatca ggcttcttga agtgttcacg tacattacgc taacacgata   149220
ttaataataa ctgtgctctg gtacagcgga gccagcagaa tgggaagttg tggaatgcag   149280
gcccttgatt ctgatagaag gtgtggtttg aactcacaga atgacagtt tggagggtag    149340 acatatgtca caagtcatca agattgtctt taaattcatg catagaagct aacagggtgt   149400
cataagcaag gcctgtaaaa tgtatgaggg aattcaaaga taatttatta aaagtaatt    149460 catgtttgga gttttgtgcc caaggagtc cttgatttga aaaatgggct tttgcccatc    149520
agattgtttc agggcccgtg tgtgcggagg ccctgccttg tgccccgtga gctcagcctg   149580
acagaaatcc tttggtagca cttaaggctc ctcttcctcc cattgaggca gggaagactc   149640
tgggttctgc aggcagaggt ggttgtgggt gtcttgctgc tcttgttgac atgtgggctc   149700
tccttccagg aagacacaga gaggacccag atcaacgtcc tggccgtgca ggccatcacc   149760
tcactggtgc tcagtgcaat gactgtgcct gtggccggca acccagctgt aagctgcttg   149820
gagcagcagc cccggaacaa gcctctgaaa gctctcgaca ccaggtttgc ttgagttccc   149880
acgtgtctct gggacatagc aggtgctggg gacagtgggt tccccgctga agcgtccagc   149940
agcttcaacc aggccgtttt ccttcattgc tagaattgaa acaccgtcc gtgtggcctg    150000 tgcaggagat gcagacccaa aggtggcctc ctggtcagtg agaagctgga aacgtgacag   150060
gaactgacgt ggggttattg agcatttagg ggaagacgtt agcagagcag gaatgagcag   150120
gcaactagta gaacacccac ttaagggctc acggacaggt gctcacttag gaagtgagtt   150180
tcatttggta ttacaccagg ttcctttagg caaagcggag ggaaagttct ggtgtttttc    150240
acttgtaaga ttttgaagga aacaaaacac tcttaccctt ttttctaaaa tgtaggtttg   150300
ggaggaagct gagcattatc agagggattg tggagcaaga gattcaagca atggtttcaa   150360
agagagagaa tattgccacc catcatttat atcaggcatg ggatcctgtc ccttctctgt   150420
ctccggctac tacaggtacc tgaggaaag ggtgcggggg agcggttgta cttgggctag    150480
aatgagagaa gactggcatg ctcaccacac cagtgatgcg ggaagacctg agtgtggtct   150540
gagttggagg ctgtggtgct aaatacgctg cccctttcat aagcaggagt cttagtcagg   150600
cccagggagg aagtaaaatc tggaaatgaa tgagaagcat tctctcctgc cagtcaagaa   150660
atgagaagcg aaagaattct cacgggctgt aagaccagca ggatttaaaa gttgaattag   150720
ttgcttatgt taagaactca accaagttca tctacacaag ctgaatctcc agcttttcct   150780
aagaaaccat gtgtggcagt ggctgcaggg cagggcacag ctgggcctga gcaccccgct   150840
ccctgcacct ctcccctccc tgggccctgc ctgtcactgc ccactctccc accaagcctt   150900
ccggttgtgt gcctgcccta tcacaggcat cggagcttgt cacctggttt aaaagaagag   150960
agttgtgtgg ggatttggga tgcacgtttt tcactcaaaa gtattttagc gtagagctct   151020
gtgattccgt agctatttag gagtttaagc accttgaagg ctttaattgc agaaagttct   151080
```

```
atgtggacgt gcaatgtgtt atacgcagtg tctatgagac tcaaatgttt attagggcgt   151140
tgaagtaaac tgagcacttg gagggccatg gatccagcct tcaaggagct cataagtcag   151200
gaggacccag gagcaatgac ctgtcataga aggcagaaaa gaggggcaca gaggtgggtg   151260
ggaggcatac acaggcagct cctggagctc caagggagc aagtgcttcc agggaagggg   151320
gcgtggaggc ccctttggag gaggcaagtt gatctggggt ctggcagagg gttagctggg   151380
gacatttagc gggaggctgg tgcccgggaa ttgggggat gcccagcaga aagacatgag   151440
gaggctggcc tggggcgtgg ggggtgtga aaggttaagt gggggcatta tcctgctccc   151500
gctcctgccg gctgtatctg gtcagcctgg gcaccgaggt ggggttctgg aaggcactgt   151560
tcaccaaaat gcttatctgg gtcccccaga gagcttgcct gcctggactg tcggctcgcc   151620
tgcaactgct gactcctaag cttttgcagc tcagcccaca accagttcct attcacagag   151680
gtgggagctg aggggtgaca agtgactgct gcagtcttat ttgtcataga gaaaaagtga   151740
cagagtccag cttgcccact ggccctgcca gcttaactgg ttataaagtg acaaatcccc   151800
aagacccaca gggctctgca caacctgggc cctcctgcca gtggcggcga gggcaggtgg   151860
ctcacggctg ggtgcctgtc tgggcaggag ctgggctggt atggggtggg cctgcggccc   151920
tgcccccctg tgcagatcaa gactcagggt gctggtgttc acaggtgccc tcatcagcca   151980
cgagaagctg ctgctacaga tcaaccccga gcgggagctg gggagcatga gctacaaact   152040
cggccaggtc agtctcgcgc ccccgccgcc tggcctctgt ccgtttctgt cctcagactt   152100
tggcgcttga cacacccagg agaaaagctc agtgcacttt ttaaatgaaa ggaagttttc   152160 cttttttta aaaaaaatt taatgttcat tgtttttatc tgttttattc ctaggtcccg   152220
caagcagagg aagcattagt tttgtttta tttatgttct gtattccaga aagtagttaa   152280
gagacctcac atgtagcgat agagatgtgt gtaagagaca gtgagagggc gtgacttgga   152340
cttaagcaag gaccgtgaga cacaaaagg ggggtgagga cagagtggag tcagctgaaa   152400
tgctcaggag gaagtagacg ccatgaaggg ccatggtatg ggggccgca ggcgtggccg   152460 tgagtgtccc tggggccagc tcttgggggg ctccctgagt gtccctgtcc ctgtggccag   152520
ttctgggtgg gagccccgtg tgcaggcaga cagctcggcc acttcctagc aggtcacatt   152580
ggtctgtgct tctgtttcct cctcagataa gtgaagggat tcaagggtct gggtgtggtg   152640
gctaacacct gtaatctata acattttagg aggctgaggc aggaggctta cctgagctca   152700
ggaggttgag gctgcagtga gccatgattg caccactgca ctccagcctg gcaacagac   152760 cagtactctg tcccttaaaa aaaaatgtaa acagaaacgt agggccattt gcatatgatg   152820
gcacatggcg tggagcccta caggtgtatg ctgggcgggg cccggctgtg ctggccgact   152880
tgcacctttc cctccacccc ggtgctgtgt ctttcgctca ccgggttcct gatttagtga   152940
aagcagttgt gcaggacagt tctctttgta gcttttgttt ctgtggaaat gggtcagaat   153000
atggtgttta gaaacactta tgagctctga gagtttcctc ttctgagttc ctggcctgca   153060
gccttcacag cagaaaccct gtgatgtcac aagcctgttt ctgttccctg ctctctgcct   153120
gtactgtcct gttttgtgcc tgccggtttc agtgacagga agcagggagc tactggacca   153180
gcctgtattt ttctagacat agttggaaaa agaagtccca ctcttctgtc ctttcacctt   153240
tgacagatgt ttccaccca agataagtga aaatgaccaa taggatgcac tgtatttttc   153300
atgaaagtgt ttctgaaggg caggctgaga gtgagaggcc tggggctcac tgggtgcctc   153360
tggccttgtc ctgggcccag ggacactggt ctgtgcccga ggtattccct atcccccaa   153420 ccccgctgca tttggccaca tccttcaatg tttgcgttgt gtccagcgtc cgcaaaccaa   153480
```

```
ctgtcatggg atcatactgg ggctgaagta cggtcccacc cctgccctgt ctggggctga    153540
agtacagtgc caccectgcc ctgtctgggg ctgaaggaca gtgccacccc tgccctgtct    153600
ggggctgaag tacagtgcca ccectgccct gtctggggct gaaggacagt gccacccctt    153660
ccctgtctgg ggctgaagga cagtgccacc cctgccctgt ctggggctga aggacagtgc    153720
caccectgcc ctgtctgggg ctgaaggaca gtgccacccc tgccctgtct ggggctgaag    153780
gacagtgcca ccectgccct gtctggggct gaaggacagt gccacccetg ccctgtctgg    153840
ggctgaagga cagtgccacc cctgccctgt ctggggctga aggacagtgc caccectgcc    153900
ctgtctgggg ctgaaggaca gtgccacccc tgccctgtct ggggctgaag gacagtgcca    153960
ccectgccct gtctggggct gaaggacagt gccacccctg ccctgtctgg ggctgaagga    154020
cagtgccacc cctgccctgt ctggggctga aggacagtgc caccectgcc ctgtctgggg    154080
ctgaaggaca gtgccacccc tgccctgtct gggatgttta gccectagat gccactggac    154140
tgagccgcta cttgcttttg ggaaagaggg gtggggggtta gggtctggg cgaggggagt    154200
gcagggcctc ctccttggcc tgagagctgt tcatacagac tcctcgccca ctccctgcag    154260
ggtgctgggt cccagggggg aaatggccct tggtgccaag aacgtgagtt ggggctagtg    154320
ccagtgatga tggagaacag cttttatgg gcacacagcc cacagcactg tgccaagtgc    154380
tcgaggcttc ccgagaacca ggcagaaagg aggacagtcg aggtgtgctg actgcgtggt    154440
ggctgcgtga tctagagcgc gggtcacaaa ggcgcgaggg agctctggcc ttgggtttac    154500
cgcaatgact gccagtgcgg gagactggaa aaggaatctc acgtattggt tccgtgtttt    154560
ggggactcca ttcagatgtc acttaggagt gaaagcatcc cttcgtagag cctctttctg    154620
tgtcaccctc ctcagctgct cctggggttg actggcccct gattcatgcc tttagcatgt    154680
gctggagctt cccagcagct gtccagcccc tgccccaccc tctctgtggg ctcccttgcc    154740
cgtaacctgg ggtgtctgaa cgacccttgc taagggcag actgttagac ggtaggcatg    154800
tgctgagtcc cagtggccac acccacccac caggagcctg gcactgtggc cgcagcactg    154860
agcagtgccc cgtttctgtg gcaggtgtcc atacactccg tgtggctggg aacagcatc    154920
acaccctga gggaggagga atgggacgag gaagaggag aggaggccga cgcccctgca    154980
ccttcgtcac cacccacgtc tccagtcaac tccaggtttt ccaatggcct ttttctttt    155040
aacagaaatt tgaaatttct tatcagtcat ttgatttgtt tgaggtgctt cttgaaatga    155100
gcctctcatc tcatgtactt ggaaaatacc catctcgcat attccacagg aaacaccggg    155160
ctggagttga catccactcc tgttcgcagt ttttgcttga gttgtacagc cgctggatcc    155220
tgccgtccag ctcagccagg aggaccccgg ccatcctgat cagtgaggtg gtcagatccg    155280
taagtgagcc ttcccattcc cctcacacct gcacgtgcca cacgcaccac acacgccaca    155340
caccccacac acacacaccg cccacacaca tgccacttgc acacacaccc ctcatgcatg    155400
caacacacac acaggccaca cgcaccatag acaccacaca cacatgccac atgcacacac    155460
atacacggca tgcaccatac acacaacaca cacagcacac atgccacaca cacacgccac    155520
accacatgca ccacacacat gccacatgca cacacactcc acatgcatgc accacacaca    155580
cacacacaca ccacacacac cacatgcacc acaccacaca ggttacatgc acacaacaca    155640
cacatgccac gtgcacacac cccacacacc acatgtatgt gccacacaca gcacacaacc    155700
acacacatgc accacacaca tgccacatgt gcatgcacca gacacatggc acacactaca    155760
cacacgccac gtgcacacac cccacacaca tgtacgcacc acacacatgc cacacacaca    155820
```

```
tgcaccacac acatgccaca tgtacacaca tgtatataca cacccacac cacacacaca    155880 ccacttgcac accacgcaca cacaccacat gcgcacacac acaccacata cgccacatgt    155940
acacaccata cacacaccat acatgcacca cgtgtaccac gcacccacac agacacagca    156000
cacgcataca ccacacacac acgcacacat gcgtcccgca cagtaatgtc tcttgggtgt    156060
aagaacacga cttgccagta gtagcgttct ggatgcgttg cctggattct aacagcgcga    156120
ttctcccctt gccctcctgg ttttccacat ctccagcttc tagtggtctc agacttgttc    156180
accgagcgca accagtttga gctgatgtat gtgacgctga cagaactgcg aagggtgcac    156240
ccttcagaag acgagatcct cgctcagtac ctggtgcctg ccacctgcaa ggcagctgcc    156300
gtccttggga tggtaagtga caggtggcac agaggtttct gtgctgaagc cacggggcc     156360 catctgcctt gggacctggt gttggccaga ggtgccgggt gcggctgcct ccttccaaga    156420
gttgacccga accggactcc acggcccacg tgagctgcag tgcttctcag atggaggggg    156480
ttcagcgacg gtcagtgcca ttcacaggtc actgtgatgt gggttgtggc ggccaagcca    156540
tggtttgggg tcccgtatcc ctgggcttat gacatcattg tagtagccca tcccacaga     156600 accacggtgt gtggtggcgc tgaggcatcg tagatggtgg aaatgctact ggcttcccca    156660
tgctctgccc tgaggcctga ctgcctcact cccttctca gttatgttcc aggcccccg      156720 agcttcctgg ctggacagct tctctcctgg gggccgtttt gtcacagtga ccctgtgttt    156780
ctagtcccaa atctgggtgc tatagtctct ttttagcgtg gtggttgtct tagtcttttt    156840
tggctgctac cacaagttac cttagactgg gtaatttata aacagtggaa atttacttct    156900
caccgttctg ggggctggaa gttttcatgg tcaaggtgcc agcagatttg gtgtgtgatg    156960
agggctgctc tctgcttcat agatggcatc ttctggctgg gtcctcacgg tggaaggagt    157020
gaacaagctc cctcaggcct tttagaaggg ccccaatcca caagggctct cccatcatga    157080
cctcatcacc tcccaaggcc ccaccttctt gtactgtggc actgcaaatt aggtgtcagt    157140
gtaggagttt caggagggat agaaacattc agaccatccc agcggtcaag tgttcatcct    157200
cttgagttcc tccttattct gcttctggtt tatcaggatt cagccagtgc agcatggtac    157260
ctgtattctg tggcacatca ccacatggta tttgccaagt atccatcacc tgcacacgtg    157320
aaatcattgc ccgtgggtcc cgacatctgg cgaagcatat tcaaggatgg cagaactgtc    157380
agagctggca cctctggttc cttgtcatgt ggcattacct agtaatccat tttatgatag    157440
caatggaaac tcatttcttc aacaaacacc tgagtggctg ccgtgtgcca gccgtctggg    157500
gcccttggtg agaatggcat ggtggtgccc atcagggcct gcctagcccg tgctctggac    157560
gggctcctgt gtgtcaggaa cgacaatgct gtcatgacgg tgaatgattt ttttttttgc    157620
catcactcca gccgctaaca tttgcggagc tcttcctccc gcaccccac ctgacaaggc     157680 caagggtgac cttggcccca ccctaggcgg ccaaggtcag aggttagctg gcttgtctgg    157740
gtcacacaaa atgcagcaga ggttgaggtg agcacatgtc cgtgacctgg agcctgactc    157800
cctctctgcg agtcttgact gctcttgcct agactctgtc ctccccgagc ccaaacgcca    157860
gtcatcttcc cttgtgggtg tccttcagcc tggtgccatg ctggtgactc agcagccgtc    157920
cagggagtgg aaacaattga gtgtgtgggt tccctgtgtg ggcatctctc ttcacggcga    157980
acaccctctg ggtgttgccc acgcgatgtc aaagcggctc ttggaagggg tccttctcct    158040
ttgtgggaag tttcagctgc tgggctaact tgaattgtaa ctgtggtttt tgctcaggcc    158100
ccagatcccc ctaggcaagt gttgtgccat cagtaatcaa atgagaaata atcatttga     158160 aaagcagatc ctaaggcagg atggtcatgg acactcactc ccagctcttt gtgcactcat    158220
```

```
gctttctgga agatggccat cctctgtgaa ggttttcagc gcgtcatgct tggtacccac    158280
gtatccagag catgtcgttt tgaggtattt gcccaccgtt gtgaaatccg tgccaccgca    158340
gagcaggtcc tgatgtgggg ctttcagaag tgggacctgg ggccgtacgc agtccttagg    158400
gaggggccgt gtggcgttgt gcgtgtgagg ggatagcaca gggtgaggtg ggggcccaag    158460
aaggaagtga cccacaaaga acagcctcct cttttggtcc ttgttcctgg gatggctggg    158520
agtggcttct gtgtcgtccg gccatttccc ctgcggagag gctcctacca ctgccgagaa    158580
cctcatcatt ccacaaaaac aagaggccgc ctggccatcc agcgctccat gggaattctg    158640
tgtccccata gtcttgggct gaaggagggt gacattcctt gctgacttct gcagggtct     158700 cctcactgtt aaagagcaga ttgaaagtga agaacgtggg ctaagtgttt aggtcgatat    158760
ttaaccctgc taggttttgg atactaagtg aaattgaggc cattttggtt gaagttgaca    158820
gaaaccacta tcagggatcc ccaagactac cccaggcttt tctagaaaga ctctcagcta    158880
agatgtgtta tggtaaaagc acacaaaaca aaatcagcaa agaaaattag caagggcaga    158940
ggcccatggg gcgatgtccc gaggacacca ggcttgagct tccagaatcc tctcccagcg    159000
gggtcgtgca ggacgcactt aactccccgc acagtgagcc gtgacagcgc gtgtgcagtg    159060
tcgtcgccag gaaagcacac tagagactcg gtgccagggt ttttactggg ggctgggcac    159120
atgggcaccc tctgcctgcc tcgtgcccag actctggact cccggaggga aggcaagttc    159180
tcagcaccaa ccctggtgcc cacacaagca gctgagcaca gggagcccct cctcagtgag    159240
gatggtgggc accgtcccaa caccagccag ggggccagcct tgcacacagg cctctcagga    159300
tggtctccgg cctgctgtgt agtctcttct gcacacaagc gtgagggcag cgccccgcc    159360 tcggctgtgg ggaggagcca ctgggacgtg agctctggtg gcatgcagca gcttttgtct    159420
gtgtgtgcct aggacaaggc cgtggcggag cctgtcagcc gcctgctgga gagcacgctc    159480
aggagcagcc acctgcccag cagggttgga gccctgcacg gcgtcctcta tgtgctggag    159540
tgcgacctgc tggacgacac tgccaagcag ctcatcccgg tcatcagcga ctatctcctc    159600
tccaacctga aagggatcgc ccagtgagtg ggagcctggc tggggctggg gcggggtct     159660 cagaatgagc tgtgaaggaa gcagcatcac cctctccaag tgcccaggct cctggccaga    159720
tggcaggcca ggtatcagtg ggaacccagg tgggtgccat ggctgaggtc agtgagacgc    159780
aagagcacag gtgcgtccta gaggcttcct cgggcacctc cagcgagctg gagctctcgc    159840
ctctgctgct gtctcatgtg gcgcttagca cactctccca cgtgcccatt cctgactctg    159900
ctctcgaggc catcggctct cattctctgc tcccagaacc ctgttattac ccaggctagc    159960
ctcctctctg caccttcccc gccctggccc agtacctccc tcttgtttcc actgtgattc    160020
cgacctcacc ttatcttaaa gctgctggac ggcaggttct gtacacacgt gtccttgaca    160080
aagcacggct ggtgccgcaa ccctcagcg agcaagtcaa gctcttcaca gcgatgtctt     160140
acaagcgcag agggctctgt gacaccctgg tctcaccgcc actcttccaa agtcgcagag    160200
gctttagcag agatgggccc agcctctctg agtcataggc ttctgcacac gggagctgtc    160260
tttagaggga gggtggaatt tcatcagcca cccacatggg ggagttgagg gcaagaatta    160320
ggagcaaaga tgggaagggg tctgggagga atggccagtg atccccttg acaagtgggc      160380 aggaaacggg ggctaggtca aagttgagtg gaagacctgg agggagacgg gaaggtctct    160440
gtaggcacag ttcagacagg agggaggtgt gagccagggc acatgccggt ggccgtctgg    160500
caggatttgg gacatgctgg agcagggaca gcggctcatc aggggccatt gccctcatcc    160560
```

```
aggccagagt gtcacaagcc cgtggggagg cccttctcgc ctgtcatcct tgctgggcag   160620
tgggtgctgt gctagcagga caggcggacg gctggcaact gtctctgcat ccctggagcc   160680
tggcataggg ccaagtcaca cggggcacag gcctgcaaat caggcacata tgttggtgca   160740
gtgacgtgat tttgggggc agccccagaa caggccccag acacaggcca aagccctgcc    160800
tgtgctggtg tgttgggctg ttctatggct cttgctgtgg gcatggagga ctcagggaag   160860
gagagttgag gtggtccagg agttgcgttt gggatgcaga gagcttgtgg catccaggta   160920
gaaatggtgc gtggggctga cctcagcacc atgggcagag gggccgtgtc acgtgcctcc   160980
gaggtggagg tgggaccacg tggtgacaga tatacgcatc actgggcacg ttttgtggg    161040 tgttgggggg catcgtattg gctcctctgt tcacagtggc cactcattca gtccctggct   161100
accaggtcct cactgtgcca tggggaaggc cggcgctgtc gggggatcac agaaggcagc   161160
acgtcatgat ggcatgtgcc atgaaggaaa agcacagggc actcaggaag tagaggggac   161220
tggcctgggg tgtgggaatc tagggcctcg ttgggaca gagagaggaa gtgtgtggtg     161280
gccagcatgg aggtggccac aggggaggct gagttaggcc gagagggcag ggcgttgggg   161340
aggtagacgg gctcagccac tcagggagtg gtcaagcaga ggctgaaggg tcaggccagg   161400
ttgcaggggc ctgggggagc cactcagggt aggcgctccc gggagcccgc ctggcccata   161460
gctctacact cccgcgtggg gccggacatg ctgtgaagcc ctctccacgt tggatggggg   161520
tggctgagcc tggatgctgt ctcccgtttt cagctgcgtg aacattcaca gccagcagca   161580
cgtactggtc atgtgtgcca ctgcgtttta cctcattgag aactatcctc tggacgtagg   161640
gccggaattt tcagcatcaa taatacaggt gagtgggccc tggctgtctt cctctgcaca   161700
cggggagtgg gcttcccttc tcttttcctt gcaggatcat accagtgggc cagttttgac   161760
ttggtcggga ggaggcatga acacctgaga ctgtgcagcg attctttgac acagaggcct   161820
ttctccctgt gcagatgtgt ggggtgatgc tgtctggaag tgaggagtcc accccctcca   161880
tcatttacca ctgtgccctc agaggcctgg agcgcctcct gctctctgag cagctctccc   161940
gcctggatgc agaatcgctg gtcaagctga gtgtggacag agtgaacgtg cacagcccgc   162000
accgggccat ggcggctctg ggcctgatgc tcacctgcat gtacacaggt gagcatgtac   162060
acggtgccca taaggccagc ccaagtcctg ttcaagggag gcaggagcat gctcactcaa   162120
gggacctcga ctaggtgccc tctgatttca cacttctggt gttgcccaa gccgccccca    162180 tcaccttgca agaaaggctc tggagccccc agggctggag tacctggtca gggttgaccg   162240
tccctgtggt cactcatccc atgtggctga gctgggctgg gtcctgggca agcaaggggc   162300
tgatatcacc tgcttcaga tctccaggga ctcactggac ccctgtgtac aaagcactgt    162360
ctacagagcc tattgggttg tatagaggta accttcgtac tgaacacttt tgttacagga   162420
aaggagaaag tcagtccggg tagaacttca gaccctaatc ctgcagcccc cgacagcgag   162480
tcagtgattg ttgctatgga gcgggtatct gttctttttg ataggtaaga agcgaagccc   162540
catccctcag ccgttagctt ccctagaact ttggcctgaa gctgtgcttt tgtgtgtgtc   162600
tgctgatccc ctggcgctgt tgctggagtc ctgccagtga ttccccacca cagcctgacc   162660
atgggctgcc ttggctcagg gttccactgg cgagctggtg gtccttggac cccagcactc   162720
aggtgtagcg ttgaccagtt ccaaggttgt cccagtgcct gcccatctct cctgagggct   162780
cagggacagt acctggcagt tgggggtgtg gcaggggca ggaatgacca gcctctggga    162840
gggtggggca aagcctgta cagtgaggag gagctggctc agcctggctg cctatcgtga    162900 gagggagcc cacggggctg tgggaggggg gccgtggtgc ctgtgagcag ggtgaggagc    162960
```

```
agcggcagga ggatgaaggt ggaacccaca catgcatctt tgagacccgt gtggtcagtg   163020
gcttctgccc cccaccaccc cccactgctg tgcgtgcata gaattggctt ccctcacctg   163080
ctctggaagt gggttaggag cttggtaggg cttttttctca aggacaaggg cccctgattt   163140
gctctcaggc ctcagtcctg cgacatggt ggatctggag ccttgttgca ctgccttgcc   163200
tgtgctctcc aatcagggtg gccagtgggg agccatttgg cttttctcaa gagcatactc   163260
aggtggacct tgctccactg tttgaccaga tgaggcattc tgaacagcca agcctgtgct   163320
ggtctgtttt catgttgatt ttttttttc ttttcttttt gagatggagt ttttcccttg    163380
tcacccaggc tggagtgcaa tggtgtgatc tcggctcact gcaacctccg cctcccgggt   163440
tcaagtgatt ctcctgcctc agcctcccta gtagctggga ttacaggcac acaccaccat   163500
gcccagctaa ttttttgtgtt tttagtagag acggggtttc accgtgttgg ctgggctggt   163560
ctcgaactcc tgaactcaag tgatccaccc tccttggcct cccaaagtgc tgggattgca   163620
ggcgtgagcc actgcgcccg gccccatgt cgatttttaa atgcacctct gcatcgttct    163680
tcagtcccca tatgctcact gagcaccact gcgactggca gacgggcaca gggaggcgcc   163740
acgaccagtc ctggccttca aggggcttgt ggtctagtgg gcccaatgct aggtggcgag   163800
tgctccaaag agtgtggtgc acgccttccg cttgaccgct ctccagacgc cacagggagg   163860
cacctcgcag ctgaccacag atttctctct gtggagcagt gtcttcagag cggctgccat   163920
gccactgctg ggcgagggtc tgcgggcggg tagagccagg agcacctgtg aggaagtgca   163980
ctgccatttt cgtagctgct tcccgtgtgt ctcagttaca cacggctggc atgtgtgcac   164040
tgatgagacg ggaacgtgat ggttgctttt cagcactgaa agggatactg ctcaggggc    164100 gtgtttcagg atctggttag ggaagaagca gcgagagcac agatggggcc ctgtgtggta   164160
acaagaaaaa agtcctggtt gacaacagtg ccacgaagcg ttagaacaca tagggatgtt   164220
tgtggagcat ttgcatgtgg aaagcagcaa aaacataatg ggaacgggtt cttttgttat   164280
gatttttaaa aatctctttt gtaacatcct tcccgctgcg ccgtttctgc atattccttt   164340
atgtagcttt caaactcctc ttaggagttc tggtccctac agggcgtggg agccaggct    164400 ttacgtagct ttcaaactcc tcttaggagt tctggtccct acagggtgtg ggagcccagg   164460
gcctgtgccg agcagcctgc ctccacgagc tagacagagg aagggctggg gttttgcctt   164520
tttagtctca aaattcgtac tccagttgct taggctctga cttcccac ttggaaagtc     164580 cctcacggcc gagggtcct cccagccctg atttcacatc ggcatttttcc ccagtattag   164640 agccaaggcc ctccgcgggc aggtgggggca gctgtgggag ctggtgccag tctctgacct  164700
gcgtccctcc tcccaggatc aggaaaggct ttccttgtga agccagagtg gtggccagga   164760
tcctgcccca gtttctagac gacttcttcc caccccagga catcatgaac aaagtcatcg   164820 gagagttttct gtccaaccag cagccatacc cccagttcat ggccaccgtg gtgtataagg   164880
tgaggttgca tgtgggatgg ggatggagtg ggaaagcctg gaggtggagt tgcctccgac   164940
ttcccagcag attcgccagc agagcccagc tcctccgctt taaagcagca atgcctctgg   165000
cccccacccc acccccgcca cccaggcgca gcaggtgctt cccgtccccc cagccctgac   165060
actcaggcac ctgcttgctc cttgcaggtg tttcagactc tgcacagcac cgggcagtcg   165120
tccatggtcc gggactgggt catgctgtcc ctctccaact tcacgcagag gccccggtc    165180 gccatggcca cgtggagcct ctcctgcttc tttgtcagcg cgtccaccag cccgtgggtc   165240
gcggcgatgt atcctctctg ggtccctggt gctggccccg tttcccttgt caacaccgag   165300
```

```
gctcatgttt catgataagg tttttgaaacc taacctttgc aaaaacccca cagatgccag  165360
ggtgacaggc cctcagcccc agggaagtaa aatgctgaca ggggtacaga aaggagcacg  165420
tccagacatt tgctgaccag ggcctctcag aggggccggt gtatggcagg agggtcgcag  165480
ctgaggggcc tttctgtgga gggcctgggt gaggggagcg agggtgggcg gtggtctctg  165540
cagacgtccc gcccactcgc gggctctgtg tggctgggct tctcctgaca ctgcttctca  165600
ttagctttgg tcattgtgcc tcgatcgccc tctcggggaa aggcttaagt aaagatccag  165660
ttcccacccc cagatgctgg ctgccaggag tttcccttc cacagcccttccccaagaca  165720
gaccacaaga gcctccaagc agcacagttg tcctggtgct gacagcacag ccttgcccgg  165780
cgtgcctggc acggctctgc cctcactgca ttggagcagg gctagtggag gccagcggaa  165840
gcaccggcca ccagcgctgc acaggagcca ggcaggtga gtgctgccga gtgggtgccc  165900
tgcctgcagg gcatccagcc agccaagggt tgcaggaatg gaggtggagg cgctgatgca  165960
gctggaggca tccaggtggc ccttccgggg ctctgctcgc tctccaggct ccctggaccc  166020
ctttgtagac tgtttcagga gaggaactcc caggtgagga cagggaggca gcattcccct  166080
catttgccgg cctttttcct taactcctgc accagcctcc cacatgtcat cagcaggatg  166140
ggcaagctga gcaggtgga cgtgaacctt ttctgcctgg tcgccacaga cttctacaga  166200
caccagatag aggaggagct cgaccgcagg gccttccagt ctgtgcttga ggtggttgca  166260
gccccaggaa gcccatatca ccggctgctg acttgtttac gaaatgtcca caaggtcacc  166320
acctgctgag cgccatggtg ggagagactg tgaggcggca gctggggccg gagcctttgg  166380
aagtctgcgc ccttgtgccc tgcctccacc gagccagctt ggtccctatg ggcttccgca  166440
catgccgcgg gcggccaggc aacgtgcgtg tctctgccat gtggcagaag tgctctttgt  166500
ggcagtggcc aggcagggag tgtctgcagt cctggtgggg ctgagcctga ggccttccag  166560
aaagcaggag cagctgtgct gcaccccatg tgggtgacca ggtcctttct cctgatagtc  166620
acctgctggt tgttgccagg ttgcagctgc tcttgcatct gggccagaag tcctccctcc  166680
tgcaggctgg ctgttggccc ctctgctgtc ctgcagtaga aggtgccgtg agcaggcttt  166740
gggaacactg gcctgggtct ccctggtggg gtgtgcatgc cacgccccgt gtctggatgc  166800
acagatgcca tggcctgtgc tgggccagtg gctgggggtg ctagacaccc ggcaccattc  166860
tcccttctct cttttcttct caggatttaa aatttaatta tatcagtaaa gagattaatt  166920
ttaacgtaac tcttctatg cccgtgtaaa gtatgtgaat cgcaaggcct gtgctgcatg  166980
cgacagcgtc cggggtggtg gacagggccc ccggccacgc tccctctcct gtagccactg  167040
gcatagccct cctgagcacc cgctgacatt tccgttgtac atgttcctgt ttatgcattc  167100
acaaggtgac tgggatgtag agaggcgtta gtgggcaggt ggccacagca ggactgagga  167160
caggccccca ttatcctagg ggtgcgctca cctgcagccc ctcctcctcg ggcacagacg  167220
actgtcgttc tccacccacc agtcagggac agcagcctcc ctgtcactca gctgagaagg  167280
ccagccctcc ctggctgtga gcagcctcca ctgtgtccag agacatgggc ctcccactcc  167340
tgttccttgc tagccctggg gtggcgtctg cctaggagct ggctggcagg tgttgggacc  167400
tgctgctcca tggatgcatg ccctaagagt gtcactgagc tgtgttttgt ctgagcctct  167460
ctcggtcaac agcaaagctt ggtgtcttgg cactgttagt gacagagccc agcatccctt  167520
ctgcccccgt tccagctgac atcttgcacg gtgaccccett ttagtcagga gagtgcagat  167580
ctgtgctcat cggagactgc cccacggccc tgtcagagcc gccactccta tccccaggcc  167640
aggtccctgg accagcctcc tgtttgcagg cccagaggag ccaagtcatt aaaatggaag  167700
```

```
tggattctgg atggccgggc tgctgctgat gtaggagctg gatttgggag ctctgcttgc    167760
cgactggctg tgagacgagg caggggctct gcttcctcag ccctagaggc gagccaggca    167820
aggttggcga ctgtcatgtg gcttggtttg gtcatgcccg tcgatgtttt gggtattgaa    167880
tgtggtaagt ggaggaaatg ttggaactct gtgcaggtgc tgccttgaga cccccaagct    167940
tccacctgtc cctctcctat gtggcagctg gggagcagct gagatgtgga cttgtatgct    168000
gcccacatac gtgaggggga gctgaaaggg agcccctcct ctgagcagcc tctgccaggc    168060
ctgtatgagg cttttcccac cagctcccaa cagaggcctc cccagccag gaccacctcg    168120 tcctcgtggc ggggcagcag gagcggtaga aaggggtccg atgtttgagg aggcccttaa    168180
gggaagctac tgaattataa cacgtaagaa aatcaccatt ccgtattggt tgggggctcc    168240
tgtttctcat cctagctttt tcctggaaag cccgctagaa ggtttgggaa cgaggggaaa    168300
gttctcagaa ctgttggctg ctccccaccc gcctcccgcc tccccgcag gttatgtcag    168360 cagctctgag acagcagtat cacaggccag atgttgttcc tggctagatg tttacatttg    168420
taagaaataa cactgtgaat gtaaaacaga gccattccct tggaatgcat atcgctgggc    168480
tcaacataga gtttgtcttc ctcttgttta cgacgtgatc taaaccagtc cttagcaagg    168540
ggctcagaac accccgctct ggcagtaggt gtcccccacc cccaaagacc tgcctgtgtg    168600
ctccggagat gaatatgagc tcattagtaa aaatgacttc acccacgcat atacataaag    168660
tatccatgca tgtgcatata gacacatcta aattttaca cacacacctc tcaagacgga    168720
gatgcatggc tctaagagt gcccgtgtcg gttcttcctg gaagttgact ttccttagac    168780
ccgccaggtc aagttagccg cgtgacggac atccaggcgt gggacgtggt cagggcaggg    168840
ctcattcatt gcccactagg atcccactgg cgaagatggt ctccatatca gctctctgca    168900
gaagggagga agactttatc atgttcctaa aaatctgtgg caagcaccca tcgtattatc    168960
caaattttgt tgcaaatgtg attaatttgg ttgtcaagtt ttgggggtgg gctgtgggga    169020
gattgctttt gttttcctgc tggtaatatc gggaaagatt ttaatgaaac cagggtagaa    169080
ttgtttggca atgcactgaa gcgtgttct ttcccaaaat gtgcctccct tccgctgcgg    169140
gcccagctga gtctatgtag gtgatgtttc cagctgccaa gtgctctttg ttactgtcca    169200
ccctcatttc tgccagcgca tgtgtccttt caaggggaaa atgtgaagct gaacccctc     169260 cagacaccca gaatgtagca tctgagaagg ccctgtgccc taaaggacac ccctcgcccc    169320
catcttcatg gaggggtca tttcagagcc ctcggagcca atgaacagct cctcctcttg    169380
gagctgagat gagccccacg tggagctcgg gacggatagt agacagcaat aactcggtgt    169440
gtggccgcct ggcaggtgga acttcctccc gttgcggggt ggagtgaggt tagttctgtg    169500
tgtctggtgg gtggagtcag gcttctcttg ctacctgtga gcatccttcc cagcagacat    169560
cctcatcggg ctttgtccct ccccgcttc ctccctctgc ggggaggacc cgggaccaca    169620
gctgctggcc agggtagact tggagctgtc ctccagaggg gtcacgtgta ggagtgagaa    169680
gaaggaagat cttgagagct gctgagggac cttggagagc tcaggatggc tcagacgagg    169740
acactcgctt gccgggcctg ggcctcctgg gaaggaggga gctgctcaga atgccgcatg    169800
acaactgaag gcaacctgga aggttcaggg gccgctcttc cccatgtgc ctgtcacgct     169860 ctggtgcagt caaaggaacg ccttcccctc agttgtttct aagagcagag tctcccgctg    169920
caatctgggg ggtaactgcc agccttggag gatcgtggcc aacgtggacc tgcctacgga    169980
gggtgggctc tgacccaagt ggggcctcct tgtccaggtc tcactgcttt gcaccgtggt    170040
```

```
cagagggact gtcagctgag cttgagctcc cctggagcca gcagggctgt gatgggcgag    170100
tcccggagcc ccacccagac ctgaatgctt ctgagagcaa agggaaggac tgacgagaga    170160
tgtatattta attttttaac tgctgcaaac attgtacatc caaattaaag gaaaaaaatg    170220
gaaaccatca gttgttgctg tgtgaggctt gctttgcttc atgagaacct agaccttgct    170280
gagctggagt cttaggaagc agtctcctaa gtgcttctcc agcagggcca gaaactgtcc    170340
caccagctaa catctggcat tatggagggt cccccaggca gctgccagca gggacaggcc    170400
ccgtgttttc tgtagccagg gatgaggaag tggccccagg gcatgggcct ggctgggtgc    170460
ttctgcaagg gccttcccaa accacagtac aggtggtctt cctgccctgc agatgggagc    170520
tgtgggagct gctggagctg ctggagcctt catggtcaag tgacatcata agcttatatg    170580
acatacacaa gcctcaggac ttggcccatg gcactgaagc aggtcatcag gcccagcaca    170640
gagactagag ctgtgttctc acagggccca ccacccttcc acctccttgg ccattgacac    170700
ctgcgtccct ggcccagctg ctcccaggta accccccaaag cagctggcac atcccacctc    170760
tggtgtggcc ggggctgctg tgtgtccgca gggcctgccc cgtctattct agcttgtttg    170820
tcctgtctga accagcgcct actccaagaa gcctctgctc agcccagcgg ggatgcttct    170880
aagctccgga cgagcctctc ggaagccttg gtgattggtg gtgtagtcat cttgggatgc    170940
agatgtctta ccaacctgca agaacaaaaa ccctgtggct tcctctggtg cagggtattt    171000
agtcaatgtt tgctgaggtc ccgtctggtt ctggctaatt ggcaggggtc gtccacccat    171060
tctttccctg ctctgctgtc tgtgccagga gagacggggg ccagtcggcc aaggggccag    171120
ctcctgctgc ctgctcctct tgggcacgtg cgggggcccc ctttctctga gcagggatag    171180
ggatcagtct gccggaggga tgtggtggac aggcctaaag catttggggc ggggcatgcc    171240
acttgagctc cctaaatctg tctcctcata ggtgacaccg ctccagggcc ccccagtggc    171300
ctctcctttc agagctacct aaattctggt cacttcagag aaatggagca cccccttctc    171360
cctggtccag gtgtggacag cctggcacac tgagcacacc tggcatggct ggtaatttca    171420
gaaagaagag gggccggggt ccagtgggaa gcagcggtga acccctcgtg agtgggcttt    171480
gcagtccctc cccatgccac ggcagagctg ccctcaacac agccttcctc ttcctcatcg    171540
gagagcacac cctgtcccct tgccgagctg tgccctgtgc cttcggtggt atttgatttt    171600
ggctgctact ggctttgttg ggatctggaa gtcgcttccc ctgcgtgtg cgtggagcac    171660
tgtaagtcag atgagggaag tagccagggt gaggtgagta ccgggtggag ccgccactga    171720
agggactggg tagggggggcc ttgcctctac atgatgtgac acagccaacc gaggacagag    171780
gaagcccgt tcctgggggt gtggggtgca cccctcaggg aagcctgcag tggggcctga    171840
ggaaaggcat cctccgcgag cccacgagtc tggtccatga gcaccgtgac agtgtctgtg    171900
ggtagaggtg gacccggcct tgtgtcatca ccaggacctc ttttgggaaa ccatgtggac    171960
atcgcttgcg ggtccccccag gctctgcagc cccagcagcc t                      172001
```

<210> SEQ ID NO 3
<211> LENGTH: 10081
<212> TYPE: DNA
<213> ORGANISM: Mus musculus

<400> SEQUENCE: 3

```
gcactcgccg cgagggttgc cgggacgggc ccaagatggc tgagcgcctt ggttccgctt      60
ctgcctgccg cgcagagccc cattcattgc cttgctgcta agtggcgccg cgtagtgcca     120
gtaggctcca agtcttcagg gtctgtccca tcgggcagga agccgtcatg gcaaccctgg     180
```

```
aaaagctgat gaaggctttc gagtcgctca agtcgtttca gcagcaacag cagcagcagc    240
caccgccgca ggcgccgccg ccaccgccgc cgccgcctcc gcctcaaccc cctcagccgc    300
cgcctcaggg gcagccgccg ccgccaccac cgccgctgcc aggtccggca gaggaaccgc    360
tgcaccgacc aaagaaggaa ctctcagcca ccaagaaaga ccgtgtgaat cattgtctaa    420
caatatgtga aacattgtg gcacagtctc tcagaaattc tccagaattt cagaaactct     480
tgggcatcgc tatggaactg tttctgctgt gcagtgacga tgcggagtca gatgtcagaa    540
tggtggctga tgagtgcctc aacaaagtca tcaaagcttt gatggattct aatcttccaa    600
ggctacagtt agaactctat aaggaaatta aaaagaatgg tgctcctcga agtttgcgtg    660
ctgccctgtg gaggtttgct gagctggctc acctggttcg acctcagaag tgcaggcctt    720
acctggtgaa tcttcttcca tgcctgaccc gaacaagcaa agaccggag gaatcagttc      780
aggagacctt ggctgcagct gttcctaaaa ttatggcttc ttttggcaat tcgcaaatg     840
acaatgaaat taaggttctg ttgaaagctt catagcaaa tctgaagtca agctctccca    900
ccgtgcggcg gacagcagcc ggctcagccg tgagcatctg ccaacattct aggaggacac    960
agtacttcta caactggctc cttaatgtcc tcctaggtct gctggttccc atggaagaag   1020
agcactccac tctcctgatc ctcggtgtgt tgctcacatt gaggtgtcta gtgcccttgc   1080
tccagcagca ggtcaaggac acaagtctaa aaggcagctt tggggtgaca cggaaagaaa   1140
tggaagtctc tccttctaca gagcagcttg tccaggttta tgaactgact ttgcatcata   1200
ctcagccacca agaccacaat gtggtgacag gggcactgga gctcctgcag cagctcttcc   1260
gtaccctcc acctgaactc ctgcaagcac tgaccacacc aggagggctt gggcagctca   1320
ctctggttca agaagaggcc cggggccgag gccgcagcgg gagcatcgtg gagcttttag   1380
ctggaggggg ttcctcgtgc agccctgtcc tctcaagaaa gcagaaaggc aaagtgctct   1440
taggagagga agaagccttg gaagatgact cggagtccag gtcagatgtc agcagctcag   1500
cctttgcagc ctctgtgaag agtgagattg gtggagagct cgctgcttct tcaggtgttt   1560
ccactcctgg ttctgttggt cacgacatca tcactgagca gcctagatcc cagcacacac   1620
ttcaagcaga ctctgtggat ttgtccggct gtgacctgac cagtgctgct actgatgggg   1680
atgaggagga catcttgagc cacagctcca gccagttcag tgctgtccca tccgaccctg   1740
ccatggacct gaatgatggg acccaggcct cctcacccat cagtgacagt tctcagacca   1800
ccactgaagg acctgattca gctgtgactc cttcggacag ttctgaaatt gtgttagatg   1860
gtgccgatag ccagtatttta ggcatgcaga taggacagcc acaggaggac gatgaggagg   1920
gagctgcagg tgttctttct ggtgaagtct cagatgtttt cagaaactct tctctggccc   1980
ttcaacaggc acacttgttg gaaagaatgg gccatagcag gcagccttcc gacagcagta   2040
tagataagta tgtaacaaga gatgaggttg ctgaagccag tgatccagaa agcaagcctt   2100
gccgaatcaa aggtgacata ggacagccta atgatgatga ttctgctcct ctggtacatt   2160
gtgtccgtct tttatctgct tccttttgt taactggtga aaagaaagca ctggttccag    2220
acagagacgt gagagtcagt gtgaaggccc tggccctcag ctgcattggt gcggctgtgg   2280
cccttcatcc agagtcgttc ttcagcagac tgtacaaagt acctcttaat accacggaaa   2340
gtactgagga acagtatgtt tctgacatct gaactacat cgatcatgga gacccacagg    2400
tccgaggagc tactgccatt ctctgtggga cccttgtcta ctccatcctc agtaggtccc   2460
gtctccgtgt tggtgactgg ctgggcaaca tcagaaccct gacaggaaat acattttctc   2520
```

```
tggtggactg cattccttta ctgcagaaaa cgttgaagga tgaatcttct gttacttgca    2580
agttggcttg tacagctgtg aggcactgtg tcctgagtct ttgcagcagc agctacagtg    2640
acttgggatt acaactgctt attgatatgc tgcctctgaa gaacagctcc tactggctgg    2700
tgaggaccga actgctggac actctggcag agattgactt caggctcgtg agttttttgg    2760
aggcaaaagc agaaagttta caccgagggg ctcatcatta tacagggttt ctaaaactac    2820
aagaacgagt actcaataat gtggtcattt atttgcttgg agatgaagac cccagggttc    2880
gacatgttgc tgcaacatca ttaacaaggc ttgtcccaaa gctgttttac aagtgtgacc    2940
aaggacaagc tgatccagtt gtggctgtag cgagggatca gagcagtgtc tacctgaagc    3000
tcctcatgca tgagacccag ccaccatcac acttttctgt cagcaccatc accagaatct    3060
atagaggcta tagcttactg ccaagtataa cagatgtcac catggaaaac aatctctcaa    3120
gagttgttgc cgcagtttct catgaactca ttacgtcaac aacacgggca ctcacatttg    3180
gatgctgtga agccttgtgt cttctctcag cagcctttcc agtttgcact tggagtttag    3240
gatggcactg tggagtgccc ccactgagtg cctctgatga gtccaggaag agctgcactg    3300
ttgggatggc ctccatgatt ctcaccttgc tttcatcagc ttggttccca ctggatctct    3360
cagcccatca ggatgccttg attttggctg gaaacttgct agcagcgagt gcccccaagt    3420
ctctgagaag ttcatggacc tctgaagaag aagccaactc agcagccacc agacaggagg    3480
aaatctggcc tgctctgggg gatcggactc tagtgccctt ggtggagcag ctttctctccc    3540 acctgctgaa ggtgatcaat atctgtgctc atgtcttgga cgatgtgact cctggaccag    3600
caatcaaggc agccttgcct tctctaacaa acccccttc tctaagtcct attcgacgga    3660
aagggaagga gaaagaacct ggagaacaag cttctactcc aatgagtccc aagaaagttg    3720
gtgaggccag tgcagcctct cgacaatcag acacctcagg acctgtcaca gcaagtaaat    3780
catcctcact ggggagtttc taccatctcc cctcctacct caaactgcat gatgtcctga    3840
aagccactca cgccaactat aaggtcacct tagatcttca gaacagcact gaaaagtttg    3900
gggggttcct gcgctctgcc ttggacgtcc tttctcagat tctagagctg cgacactgc    3960 aggacattgg aaagtgtgtt gaagaggtcc ttggatacct gaaatcctgc tttagtcgag    4020
aaccaatgat ggcaactgtc tgtgtgcagc agctattgaa gactctcttt gggacaaact    4080
tagcctcaca gtttgatggc ttatcttcca accccagcaa gtctcagtgc cgagctcagc    4140
gccttggctc ttcaagtgtg aggcccggct tatatcacta ctgcttcatg gcaccataca    4200
cgcacttcac acaggccttg gctgacgcaa gcctgaggaa catggtgcag gcggagcagg    4260
agcgtgatgc ctcggggtgg tttgatgtac tccagaaagt gtctgcccaa ttgaagacga    4320
acctaacaag cgtcacaaag aaccgtgcag ataagaatgc tattcataat cacattaggt    4380
tatttgagcc tcttgttata aaagcattga agcagtacac cacgacaaca tctgtacaat    4440
tgcagaagca ggttttggat ttgctggcac agctggttca gctacgggtc aattactgtc    4500
tactggattc agaccaggtg ttcatcgggt ttgtgctgaa gcagtttgag tacattgaag    4560
tgggccagtt cagggaatca gaggcaatta ttccaaatat atttttcttc ctggtattac    4620
tgtcttatga gcgctaccat tcaaaacaga tcattgaat tcctaaaatc atccagctgt    4680
gtgatggcat catggccagt ggaaggaagg ccgttacaca tgctatacct gctctgcagc    4740
ccattgtcca tgacctcttt gtgttacgag aacaaataa agctgatgca gggaaagagc    4800
ttgagacaca gaaggaggtg gtggtctcca tgctgttacg actcatccag taccatcagg    4860
tgctggagat gttcatcctt gtcctgcagc agtgccacaa ggagaatgag gacaagtgga    4920
```

```
aacggctctc tcggcaggtc gcagacatca tcctgcccat gttggccaag cagcagatgc   4980
atattgactc tcatgaagcc cttggagtgt taaatacctt gtttgagatt ttggctcctt   5040
cctccctacg tcctgtggac atgcttttgc ggagtatgtt catcactcca agcacaatgg   5100
catctgtaag cactgtgcag ctgtggatat ctggaatcct cgccattctg agggttctca   5160
tttcccagtc aaccgaggac attgttcttt gtcgtattca ggagctctcc ttctctccac   5220
acttgctctc ctgtccagtg attaacaggt taaggggtgg aggcggtaat gtaacactag   5280
gagaatgcag cgaagggaaa caaaagagtt tgccagaaga tacattctca aggtttcttt   5340
tacagctggt tggtattctt ctagaagaca tcgttacaaa acagctcaaa gtggacatga   5400
gtgaacagca gcatacgttc tactgccaag agctaggcac actgctcatg tgtctgatcc   5460
acatattcaa atctggaatg ttccggagaa tcacagcagc tgccactaga ctcttcacca   5520
gtgatggctg tgaaggcagc ttctatactc tagagagcct gaatgcacgg gtccgatcca   5580
tggtgcccac gcacccagcc ctggtactgc tctggtgtca gatcctactt ctcatcaacc   5640
acactgacca ccggtggtgg gcagaggtgc agcagacacc caagagacac agtctgtcct   5700
gcacgaagtc acttaacccc cagaagtctg gcgaagagga ggattctggc tcggcagctc   5760
agctgggaat gtgcaataga gaaatagtgc gaagaggggc ccttattctc ttctgtgatt   5820
atgtctgtca gaatctccat gactcagaac acttaacatg gctcattgtg aatcacattc   5880
aagatctgat cagcttgtct catgagcctc cagtacaaga ctttattagt gccattcatc   5940
gtaattctgc agctagtggt cttttttatcc aggcaattca gtctcgctgt gaaaatcttt   6000
caacgccaac cactctgaag aaaacacttc agtgcttgga aggcatccat ctcagccagt   6060
ctggtgctgt gctcacacta tatgtggaca ggctcctggg cacccccttc cgtgcgctgg   6120
ctcgcatggt cgacaccctg cctgtcgcc gggtagaaat gcttttggct gcaaatttac   6180
agagcagcat ggcccagttg ccagaggagg aactaaacag aatccaagaa cacctccaga   6240
acagtgggct tgcacaaaga caccaaaggc tctattcact gctggacaga ttccgactct   6300
ctactgtgca ggactcactt agccccttgc ccccagtcac ttcccaccca ctggatgggg   6360
atgggcacac atctctggaa acagtgagtc cagacaaaga ctggtacctc cagcttgtca   6420
gatcccagtg ttggaccaga tcagattctg cactgctgga aggtgcagag ctggtcaacc   6480
gtatccctgc tgaagatatg aatgacttca tgatgagctc ggagttcaac ctaagccttt   6540
tggctccctg tttaagcctt ggcatgagcg agattgctaa tggccaaaag agtcccctct   6600
ttgaagcagc ccgtggggtg attctgaacc gggtgaccag tgttgttcag cagcttcctg   6660
ctgtccatca agtcttccag cccttcctgc ctatagagcc cacggcctac tggaacaagt   6720
tgaatgatct gcttggtgat accacatcat accagtctct gaccatactt gcccgtgccc   6780
tggcacagta cctggtggtg ctctccaaag tgcctgctca tttgcacctt cctcctgaga   6840
aggaggggga cacggtgaag tttgtggtaa tgacagttga ggccctgtca tggcatttga   6900
tccatgagca gatcccactg agtctggacc tccaagccgg gctagactgc tgctgcctgg   6960
cactacaggt gcctggcctc tgggggtgc tgtcctcccc agagtacgtg actcatgcct   7020
gctccctcat ccattgtgtg cgattcatcc tggaagccat tgcagtacaa cctggagacc   7080
agcttctcgg tcctgaaagc aggtcacata ctccaagagc tgtcagaaag gaggaagtag   7140
actcagatat acaaaacctc agtcatgtca cttcggcctg cgagatggtg gcagacatgg   7200
tggaatccct gcagtcagtg ctggccttgg gccacaagag gaacagcacc ctgccttcat   7260
```

```
ttctcacagc tgtgctgaag aacattgtta tcagtctggc ccgactcccc ctagttaaca    7320
gctatactcg tgtgcctcct ctggtatgga aactcgggtg gtcacccaag cctggagggg    7380
attttggcac agtgtttcct gagatccctg tagagttcct ccaggagaag gagatcctca    7440
aggagttcat ctaccgcatc aacaccctag ggtggaccaa tcgtacccag ttcgaagaaa    7500
cttgggccac cctccttggt gtcctggtga ctcagcccct ggtgatggaa caggaagaga    7560
gcccaccaga ggaagacaca gaaagaaccc agatccatgt cctggctgtg caggccatca    7620
cctctctagt gctcagtgca atgaccgtgc ctgtggctgg caatccagct gtaagctgct    7680
tggagcaaca gccccggaac aagccactga aggctctcga taccagattt ggaagaaagc    7740
tgagcatgat cagagggatt gtagaacaag aaatccaaga gatggtttcc cagagagaga    7800
atactgccac tcaccattct caccaggcgt gggatcctgt cccttctctg ttaccagcta    7860
ctacaggtgc tcttatcagc catgacaagc tgctgctgca gatcaaccca gagcgggagc    7920
caggcaacat gagctacaag ctgggccagg tgtccataca ctccgtgtgg ctgggaaata    7980
acatcacacc cctgagagag gaggaatggg atgaggaaga agaggaagaa agtgatgtcc    8040
ctgcaccaac gtcaccacct gtgtctccag tcaattccag aaaacaccgt gccggggttg    8100
atattcactc ctgttcgcag tttctgcttg aattgtacag ccgatggatc ctgccatcca    8160
gtgcagccag aaggaccccc gtcatcctga tcagtgaagt ggttcgatct cttcttgtag    8220
tgtcagactt attcaccgaa cgtacccagt ttgaaatgat gtatctgacg ctgacagaac    8280
tacggagagt gcacccttca gaagatgaga tcctcattca gtacctggtg cctgccacct    8340
gtaaggcagc tgctgtcctt ggaatggaca aaactgtggc agagccagtc agccgcctac    8400
tggagagcac actgaggagc agccacctgc ccagccagat cggagccctg cacggcatcc    8460
tctatgtgtt ggagtgtgac ctcttggatg acactgcaaa gcagctcatt ccagttgtta    8520
gtgactatct gctgtccaac ctcaaaggaa tagcccactg cgtgaacatt cacagccagc    8580
agcatgtgct ggtaatgtgt gccactgctt tctacctgat ggaaaactac cctctggatg    8640
tgggaccaga attttcagca tctgtgatac agatgtgtgg agtaatgctg tctggaagtg    8700
aggagtccac cccctccatc atttaccact gtgccctccg gggtctggag cggctcctgc    8760
tgtctgagca gctatctcgg ctagacacag agtccttggt caagctaagt gtggacagag    8820
tgaatgtaca aagcccacac agggccatgg cagcccctagg cctgatgctc acctgcatgt    8880
acacaggaaa ggaaaaagcc agtccaggca gagcttctga ccccagccct gctacacctg    8940
acagcgagtc tgtgattgta gctatggagc gagtgtctgt tctcttttgat aggatccgca    9000
agggatttcc ctgtgaagcc agggttgtgg caaggatcct gcctcagttc ctagatgact    9060
tctttccacc tcaagatgtc atgaacaaag tcattggaga gttcctgtcc aatcagcagc    9120
catacccaca gttcatggcc actgtagttt acaaggtttt tcagactctg cacagtgctg    9180
ggcagtcatc catggtccgg gactgggtca tgctgtccct gtccaacttc acacaaagaa    9240
ctccagttgc catggccatg tggagcctct cctgcttcct tgttagcgca tctaccagcc    9300
catgggtttc tgcgatcctt ccacatgtca tcagcaggat gggcaaactg aacaggtgg    9360
atgtgaacct tttctgcctg gttgccacag acttctacag acaccagata gaggaggaat    9420
tcgaccgcag ggcttttcag tctgtgtttg aggtggtggc tgcaccagga agtccatacc    9480
acaggctgct tgcttgtttg caaaatgttc acaaggtcac cacctgctga gtagtgcctg    9540
tgggacaaaa ggctgaaaga aggcagctgc tggggcctga gcctccagga gcctgctcca    9600
agcttctgct ggggctgcct tggccgtgca ggcttccact tgtgtcaagt ggacagccag    9660
```

```
gcaatggcag gagtgctttg caatgagggc tatgcaggga acatgcacta tgttggggtt    9720
gagcctgagt cctgggtcct ggcctcgctg cagctggtga cagtgctagg ttgaccaggt    9780
gtttgtcttt ttcctagtgt tcccctggcc atagtcgcca ggttgcagct gccctggtat    9840
gtggatcaga agtcctagct cttgccagat ggttctgagc ccgcctgctc cactgggctg    9900
gagagctccc tcccacattt acccagtagg catacctgcc acaccagtgt ctggacacaa    9960
aatgaatggt gtgtggggct gggaactggg gctgccaggt gtccagcacc attttccttt   10020
ctgtgttttc ttctcaggag ttaaaattta attatatcag taaagagatt aattttaatg   10080
t                                                                   10081

<210> SEQ ID NO 4
<211> LENGTH: 168002
<212> TYPE: DNA
<213> ORGANISM: Macaca mulatta
<220> FEATURE:
<221> NAME/KEY: misc_feature
<222> LOCATION: (8794)..(8848)
<223> OTHER INFORMATION: n is a, c, g, or t
<220> FEATURE:
<221> NAME/KEY: misc_feature
<222> LOCATION: (11952)..(12155)
<223> OTHER INFORMATION: n is a, c, g, or t
<220> FEATURE:
<221> NAME/KEY: misc_feature
<222> LOCATION: (13733)..(14137)
<223> OTHER INFORMATION: n is a, c, g, or t
<220> FEATURE:
<221> NAME/KEY: misc_feature
<222> LOCATION: (17299)..(17497)
<223> OTHER INFORMATION: n is a, c, g, or t
<220> FEATURE:
<221> NAME/KEY: misc_feature
<222> LOCATION: (18993)..(19355)
<223> OTHER INFORMATION: n is a, c, g, or t
<220> FEATURE:
<221> NAME/KEY: misc_feature
<222> LOCATION: (30628)..(32144)
<223> OTHER INFORMATION: n is a, c, g, or t
<220> FEATURE:
<221> NAME/KEY: misc_feature
<222> LOCATION: (37234)..(37641)
<223> OTHER INFORMATION: n is a, c, g, or t
<220> FEATURE:
<221> NAME/KEY: misc_feature
<222> LOCATION: (56357)..(56602)
<223> OTHER INFORMATION: n is a, c, g, or t
<220> FEATURE:
<221> NAME/KEY: misc_feature
<222> LOCATION: (66208)..(66275)
<223> OTHER INFORMATION: n is a, c, g, or t
<220> FEATURE:
<221> NAME/KEY: misc_feature
<222> LOCATION: (72472)..(72756)
<223> OTHER INFORMATION: n is a, c, g, or t
<220> FEATURE:
<221> NAME/KEY: misc_feature
<222> LOCATION: (82608)..(83314)
<223> OTHER INFORMATION: n is a, c, g, or t
<220> FEATURE:
<221> NAME/KEY: misc_feature
<222> LOCATION: (108856)..(108875)
<223> OTHER INFORMATION: n is a, c, g, or t
<220> FEATURE:
<221> NAME/KEY: misc_feature
<222> LOCATION: (131686)..(132275)
<223> OTHER INFORMATION: n is a, c, g, or t
<220> FEATURE:
<221> NAME/KEY: misc_feature
<222> LOCATION: (143992)..(145163)
<223> OTHER INFORMATION: n is a, c, g, or t
<220> FEATURE:
```

<221> NAME/KEY: misc_feature
<222> LOCATION: (147895)..(148388)
<223> OTHER INFORMATION: n is a, c, g, or t

<400> SEQUENCE: 4

| | | | | | |
|---|---|---|---|---|---|
| atacaggcgt | gagccaccgc | acccagctgg | aacttaatttt | ttttaaagat | cgtgttgctc | 60 |
| tatcgcccaa | gctggagtgc | agtggtgcaa | ccatagctca | cttgcagcca | caaattcctg | 120 |
| gtttcaggtg | atcctcctac | atcagcctcc | caagaactgg | gaactaacgg | ctgtttctct | 180 |
| gctgtccttc | tcaagagaag | ggagggagac | aatgctgggt | ttcccttttgg | gacaggctct | 240 |
| gagacaaggt | ggaggtgctg | cttgtggcca | cagagcaggg | gactctgggt | tgcaggtgtg | 300 |
| gcctggcttg | agtaggcttt | agtgggcttc | tctctgcctg | caccaccccc | gggctgggtg | 360 |
| gttgtctctg | aggccaaccc | tactccctaa | tgggcaggct | ggacagctgc | cctctctgtt | 420 |
| tgcccctcta | ccacccaaaa | ggcgggaggc | tctggagacc | aggaccctgc | ctgcgccggc | 480 |
| ctgtgcccca | ggcgtgaggg | ggtgcccac | agatctctgc | tgagctgagg | ctgaatggca | 540 |
| cccccttgggg | gtcctgccag | gtcagagcag | ggtgctttcc | catacagaaa | cgcccccagg | 600 |
| tcgggactca | ttcctgtggg | aggcgtcttg | tggccacaac | tgcttctcgc | tgcactaatc | 660 |
| acagtgcctc | tgtgggcagc | gggcgctgac | catcccgggcc | tgcctcagac | cctctcctcc | 720 |
| cttccggggc | gctgcgctgg | gaccgatggg | gggcgccagg | cctgtgggca | ccgccctgca | 780 |
| ggggccgctc | cagctcactg | gggggtgggg | agggtcacac | ttggggtctt | cagatggcgc | 840 |
| cgaccacgcg | caatctctgc | gctctgcgca | ggggctcgcc | caccctctcc | ccgtgcagcg | 900 |
| agtcccccagc | aggctccccg | cagggctgtc | caggtgagcc | tggctctggc | cgcggggccag | 960 |
| tgtggcgggc | gggcaagccc | cgaggccacc | tcggctcaga | gcccacggcc | ggctctcgcc | 1020 |
| cagctccaga | cgtctgcgag | ggttccattc | cgcttgggcc | ggcgccccgc | gcgccgcgcc | 1080 |
| ctggccccgc | ccctccctca | tcccgccccc | tctgcacccc | accctccct | ggccccgccc | 1140 |
| tccgcgcccc | acctctcatc | ttcccgcccc | gcccccagcc | acgcccctca | cggtcagccc | 1200 |
| cctcccctat | ccgccccgcc | tctcatcgtc | tcgcctcgct | ccgcccctca | gccgtcccgc | 1260 |
| ccctcagccg | ccctgcctaa | tgtccccgcc | cccagcctcg | ccccgctccg | ccccagcctc | 1320 |
| gccccgcccc | gcccctcagg | cgccctgcct | gctgtgcccc | gcccagcct | cgccacgccc | 1380 |
| ctcgttacca | tgtagtcccg | cccctgtccct | tccgcgtccc | gcctcgcccc | taccccttca | 1440 |
| cagcttcgcc | ccaccccatt | acagtcttgc | cacgccccgt | ccctgtccg | ttgagccctg | 1500 |
| ctccttcgcc | caggtggggc | gctgcgctgt | cagaggcttt | ggtggctctg | tgaggcagaa | 1560 |
| catgcgggcg | cagggactgg | ctggctccct | ggccagtcat | tggcagagtc | cgcaggctag | 1620 |
| ggctgtcaat | catgctggcc | ggcgtggccc | cgcctccgcc | ggcgcagcgt | cttgagacgc | 1680 |
| aaggcgccgc | gggggctgcc | gggacgggtc | caagatggac | ggccgcttcg | gttccgcttt | 1740 |
| tacccgcggc | ccagagcccc | attcattgcc | ccggtgctga | gcggcgctgc | gagtcggccc | 1800 |
| gaggcctccg | gggactgcct | agccgggcgg | gagaccgcca | tggcgaccct | ggaaaagctg | 1860 |
| atgaaggcct | tcgagtctct | caagtccttc | cagcagcagc | agcagcagca | gcagcaacag | 1920 |
| ccgccgccgc | cgccgccgcc | gcctcctcct | cctcctcagc | ttcctcagcc | gccgcaggca | 1980 |
| cagccgatgc | tgcctcagcc | gcagccgccc | ccgccgccgc | cccgccacc | acccggcccg | 2040 |
| gctgtggctg | aggagccgct | gcaccgaccg | tgagtttggg | cccgctgcag | ctccctgtcc | 2100 |
| cggcgggtcc | cagcctacgg | cggggatggc | ggaatcctgc | agcctgcggg | ccggcgacac | 2160 |
| gaacccccc | ggccccgcag | cgacagagtg | acccagcaac | ccagagccaa | tgagggacac | 2220 |

```
ccgcccccctc ctgcggcgag accttccccc acttcagccc cggtcccgca cttgggtctt    2280
gtcctcccgc gaggggaggc agaacctcgt tgggacctgt cctgaattca cggaggggag    2340
tcacggcctc agccctctcg ccctttccag ggtgcgaaga gttggggcga aaacttgttt    2400 cttttttattt gcgagaaact agggcggggg tttaactgtg ttctgaagag aacttggaag    2460
agccgagatt tgctcagggc cacttccctc atctagtcag agagggaaga gggctggggg    2520
cgcgggacac ctcgagagga ggcggggttt ggagctagag agatgtgggg gcagtggatg    2580
acataatgct tttaggacgc ctcggcggga gtggctggag tgggggggcgg ggagtgaggg    2640 cgcgtccaat gggagattta ttttccaagt ggcatttaaa acagcctgag atttgaggct    2700
cttcctacat tctcagggca tttcatttag ttcatgatcg cggtggtagt aacacgattt    2760
taagcaccac ctaagagacc tgctcatcta agcgcaagtt agtgtgcagg catttgaatg    2820
agttgtggtc gccaaataag tggtgaactt acgtggtatt aataaaatta tcttaaatat    2880
taggaagagt tgattgaagt ttattgcctg tttgtgttgg gaataaaact aacacgttgc    2940
tgagggggag gttaattgcc gagggatgaa tgaggtatac atttttaccag tattgcagtc    3000 aggcttgcca gaatatggga ggtctgcaga ctccgtggac atctcatgtg ccagtgaaag    3060
ggtttctgtt cgcctcattg ctgacagctt gttacttttt ggaagctaga ggtctctgtt    3120
gcttgttctt ggggagaatt tttgaaacag aaaagagac cattaaaaca tctagcggaa    3180
ccccaggacg tgggagtgtg tgctgagtgt ttagcaggat ttaggaagta ctccgctgca    3240
gttcaggcct ttctcttacc tctcagtgtt ctatttccga tctggacgtg tatcagatgg    3300
catttgataa gaatatctct attaagactg attaattttt agtaatattt cttgttcttt    3360
gtttctgtta tgatccttgc cttgtcttga aagtttaatt agaagaggag gatttggaga    3420
gcagtgttag cttatttgtt agagtaaaat ttaggaataa attcttctaa aggatggaaa    3480 aacttttttgg atatttagag aaatttttaa acaatttggc ttatctcttc agtaagtaat    3540
ttctcatcct tccagaaatt taatgtagtg cctttctagg aggtaggtgt catagaagtt    3600
cacacattgc atgtatcttg tgtaaacact aaactgggct cctgatggga aggaagacct    3660
ttctgctggg ctgcttcaga cacttgatca ttctgaaaat atgccgtctc tttcctgtgc    3720
tgatttgata gaacctgcgt ttgcttatct tcaaaatatg ggtatcaaga aatttccttt    3780 gctgcccttta caaggagat agattttgtt tcattacttt atttaaggt aatatatgat    3840 taccttattt taaaaattta atcaggcctg gcaaggtggc tcatgccttt aatcccagca    3900
ctttgggagg cttaggcgga tgaatcacct gaggtcagga gttcgagacc agtctggcta    3960
acatggtgaa accccatctc tactaaaagt acaaaaatta gttggtcatg gtggcacgtg    4020
cctgtaatgc cagctacctg ggaggctgag gcaggaaaat cgctggaacc cgggaggcag    4080
aggctgcagt gagctgagac tgcgccactg cactccagcc tgggtgacag agcgagactc    4140
ttgtctcaaa aaaaaaaaa ttattatttt tgcataagta atacattaac atgacacaaa    4200
ttccgtaatt acaaaagagc aatacttaaa atatcttcct tccacccctt tcatctgagt    4260
acctaacttt gtccccaaga acaagcacta ttacagttcc tcctgtatcc tgccagatat    4320
aatctatgca tattgtaaga tagatttaaa atgctgtaaa aataaaagta gtttacagta    4380
ataatttttt ttcttttattt ttttgagat gtagtctcac attgtcaccc aggctggagt    4440
gcggtggtat gatcttggct cactgcaacc tccacctccc aggttcaaac gattctcctg    4500
cctcagcctc cagagtagct gggattacag gtgctcacca ccatgtccag ctgattttg    4560
```

```
tatttttagt agagatgggg tttcaccatg ttggccaggc tggtcttgaa ctcctgacct    4620
cggaatccat ccacctcggc ctcccaaagt gctggggtta caggtgtgag ccactgcccc    4680
tggctagaat aataactttt aaaggttctt agcattctct gaaatcaact gcattaggtt    4740
tatttatagt tattttaaat aaaatgcata tttgtcatat ttgtatgtat tttgctgttg    4800
agaaaggagg tattcgctaa ttttgagtaa caaacactgc tcacaaagtt tggattttgg    4860
catttctgtt catgtgcttc agccaaaaaa tcctcttctc aaagtaagat tgactaaagc    4920
aatttagaaa gtatctgttt ttatggctct tgctcttttg tgtggaactg tggtgtcatg    4980
ccatgcatgg gcctcagtct aagtatgagc gtatgtgctc tgctcagcat acaggatgtg    5040
ggagttccgt gtggggctgg ccacagtctc agcaaatcta gcatgcttgg gagggtcctc    5100
acagtaatta ggaggcaact gatacttgct tctggcaatt ccttattctc cttcagattc    5160
ctatccggtg tttccctgac tttattcatt catcagtaaa tatttactaa acatgtacta    5220
tgtacctagc actgttctag atgcagggct cagcagtgag cagacaaagc tgtgccctca    5280
tgaagctttc attctaatga aggacataga caataagcaa gatagataag taaaatatac    5340
agtatgttaa taagtggagg aatgtcaaag cagggaaggg gataggggaaa tgtcagggtt    5400 aatcaattgt taacttattt ttattaaaaa aaaattttt taagggcttt ccagcaaaac    5460
ccagaaagcc tgctggacaa cttccaaaaa aactgtagca ctaagtgttg acattttat    5520 tttatttat tttattttgt tttgttttgt ttttgaggc agtcttgctt tgtcagccag    5580
gctgcagtgc actggtgtga tcttagctca ctgcaacctc tgcctgttgg gttcaagcga    5640
ttcttatgcc tcagcctcct gattagctgg gattatagac atgcaccgtc ccgcctgggt    5700 aattttttt ttttccccct gagacagagt cttgctctgt cgcccaggct ggagtgcagt    5760
ggcacaatct ggctcactg caagctccgc ctcccaggtt catgccattc tcctgcctca    5820
gcctcccagg tagctgggac tacaggcgcc tgccaccacg cccagctaat ttttgtatt    5880 tttagtagag atgggtttc actgtgtcag ccaggatggt cttgatctcc tcacctcgta    5940
gtccgccccc cttggcctcc caaagtgctg ggattacagg cgtgagccac cgcgcccggc    6000 ctgtaattt ttttttttt ttttgagaca gagtcttgct ttgttgctag ctggactgc    6060 agtggtgtga tcttggcaca ctgcaacctc tgcctccgg gttcaagcga ttctcctgcc    6120
tcagcttccc gagtagctgg gactacaggc acgtgccatc acgcttggct acttttgta    6180 tatttagtag aaacggggtt tcaccatgtt agctgagatg atctcgatct cttgacctcg    6240
tgatccgccc gcctcggcct cccagagtgc tgggattaca ggtgtgagcc actgtgcctg    6300
accacgcctg ggtaattttt gtattttag tagagacggg atttcaccac gatggccaga    6360
ctggtctcga actcccagcc tcatgtgatc tgcctgccta ggcctcccaa agtgctagga    6420
ttacaggcat gagccaccat gactggccag tgttgatatt ttaaataggg tgttcaggga    6480
aggtccactg aggtgacagc tgtttttttg ggggagtgg tgggacaggg ccttgctctt    6540
taacccaggc tggaatacag catcacaatc gtagcttact gcagccttga actcctaggc    6600
tcaagtgatc ttcccacctt gacctcacaa cgtgttggga ctgtaggtgt gagtcaccat    6660
gcctggccag atgatggctt tgagtaaaga cctcaggcga gttaagagtc tagcgtaaag    6720
gtgtatggag taggggtatt ccagataggg ggaacaggtc caaagtcttc ctgtttgagg    6780
aatagcaagg gtgccatttt agttgggtga attgagtgag ggcgacattt gtagtaagag    6840
gtaaagtcca agaggtcaag gggagtgccat atcagaccaa tactacttgc cttgtagatg    6900
gaataaagat attggcattt atgtgagtga gatgggatgt cactggagga ttagaggaga    6960
```

```
ggagtagcat gatctgaatt tcattcttaa gtgaactctg gctgacaaca gagtgaaggg    7020
gaacatggac aaaagcagaa accagttagg aagccactgc agtgctcaga taagcgtggt    7080
gggttctgtc agggtaccgg ctgtgggcag tgtgaggaat gactggattt tgaatgcaga    7140
agcaactgta cttgttgaac tctgctaagt ataactattt agcagtagct ggcattatca    7200
gttaggtttg tattcagctg caagtaacag aaaattctgc tgcaatagct taaactggta    7260
acaagaaaga gcttatcaga agacaaaaat aagtctgttt ggggaaattc aacaataagt    7320
taaggaaccc aggctctttc tttttttttt tgaaatggag ttttgctctt gtcacccagg    7380
ccggagtgca atgatgcgat cttggctcac tataacctcc gcctcctagg ttccagtgat    7440
tcttctgcct cagccttcca ggtatctggg attagaggcg cacgcacacc accatgccca    7500
gctaattttt gtattttag taggcacggg gtttcatcat gttggccagg ctggtctcga    7560
actcctgacc ttaggtgatc aacccgcctc agcctgccaa agtgctgaga ttacaggtgt    7620
gagccactgc actcggtcag aacccaggct cttttttaca cttagcttgc aaacccttgt    7680
tctcattctt ttccctttgt attttattg tcgaattgta acagttcttt gtgtattctg    7740
gatactggat tcttatcaga tagatgattt gtgaaaacat tctctcttcc tttggattgt    7800 cttttactt tcttgatcat gtcttttgaa gtgtgaaagt ttttaatttt gatgaagtct    7860
agtttatcta gtttgtcctt ggttgctatg ctttgagtgt catatctaag aaatcattgt    7920
ctaatccaaa gtcaaaaagg tttacccgta tgttttcttc taagaatttt agagttttac    7980
atttaggtct gatccatttt gagttaattt ttatatgtgg ttcaggtaga agtccaactt    8040
cattcttttg catgtggtta ttcagttgtc ccagcacagt ttgttgaaga gactgtactt    8100
tccccatgga attgtcttag catccttgtt gaaaattcat tgtccttgat tgtatagatt    8160
tatttcttga ctctcagttc tacctattgg tctttatgtt gatcctgtgc cagtaccata    8220
cagtcttgat tactgaagtt tgtgtcacaa tttaaattca tgaaatgtga gttctccaac    8280
tttgttcttt ctcaagattg atttggccat gctgggtccc ttgcatttcc atatggattg    8340
taggatcaac ttgtcagttt ctacaaagaa gccaaggagg attctgagag ggattgtgtt    8400
gaatctgtag atcaacttgg ggagtattac catcttaaca gtattgtctt ccatctctga    8460
actgggcaaa ctttgtgtaa atggtcagat ttaggtattt caggctgtgt gggcacaatg    8520
tctctgtcac agctactcag ctctgccatt gtagcgtgaa atagccataa gcaatatgta    8580
tgagtgtctg tgttccagta taatttttatt aatgacaagg aaatttgaat ttcgtgtaat    8640
tttcacctgt catgaaatat tatttggttt ttttggtcaa tcatttaaaa atgtaaaaac    8700
ttttcttagc ttttgaactg gccaaacata tgcaggttat aattttccca ctcctagatt    8760
aaaatatgat aggaccacct ttgaaaagca tgtnnnnnnn nnnnnnnnnn nnnnnnnnnn    8820
nnnnnnnnnn nnnnnnnnnn nnnnnnnnaa cactttggga ggccgagcca ggtggatcac    8880
ttgaggccag gagttcgaga ccagcctaac caacatggtg aaaccccatc tctactaaaa    8940
ataaaaaaat tagctggggg tggtggtggg tgtagggtcc agcccatgg ggcttagcgg    9000 gtgttctccc cgtgcgggga gacgagagat cttaagaaat aaagacacgg ccgggcgcgg    9060
tggctcacgc ctgtaatccc agcactttgg gaggccgagg cgggcggatc acaaggtcag    9120
gagatcgaga ccacggtgaa accccgtctt tactaaaaat acaaaaaatt agccgggcgc    9180
ggttgtgggc gcctgtagtc ccagctactc gggaggctga ggcaggagaa tggcgtgaac    9240
ccgggaggag gagcttgcag tgagccgaga tcgcgccact gcactccaga cggggcgaca    9300
```

```
gagcgagact cctgtctcaa aaaaaaaaaa aaaaaaaaaa agaaaagcat gttttttttt    9360
ttttgagatg gagtttcgct tttgttgccc aggctggagt gcagtggcgc gatctcgggt    9420
caccacaacc tctgcctccc aggttcaagc gattctcctg cctcagcctc ccttgtagct    9480
gggattacag gcatgtgcca ccatgcccgg ctaattttgt attttagta gagacggggt     9540 ttctccaggt tggtcaggct ggtctcgaac tcctgacctc aggtgatctg cctgcctcgg    9600
cctcccgaag tgctgggatt acaggcgtga gccactctgc ccagccagaa agcatttctt    9660
ttttggctgt tttttgttg ttttttttaa ttaactagtt ttgaaaatta tagaagttac     9720
acatatatgt tataaaaaca tctccaagca gcacagaaga tgaaaaacaa agcccttctt    9780
gcaagtctgt catctttgtc taacttccta agaacaaaag tatttcttgt gtcttcttcc    9840
cagattttaa tatgcatata caagcattta aatatgtcat tttttgttgg cttgactgag    9900
atcacattac atacgtatttt ttttacttaa caatttgagt acaatgtgtc atggaaattg   9960
ttccatagca gtatctgtaa ttcttattaa ttgctgtgta atattgtaga atttcttttt    10020
aaaagaggac ttttggagat gtaaaggcaa aggtctccca ttattctggc tgtacaacgt    10080
tctggtgaca tattctctct accctgagag gtccccatac ccatcacctc catttcctgt    10140
aaataagtca accacttggt aaactacctt tgaatggatc cacactcaaa acatttagtc    10200
ttattcagac aacaaggagg aaaaataaaa taccttataa agcactgttt catatgtatt    10260
aaattggatc aatttgcgtg ctagaatgta tgttagagac atgatatgcc cataggtcct    10320
tgctatcacg gtgaggtctc agggacagca gtttggtatc atttggtatc tcataagcag    10380
actctgtctg cctgacttaa caaatcagag tctgcgtttt aacaggttca gtgagtgact    10440
tacatgcaca ttggagtttg ggaagctcca ctataggtgc ttagaccttt cctttgttgt    10500
tgctaataac aatgcaagca tttggaggag agacctgtgt tgctcgtatg tgtccaggtg    10560
tagctgaggt ggccttgctt gtctgctgta gggccattga gcatttgcgt agctgtgatg    10620
aatgagctga ggtgagcctg cggagagctc ccagccattg gtagtgggac ttgcttagat    10680
gaactagaag gacctgagca tccactttgg ggaaaaacaa ccgaatgaag ggagaggcaa    10740
catgcagttt tatttagggt acgaaggaga gctgtggtta aaggtgaaca tttgagtgga    10800 aaggggggcaa cccatgtgtg gagcgggaga agagcggtcc aggcagagtt aacagaaggc    10860
agaaatgctt tccatctttg aaaactagga aggatgccag tggctgaagt aagatgaagg    10920
acagaaatag gggatgaggc ttcgagagat gagaggttag agacgagggt cttgtgcacc    10980
aagataagct tgtgtggtca aaacaagtag tttcgttttt gttttaaaa gatcactttg     11040 gctgggtgca atggttcatg cctgtaatac cagtactttg agaggctgtg gtgggaggat    11100
tgcctgaagc caggggacca gcgtagccaa catagcagca cctataaggt ctctacaaaa    11160
aacttttaaa aagtagctgg gtgtagtggt gtgtgcctgt agtcccagcc acccaggagg    11220
ctgaggaggc tggagggttg cttgagtcca gcagtttgag gctgcagcga gcaatgattg    11280
tgccactgca ctacagcctg gcatgagag tgagaccctg tctctaaata tatgtgtata     11340 tataaagaa aagatcactt tgacaacacc acatgctggt gaggatttag aaaaactagg     11400
tcacttattg ctggtgggaa tataatatag tacggccact ctggaaaaca gtttggcagt    11460
ttctcataaa actgaatgta caattagtat acaacccagc aactcctgca atcctgcgca    11520
ttaatcctag agaaatgaag ccttcatgtt cacataaaaa cctatactca agcgtgcata    11580
gcagctttac ccataatatc taagaactgg aatcagctca gatgtccttc tgcaggtgaa    11640
tggttaaact actcagtaat aaaaaggaat gatctactga tagcatgcaa cagtgtaggt    11700
```

```
gaagttatgc taatgaaaaa agccaatccc aaaaggttac atattatatg attctatgta    11760
tataacgttt tggcagtgac acagttttag ggatggagaa tagattagtg gttgcctggg    11820
gttagagatg gggttgtaga gtaggttagg ggtggcagag gagagaaaag agagggaggc    11880
gagtgtggtt ataaaaggac aacacagggg gatacttgta acagaaatgc tttgtctttt    11940
ttttttttt  tnnnnnnnnn nnnnnnnnnn nnnnnnnnnn nnnnnnnnnn nnnnnnnnnn    12000
nnnnnnnnnn nnnnnnnnnn nnnnnnnnnn nnnnnnnnnn nnnnnnnnnn nnnnnnnnnn    12060
nnnnnnnnnn nnnnnnnnnn nnnnnnnnnn nnnnnnnnnn nnnnnnnnnn nnnnnnnnnn    12120
nnnnnnnnnn nnnnnnnnnn nnnnnnnnnn nnnnngctca ctgcagcctc tgcctctggg    12180
gttcaagcga ttcttctgcc tcagcctcct gagtagctgg gactacaggt gcacgccacc    12240
atgcccggct aattttttgta tttttagtag agacagggtt tcatcatgtt ggccaggctg    12300
gtcttgatct cctcacctca tgatccgccc acctcgccca cctcggcctc ccagagtgct    12360
gggattacag gctgagcca ccgcgtccgg cctattttat ttttttgag acagagtctc     12420
actctgtatc ccagactgga gtacagtggc gcgatcttgg ctcactgcag cctctgcctc    12480
tggggttcaa gcgattctcc tgcctcagcc tcctgagtag ctgggactac aggtgcacgc    12540
caccatgccc ggctaatttt tgtatttta gtagagacgg ggtttcacca tgttggccag    12600
ggtggtcttg atctcctcac ctcatgatcc gcccacctcg gcctcccaaa gtgctgggat    12660
tacagggatt tttgtgtttt tcgtagagac agggtttcat tatgatggcc aggttggttt    12720
tgaactcctg acctcctgtg atctgctggc ctcgcctccc aaagtgttgg gattatagac    12780
gttgagccac tgcactcggc caaggaaaga gatgctttgt cttgagtgtg gtggtgtata    12840
gaaattgtat agaactaagg ctgggcacgg tggctcactc ctgtaatccc agcattttgg    12900
gagaacgagg tgggcagatc gtgagttcag gagattgaga ccatcctggc taacatggtg    12960
aaaccctgtc cctgctaaaa ataccaaaaa ttggccgggc gtggtggctc acgcctataa    13020
tcccagcact ttgggaggct gaggcgggtg gatcacgagg tcaggagatc gagaccatcc    13080
tggctaacac agtgaaaccc tgtctctact aaaaatacaa aagcaaaatt agccgggcgt    13140
ggtggcgggc gcctgtagtc ccagctactt gggaggctga acaggagaa tggcgtgaac     13200
ctgggaggtg gaggttgcag tgagctgaga tcgcgccact gcactccagc ctgggcaaca    13260
gagtgagact ctgtctcaaa aaaaaaaaa aaaagaaat tgtatagaac taaatacaca      13320
aatgaacaac aataaaactt gaaactctaa gtaagatcac tggattgtat cagtgtcaat    13380
attctggttg tgataatgta gtatattaaa tagttttgca aagtgttacc attggggaaa    13440
actggataaa gggcacactg gatctctgtt atttcttaca actgcacgtg aaccaataat    13500
tatcttaaaa aaacttcaat tcaaaaaagt ctgccctgat ccagttggga ggctactgaa    13560
gtaatcaaag ctagacatgc tggtgtcttg tgactggtag cagtggtgat ggtaagtggt    13620
cagattctgg atctcttgga gaaagatctg acaagatttg cagattcttt aaaaaaatg     13680
agattaggct gggcacggtg gctcacgctt gggaggctga ggagggcgga tcnnnnnnnn    13740
nnnnnnnnnn nnnnnnnnnn nnnnnnnnnn nnnnnnnnnn nnnnnnnnnn nnnnnnnnnn    13800
nnnnnnnnnn nnnnnnnnnn nnnnnnnnnn nnnnnnnnnn nnnnnnnnnn nnnnnnnnnn    13860
nnnnnnnnnn nnnnnnnnnn nnnnnnnnnn nnnnnnnnnn nnnnnnnnnn nnnnnnnnnn    13920
nnnnnnnnnn nnnnnnnnnn nnnnnnnnnn nnnnnnnnnn nnnnnnnnnn nnnnnnnnnn    13980
nnnnnnnnnn nnnnnnnnnn nnnnnnnnnn nnnnnnnnnn nnnnnnnnnn nnnnnnnnnn    14040
```

```
nnnnnnnnnn nnnnnnnnnn nnnnnnnnnn nnnnnnnnnn nnnnnnnnnn nnnnnnnnnn    14100
nnnnnnnnnn nnnnnnnnnn nnnnnnnnnn nnnnnnnttg ataatttata aaatgtgatt    14160
atagaatgct gtagtgtcct tgagtttaca tgcccttcct tacacttgtg tgcctgtgca    14220
gatgccttga tttcacaatt agaggaggct gactgagatt tgtttaattt ttttttttt    14280
tgaggcagag tcttgttatg tcccccaggc tagagtacag tagcgcaatc ttggtgcact    14340
gcaacatccg cctcctgggt tcaagcaatt cttctgcctc agcctcccga gtgcctggga    14400
taacaggtgc cagcccccac gcccagctat ttttttgtatt tttagtagag acgggatttc    14460
accatgttga ctgggctggt ctcaaactcc tgacctcaga tatctgccgc cccagcctcc    14520
caaagtgctg ggattacagg cgtagccaca cctggccgtt tgttttaatt tttaaggtga    14580
cgttaaagtg actgcattta ccaaaagtgg ttgagaagcc aggactgttc ttatcctgtt    14640
tttccagttc ttgctcagag caaggtggtt tattttcac ttaattacca tacttacttt     14700
tcatgtagaa caagtcagtt tgagttatca gttcatcatc taactaaatt ccatggggga    14760
aggaatagtt ttagtttctt aaacttccaa ggttgcttat tggacaaaat gagatagcaa    14820
ggcggtgttt ttaagttaga ttttttattt ctttggtaat ataattttct caaaaactta    14880
gtagtctttt agtttagttg ttttagttg gtcctatgtt ttgcatcccc cctctctact      14940
tttattttga tagtgccaat tgcgaagaca tctgaagcca taggtttggg tgggaaggcg    15000
gcacctttag cctgattatc tttgccaggc tgttatctc cttttgcttg gctgagaagt      15060
cttaatagga ggcttattcc cagctacttg gggacataga agcggttagc tattgttcat    15120
gttttactga ggtctgtgtg gtatgttgac tgcagtcagt tactggtttt gagaattgaa    15180
ggcagcctgg tatatagagt aggtattata ttgtgtttct ttgaattgaa tttcctatct    15240
cttgtaatct ttgccatcat cttctgtgaa agaaaaaaag tttctatcaa actataccat    15300
tggttgtaag atgcagttcg gctttagtga tgctaacaca tgatccaaac gtgaaactga    15360
gtattggtga aatacagagg agatttaaag ccagaagacc tgggtttaaa tgctggctct    15420
atgacttcaa atctgtgtgt tcttgggcac gtcatggttg gcacttcaat ttcttctctc    15480
tgtaatgggg gaaatgaggc cagtcatggt ggctcatacc tatgatccca gcactttggg    15540
ggccaagatg ggaagatcgc ttgaggccag gaggttgagc aattgggcaa catagtgagg    15600
ccccgtctct acaaaacatt taaaaaaaat tagccaggcc cagtggtgca tgcctgtggt    15660
ccccaccact caggaggctg agatgggagg atccttttcag cccaggagtt taaggctaaa    15720
gtgagccatg attgtgctac tgtactctag cctgggcagt agagcaagat cctgactcta    15780
aaaaaagta aaatgaaata aaatgggga aatgaactgc tttagtaaca tcatctgttt       15840
tttctgtgag cagtgtagct tgaaagccat tggtgaactc atgcactgtg cttccctgtc    15900
cagatcccca ttctgccccc agcatggagt ataacagttt attagtagta gtcgagaaac    15960
cctcattgaa tgaatgaatg agatgtagaa gtaagtggag tgggtaattg aacacatatt     16020
catttccttt tctttttct tatttttaga aagaaagaac tttcagctac caagaaagac      16080
cgtgtgaatc attgtctgac aatatgtgaa aacatagtgg cacagtctgt caggtaattg    16140
cactttgaac tgtctagaga aaataagaac tttgtatatt ttcagtctta atgggctaga    16200
atattctgtg tcccagttat tttaaatgga ttcaaaaatc cttgaagaag gaccctttc     16260
ccatatttct ggctatatac aaggatatcc agacactaaa atgaataatg ttcccttttc    16320
gtaatctttt atgcaaaaat taaaaccatt atggtaattg aacaacatgt ttatgtttag    16380
ttaacaccct tagcaactat agttatttta aaatcctgtg tggtttgata ttttttgcgtt   16440
```

```
tattgtaaca gtgggaacag cacaaggcgg tccactttgt ctctctcatt ttgcagtttg    16500
ctgtcctgtt gtgctggtgc tcctagcagt ggctggagcc cacttctctg tgctttggga    16560
ttagtggggt catggggcat tgactggagg tcagctttcc ttgcttgatc tttctcactg    16620
gggtgaacta gcagcacctt cttttgtagc tgctttgctt ttggctatct ttctgaccgt    16680
tgttcctagc agctgtagat ggtaaatatg tttaggcctg ttttccaatgg ctgagtagga    16740 gacatatgca cctatgatat ctgaattctg ttacccagat gggcgtgtgt gaaatagtta    16800
ccttgcttta ctttcccttg gaataaataa ttcatgttat tctcctggta gaagctagaa    16860
aaagctcttt atagtcagtc agaaaaaaat ttttagacaa ataatcttga ttttagtact    16920
gacaaaaatg tgtggtgatt cttttttta gtttttttg agatggagtt tcactcttgt    16980
tgcccaggct ggagtgcaat ggtgcgatct cggctcactg caacctccgc ctcctgggtt    17040
caagcgattc tcctgcctta gtcctgag tagctggggt tacaggcatg tgccaccacg    17100
cccagctaat tttgtatttt tagtagagac agggtttctc catgttggtc aggctgatct    17160
caaactccca acctcaggtg atccgcccgc ctcagcctct caaagtgctg ggattacagg    17220
cgtgagccat gcacctggt gattcatttg tttttttaaa aatttcctct tggccattgc    17280
ttttcactgt tttctttnn nnnnnnnnn nnnnnnnnn nnnnnnnnn nnnnnnnnn    17340 nnnnnnnnn nnnnnnnnn nnnnnnnnn nnnnnnnnn nnnnnnnnn nnnnnnnnn    17400 nnnnnnnnn nnnnnnnnn nnnnnnnnn nnnnnnnnn nnnnnnnnn nnnnnnnnn    17460 nnnnnnnnn nnnnnnnnn nnnnnnnnn nnnnnntgt agaaatattg tgggaagaaa    17520
atgaaataac aaatgagcat gtgtcctgaa aataaaaata taaaaattct aagttagcat    17580
gctattgtag aatacaacac tatgataaaa gtagggaaaa aaagtttga attccacgtc    17640 tgctgcctgt gtaagctggg tgactttaga taagctttaa cgtgtttgag ccttactggc    17700
tcatgtttga agtgtaatcc ctcgttacac agttcttgtg ggatcagacg atgcatgtga    17760
aacactgtga agaagtaact gcgatagatg tgttcattag ccgcctgaac gggaagcaca    17820
tcccattgcg atgcccatca tccaaagcta tatgttatct ttactttttt tgtttttttg    17880
agacagagtc tcactctgtc gcccagactg gagtgcagtg gcgccatctc ggctcactgc    17940
agtttctgcc tcctgggttc acgccattct cctgcctcag cctcccaagt agctgggact    18000
acaggtgccc gccaccacac ctggccaaat ttttgtattt ttagtagaga cagggtttca    18060
ctgtgttagc caggatggtc tcgatctcct gacctcgtga tccgcccacc tcagcctctc    18120
aaagtgctgg gattacaggc gtgagacact gtgcccagcc atcttcactt tcttgtgaa    18180 atgatgactc taaatgtttg gcaaacattt ggtgattgtt catctgattt ccactatcca    18240
ggtctcagag aatataattt atctctgaaa gcttattgac ccaggaaaca agatctcttc    18300
caatctgagt acatcaggct ttattcttgt cattttgtct tttgagaatt tcaaatgga    18360 attcatggaa tgttggctca tattcacata ttagtaaagt acgctgagac atcttaagat    18420
tgatttgtgg ttctatttgc catattaaat caaaataata actgttaatg gttttctttt    18480
tttttttttt tttttttgag acggagtctt gctctgtcgc ccaggccgga gtgcagtggc    18540
ccgatctcag ctcactgcaa gctccgcctc cgggtttat gcattctcc tcctcagcc    18600 tcccgagtag ctgggactac aggcgcccgc tacctcgccc agctagtttt tttgtatttt    18660
ttttagtaga cgggggttt cgcccgtgtt agccaggatg gtctcgatct cctgagctcg    18720
tgatccgccc gtctcggcct cccaaagtgc tgggattgag ccaccgcgcc cggcctgtta    18780
```

```
atggttttca cattagtctg tctcttgttt ttatggagta atgctgagag ttcattatgc    18840
ttcttgttct acagaagagc atgttaaaag gatttttttgg gatcagagag gttatccatg   18900
gtttcatagg atactctgta cttttgcaggg atttcagggt atatagccaa aggtgatatt   18960
ttatataaat atgttttatg gaaacttact gannnnnnnn nnnnnnnnnn nnnnnnnnnn    19020
nnnnnnnnnn nnnnnnnnnn nnnnnnnnnn nnnnnnnnnn nnnnnnnnnn nnnnnnnnnn    19080
nnnnnnnnnn nnnnnnnnnn nnnnnnnnnn nnnnnnnnnn nnnnnnnnnn nnnnnnnnnn    19140
nnnnnnnnnn nnnnnnnnnn nnnnnnnnnn nnnnnnnnnn nnnnnnnnnn nnnnnnnnnn    19200
nnnnnnnnnn nnnnnnnnnn nnnnnnnnnn nnnnnnnnnn nnnnnnnnnn nnnnnnnnnn    19260
nnnnnnnnnn nnnnnnnnnn nnnnnnnnnn nnnnnnnnnn nnnnnnnnnn nnnnnnnnnn    19320
nnnnnnnnnn nnnnnnnnnn nnnnnnnnnn nnnncctgt agtcccagct actcagaagg     19380
ctgaggcagg agaatagcgt gaacccggga ggcagagctt gcagtgagcc gagatcgccc    19440
cactgcactc cagcctaggt gacagagtga gactctgtct caaaaaaaaa aaaaaacaaa    19500
aaacaaaaa aaccaaaacc ttatgtatat tgtgaaaatg tagtctgctt taagctctct    19560
aaagaggtct aagttactgg ttcctaagta tggatgagca tcaaaatcat ctggaaaatt    19620
tgttaaaaat acaataatga aggtacctca ctgtccttttt tcccaaacac acttctgcat   19680
tctgttttgag taggtagggc ctacacatttt ttcacaagta ttctcttggg aatacccagg  19740
aatgctcact tgagcaacct cttactaata ccatatactt tgataaagtg gctaggtaaa    19800
aataaatata taaaaatcca tcaatctccc atatattagc ataaatcagc tagaaaacag    19860
taatgtttaa agatctagtt cacagtagca ctgaagtatt gaattccaag aaattgataa    19920
gaaatatgca gaaactttat aaaaacttct gttaatgttt ctgaaagata taggtgacca    19980
cttttctagac aggaagattt tatatcatta agttgacttt tctctaaatt aacacagaaa   20040
tttaaaataa tcttgattaa aattctagta gaggtatttt tgaacttgtt cactgtaaga    20100
ataaatacat aactgcaaag aatatcttaa aatcatcact aggcccggtg tggtggccca    20160
cgcctgtaat cccagcactt ttggaggcca aggcaagcgg atcacctgag gtcaggagtt    20220
tgagcccagc ctgaccaatg tggtgaaacc ctgtctctac taaaaataca aaaattagct    20280
gggtgtggtg gtgcatgcct gtagtcccag ctacttggga ggctgaggca ggagaatcgc    20340
ttgaatccag gaggtggagg ttgtggtaag cctagatggc accactgcac cactgcctgg    20400
gtgacgagca aaattgtgtc tcaaaaaaaa aaaaaaaaaa gaaaaaaaga aaagaaatc     20460
aacgctaata tggtgagact tgatatatgt gacattaaaa tagtgattgg acattagaac    20520
aggtatagaa cagaaagaag agtgtgtgta tctgtgtgga tttatgatgg gtgtagcata    20580
ttgtattagt agggaaatga gggaaatgat atatttcttt gactttggga caacattata    20640
tctctacctc atattgcaaa caagcataaa attctgatta attacctaaa tgtgaaaaaa    20700
tgaaatactt tcttcaaaaa atgtaatctt agtttgagga agactaacat tatgaaggaa    20760
aaacctgttt tgactggaat atagttcaat atgtcaaaat ccaccttcaa caaaattgaa    20820
agtaaattga acttggggaa agtattgata gcatgtagat caaaggttac tagcctgtgt    20880
aaagagcaat tataaatcat taagaaaaga ctgtcaaccc gtcggcacct tgttctccga    20940
ctcccagcct ccagaactgt gacgagtaag tgcctgttgt ttaaaacacc tagtctatat   21000
gtactatttt gttatagcaa ctcaagctga ttaggaccct agtaatcagt agactgagac    21060
taaaacaaaa ataagaacct tttttacctg tcaagttggc aaacattaag aatatgcaga    21120
ttttttgtcag aggtgataca acctttaaga aggcaatttg ggaaaacata aagctttaga  21180
```

```
ttattaatgt gtctgatcta gggcacttac cctaggaaag tgtgtaatga tattggtgca    21240
ctgctgttca tcccattaga aaataaaaat aaccttaata gcttaccact aaaagggga     21300
ttgaaaaatt aagatacatt tatttattta tttattgaga cagagtcttg cactgttgcc    21360
tgggccggaa tgcaatggtg cgatctcagc tcactgctac ctccgcctcc tgggttcaca    21420
tgattctcct gcctcagcct cccgagtagc tgggaataca ggctcacacc tccacaccca    21480
gctaattttt tgtattttta gtagagatgg ggtttcactg tgttgaccag actggtctcg    21540
aactcctgac cttgtgatcc atcccctcg gcctcccaaa gtgtcaggat tagaggcgtg     21600
agccattgta cctggccaga tacatttata caagagagtg ttagttaaca ttcatagatt    21660
ttttttttct tgtttacttt ttattaaaaa aattttttt tagagacagg gtcttactct     21720
gtcacccagg ctgaatgcag ttgcacaatc gtagcccact gcagcctgaa ctcctgggcg    21780
gaagtgatcc ttctgcctca gccttttgag tacctggggg actttaggca gtgctgctat    21840
atatacctgg ctaagtttta aatgttttat agatgggatc ttgctatgtt gcccaggctg    21900
gtctagaatt cctgggccca agcaatcctc ccaccttggc ctcccaaagc actgagatta    21960
caggcattga gccaccactt ctgatcaata gatatttata tttgtgactg aaaatatat     22020
taacaatgtg ttaaaaaatt cagttaaaaa ataatgaaag attttgctt ctagctaaga     22080
tagaataaca aggacagcat ttatcttctt gccttgaaat agttgaaaat ggataaaata    22140
tatgtaacag tggttttcaa gttattgggc attaggcaaa aagagtagt tatcacagga     22200
aaattaatgt ggagagccct acaatttcct tacattgctg cctggccatg gcaagaggaa    22260
aaactgaaag gaaactgagg ctgagccagt ggtttgctgg gttgaggagg cagagctggg    22320
agtccagaga tgcaaggtgg ctagagcccg tatggaaaaa taccagggaa gagagctgca    22380
gagggagctc cggagaactg cacagtaccc tctcatgtgt gtagctgagt attgatgagc    22440
acatgctggt gaggaaatga cccagggctg caggtagaac cacttaaaag gattagaagg    22500
aacaattgct gcaactcaca cagggccagg aagaatttct ttttttttt tttttttt      22560
gtattttag tagagatggg gtttcaccat gttagccagg atggtctcga tctcctgacc     22620
tcgtgatccg cccgtctcgg cctcccaaag tgctgggatt acaggcttga ccaccgcgc     22680
ccggccaaag ggccaggaag aatttctaat cacacaagtc ggagtggaaa acctcggctc    22740
tcatagagca gcaggtagag tactcagaag ggtttgcctg cctagcccca gactaagttt    22800
cgttactctg accccgccta atattaaaaa aagattaatt aaattaattg tttgcaacaa    22860
aagtaatata tttcagtgtt tataacgtgt agaagtgaat tgtatgacaa tagcataaag    22920
gctggaagag cagaaattga catgtatttg tgctggacag aataatgttc ccctcttttc    22980
ccaaaagata tcgagtccta atccctggaa cctgtaaatg ttactttata aggaaaatgg    23040
tttcatggtg tgattaaaatt caggatcttg agatgagggg gctgtcttgg atgatttggg   23100
taggcactaa atgcaatcac atgtgtatgc aaaggaggca gagggagatt ttacatacac    23160
agagaaggcc atgtgaagat agaacagaaa gatttgaagg tgctggcctt gaaaattgga    23220
gtgatgaagc tataagccaa ggaatgcagt agccaccaaa gctggaagag gtaggagcaa    23280
ttctccttca gagcctactc cagagggaac gtggtgctgc cagttcctta atttcagctc    23340
agtgatacta attttggact ctggtctctg aaactgtgaa agaataaatt ttttttgttt    23400
gtttgtttaa gccacacagt ttgtggtaat ttgttacagc agctgcagga aactaattta    23460
tgctgcatgt gaaatggcat aatatcatta agatagattg tgataaaggt acatagtata    23520
```

```
aacaattaag caacaactaa aagcacaaca aggagttata gctaatgaac caaaaaagga    23580
gattagaatc ataaaaatag tgaatcccaa agaagccaga aataggggaa gaggcaaata    23640
aaggaaagaa agagcttgat ggtagattta aacctagtta tgtcaaaaag gacattaaat    23700
gtaaaagata tttttcggat tgaatggaaa agtaagaccc agtatatgct gctgcctgca    23760
agaaacatat tctaaatgta aaggcaaaaa tagcctacaa gtaacagaac agaaagaagt    23820
tcaccgtgct tacaagaatt agatgcaagc tagactggtt ctgttaatat cagacaaagt    23880
ggatttcaga gcaaaggcta ttgcctagga tgagatggtc gtttcataat aacgaagggg    23940
attcgttcat cagccgcaca taacaaactg aaatatttat gcacctgact acggagctaa    24000
aatacacgaa gcaaagccta acaactacga gtagacacag gcaaatccac agtgagagag    24060
atttcagtgg cttctctcag tgatttgtag aacacgtagc cataatatct ggatctagaa    24120
cagttgaaca acactgtccc tatgcaacct gattggcttt tacaggacac tccacccggc    24180
accagcagaa gagacactct ctcaagtgct cacagaatgt ctgccaagat agagcagatg    24240
ctgggccata aaacaagtct ctaaattaaa cgcattcaaa ttattcagag tacgttttcc    24300
gacctcagta tcattaagtt ggaatatatt ataggaagat aacctggaaa agcctcagat    24360
atgtggaaaa actcatttct aagtggccca tgggtcagaa gtgaagtcaa aagggaaaac    24420
tgaaaatctt ttggattgac tgatatgaaa acaatagatg tctatacttg tggggtgctg    24480
ttacagtata gtaaagggaa atttctagca ttaaatgcct gttttagtaa agaaagattt    24540
caaatcaatg acctcagctt ctaccttggg aaacttgaaa atgacaagca atggaatcc     24600 agagttacca gaaaggccag gtacagtggc tcatgcctgc aattctgcca ctttgggagg    24660
ccaaggcagg cggattgttt gagactggca gttcaagacc agcctgggca gcatagggag    24720
actccatatc tacaaaaaac acagaaaatt agccaggtgt ggtggcatgt gcctgtagtc    24780
ccagctaacc aggagtctaa ggtgggagga ttgcttgagc ctgggaggtt gaggctgcag    24840
tgaactgtga ttgtgccact gcgctccacc ctgggcaaca gaatgagacc ctgtctcaaa    24900
aacaaaaaca gttactagaa gaatggacat catagagata agagcagaag tcagtaaaat    24960
agaaaacaaa aatacataga aaatcaataa aaccaaaagc tagttcatca agaacatcaa    25020
taaattggtg agactaatag gaaaaaaagt gaagtcacat attatcaata tcaggaatga    25080
gggagatgac agtagtatag attatataga tattaaaagg gctatatgag gcaggtgcgg    25140
tggctcacgc ctgtaatccc agcactttgg aaggccgagg tggacagatc acctgaggtc    25200
aggagtttga gaccagcctg cccaacatgg tgaaactccg tctctactaa aaatacaaaa    25260
attagctggt catggtgcca tgcgcctgta gtcccagcta ctcgggaggc tgaggcagga    25320
gaattgcttg aacctgagag gcagaggttg cagtgagctg agatggcgcc attgtgctcc    25380
agcctgggtg acagagtgag actccgtctc aaaaaataat aataataaaa aggactatat    25440
gggaatatta tgaacaactt tatgccaata aatttgataa cttatagatt aaatggataa    25500
gttccttgaa agacacacaa actattaaag ctctctcaag aagaaataga taaactgatt    25560
agccctatat ctattttatt aaatttaaat gtaaaaatca atatttagtt actggaaaac    25620
ttttaagtgt ggttggaaat ggtatatgaa cttttttcaac tgaattttat gaaggctaat    25680
cacaggtaaa ggttttctga tgaaaattta gtgtctgaat tgagatgtgc tgtaaaaaat    25740
gttgttatgt atcttaatca tttcttcaca ttaattacat gttgaaataa tactttgggt    25800
gtattgggtt aaatgaaata ttatgaaaat cttgcctgtt ttcttttac tttttgatgtg     25860 tcacctggga aataaaaaag tgtgacttac attctgtttc tgttgacagt actgctttgg    25920
```

```
agtgcagtgt tggaatgatc tagcatttcg aagacctttc ctcccttcgt tattcagggc   25980
tgtattccac atagataagt ctgaaatact gctaagtggc acgttttgtt ttgtgctttt   26040
gtaagtttgt tgatcgttac tgatgtggac ctttggtgcc tcttaggctc atggctatct   26100
tccaaccatt gtttgcaatt tttacctaga gataaagaga aaaagagatt tggtttcaga   26160
gtaagttaga ttgagatcat gaaagagcaa tctcattttg atgcttcaaa aatagcacat   26220
cccccgtatt actgggattt gctattcttg ggcttacttc aagaacatcc ttgtgttgct   26280
ggtttggatg cttccgaatg ctgtgaagtc agtttcatgg acgtggctca tcagtttagc   26340
tctcttggct ttgtttaggc agttggagca tgatagcctg aacagcttct ctcaattaaa   26400
catttacaaa tcgtttacga atagtaaaca aactccaggt tttgtgactc tttgatagtt   26460
catctagcac aacaaaaaca caatgtgacc atgatcacct ggcatcttag ggtgaaatac   26520
tttggcccag actgaaagca aaattaaaaa ggggcaagag agatatactg ctgaactgat   26580
tttcaaggtt ccaagaatat cataggttaa gagtaaaagt aaacttttga cagagagcag   26640
cgggttttct gggattgaag tatctgaagt tttcaaacga aaatttaaaa agaaaaaatg   26700
agaattgcct tataagtaca atctcttctt ttttaaaaaa taaactttat tttggaatag   26760
ttttaggttt atcgaaaaaa attagggtag agagttttca tatccctac atccggttac    26820 cccagttatt atcttaatta agtgtgagac attttcatgt ttaatgaatc agtatcgata   26880
tgctgttaac taaagtgcag actttattaa gattttctta atttctatgt aatgtccttt   26940
ttctgttcca gaattccgtg caggacaccg gatacctcat tacatttcat tgtcatgtca   27000
ccttaggctc ctcttgacag tttctcttct tttttgctta gaaattctcc agaatttcag   27060
aaacttctgg gcatcgctat ggaactttt ctgctgtgca gtgatgacgc agagtcggat   27120
gtcagaatgg tggctgatga atgcctcaac aaagttatca agtaagagc cgtgtggatg   27180 gtgttctcag aaatgtcatt gttgtaggct aagagaagca gccatcgttg agtgttcttc   27240
tgtttggagc ccctgaggat gtctgcactt ttttccttc tggtgtgtgg tttggaggtg   27300
ctctggtatc tgcccgcatt gcttgccaca cctgcctggt cagaaggaac tgtgttgacc   27360
cttgtgcctg catggtgcct aggtcaatga agggaaccaa tggtgaccac tggatgctcc   27420
tgggaaaatg tcactacagg taccagagaa gccagagcta tgcccacatt ttttttttt    27480 ttttttttgag acggagtctc actctgtcgc ccaggctgga gtgcagtggc gcgatctcag   27540
ctcactgcaa gctccgcctc ctgggttcac gccattctcc tgcctcagcc tcccgagcag   27600
gtgggactac aggcacctgc caccgcgccc ggttaatttt ttgtattttt agtagagaca   27660
gggtttcact atggtctcga tctcctgacc tcgtgatccg cccgcctcag cctcccaaag   27720
tgctgggatt acaggcgtga ccaccgcgcc cggcgctat gcccacattt ctatgagtct    27780
cagttttctt aactataaaa tgggatcaaa gttttgtgg catgcgtatg agtgtgtgtc    27840
tgtgtgagga ttaaatgcac taattgccac taccggatcc tcaaagtggt aagaagtatt   27900
cttattaatc atgacatcct cacactctta tgcagcaaga ttgatgggtg tggcactgct   27960
tctctttttc catcacatgg attccatgct atccttttgc ccagggaatc tttcctttgt   28020
ggccagcact ttgttgtttg gctcatcacg ctttctgtgg gcaggacgct ggcttctctg   28080
gagtcttggg attctagctc cctctcttgt ccctagagtg gtcactgtct tctctctctg   28140
cttgcaattc ttgctttgct cgcatctcac tcatgcggtg acctgtatca gtttcacctt   28200
gttctccgtg cctgctggtc gttggcacca cttgcctgtg gatggcatcc catagcgtat   28260
```

```
ttagggcctg cttccccagt taagcttgct tttccacagg cctgaatatc cttgcttgct    28320
tctgttattc ccactggcag gaccacggcg gtcttttttg gatgagacag ggtcttgctc    28380
agtcacccag gctggagtgc agtggctgat cacggctcac tgcagccttg agctactggg    28440
ctcaagctat catcctggcc tggcttcttg agtagctggg actacaggcg tgcaccacca    28500
tgcccagcta attttaaaaa ttatttgtag atatgggatc tcgccaggtt gcccaggctg    28560
gtcttgaaca cctgggctca agtaatcctc cctccttggt ttcacaaagt gccgggatca    28620
caggtgtgag ccactgtgcc tggcccttga tgtttcagtt cttgatattt gatcctcaga    28680
gtcagaaagt ctaaaaagag gactatccca ggttgccttg gttcacggca aatgggacgt    28740
taagagggca gagaaaacaa tatgaccaga aacgcttcta atattggtca tttaacgtgt    28800
aagtattgtt cttttttaaa cctccttcat cttttttctag ggattgctgg acacagtggc    28860
ttggtgtgtc tgagggctgt aggccatggc cctgggttgt ggttttaggt ctcaggtgct    28920
cttcctggtt gtctccttgc ttctttccca tttcctcttc tttgtttcca gccatttctc    28980
cctttttgctt aagtttggtg cagcagggtt tggctgctct cagattgctg cttcctcaga    29040
tgatgcagtt gccaggccca gtgggctggc agtgggatca ggatctgact aggtttgctc    29100
tcactgtggc agaggagggg caggcgtggg agagcacgtg tgaccccagg ccaggtgtag    29160
ggagcccagg catggtcact tagccttcag gtcctagact ttgtcttctc atgagtgtgg    29220
ctgtgtgtgt atggtgagaa ccaggttcta cgtagcccaa gaaaatgtag agaaatgcac    29280
tgggtatctg acatagcctg gcagcacgcc tccctcaagt aggttagtct caggcggtga    29340
agcatgtatg tccagcaaga acttcatatg tggcataaag tctccgttct gtgcggcact    29400
gacaaatcac caccgtcagg aggctgaagt aatttctgtc tagggaggca gggaaggctt    29460
cctggagaca gtagccaata ggtgaaaggg tagattggag accttcttaa tcatcaccgc    29520
ctcttggttc gaggggtgcc aggaagctgt ggaggctgag aggaggggga acccatctta    29580
tgctgccaga gagtgggaca ccctgagggt caggtcaagg ggttgtacct tgttgggtgg    29640
agaattaggg gctcttgaag acttttgatg tggtcagggg agtgtatcat ttaggaagag    29700
tgacctggta aggacgtggg atagaggagg acagaggtgg gagggagtct aggtgggagt    29760
gagtgggccc agcaggagtg cagggcctcg agccaggatg gtggcagggc tgtgaggaga    29820
ggcagccacc tgtgtgtctg cggaagcagg ggcaagagag aagaggccag cggcgcgccg    29880
ccatcaccca gcaactggcg tagattgtga gagcccattc cctgcttta ggaggggccg    29940
agttttagtt ttctcttata aaataaactt ggtatttgtt tacaaaacat ttgtaaagct    30000
aaatcaaggt ttgataaggc ttctagtttt atttaagaag taatgtttaa ataaatgtcc    30060
aattcgcttt gcttatttaa ggactttcag tacaaacttc aacaacagga tcaggattta    30120
aacatttctg agatgttatt acccctcaga atttcccaga acgtgatctg gttttgattt    30180
tcaagcttgc tgacccagta ggttaaccca caaattttac taagatacac ctcagtccat    30240
ttatatcgac tgcccatgtc acggtcaaag agatcatcga ctgatgtttg gcacagcttc    30300
ctccctcttg ggtgggcaag catttggaag agaaggctcc catgggtgag agtggggcac    30360
cagagtcttc cccgtcctgt cccctggctt gagaaaccct tctctaatgt ggactttgtg    30420
ccgttagcat cgttactggc ttgaagttga ccatgtggac ataatttctg gtttagcctc    30480
acaagtgagc aaggagggtt gagagatgtg ctgtgaggaa catggggccc ccgctggccg    30540
tgggctctgg gtcagggggg caggggacca tgggcatacc tgacagtgag gaggggccac    30600
acctgcagaa agcatgcggg actcggcnnn nnnnnnnnn nnnnnnnnnn nnnnnnnnnn    30660
```

| | |
|---|---|
| nnnnnnnnnn nnnnnnnnnn nnnnnnnnnn nnnnnnnnnn nnnnnnnnnn nnnnnnnnnn | 30720 |
| nnnnnnnnnn nnnnnnnnnn nnnnnnnnnn nnnnnnnnnn nnnnnnnnnn nnnnnnnnnn | 30780 |
| nnnnnnnnnn nnnnnnnnnn nnnnnnnnnn nnnnnnnnnn nnnnnnnnnn nnnnnnnnnn | 30840 |
| nnnnnnnnnn nnnnnnnnnn nnnnnnnnnn nnnnnnnnnn nnnnnnnnnn nnnnnnnnnn | 30900 |
| nnnnnnnnnn nnnnnnnnnn nnnnnnnnnn nnnnnnnnnn nnnnnnnnnn nnnnnnnnnn | 30960 |
| nnnnnnnnnn nnnnnnnnnn nnnnnnnnnn nnnnnnnnnn nnnnnnnnnn nnnnnnnnnn | 31020 |
| nnnnnnnnnn nnnnnnnnnn nnnnnnnnnn nnnnnnnnnn nnnnnnnnnn nnnnnnnnnn | 31080 |
| nnnnnnnnnn nnnnnnnnnn nnnnnnnnnn nnnnnnnnnn nnnnnnnnnn nnnnnnnnnn | 31140 |
| nnnnnnnnnn nnnnnnnnnn nnnnnnnnnn nnnnnnnnnn nnnnnnnnnn nnnnnnnnnn | 31200 |
| nnnnnnnnnn nnnnnnnnnn nnnnnnnnnn nnnnnnnnnn nnnnnnnnnn nnnnnnnnnn | 31260 |
| nnnnnnnnnn nnnnnnnnnn nnnnnnnnnn nnnnnnnnnn nnnnnnnnnn nnnnnnnnnn | 31320 |
| nnnnnnnnnn nnnnnnnnnn nnnnnnnnnn nnnnnnnnnn nnnnnnnnnn nnnnnnnnnn | 31380 |
| nnnnnnnnnn nnnnnnnnnn nnnnnnnnnn nnnnnnnnnn nnnnnnnnnn nnnnnnnnnn | 31440 |
| nnnnnnnnnn nnnnnnnnnn nnnnnnnnnn nnnnnnnnnn nnnnnnnnnn nnnnnnnnnn | 31500 |
| nnnnnnnnnn nnnnnnnnnn nnnnnnnnnn nnnnnnnnnn nnnnnnnnnn nnnnnnnnnn | 31560 |
| nnnnnnnnnn nnnnnnnnnn nnnnnnnnnn nnnnnnnnnn nnnnnnnnnn nnnnnnnnnn | 31620 |
| nnnnnnnnnn nnnnnnnnnn nnnnnnnnnn nnnnnnnnnn nnnnnnnnnn nnnnnnnnnn | 31680 |
| nnnnnnnnnn nnnnnnnnnn nnnnnnnnnn nnnnnnnnnn nnnnnnnnnn nnnnnnnnnn | 31740 |
| nnnnnnnnnn nnnnnnnnnn nnnnnnnnnn nnnnnnnnnn nnnnnnnnnn nnnnnnnnnn | 31800 |
| nnnnnnnnnn nnnnnnnnnn nnnnnnnnnn nnnnnnnnnn nnnnnnnnnn nnnnnnnnnn | 31860 |
| nnnnnnnnnn nnnnnnnnnn nnnnnnnnnn nnnnnnnnnn nnnnnnnnnn nnnnnnnnnn | 31920 |
| nnnnnnnnnn nnnnnnnnnn nnnnnnnnnn nnnnnnnnnn nnnnnnnnnn nnnnnnnnnn | 31980 |
| nnnnnnnnnn nnnnnnnnnn nnnnnnnnnn nnnnnnnnnn nnnnnnnnnn nnnnnnnnnn | 32040 |
| nnnnnnnnnn nnnnnnnnnn nnnnnnnnnn nnnnnnnnnn nnnnnnnnnn nnnnnnnnnn | 32100 |
| nnnnnnnnnn nnnnnnnnnn nnnnnnnnnn nnnnnnnnnn nnnnggtggg agaatcactt | 32160 |
| gaacctgggc ggtggaggtt gccttgagcc gtgatcacgc cactgcactc cagcctgggc | 32220 |
| aacaaagtga gacttcgtct caaaaaataa aaataaaaat gaaataaaat cagtccgggt | 32280 |
| gtggtggctc gtacctgtag ccccagcact tcaggaagct gaggcaggtg gattgcttga | 32340 |
| gaccaggagt ttgagaccag cataggcacc atggcaaaac gctgtctgta cagaaatgag | 32400 |
| ctaggtgcgg tggtgcacaa ctatagtccc agttacttgc gaggtggagg tgggaggata | 32460 |
| aatggagcct ggaaggttga atctacagtg agctgagatt gtaccactgc ccttcagcct | 32520 |
| gggcgagcaa gtaagaccct gtctcaaaaa aaaaaattat tgactatatc ttattgtcta | 32580 |
| taatccctcc tctgtgctat tgaataccag gttttgggcc cttatttcca tcactgaaca | 32640 |
| aacttcactc tattgagcag catgtgtgga atttcatctt tattcaataa ttaacagcta | 32700 |
| ggaggaaatg ctgtttgcta gactattgct ttacttttct tcaaaaggtt actcttttatt | 32760 |
| agatgagatg ggaattaaaa atggtaactt actttatgtc tttataattg aagcccgcta | 32820 |
| gatcttaaag tagttaccag atgttttatg catttaaatg gccttttctc taaaaataga | 32880 |
| aagtaacaat gaaagaaaat gcttcgtttc tatgcaaccc tcttggtgac tagtgtgtgt | 32940 |
| gactcttaat gtgacactca ttgcaccccc tcagaatggt gcccctcgga gtttgcgtgc | 33000 |

```
tgccctgtgg aggtttgccg agctggctca cctggttcgg cctcagaaat gcaggtaagt    33060
tgtacattct ggatgttgat ttttgttggg ggccagctgc tactgatcct ttatgtctca    33120
gctcagatgt catttcagaa atctgctctg ccccttccaa attgcagtcg accttgccct    33180
gtttatgttt ccgtcatagc actaatccgt gtcagaaagt gtcacgtaca gtctgtgtgc    33240
ttgttcattt tctatcccac cctcccccaa gagacttatg ggatgtgtgc cccaggacag    33300
caggggtctt actgtcttat gctctgttgc agcctaaaca gcagtaacag tgtctgcaca    33360
tagtacttgc ttaaatgatt cttgccaaat tgttgaaggt tgaggtacca gtttcattat    33420
tgctgactat aggagttaca gcaaaatatc catttgtcta ttacatgagt taaaaatatg    33480
gttgtttcac tatgaatagt tttgtctagt caaaacagtt gtgtcttaac ggattgagaa    33540
acaaaagcag gaccactttt catcagctcc ctcctcctta acctgcagta tacgctgatg    33600
ctgatgtcct gtagaccctc agctccatcc tgagtcactg gaacgtggt ctaaaccctc     33660 attattagta tgaactgagt ttcaataaga atctcacatg ggtcgggtgt agtggctgat    33720
acctgtaacc ccagcacttc aggaggccaa ggcaggtgaa tggcttgatc cagactaggc    33780
aatatggtga aaccccgcct ctacaaaaaa tacaaaaatt agctgggcat ggtggtgcgt    33840
gcctgtaatc cagctactg gagaggctga ggtgggagga tcagttgagc ctgggaggtg     33900
gaggtcgtgt tgagccaaga tcacatcact gcactccagc ctgggcaaca gagtgagacc    33960
tgtctcaaaa aaacaaaaaa caagaaaca aaaaaaagct tatatgggtg cagaggtata     34020
atcactaagg aaatttcttt ttgtgtagtc tttttttcttt tactgtcatt tcaaaaaatg    34080 tgttatatttt ctgaagtaac acatccaggt tctccacata gcagccaaag tgaccttaaa   34140
gaacataatt gggtcttgtc attcccttat ttaaactctt gtgcccgttt cccagtgccg    34200
tttagattga ttccagactg gtaactggct ccgtcacctc agacactctg cattgactca    34260
ttagcctgat cagttcttca gatgagtcag ttttttcttc ctcctgatgg tttgtttgtt    34320
ttgtttattc ccctcagttc tcagcaaaac agtcatttcc ttagggaggt ttccctagcc    34380
tccctgtctt tccctgtccc aggagcctgg tggtgtggtc actgccctct gaggccctgc    34440
ttgttgccag gctctgccac tagagggcag ggctgcacca ctcctggcac ctcacacctg    34500
gcctgccctg tcagtgtttg ttgggtgaat tcctgtgatc tgtgactcac tgctctgtgt    34560
cctacacatt ctgcttttct tctcccctca caataccatt tataattctc cttttttcagg   34620 aaagctttat ttccattaaa acattttttgt ttttaaaatg gtattttctt acactattat   34680
tttctaatta aaaatgagtg ttttggcagg gcgtggtggc tcaccctgt aatcctagca     34740 ctttgggagg cccagatggg cggatcacaa ggtcaggaga tagagaccat cctggctaac    34800
atggtgaaac cccgtctcta ctaaaaatac aaaaaaaaat taggcgagtg tggtggtggg    34860
cgcctgtagt cccagctacg tgggaggctg aagcaggaga atggtgtgaa cccgggaggt    34920
ggagcttgca gtgagccgag atcacgccac tgcactccag cctgggcgac agagcgagac    34980
tccgtctcaa aaaaaataa aaataaaaa aaaaaaataa ataaaagta aaaaaaaaa        35040 agagtatttt aagaagtatt acgatttact gcaaataatt tttaaaccca gccttttaga    35100
tcctctgtga tcataagaga aatgaaggat gtctcccgac acttgagctt catccacatt    35160
tcattctctc gttctttcag ctgagctttg cccatcccca ttagggaccg tttggcatat    35220
gaaactggct tttcccctaac agggaatgaa ttgcttctat ttctcctgaa ggagagctgg    35280
aggaatgact tgcgttcttt tgcatacaca ggccttacct ggtgaacctt ctgccgtgcc    35340
taagtcgaac aagcaagaga cccgaggaat cagtccagga gaccttggct gcagctgttc    35400
```

```
ccaaaattat ggcttctttc ggcaattttg caaatgacaa tgaaattaag gtacgattat    35460
tgcctcagat cacaaacatg tgagtgacgc tgtgagtgag tctgtggagg gttacggctt    35520
ctgagcaggg agtcatgtgg gagcgcttct tagagtatgt tgtatgtcgt aatttagact    35580
accgtcattt gtgttatttt tgaggcacct aaagacttct ttccacttct gatttcttac    35640
tgtggggtga agagttgaat tgggagatgg tttatagatg cacattcaaa aggcatattt    35700
ccagagcaga ttggttttca gtgtattaga gtgactgttt aacctagctg tggaaagatg    35760
gctgtgccag gactgcaggt aggagaaagc tcactgacga ggccttgtgg gtctgaacat    35820
cctgcagcta tcagggcctg ttggctccct gttgtgcatt ccaacaaacc accttcaaac    35880
ccactttagt gtttgtttat aatgtccaga aatagtgacc ctgtcacatg ctctacagat    35940
tacaggattc ctagcctctt ccttttggt gggtcagtcc tgggtttgag cccaagtggc    36000
cctcttggaa ggtgatgata cacagtgggt agagtggaat cagatggact tggattagaa    36060
ttctgtccgc tttactggtt cttttcctct aggcaaacta ccaacagct ctaagctatt    36120 tccttcgtat tctgaaaact aagccttaat gggacccata tcgggcaatt ctgagagtga    36180
aataaatgaa tatgtgttag cgtgtagcat agtcgcccac aggaagggct tagatgttag    36240
ctgctactgc tcttattagc tgaatgactt ggaataaagt gttagcctct ctcatgtttt    36300
tttctctgag ctttgaagtt ttcttgttaa tactaaggag atattcaaac tagtcatggg    36360
gttttggaat gacgaaggga gatcatgaat ctaaagaatt tagtgtggta attcatcatg    36420
ctcagtaaat ggtagctgct gcttgctgtt atttttatta ccatctcttt ggagtgggag    36480
taggtctcct ttgtggtcag aggctgtgag agctccgcag cgccagtctg cccgtcagta    36540
caccgggctc tgatgaaggc agttccctct gtggtatctc tggctgtcag agctcagatg    36600
atagatggtg ttttgtact ctcagttctc atcattttca tgatttcgat cactatttga    36660
gtatgatgat gctaacactt tgttgaacat agagtccatt aattacttcc ttcctgaacc    36720
ttaggtattt aaaaaaatct attctgctac ctctctgctc atttatgatt attcagattt    36780
attatcaaga gcctggtaca gtggcttgtg cctataattg tagctacatg ggaagctgag    36840
gtaggaggat tgctggaggc caggagtttg agaccagcct gggtaacatg gtgagaccct    36900
atcgctaaaa aatgaaaaaa gttagctggg catgatggca cgtgcctgtg gtcctagcta    36960
ctcaggagac tgaggcagga ggattgcttg agcccaggag ttggagttcg aggctatact    37020
gagctgtgat tgtgccacca cactctggga tgggtggcaa agaagatgc catttcttca    37080 aaacaaaaca aaacaaaaaa aggtattatc ggtgaaattc aatagtacca acaggattat    37140
aaacaaagat agttctcttc ctactttttc tcttaatcct tgtgtctcag aggcaaacat    37200
aactcttagt gtttcttcca atatttactt cgannnnnnn nnnnnnnnnn nnnnnnnnnn    37260
nnnnnnnnnn nnnnnnnnnn nnnnnnnnnn nnnnnnnnnn nnnnnnnnnn nnnnnnnnnn    37320
nnnnnnnnnn nnnnnnnnnn nnnnnnnnnn nnnnnnnnnn nnnnnnnnnn nnnnnnnnnn    37380
nnnnnnnnnn nnnnnnnnnn nnnnnnnnnn nnnnnnnnnn nnnnnnnnnn nnnnnnnnnn    37440
nnnnnnnnnn nnnnnnnnnn nnnnnnnnnn nnnnnnnnnn nnnnnnnnnn nnnnnnnnnn    37500
nnnnnnnnnn nnnnnnnnnn nnnnnnnnnn nnnnnnnnnn nnnnnnnnnn nnnnnnnnnn    37560
nnnnnnnnnn nnnnnnnnnn nnnnnnnnnn nnnnnnnnnn nnnnnnnnnn nnnnnnnnnn    37620
nnnnnnnnnn nnnnnnnnnn nggagtacaa tgacatgatc ttggctcacc acaacctccg    37680
cctcccgggt tcaagcgatt ctcctgcctc aatctcctga gtagctggga ttacaggcac    37740
```

```
gcaccaccat gctcggctaa ttttgtattt ttagtagaga cggggtttct ccagattggt   37800
caggctggtc tcaaactcct gacctcaggt tatccaccca cttcagcctc ccaaagtgct   37860
gggattacag gcatgagcca ctgcacccgg caacttccac atttctcagt aacatgcttc   37920
tactgctttt ttttttttt tttttcaat tttagacatt ttttactttc acactataat    37980
tctatcagaa ttcagtatgt acattattat acctaagtaa atagtcatgg ttggttgtgt   38040
attatatttc tttgtatttc ttatttgatg agagagctgt gttttttgct gtgggttgaa   38100
actgtggaga gaggacatgg ggaggggaag gaagacagat gaagttggtg actgtacctt   38160
cctggccata gctgggttct cagcaccctg ggatctgctg atcacctgct cgtaggccaa   38220
gccactagcg aagttctagg tgacccagtg ctggggatgg gggggtcacc tgcaaggtct   38280
agtcatggag gtgggggcta cagtgttggc ttgtgctggg gccagcatcc ttaggaatgc   38340
atcttggagg aggaggagac agccacccac ttcttgactg gggccttcag cagtgccagc   38400
ttcttgggca gactggtgct ggctttcatc accacatcgt gttcaatctt cttccagatc   38460
ctgacttcta ggttcacctt tccttagacc ccggttcctt tcagaggctg tcgctctgcc   38520
ttgctctttg ctggcttgtg ccttgattat atgtctttgt acaactttt gttttcctgg    38580 agttaatcct cacatctgtt ttcctagagt gaattgttac ctttatatca cttgcttatt   38640
attctttgac ctttttttct tctcacacct tccaacttct ttgtaaaatg tgtttagtac   38700 aattttcat gacaggtaat ttaccaaatc agttttccc cagtgcagtc atccatcttg     38760
agttacccag ctcgctgccc cagtctgggc ggattgctct tcaggtctgt tgtacacttg   38820
tatcctagga cttctctttg ccatcagcct ggaatttcct ttgcagttct cctgttggat   38880
gcccagttcc tacatgccat atgtttatct ttctatcctc tagtagcttt gtgagagaag   38940
atgaatggga ggtaaattgt ttggagtttt gcattcataa aaatgccatt ttttctcgcg   39000
tacacttggc tgagtatagt gttctggggt agaaatcatt tttcctcaga aatgtgaagt   39060
cttttcccgt tgtcttaaag tctccaacat aacccaattc cttaacccat gaatgtgctt   39120
ttctctggaa gctttccatt tttggggagg tgaagtgcta ggtacttagt aggccttta    39180 tttttattt ttatttgttt tttgaggcgg agtctcactt tgtcgccgag gctggagtgc    39240
agtggcatga tctcggctca ctacaagctc tgcctcccag gttcacgcca ttctcctgcc   39300
tcagcctcca gtagctggga actacaggcg cacaccacca cgcccggcta gtttttttt    39360 tgtatttta gtggagacgg ggtttcaccg tgttagccag gatggtctcg atctcctgac   39420
ctcgtaatcc gcctgcctcg gcctcccaaa gtgctgggat tacaggcgtg agccaccgcg   39480
cccagccagt aggccttta atttggaaac ttatatactt cagttctggg aaaattttct   39540
tacatttctc tgataaattc ttgcctttta ttttctgtgt tctctccttc tgaaattagt   39600
tagttggatg ttggtcctcc tgggttgact cacatcttac cttttctttt ttctggtact   39660
ttttagatat ccatctcaaa ctcttctatt cagtgttatg tttttaactt ctttcttttc   39720
tttgtctctt gatgggtct tgcttgttg cccaggttga ggtgcagtgg tgcaatcata     39780
gctcactgca gcctccaact cctgggctca agcaaccgtt ctgccttagc ctcccaagta   39840
gttgggacta caggtatgca ccaccatgtc cagctatttt ctttactttc tttcttttt    39900 ttttttttt ttgagatgga gtgctgctct gttacccagg ctggagtgca gtgatgcgat    39960
tttggctcac ttaagcctct gcctcccagg ttcaagcaat tctcctgcct cagcctccta   40020
agtagctggg attataggtg tgcaccacca cgcccggcta ttttttgtat ttttagtaga   40080
gacggggttt cgccatgttg gccaggctgg tctcaaacac ctgacctcag gtgatccacc   40140
```

```
tgcctcagcc tcccacagtt ctgggattac aggcgtgagc ccatcattaa atctttaaat    40200
actagtatct gtaagtcttt tcctcttgag tcagccagta tccctggaag gaaattcctc    40260
attttcctgc ttggagacta taagcttggc tgtgtttatc ctgcaaccgg ggactggaag    40320
gggatggaag gggactgaca ctgttgctgg tcagggcgcc ctcttttttgt tttctgtatg    40380 catctcacat ctgtcctcag ttatgtaaac acctcttgag attatccctc tcagtctttg    40440
ctggaggtgg ggaaggggct gcttcctggg ctgccttgga ttggagggga gacctcaggc    40500
gagtgggtgg gaatttgccc aaggagccat gagacaagcc actgttccac cctctccgtc    40560
cctccacttt cagatgtatg tggtgcctcc aaagcccgag tgcttcttgg agttctgtgg    40620
cttgaataag cttgcttttc actggtatcc ctcataccttt ctcccccatc cccagcaaag    40680
cttgcatttg aacttcttcc catgggctaa caaatcagtc agttatgtag cccttgttac    40740
tttttagctt ccgaagtttt gttgacacac gtagtctgct agtgtccctg ttctgttctt    40800
tctgtccgtg tacattatg ctttatacaa cttctttaca tgattttcgt ggggtttctg    40860
ggtagcagag cttcacatgt tcaatccagc atgttggatt agaagtctcc caccctctgg    40920
tgtattctca ttctcagaat tacctgccaa acaccgatac tcccttgttt ttccttttcc    40980
tgacaggaaa tgtacatacc agacaggaca gaaatcatta gtgtatccct tggtgaataa    41040
ccacaaagtg atcttaccct cgtaaccacc acccaggtca agacagagta ttaccagcac    41100
tcagaagcct cacccccatc ctcccatcac tgcttcttcc ttcctcccca aggtcatgac    41160
tgtcctggct tctaatgcca gagtctgttt ttaaattctg tgtacataga ccatatagta    41220
tgtattcttt ttgtctggtt tcttttgctc gacagtaatt tcttaagagt cttctatatt    41280
atcgtgtgta ttagtagttc ctgtagtttt aggagcttca tagcattcca ttgtaggtat    41340
ataccacagt ttattcattg tgttatcact gggttgtttc tagttcttgg ctattgtgag    41400
caatgctact gtgaccactc tcaggtgttt ttttggagc acatgtgcag gtttccatca    41460
tgcgcagcta gaggtggagt tgttgggtga tagggtgtat gcatgtcagc tgcagcagaa    41520
actgccaaat agctttcctg agtgcttgta ccagctcacc ctttggttgc tgcgtatggg    41580
gactccggga gctctggtcc tcgctagcac ttggaattgc tgatgctttt acttttagcc    41640
ttcctgatgg gtattttctg gaatcacatt atgattttaa tttccgttcc ttaaagtacc    41700
cttgactctg aagtttaatg attaatgcat ctcttccttt ttgaagtact ctgaaaggta    41760
tgttgtgcat gtgttgaaaa ctggagctat ctagtctaaa atacagtgta cctcctccct    41820
gtttgaagag ttgtagcatg gcctcggggc ctcctgttag gtgccttgga aagggattc    41880 ttgggattgt agagattaga cctgaggagg ccccttggag ctctcagact aaattttgtt    41940
ctttattatt ccaaactatt taagctcacc gtgtgctgac tcatcataat aatgagtagc    42000
tctcattgtg cttgtatatt tggaccaata gaatgatttt ttttttttga gacatagtct    42060
tgctctgtca cctaggctgg agtgcaatgg cacaatcttg gctcactgca gcctctgcct    42120
cccaggttca agcgattctt gtgcctcagc ttctcgagta gctgggactg caggtgtgta    42180
ccaccatgcc tggctaatgt ttgtatttt agtagaaacg gggtttcacc atgttggcca    42240
agttggtctc aaactcctga cctcaagtga tctacccgct taagcctccc aaagtgctgg    42300
gattacaggc gtgagccgct gcgcttggcc aaagtagttt tttaagatgt gaatatcttt    42360
tcttgcagct aaaaaagttt gtcagagata attctacttt attctccagg tggttttttca    42420 gggagaaatt ggaggcagta aaccacgggg ggagtcctgt ggcttggtgg gtgggtgggg    42480
```

```
gaggtgtggc tggggtgggg agaagtcctg tggctcgctg ggtttggggg gagctgtggc   42540
tggggtgggg agaagtctag tggctggggt ggggagaagt cctatggctc ggtgggtggt   42600 ggggagctg tggctggggt ggggagaagt cctgtggctc ggtgggtggt ggggagctg    42660 tggctggggt ggggagaagt cctgtggctc ggtgggtggt ggggagctg tggctggggt    42720 ggggagaagt cctgtggctc ggtgggtggt ggggagctg tggctggggt ggggagaagt    42780
cttgtggctg gggtggggg cagtcctgtg gctggtgtct catcatgtgc ctaacagtgt    42840
ccagaggtct cgtgtaaatt ccctgggagt cgataagcct ctgagaaaca gatgatgcta   42900
accacgctgt ggaagagaaa cttgtttata aatcagatgt ccgttactgg tttactgctt   42960
gtttgcccag gcatagctcc gacagagtcc ccgactcata gtgattgctc agtgcgtgct   43020
gaacaatgat tggaatcaag tcatggctca gagcatagtt ttgaataatg ggaaattgat   43080
gttcttaagt aacatagtca ccaagataat gcaactagat gagtcacccc ttttcaattt   43140
taggatattt ttatcaagat ttaagtggtc atcattagaa ttatagcagt ttctcctttg   43200
gattgttcta gaggcccagt gagaaagtat tccctaattt ctcaggagaa cagttgtggg   43260
tagtgtgctg tcatgtccag ttaaattgca gacgtttccg gttgaagata ttccagtcct   43320
gagaactttg tgacattagc aggactttta caagccatct cttagggtgg ggcattactg   43380
tagttggctg gtactctttt ctccttaact ttgtcatttg ttgatttttt ttttttaact   43440
gtccccaaac actgtgggca gacagtatct agaattgagg cctccacccc tgcagagagg   43500
acgtggatgc tgagcagtcc ccgagtgaag attataaaga agcaaataga gtacacgtgt   43560
ctgtgaactg ttcttgagtc tcccaaattc ggggtacttc tgttcagcta taggaaaagc   43620
ctcaaactgt ttatactttg caagaattgg aaacttctaa ttcaagttaa gttttacgga   43680
atgcatggta agcttcatag gagcttcatc ttttatctgc ttggactttt gcttctatag   43740
gttttgttaa aggccttcat agcgaacctg aagtcaagct cccccactat tcggcggaca   43800
gctgctggat cagcagtgag catctgccag cactcaagaa ggacacagta tttctatagc   43860
tggctactaa atgtgctctt aggtaaggtg gaggcataca ggtggaaggg tctccagcat   43920
gtattcatga tagacccttg aaataattaa aatcagatga tccctcagct tctagaccag   43980
gctatttggc actggttgac tgaatgtgaa ctgcattggg actgctgtga gcacgcatgg   44040
gtctctgtga ccctgcagat gcagccatgc ccagggacac ctagctgggc agtgggtgtg   44100
ggctggtgtg agccctgcct gccacccagg gcctggtcct ccgtctgtgc cggccctgac   44160
tacggtgagt ctgtgaggct tgagactgtg ccttgggtcc ctgtgggttc tctgtaggtc   44220
agttgacagt ttctcctgtt gtttgggtaa ctgtggaaat gaacactggc aagtgctgaa   44280
gtgagcactg gacgcgtgat atggaccctg ccaagccagg gatatgggtg tgtagccact   44340
cccagtgggc ctcatggtgt actcgttcac ggtcatgttt gtgccatatt gatctcttgg   44400
gatctcttct tttttaacaa attaagcggg gaatctccaa acagtgagtt ggatgttaag   44460
atatcttgct gctgcccca caggcttact ggttcctgtc gaggaggagc actccaccct    44520
gctgattctt ggcgtgctgc tcaccctgag gtatttggtg cccttgctgc agcagcaggt   44580
caaggataca agcctgaaag gcagcttcgg agtgacacgg aaagaaatgg aggtctctcc   44640
ttctgcagag cagcttgtcc aggtaggagc acagggttta ctctaggcct ggcatgtgaa   44700
caactgacat ttgaagaact gattactttg gaagagaagc ggcagaaccg agggttagag   44760
gtgtggactc tggagctgtg ctgctcggtt ccgaccctag gtgctgacct ctagctgcct   44820
tccttctgta tgccattgtc accgtgagtc agatgcaggt gatgcctctt caggtgccac   44880
```

```
tctgtttcta aaaccagagg tcacgatatg tgttcataca cccagtaaat actgattgag   44940
cacccactgt gtgctcgggt ctggggtagg tgctgggggt cctgtggtga atatttccgc   45000
tgcagcctct gccctgtgga gcctgtggcc tggtgcactg gtcgaggcag ggtggtatgc   45060
cccctcaggg aggtggggac gtggtccttc ggggtgtcag aacaaaatgt tggaacttct   45120
ctttccaatg cagagaaacc ctgcagtaat tctaatgtac tgtgattggc agttgacttc   45180
agttcttgtt agcgtgctta ctcaggttat tttcactaac tgtgtaacag tgcagcctca   45240
ttttaagcaa ttgaatttt tgaactttac ttaaaatatt aggtcagggt tttattgtg   45300
cttaacatgt gccatttagc taaattttgt aggatataaa attgtaagtg acttaaaatg   45360
attcttgcat agaatcatga attgaagata atgctaataa tttaagcact gagttaggta   45420
gtgtttgtga agtgcttaga atgcttcctg gcacatgtga aggccatgta agtgctgctt   45480
attgataaac agctgagcaa gagtgaactc taagaaatga atggggctga gagttctatt   45540
ccacccagct gcccttttggt tattttacag aataaaagca gagtctcatg ggatatgaca   45600
tttaattata tttccttcac aaaaaacact gctgaatatt tgtggagta aaaagggtgt   45660
agccatggca ataatacatt taaaatatag tttatttcat ctttacctta cctgtttttt   45720
tttttttaagc tagctttata ttgagaattg catacatgca aaagtatcaa gtcatgacca   45780
gttacatttc atttataatc ctacttctcc ctttttttt ttattatttg gaagcaaacc   45840
acaatcatcc tcttacttca tctataggta tttcagtatc tctatagatg aggactcttt   45900
tttatttta aaacttaatg atggtcaggc gcagtggctc atgcctgtag tcccagaact   45960
tgggaggcc aaggcgggca gatcacttga gcctaggagt ttgagaccaa cctgggaaac   46020
atggtgaaac cccatgtctt taaaaaaaaa aaacaaagtc agccaagtgt ggtgatgcat   46080
gcctgtagtc ccagctactt gggaggctga gatgggagga tcacatgagc ctggaaggtc   46140
gaggctgcag taagccatga ttgtaccact gcactccagc ctggttgatg gagcaagatt   46200
ctgtctcaag aaaacaaaac gaaactccaa aacaatgtca caaaacagtg ccattgttag   46260
acctgaaaat attaaacatt tcctacatca aatacccact aactcattgt caatttttct   46320
ctctactctt ttggaatcag catataaata aaattggttg ataaggattg taaatctctt   46380
tgatcaactg gttctcctcc atccgaattt ttttttccct ttagagttca tttattgaga   46440
aaccagatta tttgtcttct aagttttcct gtggtctgat atactgctta catctccatt   46500
gtgtaaatta acacctttt ctgttctctg tatttcctgt acatcaataa ttggaggaaa   46560
aacctggtca gatttagtgt atattttata tctgagttca gtatttcgta tataatattt   46620
taaggtaaga gtatactctt ttaaaaagtg ttgagactat atgctcaatt tttttttaaca   46680
gatgcttttg aaaaggctgc ttgatcataa aagtttagag accattggtc tgttgggaga   46740
agcaaataat tacgaaacag tttagcaagg ttaaggtgca catggtaggg cctggagagg   46800
ttcagtcgtg agccgtcact gatgggcacg tggaatctga cccggcacag agagctggga   46860
gaagacagga gctttataga cagaaaacgt ggtctttgcc aagtcccggg agtgaaagag   46920
tgagagaatg ctcacagcac atgagtgtgg gtgcgtagac agagcaacgg tgggtcctga   46980
aaaggcctcc aggctttctc atagattagc aagagtgttg gttatggagg tcagaaggag   47040
gtcgaaactg tgttaaattg ggattgcagt aatcctggaa ggacagagat agagggtgaa   47100
ggggaaaaaa gggtatggat gtgagactta attgctgatt ttcttaatac ctttctccaa   47160
agtaaataaa tgatatggca cattttttgaa ctagcaaact ctagatatga ttatctgtat   47220
```

```
aacatatctt actccatctt cttttgacta ataactgttc ttaattaaat tactgtgaga    47280
tgttcaattc agcaaatgta gtttggctaa ctatatttaa ttagaattta atataatcct    47340
aggcctggcc aaactattaa gcaagtgtgg gcaaaatatt gataatttta gatatgcagg    47400
agctcagttt ctttctatgt gtgcttttttg aaaaagaaag aaattgaaaa atagaggaag    47460
ccctgaaatc caagaaacaa agtctctcat ctaggcatgc aataaaagca attctaggat    47520
gattgttgtt cggcatgtag tttgttagaa aacattcttc ttgaataaat agtatgccta    47580
agaaagtggg cagagggaag gcatatgcat atattattaa caaggaggga gaaaaaggca    47640
attagtaacc atccatagga gagccagcaa gattttataaa ggaaatttgt gatccaagta    47700
tgaagcaaaa taagatgcat aataaatttt aagcaagtaa tagattacag taagagaacc    47760
catttgacca ttaattttgg ggcattttct ttcaaatgac atggagtagt aatgaaatat    47820
ttctttcttt ctgagtctag gttattgtga ctggactcag aaagaaagat ttcattattg    47880
cagtgaataa cattttttgaa cattattcat aaattatgca gtaataacaa tttatgaaca    47940
catgatacat aagatacata ctgtttattt ttaattaagt ttttcagctc aacttctcgg    48000
cagggaacat taaatgtaaa tagtgttacc tagtagcatg taaatggaaa tctccatagt    48060
atgaaagcag tgctgttgct aacagaattt aggaggcgac agatgaggtg aaggaaatgt    48120
gggtgccgat ttccttatta cattgagagg agccaggaga ttctttgttc aaaatagatg    48180
gcttaagaag tcaaggtata agctgattac ctagagcagg tacccacaaa tgttttgtgt    48240
aaggggccag atagtaaata ttttcagtct tgcaggccat tccaagtctg tggcaactag    48300
gccccactac cttcgtagca cgaaagcagc cacaggcagc ccataaacgt ggctgtgttc    48360
cagtgaaact ttatgtacaa aagcaggtgc gggccagacc tgacctgtgt actgtggttt    48420
gatgacctgg gattcagggg tataggagtt accatcagag gagctgaaag tgagactttt    48480
tactttatac tcttctacac tgtctgattt tttaaaaaag aaacatatgt attttataat    48540
attgaagatg gggttggcaa atagcaaata aaaatacagg atgccagtga aatttgaact    48600
tcagataaat tatgagtaat tttatgatgt aagtatattc caaatcctgt gggacataca    48660
ctacaaaatt atttgttgtt tctttacaat ttaaatttaa ctgggtgccc ttgtcttttta    48720 tctggcaact ctaattaaag ggaaaaagaa taaattcatt atgttcatat aatgtgatac    48780
agcaggggtc cccagccccc acgctgcgga gcggtattgg tccatggcct gttaggaact    48840
aggctgccca gcaggaggtg agcagcaggt gagctggcat tcccacctga gctccgcctc    48900
ctgtcagatc agtggcagca tttgattctc atagtgcaaa ccctattgtg aacagcacat    48960
gtaagggatc tagattgtgt gctccttatg agagtctact gcctgatgat ctgaggtaga    49020
acagtctcat cttgaaacca tccccctggcc ctgtggaaaa attgtctccc atgaaaccag    49080
tctctggtgc cagaaaggtt ggggagcact gtgatatagt attgaaagtg ctgataaatg    49140
tggctactgc ctttaaaatg tctggtagct ctttctcagt ggcactcata atagtgtttt    49200
ttgattttta aatgtgtgtc aagctaactc tcccctcagt gtatgctgga ctttattttc    49260
cctttcctag tcaccagttt tgggaaatag agatcttcat tctcatgctg cttctctagt    49320
ggaagtgctc catttatttt taaggaatga atataacaat gaaaaaatca tgggaattca    49380
gaaaacaaca tggaaggtaa cgatcacatt ggtagaagtg atagggaaat atttaggggg    49440
agaaattaag gtgtaaactt tgccaacgaa gtcctgttaa aaaaaaaaaa gtgaagctta    49500
ggatgcattt tataaactct gaccagaaca cctgtgtttc tctgtttcta ggtttatgaa    49560
ctgacgttac atcatacaca gcaccaagac cacaatgttg tgaccggagc cctggagctg    49620
```

```
ttgcagcagc tcttcagaac gcctcccccc gagcttctgc aagccctgac cacagtgggg   49680
ggcattgggc agctcaccgc cgctaaggag gagtctggtg gccgaagccg tagtgggagt   49740
attgtggaac ttataggcaa gttattagta aggtctactc ttacagttaa cttttcagtg   49800
atactagtta ccctctattg atgatgggcc tgccctgtgc taagcagtct gcattgcatc   49860
ttccttgcca aaacttataa tacagatttc atctttattt tataaatagg ggagttgggc   49920
tgggtgtggt ggctcaggcc tgaaatttca gcactttgga aggatcactt cagcccagga   49980
gtttgagaca gcctggccaa gtgagaccct gtctctccaa aaaaaaaaa aaaacaaaa    50040
actgggcatg gcggcacgtg cctgtagtcc cagctgcttt ggaggctgag gtggtaggat   50100
tgcttaagcc caaaaggttg aggctgcagt gagttgtgat ggcagctgca ctgcagcctg   50160
gtgaccgagc aagatgctgt ctcaacaaaa tttaaaaatc aaagaagaga attaaagttt   50220
agaaggttag gtggcaaaat gaggccacac atttaaagcc cctcctcctg attctttctc   50280
taccttgact gcctcctgtg gtggttcagt tgctgagaaa tgaaacagt agggaaggcc   50340
gggtgcggtg gctcaagcct gtaatcccag cactttggga ggccgagacg gcggatcac    50400
gaggtcagga gatcgagacc atcctggcta acaccgtgaa accccgtctc tactaaaaaa   50460
tacaaaaaac tagccgggcg ccgtggcggg cgcctgtagt cccagctact cgggaggctg   50520
aggcaggaga atggcgtaaa cctgggaggc ggagcttgca gtgagctgag atccggccac   50580
tgcactccag ccggggcaac agagcgagac tccgtctcaa aaaataaaa acaaaacaaa    50640
acaaaaaaaa aaaaaaaaag aaaatccatc tgtccccagc tctgcatctg cctccactgc   50700
ccagtctgct cctctccatg cgcttggggc tgggccctgt ccaccatgc agtgctgccc    50760
tggagcagtg agcttagtgg gtcctttctg gcatgagagc tgcctttggg agctggagtg   50820
ggtgggaatc tctgaatccc agcctctacc gctgggtctg gtgcctagca ggctatggat   50880
aagcttttgc tgactctagc ctcccctagg ccactgcagc gtggtcggtg tagtgcactg   50940
cgtgtgcagc atggccttta ctcacagcct ccacattaga gagaatctga ctgaagtctc   51000
gttgctgcct cgtgtgagca taatgtttg ccggaaccat gagcaggaaa tattaatctg     51060
ccttgtttcc tgtcctttac actgaagaat ctttttctgt atgggatgca tgccttacaa   51120
ataatgagtg gaaatactca tcgctaatga aaagttatac ctgattgtta gtctaccaaa   51180
taatctgaga tttctaatac ttttaatttg gcttttaaaa tgcaatttat cttagctttt   51240
ttgacttctt aggtcatatc tttagaacta tgtatttgaa tgttaatgta attttcatat   51300
tgaaattaaa atgttgaact gtgatgttaa gtgcttcctg tggaaataca ttcacatttg   51360
attcaacttt gaatcaagct gtttgaagat tttcacattt cttctagatt ttatcagctt   51420
gttactttat ctgtcacttt ctgtgattta cagctggagg gggttcctca tgcagccctg   51480
tcctttcaag aaaacaaaaa ggtgattatt tcagaaatca gagtcttgtg ttgaatctta   51540
ctgatttcct tgtatttctg taatgtaatg tatcttgtat ttcttgtaat actgtattgg   51600
actctgtgta tgtatatatc ttctcagtgg agtgattgta tgtgtgaatg ttgctggaat   51660
ctgataacaa ggcctgaata gttttatagg gtggcttta acagttactt tcatatcaga    51720
attgctttgt catacatttt gaatgcatca taaatttcta atgttcgggg tcagcagact   51780
ttttctgtaa agggacagag tgcaaacatc ttagctttat gagccatatg gtctcttttg   51840
caaccattca gctctgccct gtggcaggaa tgcagttgca gacaatacac gagctactgg   51900
ccagccatgt tccagtagaa ctttacttac aggaacaggc aggctgtagt ttgcccatac   51960
```

```
ctgccttagg gaatgtgttg ttatatttta tgaagttaac ttaccttccc agtgaatttt    52020
gtttagcatt agtcaggaat attattaagt agcttctttt ccagcctggg caatgtcatg    52080
agacccggtc tctaccaaaa caagaccaaa caaaaaaaca gccaggcatg gtggcatgtg    52140
cctgtagcct cagctgctgt tctggaggct gaggcaagag gattgtttga gcccaggagt    52200
ttgaggtcac agtgagctgt gatcatgcca ctgcactcca gcctgggcaa cagaatgaga    52260
cctcgtgtcg ttaaaaaaaa caacaaaaaa agtttccttt gttggactgt tttaatttgg    52320
acctggttat cattttttcag ccatatctaa ctttgtacat atcagaatgt tctgataaag    52380
cttaactttt attaaagtgt ttctgatagt tttggtacac attatcattt gcaatgccag    52440
ttattttctt ttccagtggg gatttgcata ggaaaaaaat tgctgtcact ttctattttg    52500
aaatcttaaa agactgatcc ttttttgtgt catgatttga gtgtttaatt gagagcctaa    52560
tgcctaatat tatttgcagt attgaatggg atcttaacag gaataacatt ctagccttca    52620
ttgaattaag taaacatttc ttgaaagaac ttggaatcta taatatttgg gtcatcacag    52680
tatgagatac ttaatcaaat ttgagatttt agtgaaacat tgttgaaaag ccaaaaagat    52740
tctaggaaaa attcatctct atattcttga attaggagag attttcggac ctgtgactaa    52800
gttactctga cacttgtttg tttcttagtc actcttccca gtggcagtga aaagaagat    52860 gactggttca cattgttgag attagtttat cctcttctgg ctaggacatg ggatatatcc    52920
tgtctctttt aagccctttt ggtattttt cccccattta gagctgtgtc ttcaaactgt    52980
tttgttatag ctggaaaatc cttttttaa gtgaaatctg cccaaattat aagacagatg    53040
aaagtagagt tgtgttggat ataggattag ggtgcaagtg gcgggggtgt cctggagcct    53100
ctcttctgag ggcagcctag cgcttgtgcc tttgaggaaa ttaccctggg gatggtctat    53160
ggaacatatt tgcaaaccac tgattgaaa gatagagatg gcttttgtta agatctgaat    53220 tcacctttt ggcatttat ttgatttctc aagggaaaga acttattttg taataaagtt    53280
tccttttatt tagtagatag gccaagttgc tgtgttaatt taacctagag tttgggtttc    53340
ctttgctaat ttttttcacc tttaatgtca catcattgta aatttgtgga agttatactt    53400
ctgacttatt ctttgaagag cagaaattag aaatttccaa taattatttt gatagtgtca    53460
tttaatgaca ttaatatgta atgtagccac aaagatttaa tgagttcagt taagtcatat    53520
taagactgtt ggtttcattt gttttcatta atgtaattct gaagatgaac aataaaatgt    53580
atttttagaa ctttcaagtg aaatattatt tcatccttcc agatcatata atgcttgagt    53640
tctgattgtt aatcataaag tcaagaaaat taaagataa taaatgaaa gtgacttta    53700 ggtgttagag ttttatgtac aaattctggt gtgtcattgg agctatcaca tgaatattc    53760 aaaggccaat agcattgggt ctttacagtt aaaacttact attttaagt ttaagtagta    53820 ctatagatta tttaataatc gaaatcaata aatattaatt attaaaatgt tttgtggtat    53880
actttgagaa tcattgcttt taacttttc catataggtt tattaacttt aatagcattc    53940
taaacataac atctctacat tctttgtgtt taatactgta gaggtataaa aatacttata    54000
tatgatgata aaccatatta gagtaaatta aatattctta tgagtttcat tttagagtgc    54060
atttacttaa ttttgaaatc cttattttta gcaaactaaa ggaatgttgg tacattattt    54120
actaggcaaa gtgctcttag gagaagaaga agccttggag gatgactctg aatcgagatc    54180
ggatgtcagc agctctgcct ttgcaggtag ttctcactag ttagccactg atgtggacct    54240
tcactctctg ccgtccaccc catgcccttc ctgcctgtcc cctgcacct ggtggacagc    54300 acaactgggg gcagcagtgg acccaggttg cttaaatggg ggatatttgg gcttctttca    54360
```

```
taatacttac tctgaagctt gtgtgtctgt ggtgtttgca tcatatattt gctgttttct    54420
gtggtttaga ctgttttaaa attaggttta tgctccttga catagggct ttgtgagtag     54480 ggatggcacg ttgaaacgtc tcatgagttg gatgggttat gctggggtt ggaaatggga    54540 tgaaaaattg tgggatgaaa aattgcctat ggatagttta acttgaaaga atctgccttt    54600
gtttacagat agttatcttt tttttttttt tttgagataa agagtctcac tctgtcaccc    54660
agtgccgata cccaatgtca ctggcatgga gtggtgtgct cttggcgcac tgcagcctcc    54720
gccttctggg ttccagccgt tctcctacct cagcctccca agtagctggg actacaggtg    54780
cccgtcacca cggctggcta gttttgtat tttttgtaga gacgaggttt taccatgttg     54840
accaggctgg tcttgaagtc ctgacttcaa gtgatccgcc tgtctcagcc tcccacagtg    54900
ctgggattac aggcgtgagc cactgtgcct ggccagttac agacagttat ctaatgaaat    54960
tctctgtgta ctttataaaa gataaggatt aacttaaggt actaataact ggattatatg    55020
agggtggttt tggttgtata atcctatcta aaagaatatt ttagctgtaa ctgaaagtaa    55080
gacttaaata tttagggagg aaaatctgaa taattctagt agtaattatt tacaaaataa    55140
aaatagattt tatttttgat tacacaaatt aaacaacaat aaaacatcac agcgatctag    55200
actagtataa aggtcacacg cttaccaacc caaccgcccc aggagtgacc actgccaaca    55260
gcttcgtgtt gaccttttg ccatgatttc tatatagtct tttttgtttt taaatggtaa     55320
ttaaaaaagt caactaggaa aatgtgttag aagtttatct tccaggagaa taataggact    55380
ggagtcgaga tcttgaacgt ggcttggaag aaggcaagcc caccccagag agattacagt    55440
tgttcgggac cactgcttgc ttagaggacc tgcgtgtctg ggaccgccta gttttgtgcc    55500
cctgactagg ctgcccctta attacgaacg tctttataaa ttgccctagc cagggcttgg    55560
agtagttggt taagaacttg aacttcagtt tttgcagtga aacaccgttt gagaatatta    55620
ccttctgata agccttattt tattaagatg ggtactgtag cgagaggcag tgtgagtggt    55680
acatgaggga tgcactgctg tcctgcattt cactgtcttc aggatgctat gcagtgatga    55740
catttggaaa catttcatca aacattccat caaatggaaa cattggatga cagtggaact    55800
ttgtgttatt ttgcaagcct ttgattccat attgaatgtt ttctctcgcc atttgacaaa    55860
tgagtgtttc tctgtcttca gcctcagtga aggatgatat cagtggagag ctggctactt    55920 cttcagggt ttccactcca gggtcagcag gtcacgacat catcacgag cagccacggt     55980 cacagcacac gctgcaggcg gactcagtgg atctggccag ctgtgacttg acaagctctg    56040
ccacggatgg ggatgaggag gatatcttga gccacagctc cagccaggtc agcgccgtcc    56100
catctgaccc tgccatggac ctgaatgatg ggacccaggc ctcctcgccc atcagcgaca    56160
gctcccagac caccaccgaa gggcctgatt cagctgtcac cccttcagac agttctgaaa    56220
ttgtaagtgt gcggaggggc ctgccatctt ttattttta tttgagacag agtctcactc     56280
tatagtgcag tggaggccgg gcacagtggc tcacgcctgt aatcctagca ctttgggagg    56340
ccgaggtggg cagatcnnnn nnnnnnnnnn nnnnnnnnnn nnnnnnnnnn nnnnnnnnnn    56400
nnnnnnnnnn nnnnnnnnnn nnnnnnnnnn nnnnnnnnnn nnnnnnnnnn nnnnnnnnnn    56460
nnnnnnnnnn nnnnnnnnnn nnnnnnnnnn nnnnnnnnnn nnnnnnnnnn nnnnnnnnnn    56520
nnnnnnnnnn nnnnnnnnnn nnnnnnnnnn nnnnnnnnnn nnnnnnnnnn nnnnnnnnnn    56580
nnnnnnnnnn nnnnnnnnnn nnccacccat cttggcctcc taaagtattg ggattatatt    56640
tgtgagctac catgcccaac cctactgtct gccatctttt gagctcttcc ctggagaccc    56700
```

```
agacctgaac cctcctgctt gttctcttct tgtctaatac ccctaatgac agcgcagctt    56760
agatcactag tggagagctt gacctcatct gataccttca ctgaagggaa cagcttagtg    56820
tcttttccac tgaacactga ggtaaaaaat tggaatagtt gattatgtga actctgctaa    56880
aattgagtgc atttacatt tttaaggcc ttttaggcc ctggttaaat aattatttt    56940 aaaaatcctg aaggagccta ttataaacag atctgtggtc ttaatgaaat gtgattaata    57000
ctgtgcatta ttttaagaac ttttgacttt tcaaaaaact tttacaacat ttcccatttt    57060
atagcagcat aggtgtaagt acctctcatc cctgagttag tggacaagaa accctcatgg    57120
atagtctaat aacgtttggt acaagtctat gttgttttat actccatttt attttcagtt    57180
ttaaaaactg gttaaatatg tgtaacataa aatctaccttcttaaccatt ttttacgtat    57240 gcagcttgct ggaataaata attaaataat gtcatggaat catcgctcca cccatctgtg    57300 taacctttg atcatgtgac actgaagctc tgttcccatt gaactctcta ttcctccttc    57360
cccgccaagt ccctggcaac caccattctt ctttctgtct tctgaatttg actactttag    57420
gttctcatat actttagggt cacaccgtat ttgttttagt tagcataacg tccgcaaagc    57480
tcatgcatat tgtagcctgt gttgaacttc ctaatgtttc aggccaaatg ctattccatt    57540
gtatggatag gccacatttt gcttttccat ttctctgtcc atggacactt gtattgcttt    57600
catgctttag ctattgtgaa tcgtgctgtt atgaacatgc gtgtacaaat gtctcctgga    57660
gactctgctt tccatttttt tggctaaata cccagaattg gagttgcttt tacattctga    57720
ttttaattta aaacatttat atcattgagt gttttactta atagtataat agttagcaaa    57780
ctaatatttt ggtaataatt tgctggtagt tttagagtcc attgctcagt ttttttaggt    57840
aaattacaca ggacatttca agtggacgtg gaacaacttg tgatatggaa tcatgcccca    57900
agctgatggc taaacatacg aaataccatg ccctaaattt agtagattta gtctttgcaa    57960
tttaggagat aacctgttat attgttaggt ttttgtctaa aagctttgtc ctcatatttc    58020
caacttgctg taaaatttgt tcgtgaagac aaatattttt gtatgggttt tttcttttt    58080 atattaaaaa gaaatgtcca cattggaatt ttttggagt ttttagagct aatagagctt    58140
ttcataatgt agtgggaatg agtgatcagt aagctcttag cagtttccat gcacacattt    58200
ctgtgcattg aaataaatga cagatgagta catttgtgtt ctgtgtgtaa aacgtgctct    58260
ttcttcgttg catttccatg ttggagggct tgtctcttgg tgatcacact tcaaaattct    58320
cacagccccc cttgaaccgt ttaggtgtta gacggtaccg acaaccagta tttgggcctg    58380
cagattggac agcccagga tgaagatgag gaagccacag gtgttcttcc tgacaaagcc    58440
tcggaggcct tcaggaactc ttccatgggt atgtggacca caggtgacgc gctacaaagt    58500
ggtcttgtat tcaggcctgg acatcttaat tatatctttg ctctcaagaa gaaatccttt    58560
gatattgttt tctgagttct gaatagctga tgaaaatgac caattgagga ataatcatac    58620
tttttcttca tctaaatctt acgcttttga gttatcttag cataaatgta taattgtatt    58680
ttaagtggaa atttgtcact taatcttgat ttctctgttt ttaaagccct tcaacaagca    58740
catttattga aaaacatgag tcacagcagg cagccttctg acagcagtgt tgataaattt    58800
gtgttgagag atgaagctac tgaaccgggt gatcaagaaa acaaggtgag ggacataggc    58860
ttgagacaac ttggtgtttc tgagcttgtg tgaggattta aaatcgccct ggctactatc    58920
tactttattg ctttcccatc cctgggcctt taaatttccc cttaaatac cagctcttcc    58980 caggcctgtt gttttccgcc tttcaggtgc tactgacagc gttaagaatt gcctgagttc    59040
tgcctccttt gagagtgtgc cccagagaaa tctattctgt actgagtgtt tccttgtctg    59100
```

-continued

| | | | | | |
|---|---|---|---|---|---|
| atttcttggg | ccattcattt | gatggctgcg | tatggccttg | caccatgttt | tggttctatt | 59160 |
| gaactgtttt | aaaagtctct | gtttatatta | ccttttaca | tgtaaatgta | actgtcttca | 59220 |
| cttttaattg | ctcaagggca | aggaatagcg | tttcacagtt | tctcccagca | atcagaatta | 59280 |
| cagcctttgg | catctccctg | tctaccaggc | ccagttcgtc | ttagctttgg | gcttccccag | 59340 |
| gctgttacct | ttccctgagt | agcttctgct | tgtcctgtag | aagaccactc | atgctttgct | 59400 |
| tccagagcag | ccttttctga | atgcctggtg | tcaggtgcct | tcttactgtg | cccaccctcc | 59460 |
| ctgcatgctg | catttatccc | ctgccacagc | cctgggaccc | tgtgtccagc | tgcctctgac | 59520 |
| ttgtctgttt | ctgcttggtc | atggtctctg | tgaggtcagg | tgtgcatatg | agcacagacc | 59580 |
| agggcatctc | tttatcccca | gcacccagtg | taagtgctac | tctaggacta | tttgttgaat | 59640 |
| gaactaatgc | atgaatgtat | tggttgagta | tgagacaaac | aagtgtcact | gtctcctttc | 59700 |
| tagccttgcc | gcatcaaagg | tgacatcgga | cagtccactg | atgatgattc | tgcacctctt | 59760 |
| gtccattgtg | tccgccttt | atctgcttcg | tttttgctaa | caggggg aaa | aaatggtgag | 59820 |
| tacaaaaggg | gacgtgcaga | gttgaaggaa | ataactaggt | ttcagaggtc | aacttggtgc | 59880 |
| ccgtttagta | ctgtgtgtag | cagaggcagt | agaatctgag | gatgagtttg | gttttcacta | 59940 |
| gccaagggga | agggaggaaa | tgatgggagc | aggtaggtta | ctgggtctgg | ttttgttcat | 60000 |
| ttgaaaacaa | tctgttgttt | gaggctgaag | gtggcttggg | tgatttcttt | gcagtgctgg | 60060 |
| ttccggaccg | ggatgtgagg | gtcagcgtga | aggccctggc | cctcagctgt | gtgggagcag | 60120 |
| ctgtggctct | ccacccagaa | tctttcttca | gcaaactcta | taaagttcct | cttgacacca | 60180 |
| cagaataccc | tggtatgtta | aaagttcaca | tcttattttc | tcagatttaa | tcattattgt | 60240 |
| aaaaacgatt | tcagtattga | ctattttagt | tttagagcgg | tgttttgagt | ttatttggga | 60300 |
| tttttttttt | tttttgagac | ggagtctcac | gctgttgccc | aggctggagt | gcagtggcgc | 60360 |
| gatctcggct | cactgcaagc | tccgcctcct | gggttcacgc | cattctcctg | cctcagcctc | 60420 |
| ctgagtagct | aggactacag | gcgcccgcca | ctgcgcccgg | ctaattttt | gtattttag | 60480 |
| tagagatggg | gtttcactgt | ggtctcgatc | tcctgacctt | gtgatccgcc | cgccttggcc | 60540 |
| tcccaaagtg | ctgggattac | aggcttgagc | caccgcaccc | ggcctatttg | ggatatttga | 60600 |
| cccgcgttgt | agctcttcag | aaaacacatg | aatagtgaag | ttctttgttt | catggtttct | 60660 |
| ctttagatga | aatccgtaga | ggaaaaaaat | agaaacctca | gcacgtaaga | gccaacttat | 60720 |
| atacgcatcg | gatttaaacc | taaagcacaa | attgtgcatg | gtcacggtgg | cgctgagtca | 60780 |
| cactcagcca | ggccaggcat | tcacactcag | ggtgagtggg | caccaggact | ggctgaggca | 60840 |
| gcagtggacc | cgtgtctgca | ccctgcccat | gcttattgtg | gagccttctc | gctcgctctc | 60900 |
| tttctttggg | tgagaggta | cacttgtgtt | tttgaattta | tatgaggtaa | gggtttatat | 60960 |
| ataggttttt | ttctaatctt | tttttaagtg | gaatctggaa | ttttaatcag | atttactatc | 61020 |
| tgacagccta | gaattataat | ccagaaagtc | tgtggtattg | aggacatatt | ggcaatatga | 61080 |
| tgaatctgta | atccttaaat | cctgaaactt | tttttttttt | ttaatcactt | agggttatta | 61140 |
| tagtgaagtc | atttctgaat | ttggatcttc | tcttcatacc | tcttttctc | tttcctgaga | 61200 |
| attaagcttt | tgttttgagt | tagaaagttg | atagtaggaa | attgttccat | ggctgggcaa | 61260 |
| tttatctcca | cagaggaaca | atatgtctca | gatatcttga | actacatcga | tcatggagac | 61320 |
| ccacaggttc | gaggagccac | tgccattctc | tgtgggaccc | tcatctgctc | catcctcagc | 61380 |
| aggtcccgct | tccacgtggg | agattggatg | ggcgccatta | gaaccctgac | aggtagtggc | 61440 |

| | |
|---|---|
| cagtttttca gctgtgtttt ttctagatat ccttactaag gtttccgttt ccatgacgat | 61500 |
| gtttgtttct gttcttctgt caggaaacac attttctttg gcggattgca ttcctttgct | 61560 |
| gcggaaaaca ctgaaggacg agtcttctgt cacttgcaag ctggcctgta cagctgtgag | 61620 |
| ggtgagcgcg atctctgtgg agccattgct tcacttagtg ggcattttat cattgctgca | 61680 |
| attacaattg gagcttaata ggaaatattt ccatacactc taaagctgta accagtaata | 61740 |
| tccaccatgt atccatctct tagctttaga aagaaaacat tgccagtaaa gttaatgctt | 61800 |
| cataaacttc agtttaagtt ttaattctca gaatatttgt ttgaaataga cttcttccta | 61860 |
| aaggatatat ttagaaataa cctatcatta catgtaaagt ctgttgaata tgctgggcac | 61920 |
| ggtgactcat gcctgtaaac tgagcacttt gggaggccaa ggtggaagga ttgcttgagc | 61980 |
| ccaggagttc aagactatgg gcaacatggt tgatcctgtc tctacagaaa attaaaaaga | 62040 |
| aaaaaaaaaa ttaactgggc gtggtggtgc atacctgtag tctcagctac tcgggaggct | 62100 |
| gaggtggggg gattacttga gccccggaga tgaaggctgc agtgaggcat ggctgcatca | 62160 |
| ctgccctcta gcctgggcaa cagagtgaga ctgtctcaaa ataatagta ataataatcc | 62220 |
| gttgaattaa aaaaaacccc aaaaaccact gtgttaggcc catggtgtag taagagttaa | 62280 |
| agtgagcctt agggattatt tactcaacct ctgtgtttgt atgaagtgga atggccccag | 62340 |
| ttctttaagt gatagcatgt tgaacctttc cataccagct ggctcgtaag tcacaactgg | 62400 |
| ccagtcaaca agagtcaaaa ttaactagta aaaatcaaag caaaaaactt agaattgtcg | 62460 |
| aatttgtgcg atacctcccc cttttaaaat gtcatgcctg acagtaattt ttccctagtt | 62520 |
| tccaggtttt gtttcagtca attgtgtctg tcttgagcag aaggaagcgt gctaacagct | 62580 |
| cagtctcatg gctagctggg ggtctatgtg tcagccatgc atgtgatggt gcccctgggt | 62640 |
| gcctgaggct gcaggggagg ggtacagcag taggggcctg ttctgttctc ccgtgccttg | 62700 |
| gagtacatag tgatatagtg gggtggtcct tggtgtaggt ccctcgttcc taccctgggt | 62760 |
| ctgcgattta tttagaagtg gtgttggagc tgtgcggcag gccccttttgt aactgatcaa | 62820 |
| tgtttgtgaa gttgccgttt gagaattgaa accatgacat aagcagaaat ggaagaaaag | 62880 |
| aaccagttat ttgaaaggga cacattcact tttaagcttg tatttactga gataaaatat | 62940 |
| ataccatcag tgttcttgag aggtgtggga aaagtgcaac atcctggttg cagttaaacc | 63000 |
| cagaacgttg tgtgttgaag actgacagtt ctcaaaccgt caagacgcgg gtactgagtg | 63060 |
| ggactaacct gctgccctct tgcctcggac cttgtgttcc agcattgtgt catgagtctc | 63120 |
| tgcagcagca gctacagtga gttaggactg cagctgatca tcgatgtgct gactctgagg | 63180 |
| aacagttcct attggctggt gaggacagag cttctggaaa cccttgcgga gattgacttc | 63240 |
| aggtaagtga gtcacgtcca ttagatttca tgaactaagc tcaattgaaa gtcctggggt | 63300 |
| cacttggtat aaggaatgat gttatcaagt accctgccca tcagaaatct gagcggttta | 63360 |
| ggtagatgac agtgattttc tcccccccagt ggcttttgc tgaacctcgc cctatgcgtg | 63420 |
| gattttattt tattttatta tttatttaga gacatgatct tgctctgttg cccaggcttg | 63480 |
| gatgcagtag cacagtcata gctcactgta gctttgaact ccaggactcg agtggtcctc | 63540 |
| ctgcctcaga ctcccggtta gctaggacaa taggtgtgtg ccatcacact ggctaatatt | 63600 |
| ttatttttg tagaaatggg gtcttgctct gttgcccagg ctagtctcat ctcctgagct | 63660 |
| caattgatcc tccaatcatg gcctcccaaa gtgctgggat tacaggcatg agccactgtg | 63720 |
| cctggcctag aattttaaaa gataaataga agagtagttt tttttttttt tttgatagt | 63780 |
| cctagtcatt taagtgttct ggatagtagg aataaaagag cttagaattt ttcatctttg | 63840 |

```
tcttaaactt tttaaaaaat gtagcttatg ttaattctgc ttgttttaaa agaatatact   63900
catcattata ctgaacctag gtaagacagc tggtttatat tttgttgcaa ttaaaaaatg   63960
tgagctgtgg ttgcagtgag ccaagatcgt ggccattgca cttcagcctg gcgacagagc   64020
gagactccgt ctcaaaaaaa aaacaaacca aaaacgtga gctgtgttgg aactttcatt   64080
ttctaagagt aaagttttgg caggagaagt tttctgtcag tactttattt tagaagggaa   64140 attttttataa ttcaggtgtt ttgttttttgt ttttgttttt cccccaagc caccttttat   64200 agagcccttg tgggttattt tatttaatcc ttagaatgtt tataaatctg ggactgttct   64260
cggctccacc cacagatagg ggcgctgagc atgcgtgagt gggcagcaag atagcaggtt   64320
atggagggcc cagctcgccc cttctgtggt ttgagccagt tctgtacggg acttacagag   64380
tgttttgaaa tagtatttat tttgaagaaa aagaaaaaca gtttactgag tgctatctta   64440
ttgagtctgg agttgtgaga ggaatgccac ccctatttgt ttgaagccat cggccttttc   64500
tgttgtcttg agtaagtgct gcccaagggc cttccagggc gcctgactga gcctgctctg   64560
aagcaagctg gcggaaagtg tttactgagt aactaaatga tttcattgtt aaatgtgctc   64620
ttttgttagg ctggtgagct ttttggaggc aaaagcagaa aacttacaca gaggggctca   64680
tcattataca ggggtaagcg gcttattttt gtgagatact gttttacctt aaggaggtga   64740
aagtgaggct ttccttgtgg aatttctcta aatgcattca tcgtatttta gatctgttta   64800
tttcacagtt tatatcatga aagttataat tgtgtcacat ggatttaagt ctagcaatgt   64860
tgagttcttt ctcactagct ttccaaaata tcttacctaa aatttagtca aatacaagat   64920
tatgtttatt tttattatcc ttctctctaa agcttttaaa gctgcaagaa cgagtgctca   64980
ataatgttgt catccatttg cttggggatg aagaccccag ggtgcgacat gttgctgcag   65040
catcattaat taggtatttta ccagtatttt atctctttta ctttttttggt tgaagtacta   65100 aaaggtatga acatggaaag agagggaaga attcaaagga tgtagagcag tattcctgaa   65160
tctgagctca tttcagctat tctgttctta aactatcaag aaaaaaaaat ccaaaaaagt   65220
ctaaaattat aattaaaaaa acaaatatact aaccatccat tgtaaaaagt aatgcatttt   65280
cattgtaaaa atttggacta tagagaatag cactaagaag aaaaaaaatc accttcaatt   65340
ctgctaccac ctggaagtaa tcgctgttaa tattttgctg tatacttttt atgagtttct   65400
tattcaaaat ggggtcaaaa ttacatgcaa ttgtgtaacc taattttcac tgaatatttt   65460
attagcattt ttctgttatg aaacagtaat tttagttatg ggtcattgtt ttactatgtg   65520
attgtgataa aattttacat aaattttttt tggaaattaa ctattgtaca taaatgtgta   65580
taattttctt tttccgagaa ttcctggaag ttgagttagc agcccaggct ttgaattttt   65640
tttttttttt gagacagagt cttgttcgtt tgcctaagcg cgatctcggc tcactgcaac   65700
ctccgcctcc caagctattc tcctgcctca gccccccgag tagccgggat tacaggtgca   65760
caccaccaca cccagctaat ttttgtattt ttagtagaga cagggtttca ccagattggc   65820
caggctggtc tcaaactcct gacccccatga tccacctgcc tcggcctccc aaagtgctgg   65880
gattacaggt gtgaaccacc atgcctggcc aggctttgaa tttaaaaaaa atttctaat   65940 agctttatgg cggtataatt tacatttctt gaaacctact cgttttgagt gtatagtaaa   66000
cttcaatttt atcacatttc tatcacccca aaggtccttg ggcccattgc agtaacctcc   66060
ggttcccgcc cccattccta ggcagccact catctatttt ctgtcccctta agatttgtgt   66120 tttcgtcagg cacggtggct cacgccttta ctcccaccac tttgggaggc cgaggcaggt   66180
```

```
ggatcatggg gtcaggagtt tgagaccnnn nnnnnnnnnn nnnnnnnnnn nnnnnnnnnn   66240
nnnnnnnnnn nnnnnnnnnn nnnnnnnnnn nnnnnaccct gtctgtacta acaatacaaa   66300
aattagtcag gtgtggtggc gggcatctgt aatcctagct acttgggagg ctgaggcagg   66360
agaatcgctt gaacgtggga ggcgaagttg acagtgagca gagatcgtgc cactgcattc   66420
cagcctgggc agcagagaga gactctgtct gaaaacaaag atttgtattt tctggacatt   66480
ttatagaact ggggtcatag tataaatgga cttttgcatt tggcttcttt cacttaattt   66540
tgagattggg tcttgtagca tgtatcggta gtttgttcat ttttattggt gagagtatta   66600
tatgaataat accatatttt atctatccat cagatggata ttattgagtt catgttttgg   66660
ccaatttatg aattatggta ctgtgaacat ttgcctacaa gatttgtata ggcatgtttt   66720
catttctctt gagtggataa cctagaagtg gattttaaa taattttggg tacttactgt     66780
gaaactgctc ttcagaaaca taccatcgtt tgtccttcct ttcttgtctt tctctttctt   66840
tctttctttc tttctttctt tctttctttc tttctttctt tctttctttc tttctttctt   66900
tctttctaca tagacacatt ttaagaaaaa tttcagtagt ttttggggta caagtggttt   66960
ttggttacat ggctgaattt tggttgcatg gtgaagtctg agattttagt atacttgtca   67020
cccaagtagt gtatcttgta cccaatatgt agttttctgt ccctcacctt cctcccagcc   67080
tcccgccttg tgagtctcca atgtgcatta taccactctg tatgcccttg cgtactcaca   67140
gcccagctcc cacttctgag aacatactgc agaaacatac caaaggatac tcccactgcc   67200
agaatgtgat tgtgcctgat tcttctcacc aataaatatt tcaaaaaag ttaaatatat    67260 atcagttttt tgggcagaag ttgatacttc tcttattttt ttattttttt ttgagatagg   67320
gtctcactct atgatgccca gactggagtg cggtggtgcc atctagctta ctgcagtctc   67380
tgcctcccag gttcaagtga ttctcccacc tcagcctccc aagaagctgg aattacaggg   67440
gagagccact actgccagct aattttttgta ttttttggta gagatggggt ttcaccatgt    67500
tggccagact ggtctcaaac tcctgacctc aagtgatcta cctgccttgg ccttccaaag   67560
tgctgggatt acaggcgtga gctaccacac ccggctgata tttcttttta aaataactta   67620
ccttcttttg aaagtaatac atgttaaatg aacaaaattt aaggaaaata taaaaaagga   67680
aataatcttt ataatgaaac tactgaaaga aaaccaaaat tacattttgg tgcatattct   67740
ttttcgtttt catcattgta atttgcattt cttttgattac ttgtgagaca cacttttcat    67800
ttacttaaag gttcgtatga cttgcctgtt cagaaatttt gcagctttac cattttctgc   67860
aaatgatagc aacttctttt tatttttta ttttttattt tatttttatt tttttttttg     67920
agacggagtc tcgctctgtc gcccaggctg gagtgcagtg gctggatctc agctcactgc   67980
aagctccgcc tgctgggttc acgccattct cctgcctcag cctcccgagt agctgggact   68040
acaggcgccg ccacctcgcc cggctagttt ttgtattttt tagtagagac ggggtttcac   68100
cgtgttagcc aggatggtct cgatctcctg acctcgtgat ccaaccgtct cagcctccca   68160
aagtgctggg attacaggct tgagccaccg cgccggccg caacttcttt ttatttgttt      68220
gtttgtggtg acagagtctc gctctgtcac ccaggctgga gtgcagtggt ggaatcttgg   68280
ctcattgcaa ctattgcctc ctgggttcaa gcgattttcc tgcctcagcc cccaggtag    68340 ctgggattac aggaatgtac caccatgccc ggccaatttt tatatcttta gtagagatgg   68400
ggtttcgcca tgttggccag gctggtcttg aactcctggt ctcaagcggt tcccctgtct   68460
cggcttccca aagtgctggg attacaggtg tgagccaccc tacccagcca atagttactt   68520
cttatattcc agaaaaaatt gtactcatga tcaagtctcc atgaggaaaa agactttaat   68580
```

```
taaagatatt gcagtttgca gaccaatatg ataaaatagt tgattgtttc taaaagtatt    68640
actgagtaat gatggcagat ataagccctt ttgttttttgt aggaaaatgt tacccatgtt   68700
ctgcatttga attcagttta gatttgttag gaatctcagc ttaagctttg ccatctggga    68760
gtgtttggga caattttgca gacagaattg caaaagtgcc taagggatgc aactggcact    68820
cagacctgct ccttgctcag tactctgtgg acagatgttc agcgcttgtt gatgttgatt    68880
aaaaggttta gaaagagaac tttcaaagtt ggttttttaat taaagcatt aatagtgtga   68940 ataaaaaggg acttaatttt atgacagaca aagaaagta cagcacctgg cggggcgcgg    69000
gggctcacgc ctgtaatccc agcactttgg gaggctgagg caggtggatc atgaagtcag    69060
gagttcaaga gttcaagacc agcctggcca aggtggtgaa accccgtctc tactaaaact    69120
acaaaaatta gccaggtgcg ttggcaggca cctgtaatcc cgctactcag gaggctgaga    69180
caggagaatc acttgaacct ggatggcaga ggttgcagtg agccaagatt gtgccactgc    69240
actccagcct gggcaacaga gtgagagtct atctcaaaaa aagaaaaaag aaaatacagc    69300
acccagttat gtcagagtgg gtgcatcaga gagtgaccct gagattggag acgatgctgt    69360
cacgtgcttg aagaatgcta cctgagaaag ggggcgagaa gtggtgtttg ctggtaacca    69420
gaggtgttgg cttagccacc tgcagggagg gtggtctatc acaggtgagt ttcatctact    69480
ttcttaagca aatcaacctt acttttgtgt taggcttgtc ccaaagctgt tttataaatg    69540
tgaccaagga caagctgacc cagtagtggc cgtggcaaga gatcaaagca gtgtttacct    69600
gaaacttctc atgcatgaga cgcagcctcc atctcatttc tccgtcagca caataaccag    69660
gtatgctgac ccagtggcgt cctcacattg ttgggaaaat gcccttccct gatgcctttc    69720
tttaggcttt aattgaaaac atttttatttt ctagaaaaaa gctttagctc aggatgttttg   69780 agtgtaggtc attcctttga taggatattg tcattctgag gattgaccac accacctctg    69840
tatttaagcc ctgccacaat cacacagctg tgacactata aatctttaa tcgtttatta    69900 catttaatgt gctgacagtt atatttttgt gtgtgacact tacgtattat ctgttaaaaa    69960
attttcactt tagttgtgtt acctttaaag aggattgtat tctatcatgc ctgttgattt    70020
gtaggtgagc gggctattaa agtcagtgtt atttagggct atccactagt tctgtgattt    70080
gcaatgactc tccttcacat ttgttgtgga gcttttgaat atagcgtcaa atggccacat    70140
atatcccatg cttacctgat tcttaggtga gtaggacaga gtgctttaat gaagctataa    70200
tcttcagaat tctagcttgc aaaggagatt gcagaaggat aagacttgtg cttttcaatt    70260
ttgtctttta aatgttattt taaaaattgg ctttatatga tactcttttt ctgctgagta    70320
acggtatttt acagaacttg gactagatga cttctaagct taaatgatca cttgatgctt    70380 ttttttctgaa ttaggaactc agcttacaca tttcaaagtc ataattcctg aatacataac    70440
atcttttttt catgtaaaga ctgctttaaa aaacacatgg aaggtcgggc gtggcggctc    70500
acacctgtaa tcctagcact ttgggaggcc caggcgggca ggttgcctga gttcaagagt    70560
tcaagaccac cctggacaac atggcaaaac ctgcctctac taaaacataa aaaattagcc    70620
gggcgtggtg gtgggcacct gtaatcccag ctacttggga agctggggga tgagaatcac    70680
ttgagccctg gaggcagagg ttgcagtgag ccaagatggt gccattgcac tccagcttgg    70740
gctacagagt gagactgtgt ctcaaaaaaa aaaaaaaaa aaaaaaaaag ccacaaaaca    70800
acaacaacaa aaacacacgg aaacatttta tttggccacc ttagtatttc cccttcagat    70860
aattcctttg tttaaactca gaactggcat tttctctctt tgaaaagatt caggacaaat    70920
```

```
actcctttaa gataagcaga aacagtgaaa gagtatttga ttatcaggaa tttgataggc   70980
ttagaataaa ttgttgcttc ttaatgtcat ttcagaagat gaatattaat agatgccaac   71040
tgagatatca ttaaaattgg ttactactac tttgaaaagt ttcccagttc caaacttcag   71100
caggcctctt cacaattcaa cagtgcttaa ttgggacttg tgtgatagat acgattccca   71160
attgtgtagc agagtgtgct gcttagctac ctattctgtt agcattcgtg tgttaactta   71220
aaatcataat ctccttagtt ttgttgagtg tctctgtgga tgagacactg tgagggatac   71280
aaaatcagat tggctttatt caaaccattg gggtattatt tttatttttt gccttttttc   71340
catgtgttct aaaggaatta gagtttgaat ataactataa tggggatag aaatttacat    71400 gtgccatgaa gggaatgcag aaaagtgcca tgggagctca gaagtggaga aaggaatttt   71460
ttttcttgga agcaggagta acttcatgaa gcatttattt caacttagag atagtaggca   71520
atgctgtaag gggagtgtgg ctgcagcgaa agtgtttggg gcagactggg aggaagggag   71580
ggaataaatt cagccattgt tatggcataa tgatcaaaat ttattttcag cccctctttc   71640
acttaaaagt tgagactgct taacttcttt taatctttaa tcttaaactt ttaaatgcca   71700
tttgatcttt aaaagatat gttttaatag tatattttaa gtctctgtat ttttcttatt    71760
agaatataca gaggctataa cctactgcca agcataacag atgtcactat ggaaaataac   71820
ctttcaagag ttattgcagc agtttctcat gaactgatca catcaaccac gagagcactc   71880
actgtaagtc tctttcttga ttggtcttaa tgaaattata ataattttc gtgacttgta    71940 tggccagtta gttttatggt catcttatgg tgaggtgctt gtattagagc tcttacttat   72000
ctgtggggct tgctaagaaa ttgtgtttct gtgaaaagga tcttagctta ctccaggaat   72060
gtaaataact atttttttct gattattaaa gtaatacatg ccaaaagtta aaaaattcag   72120
ccaatttagg aagacataaa aatgaaaata agccaggcgt ggtggctcac acctgtaatc   72180
ccagcacttt gggaagccga ggtgggggc tcacttgatg tcaggagttc gagaccagcc     72240
tggccaacat ggtgaaaccc atctctactg aaaatacaaa aattagctgg gcatggtggc   72300
gggcgcctgt aatcccagct actcgggagg ccgaggcagg agaatcactt gaacgtggga   72360
ggcagagctt gcagtgagcc gagatcgagc cactgcactc cagcctgtgc aacagagcga   72420
gactttgttt ccaaaaaaaa aaaagagaaa gaaaactact gtcacctgca tnnnnnnnnn   72480
nnnnnnnnnn nnnnnnnnnn nnnnnnnnnn nnnnnnnnnn nnnnnnnnnn nnnnnnnnnn   72540
nnnnnnnnnn nnnnnnnnnn nnnnnnnnnn nnnnnnnnnn nnnnnnnnnn nnnnnnnnnn   72600
nnnnnnnnnn nnnnnnnnnn nnnnnnnnnn nnnnnnnnnn nnnnnnnnnn nnnnnnnnnn   72660
nnnnnnnnnn nnnnnnnnnn nnnnnnnnnn nnnnnnnnnn nnnnnnnnnn nnnnnnnnnn   72720
nnnnnnnnnn nnnnnnnnnn nnnnnnnnnn nnnnnnttta gtagagatgg ggtttctcca   72780
tgttggtcag gctggtctca aactcctgac ctcaggtgat ccacccgcct tggtcaccca   72840
aagtgctggg attacaggcg tgagccacca cacccgtctt tacatttta taataataat     72900 ttatgttgct gatattagaa aagaaccata atatccaaga attcaagaac aattaaatta   72960
tgtacatatg ctagtgtata gtgtgatgct ttggagaatt tttaacaatg tggagatata   73020
taatctgaat tgtagtattg agtgaaaaaa ggcagaatac aaacctagta gggggtatag   73080
tcggatttca gttaagaaaa ataatattta catatataca ttcctcacat tggcagataa   73140
tcaccaagat acattttggg attgtggatg attttttgtgt tctttatatt tttcaggtat   73200
tctcaaattt tctaaaatga gcaagtataa cttttgtcat cagaaaaaat aatatgcaaa   73260
agtaatgtta atttgttggt gaccaggtta aaccttttta tttttattat tatttttgga   73320
```

```
gatagagtct cgctctgttg cccaggctgg aacgcagtgg tgtgatcttg gctcactgca   73380
gcctctgctt cccggggtca aacgattctc cagccccagc ctcctgagtg gctggaatta   73440
caggtgcagg gcaccacacc tggctaattt ttgtattttt agtagaggtg gggtttcacc   73500
aggttggtca ggctggcctc gaactcctga cctcgtgatc caccctcctc ggcctcccaa   73560
agtgctggga ttacaggtgt gagccgctgc acccagccaa accttttat tttatttgac    73620 aaaagaaata cttgcatgtt atagaaaact aaatattgtt tgggctgtct gcagtatggt   73680
cttctcttga tttgttcaaa atattgtaaa ctttgatttg ttcaaaatat tgtaaacttt   73740 gcttatttt tttgttcttc ccttgctttg ttcaaaatat tgtaaacttt acttatttt    73800 ttttgttctt cccttggttt gttcaaaata ttgtaaactt tgcttattta tttttattgt   73860
ggctgacatg tgtcagacac tgttgtaggc ctgggatgta aaaacaggat tcctgccctt   73920
acggtctctg gaggctggtc agggagatga tgtggtcagc tggagctccg ctcctaaggt   73980
tgtgcagggg cagttgagag gcggaagggg gggacagcat ttcaaggtgt gggcagcaca   74040
ggagtctctc ttcattggga tataattgcc attccgataa catgtatttg agttgtctaa   74100
agtaggaagt tgtaccatgg tgggacagat atctcatggt tatcatacac agatctcagt   74160
tctcattgtt tgtacttttt ataaagggta aaggagata taattcaata aacctttgtg     74220
gtgtttgggt gtgattttat tgtttctttg ttctatagtt tggatgctgt gaagctttgt   74280
gtcttctttc cactgccttc ccagtttgca tttggagttt aggttggcac tgtgggtatg   74340 tatttttcctc agtatgtatt aatagttgtc tacaacagta taatataaac gtagttatta    74400
ggatgccctt tttctttctt tttaagtctt ttatcagttt ggcttttgca aaaatatctg   74460
atagaatact tgtttctgct gtattagttg tgtgagacta gtgacaggag ctgtgggaat    74520
tgaatgccaa atgttcttag gcattttggg gaatttgagg gtgtgatctt caagttcatc   74580
taggggaatt ttcatatgct ggcaaaatac ttttctcatt agcttgattc tttccagaat   74640
tatttgctgc atattagaag tttaggaacc ttttttcact taaatgtgat ctaacatatg    74700
aaatggtgat gatttaggaa ctactgtact tacattaaca gcttttactt aaaaatgatt   74760
ttcccccagt agatgaccct actcacatct gggaaataat ttcaagtctt ctccagcatt   74820
caggaataag ctttcattct gtgtatcaat tactgagaat gattttggtg actcacatca   74880
catttgagaa gtaaacctgt agatttcttg tgtgtgtcag tgaataacca gctgacattt   74940
gcttgaagtg gattacattc tctgctctag aatgattgct ttcccgcctt cctcacatat   75000
agactgagca actatggttt ctagtcatag gtccggcact agacttgact tctgagcaac   75060
tttggcattg gagtaaaatg tattaattta agaaagcta aaaattcatt caagtaaaca    75120
tacagttcta atactttta aagtttaaaa tatagatagg tttaagtgat aaaaaaatat    75180
gagtagacac cataatcctc atttctgtat ctgttcacaa ggggttgata tttatgagtt   75240
ctattctcca tacccattct gtgttctctt aatcctcagt cagcacctca ggtgttggg    75300 attcagttct tggtagtttg acttatactc tcttttctag gggattgagc cctgggtagt   75360
cctccttata tgagattgca atttgtcttc caataacttt tactacaaga tatgggtat    75420 taaaggatgc cattggggaa ccaagataat attagtatca ggaaaactaa ccacgtcaga   75480
cctgccccat tgggtatcaa gtatactatt tttccatagt aataaagagc tcaccccagc   75540
caattctctt ttattttgga cctgtttatt caatggcatt aagatgccca aatgtctggg   75600
tagctatctc atctccaatt cagcagaacc attgtcatat gccctagtgg aagcattcct   75660
```

```
tcattggaca cttaggcccc agtactttta ttcagatcta ctacctgatt tcatttctca    75720
aatgatttt  atggagcttt aatttatagg aaagttgtta gttgattaac agtaaaacag    75780
tttctgagct ggtataaaac atattgtgac acgcttttct cttggaattg caagagaaag    75840
gaagactgtt gtttgcttga aattttcta taatttgacc ttgcaaatgt ctgcttccag     75900
agtgcctcca ctgagcgcct ccgatgagtc taggaagagc tgtaccgttg ggatggccac    75960
gatgattctg accctgctct cgtcagcttg gttcccattg gatctctcag cccatcaaga    76020
tgctttgatt ttggccggaa acttgcttgc aggtactgag ttgaagcagg gactccgagg    76080
cttggatttt gatttcctta gggggaatgg gggtggtgag catatgaggg gaaaatacta    76140
aaaggtcatc gccagtgatg gcttgtccct ttagtcaaat ttcagatgtt acctatatgc    76200
acaaacacat gcagctgttc tgtgctgagt atttttaaagt ggcctcttcc cagtatggcc    76260
cctcagttaa ctacaaataa actcattttg aatttcatct tagtgggcac catatgccag    76320
tactgcctca ggcactggga tggtaagaaa gtataaagta tggactccat tctcaagttg    76380
gttttagatt agagggata catgtaaaca gaagtgcagt ggtcacacag agtggccatg    76440
atcactctcc ttgggcagat ttatgggctg ataggaaagg gcacaacagg gagagggtgc    76500
agcaccgtgg cgatgataat ggaggatgtg gccagcaagg aagacgcagt ccattgaaat    76560
tgattttggg agaagttgcc aatctccatg aaagaatcgg gacctgtgtt ctttgcttta    76620
ggaggctata ggagagtttc gtgaaaggga ctaaaagatg agtatttaa taagatcatt    76680
cagccaactt gaatgtgggc tggaggagaa ggtagagaga ctcaggagat taatgttgac    76740
gctaaggcaa gagatgggga gtctaaacca agataatggc tttgggattg tagggaagac    76800
actgatcgta agagaatgaa ggaggcagaa ttgccaggcc tgggtcacca actgaacttc    76860
ggttgtgaag accaagaaac ctgggatgac ttcacatcct gggcaggtgt gtggtagtga    76920
cagtcatgga aattgggaac acagatttgt ggggaagaca tcagtttgag tttgagtttg    76980
agtttgagtt tggcttatcc gttgaatatc agacacagat gtctggccaa ctctcaacat    77040
agattagggt cttaaatgac ttcagttccc caagcaattt gtccttccca tactgttggg    77100
ctagagaggt aatatctatg cccatatcac agccagtgct cctaaatctc tgagaagttc    77160
atgggcctct gaagaagaag ccaacccagc agccaccaag caagaggagg tctggccagc    77220
cctggggac cgggccttgg tgcccatggt ggagcagctc ttctcccacc tgctgaaggt    77280
gatcaacatt tgtgcacatg tcctggacga cgtggctcct ggaccggcaa taaaggtaat    77340
gtcccactta ggtgctggat taatatagcc ttaatgactg tgggtttcca gactatcttt    77400
atttagtaat ctgtctcttc tttattctct tttactttaa atgaacaaaa ttgctcagat    77460
tgtgacacta aatttaacat caaaatgtga ccatgtggcc gggtgcagtg gctcatgcct    77520
gttattccag tactttggga gactgaggtg ggcagatcac ttgaggccaa gagttcaaga    77580
ccagcctggc caacatcaca aaaccccatc tctactaaaa atacaaaaaa attagttggg    77640
cgtggtggca catgcctgta gtcccagcta cttgggaggc tgaggcaaga gaattgcttg    77700
aacctgagag gtggagtttg cagtgaacct tgattgtgcc actgcattcc agcctggatg    77760
acagagtcag gctctgtctc aaaagaaaaa aaaatgtga ccatgtgttt tacagctcct    77820
ttggtatcat cagtcactgt taccctaag agggaaatac atagctttag ttttaggttt    77880
ccatcattag ccaagaaagc tcagaattgg ttttcctggc taaagtacct cattgctgtc    77940
tccttaaatc ttagttaatg gctactgtcc tggctagcat agttatagag catgtccatg    78000
gttgtagaat gttctgccaa tctcagggac agttttgctt ttctgtgaag caataaaatc    78060
```

```
aacttcaaaa caaatgttaa ctgtttgcac aatggattta agatagacca gttcacatac  78120
tttttttttt ttttgagacg gagtttcact cttgttgcct aggctggagt gcaatggtgc  78180
gatctcaggt cactgcaact tctgcctcct gggttcaaac gattctcctg cctcagtctc  78240
tagagtagct gggattacag gcatgcacca ccacacccag ctaattttt tgtattttta  78300
gtagagacgg ggtttcacca tgttggtcag gctggtctca aactcctgac ctaaagtgac  78360
ctacccgcct tggcctccca aagcgttgag attacgggca tgagccacca cgcccagcct  78420
aagatagacc agttcactta ctgttatatc tgtttactct ctctttgctg tgtcttctac  78480
cttttaaaaat ctccccacta acttcccatt ctcctttagc tgccatcagt cacttccctt  78540
ctctgcaaac atctctggag agtctcagcc tcagcccaca gagcttccca ctgctctgag  78600
gtggaccttg tttgtaagac ttcttggccc tcttggcctg gaccctgtct actacttcag  78660
ccatccttcc ttaaccatcg ctagtggttt tgttgccac cctccatagc agcgtttccc  78720
ttccagatca tgtctttaca tctctgggca ctgctctggt cctgcctgcc tttccctctc  78780
tgtaccctgc aggccgctgc cgccatcttg agtgtcctct tcacttggct ttcagagggc  78840
ccacagagtt tcccactgct ctgaggtggg ccttgtttgc aatacttctt ggccctcttg  78900
gattactgca ctagccttt gttttggaaa cagcattttt aaaaaatttt aattttattt  78960
ttttgagata ggatgtcact ctgttgccca ggctggagtg cagtgtcatg atcgtagctc  79020
gctgtggcct tgatctccca ggctcaagtg atccttctgc ctcagcctcc tcagtagttg  79080
ggagtacagg tgtgcaccac catgcccagc tagttttttg attttttttc ttttttcttt  79140
tttttgaga cagagtctca cactgtcgcc cggactggca caatcttggc tcactgcaac  79200
aacctccacc tcccaggttc aggtgattct cctgcctcag cctcctgagt agttgggatt  79260
acaggcgcct gccaccacaa cttttgtat ttttaggaga gacggggttt caccatgttg  79320
gccagtctgg tctcgaactc ctgatctcgt gattcgccta cctcagcctc ccaaagtgct  79380
gggattacag gcatgagcca ctgctcccag ccaggaaaca gcattcttga gataattcat  79440
ataattcacc catttaaagt atataattca ttctctttag tatgcccaca gagttgtgca  79500
gccatcacca gaatcagttt tagaacccac aaaggaactc tgtacccttc acccaaaacc  79560
ttccatgccc ccagctgcag gcagccactg acctaccttc tgtctctgtg actctgcatc  79620
ttctggacat tactgtggat gggctcatac agtcagtgag cttgtgactg gtgccttcta  79680
ccaagcaggg ttttcagtgc agtagccttt cttctttt tttttttta aattgagacg  79740
gagcttctgc ctcccaggtt caagcgattc tcctgcctca gcctcccaag tagctgggac  79800
tacaggccca tgccaccatg cctggctaat tttttttt ttttgtatt tttagtagag  79860
atggggtttc accatgttag ccaggatggt cttgatctcc tgacctcatg atccgcccac  79920
cttggcctgc caaaatgctg gaattacagg cgtgaaccac cacacctggc taacctctca  79980
tgtactgtct gcggttcttc cctgatgcct tccagtccat gcaccgatt gtagcccctc  80040
atcctattat ggtttaaggt gactgtctta gtcaccatgg gttgccataa caaaatacca  80100
tagcctgggt ggcttcaaca acagaattta cttctcacag ttctagaggt taggaagttc  80160
aagatctagg actttcacct tgccctcaca tggtgagggg gtgagggagc tctctggtgc  80220
ctcttatatg tggacgctaa tctcattcat gagggtctgc cctcatgccc cagtcacctc  80280
tcaaaggccc cacctcctaa taccatcacc ctggtaatta agtttcagtg tatgaatttg  80340
ggggactata gacattgaaa ccataacaag cacttttcta aaagatcagg gagtgagtaa  80400
```

```
gtaccagagc taggacctca attccacctc tcggtcatct tgccttcact ctgctccatg    80460
atggctgcct cctagagtga tgggagcctc catgttttat attctctcat gtgttgtgta    80520
ttggagagag ttcagacttt atgaatacat ctggatttgt tgacttctag ctttgctggt    80580
aaccagctgt gaccttgagt aaattacttc atctctgagc ctgtttcctc tttttgaaaa    80640
gggagtttaa aatgctgttt tgggttgggc atggtggctc atgcctgtaa ttccagcact    80700
ttgggaggct gagatgggag gatcacttga gcttggagtt cgagaccagc ctgtgcatca    80760
tagtgtgaga tcctgtctcc tcaagaaatt aaaaaattaa ctgggtgagg taacgtgtgc    80820
ctgtgggccc atctactctg gaggctgagg tgggaggatt acttgagcct gggaggttga    80880
ggctgcagtg aactatgatt gcgccccatc ccgggtggcg agtgagaccc tatctcaaaa    80940
aaaagaaaaa aaaatgctgc tttgcacccc tttctcatgt catggtgtca tggctaacat    81000
cgaatgccct ggttgtttgc tgttggaagg cgtgggccta ggggctccct gaggactcct    81060
tccatcttca attcgttctc tgtgtacctg ttagcaagtt gtgggccagt ccctgccatg    81120
taccattgtg tgggtaaaag taaataaaat gtgtacagtg tctgaactgt acatataggg    81180
gtccaagaac aaaatgaatg acatgggtta gctcttttcta ataaatggta aaaccaaata    81240
ttctaatttt cagttttgtt atacttccat cacatgtttt tgtttttttgt ttttgttttt   81300
ctatttaggg cagccttgcc ttctctaaca accccccctt ctctaagtcc catccgacga    81360
aaggggaagg agaaagaacc aggagagcaa gcatctgtac cgttgagtcc caagaaaggc    81420
agtgaggcca gtgcaggtag gaaacagtgt ggggaaggga gggacaggag tgcagcatct    81480
gtcatgtagc aacataggat ttaagtaact tggtgtttta gagaaatata atacacatca    81540
gtaaagtgag agaaggtttc tccaggtgcg gttcaagata ttagaaacta atgactaata    81600
tacacagacc acctttggt ctgaagcatc tctaagtgcc acctgctgac acgcagcccc     81660
tgcagcctcc aggcttccag ccccagcacg gagcctcact ctcctgtgct tccctggttg    81720
cgggtgaggg ctggagaggc ctcctgattt tcagtaaggg aagtggtgta gatgcttagg    81780
aatagatata gtgagtgaaa aaattgattc tgatatgtca aaatttctga ttggaaatgg    81840
aatatttaca tttggaagaa ctaaaggaga gagaaagtgg ggataaagtc atctgagttg    81900
gaggagctta aaccatgcac aagtttggag gacctttttt taacccatga aaaggtcaga    81960
acagaagggg ctaggattta gttgtgactg cagttttttcg aattcccatc catactgctc    82020
ttggagggca gtggcagggg caggagagga gcctggcaaa gcatgaagtg actgctgctg    82080
cctctgctat ctgggtcgcc tggctgcctg tctgtacagt ctccctccaa acccattctc    82140
tcgctgtctc ttggtgccca ggggccagtg atggttctcc cgtttgtttt gtgtatatag    82200
catttatatc aaggctattt atttatttag agacagagtc ttgctctgtc gcccaggctg    82260
gagtgtagtg gtgcaatctc ggctcattgc aagctccgcc tcccaggttc aagcaattct    82320
cttgcctcag cctcccaagt agctgggact acaggtgtgc accactacac ctggctaatt    82380
ttttgtattt tttttagtag agacagggtt tcaccatgtt ggccaggatg gtcttgatct    82440
cctgaccttg tgatccacca acctcagcct ctcaaagtgc tggaattaca ggcatgagcc    82500
actgcacctg gcctatttat ttattttttaa ttgacaaaat tgtatatgtc tgtagtatac    82560
aacatgatgt ttgaaatatg tatacattgg ccaggcgcag tggctcannn nnnnnnnnn    82620
nnnnnnnnnn nnnnnnnnnn nnnnnnnnnn nnnnnnnnnn nnnnnnnnnn nnnnnnnnnn    82680
nnnnnnnnnn nnnnnnnnnn nnnnnnnnnn nnnnnnnnnn nnnnnnnnnn nnnnnnnnnn    82740
nnnnnnnnnn nnnnnnnnnn nnnnnnnnnn nnnnnnnnnn nnnnnnnnnn nnnnnnnnnn    82800
```

```
nnnnnnnnnn nnnnnnnnnn nnnnnnnnnn nnnnnnnnnn nnnnnnnnnn nnnnnnnnnn    82860
nnnnnnnnnn nnnnnnnnnn nnnnnnnnnn nnnnnnnnnn nnnnnnnnnn nnnnnnnnnn    82920
nnnnnnnnnn nnnnnnnnnn nnnnnnnnnn nnnnnnnnnn nnnnnnnnnn nnnnnnnnnn    82980
nnnnnnnnnn nnnnnnnnnn nnnnnnnnnn nnnnnnnnnn nnnnnnnnnn nnnnnnnnnn    83040
nnnnnnnnnn nnnnnnnnnn nnnnnnnnnn nnnnnnnnnn nnnnnnnnnn nnnnnnnnnn    83100
nnnnnnnnnn nnnnnnnnnn nnnnnnnnnn nnnnnnnnnn nnnnnnnnnn nnnnnnnnnn    83160
nnnnnnnnnn nnnnnnnnnn nnnnnnnnnn nnnnnnnnnn nnnnnnnnnn nnnnnnnnnn    83220
nnnnnnnnnn nnnnnnnnnn nnnnnnnnnn nnnnnnnnnn nnnnnnnnnn nnnnnnnnnn    83280
nnnnnnnnnn nnnnnnnnnn nnnnnnnnnn nnnngcactt taatatttag tatcggttta    83340
atgataatgt ttgtgccctt actgtcttta aaacattttt acgtcatccc tgtttgatta    83400
cttggtgtgc tcatgaagtt gttggccact agggaatctt aggctcagag aggttctgga    83460
attggtcagt ggtccttgaa ttagccgctc ctatgattct ctaactgatt tctcaaaaag    83520
caaacaagca accacagcaa aacagctgtg cacaccactc ttcttatttt gttattgttt    83580
tagtacttag gccgtactta tgtttgttag tcagtttctc attacttcta gttaatcaaa    83640
agatcagagg caatatttga gtattttcat actagaatgc tttaaaaaaa gtcattattg    83700
gccgggcgcg gtggctcaag cctgtaatcc cagcactttg ggaggccgag acgggtggat    83760
cacgaggtca ggagatcgag accatcctgg cgaacacggt gaaaccccgt ctctactaaa    83820
aaatacaaaa aactagccgg gcgagatggc gggcgcctgt agtcccagtt acttgggagg    83880
ctgaggcagg agaatggcgt aaacccggga ggcggagctt gcagtgagct gagatccggc    83940
cactgcactc cagcccgggc gacagagcga gactccatct caaaaaaaaa aaaaaaaaa    84000 aaaaagtcat tatttccagt aatctcttta aaacttggca agttattttg atctaaagt    84060 ttatcttttg tgtgcacatt tttaaagctt ctagacaatc tgatacctca ggtcctgtta    84120
caacaagtaa atcctcatca ctggggagtt tctatcatct tccttcatac ctcaaactgc    84180
atgatgtcct gaaagctacg cacgctaact acaaggtatg ggcctctgca tcttttgaaa    84240
atatatatgc ccacatactt atgtctaatg gatcgttgat gttttttctta tgatttgtag    84300 gacgtataag ccctttgaga tatgagttac aattcgtgtt ttcaagtttg tctttcagct    84360
ttgtttatga tagcatctgt catacaggtg ttttggattt tcatattgtt tgtactcaca    84420
gctaagattg attacgtgag agagctagga tgtgcagcca ggttattggg ggaagtggcc    84480
tcggtggagt ctggagggat ctgtgtacag gcttccttcc ctcctgtgag gctcacacaa    84540
aaatacagca acctgctggt cctgcaggtc ccctctgcct aacatgagcc acaattccag    84600
actcacagaa gcaggcgttc agcataaacc acgtgtttca aatagtctgg gcgttgtgag    84660
ccacttgtta tcagctaggg aaagttttta tgtcagtgta aggaactgtt gaccagataa    84720
ccccaagagc cggcctttct gtctagggat gttttagttt tctagttcat ttttttttt    84780 ttaactttaa aattttctat tcatctgcaa tttgttagat atgaagtacg catctaattt    84840
aattttggtt ttggttgtcc ccaatgctgt ttacagaaga attttttgc actaattggc    84900 ttaagttact tacattctca tagttctcta gtttcatttg ccatttttgtt atatcaatct    84960 atctgtctgc tcatctatta gaagcatcct ttttttcctg ttgtagacag tctcgctctg    85020
tccccaggct ggagtgcagt ggtgcaacca tgcctcactg cagtctcaac ctccagggct    85080
caagtgatcc tcccacctca gctcctgggt acctgggact acaggcatgt gccaccatag    85140
```

```
ccagctgctt tttacatttt ttgtagagac agggtctccc taagttgcct gggctggtct    85200
caagttcctg gcttaagtaa tccttcctcc ttggcctccc aaagtgctgg gattacaggc    85260
gtgagcaact gcacctggct agaagtatac ttcttagtta ttatagcttc atggtattta    85320
tgatgggatc agttctcctg ttctttagaa ttttctggat attcttcttt gttgattttg    85380
ggatgtgaac aatagaatca acttctactt gtaggttgat ttagggagaa cttataccte    85440 agatgttaag ttaccctgtc cagaatgtgg gatgctttcc tatttgttca aaacgtttta    85500
aattacctca gaagcacatg aaatttaaag gattttaaaa aaaactttaa agattatttc    85560
acatagctct tgcacatttc ttggtaaatg aatcctcagg tgttcttctg ttttgttac    85620 taatagatac ttctcatggt tgtttttttt ttttttttcc tgaaaatcat ttgtcaaact    85680
tatgtggctt cttttctgaa ggatgtttga taattttgga agatataaaa gtcttcatat    85740
tttacaaggt ttggagtctc tttaagctgc gtggttctca cgtcagctcc caaagcagaa    85800
gacggcatgt cgaaaaatgc catagagaag ctacttcttt tccacctgtt ttcagctcat    85860
atcatcttga atttcggggc accttttctat gctcctagtg cttgctgtct gtttattatt    85920
ttccttcctg aatacccctga actccagcat gttctgctgt aattctggcc tccctggcgt    85980 cttgactcc tgtttccttt gctctgtcat ccccacggtc agctcctgct gcgcagcttc    86040
tcagctgaac tgtttggagt ggctggcggg tcttgctgga tctttgagta ttgcctctgg    86100
tttccttggt tccttctgct gagttgctca gcgtctccac tccccatttc tcgtgtggcc    86160
cttcctgctc tcctctgatt cctttgtct tccctggttt cttgctttgg ttttcagtct    86220
ccgcagaact tttgccactc ttctgaaaac ccggaggct tttcatctta attctcattt    86280
catgacctct tttcccttat ttgagaggta gaccttccca tggtgagctt ctctttccag    86340
aattccatgt cttctttcc ctcccactta cctgttgtcc aggagaggtc agattgctgt    86400
gcgcattgga gaagaaccct ttcttccctg ggctcttcat ttcacatgac atcaccacat    86460
cacctcatcc cttggaccct cagtggtggc actgctggat ttttctttcc tttggctggc    86520 cttgggcac acccaggttg accctagctt agtcatggta tttagatcaa ctcacatttt    86580
cagtttctgt gtctgtctct tgcctgcttc tgactttgcc cagagaaagc ttttcacaa    86640 gggttcttag atttacgagc accttctttc ctgaggcagt gttttgcca atatttattt    86700 tcctagtcag tctcgcctta cctttcttgt tatacatgat gtcttggtc ctgacccatt    86760 ctctgagtct gtaaaataga attgctgtat aatttaatta catgaaatcc tttagaatct    86820
taatacatct tacaccaggt gtaacatttt atgatatcca aattgaacaa ccctgtgtga    86880
atttgacagt gatttctccc agggatccta atgtataagg aataggactt tgtattttct    86940
attttttgat ataccacata ccagatactg atcatgatgg acatttaacc cttttttct    87000 cattaggaaa gaaagttagg aattacatct ttcagtagtg ccagtgtgac ctgaaagatg    87060
cctttgaaag agtagttttt gtatagctat ctgaaaggaa tttctttcca agatattttc    87120
ccagtgctga caacaaacac gcagacacgc cctacaaggt caatgtacag cgccgcacag    87180
tggaggcgtc tgccgcagcc gttaatgttt gtatctttgg ttgtacttta cgagatcttg    87240
acggggccag taaccgtgtg ttctctcctt caccttctca aggtcacctt ggatcttcag    87300
aacagcacgg aaaaatttgg agggtttctt cgctcagcct tggacgttct ctctcagatt    87360
ctagagctgg ccacactgca ggacattggg aaggtctgtg tcttgttttg acgtgcgtcc    87420
tctgggctga gttcatctag gatggagtcc ggttctccag ggtgcctccg ggagactcct    87480
ccctgcgcca cggacttgca tcacaggacc cgagtctgac tctgccttag ccatgaagtt    87540
```

```
tgggggaag gttctatttg tattctgttt ttgtctgtta tcacgtatta gcttagaccc   87600
agtttagttt agaaaattgg tgggtttaaa aatgtgtttt tagagtcctt tatttcttaa   87660
tttgaccttt tcaagtggaa aggggcaaaa cagacagatg aggggcggg gcgggaggtg    87720 tgacttgctc ttttgtgcct gaggaagtaa cagagctggg gttgacagtt atattctctg   87780
gttttatgtc caggaatttc ccctgccgca cccctagttg atagcgaaaa tgttcaaaac   87840
tatgagaaag ttagaatgct gtggtaaaca ctctattatg tacacacaac ccagcttctg   87900
cagttgtttg cgtttggcta cgtttccttt ctatgtatat agccatctct ccatttacca   87960
gtacatctta ctttataatg catttaaaa ggagtgacag atgcctccct ccaccaaatg    88020
tgtgtcttca cgtgaaatac agtatgtctg atgcacttca tttgttctta tgtctttgaa   88080 tcttttatc tggacatgga cacaaggtta cctagttta atcgttacat atgttagtgc     88140
ttcttctctg ttattcctca tgttttccc atgtatctat ttagtgtgcg cagttgtcat    88200
ttttaatggc tatctagtgt cctgctgtgt tgatactcca tcgttccctt agagtaaaac   88260
ttgttgagac ttcagtaatg tcacctgctc agtgagactt tcctggccat cctttcaaaa   88320
cttgcttctc tctgtactct cttttcctgt tcatttttct ctttgaccca tagcatcgtc   88380
taacagtcaa ccttaaaata aataaataaa taaagacttc agagaaatgt ccaaatacat   88440
ggagtcagtt tgggaatgag aaatgaggat tataatccgg gatgcacggc atgtccggct   88500
gccagtgcct ctggtgaagg aaggggaagg ggaagctgtt attgtcagaa agggagagaa   88560
tcacataggc tccctggaag cagagttcgt tggctccaga ggctgaaagc cagagttgtc   88620
gtcattcact ggtggaattg taggcaccgg gcaggtgttc agttgagagt attttaactg   88680
aattgctgca gtcctccaga atggctagtg ataaatctgg tcatagaaac atgtattcac   88740
gtggaacatg caagccatgc acagcagata tgtaaaggat gtacgggaag ggtttcttct   88800
agggttgttg gaaagtcttt ggaaacagct ctaacctggg gcacataagc atgaaccca    88860 tctcccttg tgctttccta gtccaatttt gtctgggtct gacaaagtga tttgatccct    88920
gtatctgcaa ctttcacaaa acatactatt tatttatttt acttccttgt cttttcagtg   88980
cctatagcag tgcctggaag attgtggaat ttagtgaaca tttgttgaat gaatagatgt   89040
tcttgttaaa aatgagtttt agtgtctcat ttatcttaca tccacactgt ggtggagcca   89100
tattagccca tttcacgcca taactggaag ctgaaagatg tgacattctt ggggccagat   89160
aagtcagtgg cagagcctga gttaagtctc atagattttc ttttttcttt ttcgttttg    89220 gtggctagct ttggttttat ttttatttat ttatttattt ttattatact ttaagttctg   89280
ggttacatgt gcagaacgtg cagttttgtt atataggtat acatgtgcca tgatggtttg   89340
ctgcacccat caacctgtca cctacattag gtatttctcc taatgttatc ccttccctag   89400 tccctcacc ccgatgggcc ccggtatgtg atgttcccct ccctgtgtcc atgtgctctc    89460
attgttcaac tcccacttgt gagtgacaac atgcagtgtt tggttttctg atcttgtgat   89520
agtttgctga gaatgatggt ttctggcttc atccatatcc ctgcaaagga cattaactca   89580 tccttttta tggctgtata gtattccatg gtgtatatgt gccacatttc ttaatccagt    89640
ctatcatcga tggacatttg ggttggttcc aagtctttgc tgtttgggact agtgccacaa  89700 taaacatacg tgtgcatttg tctttattgt agaatgatat aatcctttgg gtatatgccc   89760
agtaatggga ttgctgggtc aaatggtatt tctagttcta gatctttgag gaattgccac   89820
actatcttcc acaatggttg aactaattta cactcccacc aacagtgtaa aagtgttcct   89880
```

```
attttttccac aacctctcca gcatctgttg tttcattaat ttttaatgat cgccattcta    89940
gctggtgtga gatggtatct cattgtgatt ttgatttgca tttctgtaat gaacagtgac    90000
gatgagcatt tattcatatg tctgttgact gcataagtgt cttcttttga gaagtgtctg    90060
ttcatatcct ttgtccattt ttagatgggg ttgtttgctt ttttttttttt tttgtaaatt    90120
tgtttaagtt ctttgtagat tctggatatt agcccttttgt cagatggtta gattgcaaaa    90180
atttttctccc attctgtaag ttgcctgttt actctgatga tagtttcttt tgctgtgcag    90240
aagctctttta gtttaattag atcccatttg tcaattttgg cttttgttgc cattgctttt    90300
ggtgttttag acattaagtc tttgcccatg cctatggcct gaatgttatt gcccaggttt    90360
tcttctagga tttttatagt cctaggtctt atgtttaagt ctttgatcca tcttgagttg    90420
atttttgtat aaggtgtaag gaaggggtcc agtttcagtt ttcagcatgt ggctagccag    90480
ttttcccaac actatttatt aaatagggaa tcttttcccc attgcttatg tgtgtcagat    90540
ttgtcaaaga tcagatgctg gtagatgtgt ggtgttattt ctgaagcctc tgttctgttc    90600
cattggtcta tatatctgtt ttggtaccat gctgttttgg ttactgtagc cttgtagtat    90660
agtttgaagt caggtagcgt gatgcctcca gctttgttct tcttgcccag gattgtcttg    90720
gctatgcagg ctcttttttg gttccatatg aagtttaaag tagttttttc caattctgtg    90780
aagaaagtca gtggtagctt gatggggata gcattgaatc tataaattac tttgggtagt    90840
aaggccattt tcacaatatt ggttcttcct atccatgaac atgaatgtt tttccatttg    90900
tttgtgtcct ctcttatttc cttgagcagt ggtttgtagt tctccttgaa gaggtccttc    90960
acatctctta taagttgtat tcccaggtat tttattctct tagtagcaat tgtgaatggg    91020
agttcactca tgatttggca caatctcagc ccactgcaac ctttgcctcc tgggttcaag    91080
gaattctcct gcctcagcct ccagagcagc tgggattaca ggcacctgcc accatacctg    91140
gctaattttt tgtattttta gtggaaacgg ggttttacca cattggccgg ctagtctcg    91200
aactcctgac ctcgtgatcc acccacctca gcctcccaga gtgctgggat tacaggcttc    91260
agcaactgcg cccagccaga ttttcagatc tccctctctt tgccctaaac cactgtgctt    91320
aataagaatt cttagtggc cagcagtctc catgtgtaac acattgtagc aaaatggaaa    91380
atattacatg ttttaaattt gagtgtgaga tatactgaaa taaaaatcat ctaaatgaga    91440
ttctttaaat aataagattt tcttttttgt atgtgggttt ttttttaaca ttattatat    91500
gactgtcgta tatagaaatg gctgttttca actacagtca gtgaatgtat caaatgctgc    91560
cttatccaaa taataaaagt aaatgattaa caagtcacaa tttagtgaag attgatgtta    91620
gttgatcttt atattcctga attagccaca tggttgtgtg tgtgtatata tgtttagagg    91680
tacatataga taataagctc atctctgaaa atttttacat ttggcataag aataactgga    91740
taattaagca tcttattctc tggcctgtgt ctttacagtt aaaggtagat ttactcacct    91800
ctccttttttt gttttttctca gttcatcttt tttgctatttt catgacggag gcccattta    91860
cctttctcgt atatcctttt gtttgtactt tggaagcctc acctgcttaa ttgttgagtt    91920
tttaatctgt ggtcttttag aggaggatgt gtagggtaga agctttcaca ggttcttctt    91980
tgcacttggc ccttggctgt tttgaggaat ctccctcact aactcacagc atagcaaggt    92040
ttgagatctc ttctgccaca cagcagttcc caggcagctg gaaagatatg cagatgctca    92100
gattgtcagg ccagccttga gatatacaaa ctactgagcc ttatctgtga ccttgcttag    92160
gtgaaggcat cagagcccct gcaccgacat gtgtaggcct ctggatgtgt gcggggctgg    92220
gtgttggggt ctgagcacaa gtgtagctgg agaggtgagc ttgttgtggt gacgggtatg    92280
```

```
agcaagtttt cttcagactt ctgtgagttt acctcgttcc aggatttaaa ggcacagaga    92340
ccttagaatt aaaatagaat cattttcttt ttctaaatag caacactagg aataaaaaat    92400
aataattcca cattctttac aggtaatgtt ttgttttttct tgtcttctaa tccttattta    92460
ttctgtactt attttatac gtatttgaaa tgtattatgt gttggagttt tcttttttgca    92520 ttatattata cacggttttt catgtaactc cttactgttc cattttatat gttttgtctg    92580
gtttatttta agactttatc agcaaatcgg gaaaccgtct ctacaaaaac aaaaacaaaa    92640
gcaaaaatag ttggccacag tggcatgcgt ctgtggtccc agctactcgg ggctgaggtg    92700
ggaggattgc ctgagcccgg gaggttgagg ctgcagacaa ccatggtcgt gtcactgcac    92760
tccagcgtgg gtgacagact ttatactgtc tgtttggggt gatttggtaa tgatatgccc    92820
tgatgtagtt ttttatatc ttgtgtttct tgtgcctggg tttattgagc ttgggtctgt    92880
ggcttcatag tatttttaaa gtttggaaaa ttttagggca ttatttcccc aaagattttt    92940
ttctgccctg ttcccctcct ttttttcctc tcttaaaggg gctgtgattt cctgaatgat    93000
tgcttagtgt tgtcccatag cttattgatg ctcttttcag tgttttttgt gttttctgtt    93060
ttctatagtt tctattattg tatttgcaag ttctctaact tttcttctac gatgtctaat    93120
gtgttgttta tctgttaatc tattgttaat cctgtccagt atttttttt tttttttgaa    93180 acagtctcac tctgttgccc atgctggagt ttagtggtac aatctcggct cactgcaacc    93240
tccacctccc aggctcaagc aattgttctg cctcagcctc ccaagtagct gggactacag    93300
gcacgtgcca ccacacctag ctaattttg tattttatt agagatgggg tttccccatg    93360
ttggccagac tggccttgaa ctctgatctc aggtgattca tccacctcgg cctcccaaag    93420
tgctgggatt ataggcatga gctaccttga ctggcccctg ttcagtgtat atcactaatt    93480 gtgttttat ctatataagt ttgatttagg tcttttaaaa atttctccct gtgtctctac    93540
ttagctttgt gaacacagtt gtaataactg ttttaatatc tttctctgct agttctaaga    93600
tcttctaata acttcctggt tctcggtgtt tttgattggt ctattgatgc tccttgttgt    93660
ggattgtgct ttcctgcctc tttgcatcgc tgccaatttt tggttggatg cccaacattg    93720 tgaatttac tttgctggat gctagacatt tttgtgttca cagagatctt cttgagtttt    93780
gctctgaggt tagttgagtt acatgtagat ggtttactct tttgggtctt gctttataat    93840
gagtactcta cctaatgaac cagaaagttc gggttttcca gtctgcctgc tgagaacggt    93900
gactgtttct agccctgtgt gagtgcccga gcgccgctcc ctctgatcct ttctgatgct    93960
tccctctgtg gcctcaggga gtttcctcac acacacagtt ctgctgagta ctcgagggt    94020 ccttccccga tctccaaggc tctctctgtc ttgttctctc ttctctggtg ctctgtccta    94080
taaactgtgg ctatcttggt ctccttagat tctcagcacc tcttcaattc agagggttgc    94140
ctgtccctcc tccttgtgcc acagcctagg aactctctta agaagtgag gtggggcagc    94200 tgtgggctc actttgtctc tcgtctccca gggatcactg tccttcatgg ctgatgtcca    94260
atgtcttaag gactctggat tttgtctgtt ttgttttttg gttggctttg tttgtttcaa    94320
acaggagggt aaacccagtt cctcactctc attgtgctca gtactggaag tctcgctctg    94380
ttatattgga tattagtatt tgtagcagag ccctggttcc ctggtacttg gggagctctt    94440
gaaaggccag aaacagcatg ctttctcacc tttcccaggg cttccgtttc tggtgcacac    94500
aaagcattcc atacacattt gttaaagttc tttgttagac aaatagtgat tcacaggctc    94560
tatttgtaat tttttcagta agcatgtatt agatatctgc tgggagctag tagaaacaaa    94620
```

```
aagtgacatg tgacaaattc aattctgaca agaacaacct taaacattta gaatataatt    94680
tgagtaaatc agaatttaa aaatgtgtgg cccttgaata tttgaaacca acaagaatct    94740
attgcttatt agtagaggat attttgttga acaagtggag agagaggcat tttcagtcta    94800
actggtgttg gcttttagca gctgttggaa accggttcat gattagccag gcagtggtga    94860
aacaggctgt gcattctgaa tgcctagatt ggtggcactc ttcgagttag catcttcttc    94920
tttcttcttt tttttgagat ggactttcac tcttgttgcc caggtaacaa ctccagtgca    94980
atggtgccat ctcggctcac tgcaacctct gcctcccggg ttcaagcgat tctcctgcct    95040
cagcctccca gtagctggga ttacaggtg tgcgccacca tgcctgacta attttgtgtt    95100
tttagtagag atggggtttc actatattgg tcagactggt cttgaactcc tgacctcaag    95160
tgatccacct gcctcgacct cccaaaatgc tgggattaca ggtgtgaacc actgctccca    95220
gccccttctt gattcttgta aaggacattg ggtgctgtac accttgttat agatgttgat    95280
aaaaattctt gtgagaatag taacgttaag gtagttgttt ggtcatttt gtctatcagt    95340 ataagataat tctaggactg atttgtggta aatcacacat tgctgtatca tagttgtgtt    95400
cactgaacat attcaggggc tttacagatg cagggctctt agctgctttg cgcacttctg    95460
aattcctgcc ctgagaacag gactggatac ctagtagacg ataggtattt gataacagtt    95520
taatgaatta atgagtgaat gaacagatac gtaggtatgt gaaagaatgg ttgtaatgta    95580
tgtaacttgg atttcaagac ttactctgtt caaataagaa atgaaaact ttcctctgat    95640 tttgctctac tatttacact ctttaaatgg aagttatctt gtacctttga tttctgtcta    95700
ggattcgtac aataatgggt catctctgag tcacttacgg tctcactgtt ctttccacag    95760
tgtgttgagg agatcctagg atacctgaaa tcctgcttta gtcgagaacc aatgatggca    95820
actgtttgtg ttcaacaagt aagagcttca ttctttcct attctgttaa gactttcagg    95880
tatgacgaca aaatgctgct actccttaag cagcaggtgc tggtggcgta atcagctggg    95940
aggattgtgg ggtccagcat agcactttc ggctcattcc atgattgagc caagaggccg    96000
accttcccgt cattccccag gaggacgagg tctgtcattg tggagagcaa aggacatcag    96060
aagctcccct gcatcctcac tcgttaactt ccagtccctc gggttttg tttagcgtgc    96120 tcaatctcat ttagaatcgc aaggaaaccc aaaactctta tttaaggtac aaacagcact    96180
tcatacaata tctcgccgag gtaataatag tgattcacag gaagaatttc acattgtgaa    96240
tctttgctaa tgtatccagt tatttacaga tggatttgat atttgtgtgg gagattctta    96300
aagtgttgtt catgccacgt tgtttgtgct tcaatttttt cactatagtt gttgaagact    96360
ctctttggga caaacttggc ctcccagttt gacggcttat catccaaccc cagcaagtca    96420
caaggccgag cacagcgcct tggctcctcc agtgtgaggc caggcttgta ccactactgc    96480
ttcatggccc cgtacaccca cttcacccag gccctcgctg acgccagcct gaggaacatg    96540
gtgcaggcgg agcaggagca cgacacctcg gggtaacagt tgtggcaaga atgctgtcgt    96600
tggtggaagc acaaagagc aagcaggaaa tactttgtaa aagaataaaa acgaaaaatg    96660
ttagccaaca tcttctaata gtctgctgta ttcaaagaac tctaggaaat atggttgatg    96720
caaagatgat ttaaggcata gcccggcctt tcaagaagtg tgtggccagt gagtgagatg    96780
ggcttgggac ttacacatct cagaggtggg ggtagaggag gaggaacact gagtgggctg    96840
agaagcagcc agctttcatt gccaaagtgt gtcagcaaac cagaaggcag ttcataatgt    96900
ccccacccgt tcaaagcaca ggccctgtag agtggtgtgg catgtgttgg tggcacttt    96960 caggcctgta acaaggatga aagaacagct tcattgcagc acagtagtgc tggtattcag    97020
```

```
aggtatatga aggtcatgga agcatcttgg atatgttacc ttgtgttttg tcaactttat    97080
gactagaaat ctcttttac ttaaatttat gtttgtgtct ttaatgcctg aatacagga    97140 cttcttaaat tgccataagt atcaacaggt atttgagtta ctaatctgta tagtagcaat    97200
aatagaatcc cttgttttc cttttataaa tgtaatgatt aaatagctac aattgaaaca    97260
ctagagtcag gagtcaagga aaatacccat gttccaggct gtatgttagt gatgtactca    97320
ctgtgtattc cagtttcagg aataagtctg tttcaatgct ttctgtaacc atttggggta    97380
ttaataagca agtgagtgta tgcatgtttg ggttaatttc atatatgtgt cttagaaagg    97440
atatcattga tgtaaatatt ttcaaggctt atcctccaaa aaaatcctgt gatttcttct    97500
aaattactga tcttttaaat gaccttcacc tttctctcaa gtctcactta agactgggct    97560
gagtagtcag tttcctgtag cagtaaaaag ctcagacttg agtagccttc cacaggtgac    97620
gagacttgat ggctgtcagg cagctgtaaa ctgtaaatag agtgtcatta tctcgagagg    97680
gtgatgctgc cacactgagt ggcctttcaa gttgtttctc agtctgacat gttctgatcg    97740
tgtgaatgtg aaattggttt gaacaggagt atatctgagt gcagaggaga ttatttaaag    97800
atattctcat tgtctgcttc ccttctattc ccatttggca gatggtttga tgtcctccag    97860
aaagtgtcta cccagttgaa gacgaacctc acaagtgtca caaagaaccg tgcagataag    97920
gtaaatggtg ccgtttgtgg cgtgtgaact caggcgtgtc agtgctagag atgaaactgg    97980
agctgagact tcccaggtat tttgcttgaa gcttttggtt gaaggctcac ttacggattc    98040
tttctttctt tctttgttt tttatagaa tgctattcat aatcacattc gtttgtttga    98100
acctcttgtt ataaaagctt taaaacagta cacgacaaca acatctgtgc agttacagaa    98160
gcaggtttta gatttgctgg cgcagctggt tcagttacgg gttaattact gtcttctgga    98220
ttcagatcag gtttgtcgct tttaatcttt catccatcat acctgtacct aatttagtac    98280
aaattaccct gaaagacact gaaatctact ttaaagaaat gtgaactgtg tttccccacc    98340
ccccatcaat tgctgctgct tatgttttc atgcacttag ctagtacaag gcccggggca    98400
tagccagcct cagcaagtcg gcatccttgc cccagctccc tggactcaag gctaacctgg    98460
ggttggctgt tagggatttc caaaggtttg tcccatccac tcgcctcccc tccaaaataa    98520
gtttgaattt aaattgtgag atttaattaa gatttattgt ttggggaaca ttttgcaaa    98580 atctagagag ttagtttaaa tggattatca attatgacta taattgatca tctgcagttt    98640
caggctatct aacaggttag cttacctctt taaaaggaa tggaatttag ccggacagta    98700
actgagaccc acgctcctgg agtccacgtg ggagccgcgt ggctctgcac aaacaagcat    98760
ttgcactctt cccctcttgg ctgcgttgcc ctcctcctgc agttgctgtg ggcactagat    98820
tctggctagt catgtccctt catgatgcac agtttcctca agattcgtgc cagttaaatc    98880 actgccttt catagtcaaa atttaactgt catctttgac ccatgatctt gggctacttc    98940
cttatgtggg gtaggaatat ttttgagata gaaatattac acttctctgt ttccttctag    99000
acaaaaatct gttaattctg ttagtaccgt gactcatctg aaagggtctg tttccctagg    99060
agaactgagg gcacgtggtc aacactgatt tcccaccatg ggtattgagg tggggtctgc    99120
ttttttttgt tttgtctttt tttttttgag acggagtctt gctctgtcgc ccaggctgga    99180
gtgcaatagt gccatctcag ctcactgcaa cctccacctc ccgggttcac gccattctcc    99240
tgcctcagcc tcccaagtag ctgggactac aggcacccac cacttcgcct ggcttatttt    99300
ttgtagagac cgggtttcac catgttagcc aggatggtct ctatctcctg acctcatgat    99360
```

-continued

```
ccacctgcct cggcctccca aagtgctagg attacaggcg tgagccaccg tgcccggcct   99420
ggggtctgct tttaatgaaa gaggcatcta ggggtgggct ttgccttggc ttgatgcttt   99480
gaacctttgt tcacaaaacc tatctgaaga aaatctgtct cagtgggcca ttgctctcct   99540
caggaaacat gcattgggaa cttcttttcg tttcctttga cactaggagg ctgcctgggg   99600
agaagccctg gtctatggct atgggcaagc aggggctgag aggagcaggc tctcagtggg   99660
gcagggtacc ccaagggaag ccagaaccct gatttgttcc attctagtga gaacaaagac   99720
tacagtctac cttttcttca gaatttccca gttctaactg gcatggtgg cacacctctg   99780
tagtcctagt tactgaggag gctgaggcgg gaggatcact tgagtccagg agtttgagtc   99840
cagcctgcac aacatggcaa ggcctgtctc taaaataata gtaataatca taatctctag   99900
ttctagccgg gcacagtggc tcatgcctgt aatcccagca cttttgagagg ccgaggcagg   99960
taaatcattt gagctcagga gtttgagaac agcctggcca acatgatgaa accccatctt  100020
tactaaaagt acaaaaatat tagctgggtg tggtggcagg tgcctgtaat cccagttact  100080
tgggaggctg aggcaggaga atcacttgaa cccgggagag gaggttgca gtcagctgag  100140
attgtgccac tgtcctccag cctgggcgag acagagcgag actgtgtctc aaaataataa  100200
taacaacctg tggttctgac tcgtcatggg taggaactga ttttctcatg tggtagttac  100260
agactatggt ctccttgggc ctgtctttag tagggaaaaa aggcaactcc ccactctaac  100320
ataaaatggg tggacttgaa tgttttatca aattctttct ttagtcgttc tactggagct  100380
ttttcttcaa tgtagaatat tctgttgctt tattatattt gtctgcaatc tccatgtgat  100440
atttccatgt tgagggagga cagccttgag gctcccccgt gctgcctgcg gcctgcagg  100500
catgtggaat tcatctttgg cctgtgcttt cttctgggtc ccggtgcccc tgcccgcgag  100560
gctcatgtcc agctgccct tgtggtggt gtgaggtcat tcctgctgtg agcgctctgg  100620
tttcatgttt gttccgattg cctttcatca gccgatcccc tttctcccag ttcttaagat  100680
tcaatacagt gacagtttta tgaacaagaa tagaactaga acagacaagc cattgaactc  100740
tatgctgata atgatttacc gagcacctgc tgtatgtttg cattccgcgc agaggctctg  100800
agaaagccgg gccatgtgct ccatgcttta tcggtggaag ctcctcatca ggttgggaaa  100860
gctgacagct gcgtagaata ccagtgtgac acaaagctgg ctcccgtgcg gcccttgcgt  100920
gttgcctctc agatggtggg aggaagaagg tcgactcctt tggggatctt actaccaaac  100980
cagtttcagg gaatctgcta ccctgtctgc cattaatggg aacagatgag tccccaaggt  101040
gtacttctgg gtattgtctg atgtcgcttg gaatttatta cttgtttttc caatgaggtt  101100
tcacctcagt gtgtagtaaa gttgttgagg ggattcctgg aggtgttcta cagttatcta  101160
ggctgatttc agaatagagt tatgcttata gtccaattta tcagctgtca agaaattcat  101220
ttaaaatttg tgcagataag caggaggaaa agaaacctgg tttttacgtt ttaatcctat  101280
tattgatgta aaatttact ttccttcccg taggtgttta ttggctttgt attgaaacag  101340
ttcgaataca ttgaagtggg ccagttcagg taatagcatt ttgttatttt agagtttttt  101400
ctccttcttg tgtacttaca tgtaatttag gttattaaga tgaatgttta aactactgtt  101460
aggcattttt gctgttttct ttaaatgaaa atctgattaa catgctgtgc attttttgctt  101520
ctcttaaaaa ttaatgtata tctcaagact tgtttggaag tagttacata tctgaaaatt  101580
ccatatgttg tcagttttca ttgcacattt caaagcattt aattatgttg acagatggcg  101640
gaatgaaatc ttgtggtgga gcactagttt ttaaatcttc ttagagaaag cagttttttat  101700
ataaggttgt ctttagtaat tattatgcac ttgtattctc tgcagctttt ttttgctaga  101760
```

```
tgttgaggtt ttaatacttc ttgctagtcc attacaggtt tataatgatt gaaagttaaa    101820
attctttagt acctgaaata cttaataaat actgtagtta ggaaaactta gtgcagaagg    101880
aaagtgttcc cagattccct ggggtctgga agcatagcgt tgttctaat cacgtgacac     101940 ctccactgtg ttttggggca agttactttt tctcttttga gtttcaattt ctacaagagc    102000
aaaggggcag agagagctag ggagattgta gctgctgtgc ctctgtgccg tcaggtgcct    102060
tctacctgct ccctctgaac ctttacacct gtcccggctc tgcacaaggg cacagatggg    102120
atgcactgtg gcagggatgg gcttagagta gatcactgac acctgttagc ttcatgtgcc    102180
ctcatgaatt attttatgtt gcttatattg atatgtatct taattttaaa agaaaggtct    102240
aaatggatgt ttttgtttct agggaatcag aggcaatcat tccaaacatc ttttcttct     102300 tggtattact gtcttatgaa cgctatcatt caaaacagat cattggaatt cctaaaatca    102360
ttcagctctg tgatggcatc atggccagtg aaggaaggc tgtgacacac ggtaatggga     102420
cacatctttc actgtcgtct tcagtgtcac gatgtgcttg gcagtgttcg ttttcttttt    102480
tttgttgttg ttgttttttt tttttgaga cggagtctcg ctgtgtctcc caggctggag     102540
tgcagtggcg tgatctcggc tcactgcaag ctccgcctcc cgggttcacg ccattctccc    102600
gcctcagcct cccaagtagc tgagactaca ggcgcccgcc accacgcccg gctagttttt    102660 tgtatttta gtagacgg ggtttcacca tgttagccag gatagtctcg atctcctgac       102720
ctcgtgatcc acccgcctcg gcctcccaaa gtgctgggat tacaggcttg agccaccgcg    102780
cccggccggc agtgttcgtt ttcatacacc cactttcaac tttgtcagtg gcggccgtgt    102840
gcgtctcagg ctctgcatat gtgtctgtgt gtctgtgtat gtgaatgtac tggttagaga    102900
cgtttcaaaa gagaagagag catattcttt actctcagca atttgtaatc ttctcaggga    102960 aaaaagttc aagaaacagt aagatagcct aaggtacaga tagattctga atataaagtt     103020
cctgttcatt cacacgaaac actaaaagtt cttcacctga tcttagccca aaggccgaga    103080
agcgatgaaa cactaaaaat tcttcagtcg aacttgctgt gaattaaatt ttgatctctc    103140
atccaggtgg tattggagat acagtttgac ttgggttcag ggctttctgt tttgcctgat    103200
gattattttg ctggagctta aataaagaca gggctccagg agatggccag ctgtgcaagc    103260
ccccagcctg tggaaggagc tagcctggtt ttatgaatga gctgtaaatc tttctttgag    103320 cttttttgaac tggtcttcca gcattgccct attgaccct ccctgactcc tttgctggaa    103380
tccgtaggct tttgaacttt gacagggaca catcctaaga cccttgcaaa cccctagatg    103440
tgagaatggc actactacat agagtctttt ccactcagcg tgtgtgcaga agaacatcaa    103500
ccatgctgtg tggcgaggca gggccttggc tgacctctca gtcaaggcct tagctttaca    103560
gagctaagcc agttagtctt tgccatggct tcacaatggc ttcaggttca cactgccaaa    103620
gtatagatta ttaaaggcat aggtgtttgg tttcctgcac ttggagggtc tttggacaga    103680
aaatcagtag gcagccaaag ccagtacttt gcgctgggaa gcttggtcgt ctgtgagagg    103740
gtcagagagg atacccatgt gtgcgcacca ccgaagggtc agtgagtctc agggctctgc    103800
gtgcatgtct cagggctgga gagagtgtgt cactgagagg tcagagtgtt tgtgcgtgtg    103860
tgtcaaagag ggttgcagtg tgcccttcac tgaggggtca gagggtgcct cacgtgtgtg    103920
tatgtgtgtg tgtcactggg tcagtgagtg ttcttgtgtg tgcatgtcac tgagaggtca    103980
gagggtgcct ttgtgtgtgt gtgctcatgt gtgtgtgcgt gtcactgagg ggtcagtgtt    104040
cctgtgtgca catgacattg agggtcagag tgtgcctctg tgtgcgtgtg ctcgtgtgtg    104100
```

```
catgcgtgac acctccactg tgttttgggg caagttactt tttctctttc tcttttactt 104160
ggtcatctgt gagagggtca gagaggatat ggtcctgtgt gcgcatgaca ctggggcaga 104220
gtgtgcctct gtgtgtgtgt gtgctcctgt gtgtgtacgt gtcactgagg ggtcagtgtt 104280
cctgtgtgcg cgtgacactg aggggcagag tgtgcctctg tgtgtgtgtg tgtgctcctg 104340
tgtgtgtacg tgtcactgag gggtcagtgt tcctgtgtgc gcgtgacact gaggggcaga 104400
gtgtacccgt gtgccaatga aaggcatttc ttattttttt ttatatgtgg tcacagtaga 104460
ccaattaatt tattttgact cctgttttag accaaaataa gacctggggg aaagtccctt 104520
atctatctaa tgagagagtg agtttactta aaaaagcata ataatccagt ggctttgact 104580
aaatgtatta cgtggaagtt tttattgtct tttcagatga atcaaataga ttattctcga 104640
gaccaggaat ggtgctgttt tggttatttg ggaagtttta tcattttcaa attgaccttt 104700
gaatttgagt caccttttt cagaagtggt gttaaattac aggagcccta ggttttttt 104760
cctttttag aagccatcac aaaatgatcg gtgttcagag gaaagctttt gatcttccac 104820
aatggtataa tgattgataa ccttaattca tctcttacca taaaccaagt atgtgtaagg 104880
gttttcttta tttcttgata tcattttgta gatgttgaga gcagttttcc aaatgtaatt 104940
tccatgaaat gcctgatgag ggtacccttt tgtccccaca gccataccgg ctctgcagcc 105000
catagtccat gacctttttg tattaagagg aacaaataaa gctgatgcag gaaaagagct 105060
tgaaacccaa aaagaagtgg tggtatcaat gttactgaga ctcatccagt accatcaggt 105120
aagaggaatg tgtgttggaa ctgtcgtgga tactttattg acccgtacag atggaaggaa 105180
gtgccatgtg gtaacactca ctgttaaccg tgctactttg aactaggttt gagctttctg 105240
aggcctgggg agatgctggg gcagcggcgg gtgcaggggg aggtgggggc gggggacagg 105300
cgtggtggca ggaggtatca ttggtgttta tccttccttt ttttttttt tttttgagat 105360
ggagtctcac tccgttgccc aggctggagt gcggtggcat gatcttggct cactgtaagc 105420
tccatctccc gggtttaagc gattctcctg cctccacctc ccgagtagct gggattacag 105480
acatgcacca ccatgcccag ctaattttt ttttttttt tttgtatttt tagtagagat 105540
gggggtttcac catgatggcc aagctggttt caaactcctg acctcaagtg atccgcctgc 105600
ctcggcctcc caaagtgctg ggattacagg cgtgagccac cgcgcccggc ctggtgttta 105660
tctttaaagt gggtacagcc acaggggttc acctgactcc tggtctgaga gtcacaagat 105720
cgttcaagat agtgaggccc tcttttccaa aacaaggacc aaaaatcagt tgacagtgtt 105780
ggtcaagatg gtagaaacct aaaatgatag aaatctcaac tctgaaataa aaactttatt 105840
tgcatatttta tttaccacta ttttgacata gggctaaggt cttttcttt gagctagttt 105900
ctggttttgt tttcttaagg tggcataaga attcaaagac attttgagga aaactgagtg 105960
tagaaatctc tctttttaa tgacttctct tttctttcag cttgtactgt tgtgtagccc 106020
tcgcttattt tgtcaattct ttttagctgt ttgtctttga atctttatga agccatagct 106080
tttctcataa gaagcagcac tttctttgtt cattcatatt ttaattaact cctgtagtat 106140
ttaaatactt aatgcctaat taaatcacat aattgcaatg caaaagtaca tgtatcataa 106200
agaggtctga aaatgagcaa ctggcaagca ggtggctgca ggcagagctg gctggtgggg 106260
tgggtgtcct ggagaagagc tcatcagctg catgttcagt gagctctgga tatctctgtg 106320
taaaaatgat cactaataaa cttgtgctca actgtgcaca cttccggaaa ggagatgctg 106380
ttcagtagat tgcctctgca gagaacacag aattgaaggg aatttccaca aaggcggtga 106440
gccgcctgca gaatagttta gtcaaggctg tgtttgaatt ttgccaaaga ttaatataca 106500
```

-continued

```
tttattttt  tcatgctgtg  ccttttctct  gattgtgaaa  tattataaat  tctatccaaa  106560
taacaatgat  ggcaagtcct  cctgagcaaa  gtgtgcagct  tgcatgtgtc  ctagaggaac  106620
tcgtgtttcg  ttctgattcc  cctgcatttc  tcatgtcata  gagtggggat  tgcatccgtg  106680
tcccctgtc   ctcgtgggga  tcacatctgt  ttggatccta  gagtcttcaa  gctgagctgg  106740
gacaagtgta  acagatggac  acatgggggt  ggaaaggcgc  ctctaggcag  cagactctct  106800
aattgtgcac  actcttatag  gtgttggaga  tgttcattct  cgtcctgcag  cagtgccaca  106860
aggagaatga  agacaagtgg  aagcgactgt  ctcgacagat  agctgacatc  atcctcccaa  106920
tgttagccaa  acagcaggtt  tgtccccgca  gccttggctc  gttgttgcat  agtgatggta  106980
gcttaaggtc  cttgtgaaag  gtgggtggct  ggaatcagct  cttccttcaa  tcctaatctg  107040
tgctttgata  gcagttctcc  atgctagtca  tggggcaact  gacttcattt  cttctcataa  107100
tgccatctca  ggttggtatt  gcccacctcc  tttacggggg  gaactcatga  ctcagagagg  107160
ttatggaggc  gatcaggcag  cacacagctt  tagagtgctg  gggtgagggc  gggccaagtc  107220
tgactctaaa  gcccgaaccc  ttacctccta  tactgcctcc  tgcattctgg  tcaacgcagt  107280
gttttatttg  gtggttacat  ttttgttttt  gttaccttac  tacttgtaat  ttagcagttt  107340
tcctttcctt  tcctttccct  tcctttcctt  tttccttctt  tctttccttt  ctgacagggt  107400
ctcgctctgt  cactcaggct  agagtgcagt  cgtgtaatct  cactgcaact  tccgcctccc  107460
aggttcaagc  aattctccca  cctcagtctc  ccgagtagca  aggaccacag  gtgtgcacca  107520
ctacacctgg  ctagttttt   gtattttag   tagaggcgag  gtcttgctgt  gttgcccagg  107580
ctggttttag  actcctgggt  gcaagtgatc  caccaacctt  ggcctcccaa  agtgctggca  107640
ttacaggtgt  gagccacctc  acctggccta  ttcatcacta  atcagaattt  ctatgatcaa  107700
atgacatgaa  ttgttgtttc  cacaaatgca  gtggaaggaa  atggcctggc  agtaccaatt  107760
ttggaagcaa  caggccccca  gtcaggcaca  ggacactgtg  cccccagtgt  agcagcatct  107820
ctatctcaca  gagaaggtgg  tgcgtcctcc  tcaaggcagc  tccgccagaa  aatctcatga  107880
gcggcctggc  acggcttgag  gttgcctttt  aaatggactc  agcaaataca  tgtttgttca  107940
tcttgattat  acacaataaa  caactactct  gtatagtaca  agtagtccgt  ggttttttgc  108000
atttgattta  aaccagagac  atgtgatatt  gatggttact  gccttcatga  ctgcaccccc  108060
atcctgattt  cataatagaa  tgttatcctg  agaccagtta  gacaatgaaa  cagggatctt  108120
ggcttctggt  gagactgaca  gcagttttag  cgtggtcagg  gtctccctgc  ccacagatgg  108180
tgttagaatg  gtgctctgga  agctttattc  cattatcttc  tgtgcataat  ctgagtagag  108240
tggagattga  aggcctgaat  gcatagtaaa  tatctgactt  aatttctgcc  gcaatggaaa  108300
ttgtgcgata  aaacatttat  gaaatgcgta  gcacagcccc  ggccaggtag  ctcagcacag  108360
gagcctgttg  cattcagaag  tagtgctaga  tactatcctg  ttactggcag  tacatacatc  108420
agtgatcaga  gcagattcaa  gaaagacccc  ctgccttctt  ggagtgaagg  ttttgttggg  108480
atggggtgag  gggacagaca  atagaaaaac  cagtgagtga  agtctctacc  atggcagctg  108540
atcagggacg  ctgtacagaa  gaatcccgga  gggaagagag  ttaggtggtt  tcggcggcgg  108600
agtggcattg  ttcagttggt  gatgagaaac  gttgtggtga  tctggtgaca  tttgagtgaa  108660
tttgcagaaa  ggaaagatac  aagcctagga  gataccctggg gaggagcat   tccaagaaga  108720
gcaaacagct  gcaaaggccc  tgggggggaac gtgctgttag  ggtaaaagca  atggggtgg   108780
aggagtgggg  cagctatgcg  gagggaaggg  agcgaggcct  ggtggggtga  ggccagcatg  108840
```

```
gaggagcctg agaggnnnnn nnnnnnnnnn nnnnnctccc aaagtgctgg gattacaggt    108900
gtgagccact gcaccccggc ctgttttttt tagagacgga gtcttgctct gtcgcccagg    108960
ctggagtata gtggtgcgat ctcggctcac tgcagcctcc gcctcccgga ttcaagcgat    109020
tctcctgcct cagcctcctg agtagctggg actacaggcg tgtgccactg tgcctggcta    109080
attttttgta gagacggagt ttcaccgtgt tagccaggat ggtctcaatc tcctgacctt    109140
gtgatccgcc cgtctcagcc tcccaaagtt tacaggtgga ttacaggtgg ctcccacacc    109200
gagccaagag tttgcatttt taacaaattc caggtgata ctaatgctgc ttttctggga     109260
ccacactttg agactcagtg atagaaagat ttattggtag atagtaaaa taggagtaat     109320
ttttttttc cacaaaattg gcaattgggg gaaatttaat cttccttttt tctttagcta     109380
tgacttattt attctgttta ttttaggcat ctgtgagcac tgttcaactg tggatatcag    109440
gaattctggc cattttgagg gttctgattt cccagtcaac tgaagatatt gttctttctc    109500
gtattcagga gctctctttc tctccatatt taatctcctg tccagtaatt aataggctaa    109560
gagatgggga cagtaattca gcactagaag aacacagtga agggaaacaa ataagaatt     109620
tgccagaaga aacattttca aggtatgctt tctatctgag cctgtaacta acccatgcct    109680
tttgggaagt cacttggtat ttcatgatca gttaagtctg gaataacacc tggtctcgct    109740
tcagttctga gctgggtaaa gaagtctgta tcagtgtaat tttctaatcc atcctggctt    109800
atctgtggct cctgtttcat acctctcttg aggttctgtc atgttctgtc tcttgtcctc    109860
agcagagatg ctacagcagt ggcttgctca ggtaggacag ggcagtgggg tggctgtcct    109920
gggggcaggc agtaggcgtg cattgccttc agggaagtta aaacccaaga gaagccacag    109980
aaagtgaatc ttatattctc accatgtgcc ggcagtttta cacgctgtca gtaataaaat    110040
acttctccct gcaaggcaga ctgcctccag taaatacctg tagtatcaaa tcctgtcttc    110100
cctcataaat tgttgggaag ctccctcagg acagtggtca ggcactcgta aatgcttgct    110160
gcctagatgg gtccctctcc acctctgctg gattctgagc attcactgag ttagagctgc    110220
tgctgcaaat gtgctacttc tgcctgagtg gctgtgactt catgcagccg tcatttggtt    110280
tgtcgtcagt gaagatgccc tgtgttgtcg atggagataa gcccagtaag cctgctgggc    110340
accttttttgt ttgcgggttc agcaggcagc ccgtggcttt ccctctgttg cattgaagca    110400
gctggctaaa actgatggta cattaaaattc ctatgacaga tgatcagctt gtatttgtgt    110460
aatggtgtac agtttacaaa gcttaaaaaa atactacctg ccatttcatc ctcagcgagg    110520
aaggtgatac acagagagga aaagtgactg tatccaaggc gatggtgtta cgcgtttcac    110580
tttaacggtt taatgtactt tacttctatt tttactttat atttaccaca tatattttca    110640
tatatacttg gcataagtgc tttatagtag tcacctaatt cactgtcacc cttttttgttt    110700
cttggaaggt ttctattaca actggtgggt attctttag aagacattgt tacaaaacag     110760
ctgaaggtgg aaatgagtga gcagcaacat actttctatt gccaagaact aggcactctg    110820
ctaatgtgtc tgatccacat cttcaagtct ggtaggtaaa tcacattagt cttcctcgag    110880
tatctcaatt ccccattctg cactgtacgc tcttagagtg taggagctat gctgcccggt    110940
agaaactctg tcttgcccag agtgccagtt gaaaatgttt gttgctataa gagtcagcct    111000
gatccatatg acccagcagt tctactcttg ggtatgtacc caaaagaatg gaacgcaggg    111060
tggtgaaaag atgtttgcat gccagcgttc atagcagcgt tattcacagc agctaaaatg    111120
tggaagcaac tgaagtgtcc attgatggac gaatggataa gcaaaatctg gtgtatactt    111180
agagtggaat attattgaac cttaatattc aataacctta aaggacattc tgacacgtgc    111240
```

```
tacaacatgg gtgaccccta aggacattat gctaaatgaa ataagccagt cacaaaagga  111300
caaatactat gtgattcctc ttatatgagg gacctggagt acttaattca tagatacgga  111360
cagtagagtg gtggttgcca ggggctgcgg gggaggggag ttgtttttac aagatgaaaa  111420
gagttattct agaaacgaat ggtggggatg gttgtataac agtgtgaatg tatttaatgc  111480
tactgaactc tacagttaaa aatagttaag atgagccagg tgtaatggct catgcctgta  111540
atccaagcac tttgagaggc caaggcagga ggactgcttg agccaaggag tttgagacca  111600
gcctcagcaa catggcaaga ccccatctgt acaaacagac tagccaggga tagtggtgtg  111660
cctgtggtcc caactactca ggacactgag gctggtggac cgcttgagct caggaggtca  111720
aggctctagt gaagtatgtt catgcctctg cactccagcc tcgactacag agtaagaccc  111780
tgcctcaaaa aaacaaagca agacaagacc caaaaatggt taagacgggc caatcacact  111840
ggcttactcc tgtaatccca acacttcggg gggtcaaggt ggaaggatca cttgaagcca  111900
ggagcttgaa accagcctga gcaacatagt gagacccta tctctacaaa gaaaataaaa  111960
aactagctag gtatggtagg cacatgcctg tagtcccagc tacttgggag gccgaggcgg  112020
gatgatcgct tgagcttgag accagcctgg aaaacatagg aagagactcc atctccacaa  112080
aaataaaaaa aataaaaaaa ttatccaggg gtagtgacgt gagcctgagc ccaggaggtc  112140
aagctgtagt gagccacgat cgtgccactg cactccaacc tgggcgagag atcgagacca  112200
tgtctctaaa gaaagaaaat tacaaggaca gtgaacccaa gaaagtcagt tgtgcagcaa  112260
gcatagaaag caaccagtcc aaattaggac agtgtgtttt ccaagaagaa cgatcatttg  112320
tcatgagaat gctttgcttt aaataaatga gtaaataggt agaagactag ttctagggga  112380
taggcacgtc tttcttctct caacaagaaa aagaaaggc aattctaatc tctaggaaaa  112440
gcaaatagca ttaagtcatg gtccaaatat gaggcaaacc aaaatatggc ttgattttc  112500 agcagttgat ctgttggaag cccttgatat taaaaaggtt ctcctttaag cagtttaggg  112560
gtcatgatca aagacccata gaaagagatg ccatcctttt aggatccttg gctctcttgg  112620
gaactgtatt cacgtagtca taatgtaagt attgcttgag cttttcatttt tggaatcaat  112680 atgtgactga aacactgaag acttactgac ttaattatgg tttcagaaca gaatgaaaat  112740
gtcttcagtt ctgatgaata taaaaggaaa actaaccaag ttaatttggc aagtagatgg  112800
tagagatggg gtgggaatgg aagggggcact aaaatcctta cctagcattg ttggagttac  112860
atgattacat catctgaagt tgacagacca aaatatagag gcttcaaagg tatccagata  112920
gagctaaaca tgtaactcag attgttagga ggtagtataa atgagccaaa tctcctcttt  112980
attaccgtag agttaatggg taatgtctaa agttgtctga agtctgtaaa tcatgacaaa  113040
ttatgatgtg gtgattgtat tcaacagtct ttcagttgca gggataaaac cccaatttaa  113100
actagagtaa gagaaagaat ttgttggttt gagctcctgg aaagtgcagg caagggtagt  113160
tggtaggact gcatctagtg ttataattct atggtctgca ttgtatattt atgcatatca  113220
gctctgcttt cttctcttaa tttgtatact tttaaaattt tattttaaag atagggtctc  113280
actttgtcgg ctacgctgaa gtgcagtggt gtgaagtgca gtgcgaggct cgctctagcc  113340
tcgaactcct gggctctaga gttcttcctg cctcagcctt ctaaggagct gagacaatag  113400
gcattcacca ccatggctgg ataggtttta aaattctttt gtagaaatgg aggccttgtt  113460
atgttgccca ggctggtctt taactcctag cttcaggcga tcctcctgcc tctgcttccc  113520
aaaatgctga ggttataggt gtgagccacc gcgcccagtc tcatctctgc ttcctgtctt  113580
```

```
agcccctcaa gtaggcatgt gattggcctt gcataagtca tatgggtgac cataaaccgc 113640
tgaatgctct ggtccacctg ggccaaatgg gagactggac agcattccat tgacgaggag 113700
gtggggcttg tctccgggag taagggagag gagcgcatgc agtaactgat ggtctgctgc 113760
acgggatagc ggcgcatcag ttagaatttt gaaggtaact accagaactg aaaacagaaa 113820
agataacaag tagttgcctt aaaaagggat ggggcagggt gcttttgtga tcagaaactc 113880
ctttctctta ttggattttt gtacacattt tgcggacata cccttagagt aaagataatt 113940
agcattttca gccttggtcc atttgaggag tggcccgcct ccctgctagc aggctctggg 114000
tctgctaggt tcagttgagc atcctggctc ttgcctgcat ggaacttaca gtcagtgcgt 114060
cagtatcaca agtcttaata tttcctatga aggaaaacaa tagtgcagtg acagacaaaa 114120
tgggtgggcg ggcagaggca ggatttccga gggggagaag tagctagctt tttgcagaga 114180
aatgttccgg cacccgagag agcagctgag agtgcaggca ggcaggaggc gagtggggcc 114240
tggccgcaca gcgtcacaga gtcccagaga aaggggcctc ttcatggcca ctgcattcag 114300
ctgctgtcac cctccacaca agccatggcc aaaatttaat tttgataatg gactctagtt 114360
tttgagcctt acttgctatt attgaaagaa ttttcttgtt tcttttttaaa gatcttcaga 114420 ttatgcttca ctgaccactg taataagttt aaagttgaga aaatatgcct tgttaatgaa 114480
tgataggtca attttagtat attggtcatt ttaatatttt gccaccagtt ggtttgaatc 114540
tgatgccagg aggagacagc ctcatttctt ttttttttt tgagacgag tctcgctctg 114600 ccgcccaggc tggagtgcag gggccggatc tcagctcact gcaagctccg cctcccgggt 114660
tcacgccgtt ctcctgcctc agccgcccga gtagatggga ctgcaggtgc ccaccatctc 114720
gcccggctag ttttttgtat tttttcagta gagacggggt ttcaccgtgt tcgccaggat 114780
ggtctcgatc tcctgacctc gtgatgcgcc cgtctcggcc tcccaaagtg ctgggattac 114840
agacttgagc taccgcgccc ggccgagaca gcctcatttc taaggactag tcttgccttt 114900
gtgggataag ggtggtgtgt tctgtgtctt tctacatgtc cgagcgatct ctgcagctca 114960
aaggtgttca ctgtcttatt gtgctgattt cctcttcttc catctcaaaa ttgaggcaaa 115020
atactttcac tattgaagtg ttgtccagta gaacttccag cagagacggg atgtctgcac 115080
tgtctaattt agttgccttt agccacgtgt ggtgttccat acctgaaatg tggctggtct 115140
gattgggtag cttaatttat aattttattt aattttaatt aagttgaac agctctgtgt 115200 ggatagtggc tcctgtatga aactgcaggt ctgttgagaa gcatctttac tggagagagt 115260
ggagggcttg gaggggggcac atgggttttcc tgctgctatc tttgacccta tttaattggc 115320
ccaacatttg caagtaagtt gtctgtgcgt gtatatataa atgtctgttt ctgtcttctt 115380
gtttcgtttg actgcattta tttgaaagac actaggtggc agaattactg tatttggttg 115440
gtttaaagat aagagttgaa gtaatccgtc ttgtgttttt atatcggtaa ggtgtgttta 115500
gcatgtaaaa ttggtaattc gtattcacgt actgcttaaa caaaggctaa gaattccacc 115560
catacactga aaatggagac ctttgaattt gtccatttca ggcattactt cttaaacaat 115620
acctggttca ggaactagtc agaatggcac ccttgacttt tagtttcctg cttttccttt 115680
tgttggggga ggagggtatt tagctcaaag gtgtgtgcct atttcagatt ccatctagga 115740
gaagcagaat agccaagaca gatacctgtc ctcctgttta caacatttgg ggtaaccagc 115800
atccctctcc tttggtccaa gatagacggg tttagaaaca gatgatggta ccagaggccc 115860 cggggggtgga agcatcagct ttgttgttg tccatgtggc tggattagag ctgtctggct 115920
ttgtagcctc aacacggccg tccagctttg ctcagtatga ttttcaagga cacatcttgt 115980
```

```
gcccttccct gcctgccatc cagaccatac ccagtcaggg tggcaggaac tgctgcccct 116040
tcctccctga gtcctggtcg tgggtggtgg agaggtacca tgaccctcac ggaggcctgc 116100
tcacccttcc tctgcggcag aggcgatggc tgcacgacag ctctttccct gtcctttcca 116160
aagcgtccat ggttccactt gatggggcaa agcaggaata ctggaagaga aagtggtcct 116220
ttctatagta ataaagttga cattgattca agttcaccct tggggaaagg acagggccac 116280
taacaattat aatgctggaa gcagtggaat tttctcatgg gtatatagta ggtttaattt 116340
taattatccc agttaattct tagaacagct ctgtgaagta tttccccctt tctgcttgag 116400
ttctaaaaga tcctatgcca aaaccaagaa tgaaaaccca agcattcttt cttgctcatc 116460
gatctttctc tcatcgggcc acttcttggg ttgttagtgg tgaatgtagc cgctggcaat 116520
tgcagaatac ccaccatggg ccccagtcac tgtgtggcgt ggattagagg tggttctctc 116580
catgtcatag ccgaacaagc ccagcccaga gaggtttctg ccctaggagc tcttgatggt 116640
ggaattggga tgcgatccca catcctgcct gtgttttgaa agcagcattc ttcatttcca 116700
gttcctgctt ccgttgttcc ttttagtatt tctttgttta actcacgaaa tcaggacttg 116760
gggagctgct gcgtgcagct gtagctgttt ctctgggtgc agcctgcatc caccttcctg 116820
ccccctcct tactgccatc gtggtctctg ggcacttggt ccctttctct tcccccgagt 116880
cccttggct cccctgtgcc acccttgtga tccacaggct ctgccttctt tctgtctgag 116940
actgctgctc atcactaccc gggaccttag gaagggaggt tcctccgaga agcatcttct 117000
aatctcagcc acgttctcaa tgccgctgtt ggctttgtta aataatggta gctactgtaa 117060
caaataaacc aacatttcca tggcttcaca ccagagaagg ttgtttcttg gttttatgac 117120
aatgtgttga gggtgtttct ggttcacgga tggttttcct ccatgtggga attcgggac 117180
ccaggctcct ttccttcttt tggttctctt ctctgggcct ccacatcctc tgtgtctagt 117240
tggggacaag gagagggaag gtagagaaga aggctctgtg gccttggaca agtgacatgc 117300
atgcctttgc tggtgttctc tgctggtggt gggtcacagc cccaccccgt acgaggggac 117360
tgggagacgt cgtcctgctg cctcccagca gcaagcagca ctgtggtctc tgatgtgttt 117420
tctatgagga taaaacagg cgattccagg atgagtaaag tcaggaaac ccttggaagg 117480
aggtgaccag gcaggtgtca ccatgggatt agtggtggct tcagaatgag ccgccaagag 117540
tgcagtgcct tctaaagctt ttgctattct gatatgccca caccatgccc agcaggtgtc 117600
tgccttgctc tccgcagaga gagtgatgaa tccttctcgt gaacctctgt cccgttcttc 117660
ctccctccac ctggaaggga ccctgggttc cttgaaacat cccggtggaa caggggacct 117720
tctgtcctgt ccctaagctc agcctcatcc tcctgccagc ttcccaaccc ctcttatgtc 117780
tgcttcctca cgccacatcc ttctggattc tctggaattg aatttgcct ttgatgctta 117840
tttaaaaata tccattgcag gccaggtatg gtggctcaca cctgtaatcc tgtgcacttt 117900
gggaagccaa ggcgggcaga ttgcttgaac ccaggagtct gagattagcc tgagcaacat 117960
ggtgaaatcc tgtttataga gaatacaaac agggcatggt ggcgcacacc tatactccca 118020
gctagacagg atcgactgag ccctggaggc cctggaggcc gaagctgcag tgggctgtga 118080
tcgtgccact gtattcccgt ctgggcaaca gagtgagacc ctgtctttaa aaaaaaaaaa 118140
aaatccattg catacttcac cacagtgaaa cgtgtgtctt atctttcctt tccggcctgt 118200
agctgctctt ttgcacttat agccgcacta agtcaacctt aaattaaaag caaaccagca 118260
cttcctgtgc tcttctgctt ccttcatgag ggtccctccc tctgtgtacg ctccattctc 118320
```

```
attgccccgg tggtttgttt ccctcttggt tctcaagctg tggcagcctg cctcttatca   118380
tctttactga aaagtccttt gcagaggctg cctgtgttct ttctttctcg gtccctctca   118440
tcctgggccc cccagcttga tgctgtgggg ctgccctctc ctcactcagt agcttgcagg   118500
gtcttctctg tctagccact taattggttg tgttccccga gttgctgtcc gtggtctctc   118560
gtcactgttt tctctgtgtc tctgcctctc tcctcggcct tggtaggtct ctccccttttg  118620
tgaccctggc tgttgctctc gtggacaact ttctcttgct ggtccgcgta gtcctggcat   118680
ccagcttctc aacatgggac ttgtcctgcc agtacctcag acttacgctg aaaattgaac   118740
tagcaccact gtcactctcc aggacctctt cttgttaatt aggtcattag ggatgttcga   118800
aatcccagca tcattgtcca ttcctcctcc tgccagccca gggaccctga ccttacctcc   118860
tcctctccat ctaccgggag gtggctctca gagtccgtct catcttccac ccgaacttcc   118920
ctacagactc cccgctgccg ccccaggggc tgagcacttc ctccgtgcct cgtgcagcgc   118980
tgagcccttt acctgggttc tcctgttttgc tccttattgc aacccctgtgg acagatactg  119040
ctcttaattc catcttaaac ctgaggaagc tgaggcccca ggtaaggtgc atccaaggtc   119100
actcaggtag taaactgtag agccacgatc cgaaccaggc agtctgattc ggagcctgtg   119160
ttgacactca gccacctaga acacagctca gattgtgggg ttctattacg tgttcaaaac   119220
cgccacatcc cgggtctgtc cctgcacgtg ccctgtggcc tggctgcatc ttcttgaagg   119280
cagcgcatgc gtcttcactc aaggggccca tgcaggaaag agggcccac agaaggacga   119340
ggccagtgca gaatgggctg gaggggacga tgctgactgt gaagcaagtg tagagaaatc   119400
ccaggaaacc tggaggaacc agagacaggg cattagaact catcgttgtg acctggtctg   119460
tattctctga gtgtgctgct gcttttagct cgcttcctta gtctcaggtt gtagtttaag   119520
gcattgtgga gccctaaaaa gcctctactc tgttttttgcc tgtttcggga ccctttcact  119580
tcggggatgt gttgaatttt ttgttttttgt tttttaattt tttgagatag agtcttgctc  119640
cattgcctag gctggagtgc aatggcacaa tcttggccca ctgcagcccc tgcctcctgg   119700
gttcaagcga ttcttgtgcc tctgcctccc aagtacctgg gattacaggc gcccgccacc   119760
acgcctgacc aatttttata ttttttagtgg agacagagtt ttgccatgtt ggccaagctg   119820
gtctcgaact cctgacctca agtgatccac ccacctcggc ctcccaaagt gctgggatta   119880
taggcatgag ccaccatgcc cggcctgaaa tttaatcaga aataaaattt tgaccccaac   119940
aatgatgcta ggaggcccag atctggggga gagggcaacc ttggccagat gggcctgtct   120000
ctgtttccca agtcttgctg cctctcccctg ctgtgctttg cagcctgtgc atgtctctgt   120060
gcctctgatc ttgttcatcc agaggagagg atagaatcaa gtcatgattc ctggagccct   120120
gagaagaatg ctgtggagaa acttgcaggt agactctaac tgagtgtgtg gctgaggtgc   120180
cagcattgtg tgtggggagg ctgaccgctt ggcctgccca ggcccaggat gctccatggc   120240
cgggcacaga ggcaacttgg ctgtcaggtg tcaggagcct gcagagagca cacagcctgg   120300
accgcagggc gctgcccatg ttcttccagc acctgtcctg cttgctcacc tggcctctta   120360
cagcatttct gtccctcagt tcttagcaag cccaggagct gttcaggttg gcaggtgccg   120420
agtgctgttc ctgcctgtgt agctgtggct cagtcctgtg gggggccccg ctgtggcctg   120480
agtgcagtga ttcgaggtgc cgagtgttcc ctgactcgtt ctgcaggagc tgtgttcaga   120540
cttttcacagc tcttggcttg gagcttctgg agggcttggc attgccaacc agtgcagggg  120600
tggacagtgg gagaggagga atgctagctt tcttgaccag tccattaaat aaatgggata   120660
ttggccgggc acggtggctc acgcctgaat cccagcactt tgggaggctg aggcgggtgg   120720
```

```
atcacgaagt caggagttcg agaccagcct ggccaacatg gggaaacccc ctctattcta 120780
aaaatacaaa aattagctgg gcgtggtggc agacacctgt aatcctagct actcgggaga 120840
ctgaggcagg agaataggtt gaaaccagaa ggcggaggtt gcagtgagcc aagatcatgc 120900
cactgtactc ccacctgggc aacaagagtg aaactccatc tcacaaaaaa aaaagcagaa 120960
tgtctgtttc tgcttagaaa aatcagaatt ttctaaatgc caggtgcttt gaatatgtaa 121020
gtatgggaaa caactcagcc tgtttcattt ttatgtaaaa tctccacgta gccatgtggc 121080
actggaccga gatgaaagca aagacatttc tccttctgaa cttttgtttct aggaatgttc 121140 cggagaatca cagcagctgc cactagactg ttccgcagtg atggctgtgg cggcagtttc 121200
tacaccctgg acagcttgaa tttgcgggct cgttccatga tcaccaccca cccggccctg 121260
gtgctgctct ggtgtcagat cctgctgctt gtcaaccaca ccgactaccg ctggtgggca 121320
gaagtgcagc agaccccgaa gtaggttcat aatgcccaca gcccagggcg ctggcccagc 121380
actctgtcct gagactccca gtaacctgag attgggccac cgttacagca ttttcatttt 121440
ccattttttg tgagggcttg taaaatttct gctgcatatt aatattcctt tcatggacag 121500
catattgtag agacaaacat gcggtccagc caaaggcatt cagaatagca attgctttct 121560
aaatgtgatt ttctttggca agttctttga caccattcca tcttgtggat tatgcttgtc 121620
atgctgtgtg gctcctacta agttctagtc cttcagttgg ttccatagcc agacatgttg 121680
caatgtctta acttcattat aaattaaatg tggttctggt tattcttaga taatggagta 121740
acgatttagc aaatttcaaa acctcttgga aatattattt gaccattcaa aaagacttac 121800
taagtctctc attatgggtg gccctctttt tgtaaaaggt tttcaggctt aagctccatt 121860
tctaggtgct ccaacactct gttatttgta tacacgtgga aataaaagct gtgacatccc 121920
cgccctagct gaatcctcag cacagtgttt ctggaaggct caagatccca cactgggaa 121980 aagaagttcc agagagaaaa gagggcaggt gctgccgtgc ctctctgctc agtatggata 122040
ctgggccatg tgcggccagg gcttgcagta gggccagttc atggcactca gctggaaagt 122100
ccactgttgg cgggcattcg taaccatcca ctctgtgccg tatgtagtgg ggtgtggcat 122160
ccaagtattt gaaatcagcc gcgtgcagag aaatcagccg cggatgcagc agatcactct 122220
ttttctgaca ggcctgctca ctctgatgtt atatcagaaa gctctgaatc tgggaattgt 122280
gttccctgaa ttggaataac agaaatgctt agatgatcag tgtttaaaag aaataaacca 122340
aaggtaaatt tagtttggaa ttcagcaagc gtcttcattc agccctctga gggcaaacta 122400
cagcttttca taaatgtagg taaattctct gtttcttgac cccttctgac ccagtttttcc 122460 tttataacct tctgtattgt tccattatcc tgaaataaca ttaatagatt aggctgggtg 122520
tggtggctca tgcctataat cccagcacct gggaggcca aggcgggagg atcacctgag 122580
gccaggactt cgagaccagc ccagcctggc aacatggtg aaaccctgtc tctactgaaa 122640
ataacaaaaa ttagccaagc gtggtgacag gtgcctgtag tcccagctac tcagaaggct 122700
gaggcaggag aattgcttga acccaggagg caaaggttgc agcgagctga gatcacgcca 122760
ctgcactcta ggctgggtga cagagtgaga ctccatctca aaaaaaaaa aaaaaattaa 122820 tggatcaatg gatttttaac ctaatagtta aattaaaaaa atatcattct ttaatggtaa 122880
tgtaaaggta aaattaagag aagataaat gtaacaagca ttttagtatg tgagtgtcca 122940
aggtctccct gtggtggaag gaaaaaataa atccccataa gtgtccacga tgctcataga 123000
gagcagagct gttccggttt aaaccgctgc tcttaggact gtgttttttcc agctatgggt 123060
```

-continued

```
ggtgggggat gagtaccttt ttatttccat gagatgagaa aaatgaatta ctagaagtat   123120
gaagcacaaa acacagctgc tctttttta  tctggactca gcagctataa aattgctcta   123180
tccagttgca gaagttcctg ctgcttaccc ttgatgcccc ctcggttagt gtgcatctcc   123240
tttcaggctg gctcccagat gggagctggc tccaggcgac actgggtgct ctgctccagg   123300
aggtccttgt gtgggccta  ccccggccta gcccctctct tatggactct gtcaccatgg   123360
gtttgattca ctcaatctgt cttaccttt  ggtgagctgt tagagtcctg cctatacttc   123420
agcacttgtg ggtgtgttgt ggtacacatg acatgttggt cacttcccag ctcatcttgt   123480
tctgagtcac cctggatttg gtacgttcat tcgccactag tagctggcgg tatatggcct   123540
gcgatttgga ggacttgtgc tgctacaaat tggggctgaa tttgagttga cactggccct   123600
tctttatgtc tactgctaat atttgaattg caaatgctgc ctcttctctt tcagaggctc   123660
attaccctat agctgtatta ttgcaaagta cataattaca gcttgagtgt aagtcacgct   123720
gggctggcag gacagccaac tgagaaaggg caagtttcct gttagttttc acattgacac   123780
ataatttaca atacagtaga atgtactttt gtatcaactg tagtcagtaa cagccccctc   123840
ccccaaccac ataagatata gagcagtgct gtcgcttcac atagttccct cttcctctgc   123900
catgtcccgc cctccccagg tctaaccacc aatccgtgct ctattcagcc cattgcagag   123960
ggtcatagaa atagaatcta caggctgggt gtggtggctc atgcctgtaa tcccagtgct   124020
ttgagaggct gaagtggaag gatcacttga ggctaggagt tcgagactag cctgggctac   124080
ctagcaagac cccatctcca gaaaaaaaaa atttgaaaat tacaagcatg tccctgtagt   124140
tccagctgct tgggaagctg aggcgggagg atctcttgtt gaggttacag tgagctatga   124200
tcgtgccact gtgctccagc ctgggtgaca cagcaagacc ttgtctttgg gaaaaaaatt   124260
aagaaagaga tggaaccaca cagtgtgcag ccttttgagt ctggcccctt gcagtgagcg   124320
gtgtctaccg tcatgcgttg cacacgtgtt ggtggctggc ttcttgtgac tgctgagcat   124380 tatatgctg  ggctgtagat tgctttcact tcaccagttg ggaaacagag aaaaggcagt   124440
ttttaaaaag tttaaatctg tagaattttg gtttttacca gttctcttct aaatcctgag   124500
ggattacagg aaaagttgtt gtatttcaga atattcttag cttgatgtga cctctctccc   124560
tgttaaggcc ctttgctgca atgggaagga cgtcgtcctc ggtcagaccc tgaaggtcag   124620
aggggcactt tgggagtgtg tcaacatttt aactgtatgg actagagcca agagtctcaa   124680
gatttataat tcccacctat tcaaaagaa  aaataataa  taataaagtg agaagaagtc   124740
aatgtaaagt gaaataacct gtgttggtgg ggaagaagtg tttttaaaca gaatttccat   124800
aatgtatacc ctgaacgtgt ttagagtggt gatgtttcat tgggaaacga acagtaaaac   124860
atgaaagcag ggagattttc tttctggcag ttggcaactt tcatggcaga tggggaattt   124920
gaaaagcaat tgctcaatta tcaaacatag ccagtgtgag ttctgaaata aggtgctga   124980 ttgaatgtgc agctttatgg tggattttgt cattcaggca agcattttaa ttttctgcct   125040
gttaaattct gttttcttta gttttcata  tgtggtttat tgtagcttgg gaatagataa   125100
ctgagagtat atattacaca tacaacattc tgatatggca atatttaaac caacttgtct   125160
gttttagaac tagaattaaa cataatcatc ttcagtattt tgcaaataag ctcactgcca   125220
tccagaaaca ttgtcaatgc atctgttgct ccttctagaa gacacagtct gtccagcaca   125280
aagttactta gtccccagat gtctggagaa gaggaggatt ctgacttggc agccaaactt   125340
ggaatgtgca atagagaaat agtacgaaga ggggctctca ttctcttctg tgattatgtc   125400
gtaagtttga aatgcctgta aacggggttg agggaggtgg ggaccgggag aacatcctga   125460
```

```
gtagatgaca cttgcctgga ccctctggaa cccagactgc ccagtgtcct gccagctcca   125520
tcaaaactaa atctggaatg aatgtttact tctgctctga catataattg gagaccgggc   125580
ctggccttcc agtcactgga ttctaagctg gactgtgaga gttgatgcag ctgactcatt   125640
tatcaaatgc ccagctattg gcttcacgcc tacacgatgc tgggcatatt tgttaattca   125700
agggaagcaa tggaataata ataactaatg atttgaaaaa caagataagt gcattgacta   125760
tagtggggtt ctgattttaa attttttaaa aaagtaatac caggagcagt ggcttacgcc   125820
taaattctag caactcgaga ggctgaggtg gaaagatcac ttgagcccag gagtttgaga   125880
caagcctggg ctacggtgta agacccccat ctctaaaaaa ataaaaaatg aaaaattatc   125940
caagtgtggt ggctcgtgcc tgcaatcaca gcttcttgag aagctgaggc cagaggatgg   126000
ctagagcgtg ggagttcgag accagcctgg caacacagag aaaccctgcc cctaccgaaa   126060
gaaagaaaaa ttagcctgat ggtggtgcgt gcctgtggtc ccagctacct gagagactga   126120
gaagggagga ttgcttgagc ccagaagttt gaggctgcgg tgagccgtga ctgtgtcact   126180
gcactttagc ctgggtgaca aggcgagacc cctgctctaa aaacaatttt ttttaagtta   126240
atttgtagaa aaggtgttag atgttcattg ccgtattta tgatggattc ctgtttaaat    126300
gccattctct taaaaaaaaa aaaataactt gtaggagttt ttaaccgtaa aattagcatc   126360
acatgtttac catggagaat ttacaaaaaa caaacagagg aaaataaaac ctctgtaatc   126420
atactactca gagataactt gctgttagat ttcggtgtag atctaatact tttctgtat    126480 ttatattaaa aatacttaaa acatatacat ttctttgtta caaacatggt atcttataga   126540
tagtgctgtc acatagcaaa acagtgttaa atattctgaa tcagaaaagg aagccgactc   126600
tccaactgaa agaggtgtta tcctagagac ttttttctggt gatggcaatt tgttaatatt   126660 cacttttgc tttacattct gtattgaaat agttttttctg ttttgttcta cttttaagga   126720
taatataatt gtatcatgct gttttttcaca gaaatgtaag aaaaaaagat attaattttg   126780
taagttaata gaggttgagc atcccaaatc caaaaatctg aaatcccaga tgctccaaat   126840
tctgaagctt tttgagtgct gacattatgt tcaaaggaaa tgttcattgg aagatttcag   126900
attttttgat ttagggagct caacaaataa gtataatgca catattccaa aacctgaaaa   126960
aaatcctaca ttcagaatac ttctgatccc aaacatttca gataagggtt attcaacctt   127020
tactgtcaga tgatcccaaa tgaaaaatat taatcgttaa ccaaatgtca aggaattgat   127080
cacattttac agtttctgcc taggattatg aatcaagatg aaaaggctct gcgtgtttaa   127140
aaatatatat attttattt tcttataaat cttaaatgta tcaacactta agatgtattt    127200
gatatgtgga atccattcat attttggatt aaacaattct gtcaagaccg tggcagtgat   127260 agaggattt ttttttcccac tgaactatca caaaattgga aaaagagtaa ttggagaacc    127320
ccactggctt ggccagctcg aagccccgga gggggcaggc agtgctgtgg atgggagcgt   127380
cgcagtacca cgctgcccct cctgcccatg gatctctgag gcctgccttt gtcctttgac   127440
ccttggccat ttgttagtgt ctctgagagc tggactgctg taccctactt ccccagggg    127500 gcctgacttc acacagcctc tgctgcagtg cgtggttgga ggtgacggcc ttggtaaatc   127560
cagtttcctg cctcctcaat tatttgtgct catacactgt atattttta gtgaggttta    127620 tatttgagat gtgttttctc cttcttaccc tttctggcct ttctatggat taatacctgg   127680
tctcttcttg tgtacttgaa agtgaatctc tcatcgtatt tttccttagt gtcagaacct   127740
ccatgactcc gagcacttaa cgtggctcat tgtaaatcac attcaagatc tgatcagcct   127800
```

```
ttcccacgag cctccagtac aggacttcat cagtgctgtt catcggaact ccgctgccag   127860
cggcctcttc atccaggcaa ttcagtctcg ttgtgaaaac ctttcaactg tacgtcttca   127920
tcctgccaac aattgccagt tgcagttttc tctgccttaa aaatggagta ttgaaatttt   127980
taactttaat ttctgactgg caaaatagtc atcttttgtt cttttccttc tcgctgttag   128040
ccaaccactc tgaagaaaac tcttcagtgc ttggagggga tccatctcag ccagtcggga   128100
gctgtgctca cgttgtatgt ggacaggctg ctgtgcaccc ctttccgtgt gctggctcgc   128160
atggtcgaca tccttgcttg tcgccgggta gaaatgcttc tggctgcaaa tttacaggta   128220
ttgggaaaag aaaccctgat attgatttat attgaaaatt tagcaggcca agcaaaacag   128280
gtggctgcct ttttcctcca taggtgtggt cttgacacgg tcaccaatag aaacatggaa   128340
atatctgcaa acttgccatt cctcgtgtgt ctgatctgtt tcttgaactt ttttctagtc   128400
tgtccttact aggatgaact gtacacatca gtttatcctt tttaaatgag catgaggtta   128460
ttttggggttg tacagtgtca caaacacact aatgtgtttt tgtctattag agcagcatgg   128520
cccagttgcc aatggaagaa ctcaacagaa tccaggaata ccttcagagc agcgggctcg   128580
ctcagaggta atgctggaaa cacaggtcat ccttgtgtta ggagaaccca ggatataaaa   128640
gatatagatt tgtgcgggaa taaattcaca ggacaagaaa ttgatgtgcg ttataggtgg   128700
gtttgctgca gaagtgccat aatagaaagc ttcctacttt taaaacaacc agatctcact   128760
ttatatggag taaaggacaa ccagcaggat cacgtctatg acatgagtgg aggcagtttg   128820
cactcctttt ggctgtttga gaggtagtat ttagaatgcc tgtattcact gtcctgtgat   128880
gagtgggaaa ataggttatc agctttatct tagcaaaatc aaagcatatc atctaattgc   128940
taaacaagag ttggcaaatc tgaaagacat tactgaatcc ttggcatgca ggacttacat   129000
ctgcatcccg ttgccatttt ttctcttcaa agcatttaat cacttagttg tgtttgcaaa   129060
gtcttttaga agcctttatc agaaatcctt acatctccta tgtgagtgta tttccatgac   129120
tgcaaaataa gttaaacttt tacctttttt cttcccttgg tgggggcgga aattgtgtgt   129180
gtgaaaggga aagagagaca gcagagaagg agaatataat tatcatgctg tgtcctttga   129240
gctgaaattg caaaaaagaa aacacacaca cacatgcttt gatttcagtc ttaagagtac   129300
cttgttgatg gtgttttttaa atgggattgg gcacaattag gtggacagtt tggggcgatt   129360
tttcggtctg tagggccaag ctgttttgta atttgcttta taaagttgtc actctctcatag   129420
catatggtgg cagataaact attattactt tttgacccta gacttagtct tcagtccaga   129480
tgagggagat taaagagatta taaatatctt gtgccagatg aggtgatttt attttgaaat   129540
gaccataaat tcctatcagt tgtcttactg ggatatttga tagtggagtt tgtgcatttg   129600
agtcttagat gatctgtttt acgtttatta agaaagcctt tattagcttt tataccatgt   129660
atggactgtt gcaatgtttg agtataaatg aaatttctgg acaatattaa tggagtacaa   129720
actgtgatac cttagaagta aactagggcc tgcgtttata tcatgacctg tttgagtgtt   129780
gatgagaaaa tagctgtgaa gaaaaagttt taaacaagtt tcattttcct ttaagaagcc   129840
actaatagtg catccttagg gtgtatattt ctagaatcct agtgtgcaga gtttagacta   129900
agactaaaaa aaaaattgca ctgtaatttc cttttttgttt gtattttaga caccagaggc   129960
tctattccct gctggacagg tttcgtctct ccaccatgca agactcactt agtccctctc   130020
ccccagtctc ttcccacccg ctggacgggg atgggcacgt gtcactggaa acagtgagtc   130080
cggacaaagt aagtgtccag cgtgtctgca tgcgaggcac agggcagagt gcctctgtca   130140
cctgaggcag atacagagag tgcagaggag gtgcggtgga cccaaggagt gctggcgctc   130200
```

```
tgctcggctc aatgaagccg tggttagaga cctgggggga ccatcaatgt ccgagggagc   130260
aaagcagtgc tgatgtggga ccgtttcggt aggagtgcga ggtgagtcgt tagtgggtga   130320
ctcaagggaa agtcaattgt ggcctgcagg cccctgactg cacaggcctt caagcacatg   130380
tcagtgcatt tagcctccct ccatcgcctc ataccttctg gccacctgtg agttgcactg   130440
ccactgccag ccatactggt atgttgtcag cacctccact gctcatacct caccgttagg   130500
gaccacttgg ggccttggta gagccttggt actctacttt cctggagaga gttcagctta   130560
tgaatatgaa tttagatttc aaaaaccagc agcccaagta taagaaagcg aaggttcagt   130620
cctgccgcct taggctctat ttgctaagca tctgccctgc cctgccctgg ttgctgggaa   130680
gagatgagca aagcagacag cccaggagag gatggcaaag gggccgctaa cccttagtag   130740
tttagctata tttggaagga ctattagaaa ttcaccaggt gaaggggag gccgtgagag    130800
tacccaggta ggtaacagaa gtccaaagag gaagacctgt ggtgtggtga gctgtatagc   130860
cacaacatgc cggccggagg ccctctcagt tagcctagtg cagtgttccc aagcactggc   130920
ctaggcctgt agctccaggg atgtgaagtc cccttgaacg ccacccatca tgttcccctt   130980
attcatcttt ttcttcccag gactggtaca ttcatcttgt caaatcccag tgttggacca   131040
ggtcagattc tgcgctgctg gaaggtgcag agctggtgaa tcggattcct gctgaagata   131100
tgagtgcctt catgatgaac tcggtacggg gggagcagcg gaagcaagga atcctcagct   131160
tttcttgtga cttccaagtg ggatttgtct cctcatgtga cccacttgtt gacaacacat   131220
gttgaggact ccactctgga tggggacggg atgacggaga gactccactc tgaatggggc   131280
tgggaactgg ggaggactcc atttcagggg gccgggacat gggggatatg ctgatcgaga   131340
ttgtttcagc cacattagaa tccaaggagg caagtcgatt tcactcaacc tttcatgcat   131400
ttaaagaaaa tggaggtggt cttagattac agtcatttca ctggtttgtt ctcatggcag   131460
tgaggaaggg tattgggatt ggtgtctgtc ttaattcagg atctttgaga agatggagag   131520
cactccctca gggattagga gagactcgag atggaaatga agattttact acttacaggt   131580
cctggcgggt acatggcatg cccagaggcc cctcacacgt ggaagttggg ggcatgtgag   131640
ggaatgaagt gtggtcctgg gcactagggt gggggacctg agcggnnnnn nnnnnnnnnn   131700
nnnnnnnnnn nnnnnnnnnn nnnnnnnnnn nnnnnnnnnn nnnnnnnnnn nnnnnnnnnn   131760
nnnnnnnnnn nnnnnnnnnn nnnnnnnnnn nnnnnnnnnn nnnnnnnnnn nnnnnnnnnn   131820
nnnnnnnnnn nnnnnnnnnn nnnnnnnnnn nnnnnnnnnn nnnnnnnnnn nnnnnnnnnn   131880
nnnnnnnnnn nnnnnnnnnn nnnnnnnnnn nnnnnnnnnn nnnnnnnnnn nnnnnnnnnn   131940
nnnnnnnnnn nnnnnnnnnn nnnnnnnnnn nnnnnnnnnn nnnnnnnnnn nnnnnnnnnn   132000
nnnnnnnnnn nnnnnnnnnn nnnnnnnnnn nnnnnnnnnn nnnnnnnnnn nnnnnnnnnn   132060
nnnnnnnnnn nnnnnnnnnn nnnnnnnnnn nnnnnnnnnn nnnnnnnnnn nnnnnnnnnn   132120
nnnnnnnnnn nnnnnnnnnn nnnnnnnnnn nnnnnnnnnn nnnnnnnnnn nnnnnnnnnn   132180
nnnnnnnnnn nnnnnnnnnn nnnnnnnnnn nnnnnnnnnn nnnnnnnnnn nnnnnnnnnn   132240
nnnnnnnnnn nnnnnnnnnn nnnnnnnnnn nnnnngagaa acctcctggt gctttagccg   132300
tgcgttgata cacagcagat gggagggaag tgggcacccg ggaggacaaa tgcatgtaga   132360
ggctgggggt ggaggcaggt gttcatgaaa agagaccttta cagggagggc aacacaacag   132420
tgtgttctga tgtactgaag agctagactg aaaagaacag gagaattcac ccaaaatcca   132480
tttactaaaa ttgttttatcc ttttttttt tgagacgaag tctcgctctt gtcccccagg    132540
```

```
ctggagtgcg atggtagatc ttggctcact gcaacctctg cctcctggat ttaaacaatt    132600
ctcctgcctc agcctcccga gtacaggcat gcgcccacca cgcccggcta attttttgtat  132660
ttttagtaga gacgcggttt caccgtgttg gccaggcttg tcttaaactc ctgacctcag    132720
gtgatctccc tgcctcagcc tcccaaagtg ctgggattac aggcctgagc cactgcgccc    132780
ggcctaaaat tgtttatctt aagattcatg cagtgaaaac taacttactg agtgataaat    132840
ttgcttagtg atctgtttat taggttttct aaatttgcta attgggcttt gaacagctgt    132900
aaaagttctg actgtaaaag aaagctgcaa cttttggcat tcatgatgct tttctgaata    132960
ttaaactaag atagatgttt tacctgaaga attggccccc aatcttataa atggctaaac    133020
aaaaaaggtt gctaaaacat aatccaaatt gtcataggaa ataccatttt tccaaccaaa    133080
attttgtcat tcatatggct acttttactt atttcagctg catttgacca tcttttcaa     133140
acttcaggga tggctggtgt atcaccgaga tcttggatga cactttagct ttgattttct    133200
gtttttatga attaaaattg tcataccaaa attttactt caagcaaatc caagagcata     133260
aaaaattaaa atatcactta aagtaccaag agagaacaga aatatatttt actaagcgta    133320
cgttgaatga agttgttcaa atatttgtaa caggcataga gtagaatttt cttaaaaaca    133380
ttttttgatgg tataccaatc tgtgttttct cagaaacatt tgccttattc ttttttctgt   133440
tgtgtttttc ttacctgatt gaaagctcct aatctgttgt tattgtttgt ttaaccttta    133500
atgctctgat ttcaggagtt caacctaagc ctgctagctc catgcttaag cctagggatg    133560
agtgaaattt ctggtggcca gaagagtccg ctttttgaag cagcctgtga ggtgactctg    133620
gcccgcgtga gcagcaccgt gcagcagctc cctgctgtcc accacgtctt ccagtccgac    133680
ctgcctgcag agccggcggc ctactggagc aagttgaatg atctatttgg taattaaaat    133740
taaaatttat cttatttta gaaaggttcc agggccagta tagtactttg caccaagtaa     133800
atatacaata aaggcggtgg atctaataca gcgaaagcgt ttacagaggc agctaaagag    133860
cagcactggt ggcctcagcg cagaatttct tcctgcgtgt ttgccacttt gccgttcatt    133920
gacgtggtca cggacatagg gctctaagcc cttgaggaag gctgggccag acctcagggg    133980
agatgcagcc ccaaaactaca tgcagtcatg tggatggatg cgtagatgtg ccattgagga    134040
gcaatgtctt gtgctttcat cagattctca aagaattgct tgactgcctt tcgaaggtgt    134100
tgcatctgtg ctcatgtttg cacccaccca cgagggcctt ctgtttcagg ggatgctgcg    134160
ctgtatcagt ccctgaccac tctggcccgg gccctggcac agtacctggt ggcggtctcc    134220
aaactgccca gtcacttgca ccttcctcct gagaaagaga aggacaccat gaaattcgtg    134280
gtggcaaccc ttgaggtaag aggcagctcc ggagctcatt gttgctgtgg gaggggacac    134340
ggggctgaca ctggagaggg taaagcagtt ttatttgaaa agcaagagct ctgaccaatc    134400
cagtcactat tctgtctcag cctggcagta agtcttgtca ccgtcaagtt attgtagcca    134460
gccttcaccc ttgcctcgcc actcctcacg gtggcctgtg aggtcagcca ggtccccttc    134520
tcatctgcac ctccagtgtt atgtggatcg taatttaga gacttgaaaa ataaccatct    134580
gtaggtactt tgtgtcttaa gttggcctgg acatgtcagc caaggaatac ttggtttgtg    134640
ttagtgcttg taattagccc ccaaaacatg tacacattct ggatgcatta aactcaggcc    134700
tgtatcctta aagggccatc tctgtgctgc ctgccctcag cagggacaca ctttgcagac    134760
ccacagaggc tccgcctcca cctcacacca agaaagggga ggagtccaaa gggcatcagt    134820
gccgttactc acaaaatgat aaatacaccc ttattctgaa ccaggtggag tcagatggtt    134880
tgtgatccct gtcctttagg tttcagctta gtggggaagt gggaaagcca gcgtgtgatc    134940
```

```
acagcacagg gtgattgctg ccgattatat tatgtgcctg ctgtgtgcag gacaacatac   135000
tttacacgca tcatcttatt tgactctcac aactccctgt gagataggct ctgttactcc   135060
catttgacag gtgaggagag caaggcttag agaatttcag tgacttgccc aggtccactg   135120
agctaggaag tagccattct ggcgtttgaa ctcaaggcct gctatcccta gaacccacgc   135180
tctcaaattc aacctctgag gctatgccag aggcaagccc cagtgctgtg ggcgccccag   135240
ggaagaacct ctggcctggt ggccacgtag cccaggagag atgtctacag gagcccacag   135300
cgctgaagga gagaagggca gcagagttaa gggggcattc tggcagagag gggactggca   135360
ccttggggaa tagctgggtc aggactgaat gtcatggagt caggtcagag ctgtccttct   135420
ggagggcaag ggcatctgga cctgcttccc ctcaatgctt tggacggttc caccacaact   135480
gattcacacg gcctccccaa atgaaggtac acgagcgggc attctgtgac ttggtacttc   135540
cctttaggcc ctgtcctggc atttgatcca tgagcagatt ccgctgagtc tggatctcca   135600
ggcagggctg gactgctgct gcctggccct gcagctgcct ggcctctgga gcgtggtctc   135660
ctccgcagag tttgtgaccc acgcctgctc cctcatccac tgtgtgcact tcatcctgga   135720
ggccggtgag tccccatccg tgaacaatgg gttcctatcc tagttcctgt ctagttcacc   135780
atgtttatat tttgtgctgc ctgtttgcca ggtactaagc taggaattgg ggatggagag   135840
gtagataaaa tacgcattag gaagggctgg gctccatctc tttttttttt ttttttttt   135900 tgagacggag tctcgctctg tcgcccaggc tggagtgcag tggccagatc tcagctcact   135960
gcaagctccg cctcccgggt tcacgccatt ctcttgcctc agcctcccga gtagctggga   136020
ctacaggtgc ccgccacctc gcccagctag ttttttcgtat tttttagtag agacggggtt   136080
tcaccgtgtt agccaggatg gtctcgatct cctgacctcg tgatccgccc gtctcggcct   136140
cccaaagtgc tgggattaca ggcttgagcc accgcgcccg gccggctcca tctcttactc   136200
tccaatatat tggagtctac actgaatttt aacttgaatt tgcttttta gtcattttat   136260 ttagattttg gaatttcagc tttcatcaaa attacttcta aattttatgt ctctgtgatc   136320
tttggtctta gctgactgtt ttatgcattt agtcttatat gatcgaaagg ttagtaagat   136380
tacgttcaga agattgtttt ctgttcaaat gcttgtttct atactgcact ataatattaa   136440
cgtactgtaa aataaaagtg gcttattctt ttcaaggaac agtatcctca acaagggtta   136500
ttagccacaa tttttaaaaa attggacatc atggtttaca tgttggaggg cattttgaag   136560
ctttgtattt tcaaattaaa cattatagag tgatgttttg atgtttcata attgttttca   136620
tctgtgcatt tgtggccagc ttgaaaacaa agatccaggg attaatactt aaaagccaga   136680
cttcttgggg gttatagaga tgattttggt agtaatgaat cttgagccgt ctgataataa   136740
cctcggggtg agagatggcc aacaggagag agtcgaggga cttacaaatc tgaatgaaat   136800
ctgaagtaca aatcttcaga catatgccac taaccaagag attggtacct cagtctaata   136860
ttgtctgttt gtctaaaatt ggttctaaga aatctaggct catctgtcta tcccttttgaa   136920 cttttgtgag gctgcacaaa tgtaaaattt tgaatgaaaa gcactgatgg aagtctgtgg   136980
aaattcttct gtttgttctg ttgtaatttt agttgcagtg cagcctggag agcagcttct   137040
tagtccagaa agaaggacaa ataccccaaa agtcatcaga gaggaggagg aggaaataga   137100
tcctaacaca cagagtaagt ctcaggaccc attctttctt acatgtggtt cctccaagac   137160
ttaaaagtca ttcacagaga cgtgcgccgt ggtgagtgtg cactcctgga agcgcaccgt   137220
agctcggctg tgtcctgctg ctcctcccct gccgtgggag gctttagtcc attgctttgc   137280
```

```
cacactctttt tgtttcaccg tatccctgtg catgcggctg tttctgaccc tacagagcag   137340
ctgggatgcc tctgggggag cccttccccg ctccagcact tccacatgcg gttactctgg   137400
gctcctggag ggcagggagc aggtttgtct tctctgtgtt ctcagaaatt aatgcttggc   137460
ccctggtcag caagcagcaa ccttttgttg agtgatactg aataaataca tgtttcccac   137520
atgagtattc agtaacctca gtgtcaggtt caggcatctg ttttggtgga tatttaaaag   137580
aaaattccac ttttcctaca gaaaaaaaaa aataaataaa tctaaatccc agtgatttaa   137640
gccagttata gacttagaca tatactacgg cttttcatgc cctttcctcc cagttctaga   137700
gtagtatttt actaggaaaa tggtggcaat gcctgttgag aggaaaagtt tttggccaag   137760
tgtctttcgt tcttgccagg ggcctaggc tgctggggct acttcagttt ctttagccca    137820
gtgtctggca gggaatgctc cctgtagcct gtcccacaga ggcagggtg cctcacctgg     137880 ggcctgtcca cgcattttac acagcaccct tacttggagc atcaggcatc ttttccgcgt   137940
tccgtggctc aggaaacaca ccttttcaat catgagttcg ccagtgcttt tgggcttttt   138000
ctcccagctt ttgtgcaatc ctagttatgg atggagtttt cctgccttta gtcttctgca   138060
tagtactttt ttcttctggt tcccggttcg aggttttgta attaaagaat gacccagaag   138120
cagtggcatt ttcttttctt ttctttcttt ttttttttg agacagagtc tggctctgtc    138180
gtccaggctg gagtgcagtg gccggatctc agctcactgc aagctccgcc tcccgggttc   138240
acgccattct cccgcctcag cctcccgagt agctgggact acaggcgccc gccacctcgc   138300
ccggctagtt ttttgtattt tttagtagag acggggtttc accgtgttag ccaggatggt   138360
ctcgatctcc tgacctcgtg attcacccgt cttggcctcc caaagtgctg ggattacagg   138420
cttgagccac cacgcctggc cagcagtggc attttcatac acagccaagg tcttctctga   138480
atttttatct cgaacctctg tgggtccttc aggcttcagt tgtgatttc atgatttctt     138540 gttgctacct aaggaatatg aaaacaccca cctccctact ctgcgtcttc cagccgatgg   138600
cacctcaggc tcttggtcct gtgcttctgt ggcgaggata agaatagtgc caaccatgtg   138660
gattgagata gatcagttag tccatccatg tcaagcacct ggaatggatg acagtcttgt   138720
tgtgaatact caacagatgc taccatgact ttagttagat ttccattgct ttgaaacagt   138780
tgagacatct cagagctttg agccagagca gtgggccctg atgcaggttc tgtttggttg   138840
aagatgattg tgcttattcc ctgtggccct tgtagaccgg agtgggaagc ttgcttgatt   138900
ttaatcacct cgataggatc ttacttctta aaggtcatcc aataaataat gagccaactc   138960
attagcctgg ggcttaattg cttaagtcca atgagaagtc attctctatc ctaggaagtt   139020
gcccaaactg tagaatctcg tggcctgtgg gtagtagcca cttactacac attcactgac   139080
tcaacgaatc atatttttag tagatacaat attctagact caagacacca tgatgtggat   139140
cttcccaggg gtgtgacgtg ttcctcggcg tctgccttgg gagtttccat ttccatcaga   139200
accatgcccc agggccctca aacactctga tctaggaaag ccagtgaagc aaggatgaca   139260
gcgtggccct ttgataccag ctgagggaca gacacaggtc ctgggagacc agagaaagac   139320
aaggggcaga ggaagtgtcc tagagggtgg gccagagggc tgggaacgaa ggccagagct   139380
caggttcagg accattccag caatcccagc agaaaatggg gaggattgta tggtataggc   139440
ggatatgaag gaggtagact ctgcaagctt tcagtggcca actcattcta ggtgattcca   139500
caattacagc ttgagcagct gcttgtcggt catgcttctt acactgggca agtagaatgt   139560
gttttttaaa aagtcttctc ttaaccattg cttgtttaga tccgaagtat atcaccgcag   139620
cctgtgagat ggtggcagaa atggtggagt ctctgcagtc ggtgttggct ttgggtcata   139680
```

```
aaaggaatag tggcgtgccg gcgtttctca cgtcagtgct caggaacatc gtcgtcagcc    139740
tggcccgcct gccccttgtc aacagctaca cacgtgtgcc cccactggtg agtctggtcg    139800
ttccgtgtag aagaccaagt acggtgaaac gcatgggtaa gccctgggct gggcacaccg    139860
gagagggcag ggcagagtcc ccgcggccca gaggctgcca gctgtggttc tggtgccagc    139920
tgtggttctg gtgccagctg tggttctggt gccagctgtg gttctcgtgc caggctgctt    139980
tcctcaggca ccgtatgtgg aggtcgctag tagaaatact gggttttcta aaatgaagtg    140040
aggccccaca tccctaagag attagtgtta gacttgattc taaagcaact agaccacttt    140100
gcttactggt agaccagaaa ccacactccc tcgagtgagt gagattttcc tttggaaata    140160
attcatgttt ttctacacaa ttttgctgtt gtcttcagaa tcggtttaaa gtaggtgtta    140220
ttgctgggca cagtaactca tgcctgtaat cccagcactt tgggaagcca aggcgggcag    140280
atcacttgag gtcaggagtt tgagaccagc ctggccaaca tggtgaaacc ccgtctctac    140340
taaaaataca aaaattagcc aggtgtggtg gtgtgcacct gtaatcccag ctactcagga    140400
gactgagaca ggagaatggc ttgaacccag gaggcggagg ttgcagtgag ccgagatcac    140460
gctactgcac tccagcctgg gcaacagagc aatattttgt ttcaaaaaaa aaaaaaaaa    140520 aaaaaaaaa aaagtaggtg ttattgatca ggatgcttgt ttcagataac gaagagctta    140580
gcttgaggag agtgagggtt gatggaaggg gactggcttc tgctcagtga aatggcatca    140640
tcccccacca gcctgctgaa gtaagatgat gggacctgtt ccttagggac tgcagcatcc    140700
tcaggcaaga aagaaaggcc gaccggcagg gtgtgagcca gcaggtatag gtcagtgaca    140760
atggagctgg gtcccaggga agaggcttgt ggctgcttga aagggcgcg tgcccgtctg    140820 cgtgcgcgtg tgtgtatgta cgctggagag tctggggagg cttgctccaa ggacacagta    140880
tttgatcctg agacatgagg agggttctgc cgcaggcgat gaaggtattc agatggagag    140940
ctcattcgga agaagaggcc agggcctggt ggtgctggaa gcagttgcag aacagggagt    141000
tgtaagcttt cctaggaaga gcagcaggag tgctggagaa gcaggccacc cttgctgcat    141060 ggggggttgct cttggcccca ctcttggtgc acggcgagtc actgtgagtt cgttagcatc    141120
tggttctgaa acagtaactg ctccttgga ggggctcggg gagaccatgt aggagggcac    141180
agtcaagagg tcatgctatc tggaacacac ttgaggatat gccaggacgg actgcatgct    141240
gtagataaaa ttcctctagc aagctcttaa ccggcattga ggagttccct gagtgcggtc    141300
atctggaagg cagctgtgaa aggcactgca gtctccccccc gggcaggtac caggagcaca    141360
ggggagcaga actgatttaa agagagggct ttcctgtggt gaggtgagag atgagctggt    141420
cattatcata gaacccctct gcctgtgtgc agatgcgctg tgggaatcct ggggttccgt    141480
tgggtcctct gtcacctcac tgaaggcatg tcagctgagc tggccagacc ttcagctgat    141540
cctgccactt gaacagcatc aagcctgcct ctggattctt ctgtgcacgg tgcttgtcta    141600
atcacctcat gcacagagaa ctgtacttca gagtttacag aaataagctg tatggttcat    141660
tttcgtgcct gcttgccaac aaacatatct gagctgaact tcattgaacg cctgccttta    141720
ttctaacaca ccatctgctg tttgtgggcg aggggtgctg tctctaactc ctgcctgcct    141780
ctcccagcat ccctgagtgg ggtgtgccag cagcctcagg gtgaggacag gaagtgggag    141840
ggcagagcag atttggaagg gccacttgat ggggaaggaa gtcccaggaa gcagttggag    141900
ctgttttctg ggggagaagg tgccagcttg gggacagtgt tgtagtgagg aggaagccca    141960
gtggagagaa gtggggcttc ctgcttcctc acagtgtgtc tgtcctgact cagctcgggt    142020
```

-continued

```
gatgtcactt cctttttcatc ttctcaggtg tggaagcttg gatggtcacc caaaccggga 142080
ggggattttg gcacagcatt ccctgagatc cccgtggagt tcctccagga aaaggaagtc 142140
tttaaggagt tcatctaccg catcaacacg ctaggtactc ttggggcctc tttcaggtca 142200
ccatcgtcgg gcatgtaccg ggaggaaatc cagagcccca gtactgggat cttctcattt 142260
gactccagaa aagatttaag catgataata atacaaacct gtgtgaatac attttgcagt 142320
gtcagcaaaa ctccttttac tgagaaaata gatcccagtt cctgtgtttt gtggcttgaa 142380
tcccagcttt ttatattctg ggcttgtttg aagtcaggaa agattcatgt gtaacagaca 142440
acgtgaggcc aaattctgcc ttcgattttg catttaggct caacagtggc agcgcttgtc 142500
tcggagtgtg ttctcgtgtt caccagtctg atcctgttgt gtctcactgg tgcgtttttct 142560
cacatgggaa caagcagacg ggagcagatg gagtcaagtc tcttagcact cgccttcctc 142620
agagcctaga ggcagcatgg ggagaaagcg ggcttggggc tcagacagtc ctggtctgct 142680
tccagccctc tgtagctgag cagcgcggaa caagtccttc taacctctag agaccctcag 142740
ttttgtcaaa tgtaaaatgg gagtcacgtc tatttcatag aattgttgca gatttagaaa 142800
ttacatttct tttttttttt tgagacggag tctcggctct gtcacccagg ctggagtgca 142860
gtggcgcgat ctcggctcac tccaaactcc gcctcctggg ttcacgccat tctcctgcct 142920
cagcctcccg agtagctggg actacaggcg cccgctgcca cgcctggcta attttttgta 142980
tttttagtag agacagggtt tcattgtatt aaccaggatg gtctcgatct cctgacctcg 143040
tgatccgccc acctcggtct cccaaagtgc tgggattaca ggagtgagcc accgtgcctg 143100
gcctagaaat tgcatttcta aacaagtgtt agcccttatt tctaaataag tgtcgaaatg 143160
aataagtcac cactttcgcc cctatttgat ggcaagaggt gtgatcttgt ggtgggattg 143220
taatcagtca gtcctcagtg actgtgccct gctgtggtgt ttcctggaaa gttcttgtct 143280
tgtcctagaa agtctggcag gggcaccctg tctccactgt ccagtcttct ccccaggccc 143340
ttcaggcttc tgcaaatttg aggcttgttt tcatcccaga aggttctggc agcagacgcc 143400
ttgcgtctac tgtccccttt agttaattag ataattcaat gtccaaaggg aaccctgagc 143460
aggaacctca agccagctgc ctcacggagc tcctcctctt cctcactgtg aagattggtg 143520
tcagtggcct cctggtctcc cccttgccta acacgagctc ctttgcttac ttgggtgccc 143580
ttgcccttga actccccggc agacgtgcgt gacccaagac tgtgctacag tccttgtttt 143640
tgttcatgct catcttcttc ttggttcatt gttttccctg taatgtcaat tgttttatttt 143700
gtctgtatct gtgtctgaat cagtcctgca cgctctcctt ctctctgtct tttgttcttt 143760
ctttacccag tttatcacag ggaccccccga tgtccatttc tctagttctc ctgtcctaag 143820
caccccatcc tgtctttctg gccttatcac aagtggcgtg tctgcctcag acatcatgat 143880
gggggcatga agcacagctg tcagaaacaa ctgttcgtta ggtacactcg aattcagctc 143940
atcaatagga atggagggtc tatcagatgt gttttcactg aatccctgtt cnnnnnnnnn 144000
nnnnnnnnnn nnnnnnnnnn nnnnnnnnnn nnnnnnnnnn nnnnnnnnnn nnnnnnnnnn 144060
nnnnnnnnnn nnnnnnnnnn nnnnnnnnnn nnnnnnnnnn nnnnnnnnnn nnnnnnnnnn 144120
nnnnnnnnnn nnnnnnnnnn nnnnnnnnnn nnnnnnnnnn nnnnnnnnnn nnnnnnnnnn 144180
nnnnnnnnnn nnnnnnnnnn nnnnnnnnnn nnnnnnnnnn nnnnnnnnnn nnnnnnnnnn 144240
nnnnnnnnnn nnnnnnnnnn nnnnnnnnnn nnnnnnnnnn nnnnnnnnnn nnnnnnnnnn 144300
nnnnnnnnnn nnnnnnnnnn nnnnnnnnnn nnnnnnnnnn nnnnnnnnnn nnnnnnnnnn 144360
nnnnnnnnnn nnnnnnnnnn nnnnnnnnnn nnnnnnnnnn nnnnnnnnnn nnnnnnnnnn 144420
```

```
nnnnnnnnnn nnnnnnnnnn nnnnnnnnnn nnnnnnnnnn nnnnnnnnnn nnnnnnnnnn   144480
nnnnnnnnnn nnnnnnnnnn nnnnnnnnnn nnnnnnnnnn nnnnnnnnnn nnnnnnnnnn   144540
nnnnnnnnnn nnnnnnnnnn nnnnnnnnnn nnnnnnnnnn nnnnnnnnnn nnnnnnnnnn   144600
nnnnnnnnnn nnnnnnnnnn nnnnnnnnnn nnnnnnnnnn nnnnnnnnnn nnnnnnnnnn   144660
nnnnnnnnnn nnnnnnnnnn nnnnnnnnnn nnnnnnnnnn nnnnnnnnnn nnnnnnnnnn   144720
nnnnnnnnnn nnnnnnnnnn nnnnnnnnnn nnnnnnnnnn nnnnnnnnnn nnnnnnnnnn   144780
nnnnnnnnnn nnnnnnnnnn nnnnnnnnnn nnnnnnnnnn nnnnnnnnnn nnnnnnnnnn   144840
nnnnnnnnnn nnnnnnnnnn nnnnnnnnnn nnnnnnnnnn nnnnnnnnnn nnnnnnnnnn   144900
nnnnnnnnnn nnnnnnnnnn nnnnnnnnnn nnnnnnnnnn nnnnnnnnnn nnnnnnnnnn   144960
nnnnnnnnnn nnnnnnnnnn nnnnnnnnnn nnnnnnnnnn nnnnnnnnnn nnnnnnnnnn   145020
nnnnnnnnnn nnnnnnnnnn nnnnnnnnnn nnnnnnnnnn nnnnnnnnnn nnnnnnnnnn   145080
nnnnnnnnnn nnnnnnnnnn nnnnnnnnnn nnnnnnnnnn nnnnnnnnnn nnnnnnnnnn   145140
nnnnnnnnnn nnnnnnnnnn nnnagaaaat aaggcagcag actggtgttt ctttcttttt   145200
tttttttctc ctaccttatt ttgagagagt agccagatgg tgtcttgact gatattccag   145260
agcagggaca aagcccactg aggtttgggg gctgcaatta ccaatggctg gaatgcattt   145320
gattacggtg cgttccatgt taaggatcaa taagattgtg ctctttctgg aaagtatctt   145380
ttagttttat ttattggtat tcagaggagt gtaggttgaa ttaaaatgaa aaggcatttt   145440
ataaaggccg tgagtagtac atggtttcat ttttctaatg tcttgcagag attttattag   145500
gcttctcgaa gtgttcacgt acattacgtt aatgtgatac taagagtaac tgtactctgg   145560
cacagcgaag ccagcagaat gggaagttgt ggaatgcagg cccttgattc tgatagaagg   145620
tgtggtatga actcgcagaa atgacagttt ggagggtaga catatgtcac aagtcatcaa   145680
gattgtcttt aaattcatcc atagaagcta acaggttgtc ataagcaaag cctctaaaat   145740
gtatgaggga attcaaggat aatttatcaa aaagtaattc atgtttggag ttttgtgccc   145800
aaaggagtcc ttgatttgaa aaatgggtgt tgcccatca gattgtttca gggtccgtat   145860
gtgcagaggc cgtgcctcgt gccccgtgag ctcagcctga cagaagtccc ttggtagcac   145920
ttagggactt ggttagcact tcttcccttt gaggcagggt ggactctggg ttctgcattc   145980
agagctggct gtgggtgtct tgctgttctt gttgacctgt gggctctcct tccaggaaga   146040
cacagagagg acgcagatca acgtcctggc cgtgcaggcc atcacctcac tggtgctcag   146100
tgcaatgacc gtgcctgtgg ccggcaaccc agctgtgagc tgcttggagc agcagcctcg   146160
gaacaagcct ctgaaagctc tggacaccag gtttgcctga attcccacgt gtctccagga   146220
catcatgggt gctgcggaca gtggggtccc cgctgaagca tccagcagct tcccccaggc   146280
tgttttcctt tgttgctaga attgaaaacg ctgtccatgt ggcctgtgca ggaggtgcag   146340
acccaaaggt ggcctcttgg ccattgagga gctggaaacg cgacgggaac tgacatggg   146400 ttattgggca tttaggggta aacattagca gagcaagaat gagcgggcaa gtggtagaac   146460
acccacctaa gggctcatgg acaggtgctc acttaggaag tgagtttcgt ttggtattac   146520
accaggttcc tttaggcagg gcggagggaa agttctggcg ttttttcactt gtaagatttt   146580 gaaggaaaca aaacactctt tacctttttt ctgaaatgta ggtttgggag gaagctgagc   146640
attatcagag ggattgtaga gcaagagatt caagcaatgg tttcaaagag agaacatc    146700 gccacccatc atttatacca ggcgtgggat cctgtccctt ctctgtcccc ggctaccaca   146760
```

```
ggtacctgag ggagagggtg gggggtggct gtacttgggc tgggatgaga aaagactggc   146820
gtgctcacca caccagttat gcaggaagac ctgagtgtgg tttgagttgg aggctgtggt   146880
gctaaatagc tgccccattc ataagcagga gtcttattca ggcccaggga ggaaataaaa   146940
tctggaaatg aattaggagc attatctcct gccagtcaat tctcacgggc tgtaagaaca   147000
gcaggattta aaagttgaat gagttcctta tgttaagaac tcaaccgagt tcatctacac   147060
aagctgaatc tccagctttt cctaagaaac caggtgtggc agtggctgca gggcgggca    147120
cagctgggcc tgagcacccc gctccctgca cctctcccct ccctgggccc tgtctgtcgg   147180
tgcccactct cccaccaagc ctgccagttg tgtgcctgcc ctatcacagg catcagagtt   147240
tgtcacctgg tttaaaagaa gggagttgtg tagggatctg gggatgcaca tttttcactg   147300
aacagtattt tagcatagag gtttgtgatt ccctggttat ttaggagttt aagcacctta   147360
aaggctttaa ttgcagaaag gtctatgtgg acatgcaatg tgttatacgc agtgtctatg   147420
accctcaaat gtttattagg gtattgaaat aaactgagca cttggagggc catggatcca   147480
gcttcaagga gttcataggt caggaggacc caggagcaat gacctgtcgt agacggcaga   147540
aaagaggggc acagaggtgg gttggggggca tacacaggca gctcctggag ctccaaggag   147600
agcaagtgct tccagggaag ggggtgtgga ggctccttgg gaggaggcga gttgatgctg   147660
gggtctggca gagggttagc tggggacatt cggctggagg ctgttgtctg ggaattgggg   147720
ggatgcccag cagaaagaca tgcggaggtt gtttggcctg gggcgtgggg ggtgtgagag   147780
gtcgagtggg ggcattatcc tgctcccgct cctgctggct gtatctggtc agcctgggca   147840
ccgaggcggg ttctggaaag cactgttcac agatgcttat ctgagtcccc cagannnnnn   147900
nnnnnnnnnn nnnnnnnnnn nnnnnnnnnn nnnnnnnnnn nnnnnnnnnn nnnnnnnnnn   147960
nnnnnnnnnn nnnnnnnnnn nnnnnnnnnn nnnnnnnnnn nnnnnnnnnn nnnnnnnnnn   148020
nnnnnnnnnn nnnnnnnnnn nnnnnnnnnn nnnnnnnnnn nnnnnnnnnn nnnnnnnnnn   148080
nnnnnnnnnn nnnnnnnnnn nnnnnnnnnn nnnnnnnnnn nnnnnnnnnn nnnnnnnnnn   148140
nnnnnnnnnn nnnnnnnnnn nnnnnnnnnn nnnnnnnnnn nnnnnnnnnn nnnnnnnnnn   148200
nnnnnnnnnn nnnnnnnnnn nnnnnnnnnn nnnnnnnnnn nnnnnnnnnn nnnnnnnnnn   148260
nnnnnnnnnn nnnnnnnnnn nnnnnnnnnn nnnnnnnnnn nnnnnnnnnn nnnnnnnnnn   148320
nnnnnnnnnn nnnnnnnnnn nnnnnnnnnn nnnnnnnnnn nnnnnnnnnn nnnnnnnnnn   148380
nnnnnnnntt gcagtgagcc aagatcacgc cattgcactc cagcctgggc ggcagagcga   148440
gactctgttt caaaaaaaaa aaaaaaaaaa aaaaaatctt taatgttcat tgtttttgtc   148500
cttttttattc ctaggtccca caagcagaga aaatattact tttgttttta tttatgttct   148560
ttattctaga aagtagttaa gagacctcac atgtagtgat agagatgtat ataagagaca   148620
gtgagagggc ctgagctgga cttaagcaag gaccgtgaga caccaaaagg ggtgaggaca   148680
gagtggagtt agctgagatg ctcaggagga agtagatgcc atgaagggct ctgttgtggg   148740
gggctgcagg cttggccctg agtgtccctg tggccagttg ttggggggg cccagtgtgc    148800
aggcagacag ctcggccact ttgtggcagg tcacgttggt ctgtgcttct gtttcctcct   148860
caggtaagtg aagggattta agggtccagg tgtggtggct cacacctgta atgtataaca   148920
ttttaggagg ctgaggccgg aggctcacct gagctcaggc ggttgaggct gcagtgagcc   148980
atgattgcac cactgcactc cagcctgggc aacagaccaa tactctgtca cttaaaaaaa   149040
gtgtaaacag aaacacaggg ccatttacat atgatgcac atggcaggag ccccacaggt   149100
gtatgctcag gggagggccc agctttgctg gctgacttgc acctatccct ccaccctgtg   149160
```

```
ctgtgtcttt cgctcactgg gttcctggtt tagtgaaacc agttgtgcag gacggttccc 149220
ttggtagctt ttgttgcagt ggaaatgggt caggatatgg tgtgtagaag cacttatgag 149280
ctctgagagt ttcctcttat gacttcctgg cctgcagcct tcacagcaga aaccccatga 149340
tgtcacacgc ctgtttctgt tccctgctct gtgccctgta ctgtcctgtt ctgtgcctgc 149400
tggtttcagt gacaggaggc agggagctgc tggaccagcc tgtattttc tagacatagt 149460 tggaaaaga agtcacgctc ttctgtcctc tcacctttga cagatgtttc cacctcaaga 149520
taagtggaca tggccaatag gacgcactgt acttttcctg gatgtgtttc tgaagggcag 149580
gctgagagtg agaggcctgg agctcactgg gtgcctgtgg ccttgtcctg gccccgggga 149640
cactggtctg tgcccgagat actccctatt ccccacgccc cactgcattt gcccacatcc 149700
ttcgatgttt gccctgtgtc caatgtctgc aaaccgactg tcatgggatt atactggggc 149760
tgaagtatag tgccaccct gccctgtcgg ggacgttcag cccagatgc cactggactg 149820 agccactgct tgcttttagg aaaggggtg ggggttatgg gtctgggctt ggggagcaca 149880
ggggctgctc cttggcctga gaattgttca tacagactcc ctgcccactc cctgcagggg 149940
tgctgggtcc cagggggaa atggcccttg gtgccaagaa cgtgagttgg gcctagggcc 150000
agtgatgatg gagaacagct ttttatgggc acacagccca tagcactgtg ccaagtgctc 150060
gaggctccca gagaagcagg cagaaaggag gacagtcgag gtgtgctgag cacgtggtgg 150120
ctgtgtgatc tggagcgcgg gtcacagagg cgcggggacg ctctggcctg gggtttacca 150180
caatgactgc cagtggcgga gatcggaaaa gaaatctcac gcgttggttc cgtgttttgg 150240
ggggttccgt gttttggggg gttccgtgtt ttggggggtt ccgtgttttg gggactgcat 150300
tgagatctca cttacgagtg agagcgtccc cttcgtagag cctctttctg tgtcgcctcc 150360
tcagccgctc ctggggctgg ctgactcctg atccaggccc ttagcgtgtg ctggagcttc 150420
ccagcagcag tccagccccc accccaccct ctctgtggac tcccttgcct gtaagctggg 150480
gtgtctgaac gacccttgca aagggcaga ctgttcaacg gtaggcatgt gctgagtccc 150540
ggcggccgca cccgcccacc aggagcctgg cactgtggct gcagcgctga gcagcaccct 150600
gtttctgtgg caggtgtcca tacactctgt gtggctgggg aacagcatca caccctaag 150660 ggaggaggaa tgggacgagg aggaggagga ggaggccgac gcccctgcac cttcatcacc 150720
acccacgtct ccagtcaact ccaggttttc caatggcctt tttctttct acagaaattt 150780 gaaatttctt atcagtcatt tgatttgttt gaggtgcttc ttgaaatgag cctctcatct 150840
tctgtaccca gaaaacaccc atcttgcata ttctacagga aacaccgggc tggagttgac 150900
atccattcct gttcgcagtt tttactcgag ttgtacagcc gctggatcct gccatccaac 150960
tcagccagga ggaccccggc catcctgatc agtgaggtgg ttcgatccgt aagtgagcct 151020
tcccattccc ctcacactgg cacatgccac acgcaccaca cacgctgcac acacagacac 151080
gccacaccac acgtaccaca tgcaccacac acacgtcaca tcacacatac cccacatgca 151140
cggaacacac acacgccaca tgcacacgta ccccacatgc atgcaccaca cacacacacc 151200
acatgcacac gtaccccaaa tgcacgcccc atacacctca catgcacaca taccccacat 151260
gcacacaaca cacacatgcc acatgcacac gtaccccgca tgcacacaac acacacatgc 151320
cacatgcaca cataccccac atgcacacaa cacacacacg ccacacgtgc acacacatac 151380
accacatgca ccacgcacag cacacatgcc acacgcacac acacaccaca cacacccac 151440 acagcccata caccactttc atgcaacaca caccacacac aatgccacac tcgccacatg 151500
```

```
cacacacacc acatgtacat accacacaca tgccacacgc accacacaca tgccacatgc   151560
accacacaca tgccacacca cacacaccac acacaatgcc acactcacca catgcacaca   151620
caccacatgt acataccaca cacatgccac atgcaccaca cacatgccac atgcaccaca   151680
cacaccacac acatcacata catgcaccac gtgtactatg tacacacaca gacacaccac   151740
acgcgtacac cacacacaga cgcacacacg cgtcccgcgc agtcatgtct cttaggtgta   151800
agaacacgac ttgccagtag cggcgttctg gatgtgttgc ctggattcta actgcgctac   151860 tctcccttg ctttcctggt gttccacatc tccagcttct ggtggtctca gacttgttca   151920
ctgagcgcaa ccagtttgag ctgatgtatg tgacgctgac agaactgcga agggtgcatc   151980
cttcagaaga cgagatcctc gctcagtacc tggtgcccgc cacctgcaag gcagctgccg   152040
tccttgggat ggtaagtgac aggtggtaca gaggttcctg tcctgaagcc atgtgggccc   152100
atctgccttg ggacctggtg ttggccagag gtgccaggtg cggctgcctc cttccaagag   152160
ttgacccgag ccggactcca cagcccacgt gagctgcagt gcttctcagc tggagggggt   152220
tcagcgacgg tcagtgccat ccacaggcca ccgtgatgtg ggtcgtggcg gccaagccat   152280
ggtttggggt cccgtgtccc tgggcttgtg acatcattgt agtagcccat ccccacagaa   152340
ccatggtgtg tggtagcact gaagcatcgt agatggtgga aacgcgactg gcttcccat   152400 gctctgccct gaggcctgac tgcctcactc cccctcagtt atgttccagg ccccccgaac   152460
ttcctgactg gacagcttct ctcctggggg ccattttgtc acagtgaccc tgcgtttcca   152520
gtcccaagtc tgggtgctat agtgtcttct tagcatggtg tttctcttag tctatttcgg   152580
ctgctaccac aaggtacctt agactgggtg atttataaac agtggaaatt cacttctcat   152640
agttctgggg gctggaagtt catggtcaag gtgccaacag atttggtgtt tggtgagggc   152700
tgctctctgc ttcatagatg gcatgttctc actgggtcct cacggtgaaa ggagtgaaca   152760
agctccctca ggcctttcaa aagggcccca atccacaagg gctcacccct catgacttca   152820
tcaccacccg aggccccacc ttctagtact gtggcactgc aaattagttg tcagtgtaag   152880
agtttcgggg gggatacatt cattcagacc atcccaaggg tcaagtgttc atcctcttga   152940
gctcctcctt attctgcttc tggtttatca ggattcagcc cgtgcagcac ggtacctgtg   153000
ttctgtgggc acatcaccac atggcatttc ccaagcatcc atcagctgta cacatgaaat   153060
cgctacctgt gggccccgac tgctggcaaa gcctattcaa ggatgtcaga actgtcagag   153120
ctggagcctc tgggtctttg tcatgtggca ttacctagta atccatttta tgatagcaat   153180
agaaacgcgt gtcttcaaca aacacctcag tggctgccgt gtgccagccg tctggagccc   153240
ttggtgagaa tggcatggta gtgcccatca gggcctgctt accccatgct ctggatgggc   153300
tcctgtcagt aacaacgctg tcgtgacagt gatgatgttt ttttgccgtc actccagctg   153360
ctaacatttg cggagctctt cctcctgcac cccacctgac aaaggcaccc taggcggcca   153420
gcgtcagagg ttagctggct tgtctgggtc acacaaaatg cggcagaggt gggactgagc   153480
ccatgtctgt gacctgaagc ctgactccct gcgagtcttg actactcttg cctggactct   153540
gtcctccccg agcccaaact ccagtcatct tcccttgtgg gtggccgtca gcctggtgcc   153600
gtgctggtga cttggcagcc atccagggag tggaaacaat gaacgcgtgg gctccctgtg   153660
tgggcatctc tcttcactgc gagcaccctc tgggtgttgc ccacatgatg tcaaagcggc   153720
tctcggaagg ggtccttctc ctttatgggg agtttcagct gctgggctaa cttgaattgt   153780
aatgtggttt tgtgctcagg cccagagctc cttaggcaag tgttgtgcca tcagtaatca   153840
aatgagaaat aatcattttg aaaagcagat cctaaggcag gatggtcatg ggcactaatt   153900
```

```
cccagctctg tgcatctttc ttgaagacgg tgatcctctg tgaaggtttt cagcatgtca 153960
tgcttggtac cagcgtatcc agagcatgtc attttgaggt atttgcctcc tgttgtgaaa 154020
tccgtgccac ctgagagcag gtcctgatgt gggactttca gaggtgggac caggggccgt 154080
gggagcgcag tccttaggga ggtgccgcgt ggcgttgtgt gtatgagggg atagcacagg 154140
gtgaggtggg ggcccaagaa ggaagtgatc caccaaagaa cagcctcttt cggtcctcat 154200
tcctgggatg ggtgggagcg gcttctgtgt cttccggtca tttcccctgc ggagaagctc 154260
ctgccactgc caagaacctc atcttgttcc acaacaagaa gaggctgcct ggccatccag 154320
cgctccatgg gaattctgtg tccccatagt cttgggctga agagagcga ataccttgg 154380
tgacttctgc aggggtctcc tcactgttaa agagcagatt gaaagtgaag aatgtgggct 154440
aagtgtttag gtcgatattt aaccccatta ggttttggat actaagtgaa attgaggcca 154500
ttttggttga aggttggcat aaactactat cagggatccc caagactacc cccaggcttt 154560
tctagaagga ctctcagcta agatgtaata cagtaaaagc acacaaaaca caatcagcaa 154620
accaaatcag caagggcaga ggcccatggg gcggtgtccc gaggaaacca ggcccgagct 154680
tccagaatcc tctcccggcg gggtcgtgca ggacacactg agctccccca gagtgagccg 154740
tgacagcgtg tgcagtgtcg tcaccaggct caagcttcca gaatcctctc ccagtggggt 154800
cgtgcaggac gcactgagct cccccagagt gagctgtgac agtgtgtgca gtgttgtcac 154860
cagggaagcc cactagagac tcggtgccag ggttttgact gcgggctggg cacgtgggca 154920
ccttctgcct gcttcgtgcc catactctgg actcccagag ggaaggcaga ttctcagcac 154980
aaacaccgtt gcccacacaa gcagctgagc acagagagcc cctcctcagt gaggatggtg 155040
ggcaccgtcc cgacaccagc caggggccag ccttgcacac agacctctca ggatggtctt 155100
gggccgtgca cacaagcatg agggcagcgc accgcccccg cccctccttg gctgtgggga 155160
ggagccactg gggcgtgagc tctggtggca tcagcagctt ttgtctgtgt gtgtctagga 155220
caaggtcgtg gcggagcctg tcagccgcct gctggagagc acactcagga gcagccacct 155280
gcccagcagg gtcggagccc tgcacggcat cctctatgtg ctggagtgcg acctgctgga 155340
cgatactgcc aagcagctca tcccagtcat cagtgactat ctcctctcca acctgaaagg 155400
gatcgcccag tgagtgggag cctggctggg gctaggacgg gggtctcgga atgagctgcg 155460
aaggaagcag catcaccctc tccaagtgcc caggtccctg gccagatggc aggcaggtgt 155520
cagtgggaac ccaggtgggc gccatggctg aggttggtga gacgcaaggg cacaggtgtg 155580
tcctagaggc ttcctcgggc accccagtg agctagagct cctgcctctg ctgctgtctc 155640
atgtggcgct gagcacattt ccccatgtgc ccattcctga ctctgctcgc gaggccagcg 155700
gttctcattc tctgctctca gaaccctctc ctcattaccc aggccagcct cctctctgca 155760
ccttccccgc cctggcccag cacctcccctc ctgtttccac tgtgactccg acctcacttt 155820
atcttaaagc tgctgggcgg caggttctgc acagatgtgt ccttgacaaa gcacggctgg 155880
tgccacaacc ccttaacgag caagtcaagc tcttcacaac gatgtcttgt gagtgcggag 155940
ggctctgtga caccctggtc tcacctccgc tctcccgaag tcgcagaggc tttagcagag 156000
atgggcccag cctctctgag tcacaggctt tagagctgtc tgtagaggga gggtagaatt 156060
tcatcagcca cccacatggg ggagttgagg gcaagaattt ggagcaaaga tgggaaaggg 156120
gctgggaaga atgccagtg atccccttg acaagtgggc aggagatggg gccgggtca 156180
aagttgagtg gaagacttgg agggagatgg gaagatctct gtaggcacag ttcagacagg 156240
```

```
agggaggtgt gagccagggc actggctggt ggctgtctgg caggatttgg gacatcctgg    156300
agcagggaca gtggctcaac aggggccatt gccctcatcc aggccagagt ggcacaagct    156360
tgtggggagg cccttctcgt ctgtcatcct tgctgggcgg tgggtgctgt gctagcagga    156420
cgcaggacag gcggacagct ggcaactgtc tctgcatccc tggagcctgg catagggcaa    156480
gtcacacggg ggacacaggc ctgcaaatca ggcacatgcg ttggtgcagc gaggtgattt    156540 tgggggggcag ccccacaaca ggccccaggc acaggccaaa gccctggctg tgctggcgtg    156600
ttgggccgtc tatggctctt gctgtgggca tggaggactc aggaaaggag agttgaggtg    156660
gcccaggagt tgcgtttggg atgcagagag cttgtggcat ccaggtagaa atggtgtgtg    156720
gggctggcct cagtgccatg ggcacgggct gtgtcacatg cctccgaggt agaggtggga    156780
ccacgtggtg atggatataa gcatcactgg gcacatttct gtgggtggag ggggcatct    156840 tactggctcc tctgttcaca gtggccactc attcagtccc tggctaccgg gtccccattg    156900
tgccatgggg aaggcaggtg ctgtcggggg atcacacaag gcagcacgtc atggtggaat    156960
gtgccacgaa ggaaaagcac agggcactca ggaagtagag gggactggcc tggggtgtgg    157020
gaatccaggg cctctttgag ggacagagag aggaagtctg tggtggccag tatggaggtg    157080
gccacagggg aggctgggcc aggccgagag ggcagggcgt ggaggaggta gacgggctca    157140
gctatccagg gaggggtcga gcagaggctg aagggtcagg ccaggttaca ggggcctggg    157200
gagccacaca gggtaggtgc ttccgggagc cagcctggcc cgcagctctt cactcccgcg    157260
tggggccggg catgctgcga agccctctct acgttggatg ggggcggctg agcctggctg    157320
ctgtctcccg tttttcagctg cgtgaacatt cacagccagc agcacgtact ggtcatgtgt    157380
gccactgcgt tttacctgat tgagaactat cctctggacg tagggccaga attttcagca    157440
tcaataatac aggtgagtgg gccctggctg tcttcctctg cacacgggga gtgggcttcc    157500
cttctctttt ccttgcggga tcataccagt gggccagttt tgacttggtg gggaggaggc    157560
atgaacacct gagaccatgc agcgacagaa acctttctcc ctgtgcagat gtgtggggtg    157620
atgctgtccg gaagtgagga gtccaccccc tctatcattt accactgtgc cctcagaggc    157680
ctggagcgcc tcctgctctc tgagcagctc tcccgcctgg atgcagaatc cctggtcaag    157740
ctgagtgtgg acagagtgaa cgtgcacagc ccgcaccgcg ccatggcggc tctgggcttg    157800
atgctcacct gcatgtacac aggtgagcag gtacacagtg cccgcaaggc cagcccaagt    157860
cctgttcaag ggagacagga gcatgctcgc tcaaggaacc tagactaggt gtcctctgat    157920
ttgacacttt tagtgttgcc ccaagctggc cccatcacct tgcaagagag gctctggagc    157980
ccccagggct ggagtacctg gtcagggttg accaccctc tggtcactca tcccatgtgg    158040
ctgagctgtg ctgggtcctg ggctagcgag gggctcacat cacctgctgt caggtcttct    158100
ccagtgattc attggactcc tgtgtacaaa gcactatcta cagagcctgt tgggttgtat    158160
agatgtaacc ttcgtactga acacttttat tacaggaaag gagaaagtca gtccgggtag    158220
aacttcagac cctaatcctg cagccccaga cagcgagtcg gtgattgttg ctatggagcg    158280
ggtgtctgtt cttttttgata ggtaagaaac gaagccccat ccctcagccg ttagcttccc    158340
tagaattttg gcctgaagct gagcgtttgt gtgtgttggc tgatcccctg gcgctgttgc    158400
tggagtcccg ccagtgattc ctgaccacag cctgaccgtg ggctgccttg gctcagggtt    158460
ccactggcga gctggtggtc cttggacccc agcgctcagg tgtagtgttg accagttcca    158520
aggttgtccc agcgcctgcc catctctcct gagggctcag gcaccgcacc tggccgtgtg    158580
gggtatggca gggggcagga atgaccagtc tctgggaggg tgcggcagaa gcctgcgcag    158640
```

```
tgatgaggag ttggctcagc ctggctgcct gtcgtgagag gggagcccac gggggtctgt   158700 gggaggggt  ccatggtgcc tgtgagcagg gtgaggggca gcagcaggag gaggaaggtg   158760
aaacccacac atgcatcttt gagacccgtg tggtcagtgg cttctcctcg ctacccctcc   158820
gccccactgc tgtgcgtgaa ttggtgttga gaattggctt cgctcccctg ctctggaagt   158880
gggttaggag cttcgtaggg ctttttctca aggacaaggc tccctgattg ctctcaggcc   158940
tcagtcctgg cgacatggcg gatctggggc gttgttgtgc tgccttgcct gtgctctcca   159000
atcagggtgt cccagtcctg gcgacatggc ggatctgggg cgttgttgca ctgccttgcc   159060
tgtgctctcc aatcagggtg tccagtgggg agccatttgg cttttctcaa gagcatactc   159120
aggtggactt tgctctattc tttggccaga tgaggtgttc tgaacagctg agcctgtgct   159180
tgtctgtttt catgttttt  tttttttttg agatggagtt ttgcccttgt cacccaggct   159240
ggagtgcaat ggcgcgatct cggctcactg caacctccac ctcccgggtt caagcgattc   159300
tcctgcctca gcctcccaag tagctgggat tacaggcacg tgccaccacg cccagctaat   159360
ttttgtgttt ttagtagaga cagtgcttca ccgtgttggc cgaactggtc tcgaacttct   159420
gaactcaagt gatccaccct cctcggcctc ccaaagtgct gggattgcag gcatgagcca   159480
ccgtgcctgg cccccatgtc gattttaaaa cgcacctctg catcattctt cagttcccac   159540
atgctcactg agcaccacca cagctggcag acggacacag gaggcgcca  cgaccagtcc   159600 tggccttcaa ggggcttgtg gtctagtgga cccagtgcta ggtggcgagt gctccagaga   159660
gcgtggtgta tgccttccgc tctaccgccc tccagacgcc gcaggaggc  accttggagc   159720 tgaccacaga tctccctccg tggagcactg tcttcagcgc agccgccatg ccactgctgg   159780
gcgagggtct gcgggcgggt agagccagga gcacctctga aaagtgcac  tgccgtttct   159840 tggctgcttc ctgtgcatct cagttacaca cagctggcat gtgtgcactg atgagacagg   159900
aacatgatgg ttgcttttca gcactaaaaa ggatactgct caggggcgt  gtttcaggat   159960 ctggttaggg aaaaagcagc gagagcacag atggggccct gtttggtaac aagaaaaaag   160020
tcccggttga caacagtgct acaaagtgtt agaacacata gaaatgttta tggagcattt   160080
ggatgtggaa agcagcaaaa acataatgag aaggggttct tttgttagga ttttaaaaa   160140 tctcttttgt aacatccttc cggctgcacc atttctgcat attcttttat gtagctttca   160200
gactcttagg atttctggtc actgcagggc gtgggagcca gacagagcct atgcctagca   160260
gcctgtcttc acgagctgga cagaggagga gctgggggttt tgccttttta gcctcaaatt   160320
tcatactcca gttgcttagg ctctgacttt ccccacttgg aaagtccctc acggccaagg   160380
gtacctccca gccctgattt cacatcagca ttttccccag agccaaggcc ctccgcgggc   160440
aggtggggca gctgtgggag ctggtgccag gctctgacct gtgtccctcc tcccaggatc   160500
aggaaaggct ttccttgtga agccagagtg gtggcgagga tcctgcccca gtttctagac   160560
gacttcttcc cacccagga  catcatgaac aaagtcatcg gagagtttct gtccaaccag   160620
cagccatacc cccagttcat ggccaccgtg gtgtataagg tgaggttgca tgtgggatgg   160680
ggatggagtg gggaagcctg gaggtggaat tgaccccgac ttgccagcag attcgccaga   160740
agaacccagc tcctcccctt taaagcagca atgcctctgg ccccaccccc accccacca   160800 cccgggcaca gcaggtgctt cccgccccc  agccctgaca ctcaggcgcc cgcttgctcc   160860
tggcaggtgt ttcagactct gcacagcacc gggcagtcat ccatggtccg ggactgggtc   160920
atgctgtccc tctccaactt cacacagagg accccagtcg ccatggccac atggagcctc   160980
```

```
tcctgcttct tcgtcagcgc gtccaccagc ccatgggttg cggcgatgta tcctctctgg  161040
gtccctggtg ctggcccgt tccctcgtc aacaccgagg ctcatgttc atgataaagt    161100
tttgaaacct aacctttgca aaagccccac agatgccaag gtgacaggcc ctcagcccca  161160
gggaagtaca atgctgacag ggatacagaa aggagcacat ccagacattt gctgaccagg  161220
gcctctcaga ggggcccgtg tatggcagaa gggtcgaagc tgctaagggg cccttctgtg  161280
gagggcctgg gtgaggggag cgagggtggg cggcggtctc tgcagacctc ccgcccactc  161340
gcgggctctg tgtggctggg cttctcctga cactgcttct cattagcttt ggtcattgtg  161400
cctcgatcac cctctcgggg aaaggcttaa gtaaagatcc agttcccacc cccagatgct  161460
ggctgccagg agtttccctt tccacagccc tcccccaaga cagaccacaa gagcctccga  161520
gcagcacggt tgtcctggtg ctgacagcac agcctcgccc agtgtgcctg gcgtggctct  161580
gcccgcactg tactggagca gggctcgtgg gggcagcag acagcagga gcatcggcca    161640
ccagcgctac acaggagcca ggccaggtga gtgctgccga gtgggtgcct gcctgcaggc  161700
ctcctgcttc cttggccagc tctgcccagc tcacttctgc cctgctggcc ttccagcagg  161760
gtgtccagcc agccaagggt tgcaggaatg aaggtggagg cgctgctgca gctggagcca  161820
tccaggtagc ccttccgggg ctctgctggc tctccaggct ccctgggccc cttcgtaggc  161880
tgtttcagga gaggagctcc caggtgagga cagggaggca gcattcccct catttgccgg  161940
cctttttcct taactcctgc accagcctcc cacatgtcat cagcaggatg ggaaagctgg  162000
agcaggtgga cgtcaacctt ttctgcctgg ttgccacaga cttttacaga caccagatag  162060
aggaggagct cgaccgcagg gccttccagt ctgtgtttga ggtggttgca gctccaggaa  162120
gcccatatca ccggctgctg acttgtttac gaaatgtcca caaggtcacc acctgctgag  162180
cgccatggtg ggagagactg tgaggcggca gctggggctg gagcctccag aaatctgcgc  162240
cctgtgccct gcctccaccg agccagcttg gtccctgtgg gcttccgcac atgccgcggg  162300
cggccaggca acgtgcgtgt ctctgccata tggcagaagt gctctttgtg gtacagtggc  162360
caggcaagga gtatctgcag tcccggtggg gctgagcctg aggccttccg gagagcagga  162420
gcagctgtgc tgcacgccat gtgggtgacc aggtcctttc tcctgatgct cacctgttgg  162480
gtgttgccag gctgcagctg ctcttgcatc tgggccggaa gtcctccctc ctgcaggctg  162540
gctgtgggcc cctctgctgt cctgcagtag aaggtgccgt gagcaggctt tgggaacact  162600
ggcctgtgtc ttcctggtgg ggtgtgcatg ccacgccctg tgtctgtatg cacagatgcc  162660
atggcatgtg ctgggccagt ggctgggggt gctagacacc cagcaccatt ctcccttctc  162720
tctttcttc tcaggattta aaatttaatt atatcagtaa agagattaat tttaacgtaa    162780
ctctttctat gcccgtgtaa agtatgtgaa ttgcaaggcc tgtgctgcat gcgacagtgt  162840
tcggggaggt gggcagggcc cctggccacg ctccctctcc tgtagccact ggcatagcct  162900
tcctgagcac ccgctgacat ttccgttgta catgttcctg tttatgcatt cacaaggtga  162960
ctgggatgta gagaggcgct agtgtgcagg tggccacagc aggactaagg acaggccccc  163020
actgtcctag gggcatgctc gcctgcagcc cctccttctt gggcacagac aactgttgtt  163080
ctccacccac attagggaca gcagcctccc tatcagctga gaaggccagc cctccctggc  163140
tgtgagcagc ctccgctgtg tccagagaca tgggcctccc actcctgttc cttgctagcc  163200
ctgggcggt gtctgcccag gagctggctg gccggtgatg ggatctgccg ttccatggat    163260
gcatgcccca agggtgtcac tgagctgtgt tttgtctgag cctctcttgg tcaacagcaa  163320
agcttggcgt cttggcactg ttagtgacag agcctggcat cccttctgcc cccgttccag  163380
```

```
ctgacatctt gcacggggac ccctttagt caggagagtg cagatctgtg ctcattggag    163440
actgccccac tgccctgtca gagccgccac tcctatcccc aggccaggtc cctggaccag    163500
cctcttgttt gcaggcccag aggagccaag tcattaaaat ggaagtggat tctggatggc    163560
cggctgctgc tgacatagga gctggatttg ggagctctga gatggggcag gagctctgct    163620
tcctcagccc ttgaggcgag ccaggcgagg ttggcgactg tcatgtggct tggtttgctc    163680
atgcctgttg atgttttggg tattgaatat ggtaagtgga ggaaatgctt ttctggagtc    163740
tgtgcaggtg ctgccttgag accctcaagc ttccacctgt ccctctccta tgtggcagct    163800
gaggagcagc tgacatgtgg acttgtgtgc tgcccacata catgaggggg cgctgaaagg    163860
gagcccctgc tcaaagggag cccctcctct gagcagcctt tgacaggcct gtatgaggct    163920
tttcccacca gctcccaaca gaggcctccc ccagccagga ccacctcgtc ctcgtggcag    163980
ggcagcagga gcggtagaaa ggggtctgat gtttgaggag gcccttaagg gaagctactg    164040
aattttaaca gaaagccac cattcttccg tattggttgg gggctcctgt ttctcatcct    164100
agcttcttcc tggaaagcct gctagaagct ttgggaatga ggggaaagtt ctcagaaccg    164160
ttgctgctcc ccacccacct cccctgcagt aagttatgtc aacagctcgg agacagaagt    164220
atcacaggcc agatgttgtt ctgctagatg tttacatttg taagaaataa cactgtgaat    164280
gtaaaacgga gccattcccc ttggaatgca tatcgctggg ctcaacacag agtttgtctt    164340
ccttttgttt acgacgtgat ctaaaacagt ccttagcaag gggctcagaa caccccgctc    164400
tggcagtggg tgtcccccac tcccaaaggc ctgcctgtgt gctccagaga tgaatatgag    164460
ctcattagta aaatgacttt acccatgcgt aagtcaagta cacgtgcacg tgcatatgga    164520
cacatctgta gttttataca cgcacatctc aagacagaga tgcatggcct ccaagagtgc    164580
ccgtgtcggt tcttcctgga agttgacttt cctcagacct gccaggtaaa gttagctgtg    164640
tgacgggcgt ccaggcgcgg ggcttggtca gagcagggct cattcatggc tcactaggat    164700
cccaccggag aaaacggtct ccatatcaac tctgccgaag ggaggaagac tttgtcgcgt    164760
tcctaaaaaa cctatggcaa gcaccaatca tattatccaa attgtgttga aaatgtgatt    164820
aatttggttg tcaagttttg ggggtgagct gcggggagac tgcttttgtt ttgctgctgg    164880
taatatcagg aaagacttta atgaaaccag ggtagaattg tttggcaatg cactgaagcg    164940
cgtttctgtc ccaaaacgtg cctcccttcc gctgcgggcc cagctgagtc tgtgtaggtg    165000
acgtttccgg ctgccaagcg ctctttgtta ctgtccaccc ccatttctgc cagcacacgt    165060
gtcctttcag gaggaaaatg tgaagctgaa acccctccag acacccagaa tgtagcatct    165120
gagaaggccc tgtgccctaa aggacacccc cgcccccacc ttcatggagg ggtcattcca    165180
gagccctcga agccgatgaa cagctcgtcc tcttggagct gagctgagcc ccccacgag    165240 ctcgggacgg atagtaaaca gcaataactc ggtctgtggc tgcctggcag gtggaagttc    165300
ctccccctga ggggcggagt gaggttagtt ctgtgtgtct gtggggtgga gtcagcctgc    165360
tcctgctacc tgtgagcatc ctgcccagca gacatcctca cccggctttg tccctcccca    165420
cttcctccct ctgcggggag gacccaggac cacagctgct ggccagggta ggcttggagc    165480
tgtgctccga aggggccacc tgtgggagcg agaagaagga agatcttgag agctgccgag    165540
gcaccctgga gagctcagga tggtccaggc gagaagagga cactcgctcg ccaggcctgg    165600
gcctcctggg aaggagggag ccgctcagag cgccgcatga caactgaagg caacctgaa    165660 ggttcagagg ccactcttcc cccgtgtgcc tgtcacgctc tggtgcagtc caaggaacgc    165720
```

-continued

```
cttcccctca gttgtttcca aaagcagagt ctcccgctgc aatctgggtg gtgattgcca  165780
gccttggagg attgtggcca acgtggacct gcctacggag ggtgggctct gacccacgtg  165840
gggcctcctt gtccaggtct cattgctttg tgctgtggtc agagggactg tcagctgagc  165900
ctgagctccc ctggagccag cagggctgtg atgggcgagt cccggagccc acccagacc   165960
tgactgcttc tgagagcaaa gggaaggact gacgagagat gtatatttaa tttttttaac  166020
tgctgcaaac attgtacatc caaattaaag gaaaaacatt gaaaccatca gttgttgctg  166080
tgtgaggctt gctttacttc atgagaacct agaccttgct gagctggagt cttaggaaac  166140
tgtctcctaa gtgcttatcc agcaggggca gaaactgtcc caccagctaa catctgacat  166200
tacggagggt cccgcaggca gctgccagca aggacaagcc ctgtgttttc tgtagccagg  166260
gatgaggaag tggccccagg ggcctggctg ggtgctgctt caagggcctt cgcaaaccac  166320
agtacaggtg gtcttcctgc actgcagatg ggagctgtgg gagctgctgg atccttcatg  166380
gtcaagtgac atcataagct tatatgacac acacaagcct caggacttgg cccatggcac  166440
tggagcaggt catcaggccc agcagactag agctgtgttc tcacagggcc catgacccett 166500
ctagctcctt ggccattgaa acctgtgtcc ctgacccagc tgctcccagg taccccccaa  166560
agcagctggc acatcccacc tctggtgtgg cctgggctgc tgtgtgtccg cagggcctgc  166620
cccgtctgtt ctagcttgtt ctcctgtct gaaccagcgc ctactccaag aaggctctgc  166680
tcagcccagc ggggatgctt ctaagctcgg cccagcctct gggaagcctt ggtggtcggt  166740
ggtgtagtca tcctgggatg cagaacgaaa acctgcaaga acaaaactgt ggcttcgtct  166800
ggtgcagggt atttagttac tgtttgctga ggtcctgtct ggttctggcg aatgggcagg  166860
ggtcgcccac ccattctttc cctgctctgc tgtccgtgcc aggagagacg ggggcctgtt  166920
ggccaagggg gcagctcctg ctgcctgctg tccttaggca cgtgcaggga cccccttct   166980
ctgagcagga tggggatcag tctgccagag ggatgtggtg gacaggccca gccgggtaaa  167040
aaattccccc agttgctcaa gcatttgggg gcggggcatg ccacttgagc tccttaaatc  167100
tgtctcatag gtgacaccgc tccagggcgc cccaggggct tctcccttca gagctaccaa  167160
agttctggtc acttcagaaa aatggagcac ccccttctcc ctggtccaga tgtgacagc   167220
cagaccttg gcacacctag cacacctggc atggctggta atttcagaaa gaaaagggc    167280
cggggtccag tgggaagcag tggcgaaccc ctcatgcgtg ggctttgcga tccctcccc   167340
tgccacggca gagctgccct cagcacagcc ttcctcttcc tcatcggaga gcacaccctg  167400
tccccttgcc ggggctgtgc tctgtgcctg cagtggtatt tggttttggc tgctactggc  167460
tttgttccaa agaggatctg gaagtcgctt ccctgtgtg gagcgtggag cactgtgagt   167520
cagatgaggg aagtagccag ggggaggtga gtacccggcg gagccgccac agaaaggact  167580
gggtagggg ccttgcctcc acgtgatgtg acacggccag ccgaggacag aggaagcccc   167640
gttcctgggg gtgtggggtg cacccctcag ggaagcctgc agtggggccc aaggaaaggc  167700
gttctctgcg agcccacgag tctgctctgt gggcaccgtg acaatgcccg tgggcagagg  167760
tgggcccggc cttgtgtcgt caccaggacc tcttttggga aaccatgtgg gcatcccttg  167820
cgggtccccc aggttctgca gtcccagcgg cctggctgcc tgttgggcac atggcttgag  167880
ccgcccagag ggcccagccc tgttggcagc cacatcctct ggaggccctg ccggtggggc  167940
tggctttctc taccccacac caggcctcca agtatactgg tcggggggt ctgggccctg   168000
gg                                                                 168002
```

<210> SEQ ID NO 5
<211> LENGTH: 10295
<212> TYPE: DNA
<213> ORGANISM: Rattus norvegicus

<400> SEQUENCE: 5

```
gcactcgccg cgagggttgc cgggacgggc ccaagatggc tgggagcttt ggttccgctt      60
cggtctacct cgtagagccc cattcattac cttgctgcta agtggcgctg cgtagtgcga     120
ataggctcca agccttcagg gtctgtcctg tcgggcagga ggccgtcatg caaccctgg      180
aaaaactgat gaaggctttc gagtcgctca agtcgttcca gcagcaacag cagcagcagc     240
agccgccgcc gcaggcgccg ccaccaccgc cgccgccgcc gcctcaaccc cctcagccgc     300
cgcctcaggg gcagccgccg ccaccaccgc cgctgccagg tccggccgag gagccgctgc     360
accgaccaaa gaaggaactc tcagccacca agaaggaccg tgtgaatcac tgtctaacaa     420
tatgtgaaaa cattgtggca cagtctctca gaaattctcc agaatttcag aaactcttgg     480
gcattgctat ggaactgttt ctgctgtgca gcgacgatgc ggagtcagac gtcagaatgg     540
tggctgatga gtgcctcaac aaagtcatca agctttgat ggactctaat cttccaaggc      600
tacagttaga actctataag gaaattaaaa agaatggtgc tcctcgaagt ttgcgtgcag     660
ctctgtggag gtttgctgag ctggctcacc tggttcgacc tcagaagtgc aggccttatc     720
tggtgaatct tcttccatgt ttgacccgaa caagcaaacg accggaggag tcagttcagg     780
agactttggc tgcagctgtt cctaaaatta tggcctcttt tggcaatttc gcgaatgaca     840
atgaaattaa ggttctattg aaagctttca tagcaaatct gaagtcaagc tctcccactg     900
tgcggcggac agcagctggg tcagcagtga gtatctgcca gcactctagg aggacacagt     960
acttctacaa ctggctcctg aatgtgctcc taggtttgct ggttcccatg gaggaagacc    1020
accccactct cctgatcctt ggtgtgttgc tcacactgag gtgtctagtg cccttgctcc    1080
agcagcaggt caaggacaca gtctaaagg gcagctttgg ggtaacacgg aaagaaatgg     1140
aagtctctcc ttctgcagag cagcttgtcc aggtttatga actgactttg catcacacac    1200
agcaccaaga ccataatgtg gtgacagggg cattggagct cctgcagcag ctcttccgta    1260
ccccctccacc tgagctgctg caagcactga ccacaccagg agggctcggg cagctcactc    1320
tggttcgaga ggaagccggg ggccgaggcc gcagcgggag tatcgtggag cttttagctg    1380
gaggggttc ctcatgcagc cctgttctct caagaaagca aaaaggcaaa gtgctcttag     1440
gagaggaaga agccttggag gatgactcgg agtccaggtc agatgtcagc agctcagcct    1500
ttgcagcctc tgtgaagagt gagattggtg gagagctcgc tgcttcttct tcgggtgtct    1560
ccactcccgg ttctgtaggt cacgacatca tcactgagca gcctcgatcc cagcacacac    1620
ttcaagcaga ctctgtggat ttgtcaggct gtgacttgac cagtgctgct actgatggag    1680
atgaggaaga catcttgagc cacagctcca gccagttcag tgctgttcca tccgaccctg    1740
ccatggacct gaatgatggg acccaggcct cctcacccat cagtgacagt tctcagacca    1800
ccactgaagg acctgattca gctgtgactc cttctgacag ttctgaaatt gtcttagatg    1860
gtgctgacag ccagtattta ggcgtgcaga taggacagcc acaggaggaa gacgaggagg    1920
aagctgcagg tgttctttct ggtgaagtct cagacgtttt cagaaactct tctctggccc    1980
ttcagcaggc acacttgttg gaaagaatgg gtcatagccg gcagccttct gacagcagtg    2040
ttgataagtt tgtttcaaaa gatgaggttg ctgaagctgg ggacccagaa gcaagccttt    2100
gccgaatcaa aggtgacata ggacagccta atgatgatga ttctgctcct ctggtacatt    2160
```

-continued

```
gtgtccgtct tttatccgct tccttttgt taactggcga aaagaaagca ctggttccag    2220
acagagatgt gagagtcagt gtgaaggccc tggccctcag ctgtattggt gcagctgtgg    2280
cccttcatcc agagtcgttc ttcagcaaac tctacaaagt acctctcagt accatggaaa    2340
gtactgagga acagtatgtc tctgacatcc tgaactacat cgatcatgga gaccctcagg    2400
tgcgaggagc tactgccatt ctctgtggga cccttgtcta ctccatcctc agcaggtccc    2460
gtctccgtgt tggtgactgg ctgggcacca tcagggccct gacaggaaat acattttctc    2520
tggtggactg cattccttta ctgcagaaaa ctttgaagga tgaatcttct gttacttgca    2580
agttggcttg tacagctgtg aggcactgtg tcctgagtct ttgcagcagc agctacagtg    2640
acttgggatt acaactgctt attgacatgc tgcctctgaa gaacagctcc tactggctgg    2700
tgaggactga actgctggaa actcttgcag agattgattt caggctggtg agttttttgg    2760
aggcaaaagc agaaagttta caccgagggg ctcatcatta tacagggttt ctaaaactac    2820
aagaacgagt actcaataat gtggtcattt atttgcttgg agatgaagac cccagggttc    2880
gacatgttgc tgcgacgaca ttgacaagac ttgtcccaaa gctgttttat aagtgtgacc    2940
aaggacaggc tgacccagtc gtggctgtag caagagatca aagtagtgtt tacctgaagc    3000
tcctcatgca tgagacccag ccaccatccc acttctccgt cagcaccata accagaatct    3060
atagaggcta cagcttacta ccaagtgtaa cagatgtcac catggaaaac aacctctcaa    3120
gagtcgttgc cgcagtttct catgaactca ttacgtcaac tacacgggca ctcacatttg    3180
ggtgctgtga agccttgtgt gttctttcag ccgccttttcc agtttgcact ggagtctag    3240 gatggcactg tggagtgccc ccactgagtg cctctgatga gtccaggaag agctgcactg    3300
ttgggatggc ctccatgatt ctcaccttgc tttcatcagc ttggttccca ctggatctct    3360
cagcccatca ggatgccttg attttggctg gaaacttgct agcagcgagt gcccccaagt    3420
ctctgagaag ctcatgggcc tcggaagaag aaggcagctc agcagccacc agacaggagg    3480
agatctggcc tgccctgggg gatcggactc tggtgcccat ggtggagcag cttttctccc    3540
acctgctgaa ggtgatcaat atctgtgctc atgtcttgga tgacgtgact cctggaccag    3600
caatcaaggc agctttgcct tctctcacaa ccccccttc tctaagtcct attcgacgga    3660
aagggaagga gaaagagccc ggagaacaaa catccactcc gatgagtccc aagaaaggtg    3720
gagaggccag tacagcctct cgacagtcag acacctcagg acctgtcaca gcagtaaat    3780 catcttcact tgggagtttc taccatctcc cttcctacct cagactgcat gatgtcctga    3840
aagccactca cgccaactat aaggtcacct tagatcttca aacagcact gaaaagtttg    3900 gggggttcct gcgctctgcc ttggacgtcc tttctcagat tctagagctg gcgacactgc    3960
aggacattgg aaagtgtgtt gaagaggtcc ttggatactt gaaatcctgc tttagtcgag    4020
aaccaatgat ggcgactgtc tgtgttcagc agctattgaa gactctcttt gggacaaact    4080
tagcctcaca gtttgatggc ttatcttcca accccagcaa gtctcagtgc cgagcacagc    4140
gccttggctc ttccagtgtg aggcccggct tatatcacta ctgcttcatg gcaccataca    4200
cgcacttcac gcaggctttg gctgatgcca gcctgaggaa catggtacag gcggaccagg    4260
agcacgatgc ctcagggtgg tttgatgtac tccagaaagt gtctgctcag ttgaagacga    4320
accttacaag tgtcacaaag aaccgtgcag ataagaacgc tattcataac cacattaggt    4380
tatttgagcc tcttgttata aaagcattga agcagtacac cacgacaaca tcagtacaac    4440 tgcagaaagca ggttttggat ttgctggcac agctggttca gctacgggtc aattactgtc    4500
tactggattc agatcaggtg ttcatcgggt ttgtgctgaa gcagtttgag tacattgaag    4560
```

```
tgggccagtt cagggaatca gaggcaatta ttccaaatat attttcttc ctggtactat    4620
tatcttatga gcgctaccat tcaaaacaga tcattggaat tcctaaaatc atccagctgt    4680
gtgatggcat catggccagt ggaaggaagg ctgtcacaca tgctattcct gcgctgcagc    4740
ccattgtcca tgacctcttt tgttaagag gaacaaataa agctgatgca gggaaagagc    4800
ttgaaaccca gaaggaggtg gtggtctcaa tgctgttacg actcatccag taccatcagg    4860
tgctagagat gttcatcctc gtcctgcagc agtgccacaa agagaatgag acaagtggaa    4920
aacggctctc tcggcaggtc gcagacatca tcctgcccat gttagccaag cagcagatgc    4980
atattgactc tcatgaagcc cttggagtat aaataccctt gtttgagatt ttggctcctt    5040
cctccctacg tcctgtggac atgcttttgc ggagtatgtt catcactcca agcacaatgg    5100
catctgtaag cactgtgcag ctgtggatat ctggaatcct agccattctg agggttctca    5160
tttcccagtc aaccgaagac attgttcttt ctcgtattca ggagctctcc ttctctccat    5220
atttaatttc ctgtccagta attaacaggt taagggatgg agacagtaat ccaacactag    5280
gagaacgcag tgaagggaaa caagtaaaga atttgccaga agatacattc tcaaggtttc    5340
tcttacagct ggttggtatt cttctggaag acattgttac aaaacagctc aaagtggaca    5400
tgagtgaaca gcagcataca ttctattgcc aagagctcgg cacactgctc atgtgtctga    5460
tccacatatt caaatctgga atgttccgga gaatcacagc cgctgccact agactcttca    5520
ccagtgatgg ctgtgaaggc agcttctata ctctagatag cctgaatgca cgggtgcgag    5580
ccatggtgcc cacacaccca gctctggtac tgctctggtg tcagatccta ctgctcatca    5640
accacactga ccaccgatgg tgggccgagg tgcagcagac gcccaagaga cacagtctgt    5700
cctgcacgaa gtcactaaac ccccagatat ctgctgaaga ggattctggc tcagcagctc    5760
agcttggaat gtgcaataga gaaatagtac gaagaggggc ccttattctc ttctgtgatt    5820
atgtctgtca gaatctccat gactcagaac acttaacatg gctcattgtg aatcacattc    5880
aagatctgat cagcttgtcc cacgagcctc cagttcaaga ctttattagt gccattcatc    5940
gtaattctgc agctagtggt ctttttatcc aggcaattca gtctcgctgt gaaaatcttt    6000
caactccaac cactctgaag aaaacacttc agtgcttgga aggcatccat ctcagccagt    6060
ctggtgctgt gctcacactg tatgtggaca ggctactggg cacccctttc cgtgcgctgg    6120
ctcgcatggt cgacaccctg gcctgtcgcc gagtagaaat gcttttggct gcaaatttac    6180
agagcagcat ggcccagttg ccagaggagg aactgaacag aatccaggaa cacctccaga    6240
acactgggct tgcacaaaga caccaaaggc tctattcact gctggacaga ttccgactct    6300
ctactgtgca ggactcactt agccccttgc ccccagtcac ttcccaccct ctggatgggg    6360
atgggcacac atccctggaa acagtgaatc cggacaaaga ctggtacctc cagcttgtca    6420
gatcccagtg ttggaccagg tcagattctg cactgctgga aggtgcagag ctggtgaacc    6480
gtatccctgc tgaagatatg agtgacttca tgatgagctc ggagttcaac ctaagccttt    6540
tggctccctg cttaagcctt ggcatgagcg agattgctaa tggccaaaag agtccccttt    6600
ttgaagcggc tcgtagggtg actctggacc gggtgaccaa tgtggttcag cagctgcctg    6660
cagtccatca agtcttccag cctttcctgc ctacagaacc cacagcctac tggagcaagc    6720
tgaatgatct ctttggtgat accacatcat accagtctct gaccacactt gcccgtgccc    6780
tggcacagta cctggtggtg ctctccaaag tgcctgctcc tttgcacctt cctcctgaga    6840
aggaggggca cacggtgaag tttgtggtaa tgacacttga ggccctgtca tggcatttga    6900
```

```
tccatgagca gatcccactg agtctggacc tccaagccgg cctagactgc tgctgcctgg   6960
cactgcaggt gcctggcctc tggggggtgc tgtcctcccc agagtacgtg actcatactt   7020
gctcccttat ccactgtgtg cgattcatcc tggaagccat tgcagtacaa cctggagacc   7080
aacttcttgg tccggaaagc aggtcacata ctccaagggc tgtcagaaag gaggaagtag   7140
actcagatat acaaaacctc agtcacatca cttcggcctg cgagatggtg gcagacatgg   7200
tggaatccct gcagtcggtg ctggccctgg gccacaagag aacagcacc  ctaccttcat   7260 ttctcacagc tgtgctgaag aacattgttg tcagtctggc ccgcctcccc ctcgttaaca   7320
gctatactcg tgtgcctcct ctggtatgga aactcgggtg gtcacccaag cctggagggg   7380
atttcggcac agtgtttcct gagatccctg tagagttcct ccaggagaag gaggtcctca   7440
aggagttcat ctaccgcatc aacaccctag ggtggaccag tcgtactcaa ttcgaagaaa   7500
cttgggccac cctccttggt gtcctggtga ctcagccctt ggtgatgaa  caggaagaga   7560 gcccaccaga ggaagacacc gaaaggaccc agatccacgt cctggctgta caggccatca   7620
cctctctagt gctcagcgca atggctgtgc ctgtggctgg caatccagct gtaagctgct   7680
tggagcaaca gccccggaac aagccactga aggctctcga taccagattt  ggaagaaagt   7740
tgagcatgat cagagggatt gtagaacaag aaatccaaga gatggtttcc caaagagaga   7800
atactgccac tcatcattct caccaggcat gggatcctgt cccttctctg ttaccagcta   7860
ctacaggtgc tcttatcagc catgacaagc tgctgctgca gatcaactca gagcgggagc   7920
caggcaacat gagctacaag ctgggccagg tgtccataca ctccgtgtgg ctggggaaca   7980
acatcacacc cctgagagag gaggaatggg atgaggagga ggaggaagaa gcggatgccc   8040
ctgcgccaac atcaccacct gtgtctccag tcaattccag aaaacaccgt gctggggttg   8100
atattcactc ctgttcgcag tttctgcttg aattatacag ccgttggatc ctgccatcca   8160
gtgcagccag aaggacccct gtcatcctga tcagtgaagt ggttcgatct cttcttgtgg   8220
tgtcagactt attcactgaa cgtacccagt ttgaaatgat gtatctgacg ctgacagaac   8280
tacggagagt gcacccttca gaagatgaga tcctcattca atacctggtg cctgccacct   8340
gtaaggcagc tgctgttctt ggaatggaca aaactgtggc agagccggtc agccgcctac   8400
tggagagcac actcaggagc acccacctgc ccagccagat cggagccctg catggcatcc   8460
tctatgtgtt ggagtgtgac ctcttggatg acactgtaaa gcagctcatt ccagttgtta   8520
gtgactatct gctgtccaac ctcaaaggaa tagcccactg cgtgaacatt cacagccagc   8580
agcatgtgct ggtgatgtgt gccactgcat tctacctgat ggaaaactac cctctggatg   8640
tggggccaga attctcagca tctgtgatac agatgtgtgg agtaatgctg tctggaagtg   8700
aggagtccac cccctccatc atttaccact gtgccctccg gggtctggaa cggctcctgc   8760
tgtctgagca gctctctcgg ctagacacgg agtccttggt caagctaagt gtggacagag   8820
tgaatgtaca aagcccacac agggccatgg cagcccctagg cctgatgctt acctgcatgt   8880
acacaggaaa ggaaaaagcc agtccaggca gagcttctga ccccagccct gctaccccctg   8940 acagcgagtc tgtgattgta gctatggagc gagtgtctgt gctctttgac aggatccgca   9000
agggatttcc ctgtgaagcc agggtcgtgg caaggatcct gcctcagttt ctagatgact   9060
tctttccacc tcaagatgtc atgaacaaag tcattggaga gttcctgtcc aaccagcagc   9120 cataccaca gttcatggcc actgtagtat acaaggtttt tcagactctg cacagtgctg   9180
ggcagtcatc catggtccgg gactgggtta tgctgtctct gtccaacttc acacaaagaa   9240
ctccagttgc catggccatg tggagcctct cctgcttcct tgtcagtgca tctaccagcc   9300
```

```
catgggtttc tgcaatcctt ccacacgtca tcagcaggat gggcaaactg gagcaggtgg   9360
atgtgaacct tttctgcctg gttgccacag acttctacag acaccagata gaggaggaat   9420
tcgaccgcag ggcttccag tctgtgtttg aggtggtggc agcaccagga agtccatacc    9480
acaggctgct tgcttgtttg caaaatgttc acaaggtcac cgcctgctga gtagtacctg   9540
tggaacaaga ggctgagagg aggcaactgc tgtggctaca gcctccaggg gcctgcacca   9600
agcttctgct aaggctgcct tggacgtgca ggcttccact tgtgtcaagt ggacagccag   9660
gcaatggcag gagtgctttg caatgagagc tatgcaggga acatgcacta tgttggggtt   9720
gagcctgagt cctgggtcct ggcatcactg cagctggtgg cagtgctagg ttgaccaggt   9780
gtttgtcttt ttcttagtgt tgccctggcc atagttgcca ggttgcagct gccctggtat   9840
gtggaacaga atccgagctc ttgtaagatg gttctgagcc cccctgtccc actgggctgg   9900
agagctccct cccacattta cccagcaggt gtacctgcca caccagtgtc tggacacaaa   9960
gtgaatggtg tgggggctgg gaactgggac tgccaggtgt ccagcatcat tttccctttc   10020
tctgttttct tctcaggagt taaaatttaa ttatatcagt aaagagatta attttaatgt   10080
aactcttcct atgcccgtgt aaagtgtgtg acttggcaag gcctgtgctg catgtgacaa   10140
agtttatgga agtggatgcg ccttctggcc accactctct ctcctgtagc tactcagtct   10200
agtcgggcag gtccctcatg tagccctccc aacaccctat ggcacttgca cttcacacgg   10260 ctccttttc ttatgcattc catttgacta gcaca                              10295
```

<210> SEQ ID NO 6
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 6
tagcattctt atctgcacgg                                               20

<210> SEQ ID NO 7
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 7
acccgtaact gaaccagctg                                               20

<210> SEQ ID NO 8
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 8
ttccctgaac tggcccactt                                               20

<210> SEQ ID NO 9
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 9
ctctgattcc ctgaactggc            20

<210> SEQ ID NO 10
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 10
gcctctgatt ccctgaactg            20

<210> SEQ ID NO 11
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 11
tgcctctgat tccctgaact            20

<210> SEQ ID NO 12
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 12
ttgcctctga ttccctgaac            20

<210> SEQ ID NO 13
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 13
attgcctctg attccctgaa            20

<210> SEQ ID NO 14
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 14
tggaatgatt gcctctgatt            20

<210> SEQ ID NO 15
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 15
gtttggaatg attgcctc            18

<210> SEQ ID NO 16
<211> LENGTH: 20

```
<212> TYPE: DNA
<213> ORGANISM: Artificial sequence
<220> FEATURE:
<223> OTHER INFORMATION: Synthetic oligonucleotide

<400> SEQUENCE: 16
ccaatgatct gttttgaatg                                               20

<210> SEQ ID NO 17
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 17
gccttccttc cactggccat                                               20

<210> SEQ ID NO 18
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 18
ctgcatcagc tttatttgtt                                               20

<210> SEQ ID NO 19
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 19
cctgcatcag ctttatttgt                                               20

<210> SEQ ID NO 20
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 20
agctcttttc ctgcatcagc                                               20

<210> SEQ ID NO 21
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 21
gtaacattga caccacca                                                 18

<210> SEQ ID NO 22
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 22
```
ctcagtaaca ttgacaccac                                              20

<210> SEQ ID NO 23
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 23
atgagtctca gtaacattga                                              20

<210> SEQ ID NO 24
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 24
tccttgtggc actgctgcag                                              20

<210> SEQ ID NO 25
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 25
ttctccttgt ggcactgctg                                              20

<210> SEQ ID NO 26
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 26
tcattctcct tgtggcactg                                              20

<210> SEQ ID NO 27
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 27
attctccttg tggcactg                                                18

<210> SEQ ID NO 28
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 28
cgagacagtc gcttccactt                                              20

<210> SEQ ID NO 29
<211> LENGTH: 18
<212> TYPE: DNA
<213> ORGANISM: Artificial sequence

```
<220> FEATURE:
<223> OTHER INFORMATION: Synthetic oligonucleotide

<400> SEQUENCE: 29
tgtcgagaca gtcgcttc                                                   18

<210> SEQ ID NO 30
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 30
ttgcacattc caagtttggc                                                 20

<210> SEQ ID NO 31
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 31
tctctattgc acattccaag                                                 20

<210> SEQ ID NO 32
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 32
tttctctatt gcacattcca                                                 20

<210> SEQ ID NO 33
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 33
tctctattgc acattcca                                                   18

<210> SEQ ID NO 34
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 34
gcagggttac cgccatcccc                                                 20

<210> SEQ ID NO 35
<211> LENGTH: 18
<212> TYPE: DNA
<213> ORGANISM: Artificial sequence
<220> FEATURE:
<223> OTHER INFORMATION: Synthetic oligonucleotide

<400> SEQUENCE: 35
accttatctg cacggttc                                                   18
```

<210> SEQ ID NO 36
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 36
ctctctgtgt atcaccttcc                                         20

<210> SEQ ID NO 37
<211> LENGTH: 20
<212> TYPE: DNA
<213> ORGANISM: Artificial sequence
<220> FEATURE:
<223> OTHER INFORMATION: Primer

<400> SEQUENCE: 37
ctccgtccgg tagacatgct                                         20

<210> SEQ ID NO 38
<211> LENGTH: 23
<212> TYPE: DNA
<213> ORGANISM: Artificial sequence
<220> FEATURE:
<223> OTHER INFORMATION: Primer

<400> SEQUENCE: 38
ggaaatcaga accctcaaaa tgg                                     23

<210> SEQ ID NO 39
<211> LENGTH: 29
<212> TYPE: DNA
<213> ORGANISM: Artificial sequence
<220> FEATURE:
<223> OTHER INFORMATION: Probe

<400> SEQUENCE: 39
tgagcactgt tcaactgtgg atatcggga                               29

<210> SEQ ID NO 40
<211> LENGTH: 21
<212> TYPE: DNA
<213> ORGANISM: Artificial sequence
<220> FEATURE:
<223> OTHER INFORMATION: Primer

<400> SEQUENCE: 40
gtctgagcct ctctcggtca a                                       21

<210> SEQ ID NO 41
<211> LENGTH: 19
<212> TYPE: DNA
<213> ORGANISM: Artificial sequence
<220> FEATURE:
<223> OTHER INFORMATION: Primer

<400> SEQUENCE: 41
aagggatgct gggctctgt                                          19

<210> SEQ ID NO 42
<211> LENGTH: 30
<212> TYPE: DNA
<213> ORGANISM: Artificial sequence
<220> FEATURE:
<223> OTHER INFORMATION: Probe

<400> SEQUENCE: 42
agcaaagctt ggtgtcttgg cactgttagt                                              30

<210> SEQ ID NO 43
<211> LENGTH: 21
<212> TYPE: DNA
<213> ORGANISM: Artificial sequence
<220> FEATURE:
<223> OTHER INFORMATION: Primer

<400> SEQUENCE: 43
cagagctggt caaccgtatc c                                                       21

<210> SEQ ID NO 44
<211> LENGTH: 21
<212> TYPE: DNA
<213> ORGANISM: Artificial sequence
<220> FEATURE:
<223> OTHER INFORMATION: Primer

<400> SEQUENCE: 44
ggcttaaaca gggagccaaa a                                                       21

<210> SEQ ID NO 45
<211> LENGTH: 26
<212> TYPE: DNA
<213> ORGANISM: Artificial sequence
<220> FEATURE:
<223> OTHER INFORMATION: Probe

<400> SEQUENCE: 45
acttcatgat gagctcggag ttcaac                                                  26

<210> SEQ ID NO 46
<211> LENGTH: 25
<212> TYPE: DNA
<213> ORGANISM: Artificial sequence
<220> FEATURE:
<223> OTHER INFORMATION: Primer

<400> SEQUENCE: 46
aggagaaaaa caaagaacac cagaa                                                   25

<210> SEQ ID NO 47
<211> LENGTH: 25
<212> TYPE: DNA
<213> ORGANISM: Artificial sequence
<220> FEATURE:
<223> OTHER INFORMATION: Primer

<400> SEQUENCE: 47
caattagggc aactcagaaa tagct                                                   25

<210> SEQ ID NO 48
<211> LENGTH: 22
<212> TYPE: DNA
<213> ORGANISM: Artificial sequence
<220> FEATURE:
<223> OTHER INFORMATION: Probe

<400> SEQUENCE: 48
ccaactggtc ccccagccaa ga                                                      22

<210> SEQ ID NO 49

<211> LENGTH: 21
<212> TYPE: DNA
<213> ORGANISM: Artificial sequence
<220> FEATURE:
<223> OTHER INFORMATION: Primer

<400> SEQUENCE: 49
cagagctggt gaaccgtatc c                                              21

<210> SEQ ID NO 50
<211> LENGTH: 21
<212> TYPE: DNA
<213> ORGANISM: Artificial sequence
<220> FEATURE:
<223> OTHER INFORMATION: Primer

<400> SEQUENCE: 50
ggcttaagca gggagccaaa a                                              21

<210> SEQ ID NO 51
<211> LENGTH: 26
<212> TYPE: DNA
<213> ORGANISM: Artificial sequence
<220> FEATURE:
<223> OTHER INFORMATION: Probe

<400> SEQUENCE: 51
acttcatgat gagctcggag ttcaac                                         26

<210> SEQ ID NO 52
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 52
tcctagtgtt acattaccgc                                                20

<210> SEQ ID NO 53
<211> LENGTH: 20
<212> TYPE: DNA
<213> ORGANISM: Artificial sequence
<220> FEATURE:
<223> OTHER INFORMATION: Synthetic oligonucleotide

<400> SEQUENCE: 53
ctcgactaaa gcaggatttc                                                20

<210> SEQ ID NO 54
<211> LENGTH: 17
<212> TYPE: DNA
<213> ORGANISM: Artificial sequence
<220> FEATURE:
<223> OTHER INFORMATION: Primer

<400> SEQUENCE: 54
tggtccccca gccaaga                                                   17

<210> SEQ ID NO 55
<211> LENGTH: 18
<212> TYPE: DNA
<213> ORGANISM: Artificial sequence
<220> FEATURE:
<223> OTHER INFORMATION: Primer

<400> SEQUENCE: 55

```
cccaccgtgt gacatcca                                                    18

<210> SEQ ID NO 56
<211> LENGTH: 26
<212> TYPE: DNA
<213> ORGANISM: Artificial sequence
<220> FEATURE:
<223> OTHER INFORMATION: Probe

<400> SEQUENCE: 56
agctatctcc gagctgccct gattgg                                           26
```

MODULATION OF HUNTINGTIN EXPRESSION

SEQUENCE LISTING

The present application is being filed along with a Sequence Listing in electronic format. The Sequence Listing is provided as a file entitled BIOL0113USC3SEQ_ST25.txt created May 15, 2017, which is 488 Kb in size. The information in the electronic format of the sequence listing is incorporated herein by reference in its entirety.

FIELD OF THE INVENTION

Provided herein are methods, compounds, and compositions for reducing expression of huntingtin mRNA and protein in an animal. Such methods, compounds, and compositions are useful, for example, to treat, prevent, or ameliorate Huntington's disease.

BACKGROUND

Huntington's disease (HD) is a devastating autosomal dominant, neurodegenerative disease caused by a CAG trinucleotide repeat expansion encoding an abnormally long polyglutamine (PolyQ) tract in the huntingtin protein. The Huntington disease gene was first mapped in 1993 (The Huntington's Disease Collaborative Research Group. Cell. 1993, 72:971-83), consisting of a gene, IT15, which contained a polymorphic trinucleotide repeat that is expanded and unstable on HD chromosomes. Although CAG repeats in the normal size range are usually inherited as Mendelian alleles, expanded HD repeats are unstable through meiotic transmission and are found to be expanded beyond the normal size range (6-34 repeat units) in HD patients.

Both normal and variant huntingtin protein are localized chiefly in the cytoplasm of neurons (DiFiglia et al., Neuron 1995, 14:1075-81). As a result of excessive polyglutamine length, huntingtin protein forms aggregates in the cytoplasm and nucleus of CNS neurons (Davies et al., Cell 1997, 90:537-548). Both transgenic animals and genetically modified cell lines have been used to investigate the effects of expanded polyQ repeats on the localization and processing of huntingtin. However, it is still unclear whether the formation of aggregates per se is the essential cytotoxic step or a consequence of cellular dysfunction.

HD is characterized by progressive chorea, psychiatric changes and intellectual decline. This dominant disorder affects males and females equally, and occurs in all races (Gusella and MacDonald, Curr. Opin. Neurobiol. 1995 5:656-62). Symptoms of HD are due to the death of neurons in many brain regions, but is most apparent in the striatum, particularly in the caudate nucleus, which suffers a progressive gradient of cell loss that ultimately decimates the entire structure. Although the gene encoding huntingtin is expressed ubiquitously (Strong, T. V. et al., Nat. Genet. 1995, 5:259-263), selective cell loss and fibrillary astrocytosis is observed in the brain, particularly in the caudate and putamen of the striatum and in the cerebral cortex of HD patients (Vonsattel, J-P. et al., Neuropathol. Exp. Neurol. 1985, 44:559-577), and, to a lesser extent, in the hippocampus (Spargo, E. et al., J. Neurol. Neurosurg. Psychiatry 1993, 56:487-491) and the subthalamus (Byers, R. K. et al., Neurology 1973, 23:561-569).

Huntingtin is crucial for normal development and may be regarded as a cell survival gene (Nasir et al., Human Molecular Genetics, Vol 5, 1431-1435). The normal function of huntingtin remains incompletely characterized, but based upon protein-protein interactions, it appears to be associated with the cytoskeleton and required for neurogenesis (Walling et al., J. Neurosci Res. 1998, 54:301-8). Huntingtin is specifically cleaved during apoptosis by a key cysteine protease, apopain, known to play a pivotal role in apoptotic cell death. The rate of cleavage is enhanced by longer polyglutamine tracts, suggesting that inappropriate apoptosis underlies HD.

Antisense technology is emerging as an effective means for reducing the expression of specific gene products and may therefore prove to be uniquely useful in a number of therapeutic, diagnostic, and research applications for the modulation of huntingtin expression. (See U.S. Patent Publication Nos. 2008/0039418 and 2007/0299027)

Antisense compounds for modulating expression of huntingtin are disclosed in the aforementioned published patent applications. However, there remains a need for additional such compounds.

SUMMARY OF THE INVENTION

Provided herein are methods, compounds, and compositions for modulating expression of huntingtin and treating, preventing, delaying or ameliorating Huntington's disease and/or a symptom thereof.

Figure 1:
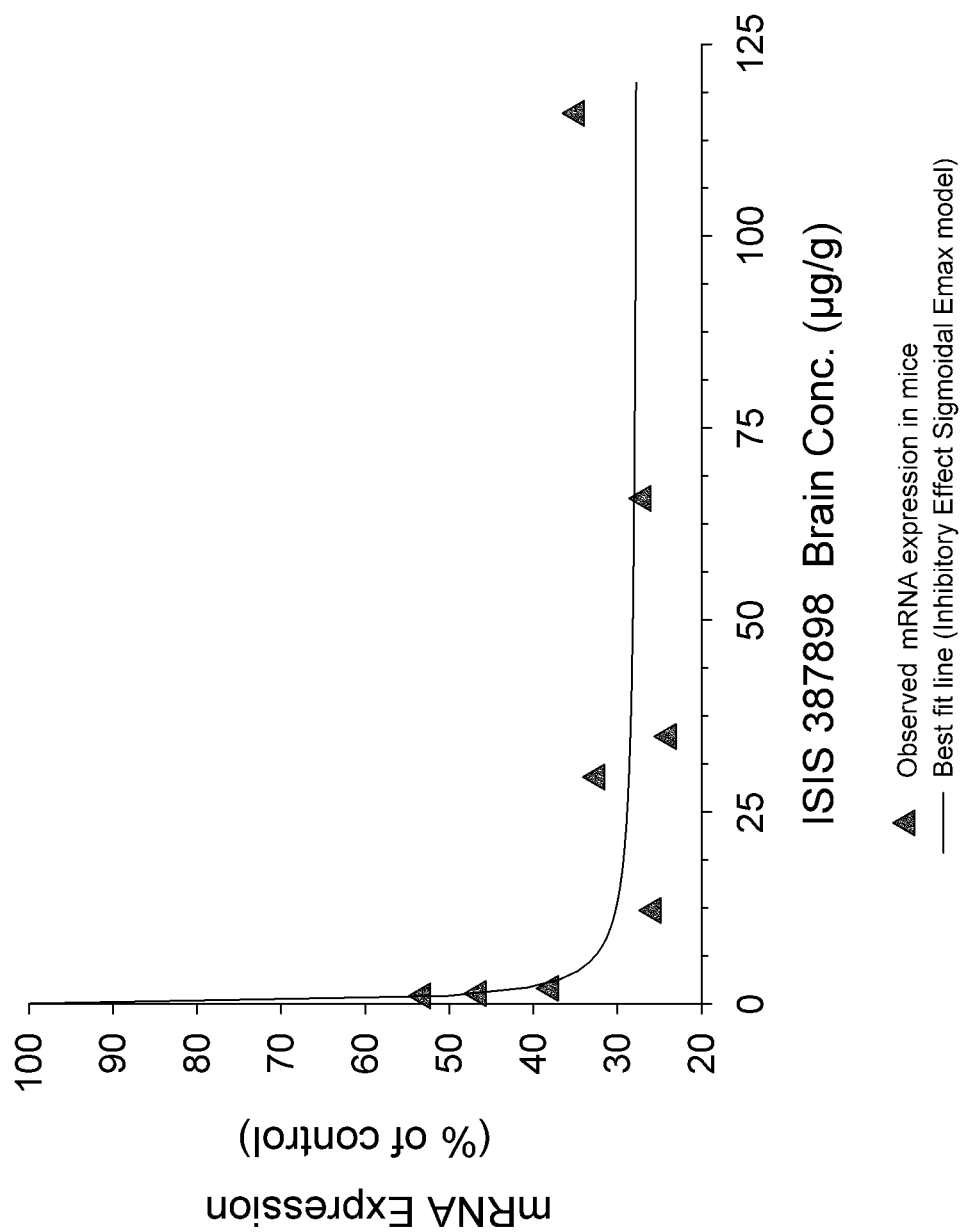
FIG. 1:
The PK/PD relationship of huntingtin mRNA expression in intrastriatal tissue with ISIS 387898 concentration in mouse brain. C57/BL6 mice were administered a single bolus of 50 µg of ISIS 387898 and huntingtin mRNA expression as well as the concentration of the antisense oligonucleotide in the tissue were measured. The $EC_{50}$ of ISIS 387898 was also calculated.

Comparison of huntingtin mRNA expression in posterior cortex tissue and ISIS 388241 concentrations at various time points. BACHD mice were administered intracerebroventricular infusion of 50 μg of ISIS 388241 for 2 weeks, and huntingtin mRNA expression as well as the concentration of the antisense oligonucleotide in the tissue were measured. The duration of action (as measured by htt mRNA expression) of ISIS 388241 (dashed line) was observed to be longer even after the concentration of the oligonucleotide (solid line) in the tissue.

FIG. 6:

Comparison of huntingtin mRNA expression in posterior cortex tissue and ISIS 443139 concentrations at various time points. BACHD mice were administered intracerebroventricular infusion of 50 μg of ISIS 443139 for 2 weeks, and huntingtin mRNA expression as well as the concentration of the antisense oligonucleotide in the tissue were measured. The duration of action (as measured by htt mRNA expression) of ISIS 443139 (dashed line) was observed to be longer even after the concentration of the oligonucleotide (solid line) in the tissue.

FIG. 7.

Effect of antisense oligonucleotide treatment on the motor performance of BACHD mice using the Rotarod assay. BACHD mice were treated with 50 μg/day ICV of ISIS 388241 or PBS for two weeks. Control groups of non-transgenic littermates were similarly treated with ISIS 388241 or PBS. The accelerating Rotarod assay was then performed. Animals were placed on the Rotarod at a speed of 2 RPM; the Rotarod accelerated to 40 RPM over 5 minutes. The duration to fall was recorded. Baseline values at 6 months age were taken before the treatment and the time points given are the age of the mice at which the assay was conducted. The bars represent the duration to fall in seconds by BACHD mice treated with ISIS 388241 (black); by BACHD mice treated with PBS (hashed); and by non-transgenic littermates treated with PBS (white). ISIS 388241-treated mice displayed increased duration of fall and, therefore, improved motor performance on the Rotarod, compared to the PBS control.

FIG. 8.

Effect of antisense oligonucleotide treatment on brain weight of R6/2 mice. Six-month old R6/2 mice were treated with 50 μg/day ICV of ISIS 388817 or control oligonucleotide ISIS 141923 or PBS for 4 weeks. Control groups of non-transgenic littermates were similarly treated with ISIS 388817 or PBS. A control group of eight-week old pre-symptomatic R6/2 mice were included in the study and not given any treatment. The bars represent the brain weights of eight-week old untreated R6/2 mice; R6/2 mice treated with ISIS 141923; R6/2 mice treated with PBS; R6/2 mice treated with ISIS 388817; non-transgenic littermates treated with PBS; and non-transgenic littermates treated with ISIS 388817. There was an increase in brain weight of R6/2 mice treated with ISIS 388817 compared to the PBS control.

FIG. 9.

Behavioral characterization of antisense oligonucleotide-treated YAC128 mice using the Open Field assay. Five month old YAC128 mice were treated with 50 μg/day ICV of ISIS 388241 or control oligonucleotide ISIS 141923 or PBS for 14 days. A control group of non-transgenic FVB/NJ littermates were included in the study and not given any treatment. Mice were placed in an open field arena that uses photobeam breaks to measure horizontal and vertical movement over a 30 min test session. Data was analyzed using Activity Monitor software to examine total ambulatory movement within the arena and movement within the center of the arena as a measure of anxiety. The bars represent time in seconds spent at the center of the field by FVB/NJ mice, YAC128 treated with PBS, and, YAC128 mice treated with ISIS 388241. YAC128 mice treated with ISIS 388241 spent more time in the center and were therefore deemed less anxiety-prone than the PBS control.

FIG. 10.

Behavioral characterization of antisense oligonucleotide-treated YAC128 mice using the Elevated Plus Maze assay. Five month old YAC128 mice were treated with 50 μg/day ICV of ISIS 388241 or control oligonucleotide ISIS 141923 or with PBS for 14 days. A control group of non-transgenic FVB/NJ littermates were included as untreated control. Mice were placed in the center of an apparatus which consisted of two open arms and two closed arms each measuring 65×6.25 cm and elevated 50 cm above the ground. The location of the mice on the apparatus and amount of time spent in the open arms was recorded over a 5 minute test session as a measure of anxiety. The bars represent the percentage of time spent in the open arms by FVB/NJ control, YAC128 treated with PBS, and YAC128 mice treated with ISIS 388241. YAC128 mice treated with ISIS 388241 spent more time in the open arms and were therefore deemed less anxiety-prone than the PBS control.

DETAILED DESCRIPTION OF THE INVENTION

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques may be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O(CH$_2$)$_2$—OCH$_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"5-methylcytosine" means a cytosine modified with a methyl group attached to the 5' position. A 5-methylcytosine is a modified nucleobase.

"Active pharmaceutical agent" means the substance or substances in a pharmaceutical composition that provide a therapeutic benefit when administered to an individual. For example, in certain embodiments an antisense oligonucleotide targeted to huntingtin is an active pharmaceutical agent.

"Active target region" or "target region" means a region to which one or more active antisense compounds is targeted. "Active antisense compounds" means antisense compounds that reduce target nucleic acid levels or protein levels.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing a pharmaceutical agent to an individual, and includes, but is not limited to administering by a medical professional and self-administering.

"Amelioration" refers to a lessening of at least one indicator, sign, or symptom of an associated disease, disorder, or condition. The severity of indicators may be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more pharmaceutical agents to an individual. The two or more pharmaceutical agents may be in a single pharmaceutical composition, or may be in separate pharmaceutical compositions. Each of the two or more pharmaceutical agents may be administered through the same or different routes of administration. Co-administration encompasses parallel or sequential administration.

"Complementarity" means the capacity for pairing between nucleobases of a first nucleic acid and a second nucleic acid.

"Contiguous nucleobases" means nucleobases immediately adjacent to each other.

"Diluent" means an ingredient in a composition that lacks pharmacological activity, but is pharmaceutically necessary or desirable. For example, the diluent in an injected composition may be a liquid, e.g. saline solution.

"Dose" means a specified quantity of a pharmaceutical agent provided in a single administration, or in a specified time period. In certain embodiments, a dose may be administered in one, two, or more boluses, tablets, or injections. For example, in certain embodiments where subcutaneous administration is desired, the desired dose requires a volume not easily accommodated by a single injection, therefore, two or more injections may be used to achieve the desired dose. In certain embodiments, the pharmaceutical agent is administered by infusion over an extended period of time or continuously. Doses may be stated as the amount of pharmaceutical agent per hour, day, week, or month.

"Effective amount" means the amount of active pharmaceutical agent sufficient to effectuate a desired physiological outcome in an individual in need of the agent. The effective amount may vary among individuals depending on the health and physical condition of the individual to be treated, the taxonomic group of the individuals to be treated, the formulation of the composition, assessment of the individual's medical condition, and other relevant factors.

"Huntingtin nucleic acid" means any nucleic acid encoding huntingtin. For example, in certain embodiments, a huntingtin nucleic acid includes a DNA sequence encoding huntingtin, an RNA sequence transcribed from DNA encoding huntingtin (including genomic DNA comprising introns and exons), and an mRNA sequence encoding huntingtin. "Huntingtin mRNA" means an mRNA encoding a huntingtin protein.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region may be referred to as a "gap segment" and the external regions may be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Hybridization" means the annealing of complementary nucleic acid molecules. In certain embodiments, complementary nucleic acid molecules include an antisense compound and a target nucleic acid.

"Immediately adjacent" means there are no intervening elements between the immediately adjacent elements.

"Individual" means a human or non-human animal selected for treatment or therapy.

"Internucleoside linkage" refers to the chemical bond between nucleosides.

"Linked nucleosides" means adjacent nucleosides which are bonded together.

"Mismatch" or "non-complementary nucleobase" refers to the case when a nucleobase of a first nucleic acid is not capable of pairing with the corresponding nucleobase of a second or target nucleic acid.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"Naturally occurring internucleoside linkage" means a 3' to 5' phosphodiester linkage.

"Natural sugar moiety" means a sugar found in DNA (2'-H) or RNA (2'-OH).

"Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid may also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleotide" means a nucleoside having a phosphate group covalently linked to the sugar portion of the nucleoside.

"Oligomeric compound" or "oligomer" means a polymer of linked monomeric subunits which is capable of hybridizing to at least a region of a nucleic acid molecule.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical composition" means a mixture of substances suitable for administering to an individual. For example, a pharmaceutical composition may comprise one or more active pharmaceutical agents and a sterile aqueous solution.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum may indicate liver toxicity or liver function abnormality. For example, increased bilirubin may indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of a pharmaceutical agent that provides a therapeutic benefit to an individual.

"Treat" refers to administering a pharmaceutical composition to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds, and compositions for inhibiting huntingtin expression.

Certain embodiments provide antisense compounds targeted to a huntingtin nucleic acid. In certain embodiments, the huntingtin nucleic acid is any of the sequences set forth in GENBANK Accession No. NM_002111.6 (incorporated herein as SEQ ID NO: 1), GENBANK Accession No. NT_006081.17 truncated from nucleotides 462000 to 634000 (incorporated herein as SEQ ID NO: 2), GENBANK Accession No. NM_010414.1 (incorporated herein as SEQ ID NO: 3), the complement of GENBANK Accession No. NW_001109716.1 truncated at nucleotides 698000 to 866000 (incorporated herein as SEQ ID NO: 4), and GENBANK Accession No. NM_024357.2 (incorporated herein as SEQ ID NO: 5).

Certain embodiments provide compounds comprising a modified oligonucleotide consisting of 12 to 30 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the modified oligonucleotide comprises at least 9, at least 10, at least 11, or at least 12 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, or at least 12 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 15 to 25 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the modified oligonucleotide comprises at least 9, at least 10, at least 11, at least 12, at least 13, at least 14 or at least 15 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, at least 12, at least 13, at least 14 or at least 15 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 18 to 21 linked nucleosides wherein the linked nucleosides comprise at least 8 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22, and 32. In certain embodiments, the modified oligonucleotide comprises at least 9, at least 10, at least 11, at least 12, at least 13, at least 14, at least 15, at least 16, at least 17 or at least 18 contiguous nucleobases of a sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32. In certain embodiments, the nucleobase sequences are those recited in SEQ ID NOs: 24, 25, 26, 6, 12, 28, 21, 22, 32, 13. In certain embodiments, the modified oligonucleotide comprises at least 9, at least 10, at least 11, at least 12, at least 13, at least 14, at least 15, at least 16, at least 17, or at least 18 contiguous nucleobases of a sequence selected from among the nucleobase sequences recited in SEQ ID NOs: 12, 22, 28, 30, 32, and 33.

Certain embodiments provide compounds comprising a modified oligonucleotide consisting of 12-30 linked nucleosides wherein the linked nucleosides comprise at least an 8 contiguous nucleobase portion that is complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828, 4928-4947 of SEQ ID NO: 1. In certain embodiments the region is selected from 4384-4403, 4609-4628, 4610-4629, 4860-4877, 4862-4881, 4925-4944, 4928-4947, 4931-4950, 4955-4974, and 5809-5828 of SEQ ID NO: 1. In certain embodiments the region is selected from 4862-4881, 4609-4628, 5809-5828, 5809-5826, 5801-5820, and 4955-4974. In certain embodiments, the modified oligonucleotide has at least a 9, at least a 10, at least an 11, or at least a 12 contiguous nucleobase portion of which is complementary within a region described herein.

Certain embodiments provide compounds comprising a modified oligonucleotide consisting of 15-25 linked nucleosides wherein the linked nucleosides comprise at least an 8 contiguous nucleobase portion that is complementary within the region selected from nucleotides 4384-4403, 4609-4628, 4610-4629, 4860-4877, 4862-4881, 4925-4944, 4928-4947, 4931-4950, 4955-4974, and 5809-5829 of SEQ ID NO: 1. In certain embodiments, the modified oligonucleotide has at least a 9, at least a 10, at least an 11, at least a 12, at least a 13, or at least a 15 contiguous nucleobase portion of which is complementary within a region described herein.

Certain embodiments provide compounds comprising a modified oligonucleotide consisting of 15-25 linked nucleosides wherein the linked nucleosides comprise at least an 8 contiguous nucleobase portion that is complementary within the region selected from nucleotides 4862-4881, 4609-4628, 5809-5828, 5809-5826, 5801-5820, and 4955-4974. In certain embodiments, the modified oligonucleotide has at least a 9, at least a 10, at least an 11, at least a 12, at least a 13, or at least a 15 contiguous nucleobase portion of which is complementary within a region described herein.

Certain embodiments provide compounds comprising a modified oligonucleotide consisting of 18-21 linked nucleosides wherein the linked nucleosides comprise at least an 8 contiguous nucleobase portion that is complementary within the region selected from nucleotides 4384-4403, 4609-4628, 4610-4629, 4860-4877, 4862-4881, 4925-4944, 4928-4947, 4931-4950, 4955-4974, and 5809-5829 of SEQ ID NO: 1. In certain embodiments, the modified oligonucleotide has at least a 9, at least a 10, at least an 11, at least a 12, at least a 13, at least a 14, at least a 15, at least a 16, at least a 17, or at least an 18 contiguous nucleobase portion of which is complementary within a region described herein.

Certain embodiments provide compounds comprising a modified oligonucleotide consisting of 18-21 linked nucleosides wherein the linked nucleosides comprise at least an 8 contiguous nucleobase portion that is complementary within the region selected from nucleotides 4862-4881, 4609-4628, 5809-5828, 5809-5826, 5801-5820, and 4955-4974. In certain embodiments, the modified oligonucleotide has at least a 9, at least a 10, at least an 11, at least a 12, at least a 13, at least a 14, at least a 15, at least a 16, at least a 17, or at least an 18 contiguous nucleobase portion of which is complementary within a region described herein.

In certain embodiments, the modified oligonucleotide consists of a single-stranded modified oligonucleotide.

In certain embodiments, the modified oligonucleotide consists of 20 linked nucleosides.

In certain embodiments, the nucleobase sequence of the modified oligonucleotide is at least 90% complementary over its entire length to a nucleobase sequence of SEQ ID NO: 1, 2, 3, 4 or 5. In certain embodiments, the nucleobase sequence of the modified oligonucleotide is at least 95% complementary over its entire length to a nucleobase sequence of SEQ ID NO: 1, 2, 3, 4 or 5. In certain embodiments, the modified oligonucleotide is at least 99% complementary over its entire length to SEQ ID NO: 1, 2, 3, 4 or 5. In certain embodiments, the nucleobase sequence of the modified oligonucleotide is 100% complementary over its entire length to a nucleobase sequence of SEQ ID NO: 1, 2, 3, 4 or 5.

In certain embodiments, the compound has at least one modified internucleoside linkage. In certain embodiments, the internucleoside linkage is a phosphorothioate internucleoside linkage.

In certain embodiments, the compound has at least one nucleoside comprising a modified sugar. In certain embodiments, the at least one modified sugar is a bicyclic sugar. In certain embodiments, the at least one bicyclic sugar comprises a 4'-CH(CH$_3$)—O—2' bridge. In certain embodiments, the at least one modified sugar comprises a 2'-O-methoxyethyl.

In certain embodiments, the compound comprises at least one at least one tetrahydropyran modified nucleoside wherein a tetrahydropyran ring replaces the furanose ring. In certain embodiments, the at least one tetrahydropyran modified nucleoside has the structure:

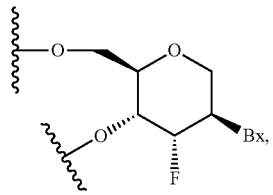

wherein Bx is an optionally protected heterocyclic base moiety.

In certain embodiments, the compound has at least one nucleoside comprising a modified nucleobase. In certain embodiments, the modified nucleobase is a 5-methylcytosine.

In certain embodiments, the modified oligonucleotide of the compound comprises:
(i) a gap segment consisting of linked deoxynucleosides;
(ii) a 5' wing segment consisting of linked nucleosides;
(iii) a 3' wing segment consisting of linked nucleosides, wherein the gap segment is positioned between the 5' wing segment and the 3' wing segment and wherein each nucleoside of each wing segment comprises a modified sugar.

In certain embodiments, the modified oligonucleotide of the compound comprises:
(i) a gap segment consisting of ten linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:
(i) a gap segment consisting of eight linked deoxynucleosides;
(ii) a 5' wing segment consisting of six linked nucleosides;
(iii) a 3' wing segment consisting of six linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

In certain embodiments, the modified oligonucleotide of the compound comprises:
(i) a gap segment consisting of eight linked deoxynucleosides;
(ii) a 5' wing segment consisting of five linked nucleosides;
(iii) a 3' wing segment consisting of five linked nucleosides, wherein the gap segment is positioned immediately adjacent to and between the 5' wing segment and the 3' wing segment, wherein each nucleoside of each wing segment comprises a 2'-O-methoxyethyl sugar; and wherein each internucleoside linkage is a phosphorothioate linkage.

Certain embodiments provide a composition comprising a compound as described herein, or a salt thereof, and a pharmaceutically acceptable carrier or diluent. In certain embodiments, the composition comprises a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32 or a salt thereof and a pharmaceutically acceptable carrier or diluent.

Certain embodiments provide a composition comprising a compound as described herein, or a salt thereof, and a pharmaceutically acceptable carrier or diluent. In certain embodiments, the composition comprises a modified oligonucleotide consisting of 12 to 30 linked nucleosides and having a nucleobase sequence comprising at least 12 contiguous nucleobases of a nucleobase sequence selected from among the nucleobase sequences recited in SEQ ID NOs: 12, 22, 28, 30, 32, and 33 or a salt thereof and a pharmaceutically acceptable carrier or diluent.

Certain embodiments provide methods of treating, preventing, or ameliorating Huntington's disease.

Certain embodiments provide methods comprising administering to an animal a compound as described herein to an animal. In certain embodiments, the method comprises administering to an animal a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 and 32.

Certain embodiments provide methods comprising administering to an animal a compound as described herein to an animal. In certain embodiments, the method comprises administering to an animal a modified oligonucleotide consisting of 12 to 30 linked nucleosides and having a nucleobase sequence comprising at least 8 contiguous nucleobases of a nucleobase sequence selected from among the nucleobase sequences recited in SEQ ID NOs: 12, 22, 28, 30, 32, and 33.

In certain embodiments, the animal is a human.

In certain embodiments, the administering prevents, treats, ameliorates, or slows progression Huntington's disease as described herein.

In certain embodiments, the compound is co-administered with a second agent.

In certain embodiments, the compound and the second agent are administered concomitantly.

In certain embodiments, the administering is parenteral administration. In certain embodiments, the parenteral administration is intracranial administration. In certain embodiments, the intracranial administration is intrathecal or intracerebroventricular administration.

Certain embodiments further provide a method to reduce huntingtin mRNA or protein expression in an animal comprising administering to the animal a compound or composition as described herein to reduce huntingtin mRNA or protein expression in the animal. In certain embodiments, the animal is a human. In certain embodiments, reducing huntingtin mRNA or protein expression prevents, treats, ameliorates, or slows progression of Huntington's disease.

Certain embodiments provide a method for treating a human with Huntington's disease comprising identifying the human with the disease and administering to the human a therapeutically effective amount of a compound or composition as described herein. In certain embodiments, the treatment reduces a symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, sleep disturbances, impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination, dementia, a anxiety, depression, blunted affect, egocentrisms, aggression, compulsive behavior, irritability, suicidal ideation, reduced brain mass, muscle atrophy, cardiac failure, impaired glucose tolerance, weight loss, osteoporosis, and testicular atrophy.

Further provided is a method for reducing or preventing Huntington's disease comprising administering to a human a therapeutically effective amount compound or composition as described herein, thereby reducing or preventing Huntington's disease.

Further provided is a method for ameliorating a symptom of Huntington's disease, comprising administering to a human in need thereof a compound comprising a modified oligonucleotide consisting of 12 to 30 linked nucleosides, wherein said modified oligonucleotide specifically hybridizes to SEQ ID NO:1, 2, 3, 4 or 5, thereby ameliorating a symptom of Huntington's disease in the human.

Further provided is a method for reducing the rate of progression of a symptom associated with Huntington's Disease, comprising administering to a human in need thereof a compound comprising a modified oligonucleotide consisting of 12 to 30 linked nucleosides, wherein said modified oligonucleotide specifically hybridizes to SEQ ID NO: 1, 2, 3, 4 or 5, thereby reducing the rate of progression a symptom of Huntington's disease in the human.

Further provided is a method for reversing degeneration indicated by a symptom associated with Huntington's disease, administering to a human in need thereof a compound comprising a modified oligonucleotide consisting of 12 to 30 linked nucleosides, wherein said modified oligonucleotide specifically hybridizes to SEQ ID NO:1, 2, 3, 4 or 5, thereby reversing degeneration indicated by a symptom of Huntington's disease in the human.

In certain embodiments, the symptom is a physical, cognitive, psychiatric, or peripheral symptom. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

Also provided are methods and compounds for the preparation of a medicament for the treatment, prevention, or amelioration of Huntington's disease.

Certain embodiments provide the use of a compound as described herein in the manufacture of a medicament for treating, ameliorating, or preventing Huntington's disease.

Certain embodiments provide a compound as described herein for use in treating, preventing, or ameliorating Huntington's disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating Huntington's disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating Huntington's disease as described herein in a patient who is subsequently administered an additional agent or therapy as described herein.

Certain embodiments provide a kit for treating, preventing, or ameliorating Huntington's disease as described herein wherein the kit comprises:
(i) a compound as described herein; and alternatively
(ii) an additional agent or therapy as described herein.

A kit as described herein may further include instructions for using the kit to treat, prevent, or ameliorate Huntington's disease as described herein by combination therapy as described herein.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 6, 9, 10, 11, 12, 13, 14, 15, 18, 19, 20, 21, 22, 23, 24, 25, 26, 27, 28, 29, 30, 32, 33, 35, or 36, for use in treating an animal having a disease or condition associated with huntingtin by administering to the animal a therapeutically effective amount of the compound so that expression of huntingtin is inhibited. In certain embodiments, the disease or condition is a neurological disorder. In certain embodiments, the disease or condition is Huntington's Disease. In certain embodiments, the animal is a human.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 6, 9, 10, 11, 12, 13, 14, 15, 18, 19, 20, 21, 22, 23, 24, 25, 26, 27, 28, 29, 30, 32, 33, 35, or 36, for use in an animal having a disease or condition associated with huntingtin by administering to the animal a therapeutically effective amount of the compound to prevent, treat, ameliorate, or slow progression of Huntington's disease.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 12, 22, 28, 30, 32, or 33, for use in an animal having a disease or condition associated with huntingtin by administering to the animal a therapeutically effective amount of the compound so that expression of huntingtin is inhibited. In certain embodiments, the disease or condition is a neurological disorder. In certain embodiments, the disease or condition is Huntington's Disease. In certain embodiments, the animal is a human.

Certain embodiments provide compounds comprising a modified oligonucleotide consisting of 12 to 30 linked nucleosides, wherein the linked nucleosides comprise at least 8, at least 9, at least 10, at least 11, at least 12, at least 13, at least 14, at least 15, at least 16, at least 17, at least 18, at least 19, or at least 20 contiguous nucleobases of a sequence recited in SEQ ID NO: 12, 22, 28, 30, 32, or 33, for use in an animal having a disease or condition associated with huntingtin by administering to the animal a therapeutically effective amount of the compound to prevent, treat, ameliorate, or slow progression of Huntington's disease.

Certain embodiments provide compounds comprising a modified oligonucleotide consisting of 12-30 linked nucleosides, wherein the linked nucleosides at least an 8, at least a 9, at least a 10, at least an 11, at least a 12, at least a 13, at least a 14, at least a 15, at least a 16, at least a 17, at least a 18, at least a 19, or at least a 20 contiguous nucleobase portion complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 and 4928-4947 of SEQ ID NO: 1, for use in an animal having a disease or condition associated with huntingtin by administering to the animal a therapeutically effective amount of the compound so that expression of huntingtin is inhibited.

Certain embodiments provide compounds comprising a modified oligonucleotide consisting of 12-30 linked nucleosides, wherein the linked nucleosides comprise at least an 8, at least a 9, at least a 10, at least an 11, at least a 12, at least a 13, at least a 14, at least a 15, at least a 16, at least a 17, at least a 18, at least a 19, or at least a 20 contiguous nucleobase portion complementary within the region selected from nucleotides 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 and 4928-4947 of SEQ ID NO: 1, for use in an animal having a disease or condition associated with huntingtin by administering to the animal a therapeutically effective amount of the compound to prevent, treat, ameliorate, or slow progression of Huntington's disease.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a huntingtin nucleic acid is 12 to 30 nucleotides in length. In other words, antisense compounds are from 12 to 30 linked nucleobases. In other embodiments, the antisense compound comprises a modified oligonucleotide consisting of 8 to 80, 12 to 50, 15 to 30, 18 to 24, 19 to 22, or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide may have two nucleosides deleted from the 5' end, or alternatively may have two subunits deleted from the 3' end. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside may be located at the 5' or 3' end of the oligonucleotide. When two or more additional nucleosides are present, the added nucleosides may be adjacent to each other, for example, in an oligonucleotide having two nucleosides added to the 5' end (5' addition), or alternatively to the 3' end (3' addition), of the oligonucleotide. Alternatively, the added nucleoside may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a huntingtin nucleic acid have chemically modified subunits arranged in patterns, or motifs, to confer to the antisense compounds properties such as enhanced the inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE, and 2'-O—$CH_3$, among others), and bicyclic sugar modified nucleosides (such bicyclic sugar modified nucleosides may include those having a 4'-$(CH2)n$-O-2' bridge, where n=1 or n=2). Preferably, each distinct region comprises uniform sugar moieties. The wing-gap-wing motif is frequently described as "X-Y-Z", where "X" represents the length of the 5' wing region, "Y" represents the length of the gap region, and "Z" represents the length of the 3' wing region. As used herein, a gapmer described as "X-Y-Z" has a configuration such that the gap segment is positioned immediately adjacent each of the 5' wing segment and the 3' wing segment. Thus, no intervening nucleotides exist between the 5' wing segment and gap segment, or the gap segment and the 3' wing segment. Any of the antisense compounds described herein can have a gapmer motif. In some embodiments, X and Z are the same, in other embodiments they are different. In a preferred embodiment, Y is between 8 and 15 nucleotides. X, Y or Z can be any of 1, 2, 3, 4, 5, 6, 7, 8, 9, 10, 11, 12, 13, 14, 15, 16, 17, 18, 19, 20, 25, 30 or more nucleotides. Thus, gapmers include, but are not limited to, for example 5-10-5, 4-8-4, 4-12-3, 4-12-4, 3-14-3, 2-13-5, 2-16-2, 1-18-1, 3-10-3, 2-10-2, 1-10-1, 2-8-2, 6-8-6 or 5-8-5.

In certain embodiments, the antisense compound as a "wingmer" motif, having a wing-gap or gap-wing configuration, i.e. an X-Y or Y-Z configuration as described above for the gapmer configuration. Thus, wingmer configurations include, but are not limited to, for example 5-10, 8-4, 4-12, 12-4, 3-14, 16-2, 18-1, 10-3, 2-10, 1-10, 8-2, 2-13, or 5-13.

In certain embodiments, antisense compounds targeted to a huntingtin nucleic acid possess a 5-10-5 gapmer motif.

In certain embodiments, antisense compounds targeted to a huntingtin nucleic acid possess a 6-8-6 gapmer motif.

In certain embodiments, antisense compounds targeted to a huntingtin nucleic acid possess a 5-8-5 gapmer motif.

In certain embodiments, an antisense compound targeted to a huntingtin nucleic acid has a gap-widened motif.

In certain embodiments, a gap-widened antisense oligonucleotide targeted to a huntingtin nucleic acid has a gap segment of ten 2'-deoxyribonucleotides positioned immediately adjacent to and between wing segments of five chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a huntingtin nucleic acid has a gap segment of eight 2'-deoxyribonucleotides positioned immediately adjacent to and between wing segments of five chemically modified nucleosides. In certain embodiments, the chemical modification comprises a 2'-sugar modification. In another embodiment, the chemical modification comprises a 2'-MOE sugar modification.

In certain embodiments, a gap-widened antisense oligonucleotide targeted to a huntingtin nucleic acid has a gap segment of eight 2'-deoxyribonucleotides positioned immediately adjacent to and between wing segments of six chemically modified nucleosides. In certain embodiments, the chemical modification comprises a 2'-sugar modification. In another embodiment, the chemical modification comprises a 2'-MOE sugar modification.

Target Nucleic Acids, Target Regions and Nucleotide Sequences

Nucleotide sequences that encode huntingtin include, without limitation, the following: GENBANK Accession No. NM_002111.6, first deposited with GENBANK® on May 31, 2006 incorporated herein as SEQ ID NO: 1; GENBANK Accession No. NT_006081.17 truncated from nucleotides 462000 to 634000, first deposited with GENBANK® on Aug. 19, 2004, and incorporated herein as SEQ ID NO: 2; GENBANK Accession No. NM_010414.1, first deposited with GENBANK® on Mar. 23, 2004, incorporated herein as SEQ ID NO: 3; the complement of GENBANK Accession No. NW_001109716.1 truncated at nucleotides 698000 to 866000, first deposited with GENBANK® on Jun. 14, 2006, incorporated herein as SEQ ID NO: 4, and GENBANK Accession No. NM_024357.2, first deposited with GENBANK® on Jun. 5, 2008, incorporated herein as SEQ ID NO: 5.

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for huntingtin can be obtained by accession number from sequence databases such as NCBI and such information is incorporated herein by reference. In certain embodiments, a target region may encompass the sequence from a 5' target site of one target segment within the target region to a 3' target site of another target segment within the target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain embodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifically exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in huntingtin mRNA levels are indicative of inhibition of huntingtin expression. Reductions in levels of a huntingtin protein are also indicative of inhibition of target mRNA expression. Further, phenotypic changes are indicative of inhibition of huntingtin expression. For example, increase in brain size to normal, improvement in motor coordination, decrease in continual muscular spasms (dystonia), decrease in irritability and/or anxiety, improvement of memory, or an increase in energy, among other phenotypic changes that may be assayed. Other phenotypic indications, e.g., symptoms associated with Huntington's disease, may also be assessed as described below.

Hybridization

In some embodiments, hybridization occurs between an antisense compound disclosed herein and a huntingtin nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a huntingtin nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a huntingtin nucleic acid).

An antisense compound may hybridize over one or more segments of a huntingtin nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a huntingtin nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a huntingtin nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or 20 nucleobases in length comprise no more than 4, no more than 3, no more than 2, or no more than 1 non-complementary nucleobase(s) relative to a target nucleic acid, such as a huntingtin nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a huntingtin nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 15 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a huntingtin nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds can optionally contain one or more nucleosides wherein the sugar group has been modified. Such sugar modified nucleosides may impart enhanced nuclease stability, increased binding affinity or some other beneficial biological property to the antisense compounds. In certain embodiments, nucleosides comprise a chemically modified ribofuranose ring moieties. Examples of chemically modified ribofuranose rings include without limitation, addition of substitutent groups (including 5' and 2' substituent groups, bridging of non-geminal ring atoms to form bicyclic nucleic acids (BNA), replacement of the ribosyl ring oxygen atom with S, N(R), or C(R1)(R)2 (R=H, C1-C12 alkyl or a protecting group) and combinations thereof. Examples of chemically modified sugars include 2'-F-5'-methyl substituted nucleoside (see PCT International Application WO 2008/101157 Published on Aug. 21, 2008 for other disclosed 5',2'-bis substituted nucleosides) or replacement of the ribosyl ring oxygen atom with S with further substitution at the 2'-position (see published U.S. Patent Application US2005-0130923, published on Jun. 16, 2005) or alternatively 5'-substitution of a BNA (see PCT International Application WO 2007/134181 Published on Nov. 22, 2007 wherein LNA is substituted with for example a 5'-methyl or a 5'-vinyl group).

Examples of nucleosides having modified sugar moieties include without limitation nucleosides comprising 5'-vinyl, 5'-methyl (R or S), 4'-S, 2'-F, 2'-OCH3 and 2'-O(CH2) 2OCH3 substituent groups. The substituent at the 2' position can also be selected from allyl, amino, azido, thio, O-allyl, O—C1-C10 alkyl, OCF3, O(CH2)2SCH3, O(CH2)2-O—N (Rm)(Rn), and O—CH2-C(=O)—N(Rm)(Rn), where each Rm and Rn is, independently, H or substituted or unsubstituted C1-C10 alkyl.

Examples of bicyclic nucleic acids (BNAs) include without limitation nucleosides comprising a bridge between the 4' and the 2' ribosyl ring atoms. In certain embodiments, antisense compounds provided herein include one or more BNA nucleosides wherein the bridge comprises one of the formulas: 4'-(CH2)-O-2' (LNA); 4'-(CH2)-S-2'; 4'-(CH2)-O-2' (LNA); 4'-(CH2)2-O-2' (ENA); 4'-C(CH3)2-O-2' (see PCT/US2008/068922); 4'-CH(CH3)-O-2' and 4'-C—H (CH2OCH3)-O-2' (see U.S. Pat. No. 7,399,845, issued on Jul. 15, 2008); 4'-CH2-N(OCH3)-2' (see PCT/US2008/ 064591); 4'-CH2-O—N(CH3)-2' (see published U.S. Patent Application US2004-0171570, published Sep. 2, 2004); 4'-CH2-N(R)—O-2' (see U.S. Pat. No. 7,427,672, issued on Sep. 23, 2008); 4'-CH2-C(CH3)-2' and 4'-CH2-C— (=CH2)-2' (see PCT/US2008/066154); and wherein R is, independently, H, C1-C12 alkyl, or a protecting group. Each of the foregoing BNAs include various stereochemical sugar configurations including for example α-L-ribofuranose and β-D-ribofuranose (see PCT international application PCT/ DK98/00393, published on Mar. 25, 1999 as WO 99/14226).

In certain embodiments, nucleosides are modified by replacement of the ribosyl ring with a sugar surrogate. Such modification includes without limitation, replacement of the ribosyl ring with a surrogate ring system (sometimes referred to as DNA analogs) such as a morpholino ring, a cyclohexenyl ring, a cyclohexyl ring or a tetrahydropyranyl ring such as one having one of the formula:

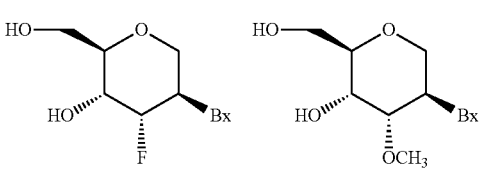

-continued

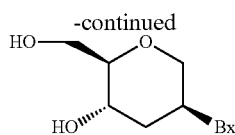

Many other bicyclo and tricyclo sugar surrogate ring systems are also known in the art that can be used to modify nucleosides for incorporation into antisense compounds (see, e.g., review article: Leumann, J. C, *Bioorganic & Medicinal Chemistry*, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified or a combination thereof) are maintained for hybridization with an appropriate nucleic acid target.

In certain embodiments, antisense compounds targeted to a huntingtin nucleic acid comprise one or more nucleotides having modified sugar moieties. In certain embodiments, the modified sugar moiety is 2'-MOE. In certain embodiments, the 2'-MOE modified nucleotides are arranged in a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., *Antisense Research and Applications*, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—CH$_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N-2, N-6 and O-6 substituted purines, including 2 aminopropyladenine, 5-propynyluracil and 5-propynylcytosine.

In certain embodiments, antisense compounds targeted to a huntingtin nucleic acid comprise one or more modified nucleobases. In certain embodiments, gap-widened antisense oligonucleotides targeted to a huntingtin nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a huntingtin nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a huntingtin nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of huntingtin nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a huntingtin nucleic acid can be assayed in a variety of ways known in the art. For example, target nucleic acid levels can be quantitated by, e.g., Northern blot analysis, competitive polymerase chain reaction (PCR), or quantitaive real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a huntingtin nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of huntingtin nucleic acids can be assessed by measuring huntingtin protein levels. Protein levels of huntingtin can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat huntingtin are commercially available.

In Vivo Testing of Antisense Compounds

Antisense compounds, for example, antisense oligonucleotides, are tested in animals to assess their ability to inhibit expression of huntingtin and produce phenotypic changes. Testing may be performed in normal animals, or in experimental disease models. For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in huntingtin nucleic acid expression are measured. Changes in huntingtin protein levels are also measured.

Certain Compounds

About seventeen hundred newly designed antisense compounds of various lengths, motifs and backbone composition were tested for their effect on human huntingtin mRNA in vitro in several cell types. The new compounds were compared with about two hundred and fifty previously designed compounds including ISIS 387916 which had previously been determined to be one of the most potent antisense compounds in vitro (see e.g., U.S. Patent Publication Nos. 2008/0039418 and 2007/0299027. Of the about seventeen hundred newly designed antisense compounds, about sixty compounds were selected for further study based on in vitro potency compared to ISIS 387916. The selected compounds were tested for systemic tolerability (see Example 3) and activity and tolerability in the brain of BACHD mice (see Example 4) compared to previously designed ISIS 388241 and ISIS 387916. From these studies, compounds having a nucleobase sequence of a sequence recited in SEQ ID NO: 6, 9, 10, 11, 12, 13, 14, 15, 18, 19, 20, 21, 23, 24, 25, 26, 27, 28, 29, 30, 32, 33, 35, 36, 10, 11, 12, 13, 18, 22 or 32 were selected as having high tolerability and high in vivo potency. By virtue of their complementary sequence, the compounds are complementary to the regions 4384-4403, 4605-4624, 4607-4626, 4608-4627, 4609-4628, 4610-4629, 4617-4636, 4622-4639, 4813-4832, 4814-4833, 4823-4842, 4860-4877, 4868-4887, 4925-4944, 4928-4947, 4931-4950, 4931-4948, 4955-4974, 4960-4977, 5801-5820, 5809-5828, 5809-5826, 101088-101105, 115066-115085, 4607-4626, 4608-4627, 4609-4628, 4610-4629, 4813-4832, 4862-4881, 5809-5828 or 4928-4947 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by the ISIS NOs: ISIS 419628, ISIS 419637, ISIS 419640, ISIS 419641, ISIS 451541, ISIS 419642, ISIS 436665, ISIS 436671, ISIS 436684, ISIS 436689, ISIS 436754, ISIS 437168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663.

Compounds described above as having high in vivo potency and tolerability were then tested by CNS bolus injection in rat to further assess neurotoxicity (see Example 5) along with several additional compounds having a nucleobase sequence of a sequence recited in SEQ ID NO: 7, 8, 11, 16, 17. Of these, ten compounds having a nucleobase sequence of a sequence recited in SEQ ID NO: 24, 25, 26, 6, 12, 28, 21, 22, 32 or 13 were selected as having high tolerability. By virtue of their complementary sequence, the compounds are complementary to the regions 4384-4403, 4609-4628, 4610-4629, 4860-4877, 4862-4881, 4925-4944, 4928-4947, 4931-4950, 4955-4974, or 5809-5829 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by the ISIS NOs: ISIS 419640, ISIS 419641, ISIS 419642, ISIS 436665, ISIS 436671, ISIS 436689, ISIS 437507, ISIS 443139, ISIS 444591, and ISIS 444661. Selected compounds were compared with previously designed compound ISIS 388241 by ICV administration in BACHD mice.

Additional studies were then run on compounds described above as having high in vivo potency and tolerability. The additional studies were designed to further assess neurotoxicity. Studies included ICV administration in wild-type mouse (see Example 16) and bolus administration in rat (see Example 17). SEQ ID NOs: 12, 22, 28, 30, 32, and 33 were selected as having high neurotolerability. By virtue of their complementary sequence, the compounds are complementary to the regions 4862-4881, 4609-4628, 5809-5828, 5809-5826, 5801-5820, and 4955-4974 of SEQ ID NO: 1. In certain embodiments, the compounds targeting the listed regions, as further described herein, comprise a modified oligonucleotide having some nucleobase portion of the sequence recited in the SEQ ID NOs, as further described herein. In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif as indicated by ISIS 388241, ISIS 443139, ISIS 436671, ISIS 444591, ISIS 437527, ISIS 444584, ISIS 444652, and ISIS 436689.

Accordingly, provided herein are antisense compounds with improved characteristics. In certain embodiments, provided herein are compounds comprising a modified oligonucleotide as further described herein targeted to or specifically hybridizable with the region of nucleotides of SEQ ID NO: 1.

In certain embodiments, the compounds as described herein are efficacious by virtue of having at least one of an in vitro IC50 of less than 7 uM, less than 6 uM, less than 5, uM, less than 4 uM, less than 3 uM, less than 2 uM, less than 1 uM when delivered to a human fibroblast cell line as described herein or an ED50 of less than 10 µg, less than 9 µg, less than 8 µg, less than 7.5 µg, less than 7.4 µg, less than 7.0 µg, less than 6 µg, less than 5 µg, less than 4 µg, less than 3 µg, or less than 2 µg by bolus injection. As described herein, ICV infusion can result in 3 to 4 fold higher ED50 values for the compounds described herein. In certain embodiments, the compounds as described herein are highly tolerable as demonstrated by having at least one of an increase an ALT or AST value of no more than 4 fold, 3 fold, or 2 fold over saline treated animals; an increase in liver, spleen or kidney weight of no more than 30%, 20%, 15%, 12%, 10%, 5% or 2%; or an increase AIF1 levels by no more than 350%, 300%, 275%, 250% 200%, 150% or 100% over control.

Certain Indications

In certain embodiments, provided herein are methods of treating an individual comprising administering one or more pharmaceutical compositions as described herein. In certain embodiments, the individual has Huntington's disease.

As shown in the examples below, compounds targeted to huntingtin as described herein have been shown to reduce the severity of physiological symptoms of Huntington's disease. In certain of the experiments, the compounds reduced rate of degeneration, e.g., the animals continued to experience symptoms, but the symptoms were less severe compared to untreated animals. In other of the experiments, however, the compounds appear to result in regeneration of function over time; e.g., animals treated for a longer period of time experienced less severe symptoms than those administered the compounds for a shorter period of time. As discussed above, Huntington's disease is a degenerative disease with a progression typified by increased severity of symptoms over time. The ability of the compounds exemplified below to restore function therefore demonstrates that symptoms of the disease may be reversed by treatment with a compound as described herein.

Accordingly, provided herein are methods for ameliorating a symptom associated with Huntington's disease in a subject in need thereof. In certain embodiments, provided is a method for reducing the rate of onset of a symptom associated with Huntington's disease. In certain embodiments, provided is a method for reducing the severity of a symptom associated with Huntington's disease. In certain embodiments, provided is a method for regenerating neurological function as shown by an improvement of a symptom associated with Huntington's disease. In such embodiments, the methods comprise administering to an individual in need thereof a therapeutically effective amount of a compound targeted to a huntingtin nucleic acid.

Huntington's disease is characterized by numerous physical, neurological, psychiatric, and/or peripheral symptoms. Any symptom known to one of skill in the art to be associated with Huntington's disease can be ameliorated or otherwise modulated as set forth above in the methods described above. In certain embodiments, the symptom is a physical symptom selected from the group consisting of restlessness, lack of coordination, unintentionally initiated motions, unintentionally uncompleted motions, unsteady gait, chorea, rigidity, writhing motions, abnormal posturing, instability, abnormal facial expressions, difficulty chewing, difficulty swallowing, difficulty speaking, seizure, and sleep disturbances. In certain embodiments, the symptom is a cognitive symptom selected from the group consisting of impaired planning, impaired flexibility, impaired abstract thinking, impaired rule acquisition, impaired initiation of appropriate actions, impaired inhibition of inappropriate actions, impaired short-term memory, impaired long-term memory, paranoia, disorientation, confusion, hallucination and dementia. In certain embodiments, the symptom is a psychiatric symptom selected from the group consisting of anxiety, depression, blunted affect, egocentrisms, aggression, compulsive behavior, irritability and suicidal ideation. In certain embodiments, the symptom is a peripheral symptom selected from the group consisting of reduced brain mass, muscle atrophy, cardiac failure, impaired glucose tolerance, weight loss, osteoporosis, and testicular atrophy.

In certain embodiments, the symptom is restlessness. In certain embodiments, the symptom is lack of coordination. In certain embodiments, the symptom is unintentionally initiated motions. In certain embodiments, the symptom is unintentionally uncompleted motions. In certain embodiments, the symptom is unsteady gait. In certain embodiments, the symptom is chorea. In certain embodiments, the symptom is rigidity. In certain embodiments, the symptom is writhing motions. In certain embodiments, the symptom is abnormal posturing. In certain embodiments, the symptom is instability. In certain embodiments, the symptom is abnormal facial expressions. In certain embodiments, the symptom is difficulty chewing. In certain embodiments, the symptom is difficulty swallowing. In certain embodiments, the symptom is difficulty speaking. In certain embodiments, the symptom is seizures. In certain embodiments, the symptom is sleep disturbances.

In certain embodiments, the symptom is impaired planning. In certain embodiments, the symptom is impaired flexibility. In certain embodiments, the symptom is impaired abstract thinking. In certain embodiments, the symptom is impaired rule acquisition. In certain embodiments, the symptom is impaired initiation of appropriate actions. In certain embodiments, the symptom is impaired inhibition of inappropriate actions. In certain embodiments, the symptom is impaired short-term memory. In certain embodiments, the symptom is impaired long-term memory. In certain embodiments, the symptom is paranoia. In certain embodiments, the symptom is disorientation. In certain embodiments, the symptom is confusion. In certain embodiments, the symptom is hallucination. In certain embodiments, the symptom is dementia.

In certain embodiments, the symptom is anxiety. In certain embodiments, the symptom is depression. In certain embodiments, the symptom is blunted affect. In certain embodiments, the symptom is egocentrism. In certain embodiments, the symptom is aggression. In certain embodiments, the symptom is compulsive behavior. In certain embodiments, the symptom is irritability. In certain embodiments, the symptom is suicidal ideation.

In certain embodiments, the symptom is reduced brain mass. In certain embodiments, the symptom is muscle atrophy. In certain embodiments, the symptom is cardiac failure. In certain embodiments, the symptom is impaired glucose tolerance. In certain embodiments, the symptom is weight loss. In certain embodiments, the symptom is osteoporosis. In certain embodiments, the symptom is testicular atrophy.

In certain embodiments, symptoms of Huntington's disease may be quantifiable. For example, osteoporosis may be measured and quantified by, for example, bone density scans. For such symptoms, in certain embodiments, the symptom may be reduced by about 15, 20, 25, 30, 35, 40, 45, 50, 55, 60, 65, 70, 75, 80, 85, 90, 95 or 99%, or a range defined by any two of these values.

In certain embodiments, provided are methods of treating an individual comprising administering one or more pharmaceutical compositions as described herein. In certain embodiments, the individual has Huntington's disease.

In certain embodiments, administration of an antisense compound targeted to a huntingtin nucleic acid results in reduction of huntingtin expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to huntingtin are used for the preparation of a medicament for treating a patient suffering or susceptible to Huntington's disease.

In certain embodiments, the methods described herein include administering a compound comprising a modified oligonucleotide having a contiguous nucleobases portion as described herein of a sequence recited in SEQ ID NO: 6, 9, 10, 11, 12, 13, 14, 15, 18, 19, 20, 21, 22, 23, 24, 25, 26, 27, 28, 29, 30, 32, 33, 35, 36, 10, 11, 12, 13, 18, 22 or 32. In certain embodiments, the methods described herein include administering a compound comprising a modified oligonucleotide having a contiguous nucleobases portion as described herein of a sequence recited in SEQ ID NOs: 12, 22, 28, 30, 32, and 33.

Administration

In certain embodiments, the compounds and compositions as described herein are administered parenterally.

In certain embodiments, parenteral administration is by infusion. Infusion can be chronic or continuous or short or intermittent. In certain embodiments, infused pharmaceutical agents are delivered with a pump. In certain embodiments, parenteral administration is by injection.

In certain embodiments, compounds and compositions are delivered to the CNS. In certain embodiments, compounds and compositions are delivered to the cerebrospinal fluid. In certain embodiments, compounds and compositions are administered to the brain parenchyma. In certain embodiments, compounds and compositions are delivered to an animal by intrathecal administration, or intracerebroventricular administration. Broad distribution of compounds and compositions, described herein, within the central nervous system may be achieved with intraparenchymal administration, intrathecal administration, or intracerebroventricular administration.

In certain embodiments, parenteral administration is by injection. The injection may be delivered with a syringe or a pump. In certain embodiments, the injection is a bolus injection. In certain embodiments, the injection is administered directly to a tissue, such as striatum, caudate, cortex, hippocampus and cerebellum.

The median effective concentration ($EC_{50}$) of an antisense compounds for inhibiting huntingtin mRNA expression was calculated after either ICV infusion or bolus injection (see Examples 9 and 10). The $EC_{50}$ for the compound after intrastriatal injection was determined to be 0.45 μg/g. The $EC_{50}$ after ICV administration was determined to be 26.4 μg/g.

Therefore, in certain embodiments, delivery of a compound or composition described herein can affect the pharmacokinetic profile of the compound or composition. In certain embodiments, injection of a compound or composition described herein, to a targeted tissue improves the pharmacokinetic profile of the compound or composition as compared to infusion of the compound or composition. In a certain embodiment, the injection of a compound or composition improves potency compared to broad diffusion, requiring less of the compound or composition to achieve similar pharmacology. In certain embodiments, similar pharmacology refers to the amount of time that a target mRNA and/or target protein is down-regulated (e.g. duration of action). In certain embodiments, methods of specifically localizing a pharmaceutical agent, such as by bolus injection, decreases median effective concentration (EC50) by a factor of about 50 (e.g. 50 fold less concentration in tissue is required to achieve the same or similar pharmacodynamic effect). In certain embodiments, methods of specifically localizing a pharmaceutical agent, such as by bolus injection, decreases median effective concentration (EC50) by a factor of 20, 25, 30, 35, 40, 45 or 50. In certain embodiments the pharmaceutical agent in an antisense compound as further described herein. In certain embodiments, the targeted tissue is brain tissue. In certain embodiments the targeted tissue is striatal tissue. In certain embodiments, decreasing EC50 is desirable because it reduces the dose required to achieve a pharmacological result in a patient in need thereof.

The half-life of MOE gapmer oligonucleotides in brain tissue is about 20 days (see Examples 9-11). The duration of action as measured by inhibition of huntingtin mRNA is prolonged in the brain (see Examples 9 and 10). Intracerebroventricular infusion of antisense oligonucleotides for 2 weeks results in inhibition of huntingtin mRNA by at least 50% in striatal tissue of BACHD mice for at least 91 days after termination of dosing. Administration by bolus injection resulted in a similar duration of action.

In certain embodiments, delivery of a compound or composition, as described herein, to the CNS results in 47% down-regulation of a target mRNA and/or target protein for at least 91 days. In certain embodiments, delivery of a compound or composition results in at least 25%, at least 30%, at least 35%, at least 40%, at least 45%, at least 50%, at least 55%, at least 60%, at least 65%, at least 70%, or at least 75% down-regulation of a target mRNA and/or target protein for at least 20 days, at least 30 days, at least 40 days, at least 50 days, at least 60 days, at least 70 days, at least 80 days, at least 85 days, at least 90 days, at least 95 days, at least 100 days, at least 110 days, at least 120 days. In certain embodiments, delivery to the CNS is by intraparenchymal administration, intrathecal administration, or intracerebroventricular administration.

In certain embodiments, an antisense oligonucleotide is delivered by injection or infusion once every month, every two months, every 90 days, every 3 months, every 6 months, twice a year or once a year.

Certain Combination Therapies

In certain embodiments, one or more pharmaceutical compositions are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, one or more pharmaceutical compositions and one or more other pharmaceutical agents are administered at the same time. In certain embodiments, one or more pharmaceutical compositions and one or more other pharmaceutical agents are administered at different times. In certain embodiments, one or more pharmaceutical compositions and one or more other pharmaceutical agents are prepared together in a single formulation. In certain embodiments, one or more pharmaceutical compositions and one or more other pharmaceutical agents are prepared separately.

In certain embodiments, pharmaceutical agents that may be co-administered with a pharmaceutical composition of include antipsychotic agents, such as, e.g., haloperidol, chlorpromazine, clozapine, quetapine, and olanzapine; antidepressant agents, such as, e.g., fluoxetine, sertraline hydrochloride, venlafaxine and nortriptyline; tranquilizing agents such as, e.g., benzodiazepines, clonazepam, paroxetine, venlafaxin, and beta-blockers; mood-stabilizing agents such as, e.g., lithium, valproate, lamotrigine, and carbamazepine; paralytic agents such as, e.g., Botulinum toxin; and/or other experimental agents including, but not limited to, tetrabenazine (Xenazine), creatine, conezyme Q10, trehalose, docosahexanoic acids, ACR16, ethyl-EPA, atomoxetine, citalopram, dimebon, memantine, sodium phenylbutyrate, rameleton, ursodiol, zyprexa, xenasine, tiapride, riluzole, amantadine, [123I]MNI-420, atomoxetine, tetrabenazine, digoxin, detromethorphan, warfarin, alprozam, ketoconazole, omeprazole, and minocycline.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references recited in the present application is incorporated herein by reference in its entirety.

Example 1: Antisense Oligonucleotides Targeted to Human Huntingtin Gene Sequences About seventeen hundred newly designed antisense compounds of various lengths, motifs and backbone composition targeting the human huntingtin gene sequence were tested for their effect on human huntingtin mRNA in vitro in several cell types. These gapmers were further designed with internucleoside linkages that are either only phosphorothioate linkages (described in Table 1) or that are phosphorothioate and phosphodiester linkages (described in Table 5). A number of the newly designed oligos and two benchmark oligonucleotides (previously designed and disclosed) are provided in Tables 1 and 5.

Gapmers with Fully Phosphorothioate Internucleoside Linkages

Certain of the compounds presented in Table 1 have a motif of 5-10-5 MOE, 6-8-6 MOE, or 5-8-5 MOE. The 5-10-5 gapmers have twenty linked nucleosides, wherein the central gap segment has ten 2'-deoxynucleosides and is flanked on both sides (in the 5' and 3' directions) by wings having five nucleosides each. The 6-8-6 gapmer has twenty linked nucleosides, wherein the central gap segment has eight 2'-deoxynucleosides and is flanked on both sides (in the 5' and 3' directions) by wings having six nucleosides each. The 5-8-5 gapmers have eighteen linked nucleosides, wherein the central gap segment has eight 2'-deoxynucleosides and is flanked on both sides (in the 5' and 3' directions) by wings having five nucleosides each. For all gapmers listed in Table 1, each nucleoside in the 5' wing segment and each nucleoside in the 3' wing segment has a 2'-MOE modification. The internucleoside linkages throughout each gapmer are phosphorothioate (P=S) internucleoside linkages. All cytosines throughout each gapmer are 5-methylcytosines. Each gapmer in Table 1 is targeted to SEQ ID NO: 1 (GENBANK Accession No. NM_002111.6) or SEQ ID NO: 2 (GENBANK Accession No. NT_006081.17 truncated from nucleotides 462000 to 634000). 'Start site' indicates the 5'-most nucleotide to which the gapmer is targeted in the human gene sequence. 'Stop site' indicates the 3'-most nucleotide to which the gapmer is targeted in the human gene sequence.

TABLE 1

Chimeric antisense oligonucleotides with phosphorothioate internucleoside linkages targeting human huntingtin gene sequences (SEQ ID NOs: 1 and 2)

| Start Site | Stop Site | Target SEQ ID NO. | ISIS No. | Sequence (5' to 3') | Motif | SEQ ID NO. |
|---|---|---|---|---|---|---|
| 4384 | 4403 | 1 | 436665 | TAGCATTCTTATCTGCACGG | 5-10-5 | 6 |
| 4511 | 4530 | 1 | 436668 | ACCCGTAACTGAACCAGCTG | 5-10-5 | 7 |
| 4599 | 4618 | 1 | 419627 | TTCCCTGAACTGGCCCACTT | 5-10-5 | 8 |
| 4605 | 4624 | 1 | 419628 | CTCTGATTCCCTGAACTGGC | 5-10-5 | 9 |
| 4607 | 4626 | 1 | 444607 | GCCTCTGATTCCCTGAACTG | 5-10-5 | 10 |
| 4608 | 4627 | 1 | 419629 | TGCCTCTGATTCCCTGAACT | 5-10-5 | 11 |
| 4608 | 4627 | 1 | 444578 | TGCCTCTGATTCCCTGAACT | 6-8-6 | 11 |
| 4609 | 4628 | 1 | 436671 | TTGCCTCTGATTCCCTGAAC | 5-10-5 | 12 |
| 4610 | 4629 | 1 | 444608 | ATTGCCTCTGATTCCCTGAA | 5-10-5 | 13 |

TABLE 1-continued

Chimeric antisense oligonucleotides with phosphorothioate
internucleoside linkages targeting human huntingtin gene sequences
(SEQ ID NOs: 1 and 2)

| Start Site | Stop Site | Target SEQ ID NO. | ISIS No. | Sequence (5' to 3') | Motif | SEQ ID NO. |
|---|---|---|---|---|---|---|
| 4617 | 4636 | 1 | 444615 | TGGAATGATTGCCTCTGATT | 5-10-5 | 14 |
| 4622 | 4639 | 1 | 437168 | GTTTGGAATGATTGCCTC | 5-8-5 | 15 |
| 4679 | 4698 | 1 | 419630 | CCAATGATCTGTTTTGAATG | 5-10-5 | 16 |
| 4733 | 4752 | 1 | 419636 | GCCTTCCTTCCACTGGCCAT | 5-10-5 | 17 |
| 4813 | 4832 | 1 | 444618 | CTGCATCAGCTTTATTTGTT | 5-10-5 | 18 |
| 4814 | 4833 | 1 | 419637 | CCTGCATCAGCTTTATTTGT | 5-10-5 | 19 |
| 4823 | 4842 | 1 | 444627 | AGCTCTTTTCCTGCATCAGC | 5-10-5 | 20 |
| 4860 | 4877 | 1 | 437507 | GTAACATTGACACCACCA | 5-8-5 | 21 |
| 4862 | 4881 | 1 | 388241 | CTCAGTAACATTGACACCAC | 5-10-5 | 22 |
| 4868 | 4887 | 1 | 436684 | ATGAGTCTCAGTAACATTGA | 5-10-5 | 23 |
| 4925 | 4944 | 1 | 419640 | TCCTTGTGGCACTGCTGCAG | 5-10-5 | 24 |
| 4928 | 4947 | 1 | 419641 | TTCTCCTTGTGGCACTGCTG | 5-10-5 | 25 |
| 4931 | 4950 | 1 | 419642 | TCATTCTCCTTGTGGCACTG | 5-10-5 | 26 |
| 4931 | 4948 | 1 | 437442 | ATTCTCCTTGTGGCACTG | 5-8-5 | 27 |
| 4955 | 4974 | 1 | 436689 | CGAGACAGTCGCTTCCACTT | 5-8-5 | 28 |
| 4960 | 4977 | 1 | 437175 | TGTCGAGACAGTCGCTTC | 5-8-5 | 29 |
| 5801 | 5820 | 1 | 444584 | TTGCACATTCCAAGTTTGGC | 5-10-5 | 30 |
| 5807 | 5826 | 1 | 387916 | TCTCTATTGCACATTCCAAG | 5-10-5 | 31 |
| 5809 | 5828 | 1 | 444591 | TTTCTCTATTGCACATTCCA | 5-10-5 | 32 |
| 5809 | 5826 | 1 | 437527 | TCTCTATTGCACATTCCA | 5-8-5 | 33 |
| 1446 | 1465 | 2 | 388817 | GCAGGGTTACCGCCATCCCC | 5-10-5 | 34 |
| 101088 | 101105 | 2 | 437441 | ACCTTATCTGCACGGTTC | 5-8-5 | 35 |
| 115066 | 115085 | 2 | 436754 | CTCTCTGTGTATCACCTTCC | 5-10-5 | 36 |

The complementarity of the gapmers in Table 1 with mouse, rhesus monkey and rat huntingtin gene sequences is further described in Tables 2, 3, and 4.

The gapmers of Table 2 are complementary with mouse huntingtin mRNA (GENBANK Accession No. NM_010414.1, designated herein as SEQ ID NO: 3). 'Mouse target start site' indicates the 5'-most nucleotide to which the gapmer is targeted in the mouse mRNA. 'Mouse target stop site' indicates the 3'-most nucleotide to which the gapmer is targeted in the mouse mRNA. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the mouse mRNA sequence.

TABLE 2

Complementarity of antisense oligonucleotides having phosphorothioate linkages with murine mRNA (SEQ ID NO: 3)

| Human Start Site | Human Stop Site | Human Target SEQ ID NO. | ISIS No. | Mouse Start Site | Mouse Stop Site | No. of mis-matches | SEQ ID NO. |
|---|---|---|---|---|---|---|---|
| 4384 | 4403 | 1 | 436665 | 4343 | 4362 | 0 | 6 |
| 4511 | 4530 | 1 | 436668 | 4470 | 4489 | 1 | 7 |
| 4599 | 4618 | 1 | 419627 | 4558 | 4577 | 0 | 8 |
| 4605 | 4624 | 1 | 419628 | 4564 | 4583 | 0 | 9 |
| 4607 | 4626 | 1 | 444607 | 4566 | 4585 | 0 | 10 |
| 4608 | 4627 | 1 | 419629 | 4567 | 4586 | 0 | 11 |
| 4608 | 4627 | 1 | 444578 | 4567 | 4586 | 0 | 11 |
| 4609 | 4628 | 1 | 436671 | 4568 | 4587 | 0 | 12 |
| 4610 | 4629 | 1 | 444608 | 4569 | 4588 | 0 | 13 |
| 4617 | 4636 | 1 | 444615 | 4576 | 4595 | 1 | 14 |
| 4622 | 4639 | 1 | 437168 | 4581 | 4598 | 2 | 15 |
| 4679 | 4698 | 1 | 419630 | 4638 | 4657 | 0 | 16 |

TABLE 2-continued

Complementarity of antisense oligonucleotides having phosphorothioate linkages with murine mRNA (SEQ ID NO: 3)

| Human Start Site | Human Stop Site | Human Target SEQ ID NO. | ISIS No. | Mouse Start Site | Mouse Stop Site | No. of mis-matches | SEQ ID NO. |
|---|---|---|---|---|---|---|---|
| 4733 | 4752 | 1 | 419636 | 4692 | 4711 | 0 | 17 |
| 4813 | 4832 | 1 | 444618 | 4772 | 4791 | 0 | 18 |
| 4814 | 4833 | 1 | 419637 | 4773 | 4792 | 0 | 19 |
| 4823 | 4842 | 1 | 444627 | 4782 | 4801 | 1 | 20 |
| 4925 | 4944 | 1 | 419640 | 4884 | 4903 | 0 | 24 |
| 4928 | 4947 | 1 | 419641 | 4887 | 4906 | 0 | 25 |
| 4931 | 4950 | 1 | 419642 | 4890 | 4909 | 0 | 26 |
| 4931 | 4948 | 1 | 437442 | 4890 | 4907 | 0 | 27 |
| 4955 | 4974 | 1 | 436689 | 4914 | 4933 | 3 | 28 |
| 5807 | 5826 | 1 | 387916 | 5763 | 5782 | 1 | 31 |
| 5809 | 5826 | 1 | 437527 | 5765 | 5782 | 1 | 33 |
| 5809 | 5828 | 1 | 444591 | 5765 | 5784 | 1 | 32 |
| 101088 | 101105 | 2 | 437441 | 4340 | 4357 | 2 | 35 |

The gapmers of Table 3 are complementary with the rhesus monkey huntingtin genomic sequence (the complement of GENBANK Accession No. NW_001109716.1 truncated at nucleotides 698000 to 866000, designated herein as SEQ ID NO: 4). 'Rhesus monkey target start site' indicates the 5'-most nucleotide to which the gapmer is targeted in the rhesus monkey gene sequence. 'Rhesus monkey target stop site' indicates the 3'-most nucleotide to which the gapmer is targeted in the rhesus monkey gene sequence. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the rhesus monkey gene sequence.

TABLE 3

Complementarity of antisense oligonucleotides having phosphorothioate linkages with rhesus monkey gene sequence (SEQ ID NO: 4)

| Human Start Site | Human Stop Site | Human Target SEQ ID NO. | ISIS No. | Rhesus monkey Start Site | Rhesus monkey Stop Site | No. of mis-matches | SEQ ID NO. |
|---|---|---|---|---|---|---|---|
| 4511 | 4530 | 1 | 436665 | 98182 | 98201 | 0 | 6 |
| 4599 | 4618 | 1 | 419627 | 101353 | 101372 | 1 | 8 |
| 4609 | 4628 | 1 | 436671 | 102256 | 102275 | 3 | 12 |
| 4610 | 4629 | 1 | 444608 | 102257 | 102276 | 2 | 13 |
| 4617 | 4636 | 1 | 444615 | 102264 | 102283 | 0 | 14 |
| 4622 | 4639 | 1 | 437168 | 102269 | 102286 | 0 | 15 |
| 4679 | 4698 | 1 | 419630 | 102326 | 102345 | 0 | 16 |
| 4733 | 4752 | 1 | 419636 | 102380 | 102399 | 0 | 17 |
| 4813 | 4832 | 1 | 444618 | 105030 | 105049 | 0 | 18 |
| 4814 | 4833 | 1 | 419637 | 105031 | 105050 | 0 | 19 |
| 4823 | 4842 | 1 | 444627 | 105040 | 105059 | 0 | 20 |
| 4860 | 4877 | 1 | 437507 | 105077 | 105094 | 1 | 21 |
| 4862 | 4881 | 1 | 388241 | 105079 | 105098 | 1 | 22 |
| 4868 | 4887 | 1 | 436684 | 105085 | 105104 | 0 | 23 |
| 4925 | 4944 | 1 | 419640 | 106844 | 106863 | 0 | 24 |
| 4928 | 4947 | 1 | 419641 | 106847 | 106866 | 0 | 25 |
| 4931 | 4950 | 1 | 419642 | 106850 | 106869 | 0 | 26 |
| 4931 | 4948 | 1 | 437442 | 106850 | 106867 | 0 | 27 |
| 4955 | 4974 | 1 | 436689 | 106874 | 106893 | 0 | 28 |
| 4960 | 4977 | 1 | 437175 | 106879 | 106896 | 0 | 29 |
| 5801 | 5820 | 1 | 444584 | 125331 | 125350 | 0 | 30 |
| 5807 | 5826 | 1 | 387916 | 125337 | 125356 | 0 | 31 |
| 5809 | 5826 | 1 | 437527 | 125339 | 125356 | 0 | 33 |
| 5809 | 5828 | 1 | 444591 | 125339 | 125358 | 0 | 32 |
| 101088 | 101105 | 2 | 437441 | 97904 | 97921 | 0 | 35 |
| 115066 | 115085 | 2 | 436754 | 110518 | 110537 | 0 | 36 |

The gapmers of Table 4 are complementary with rat huntingtin mRNA (GENBANK Accession No. NM_024357.2, designated herein as SEQ ID NO: 5). 'Rat target start site' indicates the 5'-most nucleotide to which the gapmer is targeted in the rat mRNA. 'Rat target stop site' indicates the 3'-most nucleotide to which the gapmer is targeted in the rat mRNA. 'Human Target Start Site' indicates the 5'-most nucleotide to which the gapmer is targeted in the human gene sequence. 'Human Target Stop Site' indicates the 3'-most nucleotide to which the gapmer is targeted in the human gene sequence. 'Number of mismatches' indicates the number of mismatches between the human oligonucleotide and the rat mRNA sequence.

TABLE 4

Complementarity of antisense oligonucleotides having phosphorothioate linkages with rat mRNA (SEQ ID NO: 5)

| Human Start Site | Human Stop Site | Human Target SEQ ID NO. | ISIS No. | Rat Start Site | Rat Stop Site | No. of mismatches | SEQ ID NO. |
|---|---|---|---|---|---|---|---|
| 4384 | 4403 | 1 | 436665 | 4343 | 4362 | 1 | 6 |
| 4511 | 4530 | 1 | 436668 | 4470 | 4489 | 1 | 7 |
| 4599 | 4618 | 1 | 419627 | 4558 | 4577 | 0 | 8 |
| 4605 | 4624 | 1 | 419628 | 4564 | 4583 | 0 | 9 |
| 4607 | 4626 | 1 | 444607 | 4566 | 4585 | 0 | 10 |
| 4608 | 4627 | 1 | 419629 | 4567 | 4586 | 0 | 11 |
| 4608 | 4627 | 1 | 444578 | 4567 | 4586 | 0 | 11 |
| 4609 | 4628 | 1 | 436671 | 4568 | 4587 | 0 | 12 |
| 4610 | 4629 | 1 | 444608 | 4569 | 4588 | 0 | 13 |
| 4617 | 4636 | 1 | 444615 | 4576 | 4595 | 1 | 14 |
| 4622 | 4639 | 1 | 437168 | 4581 | 4598 | 2 | 15 |
| 4679 | 4698 | 1 | 419630 | 4638 | 4657 | 0 | 16 |
| 4733 | 4752 | 1 | 419636 | 4692 | 4711 | 0 | 17 |
| 4813 | 4832 | 1 | 444618 | 4772 | 4791 | 0 | 18 |
| 4814 | 4833 | 1 | 419637 | 4773 | 4792 | 0 | 19 |
| 4823 | 4842 | 1 | 444627 | 4782 | 4801 | 1 | 20 |
| 4925 | 4944 | 1 | 419640 | 4884 | 4903 | 1 | 24 |
| 4928 | 4947 | 1 | 419641 | 4887 | 4906 | 1 | 25 |
| 4931 | 4950 | 1 | 419642 | 4890 | 4909 | 1 | 26 |
| 4931 | 4948 | 1 | 437442 | 4890 | 4907 | 1 | 27 |
| 4955 | 4974 | 1 | 436689 | 4914 | 4933 | 3 | 28 |
| 5801 | 5820 | 1 | 444584 | 5757 | 5776 | 3 | 30 |
| 5807 | 5826 | 1 | 387916 | 5763 | 5782 | 0 | 31 |
| 5809 | 5826 | 1 | 437527 | 5765 | 5782 | 0 | 33 |
| 5809 | 5828 | 1 | 444591 | 5765 | 5784 | 0 | 32 |
| 101088 | 101105 | 2 | 437441 | 4340 | 4357 | 2 | 35 |

Gapmers with Mixed Phosphorothioate and Phosphodiester Internucleoside Linkages

The chimeric antisense oligonucleotides in Table 5 were designed as 5-10-5 MOE gapmers. The 5-10-5 gapmers have twenty linked nucleosides, wherein the central gap segment has ten 2'-deoxynucleotides and is flanked on both sides (in the 5' and 3' directions) by wings having five nucleosides each. Each nucleoside in the 5' wing segment and each nucleoside in the 3' wing segment has a 2'-MOE modification. The internucleoside linkages within the central gap segment, the linkages connecting the gap segment to the 5' or 3' wing segment, and the linkages for the 5'-most and 3'-most nucleosides of each wing segments are all phosphorothioate (P=S) linkages; the internucleoside linkages connecting the rest of the nucleosides of both the 5' and 3' wing segments are phosphodiester linkages; i.e. the gapmer has a mixed backbone. All cytosines throughout each gapmer are 5-methylcytosines. Each gapmer in Table 5 is targeted to the human mRNA sequence (GENBANK Accession No. NM_002111.6, designated herein as SEQ ID NO: 1). 'Start site' indicates the 5'-most nucleotide to which the gapmer is targeted in the human mRNA. 'Stop site' indicates the 3'-most nucleotide to which the gapmer is targeted in the human mRNA.

TABLE 5

Chimeric antisense oligonucleotides with phosphorothioate and phosphate internucleoside linkages targeting human huntingtin mRNA (SEQ ID NO: 1)

| Start Site | Stop Site | Target SEQ ID NO. | ISIS No. | Sequence (5' to 3') | Motif | SEQ ID NO. |
|---|---|---|---|---|---|---|
| 4607 | 4626 | 1 | 444658 | GCCTCTGATTCCCTGAACTG | 5-10-5 | 10 |
| 4608 | 4627 | 1 | 444659 | TGCCTCTGATTCCCTGAACT | 5-10-5 | 11 |
| 4609 | 4628 | 1 | 444660 | TTGCCTCTGATTCCCTGAAC | 5-10-5 | 12 |
| 4610 | 4629 | 1 | 444661 | ATTGCCTCTGATTCCCTGAA | 5-10-5 | 13 |
| 4813 | 4832 | 1 | 444663 | CTGCATCAGCTTTATTTGTT | 5-10-5 | 18 |
| 4862 | 4881 | 1 | 443139 | CTCAGTAACATTGACACCAC | 5-10-5 | 22 |
| 5809 | 5828 | 1 | 444652 | TTTCTCTATTGCACATTCCA | 5-10-5 | 32 |
| 4928 | 4947 | 1 | 451541 | TTCTCCTTGTGGCACTGCTG | 5-10-5 | 25 |

The complementarity of the gapmers in Table 5 with mouse, rhesus monkey and rat huntingtin gene sequences are further described in Tables 6, 7, and 8.

The gapmers of Table 6 are complementary with mouse huntingtin mRNA (GENBANK Accession No. NM_010414.1; SEQ ID NO: 3). 'Mouse target start site' indicates the 5'-most nucleotide to which the gapmer is targeted in the mouse mRNA. 'Mouse target stop site' indicates the 3'-most nucleotide to which the gapmer is targeted in the mouse mRNA. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the mouse mRNA sequence.

TABLE 6

Complementarity of antisense oligonucleotides having mixed phosphorothioate and phosphate linkages with murine mRNA (SEQ ID NO: 3)

| Human Start Site | Human Stop Site | Human Target SEQ ID NO. | ISIS No. | Mouse Start Site | Mouse Stop Site | No. of mismatches | SEQ ID NO. |
|---|---|---|---|---|---|---|---|
| 4607 | 4626 | 1 | 444658 | 4566 | 4585 | 0 | 10 |
| 4608 | 4627 | 1 | 444659 | 4567 | 4586 | 0 | 11 |
| 4609 | 4628 | 1 | 444660 | 4568 | 4587 | 0 | 12 |
| 4610 | 4629 | 1 | 444661 | 4569 | 4588 | 0 | 13 |
| 4813 | 4832 | 1 | 444663 | 4772 | 4791 | 0 | 18 |
| 5809 | 5828 | 1 | 444652 | 5765 | 5784 | 1 | 32 |

The gapmers of Table 7 are complementary with the rhesus monkey huntingtin genomic sequence (the complement of GENBANK Accession No. NW_001109716.1 truncated at nucleotides 698000 to 866000; SEQ ID NO: 4). 'Rhesus monkey target start site' indicates the 5'-most nucleotide to which the gapmer is targeted in the rhesus monkey gene sequence. 'Rhesus monkey target stop site' indicates the 3'-most nucleotide to which the gapmer is targeted in the rhesus monkey gene sequence. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the rhesus monkey gene sequence.

TABLE 7

Complementarity of antisense oligonucleotides having mixed phosphorothioate and phosphate linkages with rhesus monkey gene sequence (SEQ ID NO: 4)

| Human Start Site | Human Stop Site | Human Target SEQ ID NO. | ISIS No. | Rhesus monkey Start Site | Rhesus monkey Stop Site | No. of mismatches | SEQ ID NO. |
|---|---|---|---|---|---|---|---|
| 4609 | 4628 | 1 | 444660 | 102256 | 102275 | 3 | 12 |
| 4610 | 4629 | 1 | 444661 | 102257 | 102276 | 2 | 13 |
| 4813 | 4832 | 1 | 444663 | 105030 | 105049 | 0 | 18 |
| 4862 | 4881 | 1 | 443139 | 105079 | 105098 | 1 | 22 |
| 5809 | 5828 | 1 | 444652 | 125339 | 125358 | 0 | 32 |

The gapmers of Table 8 are complementary with rat huntingtin mRNA (GENBANK Accession No. NM_024357.2; SEQ ID NO: 5). 'Rat target start site' indicates the 5'-most nucleotide to which the gapmer is targeted in the rat mRNA. 'Rat target stop site' indicates the 3'-most nucleotide to which the gapmer is targeted in the rat mRNA. 'Human Target Start Site' indicates the 5'-most nucleotide to which the gapmer is targeted in the human mRNA (GENBANK Accession No. NM_002111.6). 'Human Target Stop Site' indicates the 3'-most nucleotide to which the gapmer is targeted in the human mRNA (GENBANK Accession No. NM_002111.6). 'Number of mismatches' indicates the number of mismatches between the human oligonucleotide and the rat mRNA sequence.

TABLE 8

Complementarity of antisense oligonucleotides having mixed phosphorothioate and phosphate linkages with rat mRNA (SEQ ID NO: 5)

| Human Start Site | Human Stop Site | Human Target SEQ ID NO. | ISIS No. | Rat Start Site | Rat Stop Site | No. of mismatches | SEQ ID NO. |
|---|---|---|---|---|---|---|---|
| 4607 | 4626 | 1 | 444658 | 4566 | 4585 | 0 | 10 |
| 4608 | 4627 | 1 | 444659 | 4567 | 4586 | 0 | 11 |
| 4609 | 4628 | 1 | 444660 | 4568 | 4587 | 0 | 12 |
| 4610 | 4629 | 1 | 444661 | 4569 | 4588 | 0 | 13 |
| 4813 | 4832 | 1 | 444663 | 4772 | 4791 | 0 | 18 |
| 5809 | 5828 | 1 | 444652 | 5765 | 5784 | 0 | 32 |

Example 2: Dose-Dependent Antisense Inhibition of Human Huntingtin mRNA In Vitro About seventeen hundred newly designed antisense compounds of various lengths, motifs and backbone composition were tested for their effect on human huntingtin mRNA in vitro in several cell types. These compounds were compared to about two hundred and fifty previously designed compounds including the compound ISIS 387916 which was previously determined to be a compound of considerable potency in vivo. As shown in this example, ISIS 419640, ISIS 419641, ISIS 419642, ISIS 436665, ISIS 436671, ISIS 436689, ISIS 437507, ISIS 443139, ISIS 444591, ISIS 444661, ISIS 437527, ISIS 444584, and ISIS 444652 and previously designed ISIS 388241 were found to have similar or better potency than the benchmark compound ISIS 387916 in vitro.

A. GM04281 Fibroblasts

Cultured GM04281 fibroblasts at a density of 25,000 cells per well were transfected using electroporation with 500 nM, 1000 nM, 2000 nM, 4000 nM, or 8000 nM of antisense oligonucleotide. After a treatment period of approximately 16 hours, RNA was isolated from the cells and huntingtin mRNA levels were measured by quantitative real-time PCR. Human primer probe set RTS2617 (forward sequence CTC-CGTCCGGTAGACATGCT, designated herein as SEQ ID NO: 37; reverse sequence GGAAATCAGAACCCT-CAAAATGG, designated herein as SEQ ID NO: 38; probe sequence TGAGCACTGTTCAACTGTGGA-TATCGGGAX, designated herein as SEQ ID NO: 39) was used to measure mRNA levels. Huntingtin mRNA levels were adjusted according to total RNA content, as measured by RIBOGREEN®. Results are presented in Table 9 as percent inhibition of huntingtin mRNA, relative to untreated control cells and demonstrate antisense oligonucleotide-mediated dose-dependent reduction of huntingtin mRNA levels.

The half maximal inhibitory concentration ($IC_{50}$) of each oligonucleotide is also presented in Table 9 and was calculated by plotting the concentrations of oligonucleotides used versus the percent inhibition of huntingtin mRNA expression achieved at each concentration, and noting the concentration of oligonucleotide at which 50% inhibition of huntingtin mRNA expression was achieved compared to the control. The $IC_{50}$ is expressed in μM.

TABLE 9

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 33 | 73 | 90 | 96 | 97 | 1.00 |
| 388241 | 44 | 70 | 82 | 95 | 97 | 0.61 |
| 419641 | 26 | 32 | 71 | 90 | 93 | 1.06 |
| 436665 | 56 | 67 | 87 | 95 | 96 | 0.32 |
| 436671 | 12 | 35 | 68 | 82 | 91 | 1.55 |
| 436689 | 10 | 34 | 61 | 80 | 91 | 1.89 |

ISIS 387916, ISIS 388241, and ISIS 437507 were further tested for their effect on human huntingtin mRNA in vitro. Cultured GM04281 fibroblasts were tested in a similar procedure, as described above. The results are presented in Table 10 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 10 expressed in μM.

TABLE 10

Dose dependent reduction of huntingtin mRNA in GM04281 fibroblasts

| ISIS No. | 500 nM | 1000 nM | 2000 nM | 4000 nM | 8000 nM | $IC_{50}$ (μM) |
|---|---|---|---|---|---|---|
| 387916 | 56 | 84 | 94 | 98 | 99 | 0.34 |
| 388241 | 58 | 75 | 94 | 98 | 99 | 0.23 |
| 437507 | 61 | 74 | 85 | 93 | 93 | 0.22 |

ISIS 387916, ISIS 388241, and ISIS 437507 were further tested for their effect on human huntingtin mRNA in vitro. Cultured GM04281 fibroblasts were tested in a similar procedure as described above. The results are presented in Table 11 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 11 expressed in µM.

TABLE 11

Dose dependent reduction of huntingtin mRNA in GM04281 fibroblasts

| ISIS No. | 500 nM | 1000 nM | 2000 nM | 4000 nM | 8000 nM | $IC_{50}$ (µM) |
|---|---|---|---|---|---|---|
| 387916 | 40 | 61 | 85 | 94 | 97 | 0.70 |
| 388241 | 51 | 72 | 86 | 94 | 98 | 0.41 |
| 437507 | 30 | 55 | 71 | 79 | 82 | 1.07 |

ISIS 387916, ISIS 388241, ISIS 419641, and ISIS 436754 were further tested for their effect on human huntingtin mRNA in vitro. Cultured GM04281 fibroblasts were tested in a similar procedure as described above. The results are presented in Table 12 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 12 expressed in µM.

TABLE 12

Dose dependent reduction of huntingtin mRNA in GM04281 fibroblasts

| ISIS No. | 500 nM | 1000 nM | 2000 nM | 4000 nM | 8000 nM | $IC_{50}$ (µM) |
|---|---|---|---|---|---|---|
| 387916 | 58 | 75 | 93 | 98 | 98 | 0.22 |
| 388241 | 40 | 68 | 85 | 95 | 98 | 0.73 |
| 419641 | 37 | 58 | 86 | 92 | 95 | 0.80 |
| 436754 | 44 | 62 | 63 | 84 | 93 | 0.59 |

ISIS 387916, ISIS 388241, and ISIS 437507 were further tested for their effect on human huntingtin mRNA in vitro. Cultured GM04281 fibroblasts at a density of 25,000 cells per well were transfected using electroporation with 250 nM, 500 nM, 1000 nM, 2000 nM, 4000 nM or 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 13 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 13 expressed in µM.

TABLE 13

Dose dependent reduction of huntingtin mRNA in GM04281 fibroblasts

| ISIS No. | 250 nM | 500 nM | 1000 Nm | 2000 nM | 4000 nM | 8000 nM | $IC_{50}$ (µM) |
|---|---|---|---|---|---|---|---|
| 387916 | 10 | 9 | 61 | 85 | 97 | 99 | 0.79 |
| 388241 | 0 | 18 | 42 | 90 | 98 | 99 | 1.08 |
| 437507 | 1 | 0 | 32 | 71 | 92 | 98 | 1.30 |

ISIS 387916, ISIS 388241, ISIS 419628, ISIS 419629, ISIS 419637, ISIS 436684, ISIS 443139, ISIS 444584, ISIS 444615, ISIS 444627, ISIS 444652, ISIS 444658, ISIS 444659, ISIS 444660, and ISIS 444661 were further tested for their effect on human huntingtin mRNA in vitro. Cultured GM04281 fibroblasts at a density of 25,000 cells per well were transfected using electroporation with 156.25 nM, 312.5 nM, 625 nM, 1250 nM, or 2500 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 14 as percent inhibition of huntingtin mRNA, relative to untreated control cells, and demonstrate antisense oligonucleotide-mediated dose-dependent reduction of huntingtin mRNA levels. The data presented is the average of two experiments. The IC50 of each antisense oligonucleotide is also presented in Table 14 expressed in µM.

TABLE 14

Dose dependent reduction of huntingtin mRNA in GM04281 fibroblasts

| ISIS No | 156.25 nM | 312.5 Nm | 625 nM | 1250 nM | 2500 nM | $IC_{50}$ (µM) |
|---|---|---|---|---|---|---|
| 387916 | 19 | 22 | 44 | 62 | 85 | 0.73 |
| 388241 | 3 | 13 | 24 | 42 | 71 | 1.42 |
| 419628 | 56 | 45 | 59 | 71 | 83 | 0.20 |
| 419629 | 42 | 38 | 67 | 70 | 89 | 0.33 |
| 419637 | 24 | 17 | 32 | 61 | 77 | 0.91 |
| 436684 | 15 | 28 | 55 | 73 | 85 | 0.59 |
| 443139 | 13 | 45 | 50 | 64 | 81 | 0.61 |
| 444584 | 0 | 0 | 25 | 50 | 74 | 1.28 |
| 444615 | 36 | 35 | 37 | 38 | 70 | 0.12 |
| 444627 | 40 | 38 | 48 | 73 | 87 | 0.43 |
| 444652 | 15 | 28 | 55 | 73 | 85 | 0.59 |
| 444658 | 50 | 54 | 75 | 84 | 96 | 0.18 |
| 444659 | 47 | 61 | 69 | 79 | 93 | 0.18 |
| 444660 | 41 | 61 | 65 | 84 | 95 | 0.22 |
| 444661 | 47 | 59 | 72 | 84 | 96 | 0.19 |

ISIS 387916, ISIS 436671, ISIS 444661, ISIS 419641, and ISIS 436665 were further tested for their effect on human huntingtin mRNA in vitro. Cultured GM04281 fibroblasts at a density of 25,000 cells per well were transfected using electroporation with 13.6719 nM, 27.3438 nM, 54.6875 nM, 109.375 nM, 218.75 nM, 437.5 nM, 875 nM, 1750 nM, 3500 nM, or 7000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 15 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 15 expressed in µM.

TABLE 15

| ISIS No. | 13.6719 nM | 27.3438 nM | 54.6875 nM | 109.375 nM | 218.75 nM | 437.5 nM | 875 nM | 1750 nM | 3500 nM | 7000 nM | IC$_{50}$ (μM) |
|---|---|---|---|---|---|---|---|---|---|---|---|
| 387916 | 0 | 31 | 14 | 43 | 44 | 68 | 86 | 89 | 97 | 97 | 0.31 |
| 436671 | 0 | 0 | 21 | 31 | 54 | 73 | 77 | 83 | 88 | 97 | 0.31 |
| 444661 | 0 | 10 | 25 | 53 | 66 | 73 | 87 | 96 | 99 | 99 | 0.16 |
| 419641 | 5 | 23 | 33 | 48 | 44 | 75 | 79 | 90 | 94 | 98 | 0.17 |
| 436665 | 26 | 37 | 47 | 44 | 65 | 83 | 89 | 94 | 98 | 98 | 0.07 |

ISIS 387916, ISIS 388241, ISIS 437168, and ISIS 437175 were further tested for their effect on human huntingtin mRNA in vitro. Cultured GM04281 fibroblasts at a density of 25,000 cells per well were transfected using electroporation with 250 nM, 500 nM, 1000 nM, 2000 nM, 4000 nM, and 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 15.1 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 15.1 expressed in μM.

TABLE 15.1

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | IC$_{50}$ |
|---|---|---|---|---|---|---|---|
| 387916 | 22 | 63 | 70 | 83 | 95 | 96 | 0.62 |
| 388241 | 17 | 45 | 65 | 87 | 96 | 97 | 0.56 |
| 437175 | 47 | 31 | 56 | 60 | 79 | 91 | 1.19 |
| 437168 | 32 | 46 | 64 | 81 | 89 | 95 | 0.59 |

ISIS 387916, ISIS 388241, ISIS 437441, and ISIS 437442 were further tested for their effect on human huntingtin mRNA in vitro. Cultured GM04281 fibroblasts were tested in a similar procedure as described above. The results are presented in Table 15.2 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 15.2 expressed in μM.

TABLE 15.2

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | IC$_{50}$ |
|---|---|---|---|---|---|---|---|
| 387916 | 26 | 47 | 58 | 79 | 91 | 95 | 0.65 |
| 388241 | 30 | 52 | 60 | 81 | 94 | 97 | 0.55 |
| 437441 | 25 | 37 | 56 | 69 | 86 | 47 | 0.81 |
| 437442 | 39 | 43 | 47 | 70 | 85 | 50 | 0.59 |

ISIS 387916, ISIS 388241, ISIS 437175, and ISIS 437527 were further tested for their effect on human huntingtin mRNA in vitro. Cultured GM04281 fibroblasts were tested in a similar procedure as described above. The results are presented in Table 15.3 as percent inhibition of huntingtin mRNA, relative to untreated control cells, and demonstrate antisense oligonucleotide-mediated dose-dependent reduction of huntingtin mRNA levels. The IC$_{50}$ of each antisense oligonucleotide is also presented in Table 15.3 expressed in μM.

TABLE 15.3

Dose dependent reduction of huntingtin mRNA in GM04281 fibroblasts

| ISIS No. | 250.0 nM | 500.0 nM | 1000.0 nM | 2000.0 nM | 4000.0 nM | 8000.0 nM | IC$_{50}$ |
|---|---|---|---|---|---|---|---|
| 387916 | 40 | 45 | 47 | 76 | 92 | 96 | 0.50 |
| 388241 | 40 | 37 | 50 | 90 | 96 | 97 | 0.80 |
| 437175 | 48 | 55 | 55 | 63 | 80 | 93 | 0.37 |
| 437527 | 33 | 52 | 61 | 80 | 86 | 95 | 0.52 |

B. A549 Cells

Some of the antisense oligonucleotides described in Example 1 were tested for their effect on human huntingtin mRNA in vitro. Cultured A549 cells at a density of 4,000 cells per well were transfected using lipofectin transfection reagent with 7.4074 nM, 22.222 nM, 66.667 nM, or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 16 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 16 expressed in nM.

TABLE 16

Dose dependent reduction of huntingtin mRNA in A549 cells

| ISIS No. | 7.4074 nM | 22.222 nM | 66.667 nM | 200.00 nM | $IC_{50}$ (nM) |
|---|---|---|---|---|---|
| 387916 | 12 | 37 | 76 | 92 | 33 |
| 419640 | 21 | 45 | 73 | 93 | 27 |
| 419641 | 34 | 60 | 83 | 96 | 15 |
| 419642 | 30 | 58 | 85 | 95 | 16 |

ISIS 387916, ISIS 388241, and ISIS 437507 were further tested for their effect on human huntingtin mRNA in vitro. Cultured A549 cells at a density of 20,000 cells per well were transfected using electroporation with 250 nM, 500 nM, 1000 nM, 2000 nM, 4000 nM or 8000 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. The results are presented in Table 17 expressed as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 17 expressed in μM.

TABLE 17

Dose dependent reduction of huntingtin mRNA in A549 cells

| ISIS No. | 250 nM | 500 nM | 1000 nM | 2000 nM | 4000 nM | 8000 nM | $IC_{50}$ (μM) |
|---|---|---|---|---|---|---|---|
| 387916 | 15 | 17 | 25 | 36 | 52 | 75 | 3.09 |
| 388241 | 12 | 22 | 38 | 58 | 77 | 91 | 1.43 |
| 437507 | 25 | 28 | 38 | 57 | 58 | 76 | 1.84 |

C. LLC-MK2 cells

Some of the antisense oligonucleotides described in Example 1 and targeted to a human huntingtin nucleic acid were tested for their effect on rhesus monkey huntingtin mRNA in vitro. Cultured LLC-MK2 cells at a density of 25,000 cells per well were transfected using electroporation with 625 nM, 1250 nM, 2500 nM, 5000 nM, 10,000 nM, or 20,000 nM of antisense oligonucleotide. After a treatment period of approximately 16 hours, RNA was isolated from the cells and huntingtin mRNA levels were measured by quantitative real-time PCR. Human primer probe set RTS2686 (forward sequence GTCTGAGCCTCTCTCGGT-CAA, designated herein as SEQ ID NO: 40; reverse sequence AAGGGATGCTGGGCTCTGT, designated herein as SEQ ID NO: 41; probe sequence AGCAAAGCT-TGGTGTCTTGGCACTGTTAGTX, designated herein as SEQ ID NO: 42) was used to measure mRNA levels. Huntingtin mRNA levels were adjusted according to total RNA content, as measured by RIBOGREEN®. Results are presented in Table 18 as percent inhibition of huntingtin mRNA, relative to untreated control cells and demonstrate antisense oligonucleotide-mediated dose-dependent reduction of huntingtin mRNA levels. The $IC_{50}$ of each antisense oligonucleotide is also presented in Table 18 expressed in μM.

TABLE 18

Dose dependent reduction of huntingtin mRNA in LLC-MK2 cells

| ISIS No. | 625 nM | 1250 nM | 2500 nM | 5000 nM | 10000 nM | 20000 nM | $IC_{50}$ (μM) |
|---|---|---|---|---|---|---|---|
| 388241 | 21 | 12 | 35 | 46 | 46 | 94 | 4.1 |
| 444591 | 37 | 46 | 51 | 52 | 82 | 96 | 1.9 |
| 419641 | 32 | 52 | 69 | 87 | 94 | 97 | 1.2 |
| 444661 | 45 | 59 | 66 | 85 | 91 | 95 | 0.8 |
| 419642 | 6 | 3 | 56 | 81 | 91 | 98 | 2.9 |
| 436665 | 40 | 43 | 70 | 73 | 84 | 89 | 1.2 |
| 436671 | 31 | 51 | 68 | 82 | 90 | 97 | 1.2 |
| 436689 | 24 | 37 | 59 | 74 | 89 | 98 | 1.9 |
| 437507 | 21 | 15 | 11 | 33 | 55 | 92 | 6.4 |
| 443139 | 31 | 36 | 37 | 56 | 76 | 97 | 2.6 |

ISIS 387916, ISIS 388241, ISIS 436684, ISIS 437168, ISIS 437175, ISIS 437441, ISIS 437507, ISIS 437527, ISIS 444578, ISIS 444584, ISIS 444591, and ISIS 444607 were further tested for their effect on rhesus monkey huntingtin mRNA in vitro. Cultured LLC-MK2 cells were tested in a similar procedure as described above. The results are presented in Table 19 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 19 expressed in μM.

TABLE 19

Dose dependent reduction of huntingtin mRNA in LLC-MK2 cells

| ISIS No. | 625.0 nM | 1250.0 nM | 2500.0 nM | 5000.0 nM | 10000.0 nM | 20000.0 nM | $IC_{50}$ |
|---|---|---|---|---|---|---|---|
| 387916 | 23 | 42 | 57 | 81 | 88 | 96 | 1.95 |
| 388241 | 6 | 12 | 37 | 43 | 62 | 84 | 5.32 |
| 437168 | 72 | 47 | 60 | 78 | 83 | 92 | 1.43 |
| 437175 | 27 | 48 | 36 | 56 | 68 | 78 | 3.58 |
| 437441 | 29 | 34 | 50 | 67 | 56 | 85 | 2.43 |
| 437507 | 18 | 29 | 18 | 33 | 45 | 66 | 6.12 |
| 437527 | 36 | 36 | 48 | 57 | 81 | 90 | 2.71 |
| 436684 | 0 | 12 | 24 | 29 | 36 | 49 | n.d. |
| 444578 | 34 | 40 | 65 | 74 | 82 | 87 | 1.70 |
| 444584 | 28 | 38 | 68 | 75 | 90 | 94 | 1.69 |
| 444591 | 25 | 45 | 55 | 74 | 85 | 94 | 1.84 |
| 444607 | 41 | 54 | 76 | 87 | 92 | 94 | 0.96 | n.d. = $IC_{50}$ could not be measured for that compound

ISIS 387916, ISIS 388241, ISIS 444608, ISIS 444615, ISIS 444618, ISIS 444627, ISIS 444652, ISIS 444658, ISIS 444659, ISIS 444660, and ISIS 444661 were further tested for their effect on rhesus monkey huntingtin mRNA in vitro. Cultured LLC-MK2 cells were tested in a similar procedure as described above. The results are presented in Table 20 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 20 expressed in μM.

TABLE 20

Dose dependent reduction of huntingtin mRNA in LLC-MK2 cells

| ISIS No | 625.0 nM | 1250.0 nM | 2500.0 nM | 5000.0 nM | 10000.0 nM | 20000.0 nM | IC50 |
|---|---|---|---|---|---|---|---|
| 387916 | 35 | 44 | 68 | 74 | 90 | 96 | 1.35 |
| 388241 | 23 | 37 | 54 | 56 | 68 | 89 | 2.64 |

TABLE 20-continued

Dose dependent reduction of huntingtin mRNA in LLC-MK2 cells

| ISIS No | 625.0 nM | 1250.0 nM | 2500.0 nM | 5000.0 nM | 10000.0 nM | 20000.0 nM | IC50 |
|---|---|---|---|---|---|---|---|
| 444608 | 43 | 50 | 64 | 83 | 90 | 95 | 1.07 |
| 444615 | 29 | 45 | 55 | 76 | 90 | 97 | 1.67 |
| 444618 | 30 | 34 | 57 | 73 | 89 | 95 | 1.66 |
| 444627 | 35 | 56 | 76 | 90 | 97 | 98 | 1.00 |
| 444652 | 32 | 55 | 66 | 55 | 92 | 98 | 1.23 |
| 444658 | 50 | 62 | 80 | 90 | 95 | 97 | 0.55 |
| 444659 | 31 | 56 | 68 | 86 | 95 | 97 | 1.17 |
| 444660 | 38 | 49 | 62 | 86 | 89 | 96 | 1.26 |
| 444661 | 41 | 50 | 75 | 68 | 95 | 97 | 0.95 |

ISIS 387916, ISIS 419627, ISIS 419628, ISIS 419629, ISIS 419630, ISIS 419636, ISIS 419637, ISIS 419640, ISIS 419641, and ISIS 419642 were further tested for their effect on rhesus monkey huntingtin mRNA in vitro. Cultured LLC-MK2 cells at a density of 3,000 cells per well were transfected using lipofectin transfection reagent with 6.25 nM, 12.5 nM, 25 nM, 50 nM, 100 nM, or 200 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 21 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 21 expressed in nM.

TABLE 21

Dose dependent reduction of huntingtin mRNA in LLC-MK2 cells

| ISIS No. | 6.25 nM | 12.5 nM | 25.0 nM | 50.0 nM | 100.0 nM | 200.0 nM | $IC_{50}$ |
|---|---|---|---|---|---|---|---|
| 387916 | 1 | 37 | 37 | 53 | 84 | 90 | 35 |
| 419627 | 0 | 9 | 18 | 45 | 58 | 72 | 75 |
| 419628 | 9 | 30 | 49 | 63 | 73 | 77 | 31 |
| 419629 | 9 | 16 | 40 | 56 | 80 | 85 | 36 |
| 419630 | 17 | 8 | 43 | 58 | 71 | 81 | 40 |
| 419636 | 23 | 25 | 38 | 55 | 72 | 78 | 37 |
| 419637 | 10 | 35 | 31 | 62 | 78 | 76 | 33 |
| 419640 | 3 | 28 | 39 | 59 | 74 | 87 | 36 |
| 419641 | 11 | 34 | 51 | 65 | 85 | 87 | 26 |
| 419642 | 25 | 30 | 49 | 65 | 85 | 88 | 24 |

ISIS 387916, ISIS 419641, and ISIS 436689 were further tested for their effect on rhesus monkey huntingtin mRNA in vitro. Cultured LLC-MK2 cells at a density of 3,000 cells per well were transfected using LipofectAMINE2000 transfection reagent with 6.25 nM, 12.5 nM, 25 nM, 50 nM, 100 nM, or 200 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 22 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 22 expressed in nM.

TABLE 22

Dose dependent reduction of huntingtin mRNA in LLC-MK2 cells

| ISIS No | 6.25 nM | 12.5 nM | 25 nM | 50 nM | 100 nM | 200 nM | $IC_{50}$ (nM) |
|---|---|---|---|---|---|---|---|
| 387916 | 0 | 50 | 31 | 68 | 83 | 90 | 47 |
| 419641 | 28 | 23 | 28 | 51 | 65 | 81 | 74 |
| 436689 | 16 | 30 | 29 | 48 | 67 | 83 | 69 |

ISIS 387916, ISIS 388241, ISIS 436665, ISIS 436671, and ISIS 436689 were further tested for their effect on rhesus monkey huntingtin mRNA in vitro. Cultured LLC-MK2 cells at a density of 3,000 cells per well were transfected using lipofectin transfection reagent with 4.6875 nM, 9.375 nM, 18.75 nM, 37.5 nM, 75 nM, or 150 nM of antisense oligonucleotide. After a treatment period of approximately 16 hours, RNA was isolated from the cells and huntingtin mRNA levels were measured by quantitative real-time PCR. Human primer probe set RTS2686 was used to measure mRNA levels. Huntingtin mRNA levels were adjusted according to total RNA content, as measured by RIBOGREEN®. Results are presented in Table 23 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 23 expressed in nM.

TABLE 23

Dose dependent reduction of huntingtin mRNA in LLC-MK2 cells

| ISIS No. | 4.6875 nM | 9.375 nM | 18.75 nM | 37.5 nM | 75.0 nM | 150.0 nM | $IC_{50}$ (nM) |
|---|---|---|---|---|---|---|---|
| 387916 | 7 | 6 | 38 | 59 | 82 | 91 | 32 |
| 388241 | 0 | 0 | 5 | 35 | 62 | 81 | 60 |
| 436665 | 7 | 0 | 36 | 59 | 64 | 69 | 37 |
| 436671 | 21 | 7 | 35 | 59 | 80 | 86 | 31 |
| 436689 | 38 | 45 | 45 | 59 | 76 | 86 | 15 |

D. BACHD Transgenic Mouse Hepatocyes

Some of the antisense oligonucleotides described in Example 1 and targeted to a human huntingtin nucleic acid were tested for their effect on human huntingtin mRNA in vitro. Cultured BACHD mouse hepatocytes at a density of 10,000 cells per well were transfected using cytofectin transfection reagent with 7.4074 nM, 22.222 nM, 66.667 nM, or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 24 as percent inhibition of huntingtin mRNA, relative to untreated control cells, and demonstrate antisense oligonucleotide-mediated dose-dependent reduction of huntingtin mRNA levels. The data presented is the average of two experiments. The $IC_{50}$ of each antisense oligonucleotide is also presented in Table 24 expressed in nM.

TABLE 24

Dose dependent reduction of huntingtin mRNA
in BACHD transgenic murine hepatocytes

| ISIS No. | 7.4074 nM | 22.222 nM | 66.667 nM | 200.00 nM | $IC_{50}$ (nM) |
|---|---|---|---|---|---|
| 387916 | 8 | 19 | 58 | 89 | 40 |
| 419640 | 15 | 30 | 64 | 93 | 33 |
| 419641 | 20 | 35 | 73 | 97 | 31 |
| 419642 | 3 | 29 | 70 | 96 | 43 |

ISIS 387916, ISIS 388241, and ISIS 419641 were further tested for their effect on human huntingtin mRNA in vitro. Cultured BACHD mouse hepatocytes at a density of 10,000 cells per well were transfected using cytofectin transfection reagent with 12.5 nM, 25 nM, 50 nM, 100 nM or 200 nM of antisense oligonucleotide. After a treatment period of approximately 16 hours, RNA was isolated from the cells and huntingtin mRNA levels were measured by quantitative real-time PCR. Human primer probe set RTS2617 was used to measure mRNA levels. Huntingtin mRNA levels were adjusted according to total RNA content, as measured by RIBOGREEN®. Results are presented in Table 25 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 25 expressed in nM.

TABLE 25

Dose dependent reduction of huntingtin mRNA in BACHD
transgenic murine hepatocytes

| ISIS No. | 12.5 nM | 25 nM | 50 Nm | 100 nM | 200 nM | $IC_{50}$ (nM) |
|---|---|---|---|---|---|---|
| 387916 | 0 | 37 | 51 | 78 | 91 | 51 |
| 388241 | 0 | 10 | 45 | 70 | 92 | 68 |
| 419641 | 17 | 38 | 70 | 88 | 96 | 34 |

ISIS 387916, ISIS 388241, ISIS 419641, ISIS 436665, ISIS 436671, and ISIS 436689 were further tested for their effect on human huntingtin mRNA in vitro. Cultured BACHD mouse hepatocytes were tested in an identical manner as described above. The results are presented in Table 26 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 26 expressed in nM.

TABLE 26

Dose dependent reduction of huntingtin mRNA in BACHD
transgenic murine hepatocytes

| ISIS No. | 12.5 nM | 25 nM | 50 nM | 100 nM | 200 nM | $IC_{50}$ (nM) |
|---|---|---|---|---|---|---|
| 387916 | 19 | 48 | 64 | 86 | 93 | 32 |
| 388241 | 20 | 34 | 54 | 81 | 93 | 38 |
| 419641 | 38 | 54 | 70 | 85 | 95 | 21 |
| 436665 | 32 | 40 | 67 | 84 | 93 | 29 |
| 436671 | 32 | 42 | 58 | 78 | 91 | 32 |
| 436689 | 35 | 44 | 70 | 88 | 96 | 25 |

ISIS 387916, ISIS 419640, ISIS 419641, and ISIS 419642 were further tested for their effect on mouse huntingtin mRNA in vitro. Cultured BACHD mouse hepatocytes at a density of 20,000 cells per well were transfected using cytofectin transfection reagent with 6.667 nM, 20 nM, 60 nM, or 180 nM of antisense oligonucleotide. After a treatment period of approximately 16 hours, RNA was isolated from the cells and huntingtin mRNA levels were measured by quantitative real-time PCR. Murine primer probe set RTS2633 (forward sequence CAGAGCTGGTCAACCG-TATCC, designated herein as SEQ ID NO: 43; reverse sequence GGCTTAAACAGGGAGCCAAAA, designated herein as SEQ ID NO: 44; probe sequence ACTTCATGAT-GAGCTCGGAGTTCAACX, designated herein as SEQ ID NO: 45) was used to measure mRNA levels. Huntingtin mRNA levels were adjusted according to total RNA content, as measured by RIBOGREEN®. Results are presented in Table 27 as percent inhibition of huntingtin mRNA, relative to untreated control cells, and demonstrate antisense oligonucleotide-mediated dose-dependent reduction of huntingtin mRNA levels. The $IC_{50}$ of each antisense oligonucleotide is also presented in Table 27 expressed in nM.

TABLE 27

Dose dependent reduction of huntingtin mRNA
in BACHD transgenic murine hepatocytes

| ISIS No. | 6.667 nM | 20 nM | 60 nM | 180 nM | $IC_{50}$ (nM) |
|---|---|---|---|---|---|
| 387916 | 15 | 15 | 68 | 94 | 37 |
| 419640 | 4 | 39 | 73 | 94 | 32 |
| 419641 | 16 | 45 | 81 | 96 | 24 |
| 419642 | 23 | 39 | 75 | 93 | 25 |

Example 3: Systemic Administration of Antisense Oligonucleotides against Huntingtin mRNA in BACHD Mice Of the about seventeen hundred newly designed antisense compounds, sixty six compounds were selected based on in vitro potency compared to ISIS 387916 for testing in systemic tolerability screens.

BACHD mice were treated with ISIS oligonucleotides and evaluated for changes in the levels of various metabolic markers as well as inhibition of huntingtin mRNA in the liver. Antisense oligonucleotides which caused adverse changes in body weight, organ weight or in the levels of metabolic markers were deemed unsuitable for utilization in further studies.

Study 1.

Treatment

Nineteen groups of four BACHD mice each were injected intraperitoneally with 12.5 mg/kg of ISIS 387916, ISIS 388241, ISIS 419629, ISIS 419637, ISIS 436684, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 28 and 29 and were calculated as percent inhibition of human and murine huntingtin expression levels respectively, relative to the PBS control. All the antisense oligonucleotides effect significant inhibition of human huntingtin mRNA levels. ISIS 388241 has more than three mismatches with the murine huntingtin mRNA (SEQ ID NO: 3) and therefore did not show significant inhibition of murine mRNA levels compared to the control.

TABLE 28

Percent inhibition of human huntingtin mRNA in BACHD mice

| ISIS No. | % inhibition |
|---|---|
| 387916 | 82 |
| 388241 | 52 |
| 419629 | 80 |
| 419637 | 83 |
| 436684 | 55 |
| 444578 | 70 |
| 444584 | 62 |
| 444591 | 54 |
| 444607 | 76 |
| 444608 | 61 |
| 444615 | 89 |
| 444618 | 91 |
| 444627 | 92 |
| 444652 | 79 |
| 444658 | 62 |
| 444659 | 74 |
| 444660 | 66 |
| 444661 | 72 |
| 444663 | 77 |

TABLE 29

Percent inhibition of murine huntingtin mRNA in BACHD mice

| ISIS No. | % inhibition |
|---|---|
| 387916 | 77 |
| 419629 | 75 |
| 419637 | 87 |
| 436684 | 32 |
| 444578 | 64 |
| 444584 | 20 |
| 444591 | 32 |
| 444607 | 76 |
| 444608 | 66 |
| 444615 | 60 |
| 444618 | 88 |
| 444627 | 58 |
| 444652 | 66 |
| 444658 | 53 |
| 444659 | 62 |
| 444660 | 47 |
| 444661 | 67 |
| 444663 | 60 |

Organ Weight Measurements

Liver, spleen and kidney weights were measured at the end of the study, and are presented in Table 30 as a percent of the saline control normalized to body weight.

TABLE 30

Percent change in organ weight of BACHD mice after antisense oligonucleotide treatment

| ISIS No. | Liver | Spleen | Kidney |
|---|---|---|---|
| 387916 | −5 | −13 | +6 |
| 388241 | −1 | +14 | −5 |
| 419629 | +5 | +13 | −12 |
| 419637 | −6 | −17 | −25 |
| 436684 | −2 | −3 | +6 |
| 444578 | +11 | +18 | +1 |
| 444584 | +8 | +54 | +1 |
| 444591 | +4 | −4 | −3 |
| 444607 | +3 | +22 | −8 |
| 444608 | +6 | +18 | −3 |
| 444615 | +6 | +1 | +3 |
| 444618 | +11 | +0 | −2 |
| 444627 | +3 | −14 | +14 |
| 444652 | −11 | −4 | −18 |
| 444658 | −1 | 0 | −16 |
| 444659 | +1 | +15 | −2 |
| 444660 | −5 | +4 | −6 |
| 444661 | −1 | +7 | −1 |
| 444663 | +7 | +10 | +8 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 31.

TABLE 31

Effect of antisense oligonucleotide treatment on markers of liver function

| | ALT | AST |
|---|---|---|
| PBS | 40 | 69 |
| 387916 | 69 | 84 |
| 388241 | 42 | 76 |
| 419629 | 51 | 71 |
| 419637 | 59 | 86 |
| 436684 | 60 | 87 |
| 444578 | 62 | 93 |
| 444584 | 48 | 76 |
| 444591 | 39 | 53 |
| 444607 | 51 | 111 |
| 444608 | 48 | 75 |
| 444615 | 74 | 95 |
| 444618 | 687 | 908 |
| 444627 | 105 | 127 |
| 444652 | 54 | 64 |
| 444658 | 46 | 59 |
| 444659 | 90 | 138 |
| 444660 | 34 | 64 |
| 444661 | 49 | 99 |
| 444663 | 90 | 164 |

Study 2

Treatment

Fourteen groups of four BACHD mice each were injected intraperitoneally with 12.5 mg/kg or 50 mg/kg of ISIS 419581, ISIS 419602, ISIS 419628, ISIS 419629, ISIS 419640, ISIS 419641, or ISIS 419642 twice a week for 2 weeks. A group of four BACHD mice was injected intraperitoneally with 12.5 mg/kg of ISIS 387916 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 32 and 33 and were calculated as percent inhibition of human and murine huntingtin expression levels respectively, relative to the PBS control.

TABLE 32

Percent inhibition of human huntingtin mRNA in BACHD mice

| ISIS No. | Dose (mg/kg) | % inhibition |
|---|---|---|
| 387916 | 12.5 | 71 |
| 419581 | 12.5 | 54 |
|  | 50 | 68 |
| 419602 | 12.5 | 72 |
|  | 50 | 77 |
| 419628 | 12.5 | 65 |
|  | 50 | 76 |
| 419629 | 12.5 | 87 |
|  | 50 | 93 |
| 419640 | 12.5 | 69 |
|  | 50 | 79 |
| 419641 | 12.5 | 61 |
|  | 50 | 80 |
| 419642 | 12.5 | 76 |
|  | 50 | 83 |

TABLE 33

Percent inhibition of murine huntingtin mRNA in BACHD mice

| ISIS No. | Dose (mg/kg) | % inhibition |
|---|---|---|
| 387916 | 12.5 | 70 |
| 419581 | 12.5 | 42 |
|  | 50 | 86 |
| 419602 | 12.5 | 77 |
|  | 50 | 85 |
| 419628 | 12.5 | 67 |
|  | 50 | 86 |
| 419629 | 12.5 | 90 |
|  | 50 | 93 |
| 419640 | 12.5 | 63 |
|  | 50 | 84 |
| 419641 | 12.5 | 52 |
|  | 50 | 81 |
| 419642 | 12.5 | 56 |
|  | 50 | 83 |

Organ Weight Measurements

Liver, spleen and kidney weights were measured at the end of the study, and are presented in Table 34 as a percent of the saline control normalized to body weight.

TABLE 34

Percent change in organ weight of BACHD mice after antisense oligonucleotide treatment

| ISIS No. | Dose (mg/kg) | Liver | Spleen | Kidney |
|---|---|---|---|---|
| 387916 | 12.5 | −9 | 3 | −4 |
| 419581 | 12.5 | −2 | −6 | −1 |
|  | 50 | 14 | −1 | −11 |
| 419602 | 12.5 | 10 | 1 | −2 |
|  | 50 | 28 | 9 | −3 |
| 419628 | 12.5 | −2 | −7 | −2 |
|  | 50 | −3 | 7 | −9 |
| 419629 | 12.5 | −7 | −5 | −10 |
|  | 50 | 16 | 0 | −8 |
| 419640 | 12.5 | −5 | −2 | −8 |
|  | 50 | 1 | −20 | −4 |
| 419641 | 12.5 | −7 | −10 | −11 |
|  | 50 | −2 | −13 | −9 |
| 419642 | 12.5 | −11 | −21 | −19 |
|  | 50 | −1 | −8 | −9 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of ALT and AST are expressed in IU/L and the results are presented in Table 35.

TABLE 35

Effect of antisense oligonucleotide treatment on markers of liver function

|  | Dose (mg/kg) | ALT | AST |
|---|---|---|---|
| PBS |  | 44 | 80 |
| 387916 | 12.5 | 44 | 75 |
| 419581 | 12.5 | 56 | 101 |
|  | 50 | 390 | 281 |
| 419602 | 12.5 | 86 | 108 |
|  | 50 | 240 | 229 |
| 419628 | 12.5 | 52 | 110 |
|  | 50 | 51 | 73 |
| 419629 | 12.5 | 104 | 118 |
|  | 50 | 1262 | 1150 |
| 419640 | 12.5 | 36 | 65 |
|  | 50 | 38 | 55 |
| 419641 | 12.5 | 56 | 103 |
|  | 50 | 57 | 172 |
| 419642 | 12.5 | 40 | 64 |
|  | 50 | 47 | 101 |

Study 3

Treatment

Eighteen groups of four BACHD mice each were injected intraperitoneally with 12.5 mg/kg or 50 mg/kg of ISIS 388250, ISIS 388251, ISIS 388263, ISIS 388264, ISIS 419641, ISIS 436645, ISIS 436649, ISIS 436668, or ISIS 436689 twice a week for 2 weeks. A group of four BACHD mice was injected intraperitoneally with 12.5 mg/kg of ISIS 388241 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 36 and 37 and were calculated as percent inhibition of human and murine huntingtin expression levels respectively, relative to the PBS control. All the antisense oligonucleotides effect significant inhibition of human huntingtin mRNA levels. ISIS 388241, ISIS 388250, ISIS 388251, ISIS 388263, ISIS 388264, and ISIS 436645 have more than three mismatches with the murine huntingtin mRNA (SEQ ID NO: 3) and therefore did not show significant inhibition of murine mRNA levels compared to the control. ISIS 436649 and ISIS 436689 have three mismatches with the murine huntingtin mRNA (SEQ ID NO: 3) and therefore did not show significant inhibition of murine mRNA levels compared to the control.

TABLE 36

Percent inhibition of human huntingtin mRNA in BACHD mice

| ISIS No. | Dose (mg/kg) | % inhibition |
|---|---|---|
| 388241 | 12.5 | 32 |
| 388250 | 12.5 | 21 |
|  | 50 | 45 |
| 388251 | 12.5 | 30 |
|  | 50 | 34 |
| 388263 | 12.5 | 29 |
|  | 50 | 35 |
| 388264 | 12.5 | 35 |
|  | 50 | 42 |
| 419641 | 12.5 | 71 |
|  | 50 | 73 |
| 436645 | 12.5 | 43 |
|  | 50 | 48 |
| 436649 | 12.5 | 40 |
|  | 50 | 38 |
| 436668 | 12.5 | 45 |
|  | 50 | 69 |
| 436689 | 12.5 | 62 |
|  | 50 | 78 |

TABLE 37

Percent inhibition of murine huntingtin mRNA in BACHD mice

| ISIS No. | Dose (mg/kg) | % inhibition |
|---|---|---|
| 419641 | 12.5 | 68 |
|  | 50 | 77 |
| 436668 | 12.5 | 41 |
|  | 50 | 62 |

Organ Weight Measurements

Liver, spleen and kidney weights were measured at the end of the study, and are presented in Table 38 as a percent of the saline control normalized to body weight. Mice treated with ISIS 388263 and ISIS 436645 suffered increases in liver weight at the 50 mg/kg dose compared to the PBS control.

TABLE 38

Percent change in organ weight of BACHD mice after antisense oligonucleotide treatment

| ISIS No. | Dose (mg/kg) | Liver | Spleen | Kidney |
|---|---|---|---|---|
| 388241 | 12.5 | 1 | 6 | 9 |
| 388250 | 12.5 | 2 | 1 | −2 |
|  | 50 | 1 | 30 | 3 |
| 388251 | 12.5 | 4 | −8 | 1 |
|  | 50 | 19 | 19 | 2 |
| 388263 | 12.5 | 4 | 8 | 9 |
|  | 50 | 23 | 52 | 1 |

TABLE 38-continued

Percent change in organ weight of BACHD mice after antisense oligonucleotide treatment

| ISIS No. | Dose (mg/kg) | Liver | Spleen | Kidney |
|---|---|---|---|---|
| 388264 | 12.5 | 2 | −2 | 3 |
|  | 50 | 12 | 9 | 6 |
| 419641 | 12.5 | −1 | −9 | 3 |
|  | 50 | 2 | −4 | 3 |
| 436645 | 12.5 | 8 | 6 | 5 |
|  | 50 | 26 | 25 | 9 |
| 436649 | 12.5 | 1 | 0 | 6 |
|  | 50 | 0 | 1 | 3 |
| 436668 | 12.5 | 1 | 5 | 10 |
|  | 50 | −2 | 3 | 11 |
| 436689 | 12.5 | −3 | −5 | 4 |
|  | 50 | 6 | 11 | 5 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 39.

TABLE 39

Effect of antisense oligonucleotide treatment on markers of liver function

|  | Dose (mg/kg) | ALT | AST |
|---|---|---|---|
| PBS |  | 43 | 76 |
| 388241 | 12.5 | 43 | 88 |
| 388250 | 12.5 | 37 | 55 |
|  | 50 | 44 | 89 |
| 388251 | 12.5 | 42 | 98 |
|  | 50 | 67 | 91 |
| 388263 | 12.5 | 51 | 90 |
|  | 50 | 55 | 93 |
| 388264 | 12.5 | 31 | 59 |
|  | 50 | 65 | 90 |
| 419641 | 12.5 | 39 | 70 |
|  | 50 | 42 | 83 |
| 436645 | 12.5 | 43 | 82 |
|  | 50 | 179 | 143 |
| 436649 | 12.5 | 35 | 47 |
|  | 50 | 38 | 76 |
| 436668 | 12.5 | 36 | 73 |
|  | 50 | 28 | 57 |
| 436689 | 12.5 | 31 | 52 |
|  | 50 | 49 | 164 |

Study 4
Treatment

Eighteen groups of four BACHD mice each were injected intraperitoneally with 12.5 mg/kg or 50 mg/kg of ISIS 388241, ISIS 437123, ISIS 437132, ISIS 437140, ISIS 437442, ISIS 437446, ISIS 437477, ISIS 437478, or ISIS 437490 twice a week for 2 weeks. A group of four BACHD mice was injected intraperitoneally with 12.5 mg/kg of ISIS 387916 twice a week for 2 weeks. A control group of four mice was injected intraperitoneally with PBS twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 40 and 41 and were calculated as percent inhibition of human and murine huntingtin expression levels respectively, relative to the PBS control. ISIS 388241 and ISIS 437490 have more than three mismatches with the murine huntingtin mRNA (SEQ ID NO: 3) and therefore did not show significant inhibition of murine mRNA levels compared to the control. ISIS 437132 has three mismatches with the murine huntingtin mRNA (SEQ ID NO: 3) and therefore did not show significant inhibition of murine mRNA levels compared to the control. ISIS 437123 and ISIS 437140 have two mismatches with the murine huntingtin mRNA (SEQ ID NO: 3) and do not show significant inhibition of murine mRNA levels compared to the control.

TABLE 40

Percent inhibition of human huntingtin mRNA in BACHD mice

| ISIS No. | Dose (mg/kg) | % inhibition |
|---|---|---|
| 387916 | 12.5 | 51 |
| 388241 | 12.5 | 47 |
|  | 50 | 67 |
| 437123 | 12.5 | 0 |
|  | 50 | 21 |
| 437132 | 12.5 | 31 |
|  | 50 | 33 |
| 437140 | 12.5 | 7 |
|  | 50 | 32 |
| 437442 | 12.5 | 42 |
|  | 50 | 85 |
| 437446 | 12.5 | 39 |
|  | 50 | 70 |
| 437477 | 12.5 | 52 |
|  | 50 | 75 |
| 437478 | 12.5 | 54 |
|  | 50 | 78 |
| 437490 | 12.5 | 42 |
|  | 50 | 44 |

TABLE 41

Percent inhibition of murine huntingtin mRNA in BACHD mice

| ISIS No. | Dose (mg/kg) | % inhibition |
|---|---|---|
| 387916 | 12.5 | 48 |
| 437442 | 12.5 | 27 |
|  | 50 | 76 |
| 437446 | 12.5 | 38 |
|  | 50 | 71 |
| 437477 | 12.5 | 63 |
|  | 50 | 87 |
| 437478 | 12.5 | 60 |
|  | 50 | 89 |

Organ Weight Measurements

Liver, spleen and kidney weights were measured at the end of the study, and are presented in Table 42 as a percent of the saline control normalized to body weight.

TABLE 42

Percent change in organ weight of BACHD mice after antisense oligonucleotide treatment

| ISIS No. | Dose (mg/kg) | Liver | Spleen | Kidney |
|---|---|---|---|---|
| 387916 | 12.5 | 1 | 6 | 12 |
| 388241 | 12.5 | −3 | 16 | −2 |
|  | 50 | −6 | 10 | 0 |
| 437123 | 12.5 | −4 | 0 | 4 |
|  | 50 | 4 | 0 | −4 |
| 437132 | 12.5 | −2 | −3 | −5 |
|  | 50 | 2 | −6 | −2 |
| 437140 | 12.5 | −4 | 11 | −3 |
|  | 50 | 4 | 5 | −5 |
| 437442 | 12.5 | −10 | 9 | 3 |
|  | 50 | −3 | −20 | −10 |
| 437446 | 12.5 | −6 | 7 | 2 |
|  | 50 | −4 | 1 | −1 |
| 437477 | 12.5 | 1 | −2 | 0 |
|  | 50 | 25 | −9 | −6 |
| 437478 | 12.5 | −7 | −4 | −9 |
|  | 50 | 22 | 4 | 3 |
| 437490 | 12.5 | −5 | 0 | −5 |
|  | 50 | −7 | 3 | −9 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of alanine transaminase (ALT) and aspartate transaminase (AST) are expressed in IU/L and the results are presented in Table 43.

TABLE 43

Effect of antisense oligonucleotide treatment on markers of liver function

|  | Dose (mg/kg) | ALT | AST |
|---|---|---|---|
| PBS |  | 32 | 58 |
| 387916 | 12.5 | 40 | 122 |
| 388241 | 12.5 | 39 | 93 |
|  | 50 | 28 | 62 |
| 437123 | 12.5 | 38 | 88 |
|  | 50 | 34 | 66 |
| 437132 | 12.5 | 34 | 52 |
|  | 50 | 30 | 52 |
| 437140 | 12.5 | 30 | 62 |
|  | 50 | 40 | 63 |
| 437442 | 12.5 | 40 | 106 |
|  | 50 | 63 | 119 |
| 437446 | 12.5 | 35 | 119 |
|  | 50 | 35 | 89 |
| 437477 | 12.5 | 39 | 68 |
|  | 50 | 52 | 162 |
| 437478 | 12.5 | 37 | 53 |
|  | 50 | 55 | 71 |
| 437490 | 12.5 | 48 | 71 |
|  | 50 | 34 | 59 |

Study 5

Treatment

Eleven groups of four BACHD mice each were injected intraperitoneally with 12.5 mg/kg of ISIS 388241, ISIS 419640, ISIS 419641, ISIS 419642, ISIS 436665, ISIS 436671, ISIS 436689, ISIS 437507, ISIS 443139, ISIS 444591, or ISIS 444661 twice a week for 2 weeks. A control group of four mice was injected intraperitoneally with phosphate buffered saline (PBS) twice a week for 2 weeks. Two days after the last dose, the mice were anaesthetized with isoflurane and exsanguinated for plasma collection, after which cervical dislocation was performed and organs collected.

RNA Analysis

RNA was extracted from liver tissue for real-time PCR analysis of huntingtin mRNA levels. Human mutant huntingtin mRNA levels were measured using the human primer probe set RTS2617. Mouse normal huntingtin levels were measured using the mouse primer probe set RTS2633. Results are presented in Tables 44 and 45 and were calculated as percent inhibition of human and murine huntingtin expression levels respectively, relative to the PBS control. All the antisense oligonucleotides effect significant inhibition of human huntingtin mRNA levels. ISIS 388241, ISIS 437507, and ISIS 443139 have more than three mismatches with the murine huntingtin mRNA (SEQ ID NO: 3) and therefore do not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 44

Percent inhibition of human huntingtin mRNA in BACHD mice

| ISIS No. | % inhibition |
|---|---|
| 388241 | 53 |
| 419640 | 34 |
| 419641 | 63 |
| 419642 | 55 |
| 436665 | 63 |
| 436671 | 66 |
| 436689 | 57 |
| 437507 | 54 |
| 443139 | 39 |
| 444591 | 48 |
| 444661 | 50 |

TABLE 45

Percent inhibition of murine huntingtin mRNA in BACHD mice

| ISIS No. | % inhibition |
|---|---|
| 419640 | 24 |
| 419641 | 51 |
| 419642 | 34 |
| 436665 | 49 |
| 436671 | 63 |
| 444591 | 41 |
| 444661 | 46 |

Body Weight and Organ Weight Measurements

The body weights of the mice were measured at the onset of the study and subsequently twice a week. The body weights of the mice are presented in Table 46 and are expressed as a percent change over the weights taken at the start of the study. The results indicate that treatment with these oligonucleotides did not cause any adverse change in body weight of the mice throughout the study.

TABLE 46

Percent change in body weight of BACHD mice after antisense oligonucleotide treatment

| | day 4 | day 7 | day 10 | day 12 |
|---|---|---|---|---|
| PBS | −3 | 0 | +2 | +1 |
| ISIS 388241 | −2 | −1 | −1 | +1 |
| ISIS 419640 | +1 | 0 | +3 | +4 |
| ISIS 419641 | +1 | +1 | +2 | 0 |
| ISIS 419642 | −3 | −2 | +1 | −5 |
| ISIS 436665 | +1 | +4 | +5 | +1 |
| ISIS 436671 | +1 | +2 | +5 | +4 |
| ISIS 436689 | +1 | +3 | 0 | −1 |
| ISIS 437507 | −1 | −2 | +2 | −2 |
| ISIS 443139 | −2 | +6 | +4 | +1 |
| ISIS 444591 | −1 | +1 | +2 | 0 |
| ISIS 444661 | +1 | +3 | +2 | 0 |

Liver, spleen and kidney weights were measured at the end of the study, and are presented in Table 47 as a percent of the saline control normalized to body weight.

TABLE 47

Percent change in organ weight of BACHD mice after antisense oligonucleotide treatment

| ISIS No. | Liver | Spleen | Kidney |
|---|---|---|---|
| 388241 | +2 | +13 | −7 |
| 419640 | −2 | +12 | −12 |
| 419641 | +4 | +3 | −13 |
| 419642 | +5 | +19 | −8 |
| 436665 | −3 | +3 | −13 |
| 436671 | 0 | +1 | −18 |
| 436689 | −6 | −10 | −12 |
| 437507 | −5 | −5 | −14 |
| 443139 | −2 | −9 | −13 |
| 444591 | −2 | −10 | −12 |
| 444661 | 0 | −16 | −12 |

Evaluation of Liver Function

To evaluate the impact of ISIS oligonucleotides on the hepatic function of the mice described above, plasma concentrations of transaminases were measured using an automated clinical chemistry analyzer (Hitachi Olympus AU400e, Melville, N.Y.). Measurements of ALT and AST are expressed in IU/L. Plasma levels of bilirubin and albumin were also measured using the same clinical chemistry analyzer and expressed in g/dL. The results are presented in Table 48.

TABLE 48

Effect of antisense oligonucleotide treatment on markers of liver function

| | ALT | AST | Bilirubin | Albumin |
|---|---|---|---|---|
| PBS | 42.5 | 86.5 | 0.2 | 3.1 |
| ISIS 388241 | 39.3 | 54.5 | 0.3 | 3.0 |
| ISIS 419640 | 36.8 | 85.8 | 0.2 | 2.9 |
| ISIS 419641 | 50.0 | 71.8 | 0.2 | 3.0 |
| ISIS 419642 | 42.8 | 77.0 | 0.1 | 3.0 |
| ISIS 436665 | 51.5 | 123.0 | 0.2 | 3.0 |
| ISIS 436671 | 52.0 | 71.0 | 0.1 | 3.0 |
| ISIS 436689 | 38.3 | 75.3 | 0.2 | 3.1 |
| ISIS 437507 | 37.0 | 77.5 | 0.1 | 3.0 |
| ISIS 443139 | 41.3 | 124.8 | 0.2 | 3.0 |
| ISIS 444591 | 46.5 | 61.3 | 0.2 | 3.0 |
| ISIS 444661 | 67.5 | 109.8 | 0.2 | 3.1 |

Measurement of Kidney Function

To evaluate the impact of ISIS oligonucleotides on the kidney function of mice described above, plasma concentrations of blood urea nitrogen (BUN) and creatinine were measured using an automated clinical chemistry analyzer (Hitachi Olympus AU400e, Melville, N.Y.). Results are presented in Table 49 expressed in mg/dL.

TABLE 49

Effect of antisense oligonucleotide treatment on markers of kidney function

|  | BUN | Creatinine |
|---|---|---|
| PBS | 24.0 | 0.17 |
| ISIS 388241 | 22.6 | 0.17 |
| ISIS 419640 | 21.4 | 0.16 |
| ISIS 419641 | 19.9 | 0.16 |
| ISIS 419642 | 23.6 | 0.18 |
| ISIS 436665 | 20.2 | 0.17 |
| ISIS 436671 | 22.6 | 0.17 |
| ISIS 436689 | 19.2 | 0.18 |
| ISIS 437507 | 19.9 | 0.16 |
| ISIS 443139 | 23.3 | 0.16 |
| ISIS 444591 | 23.5 | 0.18 |
| ISIS 444661 | 25.4 | 0.18 |

Measurement of other Metabolic Parameters

To evaluate the impact of ISIS oligonucleotides on other metabolic functions in mice described above, plasma concentrations of glucose, cholesterol and triglycerides were measured using an automated clinical chemistry analyzer (Hitachi Olympus AU400e, Melville, N.Y.). Results are presented in Table 50 expressed in mg/dL and demonstrate that treatment with these oligonucleotides did not cause any adverse changes in the levels of these metabolic markers between the control and treatment groups.

TABLE 50

Effect of antisense oligonucleotide treatment on metabolic markers

|  | Glucose | Cholesterol | Triglycerides |
|---|---|---|---|
| PBS | 198 | 142 | 225 |
| ISIS 388241 | 197 | 133 | 185 |
| ISIS 419640 | 198 | 132 | 189 |
| ISIS 419641 | 188 | 140 | 219 |
| ISIS 419642 | 184 | 128 | 192 |
| ISIS 436665 | 199 | 134 | 152 |
| ISIS 436671 | 196 | 148 | 174 |
| ISIS 436689 | 194 | 132 | 174 |
| ISIS 437507 | 198 | 139 | 155 |
| ISIS 443139 | 178 | 122 | 239 |
| ISIS 444591 | 202 | 145 | 263 |
| ISIS 444661 | 180 | 140 | 247 |

Example 4: Bolus Administration of Antisense Oligonucleotides Against Huntingtin mRNA to the Striatum of BACHD Mice BACHD mice were treated with ISIS oligonucleotides via bolus administration to a defined mouse brain area, the striatum, for the purpose of screening the activity of the oligonucleotides in brain tissue against human and mouse huntingtin mRNA expression.
Treatment and Surgery Groups of four BACHD mice each were administered with ISIS 388241, ISIS 419628, ISIS 419637, ISIS 419640, ISIS 419641, ISIS 419642, ISIS 436665, ISIS 436671, ISIS 436684, ISIS 436689, ISIS 436754, ISIS 437168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661 or ISIS 444663 delivered as a single bolus injection at 3 µg, 10 µg or 25 µg concentrations into the striatum.

A control group of 4 BACHD mice were similarly treated with PBS. ISIS 388241 was administered in seven groups of 4 mice each and the results presented are the average of the data derived from the 28 mice. ISIS 419628 was administered in 2 groups of 4 BACHD mice each and the results presented are the average of the data derived from the 8 mice. Seven days after the bolus administration, the mice were euthanized using isoflurane and the organs were removed. The animals were decapitated and the brain was removed for dissection of the striatal tissue.
RNA Analysis RNA was extracted from striatal tissue for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. The results for human huntingtin mRNA levels are presented in Table 51 and are expressed as percent inhibition compared to the PBS control group. All the antisense oligonucleotides effect dose-dependent inhibition of human huntingtin mRNA levels. The results for murine huntingtin mRNA levels are presented in Table 52 and are expressed as percent inhibition compared to the PBS control group.

The effective doses ($ED_{50}$) of each oligonucleotide for human huntingtin mRNA and mouse huntingtin mRNA were calculated by plotting the concentrations of oligonucleotides used versus the percent inhibition of huntingtin mRNA expression levels of either species and noting the concentrations at which 50% inhibition of huntingtin mRNA expression was achieved for each species compared to the corresponding controls. The $ED_{50}$ (µg) for each antisense oligonucleotide is also presented in Tables 51 and 52 for human and murine huntingtin mRNA respectively.

ISIS 388241, ISIS 436684, ISIS 436754, ISIS 437175, ISIS 437507, ISIS 443139, and ISIS 444584 are each mismatched by 8 base pairs or more with murine huntingtin mRNA (SEQ ID NO: 3) and therefore do not show significant inhibition of murine mRNA levels compared to the control. ISIS 437168 and ISIS 437441 have 2 mismatches each with the murine huntingtin mRNA (SEQ ID NO: 3) and do not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 51

Percent inhibition of human huntingtin mRNA levels in vivo and $ED_{50}$ of the antisense oligonucleotides

| ISIS No. | 3 mg | 10 mg | 25 mg | $ED_{50}$ |
|---|---|---|---|---|
| 388241 | 33 | 55 | 68 | 7.4 |
| 419628 | 49 | 58 | 83 | 5.1 |
| 419637 | 40 | 62 | 79 | 6.1 |
| 419640 | 52 | 64 | 77 | 4.8 |
| 419641 | 71 | 77 | 89 | 2.2 |
| 419642 | 67 | 70 | 83 | 3.0 |
| 436665 | 52 | 71 | 60 | 5.8 |
| 436671 | 68 | 80 | 84 | 2.4 |
| 436684 | 2 | 18 | 37 | 36.9 |
| 436689 | 27 | 63 | 81 | 7.0 |
| 436754 | 31 | 54 | 61 | 10.5 |

TABLE 51-continued

Percent inhibition of human huntingtin mRNA levels in vivo and ED$_{50}$ of the antisense oligonucleotides

| ISIS No. | 3 mg | 10 mg | 25 mg | ED$_{50}$ |
|---|---|---|---|---|
| 437168 | 2 | 49 | 60 | 15.2 |
| 437175 | 0 | 53 | 64 | 12.9 |
| 437441 | 3 | 32 | 38 | 35.3 |
| 437442 | 38 | 50 | 56 | 11.9 |
| 437507 | 38 | 59 | 79 | 6.6 |
| 437527 | 37 | 47 | 59 | 11.9 |
| 443139 | 39 | 61 | 70 | 6.7 |
| 444578 | 51 | 66 | 75 | 4.6 |
| 444584 | 30 | 63 | 71 | 7.8 |
| 444591 | 60 | 54 | 70 | 5.6 |
| 444607 | 57 | 69 | 75 | 3.2 |
| 444608 | 67 | 68 | 82 | 3.1 |
| 444615 | 47 | 55 | 91 | 5.2 |
| 444618 | 57 | 64 | 83 | 4.0 |
| 444627 | 47 | 70 | 61 | 5.0 |
| 444652 | 36 | 62 | 66 | 7.8 |
| 444658 | 60 | 66 | 79 | 3.6 |
| 444659 | 61 | 67 | 84 | 3.4 |
| 444660 | 55 | 62 | 66 | 4.2 |
| 444661 | 48 | 57 | 70 | 6.4 |
| 444663 | 42 | 60 | 80 | 5.5 |

TABLE 52

Percent inhibition of murine huntingtin mRNA levels in vivo and ED$_{50}$ of the antisense oligonucleotides

| ISIS No. | 3 mg | 10 mg | 25 mg | ED$_{50}$ |
|---|---|---|---|---|
| 419628 | 50 | 55 | 83 | 5.1 |
| 419637 | 63 | 79 | 86 | 2.6 |
| 419640 | 51 | 60 | 86 | 4.9 |
| 419641 | 65 | 80 | 87 | 2.7 |
| 419642 | 69 | 73 | 88 | 2.5 |
| 436665 | 68 | 82 | 66 | 2.7 |
| 436671 | 75 | 87 | 90 | 2 |
| 437442 | 30 | 53 | 82 | 9 |
| 437527 | 67 | 73 | 90 | 2.7 |
| 444578 | 50 | 65 | 74 | 4.9 |
| 444591 | 69 | 69 | 81 | 2.8 |
| 444607 | 57 | 70 | 75 | 3.8 |
| 444608 | 70 | 72 | 90 | 2.5 |
| 444615 | 30 | 37 | 88 | 9.5 |
| 444618 | 66 | 71 | 90 | 2.8 |
| 444627 | 41 | 60 | 57 | 8.8 |
| 444652 | 47 | 62 | 66 | 4.7 |
| 444658 | 60 | 62 | 85 | 3.9 |
| 444659 | 54 | 62 | 85 | 4.2 |
| 444660 | 42 | 48 | 64 | 9.5 |
| 444661 | 49 | 57 | 74 | 5.9 |
| 444663 | 42 | 65 | 84 | 5.1 |

The ten compounds marked with an asterisk had an improved ED50 over ISIS 388241.

Example 5: Assay for Neurotoxic Effects of Bolus Administration of Antisense Oligonucleotides in the Striatal Tissue of Rats About 30 compounds were selected as having high tolerability and high potency. Compounds were then tested by CNS bolus injection in rat to further assess neurotoxicity.

Sprague-Dawley rats each were treated with ISIS oligonucleotides via bolus administration to a defined brain area, the striatum, for the purpose of screening for the induction of the microglial marker AIF1 as a measure of CNS toxicity.

Treatment and Surgery

Groups of four Sprague-Dawley rats were administered with ISIS 387916, ISIS 388241, ISIS 419627, ISIS 419628, ISIS 419629, ISIS 419630, ISIS 419636, ISIS 419637, ISIS 419640, ISIS 419641, ISIS 419642, ISIS 436665, ISIS 436668, ISIS 4196671, ISIS 436684, ISIS 436689, ISIS 436754, ISIS 443168, ISIS 437175, ISIS 437441, ISIS 437442, ISIS 437507, ISIS 437527, ISIS 443139, ISIS 444578, ISIS 444584, ISIS 444591, ISIS 444607, ISIS 444608, ISIS 444615, ISIS 444618, ISIS 444627, ISIS 444652, ISIS 444658, ISIS 444659, ISIS 444660, ISIS 444661, or ISIS 444663 delivered as a single bolus injection at 50 μg concentration into the striatum.

A control group of 4 rats were similarly treated with PBS. A group of 4 rats were similarly treated with ISIS 104838, an antisense oligonucleotide against TNF-α, as a negative control group. ISIS 387916 was administered in four groups of 4 rats each and the results presented are an average of the data derived from the 16 rats. ISIS 419628 was administered in two groups of 4 rats each and the results presented are the average of the data from the 8 rats. ISIS 419629, ISIS 444584 and ISIS 444618, which had toxic indicators in the systemic administration study (Example 3) were also tested in this study. Seven days after bolus administration, the rats were euthanized using isoflurane and the organs were removed. The animals were decapitated and the brain was removed for dissection of the striatal tissue.

RNA Analysis of AIF1 Expression Levels

RNA was extracted from striatal tissue for real-time PCR analysis of AIF1 mRNA levels. Rat AIF1 levels were measured using the rat primer probe set rAif1_LTS00219 (forward sequence AGGAGAAAAACAAAGAACACCA-GAA, designated herein as SEQ ID NO: 46; reverse sequence CAATTAGGGCAACTCAGAAATAGCT, designated herein as SEQ ID NO: 47; probe sequence CCAACTGGTCCCCCAGCCAAGAX, designated herein as SEQ ID NO: 48). Results were calculated as the percentage of AIF1 expression over that of the PBS control and are presented in Table 53. ISIS 419629, ISIS 444584, and ISIS 444618, which had toxic indicators in the systemic administration study (in Example 3), also had toxic indicators in this study (greater than 300% above saline control). Later studies showed that ISIS 444584 is neurotolerable and exhibits negligible toxic indicators (see Example 16 and 17).

TABLE 53

Percent expression of AIF1 mRNA levels in vivo as a measure of neurotoxicity

| ISIS No. | % expression |
|---|---|
| 104838 | 111 |
| 387916 | 870 |
| 388241 | 236 |
| 419627 | 168 |
| 419628 | 497 |
| 419629 | 247 |
| 419630 | 227 |
| 419636 | 464 |
| 419637 | 275 |
| 419640 | 305 |
| 419641 | 206 |
| 419642 | 173 |
| 436665 | 217 |
| 436668 | 447 |
| 436671 | 239 |
| 436684 | 700 |
| 436689 | 149 |
| 436754 | 125 |
| 437168 | 130 |

TABLE 53-continued

Percent expression of AIF1 mRNA levels in vivo as a measure of neurotoxicity

| ISIS No. | % expression |
|---|---|
| 437175 | 131 |
| 437441 | 158 |
| 437442 | 157 |
| 437507 | 133 |
| 437527 | 184 |
| 443139 | 143 |
| 444578 | 352 |
| 444584 | 317 |
| 444591 | 194 |
| 444607 | 362 |
| 444608 | 476 |
| 444615 | 645 |
| 444618 | 547 |
| 444627 | 377 |
| 444652 | 336 |
| 444658 | 364 |
| 444659 | 319 |
| 444660 | 411 |
| 444661 | 249 |
| 444663 | 448 |

RNA Analysis of Huntingtin Expression Levels

RNA was extracted from striatal tissue for real-time PCR analysis of huntingtin mRNA levels. Rat huntingtin mRNA levels were measured using the rat primer probe set rHtt_LTS00343 (forward sequence CAGAGCTGGTGAAC-CGTATCC, designated herein as SEQ ID NO: 49; reverse sequence GGCTTAAGCAGGGAGCCAAAA, designated herein as SEQ ID NO: 50; probe sequence ACTTCATGAT-GAGCTCGGAGTTCAACX, designated herein as SEQ ID NO: 51). Results were calculated as the percentage reduction of huntingtin expression over that of the PBS control and are presented in Table 54. ISIS 388241, ISIS 436684, ISIS 436754, ISIS 437175, ISIS 437507, and ISIS 443139 are each mismatched by 6 base pairs or more with the rat gene sequence (SEQ ID NO: 5) and therefore do not show significant inhibition of rat mRNA levels compared to the control. ISIS 419640, ISIS 419641, ISIS 419642, ISIS 436665, ISIS 436668, ISIS 437442, ISIS 444615, and ISIS 444627 have 1 mismatch each with the rat gene sequence (SEQ ID NO: 5) and do not show significant inhibition of rat mRNA levels compared to the control. ISIS 437168 and ISIS 437441 have 2 mismatches each with the rat gene sequence (SEQ ID NO: 5) and do not show significant inhibition of rat mRNA levels compared to the control. ISIS 436689 and ISIS 444584 have 3 mismatches each with the rat gene sequence (SEQ ID NO: 5) and do not show significant inhibition of rat mRNA levels compared to the control.

TABLE 54

Percent reduction of rat huntingtin mRNA levels in rats

| ISIS No. | % reduction |
|---|---|
| 387916 | 70 |
| 419627 | 67 |
| 419628 | 57 |
| 419629 | 85 |
| 419630 | 11 |
| 419636 | 53 |
| 419637 | 84 |
| 436671 | 77 |
| 437527 | 86 |
| 444578 | 72 |
| 444591 | 35 |
| 444607 | 57 |
| 444608 | 68 |
| 444618 | 56 |
| 444652 | 75 |
| 444658 | 61 |
| 444659 | 55 |
| 444660 | 63 |
| 444661 | 52 |
| 444663 | 59 |

Example 6: Intracerebroventricular Administration of Antisense Oligonucleotides Against Huntingtin mRNA-Tolerability Study in BACHD Mice Selected compounds were compared with previously designed compound ISIS 388241 by ICV administration in BACHD mice.

Selected compounds plus the benchmark 388241 were selected based on in vitro and systemic potency and systemic tolerability as well as CNS potency and tolerability.

BACHD mice were treated with ISIS oligonucleotides via intracerebroventricular (ICV) administration to a defined mouse brain area, the right lateral ventricle, for the purpose of evaluating the tolerability of ICV dosing in mice.

Treatment and Surgery

Groups of five BACHD mice each were administered ISIS 388241, ISIS 437507, ISIS 443139, ISIS 419640, ISIS 419641, ISIS 419642, ISIS 444591, ISIS 436665, ISIS 436671, ISIS 444661, or ISIS 436689 at 150 µg/day delivered ICV with Alzet 2002 pumps at the rate of 12 µL/day for 2 weeks. A control group of 4 BACHD mice were similarly treated with PBS. The mice were surgically implanted with the pumps in the following manner: Mice were individually anaesthetized with 3% isoflurane for pump implantation. After two weeks, the mice were anesthetized again and the pump was surgically removed. The animals were then allowed to recover for two more weeks before being euthanized.

The body weights of the mice were taken weekly during the treatment and recovery periods. After 4 weeks, the mice were euthanized using isoflurane and decapitated. The brain was removed for tissue acquisition from the anterior and posterior sections.

RNA Analysis

RNA was extracted from the right hemisphere of the anterior cortex and the posterior cerebellar section of the cannulation site for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. Results were calculated as percent inhibition of human and murine huntingtin mRNA expression compared to the control and are presented in Tables 56 and 57 respectively. All the antisense oligonucleotides effect significant inhibition of human huntingtin mRNA levels. ISIS 388241, ISIS 437507, and ISIS 443139 are each mismatched by 8 base pairs or more with the murine huntingtin mRNA (SEQ ID NO: 3) and therefore do not show significant inhibition of murine mRNA levels compared to the control. ISIS 444591 has 1 mismatch with the murine huntingtin mRNA (SEQ ID NO: 3) and does not show significant inhibition of murine mRNA levels compared to the control. ISIS 436689 has 3 mismatches with the murine huntingtin mRNA (SEQ ID NO: 3) and does not show significant inhibition of murine mRNA levels compared to the control.

TABLE 56

Percent reduction of human huntingtin mRNA levels in BACHD mice via ICV administration of antisense oligonucleotides

| ISIS No. | Number of mice | Anterior cortex | Posterior cortex |
|---|---|---|---|
| 388241 | 3 | 82 | 70 |
| 419640 | 1 | 60 | 46 |
| 419641 | 2 | 75 | 66 |
| 419642 | 3 | 29 | 42 |
| 436665 | 5 | 62 | 38 |
| 436671 | 3 | 69 | 77 |
| 436689 | 3 | 49 | 40 |
| 437507 | 3 | 77 | 66 |
| 443139 | 5 | 93 | 90 |
| 444591 | 5 | 79 | 78 |

TABLE 57

Percent reduction of murine huntingtin mRNA levels in BACHD mice via ICV administration of antisense oligonucleotides

| ISIS No. | Number of mice | Anterior cortex | Posterior cortex |
|---|---|---|---|
| 419640 | 1 | 22 | 34 |
| 419641 | 2 | 40 | 26 |
| 419642 | 3 | 63 | 71 |
| 436665 | 5 | 72 | 56 |
| 436671 | 3 | 80 | 71 |

Body Weight Measurement

The body weights of the mice were measured at the onset of the study and subsequently once a week. The body weights of the mice are presented in Table 58 and are expressed as a percent change over the weights taken at the start of the study. The body weights were considered a measure of the tolerability of the mice to the ICV administration of antisense oligonucleotide. 'n.d.' means that there was no data available for that time period.

TABLE 58

Percent change in body weight of BACHD mice during antisense oligonucleotide treatment

| | week 1 | week 2 | week 3 | week 4 |
|---|---|---|---|---|
| PBS | −1 | +2 | +6 | +6 |
| ISIS 388241 | +3 | +11 | +15 | +7 |
| ISIS 437507 | +21 | +10 | +13 | −4 |
| ISIS 443139 | +10 | +10 | +16 | +12 |
| ISIS 419640 | +21 | +11 | −10 | +9 |
| ISIS 419641 | +24 | +3 | −5 | −12 |
| ISIS 419642 | +45 | +39 | +12 | +1 |
| ISIS 444591 | +18 | +38 | +27 | +17 |
| ISIS 436665 | +34 | +43 | +23 | +9 |
| ISIS 436671 | +19 | +17 | +11 | 0 |
| ISIS 444661 | +19 | −10 | −21 | n.d. |
| ISIS 436689 | +49 | +40 | +2 | −17 |

Survival of the Mice

The survival of the mice was assessed throughout the entire study period. Table 59 below shows the survival pattern in the groups of mice treated with ISIS oligonucleotides as well as the control.

TABLE 59

Number of survivals during antisense oligonucleotide treatment

| | week 1 | week 2 | week 3 | week 4 |
|---|---|---|---|---|
| PBS | 5 | 5 | 5 | 5 |
| ISIS 388241 | 4 | 3 | 3 | 3 |
| ISIS 437507 | 5 | 5 | 4 | 4 |
| ISIS 443139 | 5 | 5 | 5 | 5 |
| ISIS 419640 | 5 | 5 | 4 | 1 |
| ISIS 419641 | 5 | 5 | 4 | 2 |
| ISIS 419642 | 5 | 5 | 4 | 2 |
| ISIS 444591 | 5 | 5 | 5 | 5 |
| ISIS 436665 | 5 | 5 | 5 | 5 |
| ISIS 436671 | 4 | 4 | 3 | 3 |
| ISIS 444661 | 5 | 5 | 1 | 0 |
| ISIS 436689 | 4 | 4 | 4 | 3 |

Example 7: Intracerebroventricular Administration of Antisense Oligonucleotides Against Huntingtin in C57/BL6 Mice Wild-type C57/BL6 mice were treated with ISIS oligonucleotides via intracerebroventricular (ICV) administration to a defined mouse brain area, the right lateral ventricle, for the purpose of evaluating the potency of the oligonucleotides against mouse huntingtin in these mice.

Treatment and Surgery

Groups of ten C57/BL6 mice each were administered ISIS 408737 (5' TCCTAGTGTTACATTACCGC 3' (SEQ ID NO: 52), start site 5263 of SEQ ID NO: 3) at 50 µg/day delivered ICV with Alzet 2002 pumps at the rate of 0.5 µL/day for 7 days or 14 days. A control group of six C57/BL6 mice were similarly treated with PBS. The mice were surgically implanted with the pumps in the following manner: Briefly, Alzet osmotic pumps (Model 2002) were assembled according to manufacturer's instructions. Pumps were filled with a solution containing the antisense oligonucleotide and incubated overnight at 37° C., 24 hours prior to implantation. Animals were anesthetized with 3% isofluorane and placed in a stereotactic frame. After sterilizing the surgical site, a midline incision was made over the skull, and a subcutaneous pocket was created over the back, in which a pre-filled osmotic pump was implanted. A small burr hole was made through the skull above the right lateral ventricle. A cannula, connected to the osmotic pump via a plastic catheter, was then placed in the ventricle and glued in place using Loctite adhesive. The incision was closed with sutures. Antisense oligonucleotide or PBS was infused for 7 or 14 days, after which animals were euthanized according to a humane protocol approved by the Institutional Animal Care and Use Committee. Brain and spinal cord tissue were harvested and snap frozen in liquid nitrogen. Prior to freezing, brain tissue was cut transversely into five sections (S1, S2, S3, S4, and S5) using a mouse brain matrix. Sections 1 to 5 were approximately 2 mm apart from each other with 51 being most rostral and S5 most caudal.

RNA and Protein Analysis

Total RNA was extracted from mouse brain and spinal cord with RNeasy Protect Mini Kit (Qiagen, Mississauga, ON, Canada) for real-time PCR analysis of huntingtin mRNA levels using an RNeasy Mini prep kit (Qiagen). Q-PCR reactions were conducted and analyzed on an ABI Prism 7700 Sequence Detector (Applied Biosystems). Mouse huntingtin mRNA levels were measured using the murine primer probe set ABI # Mm01213820_ml (Applied Biosystems) and normalized to peptidylprolyl isomerase A mRNA levels. Protein lysates were prepared from mouse brain slabs as described previously (Li S. H. and Li X. J., *Methods in Molecular Biology* (2008), 217:1940-6029). Lysates were run on 3-8% tris-acetate gel and transferred using the iBlot dry blotting system (Invitrogen). Blots were probed with anti-beta tubulin (Chemicon) and monoclonal MAB2166 antibody (Millipore) that reacts specifically with murine huntingtin protein. Immunoblots were quantified using Odyssey V3.0 software.

The results are presented in Table 60 as percent reduction compared to the PBS control and demonstrate significant inhibition of huntingtin mRNA and protein levels by the antisense oligonucleotide both at day 7 and day 14.

TABLE 60

Percent inhibition of murine huntingtin mRNA in C57/BL6 mice

|  | day 7 | day 14 |
|---|---|---|
| mRNA | 66 | 68 |
| protein | 21 | 49 |

Example 8: Intracerebroventricular Administration of Antisense Oligonucleotides Against Huntingtin mRNA in Cynomologous Monkeys Cynomologous monkeys were treated with ISIS oligonucleotides via intracerebroventricular (ICV) administration to a defined brain area, the lateral ventricles, for the purpose of screening the activity of the oligonucleotides in brain tissue against huntingtin mRNA expression.

Treatment and Surgery

Two groups of 3 cynomologous monkeys each were administered either 0.635 mg/ml (1.5 mg/day) or 1.67 mg/ml (4 mg/day) of ISIS 436689 delivered ICV with individual ambulatory pumps (Pegasus Vario) at the rate of 0.05 ml/hr for 4 weeks. A control group of 2 cynomologous monkeys were administered with PBS in a similar manner. The groups were administered ISIS 436689 bilaterally. One animal was administered ISIS 436689 at the 4 mg/day dose unilaterally to the right ventricle.

Animals were allowed 10 days to recover from surgery prior to infusion being performed. During the post surgery recovery period, the animals were maintained on PBS ICV infusion at a flow rate of 0.05 mL/h using one ambulatory infusion pump per ventricle. At the end of the recovery period, each cannula was connected to an individual ambulatory pump (Pegasus Vario) placed within a primate jacket (Lomir, PJ-02NB). The pumps remained connected until completion of the infusion period. After 4 weeks administration, the animals were euthanized and the brain, liver and kidney were harvested.

RNA Analysis of htt mRNA

RNA was extracted from the anterior caudate, posterior caudate, temporal cortex, parietal cortex, hypothalamus, mid-brain, hippocampus, and spinal cords, as well as the liver and kidney for real-time PCR analysis of huntingtin mRNA levels. Huntingtin mRNA levels were measured using the human primer probe set RTS2617 and normalized to monkey cyclophilin A levels. Results were calculated as percent inhibition of huntingtin mRNA expression compared to the PBS control and are presented in Table 61. ISIS 436689 effected significant inhibition of human huntingtin mRNA levels in the CNS.

TABLE 61

Percent reduction of huntingtin mRNA levels in cynomologous monkeys via ICV administration of antisense oligonucleotides

| | Dose (mg/day) | | | |
|---|---|---|---|---|
| Tissue | 1.5 (bilateral) | 4 (bilateral) | 4 (right unilateral) | 4 (left unilateral) |
| Anterior caudate | 59 | 49 | 85 | 12 |
| Posterior caudate | 52 | 81 | 63 | 0 |
| Temporal cortex | 10 | 34 | 41 | 31 |
| Parietal cortex | 22 | 38 | 46 | 24 |
| Hypothalamus | 59 | 71 | 35 | 100 |
| Mid-brain | 32 | 38 | 2 | 0 |
| Hippocampus | 18 | 18 | 28 | 10 |
| Cervical cord | 58 | 65 | n.d. | n.d. |
| Thoracic cord | 50 | 67 | n.d. | n.d. |
| Lumbar cord | 49 | 62 | n.d. | n.d. |
| Liver | 0 | 13 | n.d. | n.d. |
| Kidney | 0 | 13 | n.d. | n.d. | n.d. = no data

Example 9: Measurement of Half-Life of ISIS 387898 in the Striatum of C57/BL6 Mice Via Single Bolus Administration C57/BL6 mice were administered ISIS 387898 as a single bolus to the striatum for the purpose of measuring half-life and duration of action of the antisense oligonucleotide against huntingtin mRNA expression in that tissue.

Treatment

Forty C57/BL6 mice were treated with ISIS 387898 (5' CTCGACTAAAGCAGGATTTC 3' (SEQ ID NO: 53); start position 4042 of SEQ ID NO: 1 and start position 4001 of SEQ ID NO: 3) delivered as a single bolus of 50 μg in a procedure similar to that described in Example 5. Eight control C57/BL6 mice were treated with PBS in a similar procedure. Groups of 4 mice each were euthanized at various time points and striatal tissue extracted in a procedure similar to that described in Example 5.

RNA Analysis

RNA was extracted from striatal tissue for real-time PCR analysis of huntingtin mRNA levels. Mouse normal huntingtin mRNA levels were measured using the murine primer probe set RTS2633. The results are presented in Table 62 and are expressed as percent inhibition compared to the PBS control group at day 7. The inhibitory effect of ISIS 387898 was observed to be prolonged for at least 91 days.

TABLE 62

Effect of ISIS 387898 as a single bolus administration on murine huntingtin mRNA expression at various time points in C57/BL6 striatum

| Treatment | Days after dosing | % inhibition |
|---|---|---|
| ISIS 387898 | 1 | 66 |
| | 7 | 74 |
| | 14 | 68 |
| | 21 | 77 |
| | 28 | 75 |
| | 50 | 63 |
| | 73 | 55 |
| | 91 | 48 |
| PBS | 50 | 5 |

Analysis of Antisense Oligonucleotide Concentration in the Brain:

Brain tissues were minced, weighed, homogenized, and extracted using a phenol/chloroform liquid-liquid extraction method. This was followed by solid phase extraction of the supernatant on a phenyl-bonded column before capillary gel eletrophoresis electrokinetic injection. A P/ACE MDQ capillary electrophoresis instrument (Beckman Coulter, Fullerton, Calif.) was used for gel-filled capillary electrophoretic analysis. Oligonucleotide peaks were detected by UV absorbance at 260 nm.

Figure 2:
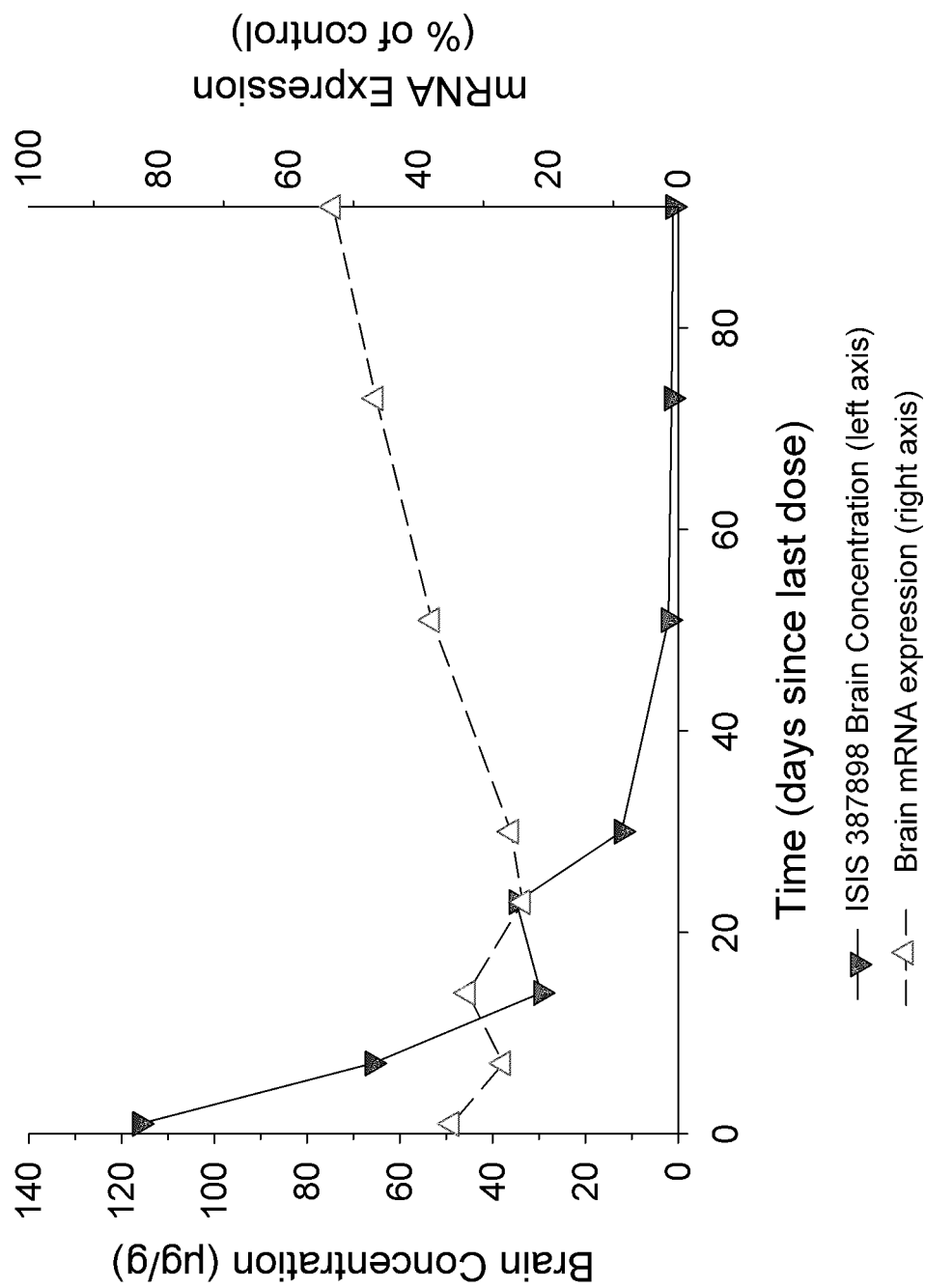
FIG. 2:
Comparison of huntingtin mRNA expression in intrastriatal tissue and ISIS 387898 concentrations at various time points. C57/BL6 mice were administered a single bolus of 50 µg of ISIS 387898 and huntingtin mRNA expression as well as the concentration of the antisense oligonucleotide in the tissue were measured. The duration of action (as measured by htt mRNA expression) of ISIS 387898 (dashed line) was observed to be longer even after the concentration of the oligonucleotide (solid line) in the tissue.

The concentration of ISIS 387898 in the brain (µg/g) was plotted against the expression of human huntingtin as a percentage of the PBS control (Table 63 and FIG. 1). The concentration of ISIS 387898 which achieves 50% inhibition of huntingtin mRNA expression ($EC_{50}$) was calculated. The $EC_{50}$ was determined to be 0.45 µg/g. The time-dependent concentration of ISIS 387898 in the brain tissue and corresponding percentage huntingtin mRNA expression was also plotted (Table 64 and FIG. 2) and the half-life of the oligonucleotide was calculated as 21 days.

TABLE 63

Concentration of ISIS 387898 in brain tissue and its effect on htt mRNA expression as a percentage of the control

| concentration (µg/g) | % mRNA expression |
|---|---|
| 0 | 105.0 |
| 25 | 28.8 |
| 50 | 28.2 |
| 75 | 27.9 |
| 100 | 27.8 |
| 125 | 27.8 |

TABLE 64

Time-dependent concentration of ISIS 387898 in brain tissue and its effect on htt mRNA expression as a percentage of the control

| Time (day) | Conc (µg/g) | mRNA % expression |
|---|---|---|
| 1 | 116 | 35 |
| 7 | 65.7 | 27 |
| 14 | 30 | 32 |
| 23 | 34.9 | 24 |
| 30 | 12.2 | 26 |
| 51 | 2.1 | 38 |
| 73 | 1.4 | 47 |
| 92 | 1.1 | 53 |

Example 10: Measurement of Half-Life of ISIS 387898 in the Lateral Ventricles of BACHD Mice Via ICV Administration BACHD mice were administered ISIS 387898 by ICV to the lateral ventricles of the brain for the purpose of measuring half-life and duration of action of the antisense oligonucleotide against huntingtin mRNA expression in that tissue.

Treatment

Twenty eight BACHD mice were treated with ISIS 387898 delivered by ICV administration at 75 µg/day for 2 weeks in a procedure similar to that described in Example 9. Twenty eight control BACHD mice were treated with PBS in a procedure similar to that described in Example 9. Groups of 4 mice each from both the treatment and control groups were euthanized at biweekly time points and anterior cortical tissue extracted in a procedure similar to that described in Example 9.

RNA Analysis

RNA was extracted from the right hemisphere, both anterior and posterior to the cannulation site for real-time PCR analysis of huntingtin mRNA levels. Human mutant huntingtin mRNA levels were measured using the human primer probe set RTS2617. Mouse normal huntingtin mRNA levels were measured using the murine primer probe set RTS2633. Human mutant huntingtin mRNA expression levels are presented in Table 65 and are expressed as percent inhibition compared to the average of that measured in the PBS control groups. Murine normal huntingtin mRNA expression levels are presented in Table 66 and are expressed as percent inhibition compared to the average of that measured in the PBS control groups. The inhibitory effect of ISIS 387898 was observed to be prolonged for 91 days.

TABLE 65

Effect of ISIS 387898 administered ICV on human huntingtin mRNA expression at various time points

| Treatment | Days after dosage | anterior | posterior |
|---|---|---|---|
| ISIS 387898 | 14 | 74 | 65 |
|  | 28 | 67 | 61 |
|  | 42 | 70 | 61 |
|  | 56 | 57 | 52 |
|  | 70 | 57 | 43 |
|  | 91 | 41 | 61 |
|  | 127 | 28 | 16 |
| PBS | 14 | 0 | 0 |
|  | 28 | 0 | 0 |
|  | 42 | 1 | 0 |
|  | 56 | 9 | 10 |
|  | 70 | 13 | 10 |
|  | 91 | 13 | 25 |
|  | 127 | 11 | 0 |

TABLE 66

Effect of ISIS 387898 administered ICV on murine huntingtin mRNA expression at various time points

| Treatment | Days after dosage | anterior | posterior |
|---|---|---|---|
| ISIS 387898 | 14 | 85 | 81 |
|  | 28 | 81 | 69 |
|  | 42 | 86 | 79 |
|  | 56 | 74 | 69 |
|  | 70 | 73 | 58 |
|  | 91 | 39 | 63 |
|  | 127 | 39 | 0 |
| PBS | 14 | 0 | 0 |
|  | 28 | 0 | 0 |
|  | 42 | 0 | 0 |
|  | 56 | 17 | 14 |
|  | 70 | 5 | 24 |
|  | 91 | 9 | 17 |
|  | 127 | 32 | 0 |

Figure 3:
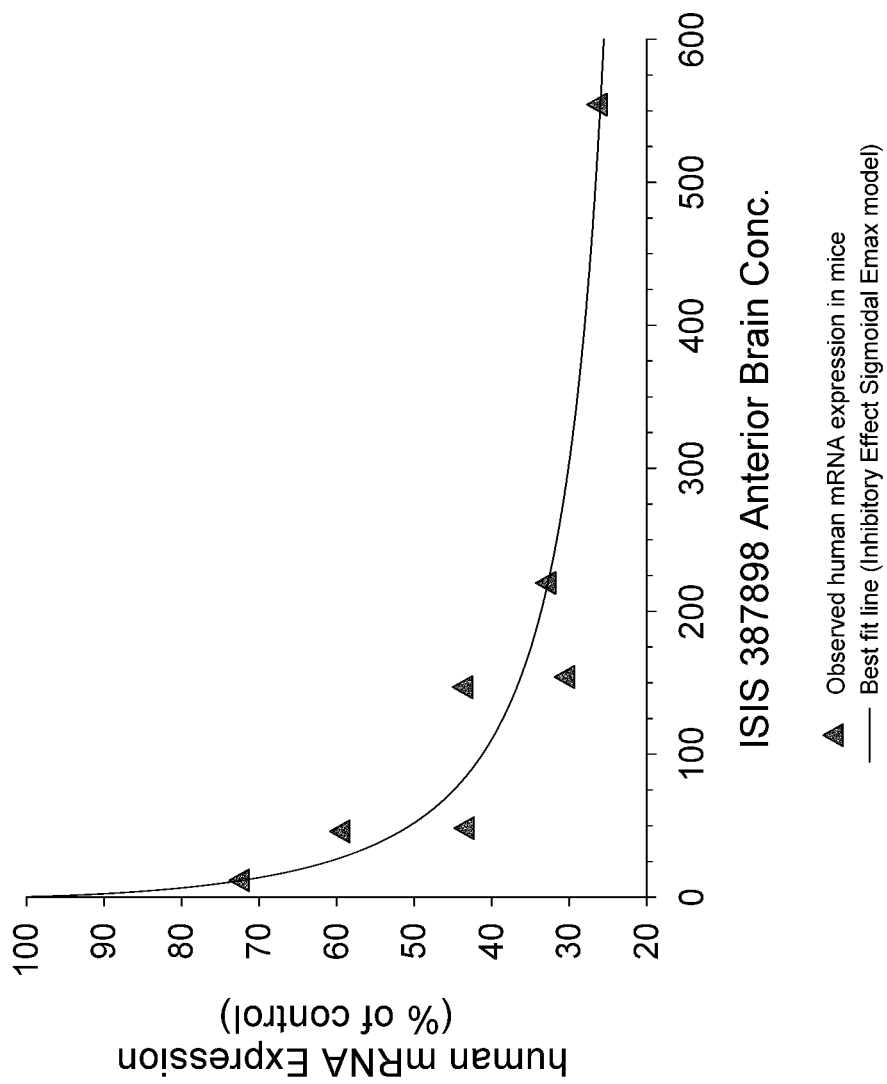
FIG. 3:
The PK/PD relationship of huntingtin mRNA expression in the anterior cortex tissue with ISIS 387898 concentration in mouse brain. BACHD mice were administered an intracerebroventricular infusion of 75 µg of ISIS 387898 for 2 weeks and huntingtin mRNA expression as well as the concentration of the antisense oligonucleotide in the tissue were measured. The $EC_{50}$ of ISIS 387898 was also calculated.
Figure 4:
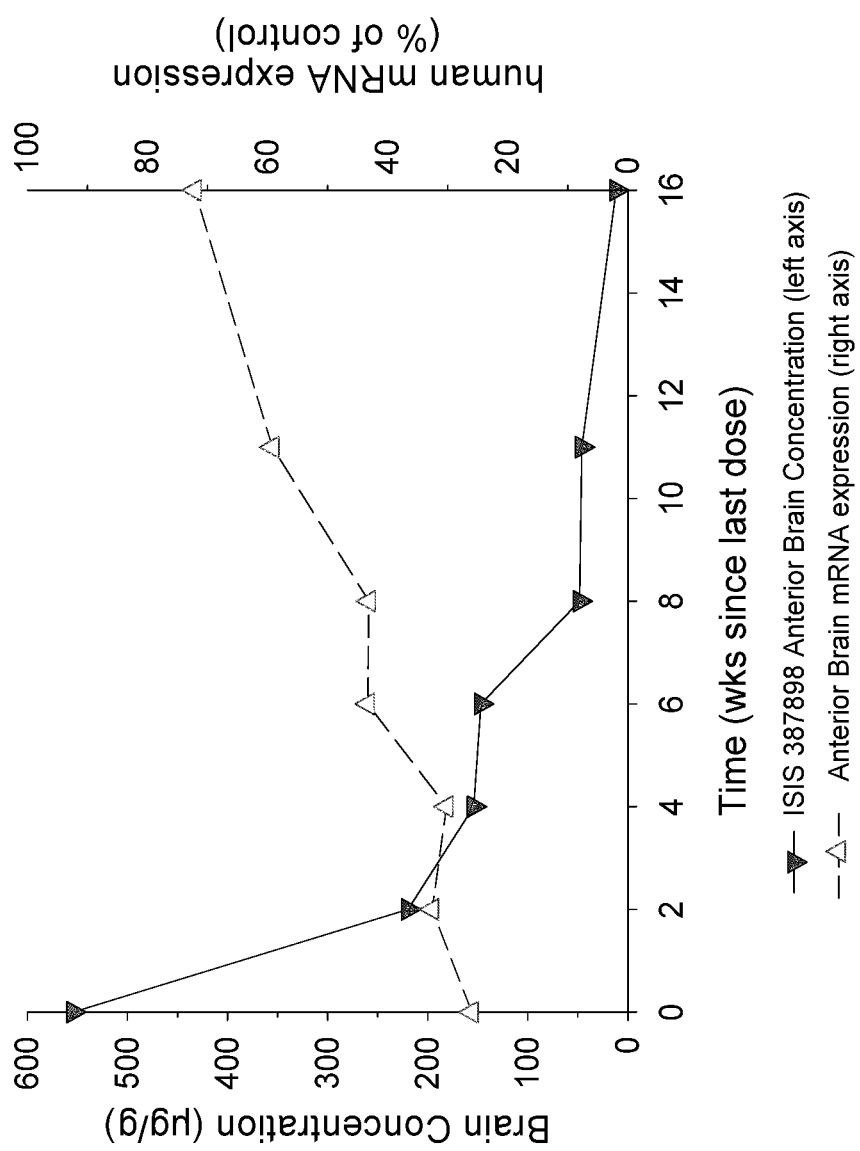
FIG. 4:
Comparison of huntingtin mRNA expression in anterior cortex tissue and ISIS 387898 concentrations at various time points. BACHD mice were administered intracerebroventricular infusion of 75 µg of ISIS 387898 for 2 weeks, and huntingtin mRNA expression as well as the concentration of the antisense oligonucleotide in the tissue were measured. The duration of action (as measured by htt mRNA expression) of ISIS 387898 (dashed line) was observed to be longer even after the concentration of the oligonucleotide (solid line) in the tissue.

Analysis of Antisense Oligonucleotide Concentration in the Brain:

Brain tissue was processed in a procedure similar to that described in Example 9. The concentration of ISIS 387898 in the anterior cortex of the brain (µg/g) was plotted against the inhibition of human huntingtin as a percentage of the PBS control (Table 67 and FIG. 3), and the $EC_{50}$ was calculated to be 26.4 μg/g. The time-dependent concentration of ISIS 387898 in the brain tissue was also plotted (Table 68 and FIG. 4) and the half-life of the oligonucleotide was calculated as 21 days.

TABLE 67

Concentration of ISIS 387898 in brain tissue and its effect on htt mRNA expression as a percentage of the control

| Concentration (μg/g) | % mRNA expression |
| --- | --- |
| 0 | 105 |
| 10 | 90.7 |
| 100 | 19.3 |
| 200 | 14.3 |
| 300 | 13.2 |
| 400 | 12.7 |
| 500 | 12.5 |
| 600 | 12.4 |

TABLE 68

Time-dependent concentration of ISIS 387898 in brain tissue and its effect on htt mRNA expression as a percentage of the control

| Days after last dose | Conc (mg/g) | % mRNA expression |
| --- | --- | --- |
| 14 | 554.3 | 12 |
| 28 | 219.8 | 15 |
| 42 | 154 | 13 |
| 56 | 146.9 | 32 |
| 70 | 48.3 | 28 |
| 91 | 46.1 | 66 |
| 127 | 11.8 | 90 |

Example 11: Measurement of Half-Life of ISIS 388241 and ISIS 443139 in the Lateral Ventricles of BACHD Mice Via ICV Administration BACHD mice were administered ISIS 388241 or ISIS 443139 by ICV to the lateral ventricles of the brain for the purpose of measuring half-life and duration of action of the antisense oligonucleotide against huntingtin mRNA expression in that tissue.

Treatment

Twenty BACHD mice were treated with ISIS 38241 delivered by ICV administration at 50 μg/day for 2 weeks in a procedure similar to that described in Example 9. Twenty BACHD mice were treated with ISIS 443139 delivered by ICV administration at 50 μg/day for 2 weeks in a procedure similar to that described in Example 9. Twenty control BACHD mice were treated with PBS in a procedure similar to that described in Example 9. Groups of 4 mice each from both the treatment groups and control group were euthanized at biweekly time points and tissue extracted in a procedure similar to that described in Example 9.

RNA Analysis

RNA was extracted from the right hemisphere, both anterior and posterior to the cannulation site for real-time PCR analysis of huntingtin mRNA levels. Human mutant huntingtin mRNA levels were measured using the human primer probe set RTS2617. The results are presented in Table 69 and are expressed as percent inhibition compared to the average of that measured in the PBS control groups. The inhibitory effects of both ISIS 388241 and ISIS 443139 were observed to be prolonged for at least 16 weeks.

Both ISIS 388241 and its mixed backbone equivalent, ISIS 443139, have more than 3 mismatches with murine huntingtin mRNA (SEQ ID NO: 5) and therefore did not show significant inhibition of murine mRNA levels compared to the control.

TABLE 69

Effect of ISIS 388241 and ISIS 443139 administered ICV on human huntingtin mRNA expression at various time points

| Treatment | Weeks after dosage | anterior | posterior |
| --- | --- | --- | --- |
| ISIS 388241 | 0 | 63 | 64 |
|  | 4 | 79 | 56 |
|  | 8 | 67 | 51 |
|  | 12 | 76 | 68 |
|  | 16 | 35 | 34 |
| ISIS 443139 | 0 | 35 | 55 |
|  | 4 | 20 | 62 |
|  | 8 | 61 | 59 |
|  | 12 | 67 | 53 |
|  | 16 | 46 | 37 |
| PBS | 0 | 15 | 10 |
|  | 4 | 0 | 2 |
|  | 8 | 5 | 0 |
|  | 12 | 32 | 4 |
|  | 16 | 6 | 2 |

Figure 5:
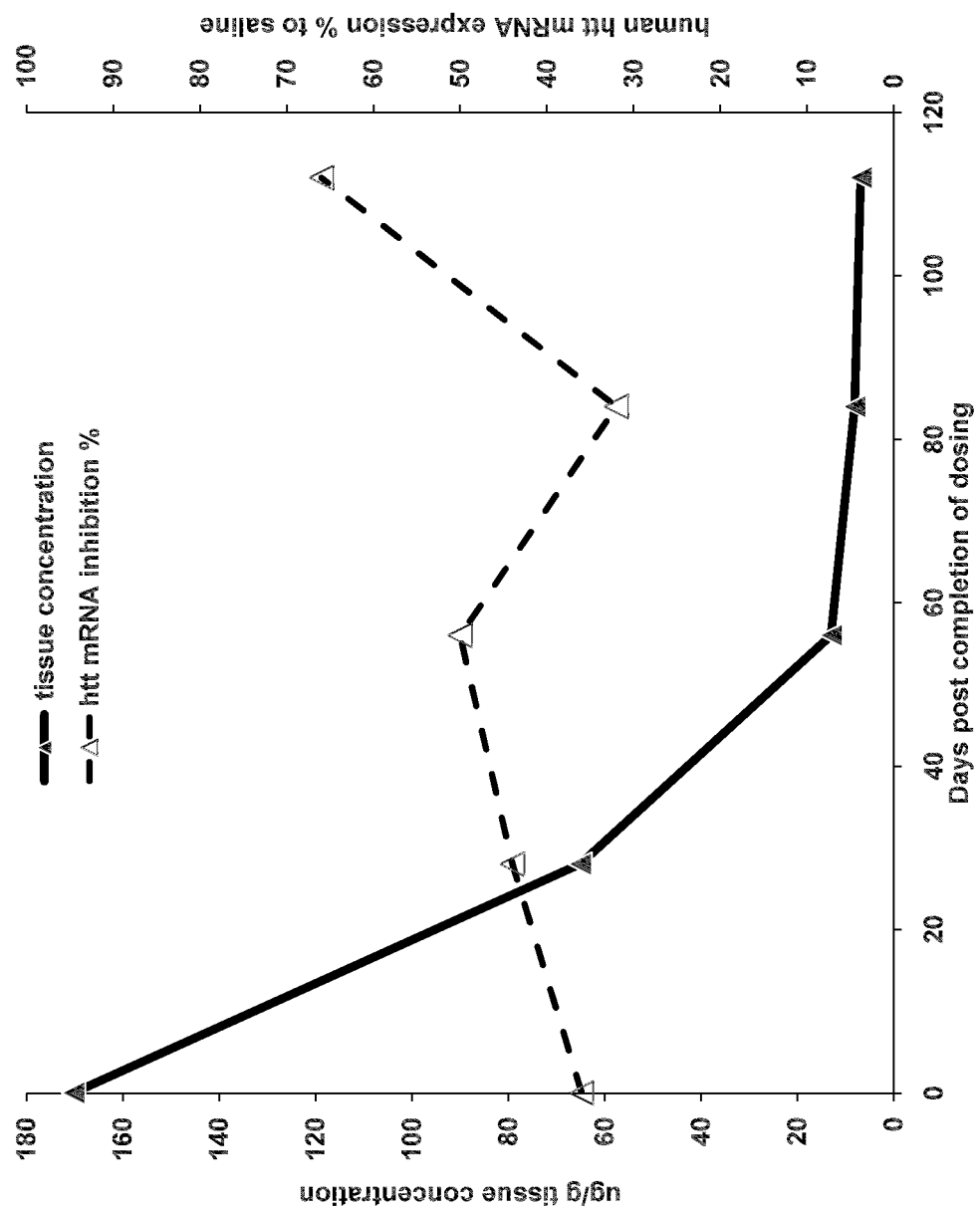
FIG. 5.
Figure 6:
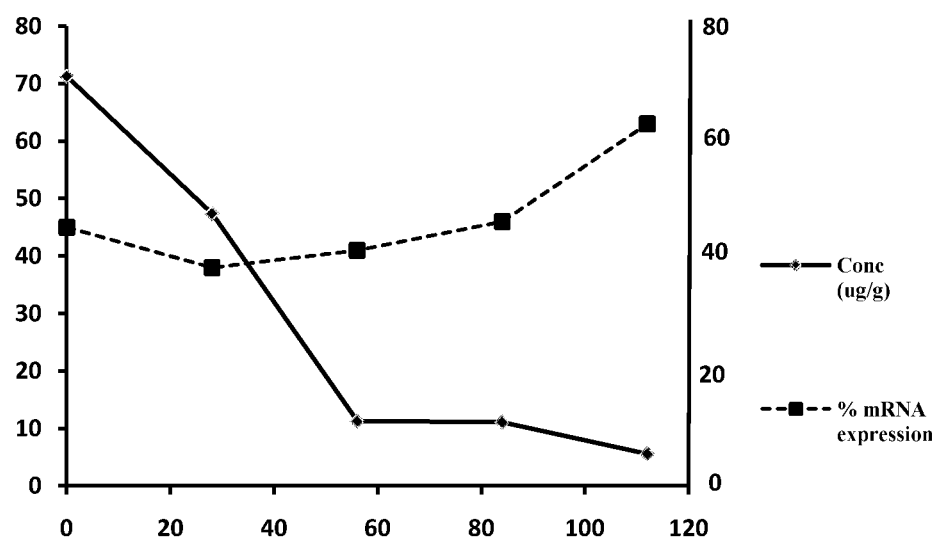

Analysis of Antisense Oligonucleotide Concentration in the Brain:

Brain tissue was processed in a procedure similar to that described in Example 9. The time-dependent concentration of ISIS 388241 in the posterior brain tissue was plotted (Table 70 and FIG. 5) and the half-life of the oligonucleotide was calculated as 20 days. The time-dependent concentration of ISIS 443139 in the posterior brain tissue was plotted (Table 71 and FIG. 6) and the half-life of the oligonucleotide was calculated as 20 days.

TABLE 70

Concentration of ISIS 384241 in brain tissue and its effect on htt mRNA expression as a percentage of the control

| Days after last dose | Conc (ug/g) | % mRNA expression |
| --- | --- | --- |
| 0 | 170.3 | 36 |
| 28 | 65.2 | 43 |
| 56 | 13 | 49 |
| 84 | 8.2 | 32 |
| 112 | 6.9 | 66 |

TABLE 71

Concentration of ISIS 443139 in brain tissue and its effect on htt mRNA expression as a percentage of the control

| Days after last dose | Conc (ug/g) | % mRNA expression |
| --- | --- | --- |
| 0 | 71.3 | 45 |
| 28 | 47.4 | 38 |
| 56 | 11.3 | 41 |

TABLE 71-continued

Concentration of ISIS 443139 in brain tissue and its effect on htt mRNA expression as a percentage of the control

| Days after last dose | Conc (ug/g) | % mRNA expression |
|---|---|---|
| 84 | 11.1 | 46 |
| 112 | 5.6 | 63 |

Example 12: Effect of Antisense Inhibition of Mutant Human Huntingtin on the Motor Performance of BACHD Mice BACHD mice were treated with ISIS oligonucleotides via intracerebroventricular (ICV) administration for the purpose of evaluating the effect of the oligonucleotides against huntingtin mRNA expression on their motor performance via the rotarod assay.

Treatment

The accelerating rotarod assay was performed on the Ugo Basile rotarod. Animals were placed on the rotarod at a speed of 2 RPM, the rotarod accelerated to 40 RPM over 5 minutes. The duration to fall was recorded. Duration to fall is defined by the animal either falling from the rotarod, or stopping their run, hanging on to the rotarod and rotating on it. Six month old BACHD mice and their non-transgenic littermates were trained to run on the rotarod for one week prior to treatment. This consisted of three consecutive trials of 5 minutes each, with a 20 minute rest period between trials. A group of 15 BACHD mice were then treated with ISIS 388241 at 50 µg/day delivered ICV with Alzet 2002 pumps at the rate of 12 µL/day for 2 weeks. The mice were surgically implanted with the pumps in a similar procedure as that described in Example 6. A control group of 14 BACHD mice were treated with PBS in a similar manner. A control group of 9 non-transgenic littermates were treated with PBS in a similar manner.

Rotarod Performance Assay

Figure 7:
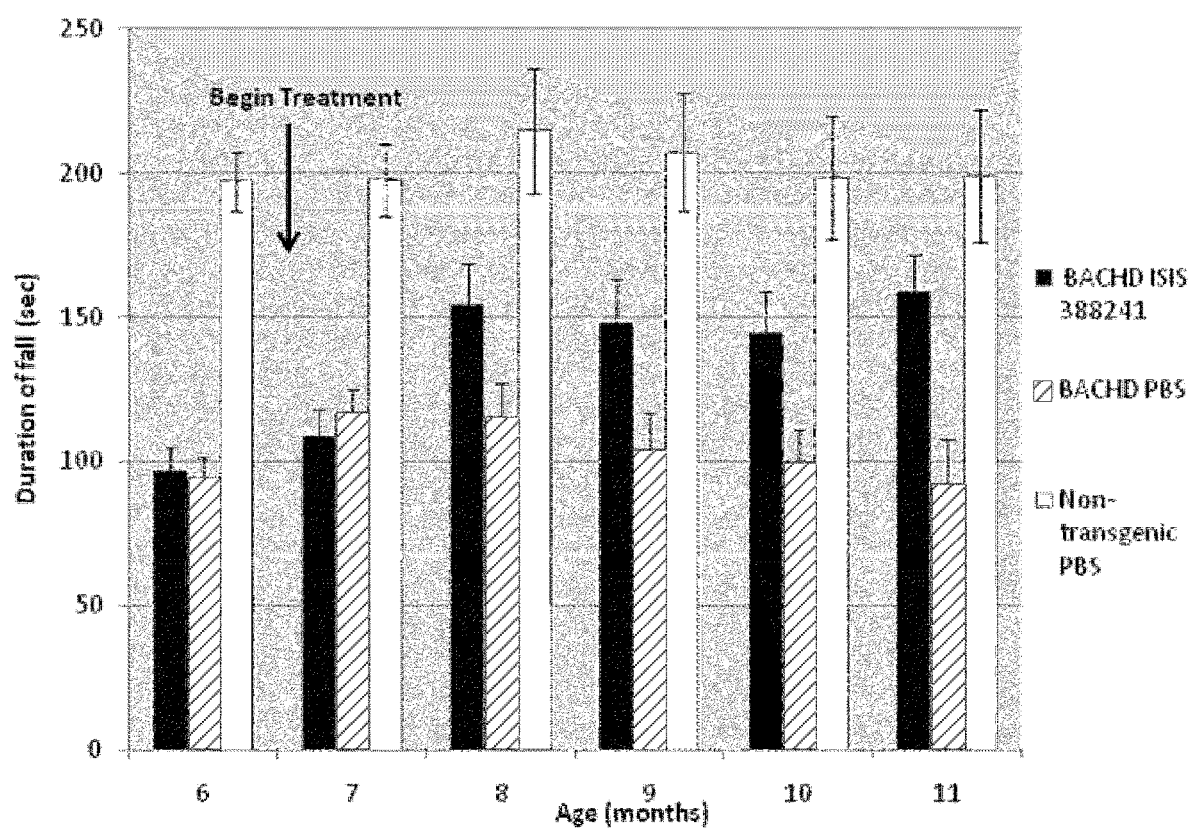

At the end of the treatment period, the pumps were removed and two weeks later, the first post-treatment rotarod assay was conducted. Rotarod behavior was analyzed monthly till the mice were 11 months of age. Each month, the animals were placed on the rotarod for three trial runs a day for 2 days. The results are presented in FIG. 7, as well as in Table 72 expressed as duration to fall in seconds. Baseline values at 6 months age were taken before the treatment and the time points given are the age of the mice at which the assay was conducted. The data indicates that treatment of BACHD mice with ISIS 388241 increased the duration to fall compared to that observed in untreated BACHD mice.

TABLE 72

Effect of antisense inhibition of mutant huntingtin mRNA on duration to fall (sec)

| | 6 months | 7 month | 8 months | 9 months | 10 months | 11 months |
|---|---|---|---|---|---|---|
| ISIS 388241 | 97 | 108 | 154 | 148 | 144 | 159 |
| PBS control | 94 | 117 | 115 | 104 | 99 | 92 |
| Non-transgenic control | 197 | 198 | 215 | 207 | 198 | 199 |

Example 13: Effect of Antisense Inhibition of Mutant Human Huntingtin and Wild Type Murine Huntingtin mRNA on the Motor Performance of BACHD Mice BACHD mice were treated with ISIS oligonucleotides via intracerebroventricular (ICV) administration for the purpose of evaluating the effect of the oligonucleotides against huntingtin mRNA expression on their motor performance via the rotarod assay.

Treatment

The accelerating rotarod assay was performed on the Ugo Basile rotarod. Animals were placed on the rotarod at a speed of 2 RPM, the rotarod accelerated to 40 RPM over 5 minutes. The duration to fall was recorded. Duration to fall is defined by the animal either falling from the rotarod, or stopping their run, hanging on to the rotarod and rotating on it. Two month old BACHD mice and their non-transgenic littermates were trained to run on the rotarod for one week prior to treatment. This consisted of three consecutive trials of 5 minutes each, with a 20 minute rest period between trials. Groups of 17-21 BACHD mice each were then treated with ISIS 388241 at 50 µg/day, ISIS 408737 at 75 µg/day, or ISIS 387898 at 75 µg/day, delivered ICV with Alzet 2002 pumps at the rate of 0.5 µL/hour for 2 weeks. The mice were surgically implanted with the pumps in a similar procedure as that described in Example 6. A control group of 20 BACHD mice were treated with PBS in a similar manner. Groups of non-transgenic control mice were also similarly treated with ISIS oligonucleotides or PBS in a similar manner.

Rotarod Performance Assay

At the end of the treatment period, the pumps were removed and two weeks later, the first post-treatment rotarod assay was conducted. Rotarod behavior was analyzed monthly till the mice were 10 months of age. Each month, the animals were placed on the rotarod for 3-5 trial runs a day for 3 consecutive days. The results are presented in Table 73 expressed as duration to fall in seconds. Baseline values at 2 months age were taken before the treatment and the time points given are the age of the mice at which the assay was conducted. ISIS 387898 (designated in the table as Human-mouse ASO) is cross-reactive for both mouse and human huntingtin mRNA and therefore would inhibit both human mutant huntingtin mRNA and wild-type murine huntingtin mRNA in the mice. ISIS 388241 (designated in the table as Human ASO) specifically targets human huntingtin mRNA and is mismatched by 8 base pairs with murine huntingtin mRNA. Therefore, ISIS 388241 would specifically inhibit only human mutant huntingtin mRNA and not wild-type murine huntingtin mRNA in the mice. ISIS 408737 (designated in the table as Mouse ASO) specifically targets murine huntingtin mRNA and is mismatched by 7 base pairs with human huntingtin mRNA. Therefore, ISIS 408737 would specifically inhibit only wild-type murine huntingtin mRNA and not human mutant huntingtin mRNA in the mice. 'Tg' indicates the BACHD mice and 'Non-Tg' indicates the non-transgenic control mice.

The results of the study indicate that inhibition of human mutant huntingtin mRNA by ISIS 388241 (Tg-Human ASO) significantly improved the performance of the mice in the rotarod assay compared to the control (Tg-PBS). The results also indicate that treatment of mice with ISIS 387898 (Tg-Human-mouse ASO), which targets both mutant and wild-type huntingtin mRNA in the mice, did not cause any deleterious effects on the motor performance of the mice and, in fact, also significantly improved rotarod performance compared to the control (Tg-PBS). The mice treated with ISIS 408737 (Tg-Mouse ASO) did not show improved rotarod performance compared to the PBS control, as expected, since the oligonucleotide does not target the mutant huntingtin mRNA. The non-transgenic controls were utilized as positive controls in this assay.

TABLE 73

Effect of antisense inhibition of huntingtin mRNA on duration to fall (sec)

| | 2 months | 3 months | 4 months | 5 months | 6 months | 7 months | 8 months | 9 months | 10 months |
|---|---|---|---|---|---|---|---|---|---|
| Tg-Human ASO | 146 | 167 | 190 | 192 | 190 | 188 | 181 | 191 | 191 |
| Tg-mouse ASO | 151 | 142 | 152 | 143 | 139 | 144 | 139 | 123 | 130 |
| Tg-Human-mouse ASO | 149 | 187 | 203 | 199 | 196 | 194 | 189 | 194 | 171 |
| Tg-PBS | 152 | 164 | 169 | 160 | 159 | 155 | 148 | 135 | 136 |
| Non-Tg-Human ASO | 212 | 223 | 234 | 236 | 247 | 248 | 245 | 247 | 235 |
| Non-Tg-Mouse ASO | 201 | 212 | 215 | 213 | 231 | 243 | 244 | 250 | 247 |
| Non-Tg-Human-mouse ASO | 220 | 240 | 239 | 224 | 243 | 244 | 246 | 229 | 235 |
| Non-Tg-PBS | 193 | 220 | 228 | 227 | 228 | 216 | 220 | 208 | 208 |

Example 14: Effect of Antisense Inhibition of Huntingtin mRNA on the Brain Mass of R6/2 Mice R6/2 mice were treated with ISIS oligonucleotides via intracerebroventricular (ICV) administration for the purpose of evaluating the effect of the oligonucleotides against huntingtin mRNA expression on brain weight and volume.

Treatment

R6/2 mice were housed in groups of up to 5 per cage (mixed genotypes, single sex), All mice were housed in shoe-box cages with sterile wood bedding covering the ground that were changed as frequently as needed to provide the animals with dry bedding. This basic environment was enriched with the addition of play tunnels, shredded nestlet, and plastic bones for all mice; i.e. an environmentally-enriched cage containing a Mouse Tunnel, (amber color, certified, transparent, BioSery Product# K3323), a Petite Green Gumabone (BioSery Product # K3214) and a nestlet (Hockley et al., Ann Neurol. 2002, 51: 235-242). Food and water were available ad libitum to the mice in their home cages.

A group of ten six month old R6/2 mice was administered 50 µg/day of ISIS 388817 delivered ICV with Alzet 1004 pumps at the rate of 0.12 µl/hr for 4 weeks. A group of two non-transgenic littermates was administered 50 µg/day of ISIS 388817 delivered in a similar manner. A control group of five R6/2 mice was administered 50 µg/day of ISIS 141923 delivered in a similar manner. A control group of nine R6/2 mice was administered PBS delivered in a similar manner. A group of eight non-transgenic littermates was administered PBS delivered in a similar manner. A group of four untreated eight-week old pre-symptomatic R6/2 were also included in the study.

Brain Weight Measurement

Figure 8:
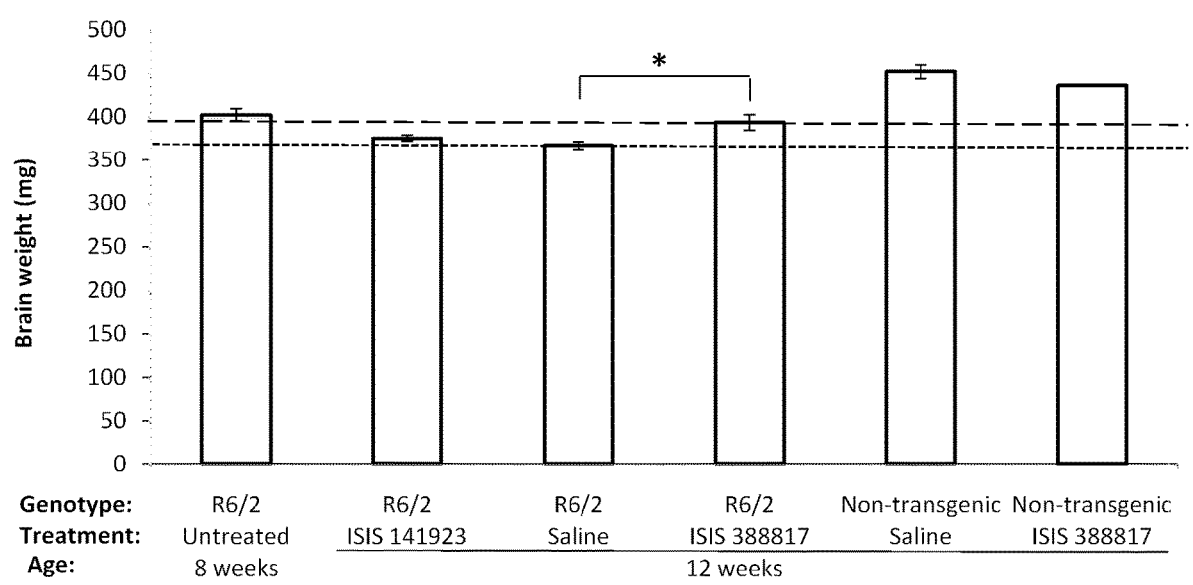

Animals were anaesthetized with isofluorane and then subjected to transcardial perfusion with ice-cold Sorenson's phosphate buffer (SPB), and fixed with 4% paraformaldyhyde in SPB. Brains were removed, and trimmed with coronal cuts immediately rostral to the forebrain (removing the olfactory bulbs) and immediately caudal to the cerebellum (removing the spinal cord). The remaining brain was weighed in mg. The results are presented in FIG. 8 and Table 74 and demonstrate the increase in brain weight in R6/2 mice treated with ISIS 388817 compared to the PBS control

TABLE 74

Effect of antisense inhibition of mutant huntingtin mRNA on brain weight (mg)

| Mouse model | Treatment | Brain weight |
|---|---|---|
| R6/2 | PBS | 367 |
| | ISIS 141923 | 375 |
| | ISIS 388817 | 394 |
| R6/2 (8 weeks old) | None | 402 |
| Non-transgenic | ISIS 141923 | 452 |
| | ISIS 388817 | 436 |

Example 15: Effect of Antisense Inhibition of Huntingtin mRNA on Anxiety Performance of YAC128 Mice YAC128 mice were treated with ISIS oligonucleotides via intracerebroventricular (ICV) administration for the purpose of evaluating the effect of the oligonucleotides against huntingtin mRNA expression on anxiety in these mice as measured by their performance in the open field and elevated plus maze assays.

Treatment

A group of seven five-month old YAC128 mice was administered 50 µg/day of ISIS 388241 delivered ICV with Alzet 1004 pumps at the rate of 0.5 µl/hr for 14 days. A control group of four YAC128 mice were similarly treated with PBS. A control group of eight non-transgenic FVB/NJ littermates was included in the study and did not receive any treatment. The mice were surgically implanted with the pumps in the following manner: Briefly, Alzet osmotic pumps (Model 2002) were assembled according to manufacturer's instructions. Pumps were filled with a solution containing the antisense oligonucleotide and incubated overnight at 37° C., 24 hours prior to implantation. Animals were anesthetized with 3% isofluorane and placed in a stereotactic frame. After sterilizing the surgical site, a midline incision was made over the skull, and a subcutaneous pocket was created over the back, in which a pre-filled osmotic pump was implanted. A small burr hole was made through the skull above the right lateral ventricle. A cannula, connected to the osmotic pump via a plastic catheter, was then placed in the ventricle and glued in place using Loctite adhesive. The incision was closed with sutures. Antisense oligonucleotide or PBS was infused for 14 days, after which the pumps were removed. The animals were allowed to recover for 2 weeks after which behavioral analysis was done and the mice were finally euthanized according to a humane protocol approved by the Institutional Animal Care and Use Committee. Brain and spinal cord tissue were harvested and snap frozen in liquid nitrogen. Prior to freezing, brain tissue was cut transversely into five sections (S1, S2, S3, S4, and S5) using a mouse brain matrix. Sections 1 to 5 were approximately 2 mm apart from each other with S1 being most rostral and S5 most caudal.

Open Field Assay

Figure 9:
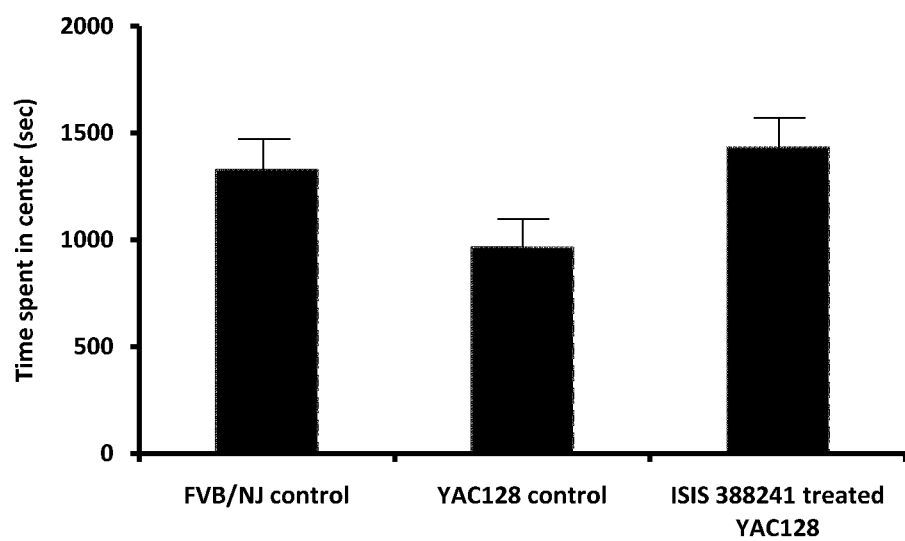

Mice were placed in an open field arena (Med Associates) that uses photobeam breaks to measure horizontal and vertical movement over a 30 min test session. Data was analyzed using Activity Monitor software to examine total ambulatory movement within the arena and movement within the center of the arena as a measure of anxiety. YAC128 control mice were expected to spend less time at the centre of the arena compared to their non-transgenic, less anxiety-prone FVB/NJ littermates. The results are presented in FIG. 9 and Table 75 and indicate that treatment of YAC128 mice with antisense oligonucleotide decreased anxiety in these mice, according to the parameters of the open field assay.

TABLE 75

Effect of antisense inhibition of mutant htt mRNA on open field performance of YAC128 mice

| Mice model | Time in center (sec) |
| --- | --- |
| FVB control | 1326 |
| YAC128 control | 964 |
| ISIS 388241 treated YAC128 | 1433 |

Elevated Plus Maze Sssay

Figure 10:
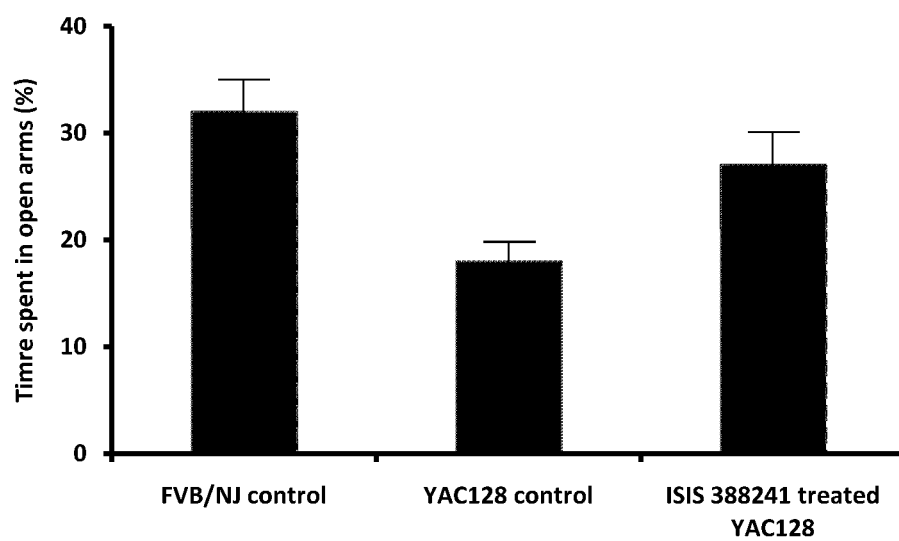

The apparatus consisted of two open arms and two closed arms each measuring 65×6.25 cm and elevated 50 cm above the ground. Mice were placed in the center of the apparatus and their location was recorded over a 5 minute test session. YAC128 control mice were expected to spend less time at the open arms of the apparatus compared to their non-transgenic, less anxiety-prone FVB/NJ littermates. The results are presented in FIG. 10 and Table 76 and indicate that treatment of YAC128 mice with antisense oligonucleotide decreased anxiety in these mice, according to the parameters of the elevated plus maze assay.

TABLE 76

Effect of antisense inhibition of mutant htt mRNA on elevated plus maze performance of YAC128 mice

| Mice model | % time in open arms |
| --- | --- |
| FVB control | 32 |
| YAC128 control | 18 |
| ISIS 388241 treated YAC128 | 27 |

RNA and Protein Analysis

Total RNA was extracted from mouse brain and spinal cord with RNeasy Protect Mini Kit (Qiagen, Mississauga, ON, Canada) for real-time PCR analysis of huntingtin mRNA levels using an RNeasy Mini prep kit (Qiagen). Q-PCR reactions were conducted and analyzed on an ABI Prism 7700 Sequence Detector (Applied Biosystems). Human huntingtin mRNA levels were measured using the human primer probe set RTS2686 and normalized to peptidylprolyl isomerase A mRNA levels.

Protein lysates were prepared from mouse brain slabs as described previously (Li S. H. and Li X. J., Methods in Molecular Biology (2008), 217:1940-6029). Lysates were run on 3-8% tris-acetate gel and transferred using the iBlot dry blotting system (Invitrogen). Blots were probed with anti-beta tubulin (Chemicon) and mouse monoclonal EM48 antibody that reacts specifically with human huntingtin protein (Millipore). Immunoblots were quantified using Odyssey V3.0 software.

The results are presented in Table 77 as percent reduction compared to the PBS control and demonstrate significant inhibition of huntingtin mRNA and protein levels by the antisense oligonucleotide.

TABLE 77

Percent inhibition of huntingtin mRNA in YAC128 mice

| | % inhibition |
| --- | --- |
| mRNA | 85 |
| protein | 86 |

Example 16: Intracerebroventricular Administration of Antisense Oligonucleotides Against Huntingtin in C57/BL6 Mice C57/BL6 mice were treated with ISIS oligonucleotides via intracerebroventricular (ICV) administration to the right lateral ventricle, for the purpose of evaluating the tolerability of the oligonucleotides in these mice.

Treatment and Surgery

Groups of five C57/BL6 mice each were administered ISIS 387916, ISIS 437527, ISIS 444578, ISIS 444584, ISIS 444607, ISIS 444608, ISIS 444627, ISIS 444652, ISIS 444659, ISIS 444660, or ISIS 444661 at 150 µg/day delivered ICV with Alzet 2002 pumps at the rate of 0.5 µL/day for 2 weeks. A control group of six C57/BL6 mice were similarly treated with PBS. The procedure for implanting the pumps and oligonucleotide administration is described in Example 6.

The animals were allowed to recover for two weeks before being euthanized using isoflurane. Brain and spinal cord tissue were harvested and snap frozen in liquid nitrogen. Prior to freezing, brain tissue was cut transversely into five sections (S1, S2, S3, S4, and S5) using a mouse brain matrix. Sections 1 to 5 were approximately 2 mm apart from each other with 51 being the most rostral and S5 the most caudal.

RNA Analysis

Total RNA was extracted from anterior and posterior cortices of the brain for real-time PCR analysis of huntingtin mRNA levels using an RNeasy Mini prep kit (Qiagen). RT-PCR reactions were conducted on an ABI Prism 7700 Sequence Detector (Applied Biosystems). Mouse huntingtin mRNA levels were measured using a murine primer probe set RTS2633 and normalized to cyclophilin mRNA levels. The results are presented in Table 78 as percent reduction compared to the PBS control. ISIS 387916, ISIS 437527, ISIS 444627, and ISIS 444652 all have one mismatch with the murine huntingtin mRNA (SEQ ID NO: 3) and therefore did not show significant inhibition of murine mRNA levels compared to the control.

The microglial marker, AIF1 was also measured by RT-PCR analysis using murine primer probe set mAIF1_LTS00328 (forward sequence TGGTCCCCCAGC-CAAGA, designated herein as SEQ ID NO: 54; reverse sequence CCCACCGTGTGACATCCA, designated herein as SEQ ID NO: 55; probe sequence AGCTATCTC-CGAGCTGCCCTGATTGG, designated herein as SEQ ID NO: 56). The results are presented in Table 79 and indicate that the tested ISIS oligonucleotides did not induce an inflammatory response.

TABLE 78

Percent inhibition of murine huntingtin mRNA compared to the control in C57/BL6 mice

| ISIS No | anterior | posterior |
|---|---|---|
| 387916 | 72 | 74 |
| 437527 | 59 | 62 |
| 444578 | 69 | 69 |
| 444584 | 0 | 9 |
| 444607 | 59 | 79 |
| 444608 | 41 | 66 |
| 444627 | 41 | 45 |
| 444652 | 61 | 64 |
| 444660 | 35 | 33 |
| 444661 | 72 | 69 |

TABLE 79

Percent increase in AIF1 mRNA expression compared to the control in C57/BL6 mice

| ISIS No | anterior | posterior |
|---|---|---|
| 387916 | 159 | 67 |
| 437527 | 102 | 77 |
| 444578 | 22 | 7 |
| 444584 | 33 | 37 |
| 444607 | 34 | 58 |
| 444608 | 29 | 1 |
| 444627 | 46 | 22 |
| 444652 | 59 | 50 |
| 444660 | -3 | 11 |
| 444661 | 67 | 62 |

Body Weight Measurements

Body weights were measured at regular intervals throughout the study period, and are presented in Table 80. These weights were utilized as an indicator of tolerability. Mice treated with ISIS 437527, ISIS 444584, and ISIS 444652 had consistent body weight throughout the study period and were deemed the most tolerable of all the ISIS oligonucleotides included in the study. 'n/a' indicates no data for that group of mice.

TABLE 80

Body weights of C57/BL6 mice after antisense oligonucleotide treatment

| | Day 0 | Day 4 | Day 8 | Day 12 | Day 16 | Day 19 | Day 23 | Day 26 | Day 28 |
|---|---|---|---|---|---|---|---|---|---|
| PBS | 105 | 108 | 111 | 114 | 111 | 111 | 113 | 114 | 112 |
| ISIS 387916 | 107 | 108 | 106 | 111 | 106 | 104 | 101 | 101 | 97 |
| ISIS 437527 | 105 | 116 | 116 | 120 | 111 | 112 | 112 | 108 | 108 |
| ISIS 444578 | 105 | 116 | 112 | 115 | 103 | 98 | 83 | 81 | 87 |
| ISIS 444584 | 105 | 117 | 115 | 111 | 105 | 105 | 103 | 104 | 102 |
| ISIS 444607 | 105 | 115 | 112 | 110 | 101 | 98 | 106 | 109 | 106 |
| ISIS 444608 | 102 | 111 | 112 | 112 | 97 | 91 | 78 | 75 | 87 |
| ISIS 444627 | 105 | 116 | 124 | 126 | 105 | 104 | 93 | 94 | 91 |
| ISIS 444652 | 106 | 122 | 124 | 126 | 119 | 113 | 111 | 111 | 108 |
| ISIS 444659 | 105 | 118 | 123 | 116 | 92 | 89 | 68 | n/a | n/a |
| ISIS 444660 | 104 | 115 | 120 | 118 | 103 | 93 | 89 | 84 | 90 |
| ISIS 444661 | 107 | 125 | 120 | 106 | 76 | 86 | 89 | 86 | 91 |

Example 17: Assay for Neurotoxic Effects of Bolus Administration of Antisense Oligonucleotides in the Striatal Tissue of Rats Sprague-Dawley rats were treated with ISIS oligonucleotides via bolus administration to the striatum, for the purpose of screening for the induction of the microglial marker AIF1 as a measure of CNS toxicity.

Treatment and Surgery

Groups of four Sprague-Dawley rats were administered ISIS 388241, ISIS 443139, ISIS 436671, ISIS 437527, ISIS 444584, ISIS 444591, or ISIS 444652 delivered as a single bolus at a concentration of 25 µg, 50 µg, 75 µg, or 100 µg.

A group of 4 rats were similarly treated with ISIS 387916, delivered as a single bolus at 10 µg, 25 µg, 50 µg, or 75 µg concentrations. A control group of 4 rats were similarly treated with PBS. Seven days after bolus administration, the rats were euthanized using isoflurane and the organs were removed. The animals were decapitated and the brain was removed for dissection of the striatal tissue. A pair of fine curved forceps was placed straight down into the brain just anterior to the hippocampus to make a transverse incision in the cortex and underlying tissues by blunt dissection. The tips of another pair of fine curved forceps were placed straight down along the midsaggital sinus midway between the hippocampus and the olfactory bulb to make a longitudinal incision, cutting the corpus callosum by blunt dissection. The first pair of forceps was then used to reflect back the resultant corner of cortex exposing the striatum and internal capsule, and then to dissect the internal capsule away from the striatum. The second set of forceps was placed such that the curved ends were on either side of the striatum and pressed down to isolate the tissue. The first set of forceps was used to pinch off the posterior end of the striatum and to remove the striatum from the brain.

RNA Analysis of AIF1 Expression Levels

RNA was extracted from striatal tissue for real-time PCR analysis of AIF1 mRNA levels. Rat AIF1 levels were measured using the rat primer probe set rAif1_LTS00219. Results were calculated as the percentage of AIF1 expression over that of the PBS control and are presented in Table 81. The results indicate that ISIS 388241, ISIS 443139, ISIS 436671, ISIS 444591, ISIS 437527, ISIS 444584, and ISIS 444652 were well tolerated in rat brain.

TABLE 81

Percent expression of AIF1 mRNA levels in vivo as a measure of neurotoxicity

| ISIS No | Dose (μg) | % increase |
|---|---|---|
| 387916 | 10 | 145 |
|  | 25 | 157 |
|  | 50 | 247 |
|  | 75 | 316 |
| 388241 | 25 | 29 |
|  | 50 | 12 |
|  | 75 | 30 |
|  | 100 | 41 |
| 436671 | 25 | 37 |
|  | 50 | 2 |
|  | 75 | 13 |
|  | 100 | 50 |
| 443139 | 25 | 0 |
|  | 50 | 7 |
|  | 75 | 167 |
|  | 100 | 26 |
| 444591 | 25 | 18 |
|  | 50 | 80 |
|  | 75 | 50 |
|  | 100 | 207 |
| 437527 | 25 | 98 |
|  | 50 | 45 |
|  | 75 | 23 |
|  | 100 | 126 |
| 444584 | 25 | −1 |
|  | 50 | 10 |
|  | 75 | 35 |
|  | 100 | 31 |
| 444652 | 25 | 17 |
|  | 50 | 46 |
|  | 75 | 39 |
|  | 100 | 48 |

RNA Analysis of Huntingtin Expression Levels

RNA was extracted from striatal tissue for real-time PCR analysis of huntingtin mRNA levels. Rat huntingtin mRNA levels were measured using the rat primer probe set rHtt_LTS00343. Results were calculated as the percentage reduction of huntingtin expression over that of the PBS control and are presented in Table 82. ISIS 388241 and ISIS 443139 are each mismatched by 6 base pairs or more with the rat gene sequence (SEQ ID NO: 5) and therefore do not show significant inhibition of rat mRNA levels compared to the control. ISIS 444584 has 3 mismatches with the rat gene sequence (SEQ ID NO: 5) and therefore does not show significant inhibition of rat mRNA levels compared to the control.

TABLE 82

Percent reduction of rat huntingtin mRNA levels in rats

| ISIS No | Dose (μg) | % inhibition |
|---|---|---|
| 387916 | 10 | 6 |
|  | 25 | 39 |
|  | 50 | 55 |
|  | 75 | 60 |
| 388241 | 25 | 8 |
|  | 50 | 23 |
|  | 75 | 27 |
|  | 100 | 19 |

TABLE 82-continued

Percent reduction of rat huntingtin mRNA levels in rats

| ISIS No | Dose (μg) | % inhibition |
|---|---|---|
| 436671 | 25 | 52 |
|  | 50 | 57 |
|  | 75 | 57 |
|  | 100 | 70 |
| 443139 | 25 | 35 |
|  | 50 | 29 |
|  | 75 | 28 |
|  | 100 | 27 |
| 444591 | 25 | 26 |
|  | 50 | 57 |
|  | 75 | 68 |
|  | 100 | 69 |
| 437527 | 25 | 40 |
|  | 50 | 55 |
|  | 75 | 60 |
|  | 100 | 74 |
| 444584 | 25 | 43 |
|  | 50 | 38 |
|  | 75 | 38 |
|  | 100 | 41 |
| 444652 | 25 | 49 |
|  | 50 | 70 |
|  | 75 | 55 |
|  | 100 | 59 |

Example 18: Dose-Dependent Antisense Inhibition of Huntingtin mRNA in Cynomolgous Primary Hepatocytes ISIS 437527, ISIS 444584, and ISIS 444652 were tested in cynomolgus primary hepatocytes at various doses. The benchmark oligonucleotides, ISIS 387916 and ISIS 388241 were also included for comparison. Cells were plated at a density of 35,000 cells per well and transfected using electroporation with 39.0625 nM, 78.125 nM, 156.25 nM, 312.5 nM, 625 nM, 1,250 nM, 2,500 nM, 5,000 nM, 10,000 nM, and 20,000 nM concentrations of each antisense oligonucleotide. After approximately 16 hours, RNA was isolated from the cells and huntingtin mRNA transcript levels were measured by quantitative real-time PCR using primer probe set RTS2686. Huntingtin mRNA transcript levels were normalized to total RNA content, as measured by RIBOGREEN®. Results are presented in Table 83 as percent inhibition of huntingtin, relative to untreated control cells. Control oligonucleotide, ISIS 141923 was included in this assay and did not demonstrate inhibition of huntingtin mRNA, as expected.

ISIS 437527, ISIS 444584, and ISIS 444652 had lower $IC_{50}$ values than the benchmark oligonucleotide, ISIS 388241. ISIS 437527 and ISIS 444652 had as low or lower IC50 values than the benchmark oligonucleotide, ISIS 387916.

TABLE 83

Dose-dependent antisense inhibition of huntingtin mRNA in cynomolgus primary hepatocytes

|  | ISIS 387916 | ISIS 388241 | ISIS 437527 | ISIS 444584 | ISIS 444652 | ISIS 141923 |
|---|---|---|---|---|---|---|
| 39.0625 nM | 0 | 6 | 0 | 0 | 0 | 0 |
| 78.125 nM | 17 | 4 | 19 | 0 | 16 | 0 |
| 156.25 nM | 6 | 0 | 27 | 11 | 12 | 3 |
| 312.5 nM | 19 | 0 | 23 | 16 | 35 | 0 |
| 625.0 nM | 31 | 0 | 37 | 30 | 50 | 0 |

TABLE 83-continued

Dose-dependent antisense inhibition of huntingtin mRNA in cynomolgous primary hepatocytes

| | ISIS 387916 | ISIS 388241 | ISIS 437527 | ISIS 444584 | ISIS 444652 | ISIS 141923 |
|---|---|---|---|---|---|---|
| 1250.0 nM | 45 | 0 | 28 | 23 | 52 | 0 |
| 2500.0 nM | 62 | 4 | 33 | 47 | 74 | 0 |
| 5000.0 nM | 78 | 54 | 55 | 42 | 86 | 0 |
| 10000.0 nM | 82 | 80 | 68 | 77 | 91 | 0 |
| 20000.0 nM | 84 | 75 | 70 | 69 | 92 | 0 |
| IC$_{50}$ (µM) | 1.4 | 5.4 | 2.0 | 4.0 | 0.8 | >20 |

Example 19: Measurement of Half-Life of ISIS Oligonucleotides in BACHD Mice Via Single Intrastriatal Bolus Administration BACHD mice were administered ISIS oligonucleotides as a single bolus to the striatum for the purpose of measuring the duration of action of the antisense oligonucleotides against huntingtin mRNA expression, or its half-life, in that tissue.

Treatment and Surgery

Groups of 25 BACD mice each were treated with ISIS 388241, ISIS 436689, ISIS 436671, or ISIS 444591, delivered as a single bolus of 40 µg in a procedure similar to that described in Example 4. A control group of 25 BACHD mice were treated with PBS in a similar procedure. At various time points, 5 mice from each group were euthanized and striatal tissue was extracted. A pair of fine curved forceps was placed straight down into the brain just anterior to the hippocampus to make a transverse incision in the cortex and underlying tissues by blunt dissection. The tips of another pair of fine curved forceps were placed straight down along the midsaggital sinus midway between the hippocampus and the olfactory bulb to make a longitudinal incision, cutting the corpus callosum by blunt dissection. The first pair of forceps was then used to reflect back the resultant corner of cortex exposing the striatum and internal capsule, and then to dissect the internal capsule away from the striatum. The second set of forceps was placed such that the curved ends were on either side of the striatum and pressed down to isolate the tissue. The first set of forceps was used to pinch off the posterior end of the striatum and to remove the striatum from the brain.

RNA Analysis

RNA was extracted from anterior and posterior sections of the striatal tissue for real-time PCR analysis of huntingtin mRNA levels. Human mutant huntingtin mRNA levels were measured using RTS2617. Mouse normal huntingtin mRNA levels were measured using the murine primer probe set RTS2633. The results are presented in Tables 84 and 85 and are expressed as percent inhibition compared to the average of the PBS control group at week 1, week 10, and week 20. The half-life of the ISIS oligonucleotides in the anterior section of the brain was calculated from the inhibition data and is presented in Table 86.

TABLE 84

Percent inhibition of human huntingtin mRNA expression at various time points

| ISIS No | Time (weeks) | Posterior | Anterior |
|---|---|---|---|
| 388241 | 1 | 72 | 91 |
| | 5 | 65 | 86 |
| | 10 | 52 | 73 |
| | 15 | 26 | 56 |
| | 20 | 14 | 53 |
| 436671 | 1 | 82 | 92 |
| | 5 | 78 | 89 |
| | 10 | 68 | 82 |
| | 15 | 61 | 77 |
| | 20 | 30 | 77 |
| 444591 | 1 | 60 | 85 |
| | 5 | 58 | 76 |
| | 10 | 48 | 60 |
| | 15 | 27 | 43 |
| | 20 | 27 | 36 |
| 436689 | 1 | 72 | 83 |
| | 5 | 72 | 87 |
| | 10 | 60 | 74 |
| | 15 | 50 | 74 |
| | 20 | 44 | 59 |

TABLE 85

Percent inhibition of mouse huntingtin mRNA expression at various time points

| ISIS No | Time (weeks) | Posterior | Anterior |
|---|---|---|---|
| 388241 | 1 | 1 | 12 |
| | 5 | 22 | 36 |
| | 10 | 17 | 14 |
| | 15 | 7 | 18 |
| | 20 | 9 | 38 |
| 436671 | 1 | 84 | 96 |
| | 5 | 77 | 80 |
| | 10 | 64 | 86 |
| | 15 | 51 | 78 |
| | 20 | 19 | 75 |
| 444591 | 1 | 74 | 95 |
| | 5 | 70 | 90 |
| | 10 | 57 | 67 |
| | 15 | 34 | 47 |
| | 20 | 33 | 38 |
| 436689 | 1 | 40 | 32 |
| | 5 | 47 | 40 |
| | 10 | 35 | 18 |
| | 15 | 34 | 22 |
| | 20 | 36 | 5 |

TABLE 86

Half-life of ISIS oligonucleotides in the anterior section of the brain in BACHD mice after intrastriatal bolus injection

| ISIS No | Half-life (days) |
|---|---|
| 436671 | 46.6 |
| 436689 | 39.4 |
| 444591 | 24.3 |
| 388241 | 25.8 |

Body Weight Measurements

Body weights were measured at regular intervals, and are presented in Table 87 as a percent of the weight of the mice at the start of the study. These weights were utilized as an

TABLE 87

Percent change in body weight of BACHD mice after antisense oligonucleotide treatment

|  | Week 5 | Week 10 | Week 15 | Week 20 |
|---|---|---|---|---|
| PBS | 8 | 19 | 26 | 28 |
| ISIS 388241 | 9 | 22 | 29 | 26 |
| ISIS 436671 | 5 | 19 | 35 | 38 |
| ISIS 444591 | 7 | 21 | 30 | 43 |
| ISIS 436689 | 3 | 18 | 31 | 38 |

Example 20: Effect of Intrathecal Administration of ISIS 437527 in Sprague Dawley Rats Sprague Dawley rats were dosed with ISIS 437527 by intrathecal (IT) administration either as a single dose, repeated doses, or continuous infusion.

Treatment and Surgery

Rats were anesthetized with isoflurane and a 28-gauge polyurethane catheter was placed into the IT lumbar space of each rat. The proximal end of the catheter was attached to a dosing pedestal that was extended through the skin for animals in groups receiving bolus injections. The catheter for animals in the group receiving continuous infusion was attached to an ALZET pump (Model 2ML1) which was placed in a subcutaneous pocket on the dorsal aspect of each animal. Post-surgically the animals received a single intramuscular dose of ceftiofur sodium (5 mg/kg) and butorphanol tartrate (0.05 mg/kg). The rats receiving continuous infusion began receiving the oligonucleotide dose immediately. The animals that would receive bolus injections were allowed a surgical recovery period of at least five days after which the patency of the catheter was evaluated.

A group of 5 Sprague Dawley rats was administered a single bolus injection of 350 µg of ISIS 437527 delivered intrathecally. Another group of 5 Sprague Dawley rats was administered bolus injections of 120 µg of ISIS 437527 delivered intrathecally three times over the course of 1 week. Another group of 5 Sprague Dawley rats was administered bolus injections of 350 µg of ISIS 437527 delivered intrathecally three times over the course of 1 week. Another group of 5 Sprague Dawley rats was administered 50 µg/day of ISIS 437527 delivered by continuous infusion at a rate of 0.01 mL/hr for 7 days. A control group of 5 Sprague Dawley rats was administered bolus injections of PBS delivered intrathecally three times over the course of 1 week. Each group was given a recovery period of 7 days, after which the rats were euthanized. The brain and spinal cord from all groups were harvested and analyzed.

RNA Analysis of Huntingtin Expression Levels

RNA was extracted from the frontal cortex, temporal cortex, and the cervical cord for real-time PCR analysis of huntingtin mRNA levels. Rat huntingtin mRNA levels were measured using the primer probe set rHtt_LTS00343 normalized to Cyclophilin levels. The results are presented in Table 88 and are expressed as percent inhibition compared to the average of the PBS control groups.

TABLE 88

Percent inhibition of huntingtin mRNA expression in Sprague Dawley rats

| Tissue | Dose schedule | Dose | % inhibition |
|---|---|---|---|
| Frontal Cortex | IT Infusion | 50 µg/day | 11 |
|  | Single IT Bolus | 350 µg | 28 |
|  | Repeated IT Bolus | 120 µg × 3 | 21 |
|  | Repeated IT Bolus | 350 µg × 3 | 0 |
| Temporal Cortex | IT Infusion | 50 µg /day | 0 |
|  | Single IT Bolus | 350 µg | 34 |
|  | Repeated IT Bolus | 120 µg × 3 | 44 |
|  | Repeated IT Bolus | 350 µg × 3 | 48 |
| Cervical Cord | IT Infusion | 50 µg /day | 22 |
|  | Single IT Bolus | 350 µg | 45 |
|  | Repeated IT Bolus | 120 µg × 3 | 58 |
|  | Repeated IT Bolus | 350 µg × 3 | 46 |

RNA Analysis of AIF1 Expression Levels

RNA was extracted from frontal cortex, temporal cortex, and the cervical cord for real-time PCR analysis of AIF1 mRNA levels. Rat AIF1 levels were measured using the rat primer probe set rAif1_LTS00219. Results were calculated as the percentage of AIF1 expression over that of the PBS control and are presented in Table 89. The results indicate that repeated IT bolus administrations lead to inflammation at the cervical cord tissues. Continuous IT administration and single IT bolus administrations were well tolerated in the rats.

TABLE 89

Percent expression of AIF1 mRNA levels in Sprague Dawley rats as a measure of neurotoxicity

| Tissue | Dose schedule | Dose | % inhibition |
|---|---|---|---|
| Frontal Cortex | IT Infusion | 50 µg/day | −36 |
|  | Single IT Bolus | 350 µg | −4 |
|  | Repeated IT Bolus | 120 µg × 3 | 41 |
|  | Repeated IT Bolus | 350 µg × 3 | −7 |
| Temporal Cortex | IT Infusion | 50 µg /day | 15 |
|  | Single IT Bolus | 350 µg | 22 |
|  | Repeated IT Bolus | 120 µg × 3 | 25 |
|  | Repeated IT Bolus | 350 µg × 3 | 76 |
| Cervical Cord | IT Infusion | 50 µg /day | 108 |
|  | Single IT Bolus | 350 µg | 72 |
|  | Repeated IT Bolus | 120 µg × 3 | 473 |
|  | Repeated IT Bolus | 350 µg × 3 | 268 |

Example 21: Measurement of Half-Life of ISIS 436689 in the CNS Tissues of Cynomolgous Monkeys Via Intrathecal Administration Cynomolgous monkeys were administered ISIS 436689 intrathecally (IT) for the purpose of measuring the half-life and duration of action of the antisense oligonucleotide against huntingtin mRNA expression in various CNS tissues.

Treatment

The study was conducted at Northern Biomedical Research, MI. Prior to the start of the treatment, the monkeys were kept in quarantine for a 4-week time period, during which standard panels of serum chemistry and hematology, examination of fecal samples for ova and parasites, and a tuberculosis test, were conducted to screen out abnormal or ailing monkeys. The monkeys were implanted with intrathecal lumbar catheters using polyurethane catheters connected to a subcutaneous titanium access port (P.A.S. PORT® Elite Plastic/Titanium portal with Ultra lock connector). For continuous infusion using an external pump, the animals were anesthetized to attach the dosing apparatus to the port. The animals were pretreated with atropine sulfate by subcutaneous injection at a dose of 0.04 mg/kg. Approximately 15 minutes later, an intramuscular dose of 8 mg/kg of ketamine HCl was administered to induce sedation. The animals were masked to a surgical plane of anesthesia, intubated and maintained on approximately 1 L/min of oxygen and 2% halothane or isoflurane. The animals received a single intramuscular dose of 5 mg/kg ceftiofur sodium antibiotic. An incision was made near the port for placement of the modified needle support. The modified needle was placed in the port and secured with sutures. Upon recovery from surgery, a jacket was placed on the animal.

Fifteen male cynomolgus monkeys were administered 4 mg/day of ISIS 436689 at a concentration of 1.67 mg/mL and at a flow rate of 2.4 mL/day for 21 days. A control group of 3 cynomolgus monkeys was administered with PBS in a similar manner for the same time period. Groups of 3 monkeys each were allowed recovery periods of 1 day, 2 weeks, 4 weeks, or 8 weeks, after which they were euthanized. During the study period, the monkeys were observed daily for signs of illness or distress.

All animals were sedated with an intramuscular injection of 8.0 mg/kg of ketamine HCl, maintained on a halothane or isoflurane/oxygen mixture, and provided with an intravenous bolus of heparin Na at 200 IU/kg. The animals were perfused via the left cardiac ventricle with 0.001% sodium nitrite in saline.

At the time of sacrifice, the brain was cut in a brain matrix at 3 mm coronal slice thickness. Several brain structures were sampled using a 4 mm biopsy punch. One 4 mm diameter sample from each structure was placed in 2 mL screw capped tubes containing 1.0 mL of RN Alater RNA stabilization solution (Qiagen, Calif.), incubated for 1 hour at ambient temperature and then frozen. Adjacent 6 mm diameter samples were placed in 2 mL screw capped tubes and frozen for pharmacokinetic analysis.

The spinal cord was sectioned into cervical, thoracic and lumbar sections, and approximately 3 mm thick sections of each area of the spinal cord were taken for RNA and pharmacokinetic analysis. These samples were processed in a manner similar to those of the brain samples.

Samples of the liver were harvested for RNA and pharmacokinetic analyses. These samples were processed in a manner similar to those of the brain and spinal cord described above.

RNA Analysis

RNA was extracted from the lumbar spinal cord, thoracic spinal cord, cervical spinal cord, frontal cortex, occipital cortex, cerebellar cortex, caudate tissue, hippocampus, middle brain, and pons for real-time PCR analysis of huntingtin mRNA levels with primer probe set RTS2617. The results measured in the various sections of the spinal cord are presented in Table 90 and are expressed as percent inhibition compared to that measured in the PBS control group at 8 weeks. The results measured in the various sections of the brain are presented in Table 91 and are expressed as percent inhibition compared to that measured in the PBS control group at 8 weeks.

TABLE 90

Effect of ISIS 436689 administered IT on huntingtin mRNA expression in the spinal cord at various time points

| Recovery period | Lumbar spinal cord | Thoracic spinal cord | Cervical spinal cord |
|---|---|---|---|
| 1 Day | 36 | 66 | 65 |
| 2 Weeks | 56 | 55 | 54 |
| 4 Weeks | 0 | 63 | 65 |
| 8 Weeks | 48 | 48 | 44 |

TABLE 91

Effect of ISIS 436689 administered IT on huntingtin mRNA expression in various brain tissues at various time points

| Recovery period | Frontal cortex | Occipital cortex | Cerebellar cortex | Caudate | Hippocampus | Middle brain | Pons |
|---|---|---|---|---|---|---|---|
| 1 Day | 53 | 37 | 8 | 21 | 19 | 24 | 22 |
| 2 Weeks | 42 | 28 | 16 | 3 | 28 | 0 | 32 |
| 4 Weeks | 47 | 32 | 25 | 7 | 22 | 2 | 43 |
| 8 Weeks | 33 | 34 | 11 | 17 | 27 | 5 | 22 |

Oligonucleotide Concentration Measurement by ELISA

Tissues (20 mg) were minced, weighed, and homogenized prior to liquid/liquid extraction using phenol/chloroform. The supernatant was removed, lyophilized, and reconstituted in human EDTA plasma (1 mL) before being analyzed using a hybridization ELISA procedure.

ISIS 436689 was detected in the tissues by hybridization to a labeled complementary cutting probe (digoxigenin at the 5' end and a C18 spacer and BioTEG at the 3' end). The complex was then captured on a neutravidin-coated plate and S1 nuclease was added to digest the unhybridized cutting probes. Since ISIS 436689 protected the cutting probe from digestion, the undigested cutting probe was used as a measure of the oligonucleotide concentration. The undigested cutting probe was detected using an anti-digoxigenin antibody conjugated to alkaline phosphatase followed by fluorogenic substrate readout. Oligonucleotide concentrations were measured in the cervical, thoracic, and lumbar sections of the spinal cord and in the liver on days 7, 20, 34, and 62 of the recovery period, and are presented in Table 92. The half-life of ISIS 436689 in these tissues was calculated from this data, and is presented in Table 93. The data indicates that the oligonucleotide was mainly concentrated in the CNS with negligible concentrations in the systemic tissues.

TABLE 92

Concentrations (μg/g tissue) of ISIS 436689 administered IT on huntingtin mRNA expression in various tissues at various time points

| Organ | Day 7 | Day 20 | Day 34 | Day 62 |
| --- | --- | --- | --- | --- |
| Cervical cord | 118.9 | 78.7 | 79.8 | 42.8 |
| Thoracic cord | 503.5 | 215.8 | 101.6 | 61.4 |
| Lumbar cord | 557.1 | 409.5 | 143.3 | 49.5 |
| Liver | 33.6 | 10.3 | 2.0 | 0.2 |

TABLE 93

Half-life of ISIS 436689 administered IT on huntingtin mRNA expression in various tissues

| Organ | Half-life |
| --- | --- |
| Cervical cord | 4.0 |
| Thoracic cord | 15.1 |
| Lumbar cord | 18.7 |
| Liver | 7.6 |

The invention claimed is:

1. A single-stranded modified oligonucleotide consisting of 18 linked nucleosides and having:
   a gap segment consisting of eight linked deoxynucleosides;
   a 5' wing segment consisting of five linked nucleosides; and
   a 3' wing segment consisting of five linked nucleosides;
   wherein the gap segment is positioned between the 5' wing segment and the 3' wing segment;
   wherein each nucleoside of each wing segment comprises a 2'O-methoxyethyl sugar; and
   wherein the nucleobase sequence of the oligonucleotide consists of the sequence recited in SEQ ID NO: 29, or a pharmaceutically acceptable salt thereof.

2. The single-stranded modified oligonucleotide of claim 1, wherein at least one nucleoside comprises a modified nucleobase.

3. The single-stranded modified oligonucleotide of claim 2, wherein the modified nucleobase is a 5-methylcytosine.

4. The single-stranded modified oligonucleotide of claim 1, wherein each cytosine is a 5-methylcytosine.

5. The single-stranded modified oligonucleotide of claim 1, wherein at least one internucleoside linkage is a modified internucleoside linkage.

6. The single-stranded modified oligonucleotide of claim 1, wherein each internucleoside linkage is a phosphorothioate internucleoside linkage.

7. The single-stranded modified oligonucleotide of claim 4, wherein at least one internucleoside linkage is a modified internucleoside linkage.

8. The single-stranded modified oligonucleotide of claim 4, wherein each internucleoside linkage is a phosphorothioate internucleoside linkage.

9. A composition comprising the single-stranded modified oligonucleotide or pharmaceutically acceptable salt thereof of claim 1 and at least one pharmaceutically acceptable carrier or diluent.

10. A composition comprising the single-stranded modified oligonucleotide or pharmaceutically acceptable salt thereof of claim 4 and at least one pharmaceutically acceptable carrier or diluent.

11. A composition comprising the single-stranded modified oligonucleotide or pharmaceutically acceptable salt thereof of claim 6 and at least one pharmaceutically acceptable carrier or diluent.

12. A composition comprising the single-stranded modified oligonucleotide or pharmaceutically acceptable salt thereof of claim 8 and at least one pharmaceutically acceptable carrier or diluent.

13. The single-stranded modified oligonucleotide of claim 1, which is capable of inhibiting huntingtin expression.

14. The single-stranded modified oligonucleotide of claim 4, which is capable of inhibiting huntingtin expression.

15. The single-stranded modified oligonucleotide of claim 6, which is capable of inhibiting huntingtin expression.

16. The single-stranded modified oligonucleotide of claim 8, which is capable of inhibiting huntingtin expression.

* * * * *